United States Patent
Bartolozzi et al.

(10) Patent No.: US 8,580,829 B2
(45) Date of Patent: Nov. 12, 2013

(54) OXADIAZOLE INHIBITORS OF LEUKOTRIENE PRODUCTION

(75) Inventors: Alessandra Bartolozzi, Norwalk, CT (US); Todd Bosanac, New Milford, CT (US); Zhidong Chen, New Milford, CT (US); Stephane De Lombaert, Branford, CT (US); Jonathon Alan Dines, Wokingham (GB); John D. Huber, New York, NY (US); Weimin Liu, Beijing (CN); Ho Yin Lo, Bethel, CT (US); Pui Leng Loke, Abingdon (GB); Tina Marie Morwick, Carmel, IN (US); Peter Allen Nemoto, Southbury, CT (US); Alan Olague, Danbury, CT (US); Doris Riether, Biberach an der Riss (DE); Heather Tye, Abingdon (GB); Lifen Wu, New Milford, CT (US); Renee M. Zindell, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 34 days.

(21) Appl. No.: 13/215,654

(22) Filed: Aug. 23, 2011

(65) Prior Publication Data
US 2012/0214787 A1 Aug. 23, 2012

Related U.S. Application Data

(60) Provisional application No. 61/511,247, filed on Jul. 25, 2011, provisional application No. 61/377,181, filed on Aug. 26, 2010.

(51) Int. Cl.
*A01N 43/82* (2006.01)
*A61K 31/41* (2006.01)

(52) U.S. Cl.
USPC .......................... 514/364; 548/131

(58) Field of Classification Search
USPC .......................... 548/131; 514/364
See application file for complete search history.

(56) References Cited

U.S. PATENT DOCUMENTS

| | | | |
|---|---|---|---|
| 6,911,444 B2 | 6/2005 | Lacrampe et al. | |
| 7,319,108 B2 | 1/2008 | Schwink et al. | |
| 2007/0105866 A1 | 5/2007 | Hutchinson et al. | |
| 2009/0192171 A1 | 7/2009 | Hutchinson et al. | |
| 2010/0197591 A1 | 8/2010 | Aspnes et al. | |
| 2011/0206652 A1 | 8/2011 | Kayser et al. | |
| 2011/0206783 A1* | 8/2011 | Burgey et al. | 424/722 |
| 2012/0214787 A1 | 8/2012 | Bartolozzi et al. | |
| 2012/0220561 A1* | 8/2012 | Bartolozzi et al. | 514/210.2 |
| 2012/0245162 A1* | 9/2012 | Bartolozzi et al. | 514/230.5 |
| 2012/0295896 A1* | 11/2012 | Bartolozzi et al. | 514/227.8 |

FOREIGN PATENT DOCUMENTS

| | | | |
|---|---|---|---|
| WO | 2006044602 A2 | 4/2006 | |
| WO | 2007056228 A2 | 5/2007 | |
| WO | 2007120574 A2 | 10/2007 | |
| WO | 2008030369 A1 | 3/2008 | |
| WO | 2008128335 A1 | 10/2008 | |
| WO | 2008156721 A1 | 12/2008 | |
| WO | 2009048547 A1 | 4/2009 | |
| WO | 2011143466 A1 | 11/2011 | |

OTHER PUBLICATIONS

International Search Report for PCT/US2011/047356 mailed on Oct. 28, 2011.
International Search Report for PCT/US2011/048743 mailed on Nov. 2, 2011.
International Search Report for PCT/US2011/052252 mailed on Nov. 2, 2011.
International Search Report for PCT/US2011/052254 mailed on Nov. 16, 2011.
U.S. Appl. No. 13/237,112, filed Sep. 20, 2011. First named inventor: Alessandra Bartolozzi.
Chabner, Bruce A. et al. "Antineoplastic Agents" Chemotherapy of Neoplastic Diseases, Goodman & Gilmans, The Pharmacological Basis of Therapeutics, (2006) 11th edition, pp. 1315-1403.
Poupaert, Jacques H. "Drug Design: Basic Principles and Applications" Encyclopedia of Pharmaceutical Technology, 3rd Edition, (2007) pp. 1362-1369.
Machine Translation of JP05112564 (May 7, 1993).

* cited by examiner

*Primary Examiner* — James O Wilson
*Assistant Examiner* — Alexander R Pagano
(74) *Attorney, Agent, or Firm* — Michael P. Morris; Usha R. Patel

(57) ABSTRACT

The present invention relates to compounds of formula (I):

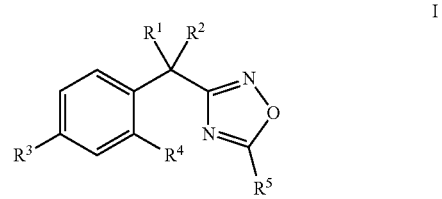

and pharmaceutically acceptable salts thereof, wherein $R^1$-$R^5$ are as defined herein. The invention also relates to pharmaceutical compositions comprising these compounds, methods of using these compounds in the treatment of various diseases and disorders, processes for preparing these compounds and intermediates useful in these processes.

18 Claims, No Drawings

OXADIAZOLE INHIBITORS OF LEUKOTRIENE PRODUCTION

FIELD OF THE INVENTION

This invention relates to oxadiazoles that are useful as inhibitors of five lipoxygenase activating protein (FLAP) and are thus useful for treating a variety of diseases and disorders that are mediated or sustained through the activity of leukotrienes including asthma, allergy, rheumatoid arthritis, multiple sclerosis, inflammatory pain, acute chest syndrome and cardiovascular diseases including atherosclerosis, myocardial infarction and stroke. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Leukotrienes (LTs) and the biosynthetic pathway from arachidonic acid leading to their production have been the targets of drug discovery efforts for over twenty years. LTs are produced by several cell types including neutrophils, mast cells, eosinophils, basophils monocytes and macrophages. The first committed step in the intracellular synthesis of LTs involves oxidation of arachidonic acid by 5-lipoxygenase (5-LO) to LTA4, a process requiring the presence of the 18 kD integral membrane protein 5-lipoxygenase-activating protein (FLAP) (D. K. Miller et al., Nature, 1990, 343, 278-281; R. A. F. Dixon et al., Nature, 1990, 343, 282-284). Subsequent metabolism of $LTA_4$ leads to $LTB_4$, and the cysteinyl LTs-$LTC_4$, $LTD_4$ and $LTE_4$ (B. Samuelsson, Science, 1983, 220, 568-575). The cysteinyl LTs have potent smooth muscle constricting and bronchoconstricting effects and they stimulate mucous secretion and vascular leakage. $LTB_4$ is a potent chemotactic agent for leukocytes, and stimulates adhesion, aggregation and enzyme release.

Much of the early drug discovery effort in the LT area was directed towards the treatment of allergy, asthma and other inflammatory conditions. Research efforts have been directed towards numerous targets in the pathway including antagonists of $LTB_4$ and the cysteinyl leukotrienes $LTC_4$, $LTD_4$ and $LTE_4$, as well as inhibitors of 5-lipoxygenase (5-LO), $LTA_4$ hydrolase and inhibitors of 5-lipoxygenase activating protein (FLAP) (R. W. Friesen and D. Riendeau, Leukotriene Biosynthesis Inhibitors, Ann. Rep. Med. Chem., 2005, 40, 199-214). Years of effort in the above areas have yielded a few marketed products for the treatment of asthma including a 5-LO inhibitor, zileuton, and LT antagonists, montelukast, pranlukast and zafirlukast.

More recent work has implicated LTs in cardiovascular disease, including myocardial infarction, stroke and atherosclerosis (G. Riccioni et al., J. Leukoc. Biol., 2008, 1374-1378). FLAP and 5-LO were among the components of the 5-LO and LT cascade found in atherosclerotic lesions, suggesting their involvement in atherogenesis (R. Spanbroek et al., Proc. Natl. Acad. Sci. U.S.A., 2003, 100, 1238-1243). Pharmacological inhibition of FLAP has been reported to decrease atherosclerotic lesion size in animal models. In one study, oral dosing of the FLAP inhibitor MK-886 to apoE/LDL-R double knockout mice fed a high-fat diet from 2 months of age to 6 months led to a 56% decrease in plaque coverage in the aorta and a 43% decrease in the aortic root (J. Jawien et al., Eur. J. Clin. Invest., 2006, 36, 141-146). This plaque effect was coupled with a decrease in plaque-macrophage content and a concomitant increase in collagen and smooth muscle content which suggests a conversion to a more stable plaque phenotype. In another study, it was reported that administration of MK-886 via infusion to $ApoE^{-/-}$xCD4dnTβRII mice (apoE KO mice expressing a dominant-negative TGF-beta receptor which effectively removes all TGF-beta from the system) resulted in about a 40% decrease in plaque area in the aortic root (M. Back et al., Circ. Res., 2007, 100, 946-949). The mice were only treated for four weeks after plaque growth was already somewhat mature (12 weeks) thus raising the possibility of therapeutically treating atherosclerosis via this mechanism. In a study examining human atherosclerotic lesions, it was found that the expression of FLAP, 5-LO and $LTA_4$ hydrolase was significantly increased compared to healthy controls (H. Qiu et al., Proc. Natl. Acad. Sci. U.S.A., 103, 21, 8161-8166). Similar studies suggest that inhibition of the LT pathway, for example by inhibition of FLAP, would be useful for the treatment of atherosclerosis (for reviews, see M. Back Curr. Athero. Reports, 2008 10, 244-251 and Cum Pharm. Des., 2009, 15, 3116-3132).

In addition to the work cited above, many other studies have been directed towards understanding the biological actions of LTs and the role of LTs in disease. These studies have implicated LTs as having a possible role in numerous diseases or conditions (for a review, see M. Peters-Golden and W. R. Henderson, Jr., M. D., N. Engl. J. Med., 2007, 357, 1841-1854). In addition to the specific diseases cited above, LTs have been implicated as having a possible role in numerous allergic, pulmonary, fibrotic, inflammatory and cardiovascular diseases, as well as cancer. Inhibition of FLAP is also reported to be useful for treating renal diseases such as diabetes-induced proteinuria (see for example J. M. Valdivieso et al., Journal of Nephrology, 2003, 16, 85-94 and A Montero et al., Journal of Nephrology, 2003, 16, 682-690).

A number of FLAP inhibitors have been reported in the scientific literature (see for example J. F. Evans et al., Trends in Pharmacological Sciences, 2008, 72-78) and in U.S. patents. Some have been evaluated in clinical trials for asthma, including MK-886, MK-591, and BAY X1005, also known as DG-031. More recently, the FLAP inhibitor AM-103 (J. H. Hutchinson et al., J. Med. Chem. 52, 5803-5815) has been evaluated in clinical trials, based on its anti-inflammatory properties (D. S. Lorrain et al., J. Pharm. Exp. Ther., 2009, DOI:10.1124/jpet.109.158089). Subsequently, it was replaced by the back-up compound AM-803 (GSK-2190915) for the treatment of respiratory diseases. DG-031 has also been in clinical trials to evaluate its effect on biomarkers for myocardial infarction risk and showed a dose-dependent suppression of several biomarkers for the disease (H. Hakonarson et al., JAMA, 2005, 293, 2245-2256). MK-591 was shown in a clinical trial to reduce proteinuria in human glomerulonephritis (see for example A. Guash et al., Kidney International, 1999, 56, 291-267).

However, to date, no FLAP inhibitor has been approved as a marketed drug.

BRIEF SUMMARY OF THE INVENTION

The present invention provides novel compounds which inhibit 5-lipoxygenase activating protein (FLAP) and are thus useful for treating a variety of diseases and disorders that are mediated or sustained through the activity of leukotrienes, including allergic, pulmonary, fibrotic, inflammatory and cardiovascular diseases and cancer. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its first broadest embodiment, the present invention relates to a compound of formula I:

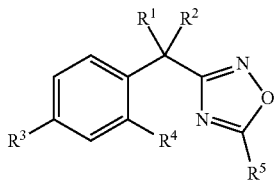

wherein:
$R^1$ and $R^2$ together with the carbon atom to which they are attached form a $C_{3-10}$ carbocyclic ring or a 5-11 membered heterocyclic ring, wherein each carbocycle or heterocycle is optionally independently substituted with one to two groups selected from $C_{1-6}$ alkyl and halogen;
$R^3$ is 5-11 membered heteroaryl ring containing one to three heteroatoms selected from nitrogen, oxygen and sulfur, wherein each $R^3$ is optionally independently
substituted with one to three groups selected from $C_{1-5}$ alkyl, $C_{3-6}$ carbocycle, cyano, $C_{1-5}$ alkoxy, $C_{1-3}$ hydroxy, amino, $C_{1-3}$ alkylamino and $C_{1-3}$ dialkylamino;
$R^4$ is hydrogen, halogen, $C_{1-3}$ alkyl or nitrile;
$R^5$ is $C_{1-6}$ alkyl, $C_{3-10}$ carbocycle, 5-11 membered heterocycle, aryl, 5-11 membered heteroaryl, —C(O)—$R^6$ or —$NR^7R^8$, wherein each $R^5$ is optionally independently substituted with one to three groups selected from $R^9$, $R^{10}$ and $R^{11}$;
$R^6$ is $C_{3-8}$ heterocycle, amino, $C_{1-3}$ alkylamino, $C_{1-3}$ dialkylamino, —NH-5-6 membered heteroaryl or —NH-5-6 membered heterocycle, each optionally independently substituted with one to three groups selected from $R^9$, $R^{10}$ and $R^{11}$;
$R^7$ and $R^8$ are each independently hydrogen, 5-6 membered heterocyclic ring optionally substituted with one to three methyl groups, —S(O)$_n C_{1-6}$alkyl or $C_{1-6}$ alkyl which is optionally substituted with 5-6 membered heterocycle;
$R^9$, $R^{10}$ and $R^{11}$ are independently selected from
  (a) —H,
  (b) —OH,
  (c) halogen,
  (d) —CN,
  (e) —$CF_3$,
  (f) $C_{1-6}$alkyl optionally substituted with one to three —OH, CN, —N($R^{12}$)($R^{13}$), aryl, —O—$C_{1-2}$ alkyl-aryl, 3-6 membered heterocycle, —C(O)-3-6 membered heterocycle, $C_{1-6}$alkoxy, —S(O)$_n C_{1-6}$alkyl or —C(O)N($R^{12}$)($R^{13}$),
  (g) $C_{1-6}$alkoxy,
  (h) —N($R^{12}$)($R^{13}$),
  (i) —S(O)$_n C_{1-6}$alkyl,
  (j) —$CO_2R^{12}$,
  (k) —C(O)N($R^{12}$)($R^{13}$),
  (l) —S(O)$_2$N($R^{12}$)($R^{13}$),
  (m) a 3-10 membered heterocyclic group optionally substituted with one to three groups selected from $C_{1-6}$ alkyl, $C_{1-6}$ alkylhydroxy, $C_{1-6}$ alkyl-$CO_2R^{12}$, —S(O)$_n$ $C_{1-6}$alkyl, oxo and —$CO_2R^{12}$,
  (n') oxo,
  (o) —C(O)—$C_{1-3}$ alkyl,
  (p) —C(O)-3-6 membered heterocycle optionally substituted with one to three groups selected from halogen hydroxy and $C_{1-6}$alkoxy,
  (q) 5-6 membered heteroaryl ring optionally substituted with one to three —$C_{1-4}$alkyl groups,
  (r) aryl;
$R^{12}$ and $R^{13}$ are each independently selected from —H, —$C_{1-6}$ alkyl, —C(O)—$C_{1-6}$ alkyl and a 3-6 membered heterocyclic group, each of which is optionally independently substituted with one to three —OH, $C_{1-6}$ alkyl, $C_{1-6}$alkoxy, —C(O)N($R^{14}$)($R^{15}$), —N($R^{14}$)($R^{15}$), —S(O)$_n C_{1-6}$alkyl, CN, $C_{3-10}$ carbocycle, —$CO_2R^{12}$, $CF_3$, 3-6 membered heterocycle, halogen; or
$R^{12}$ and $R^{13}$ together with the nitrogen atom to which they are attached form a heterocyclyl ring optionally substituted with one to three —OH, CN, $C_{1-6}$alkyl, $C_{1-6}$alkoxy, —C(O)—$C_{1-3}$ alkyl or oxo;
$R^{14}$ and $R^{15}$ are each independently selected from —H and —$C_{1-6}$alkyl;
n is 0, 1 or 2;
or a pharmaceutically acceptable salt thereof.

In a second embodiment, the present invention relates to a compound as described in the broadest embodiment above, wherein:
$R^1$ and $R^2$ together with the carbon atom to which they are attached is cyclopropyl, cyclobutyl, cyclopentyl, cyclohexyl, cycloheptyl, cyclooctyl, 2.2.1 bicycloheptyl, oxetanyl, tetrahydrofuranyl, tetrahydropyranyl, pyrrolidinyl, piperidinyl, tetrahydrothienyl, wherein each carbocycle or heterocycle is optionally independently substituted with one to two groups selected from $C_{1-6}$ alkyl and halogen;
$R^3$ is pyridinyl, pyrimidinyl, pyrazinyl, pyridazinyl, pyrrolyl, imidazolyl, thienyl, furanyl, thiazolyl, indolyl, pyrrolopyridinyl, pyrrolopyrimidinyl, pyrrolopyrazinyl, dihydropyrrolopyridinyl or pyrrolopyridazinyl wherein each $R^3$ is optionally independently substituted with one to three groups selected from $C_{1-3}$ alkyl, $C_{3-6}$ carbocycle, cyano, $C_{1-3}$ alkoxy, $C_{1-3}$ hydroxy, amino, $C_{1-3}$ alkylamino and $C_{1-3}$ dialkylamino;
$R^4$ is hydrogen, halogen, methyl or ethyl;
$R^5$ is methyl, ethyl, propyl, isopropyl, butyl, isobutyl, tert. butyl, pentyl, hexyl, cyclopropyl, cyclobutyl, cyclopentyl, cyclohexyl, cycloheptyl, cyclooctyl, phenyl, piperidinyl, piperazinyl, morpholinyl, thiomorpholinyl, pyrrolidinyl, tetrahydropyranyl, pyrrolyl, thienyl, furanyl, thiazolyl, oxazolyl, isoxazolyl, pyrazolyl, imidazolyl, triazolyl, pyridinyl, pyrimidinyl, pyrazinyl, pyridazinyl, quinolinyl, isoquinolinyl, indolyl, pyrrolopyridinyl, pyrrolopyrimidinyl, pyrazolopyrimidinyl, imidazopyridinyl, indazolyl, —C(O)—$R^6$, hydroxy or —$NR^7R^8$, wherein each $R^5$ is optionally independently substituted with one to three groups selected from $R^9$, $R^{10}$ and $R^{11}$;
$R^6$ is azetidinyl, pyrrolidinyl, piperidinyl, piperazinyl, tetrahydropyranyl, morpholinyl, thiomorpholinyl, amino, $C_{1-3}$ alkylamino, $C_{1-3}$ dialkylamino, —NH-pyridinyl or —NH-5-6 membered heterocycle, each optionally independently substituted with one to three groups selected from $R^9$, $R^{10}$ and $R^{11}$;
$R^7$ and $R^8$ are each independently hydrogen, 5-6 membered heterocyclic ring optionally substituted with one to three methyl groups, $C_{1-5}$ alkyl which is optionally substituted with 5-6 membered heterocycle; or —S(O)$_n C_{1-6}$alkyl;
$R^9$, $R^{10}$ and $R^{11}$ are independently selected from
  (a) —H,
  (b) —OH,
  (c) halogen,
  (d) —CN,
  (e) —$CF_3$, (f) $C_{1-6}$alkyl optionally substituted with one to three —OH, CN, —N($R^{12}$)($R^{13}$), phenyl, benzyl, phenethyl, azetidinyl, pyrrolidinyl, piperidinyl, piperazinyl, morpholinyl, —C(O)-3-6 membered heterocycle, $C_{1-6}$alkoxy, —S(O)$_n$ $C_{1-6}$alkyl or —C(O)N($R^{12}$)($R^{13}$), (g) $C_{1-6}$alkoxy, (h) —N($R^{12}$)($R^{13}$), (i) —S(O)$_n C_{1-6}$alkyl, (j) —CO$_2 R^{12}$, (k) —C(O)N($R^{12}$)($R^{13}$), (l) —S(O)$_2$N($R^{12}$)($R^{13}$), (m) oxetanyl, tetrahydrofuranyl, tetrahydropyranyl, tetrahydrothienyl, azetidinyl, pyrrolidinyl, piperidinyl, piperazinyl, morpholinyl or thiomorpholinyl, optionally substituted with one to three groups selected from $C_{1-6}$ alkyl, $C_{1-6}$ alkylhydroxy, $C_{1-6}$ alkyl-CO$_2 R^{12}$, —S(O)$_n$ $C_{1-6}$alkyl, oxo and —CO$_2 R^{12}$, (n') oxo, (o) —C(O)—$C_{1-3}$ alkyl, (p) —C(O)-3-6 membered heterocycle optionally substituted with one to three groups selected from halogen hydroxy and $C_{1-6}$alkoxy, (q) imidazolyl, pyrazolyl, thiazolyl, furanyl, pyridinyl, pyrimidinyl, pyridazinyl each optionally substituted with one to three —$C_{1-4}$alkyl groups, (r) phenyl;

$R^{12}$ and $R^{13}$ are each independently selected from —H, —$C_{1-6}$ alkyl, —C(O)—$C_{1-6}$ alkyl and a 3-6 membered heterocyclic group, each of which is optionally independently substituted with one to three —OH, $C_{1-6}$ alkyl, $C_{1-6}$alkoxy, —C(O)N($R^{14}$)($R^{15}$), —N($R^{14}$)($R^{15}$), —S(O)$_n C_{1-6}$alkyl, CN, cyclopropyl, cyclobutyl, cyclopentyl, cyclohexyl, —CO$_2 R^{12}$, CF$_3$, 3-6 membered heterocycle, halogen; or $R^{12}$ and $R^{13}$ together with the nitrogen atom to which they are attached form a heterocyclyl ring optionally substituted with one to three —OH, CN, $C_{1-6}$alkyl, $C_{1-6}$alkoxy, —C(O)—$C_{1-3}$ alkyl or oxo;

$R^{14}$ and $R^{15}$ are each independently selected from —H and —$C_{1-6}$alkyl;

n is 0 or 2;

or a pharmaceutically acceptable salt thereof.

In a third embodiment, the present invention relates to a compound as described in any of the preceding embodiments above, wherein:

$R^1$ and $R^2$ together with the carbon atom to which they are attached is cyclopropyl, cyclobutyl, cyclopentyl, cyclohexyl, 2.2.1 bicycloheptyl or tetrahydropyranyl wherein each carbocycle or heterocycle is optionally independently substituted with one to two groups selected from $C_{1-3}$ alkyl and halogen;

or a pharmaceutically acceptable salt thereof.

In a fourth embodiment there is provided a compound of formula (I) as described in any of the preceding embodiments above, wherein:

$R^3$ is pyridinyl, pyrimidinyl, pyrazinyl, pyrrolopyrazinyl, dihydropyrrolopyridinyl, pyrrolopyridinyl or pyridazinyl, wherein each $R^3$ is optionally independently substituted with one to three groups selected from $C_{1-3}$ alkyl, cyclopropyl, cyclobutyl, cyano, $C_{1-3}$ alkoxy, $C_{1-3}$ hydroxy, amino, $C_{1-3}$ alkylamino and $C_{1-3}$ dialkylamino;

or a pharmaceutically acceptable salt thereof.

In a fifth embodiment there is provided a compound as described in any of the preceding embodiments above, wherein:

$R^5$ is methyl, ethyl, propyl, isopropyl, butyl, isobutyl, tert. butyl, pentyl, hexyl, phenyl, piperidinyl, piperazinyl, morpholinyl, thiomorpholinyl, pyrrolidinyl, furanyl, thiazolyl, oxazolyl, isoxazolyl, pyrazolyl, imidazolyl, triazolyl, pyridinyl, pyrimidinyl, pyrazinyl, pyridazinyl, quinolinyl, isoquinolinyl, indolyl, pyrrolopyridinyl, pyrrolopyrimidinyl, pyrazolopyrimidinyl, imidazopyridinyl, indazolyl, —C(O)—$R^6$, hydroxy or —NR$^7 R^8$, wherein each $R^5$ is optionally independently substituted with one to three groups selected from $R^9$, $R^{10}$ and $R^{11}$;

$R^6$ is azetidinyl, pyrrolidinyl, piperidinyl, piperazinyl, morpholinyl, amino, —NH-pyridinyl optionally substituted with a methyl group, $C_{1-3}$ alkylamino or $C_{1-3}$ dialkylamino;

$R^7$ and $R^8$ are each independently hydrogen, 5-6 membered heterocyclic ring optionally substituted with one to three methyl groups, $C_{1-5}$ alkyl which is optionally substituted with 5-6 membered heterocycle; or $R^7$ and $R^8$ are each independently —S(O)$_n C_{1-6}$alkyl;

$R^9$, $R^{10}$ and $R^{11}$ are independently selected from (a) —H, (b) —OH, (c) halogen, (d) —CN, (e) —CF$_3$, (f) $C_{1-6}$alkyl optionally substituted with one to three —OH, CN, —N($R^{12}$)($R^{13}$), phenyl, benzyl, azetidinyl, pyrrolidinyl, piperidinyl, piperazinyl, morpholinyl, —C(O)-piperidine, —C(O)-pyrrolidine, —C(O)-morpholine, $C_{1-6}$alkoxy, —S(O)$_n C_{1-3}$alkyl or —C(O)N($R^{12}$)($R^{13}$), (g) $C_{1-6}$alkoxy, (h) —N($R^{12}$)($R^{13}$), (i) —S(O)$_2 C_{1-6}$alkyl, (j) —CO$_2 R^{12}$, (k) —C(O)N($R^{12}$)($R^{13}$), (l) —S(O)$_2$N($R^{12}$)($R^{13}$), (m) oxetanyl, tetrahydrofuranyl, tetrahydropyranyl, tetrahydrothienyl, azetidinyl, pyrrolidinyl, piperidinyl, piperazinyl, morpholinyl or thiomorpholinyl, optionally substituted with one to three groups selected from $C_{1-6}$ alkyl, $C_{1-6}$ alkylhydroxy, $C_{1-6}$ alkyl-CO$_2 R^{12}$, —S(O)$_2$ $C_{1-6}$alkyl, oxo and —CO$_2 R^{12}$, (n') oxo, (o) —C(O)—$C_{1-3}$ alkyl, (p) —C(O)-azetidine, —C(O)-piperidine, —C(O)-pyrrolidine or —C(O)-morpholine optionally substituted with one to three groups selected from halogen, hydroxy and $C_{1-6}$alkoxy, (q) imidazolyl, pyrazolyl, thiazolyl, furanyl, pyridinyl, pyrimidinyl, pyridazinyl each optionally substituted with one to three —$C_{1-4}$alkyl groups, (r) phenyl;

$R^{12}$ and $R^{13}$ are each independently selected from —H, —$C_{1-6}$ alkyl, —C(O)—$C_{1-6}$ alkyl, morpholinyl, piperidinyl, piperizinyl and tetrahydropyranyl, each of which is optionally independently substituted with one to three —OH, $C_{1-6}$ alkyl, $C_{1-6}$alkoxy, —C(O)N($R^{14}$)($R^{15}$), —N($R^{14}$)($R^{15}$), —S(O)$_2 C_{1-6}$alkyl, CN, cyclopropyl, cyclobutyl, cyclopentyl, cyclohexyl, —CO$_2 R^{12}$, CF$_3$, morpholinyl, piperidinyl, piperizinyl, tetrahydrofuranyl, tetrahydropyranyl; or $R^{12}$ and $R^{13}$ together with the nitrogen atom to which they are attached form a 5-6 membered heterocyclyl ring optionally substituted with one to three —OH, CN, $C_{1-6}$alkyl, $C_{1-6}$alkoxy, —C(O)—$C_{1-3}$alkyl or oxo;

$R^{14}$ and $R^{15}$ are each independently selected from —H and —$C_{1-4}$alkyl;

or a pharmaceutically acceptable salt thereof.

In a sixth embodiment there is provided a compound of formula (I) as described in the second embodiment above, wherein:

R[1] and R[2] together with the carbon atom to which they are attached is cyclopropyl, cyclobutyl, cyclopentyl, cyclohexyl, 2.2.1 bicycloheptyl or tetrahydropyranyl wherein each carbocycle or heterocycle is optionally independently substituted with one to two groups selected from methyl, ethyl and fluoro;

R[3] is pyridinyl, pyrimidinyl, pyrazinyl, pyrrolopyrazinyl, dihydropyrrolopyridinyl, pyrrolopyridinyl or pyridazinyl, wherein each R[3] is optionally independently substituted with one to two amino, —NHCH$_3$, —CH$_2$—OH, cyclopropyl group, cyano or one to two methyl groups;

R[4] is hydrogen, methyl or fluoro;

R[5] is methyl, ethyl, phenyl, piperidinyl, piperazinyl, pyrrolidinyl, thiazolyl, oxazolyl, isoxazolyl, pyrazolyl, imidazolyl, triazolyl, pyridinyl, pyrimidinyl, pyrazinyl, pyridazinyl, pyrazolopyrimidinyl, imidazopyridinyl, indazolyl, —C(O)—R[6], hydroxy or —NR[7]R[8], wherein each R[5] is optionally independently substituted with one to three groups selected from R[9], R[10] and R[11];

R[6] is azetidinyl, pyrrolidinyl, piperidinyl, piperazinyl, morpholinyl, amino, —NH-pyridinyl optionally substituted with a methyl group, $C_{1-3}$ alkylamino or $C_{1-3}$ dialkylamino;

R[7] and R[8] are each independently hydrogen, piperidinyl optionally substituted with methyl, $C_{1-3}$ alkyl which is optionally substituted with tetrahydropyranyl ring; or R[7] and R[8] are each independently —S(O)$_2$C$_{1-6}$alkyl;

R[9], R[10] and R[11] are independently selected from
(a) —H,
(b) —OH,
(c) halogen,
(d) —CN,
(e) —CF$_3$,
(f) $C_{1-6}$alkyl optionally substituted with one to three —OH, CN, —N(R[12])(R[13]), phenyl, benzyl, azetidinyl, pyrrolidinyl, piperidinyl, piperazinyl, morpholinyl, —C(O)-piperidine, —C(O)-pyrrolidine, —C(O)-morpholine, $C_{1-6}$alkoxy, —S(O)$_n$C$_{1-3}$alkyl or —C(O)N(R[12])(R[13]),
(g) $C_{1-6}$alkoxy,
(h) —N(R[12])(R[13]),
(i) —S(O)$_2$C$_{1-6}$alkyl,
(j) —CO$_2$R[12],
(k) —C(O)N(R[12])(R[13]),
(l) —S(O)$_2$N(R[12])(R[13]),
(m) oxetanyl, tetrahydrofuranyl, tetrahydropyranyl, tetrahydrothienyl, azetidinyl, pyrrolidinyl, piperidinyl, piperazinyl, morpholinyl or thiomorpholinyl, optionally substituted with one to three groups selected from $C_{1-6}$ alkyl, $C_{1-6}$alkylhydroxy, $C_{1-6}$ alkyl-CO$_2$R[12], —S(O)$_2$ $C_{1-6}$alkyl, oxo and —CO$_2$R[12],
(n') oxo,
(o) —C(O)—C$_{1-3}$ alkyl,
(p) —C(O)-azetidine, —C(O)-piperidine, —C(O)-pyrrolidine or —C(O)-morpholine optionally substituted with one to three groups selected from halogen, hydroxy and C$_{1-6}$alkoxy,
(q) imidazolyl, pyrazolyl, thiazolyl optionally substituted with one to three methyl groups,
(r) phenyl;

R[12] and R[13] are each independently selected from —H, tetrahydropyranyl, piperidinyl, —C(O)methyl, and —C$_{1-6}$ alkyl, wherein the alkyl group is optionally independently substituted with one to three —OH, C$_{1-6}$alkoxy, —C(O)N(R[14])(R[15]), —N(R[14])(R[15]), —S(O)$_2$C$_{1-6}$alkyl, cyclopropyl, morpholinyl, tetrahydrofuranyl, tetrahydropyranyl, —CO$_2$R[12], CN or halogen; or R[12] and R[13] together with the nitrogen atom to which they are attached form a pyrrolidinyl, piperidinyl, piperazinyl or morpholinyl ring optionally substituted with one to three —OH, CN, C$_{1-3}$alkyl, C$_{1-3}$alkoxy, —C(O)—C$_{1-3}$alkyl or oxo;

R[14] and R[15] are each independently selected from —H and —C$_{1-4}$alkyl;

or a pharmaceutically acceptable salt thereof.

In a seventh embodiment there is provided a compound as described in the embodiment immediately above, wherein:

R[1] and R[2] together with the carbon atom to which they are attached is cyclobutyl, cyclopentyl, cyclohexyl or 2.2.1 bicycloheptyl wherein each carbocycle is optionally independently substituted with one to two groups selected from methyl and fluoro;

or a pharmaceutically acceptable salt thereof.

In an eighth embodiment there is provided a compound as described in the sixth embodiment above, wherein:

R[1] and R[2] together with the carbon atom to which they are attached is tetrahydropyranyl;

or a pharmaceutically acceptable salt thereof.

In a ninth embodiment there is provided a compound as described in the sixth embodiment above, wherein:

R[3] is selected from

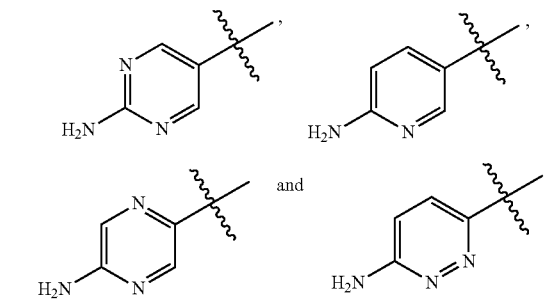

or a pharmaceutically acceptable salt thereof.

In a tenth embodiment there is provided a compound as described in the sixth embodiment above, wherein:

R[5] is selected from imidazolyl, pyrazolyl, triazolyl, thiazolyl, oxazolyl, pyrazolopyrimidinyl, imidazopyridinyl, indazolyl, pyridinyl, pyrimidinyl, pyrazinyl, pyridazinyl, pyrrolidinyl, piperidinyl and phenyl, wherein each R[5] is optionally independently substituted with one to three groups selected from R[9], R[10] and R[11];

or a pharmaceutically acceptable salt thereof.

In an eleventh embodiment there is provided a compound as described in the sixth embodiment above, wherein:

R[5] is selected from —C(O)—R[6] and —NR[7]R[8], wherein each R[5] is optionally independently substituted with one to three groups selected from R[9], R[10] and R[11];

or a pharmaceutically acceptable salt thereof.

In a twelfth embodiment there is provided a compound as described in the sixth embodiment above, wherein:

R[1] and R[2] together with the carbon atom to which they are attached is cyclobutyl, cyclopentyl, cyclohexyl or tetrahydropyranyl wherein each carbocycle or is optionally independently substituted with one to two groups selected from methyl and fluoro;

R³ is selected from

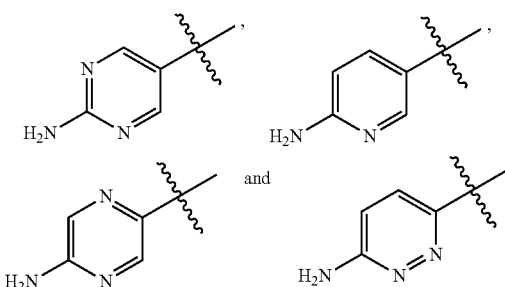

R⁴ is hydrogen or fluoro;
R⁵ is selected from imidazolyl, pyrazolyl, triazolyl, thiazolyl, oxazolyl, pyrazolopyrimidinyl, imidazopyridinyl, indazolyl, pyridinyl, pyrimidinyl, pyrazinyl, pyridazinyl, pyrrolidinyl, piperidinyl and phenyl, wherein each R⁵ is optionally independently substituted with one to three groups selected from R⁹, R¹⁰ and R¹¹;
or a pharmaceutically acceptable salt thereof.

In a thirteenth embodiment there is provided a compound as described in the sixth embodiment above, wherein:
R¹ and R² together with the carbon atom to which they are attached is cyclobutyl, cyclopentyl, cyclohexyl or tetrahydropyranyl wherein each carbocycle or is optionally independently substituted with one to two groups selected from methyl and fluoro;
R³ is selected from

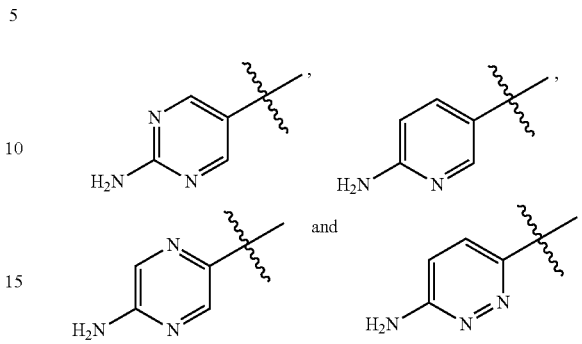

R⁴ is hydrogen or fluoro;
R⁵ is selected from —C(O)—R⁶ and —NR⁷R⁸, wherein each R⁵ is optionally independently substituted with one to three groups selected from R⁹, R¹⁰ and R¹¹;
or a pharmaceutically acceptable salt thereof.

The following are representative compounds of the invention which can be made by the general synthetic schemes, the examples, and known methods in the art.

TABLE I

| Example | Structure | Name |
|---|---|---|
| 1 | 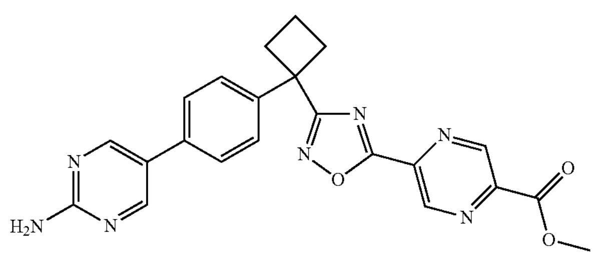 [SMILES: COC(=O)c1cnc(-c2nc(C3(c4ccc(-c5cnc(N)nc5)cc4)CCC3)no2)cn1] | 5-(3-{1-[4-(2-Amino-pyrimidin-5-yl)-phenyl]-cyclobutyl}-1,2,4-oxadiazol-5-yl)-pyrazine-2-carboxylic acid methyl ester |
| 2 | 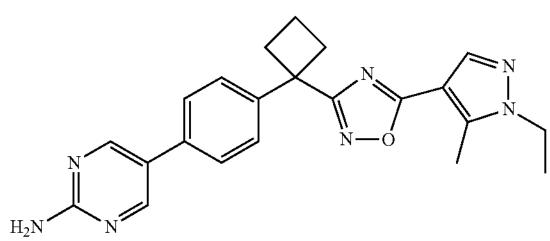 [SMILES: CCn1ncc(-c2nc(C3(c4ccc(-c5cnc(N)nc5)cc4)CCC3)no2)c1C] | 5-(4-{1-[5-(1-Ethyl-5-methyl-1H-pyrazol-4-yl)-1,2,4-oxadiazol-3-yl]-cyclobutyl}-phenyl)-pyrimidin-2-ylamine |
| 3 | 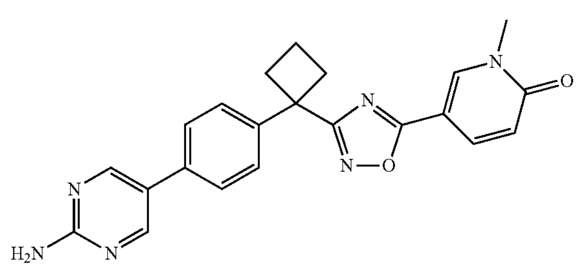 [SMILES: Cn1cc(-c2nc(C3(c4ccc(-c5cnc(N)nc5)cc4)CCC3)no2)ccc1=O] | 5-(3-{1-[4-(2-Amino-pyrimidin-5-yl)-phenyl]-cyclobutyl}-1,2,4-oxadiazol-5-yl)-1-methyl-1H-pyridin-2-one |

TABLE I-continued

| Example | Structure | Name |
|---|---|---|
| 4 | 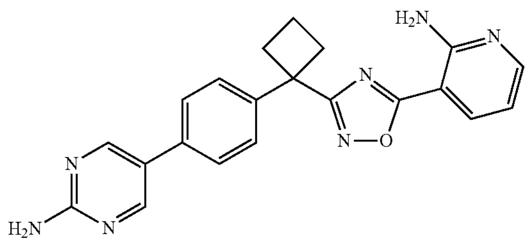 [SMILES: Nc1ncc(-c2ccc(C3(c4noc(-c5cccnc5N)n4)CCC3)cc2)cn1] | 5-(4-{1-[5-(2-Amino-pyridin-3-yl)-1,2,4-oxadiazol-3-yl]-cyclobutyl}-phenyl)-pyrimidin-2-ylamine |
| 5 | 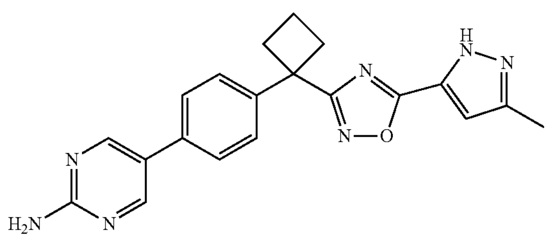 [SMILES: Cc1cc(-c2nc(C3(c4ccc(-c5cnc(N)nc5)cc4)CCC3)no2)[nH]n1] | 5-(4-{1-[5-(5-Methyl-2H-pyrazol-3-yl)-1,2,4-oxadiazol-3-yl]-cyclobutyl}-phenyl)-pyrimdin-2-ylamine |
| 6 | 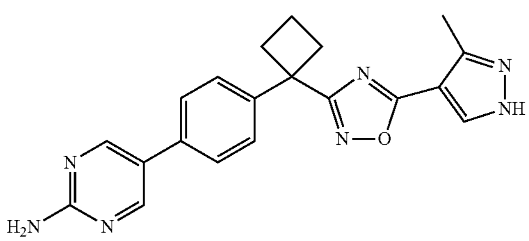 [SMILES: Cc1n[nH]cc1-c1nc(C2(c3ccc(-c4cnc(N)nc4)cc3)CCC2)no1] | 5-(4-{1-[5-(3-Methyl-1H-pyrazol-4-yl)-1,2,4-oxadiazol-3-yl]-cyclobutyl}-phenyl)-pyrimidin-2-ylamine |
| 7 | 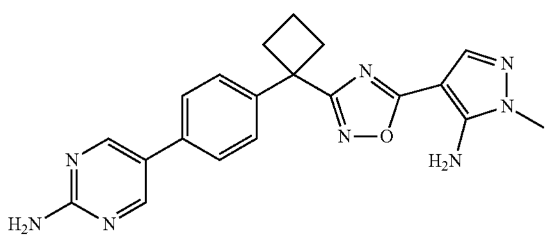 [SMILES: Cn1ncc(-c2nc(C3(c4ccc(-c5cnc(N)nc5)cc4)CCC3)no2)c1N] | 5-(4-{1-[5-(5-Amino-1-methyl-1H-pyrazol-4-yl)-1,2,4-oxadiazol-3-yl]-cyclobutyl}-phenyl)-pyrimidin-2-ylamine |
| 8 | 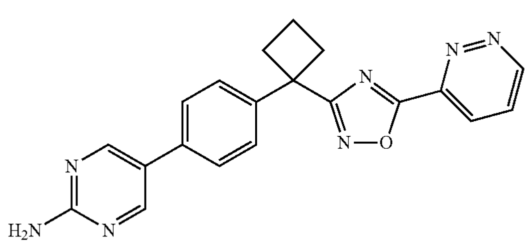 [SMILES: Nc1ncc(-c2ccc(C3(c4noc(-c5cccnn5)n4)CCC3)cc2)cn1] | 5-{4-[1-(5-Pyridazin-3-yl-1,2,4-oxadiazol-3-yl)-cyclobutyl]-phenyl}-pyrimidin-2-ylamine |
| 9 | 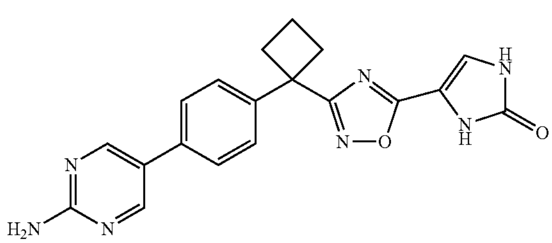 [SMILES: Nc1ncc(-c2ccc(C3(c4noc(-c5c[nH]c(=O)[nH]5)n4)CCC3)cc2)cn1] | 4-(3-{1-[4-(2-Amino-pyrimidin-5-yl)-phenyl]-cyclobutyl}-1,2,4-oxadiazol-5-yl)-1,3-dihydro-imidazol-2-one |

TABLE I-continued

| Example | Structure | Name |
|---|---|---|
| 10 | 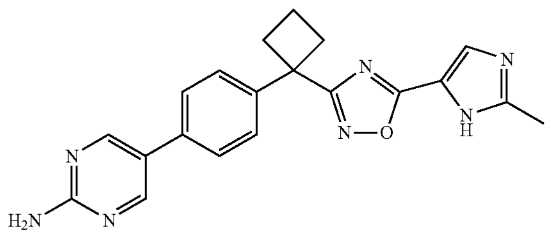 [SMILES: Cc1ncc(-c2nc(C3(c4ccc(-c5cnc(N)nc5)cc4)CCC3)no2)[nH]1] | 5-(4-{1-[5-(2-Methyl-3H-imidazol-4-yl)-1,2,4-oxadiazol-3-yl]-cyclobutyl}-phenyl)-pyrimidin-2-ylamine |
| 11 | 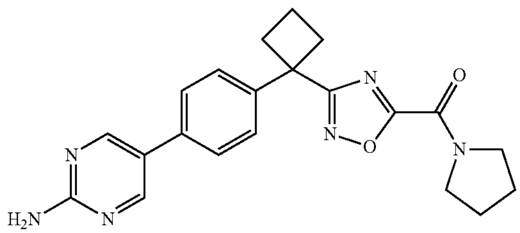 [SMILES: Nc1ncc(-c2ccc(C3(c4noc(C(=O)N5CCCC5)n4)CCC3)cc2)cn1] | (3-{1-[4-(2-Amino-pyrimidin-5-yl)-phenyl]-cyclobutyl}-1,2,4-oxadiazol-5-yl)-pyrrolidin-1-yl-methanone |
| 12 | 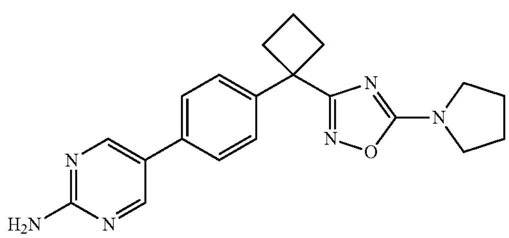 [SMILES: Nc1ncc(-c2ccc(C3(c4noc(N5CCCC5)n4)CCC3)cc2)cn1] | 5-{4-[1-(5-Pyrrolidin-1-yl-1,2,4-oxadiazol-3-yl)-cyclobutyl]-phenyl}-pyrimidin-2-ylamine |
| 13 | 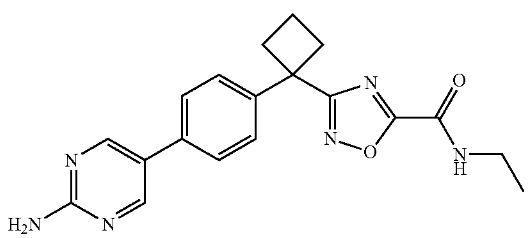 | 3-{1-[4-(2-Amino-pyrimidin-5-yl)-phenyl]-cyclobutyl}-1,2,4-oxadiazole-5-carboxylic acid ethylamide |
| 14 | 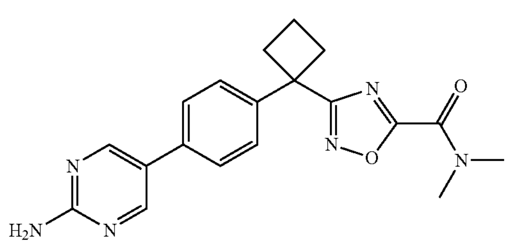 [SMILES: CN(C)C(=O)c1nc(C2(c3ccc(-c4cnc(N)nc4)cc3)CCC2)no1] | 3-{1-[4-(2-Amino-pyrimidin-5-yl)-phenyl]-cyclobutyl}-1,2,4-oxadiazole-5-carboxylic acid dimethylamide |
| 15 | 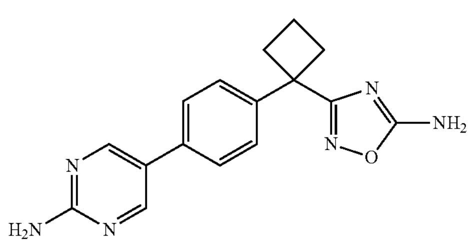 [SMILES: Nc1ncc(-c2ccc(C3(c4noc(N)n4)CCC3)cc2)cn1] | 5-{4-[1-(5-Amino-1,2,4-oxadiazol-3-yl)-cyclobutyl]-phenyl}-pyrimidin-2-ylamine |

TABLE I-continued

| Example | Structure | Name |
|---|---|---|
| 16 | 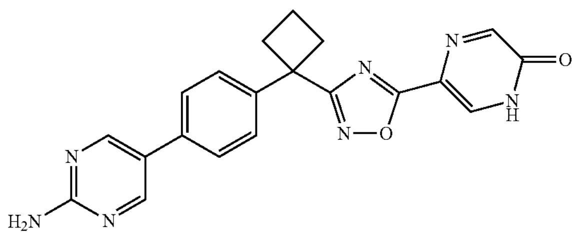 [SMILES: Nc1ncc(-c2ccc(C3(c4noc(-c5c[nH]c(=O)cn5)n4)CCC3)cc2)cn1] | 5-(3-{1-[4-(2-Amino-pyrimidin-5-yl)-phenyl]-cyclobutyl}-1,2,4-oxadiazol-5-yl)-1H-pyrazin-2-one |
| 17 | 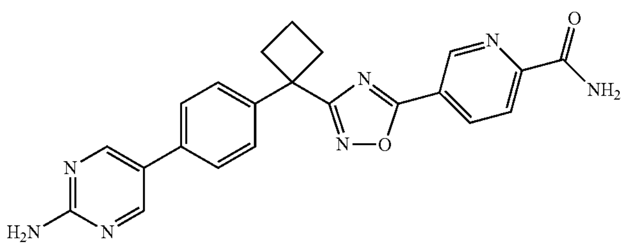 [SMILES: NC(=O)c1ccc(-c2nc(C3(c4ccc(-c5cnc(N)nc5)cc4)CCC3)no2)cn1] | 5-(3-{1-[4-(2-Amino-pyrimidin-5-yl)-phenyl]-cyclobutyl}-1,2,4-oxadiazol-5-yl)-pyridine-2-carboxylic acid amide |
| 18 | 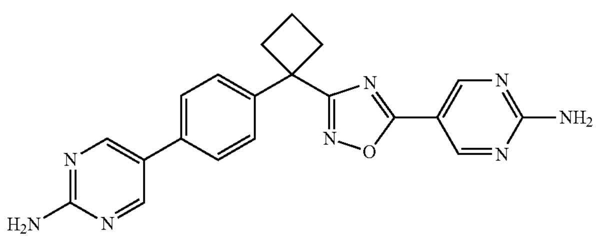 [SMILES: Nc1ncc(-c2ccc(C3(c4noc(-c5cnc(N)nc5)n4)CCC3)cc2)cn1] | 5-(4-{1-[5-(2-Amino-pyrimidine-5-yl)-1,2,4-oxadiazole-3-yl]-cyclobutyl}-phenyl)-pyrimidin-2-ylamine |
| 19 | 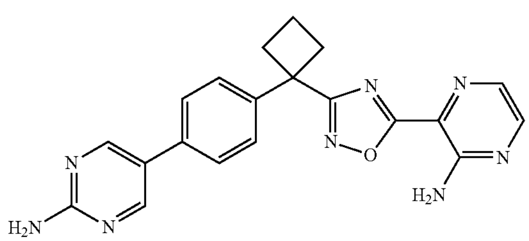 [SMILES: Nc1ncc(-c2ccc(C3(c4noc(-c5nccnc5N)n4)CCC3)cc2)cn1] | 5-(4-{1-[5-(3-Amino-pyrazin-2-yl)-1,2,4-oxadiazol-3-yl]-cyclobutyl}-phenyl)-pyrimidin-2-ylamine |
| 20 | 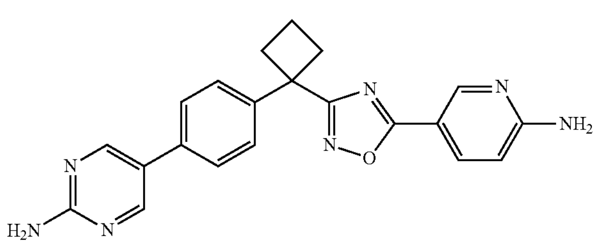 [SMILES: Nc1ccc(-c2nc(C3(c4ccc(-c5cnc(N)nc5)cc4)CCC3)no2)cn1] | 5-(4-{1-[5-(6-Amino-pyridin-3-yl)-1,2,4-oxadiazol-3-yl]-cyclobutyl}-phenyl)-pyrimidin-2-ylamine |
| 21 | 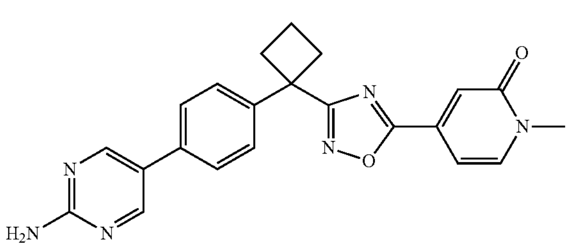 [SMILES: Cn1ccc(-c2nc(C3(c4ccc(-c5cnc(N)nc5)cc4)CCC3)no2)cc1=O] | 4-(3-{1-[4-(2-Amino-pyrimidin-5-yl)-phenyl]-cyclobutyl}-1,2,4-oxadiazol-5-yl)-1-methyl-1H-pyridin-2-one |

TABLE I-continued

| Example | Structure | Name |
|---|---|---|
| 22 | 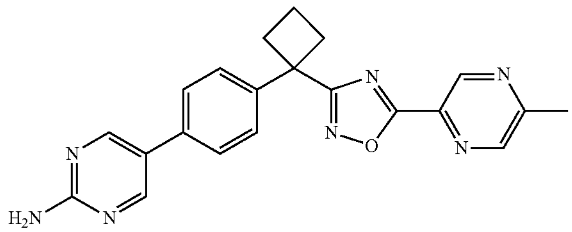 | 5-(4-{1-[5-(5-Methyl-pyrazin-2-yl)-1,2,4-oxadiazol-3-yl]-cyclobutyl}-phenyl)-pyrimidin-2-ylamine |
| 23 | 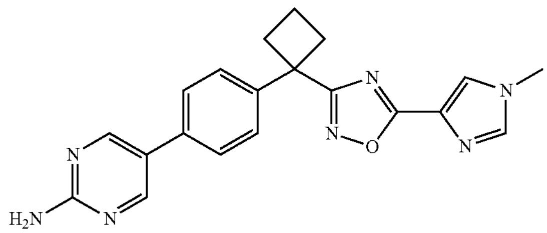 [SMILES: Cn1cnc(-c2nc(C3(c4ccc(-c5cnc(N)nc5)cc4)CCC3)no2)c1] | 5-(4-{1-[5-(1-Methyl-1H-imidazol-1-yl)-1,2,4-oxadiazol-3-yl]-cyclobutyl}-phenyl)-pyrimidin-2-ylamine |
| 24 | 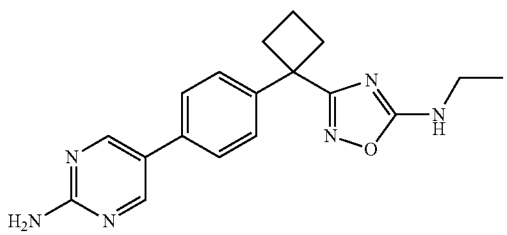 [SMILES: CCNc1nc(C2(c3ccc(-c4cnc(N)nc4)cc3)CCC2)no1] | 5-{4-[1-(5-Ethylamino-1,2,4-oxadiazol-3-yl)-cyclobutyl]-phenyl}-pyrimidin-2-ylamine |
| 25 | 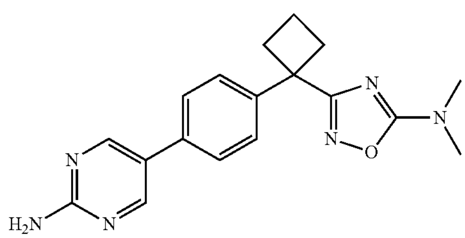 [SMILES: CN(C)c1nc(C2(c3ccc(-c4cnc(N)nc4)cc3)CCC2)no1] | 5-{4-[1-(5-Dimethylamino-1,2,4-oxadiazol-3-yl)-cyclobutyl]-phenyl}-pyrimidin-2-ylamine |
| 26 | 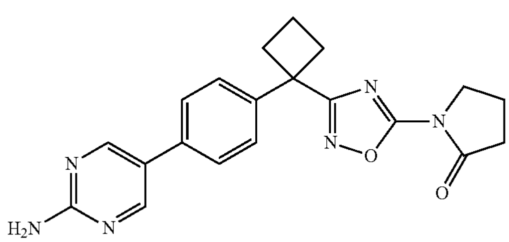 [SMILES: Nc1ncc(-c2ccc(C3(c4noc(N5CCCC5=O)n4)CCC3)cc2)cn1] | 1-(3-{1-[4-(2-Amino-pyrimidin-5-yl)-phenyl]-cyclobutyl}-1,2,4-oxadiazol-5-yl)-pyrrolidin-2-one |
| 27 | 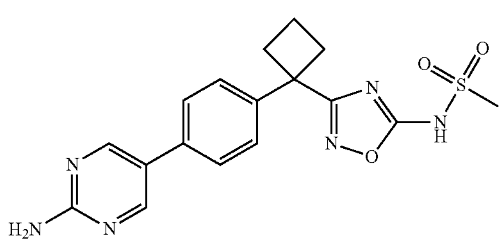 [SMILES: CS(=O)(=O)Nc1nc(C2(c3ccc(-c4cnc(N)nc4)cc3)CCC2)no1] | N-(3-{1-[4-(2-Amino-pyrimidin-5-yl)-phenyl]-cyclobutyl}-1,2,4-oxadiazol-5-yl)-methanesulfonamide |

TABLE I-continued

| Example | Structure | Name |
|---|---|---|
| 28 | 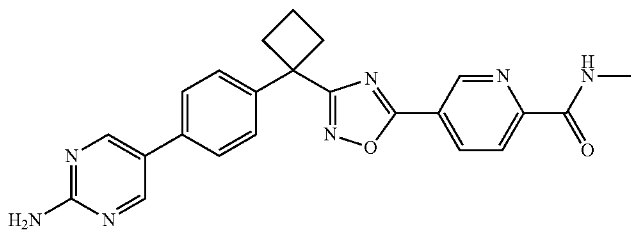 [SMILES: CNC(=O)c1ccc(-c2nc(C3(c4ccc(-c5cnc(N)nc5)cc4)CCC3)no2)cn1] | 5-(3-{1-[4-(2-Amino-pyrimidin-5-yl)-phenyl]-cyclobutyl}-1,2,4-oxadiazol-5-yl)-pyridine-2-carboxylic acid methylamide |
| 29 | 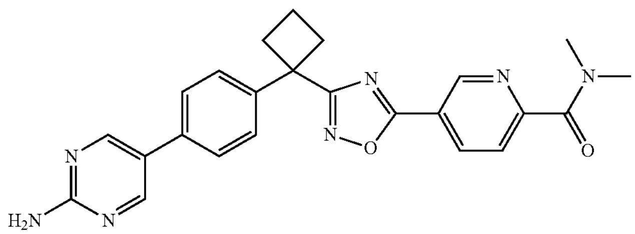 [SMILES: CN(C)C(=O)c1ccc(-c2nc(C3(c4ccc(-c5cnc(N)nc5)cc4)CCC3)no2)cn1] | 5-(3-{1-[4-(2-Amino-pyrimidin-5-yl)-phenyl]-cyclobutyl}-1,2,4-oxadiazol-5-yl)-pyridine-2-carboxylic acid dimethylamide |
| 30 | 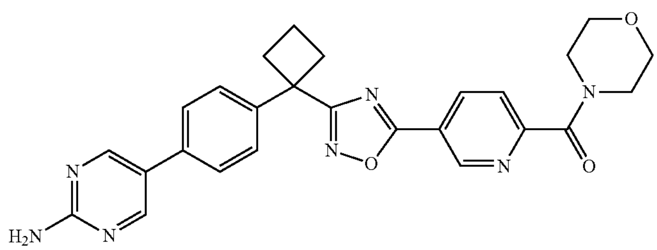 [SMILES: Nc1ncc(-c2ccc(C3(c4noc(-c5ccc(C(=O)N6CCOCC6)nc5)n4)CCC3)cc2)cn1] | [5-(3-{1-[4-(2-Amino-pyrimidin-5-yl)-phenyl]-cyclobutyl}-1,2,4-oxadiazol-5-yl)-pyridin-2-yl]-morpholin-4-yl-methanone |
| 31 | 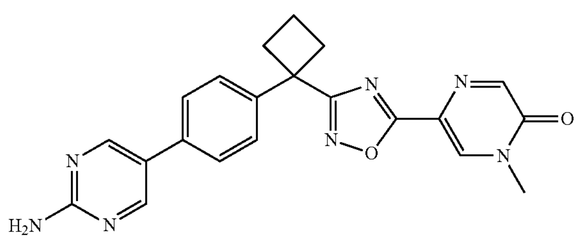 | 5-(3-{1-[4-(2-Amino-pyrimidin-5-yl)-phenyl]-cyclobutyl}-1,2,4-oxadiazol-5-yl)-1-methyl-1Hpyrazin-2-one |
| 32 | 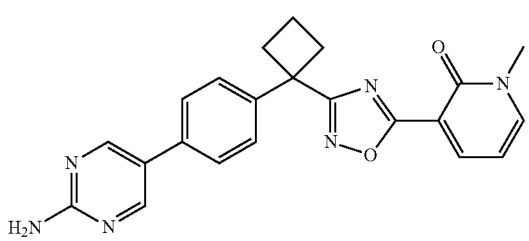 [SMILES: Cn1cccc(-c2nc(C3(c4ccc(-c5cnc(N)nc5)cc4)CCC3)no2)c1=O] | 3-(3-{1-[4-(2-Amino-pyrimidin-5-yl)-phenyl]-cyclobutyl}-1,2,4-oxadiazol-5-yl)-1-methyl-1Hpyridin-2-one |
| 33 | 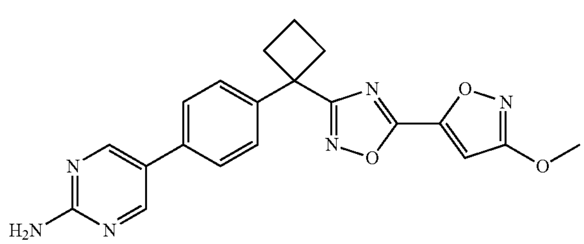 [SMILES: COc1cc(-c2nc(C3(c4ccc(-c5cnc(N)nc5)cc4)CCC3)no2)on1] | 5-(4-{1-[5-(3-Methoxy-isoxazol-5-yl)-1,2,4-oxadiazol-3-yl]-cyclobutyl}-phenyl)-pyrimidin-2-ylamine |

TABLE I-continued

| Example | Structure | Name |
|---|---|---|
| 34 | 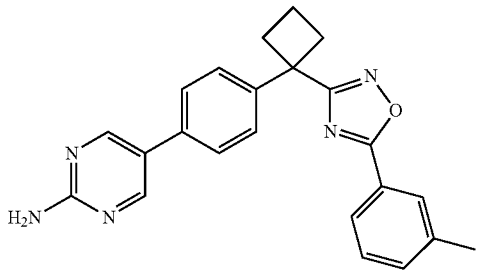 [SMILES: Cc1cccc(-c2nc(C3(c4ccc(-c5cnc(N)nc5)cc4)CCC3)no2)c1] | 5-{4-[1-(5-m-Tolyl-1,2,4-oxadiazol-3-yl)-cyclobutyl]-phenyl}-pyrimidin-2-ylamine |
| 35 | 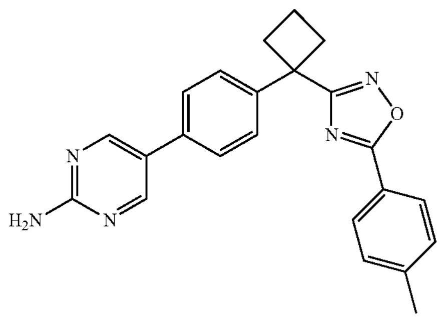 [SMILES: Cc1ccc(-c2nc(C3(c4ccc(-c5cnc(N)nc5)cc4)CCC3)no2)cc1] | 5-{4-[1-(5p-Tolyl-1,2,4-oxadiazol-3-yl)-cyclobutyl]-phenyl}-pyrimidin-2-ylamine |
| 36 | 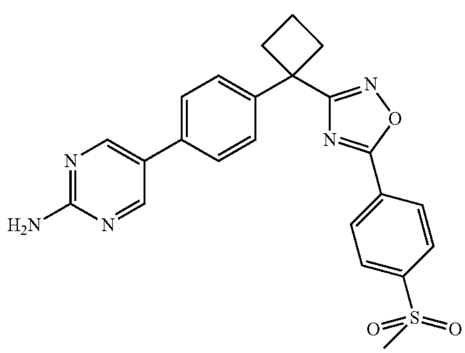 [SMILES: CS(=O)(=O)c1ccc(-c2nc(C3(c4ccc(-c5cnc(N)nc5)cc4)CCC3)no2)cc1] | 5-(4-{1-[5-(4-Methanesulfonyl-phenyl)-1,2,4-oxadiazol-3-yl]-cyclobutyl}-phenyl)-pyrimidin-2-ylamine |
| 37 | 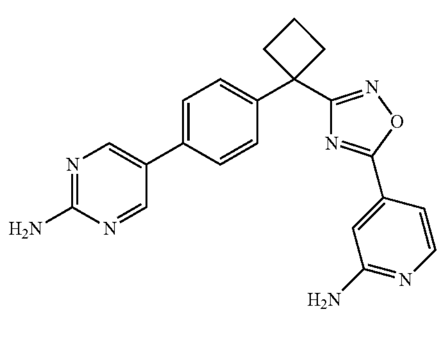 [SMILES: Nc1cc(-c2nc(C3(c4ccc(-c5cnc(N)nc5)cc4)CCC3)no2)ccn1] | 5-(4-{1-[5-(2-Amino-pyridin-4-yl)-1,2,4-oxadiazol-3-yl]-cyclobutyl}-phenyl)-pyrimidin-2-ylamine |

TABLE I-continued

| Example | Structure | Name |
|---|---|---|
| 38 | 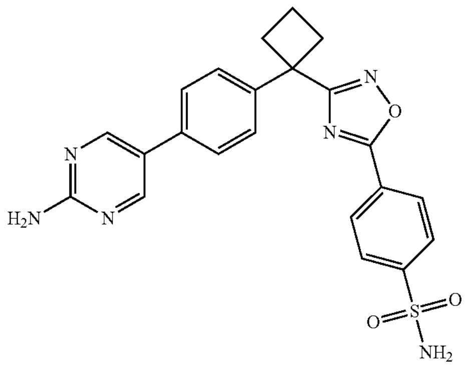 [SMILES: Nc1ncc(-c2ccc(C3(c4noc(-c5ccc(S(N)(=O)=O)cc5)n4)CCC3)cc2)cn1] | 4-(3-{1-[4-(2-Amino-pyrimidin-5-yl)-phenyl]-cyclobutyl}-1,2,4-oxadiazol-5-yl)-benzenesulfonamide |
| 39 | 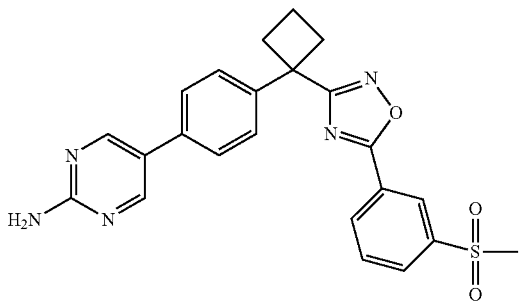 [SMILES: CS(=O)(=O)c1cccc(-c2nc(C3(c4ccc(-c5cnc(N)nc5)cc4)CCC3)no2)c1] | 5-(4-{1-[5-(3-Methanesulfonyl-phenyl)-1,2,4-oxadiazol-3-yl]-cyclobutyl}-phenyl)-pyrimidin-2-ylamine |
| 40 | 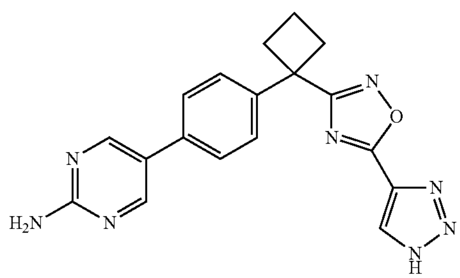 [SMILES: Nc1ncc(-c2ccc(C3(c4noc(-c5c[nH]nn5)n4)CCC3)cc2)cn1] | 5-(4-{1-[5-(1H-1,2,3-Triazol-4-yl)-1,2,4-oxadiazol-3-yl]-cyclobutyl}-phenyl)-pyrimidin-2-ylamine |
| 41 | 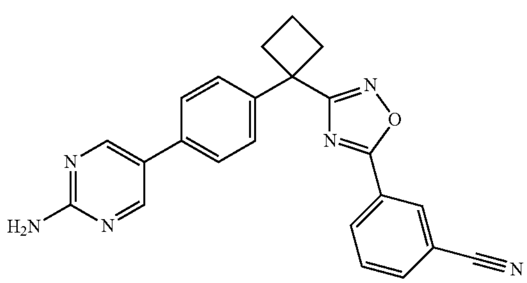 [SMILES: N#Cc1cccc(-c2nc(C3(c4ccc(-c5cnc(N)nc5)cc4)CCC3)no2)c1] | 3-(3-{1-[4-(2-Amino-pyrimidin-5-yl)-phenyl]-cyclobutyl}-1,2,4-oxadiazol-5-yl)-benzonitrile |
| 42 | 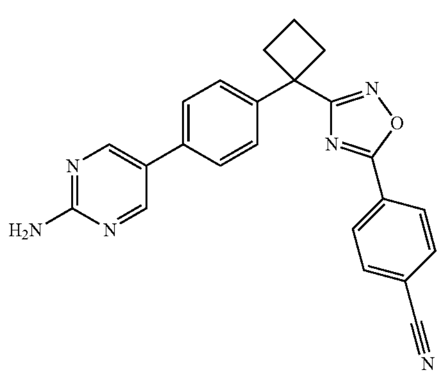 [SMILES: N#Cc1ccc(-c2nc(C3(c4ccc(-c5cnc(N)nc5)cc4)CCC3)no2)cc1] | 4-(3-{1-[4-(2-Amino-pyrimidin-5-yl)-phenyl]-cyclobutyl}-1,2,4-oxadiazol-5-yl)-benzonitrile |

TABLE I-continued

| Example | Structure | Name |
| --- | --- | --- |
| 43 | 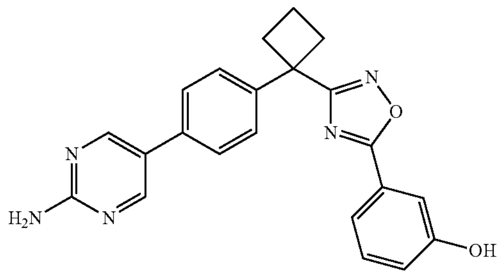 [SMILES: Nc1ncc(-c2ccc(C3(c4noc(-c5cccc(O)c5)n4)CCC3)cc2)cn1] | 3-(3-{1-[4-(2-Amino-pyrimidin-5-yl)-phenyl]-cyclobutyl}-1,2,4-oxadiazol-5-yl)-phenol |
| 44 | 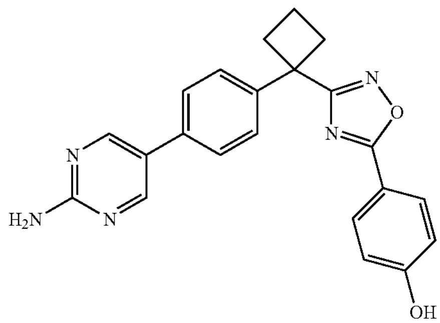 [SMILES: Nc1ncc(-c2ccc(C3(c4noc(-c5ccc(O)cc5)n4)CCC3)cc2)cn1] | 4-(3-{1-[4-(2-Amino-pyrimidin-5-yl)-phenyl]-cyclobutyl}-1,2,4-oxadiazol-5-yl)-phenol |
| 45 | 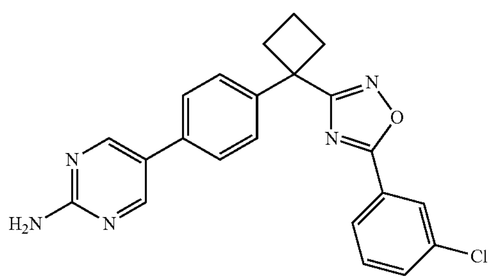 [SMILES: Nc1ncc(-c2ccc(C3(c4noc(-c5cccc(Cl)c5)n4)CCC3)cc2)cn1] | 5-(4-{1-[5-(3-Chloro-phenyl)-1,2,4-oxadiazol-3-yl]-cyclobutyl}-phenyl)-pyrimidin-2-ylamine |
| 46 | 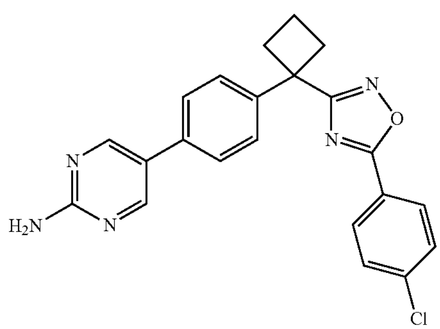 [SMILES: Nc1ncc(-c2ccc(C3(c4noc(-c5ccc(Cl)cc5)n4)CCC3)cc2)cn1] | 5-(4-{1-[5-(4-Chloro-phenyl)-1,2,4-oxadiazol-3-yl]-cyclobutyl}-phenyl)-pyrimidin-2-ylamine |
| 47 | 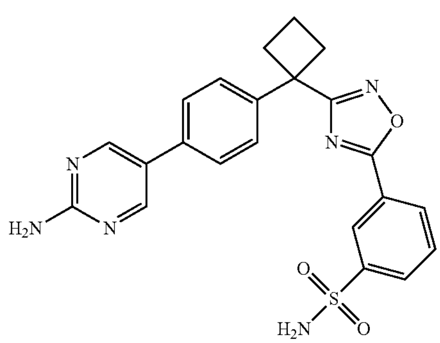 [SMILES: Nc1ncc(-c2ccc(C3(c4noc(-c5cccc(S(N)(=O)=O)c5)n4)CCC3)cc2)cn1] | 3-(3-{1-[4-(2-Amino-pyrimidin-5-yl)-phenyl]-cyclobutyl}-1,2,4-oxadiazol-5-yl)-benzenesulfonamide |

TABLE I-continued

| Example | Structure | Name |
|---|---|---|
| 48 | 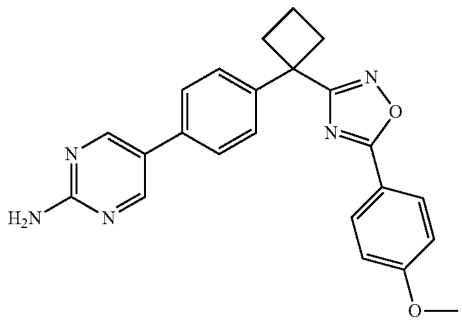 [SMILES: COc1ccc(-c2nc(C3(c4ccc(-c5cnc(N)nc5)cc4)CCC3)no2)cc1] | 5-(4-{1-[5-(4-Methoxy-phenyl)-1,2,4-oxadiazol-3-yl]-cyclobutyl}-phenyl)-pyrimidin-2-ylamine |
| 49 | 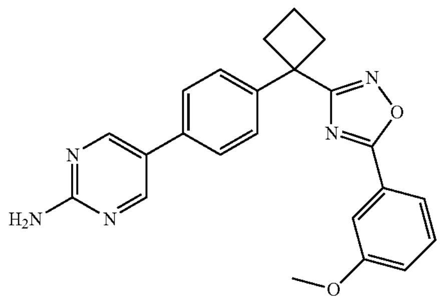 [SMILES: COc1cccc(-c2nc(C3(c4ccc(-c5cnc(N)nc5)cc4)CCC3)no2)c1] | 5-(4-{1-[5-(3-Methoxy-phenyl)-1,2,4-oxadiazol-3-yl]-cyclobutyl}-phenyl)-pyrimidin-2-ylamine |
| 50 | 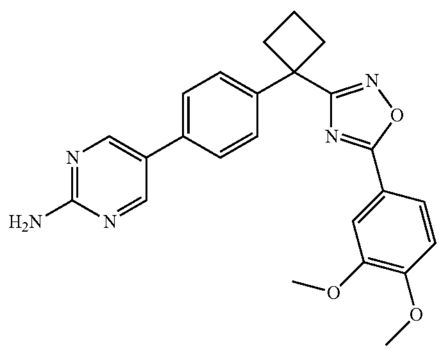 [SMILES: COc1ccc(-c2nc(C3(c4ccc(-c5cnc(N)nc5)cc4)CCC3)no2)cc1OC] | 5-(4-{1-[5-(3,4-Dimethoxy-phenyl)-1,2,4-oxadiazol-3-yl]-cyclobutyl}-phenyl)-pyrimidin-2-ylamine |
| 51 | 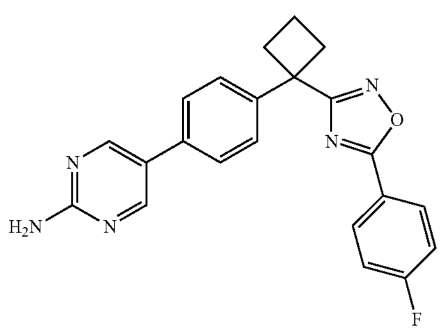 [SMILES: Nc1ncc(-c2ccc(C3(c4noc(-c5ccc(F)cc5)n4)CCC3)cc2)cn1] | 5-(4-{1-[5-(4-Fluoro-phenyl)-1,2,4-oxadiazol-3-yl]-cyclobutyl}-phenyl)-pyrimidin-2-ylamine |
| 52 | 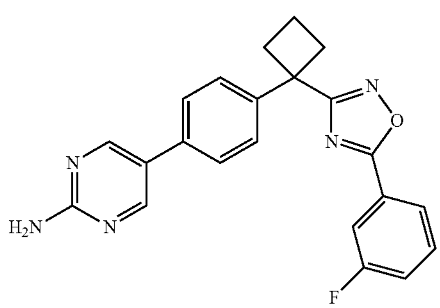 [SMILES: Nc1ncc(-c2ccc(C3(c4noc(-c5cccc(F)c5)n4)CCC3)cc2)cn1] | 5-(4-{1-[5-(3-Fluoro-phenyl)-1,2,4-oxadiazol-3-yl]-cyclobutyl}-phenyl)-pyrimidin-2-ylamine |

TABLE I-continued

| Example | Structure | Name |
|---|---|---|
| 53 | 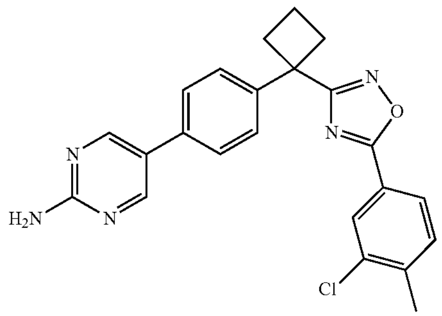 [SMILES: Cc1ccc(-c2nc(C3(c4ccc(-c5cnc(N)nc5)cc4)CCC3)no2)cc1Cl] | 5-(4-{1-[5-(3-Chloro-4-methyl-phenyl)-1,2,4-oxadiazol-3-yl]-cyclobutyl}-phenyl)-pyrimidin-2-ylamine |
| 54 | 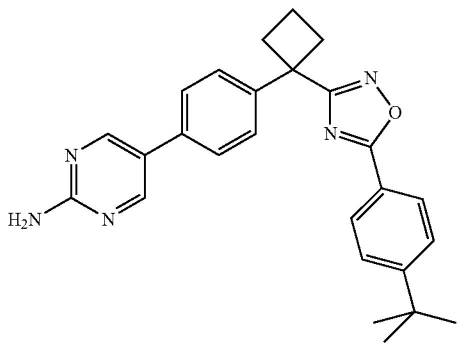 [SMILES: CC(C)(C)c1ccc(-c2nc(C3(c4ccc(-c5cnc(N)nc5)cc4)CCC3)no2)cc1] | 5-(4-{1-[5-(4-tert-Butyl-phenyl)-1,2,4-oxadiazol-3-yl]-cyclobutyl}-phenyl)-pyrimidin-2-ylamine |
| 55 | 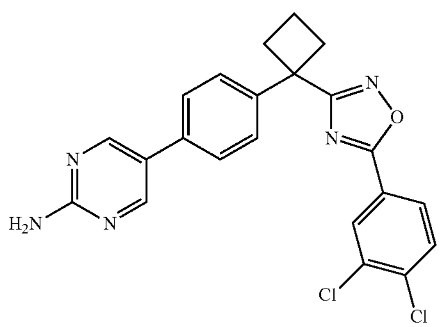 [SMILES: Nc1ncc(-c2ccc(C3(c4noc(-c5ccc(Cl)c(Cl)c5)n4)CCC3)cc2)cn1] | 5-(4-{1-[5-(3,4-Dichloro-phenyl)-1,2,4-oxadiazol-3-yl]-cyclobutyl}-phenyl)-pyrimidin-2-ylamine |
| 56 | 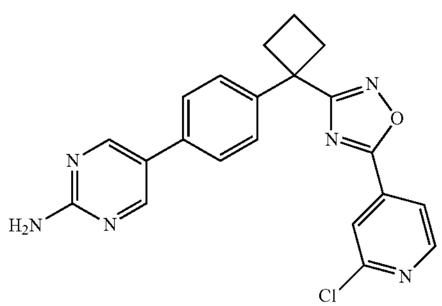 [SMILES: Nc1ncc(-c2ccc(C3(c4noc(-c5ccnc(Cl)c5)n4)CCC3)cc2)cn1] | 5-(4-{1-[5-(2-Chloro-pyridin-4-yl)-1,2,4-oxadiazol-3-yl]-cyclobutyl}-phenyl)-pyrimidin-2-ylamine |
| 57 | 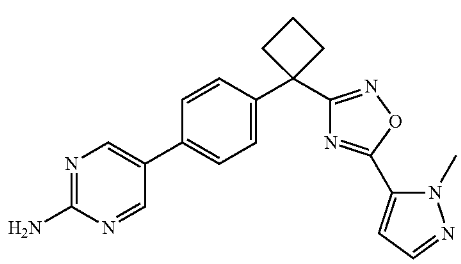 [SMILES: Cn1nccc1-c1nc(C2(c3ccc(-c4cnc(N)nc4)cc3)CCC2)no1] | 5-(4-{1-[5-(2-Methyl-2H-pyrazol-3-yl)-1,2,4-oxadizol-3-yl]-cyclobutyl}-phenyl)-pyrimidin-2-ylamine |

TABLE I-continued

| Example | Structure | Name |
|---|---|---|
| 58 | 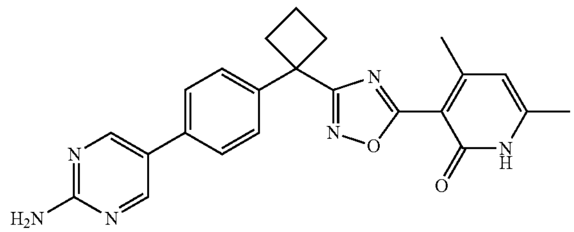 [SMILES: Cc1cc(C)c(-c2nc(C3(c4ccc(-c5cnc(N)nc5)cc4)CCC3)no2)c(=O)[nH]1] | 3-(3-{1-[4-(2-Amino-pyrimidin-5-yl)-phenyl]-cyclobutyl}-1,2,4-oxadiazol-5-yl)-4,6-dimethyl-1H-pyridin-2-one |
| 59 | 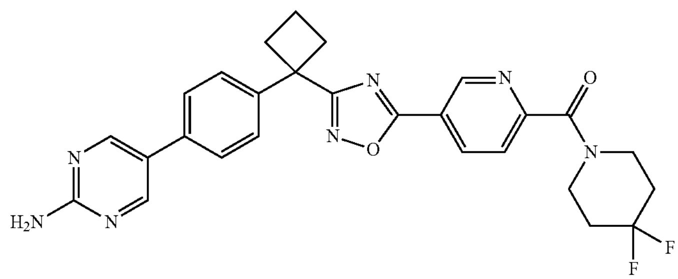 [SMILES: Nc1ncc(-c2ccc(C3(c4noc(-c5ccc(C(=O)N6CCC(F)(F)CC6)nc5)n4)CCC3)cc2)cn1] | [5-(3-{1-[4-(2-Amino-pyrimidin-5-yl)-phenyl]-cyclobutyl}-1,2,4-oxadiazol-5-yl)-pyridin-2-yl]-(4,4-difluoro-piperidin-1-yl)-methanone |
| 60 | 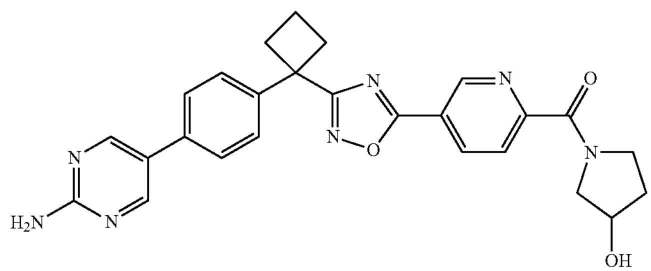 [SMILES: Nc1ncc(-c2ccc(C3(c4noc(-c5ccc(C(=O)N6CCC(O)C6)nc5)n4)CCC3)cc2)cn1] | [5-(3-{1-[4-(2-Amino-pyrimidin-5-yl)-phenyl]-cyclobutyl}-1,2,4-oxadiazol-5-yl)-pyridin-2-yl]-(3-hydroxy-pyrrolidin-1-yl)-methanone |
| 61 | 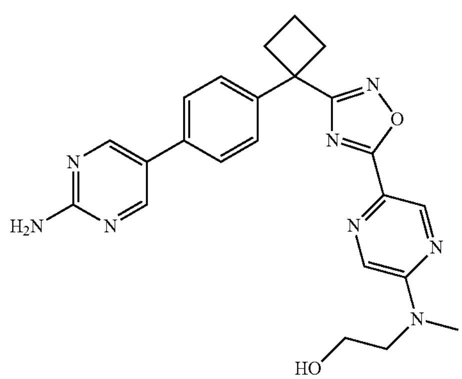 [SMILES: CN(CCO)c1cnc(-c2nc(C3(c4ccc(-c5cnc(N)nc5)cc4)CCC3)no2)cn1] | 2-{[5-(3-{1-[4-(2-Amino-pyrimidin-5-yl)-phenyl]-cyclobutyl}-1,2,4-oxadiazol-5-yl)-pyrazin-2-yl]-methyl-amino}-ethanol |
| 62 | 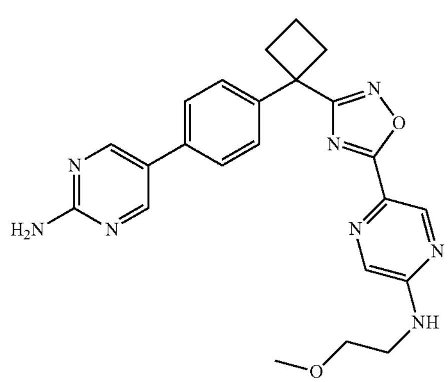 [SMILES: COCCNc1cnc(-c2nc(C3(c4ccc(-c5cnc(N)nc5)cc4)CCC3)no2)cn1] | 5-[4-(1-{5-[5-(2-Methoxy-ethylamino)-pyrazin-2-yl]-1,2,4-oxadiazol-3-yl}-cyclobutyl)-phenyl]-pyrimidin-2-ylamine |

TABLE I-continued

| Example | Structure | Name |
|---|---|---|
| 63 | 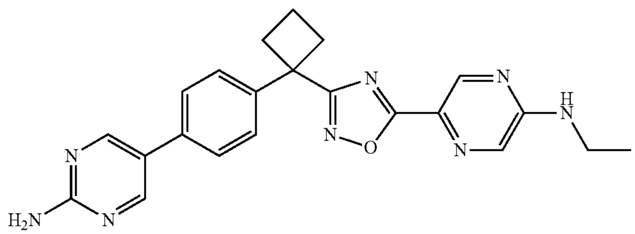 [SMILES: CCNc1cnc(-c2nc(C3(c4ccc(-c5cnc(N)nc5)cc4)CCC3)no2)cn1] | 5-(4-{1-[5-(5-Ethylamino-pyrazin-2-yl)-1,2,4-oxadiazol-3-yl]-cyclobutyl}-phenyl)-pyrimidin-2-ylamine |
| 64 | 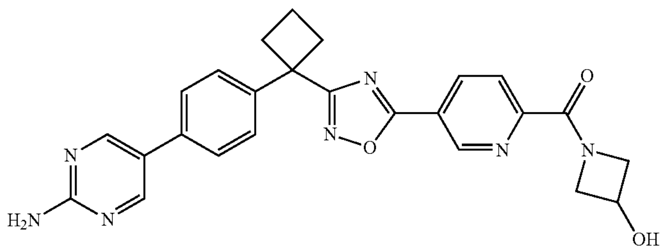 [SMILES: Nc1ncc(-c2ccc(C3(c4noc(-c5ccc(C(=O)N6CC(O)C6)nc5)n4)CCC3)cc2)cn1] | [5-(3-{1-[4-(2-Amino-pyrimidin-5-yl)-phenyl]-cyclobutyl}-1,2,4-oxadiazol-5-yl)-pyridin-2-yl]-(3-hydroxy-azetidin-1-yl)-methanone |
| 65 | 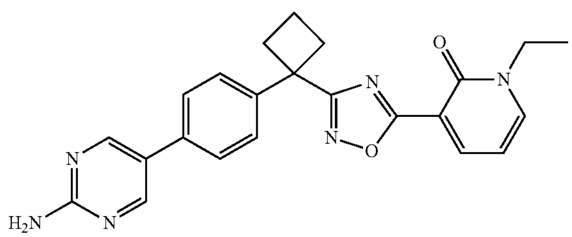 [SMILES: CCn1cccc(-c2nc(C3(c4ccc(-c5cnc(N)nc5)cc4)CCC3)no2)c1=O] | 3-(3-{1-[4-(2-Amino-pyrimidin-5-yl)-phenyl]-cyclobutyl}-1,2,4-oxadiazol-5-yl)-1-ethyl-1H-pyridin-2-one |
| 66 | 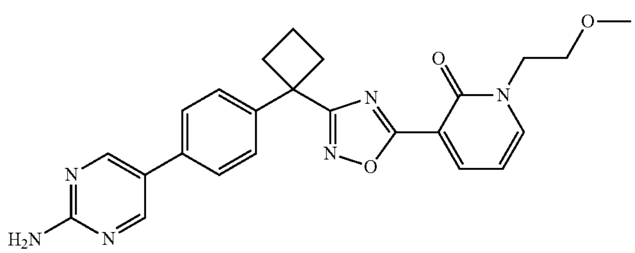 [SMILES: COCCn1cccc(-c2nc(C3(c4ccc(-c5cnc(N)nc5)cc4)CCC3)no2)c1=O] | 3-(3-{1-[4-(2-Amino-pyrimidin-5-yl)-phenyl]-cyclobutyl}-1,2,4-oxadiazol-5-yl)-1-(2-methoxy-ethyl)-1H-pyridin-2-one |
| 67 | 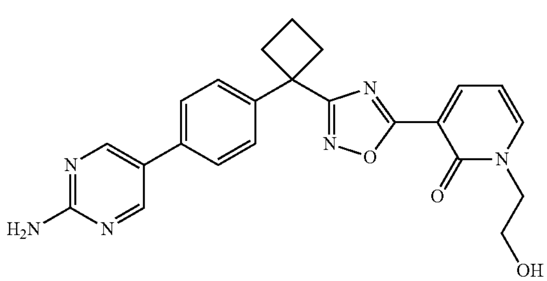 [SMILES: Nc1ncc(-c2ccc(C3(c4noc(-c5cccn(CCO)c5=O)n4)CCC3)cc2)cn1] | 3-(3-{1-[4-(2-Amino-pyrimidin-5-yl)-phenyl]-cyclobutyl}-1,2,4-oxadiazol-5-yl)-1-(2-hydroxy-ethyl)-1H-pyridin-2-one |
| 68 | 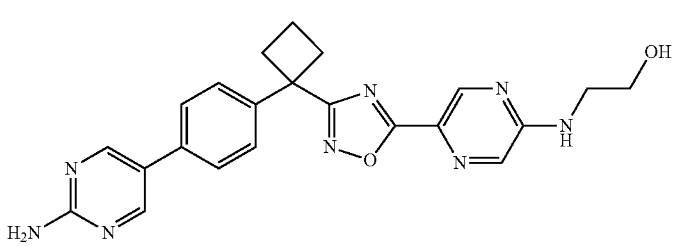 [SMILES: Nc1ncc(-c2ccc(C3(c4noc(-c5cnc(NCCO)cn5)n4)CCC3)cc2)cn1] | 2-[5-(3-{1-[4-(2-Amino-pyrimidin-5-yl)-phenyl]-cyclobutyl}-1,2,4-oxadiazol-5-yl)-pyrazin-2-ylamino]-ethanol |

TABLE I-continued

| Example | Structure | Name |
|---|---|---|
| 69 | 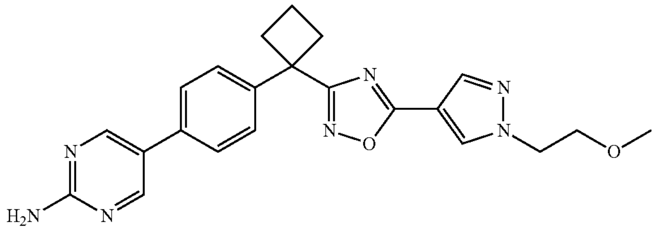 [SMILES: COCCn1cc(-c2nc(C3(c4ccc(-c5cnc(N)nc5)cc4)CCC3)no2)cn1] | 5-[4-(1-{5-[1-(2-Methoxy-ethyl)-1H-pyrazol-4-yl]-1,2,4-oxadiazol-3-yl}-cyclobutyl)-phenyl]-pyrimidin-2-ylamine |
| 70 | 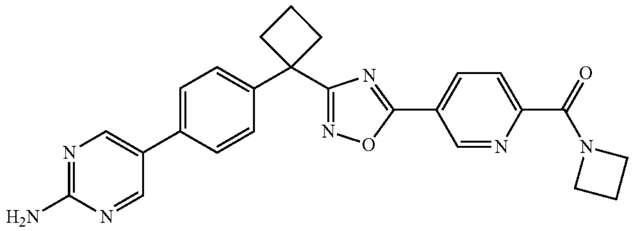 [SMILES: Nc1ncc(-c2ccc(C3(c4noc(-c5ccc(C(=O)N6CCC6)nc5)n4)CCC3)cc2)cn1] | [5-(3-{1-[4-(2-Amino-pyrimidin-5-yl)-phenyl]-cyclobutyl}-1,2,4-oxadiazol-5-yl)-pyridin-2-yl]-azetidin-1-yl-methanone |
| 71 | 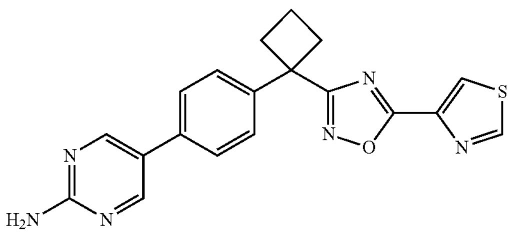 [SMILES: Nc1ncc(-c2ccc(C3(c4noc(-c5cscn5)n4)CCC3)cc2)cn1] | 5-{4-[1-(5-Thiazol-1-yl-1,2,4-oxadiazol-3-yl)-cyclobutyl]-phenyl}-pyrimidin-2-ylamine |
| 72 | 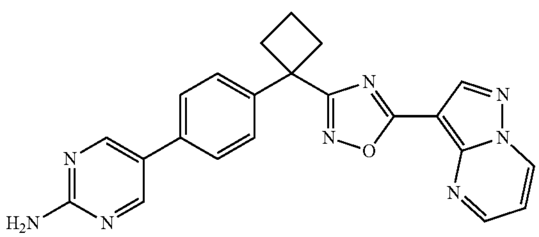 | 5-{4-[1-(5-Pyrazolo[1,5-a]pyrimidin-3-yl-1,2,4-oxadiazol-3-yl)-cyclobutyl]-phenyl}-pyrimidin-2-ylamine |
| 73 | 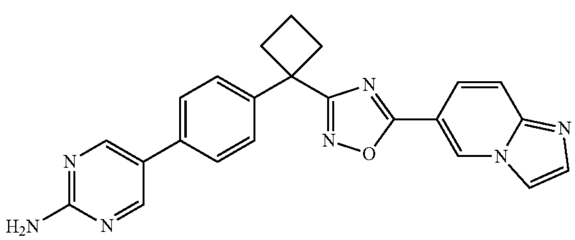 [SMILES: Nc1ncc(-c2ccc(C3(c4noc(-c5ccc6nccn6c5)n4)CCC3)cc2)cn1] | 5-{4-[1-(5-Imidazo[1,2-a]pyridin-6-yl-1,2,4-oxadiazol-3-yl)-cyclobutyl]-phenyl}-pyrimidin-2-ylamine |
| 74 | 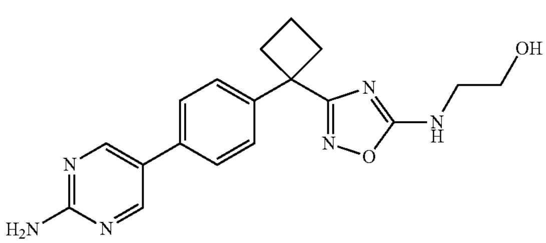 [SMILES: Nc1ncc(-c2ccc(C3(c4noc(NCCO)n4)CCC3)cc2)cn1] | 2-(3-{1-[4-(2-Amino-pyrimidin-5-yl)-phenyl]-cyclobutyl}-1,2,4-oxadiazol-5-ylamino)-ethanol |

TABLE I-continued

| Example | Structure | Name |
|---|---|---|
| 75 | 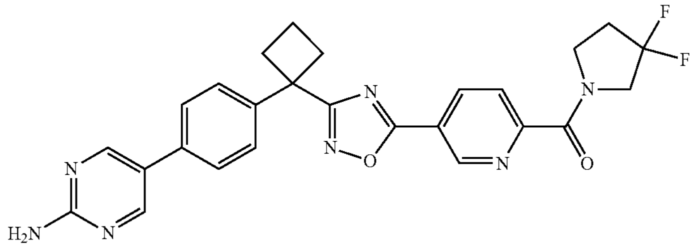 [SMILES: Nc1ncc(-c2ccc(C3(c4noc(-c5ccc(C(=O)N6CCC(F)(F)C6)nc5)n4)CCC3)cc2)cn1] | [5-(3-{1-[4-(2-Amino-pyrimidin-5-yl)-phenyl]-cyclobutyl}-1,2,4-oxadiazol-5-yl)-pyridin-2-yl]-(3,3-difluoro-pyrrolidin-1-yl)-methanone |
| 76 | 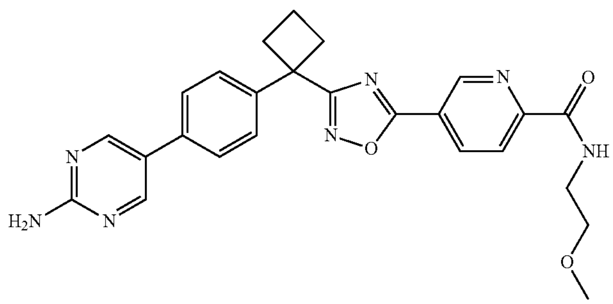 [SMILES: COCCNC(=O)c1ccc(-c2nc(C3(c4ccc(-c5cnc(N)nc5)cc4)CCC3)no2)cn1] | 5-(3-{1-[4-(2-Amino-pyrimidin-5-yl)-phenyl]-cyclobutyl}-1,2,4-oxadiazol-5-yl)-pyridine-2-carboxylic acid (2-methoxy-ethyl)-amide |
| 77 | 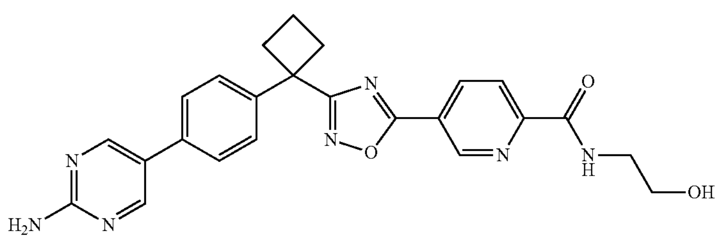 [SMILES: Nc1ncc(-c2ccc(C3(c4noc(-c5ccc(C(=O)NCCO)nc5)n4)CCC3)cc2)cn1] | 5-(3-{1-[4-(2-Amino-pyrimidin-5-yl)-phenyl]-cyclobutyl}-1,2,4-oxadiazol-5-yl)-pyridine-2-carboxylic acid (2-hydroxy-ethyl)-amide |
| 78 | 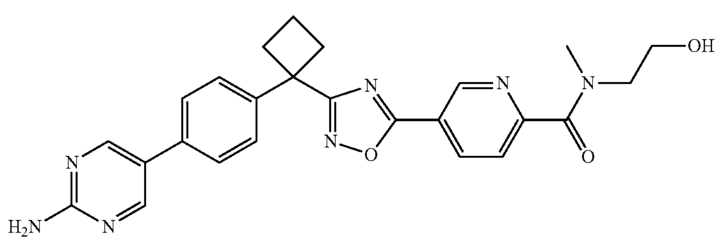 | 5-(3-{1-[4-(2-Amino-pyrimidin-5-yl)-phenyl]-cyclobutyl}-1,2,4-oxadiazol-5-yl)-pyridine-2-carboxylic acid (2-hydroxy-ethyl)-methyl-amide |
| 79 | 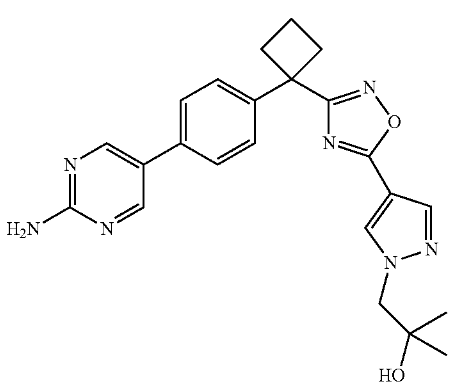 [SMILES: CC(C)(O)Cn1cc(-c2nc(C3(c4ccc(-c5cnc(N)nc5)cc4)CCC3)no2)cn1] | 1-[4-(3-{1-[4-(2-Amino-pyrimidin-5-yl)-phenyl]-cyclobutyl}-1,2,4-oxadiazol-5-yl)-pyrazol-1-yl]-2-methyl-propan-2-ol |

TABLE I-continued

| Example | Structure | Name |
|---|---|---|
| 80 | 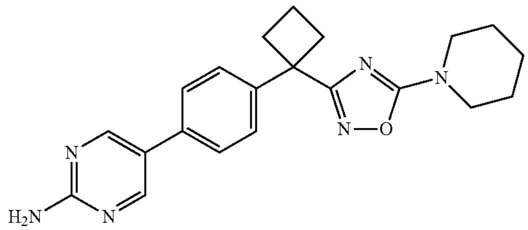 [SMILES: Nc1ncc(-c2ccc(C3(c4noc(N5CCCCC5)n4)CCC3)cc2)cn1] | 5-{4-[1-(5-Piperidin-1-yl-1,2,4-oxadiazol-3-yl)-cyclobutyl]-phenyl}-pyrimidin-2-ylamine |
| 81 | 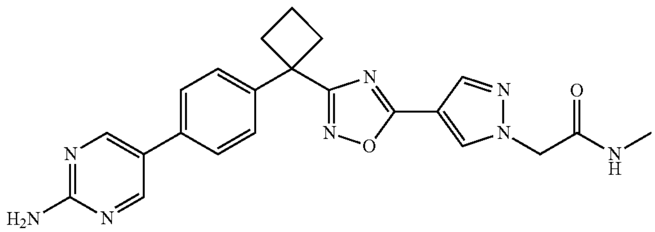 | 2-[4-(3-{1-[4-(2-Amino-pyrimidin-5-yl)-phenyl]-cyclobutyl}-1,2,4-oxadiazol-5-yl)-pyrazol-1-yl]-N-methyl-acetamide |
| 82 | 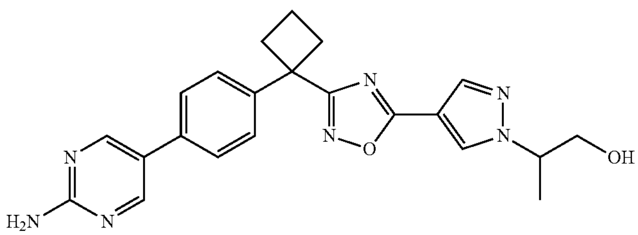 [SMILES: CC(CO)n1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-1,2,4-oxadiazol-5-yl)-pyrazol-1-yl]-propan-1-ol |
| 83 | 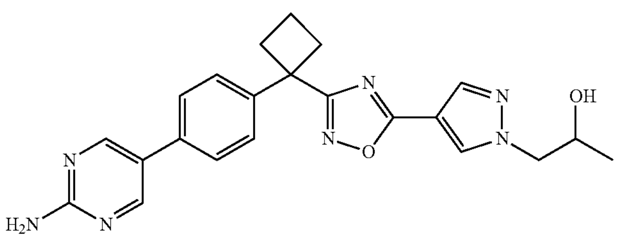 [SMILES: CC(O)Cn1cc(-c2nc(C3(c4ccc(-c5cnc(N)nc5)cc4)CCC3)no2)cn1] | 1-[4-(3-{1-[4-(2-Amino-pyrimidin-5-yl)-phenyl]-cyclobutyl}-1,2,4-oxadiazol-5-yl)-pyrazol-1-yl]-propan-2-ol |
| 84 | 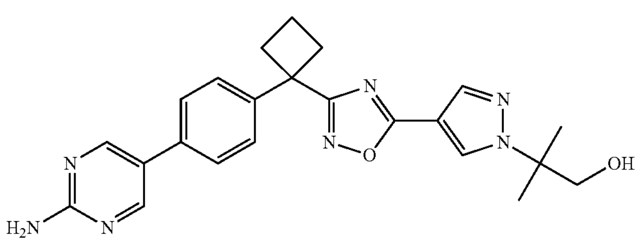 [SMILES: CC(C)(CO)n1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-1,2,4-oxadiazol-5-yl)-pyrazol-1-yl]-2-methyl-propan-1-ol |
| 85 | 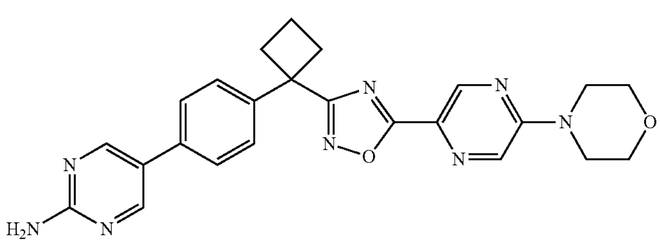 [SMILES: Nc1ncc(-c2ccc(C3(c4noc(-c5cnc(N6CCOCC6)cn5)n4)CCC3)cc2)cn1] | 5-(4-{1-[5-(5-Morpholin-4-yl-pyrazin-2-yl)-1,2,4-oxadiazol-3-yl]-cyclobutyl}-phenyl)-pyrimidin-2-ylamine |

TABLE I-continued

| Example | Structure | Name |
|---|---|---|
| 86 | 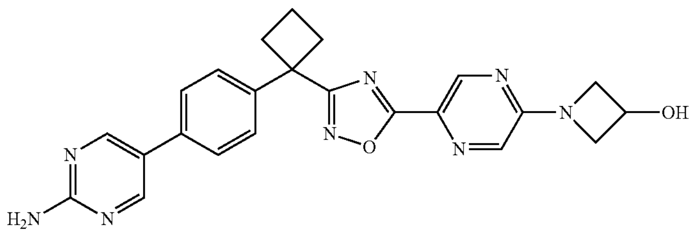 [SMILES: Nc1ncc(-c2ccc(C3(c4noc(-c5cnc(N6CC(O)C6)cn5)n4)CCC3)cc2)cn1] | 1-[5-(3-{1-[4-(2-Amino-pyrimidin-5-yl)-phenyl]-cyclobutyl}-1,2,4-oxadiazol-5-yl)-pyrazin-2-yl]-azetidin-3-ol |
| 87 | 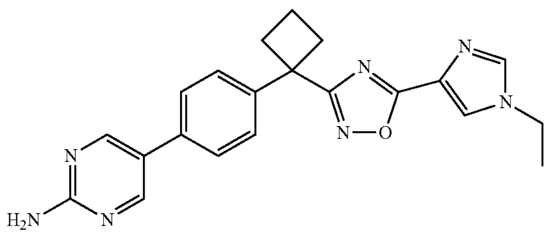 [SMILES: CCn1cnc(-c2nc(C3(c4ccc(-c5cnc(N)nc5)cc4)CCC3)no2)c1] | 5-(4-{1-[5-(1-Ethyl-1H-imidazol-4-yl)-1,2,4-oxadiazol-3-yl]-cyclobutyl}-phenyl)-pyrimidin-2-ylamine |
| 88 | 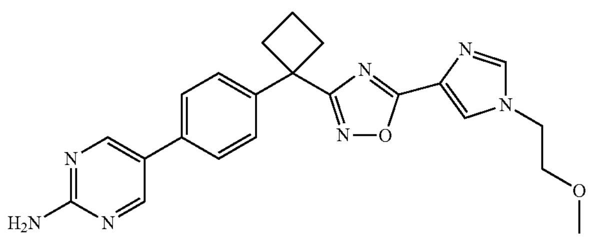 [SMILES: COCCn1cnc(-c2nc(C3(c4ccc(-c5cnc(N)nc5)cc4)CCC3)no2)c1] | 5-[4-(1-{5-[1-(2-Methoxy-ethyl)-1H-imidazol-4-yl]-1,2,4-oxadiazol-3-yl}-cyclobutyl)-phenyl]-pyrimidin-2-ylamine |
| 89 | 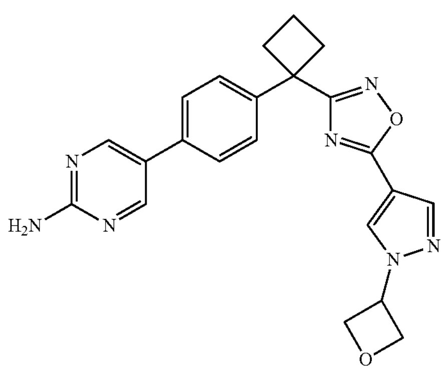 [SMILES: Nc1ncc(-c2ccc(C3(c4noc(-c5cnn(C6COC6)c5)n4)CCC3)cc2)cn1] | 5-(4-{1-[5-(1-Oxetan-3-yl-1H-pyrazol-4-yl)-1,2,4-oxadiazol-3-yl]-cyclobutyl}-phenyl)-pyrimidin-2-ylamine |
| 90 | 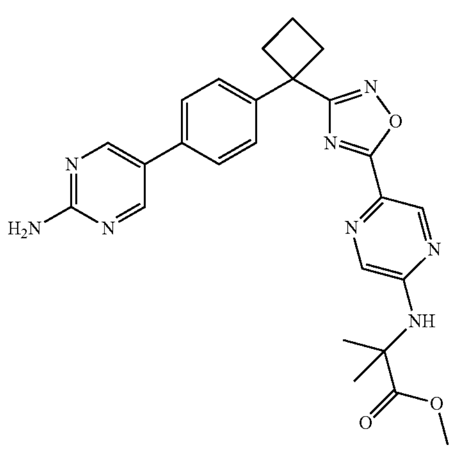 [SMILES: COC(=O)C(C)(C)Nc1cnc(-c2nc(C3(c4ccc(-c5cnc(N)nc5)cc4)CCC3)no2)cn1] | 2-[5-(3-{1-[4-(2-Amino-pyrimidin-5-yl)-phenyl]-cyclobutyl}-1,2,4-oxadiazol-5-yl)-pyrazin-2-ylamino]-2-methyl-propionic acid methyl ester |

TABLE I-continued

| Example | Structure | Name |
|---------|-----------|------|
| 91 | 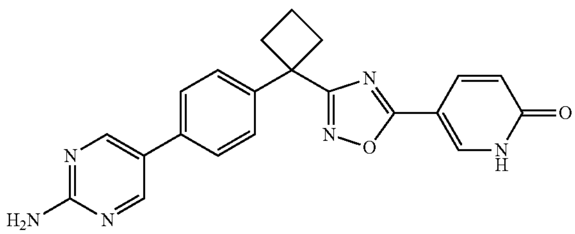 [SMILES: Nc1ncc(-c2ccc(C3(c4noc(-c5ccc(=O)[nH]c5)n4)CCC3)cc2)cn1] | 5-(3-{1-[4-(2-Amino-pyrimidin-5-yl)-phenyl]-cyclobutyl}-1,2,4-oxadiazol-5-yl)-1H-pyridin-2-one |
| 92 | 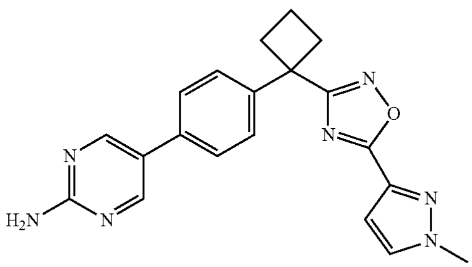 [SMILES: Cn1ccc(-c2nc(C3(c4ccc(-c5cnc(N)nc5)cc4)CCC3)no2)n1] | 5-(4-{1-[5-(1-Methyl-1I-pyrazol-3-yl)-1,2,4-oxadiazol-3-yl]-cyclobutyl}-phenyl)-pyrimidin-2-ylamine |
| 93 | 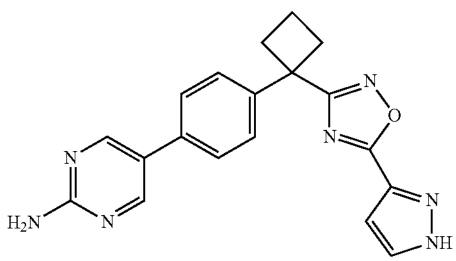 [SMILES: Nc1ncc(-c2ccc(C3(c4noc(-c5cc[nH]n5)n4)CCC3)cc2)cn1] | 5-(4-{1-[5-(1H-Pyrazol-3-yl)-1,2,4-oxadiazol-3-yl]-cyclobutyl}-phenyl)-pyrimidin-2-ylamine |
| 94 | 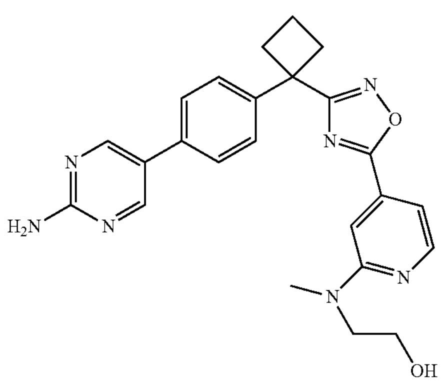 [SMILES: CN(CCO)c1cc(-c2nc(C3(c4ccc(-c5cnc(N)nc5)cc4)CCC3)no2)ccn1] | 2-{[4-(3-{1-[4-(2-Amino-pyrimidin-5-yl)-phenyl]-cyclobutyl}-1,2,4-oxadiazol-5-yl)-pyridin-2-yl]-methyl-amino}-ethanol |
| 95 | 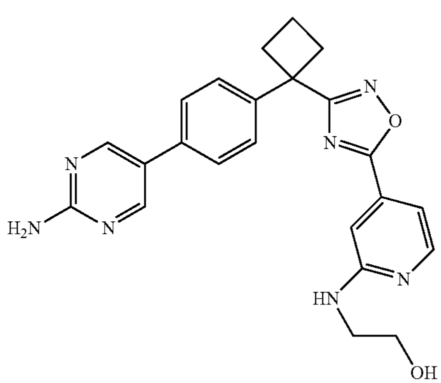 [SMILES: Nc1ncc(-c2ccc(C3(c4noc(-c5ccnc(NCCO)c5)n4)CCC3)cc2)cn1] | 2-[4-(3-{1-[4-(2-Amino-pyrimidin-5-yl)-phenyl]-cyclobutyl}-1,2,4-oxadiazol-5-yl)-pyridin-2-ylamino]-ethanol |

TABLE I-continued

| Example | Structure | Name |
|---|---|---|
| 96 | 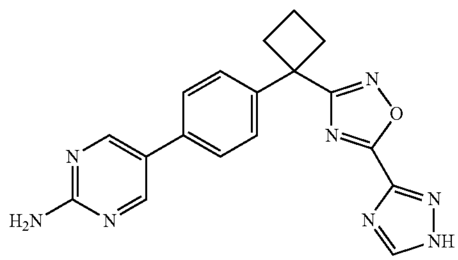 [SMILES: Nc1ncc(-c2ccc(C3(c4noc(-c5nc[nH]n5)n4)CCC3)cc2)cn1] | 5-(4-{1-[5-(1H-1,2,4-Triazol-3-yl)-1,2,4-oxadiazol-3-yl]-cyclobutyl}-phenyl)-pyrimidin-2-ylamine |
| 97 | 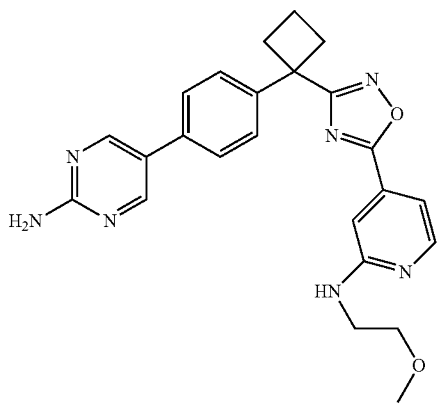 [SMILES: COCCNc1cc(-c2nc(C3(c4ccc(-c5cnc(N)nc5)cc4)CCC3)no2)ccn1] | 5-[4-(1-{5-[2-(2-Methoxy-ethylamino)-pyridin-4-yl]-1,2,4-oxadiazol-3-yl}-cyclobutyl)-phenyl]-pyrimidin-2-ylamine |
| 98 | 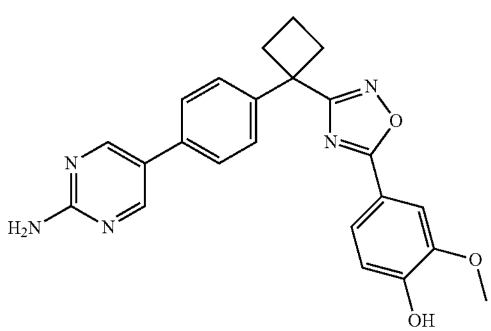 [SMILES: COc1cc(-c2nc(C3(c4ccc(-c5cnc(N)nc5)cc4)CCC3)no2)ccc1O] | 4-(3-{1-[4-(2-Amino-pyrimidin-5-yl)-phenyl]-cyclobutyl}-1,2,4-oxadiazol-5-yl)-2-methoxy-phenol |
| 99 | 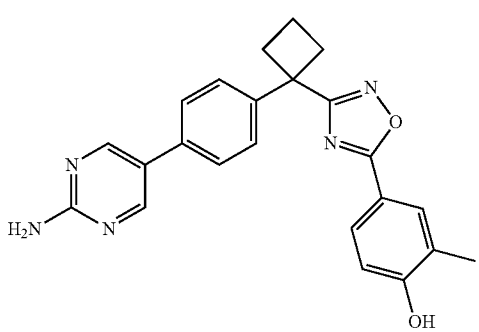 [SMILES: Cc1cc(-c2nc(C3(c4ccc(-c5cnc(N)nc5)cc4)CCC3)no2)ccc1O] | 4-(3-{1-[4-(2-Amino-pyrimidin-5-yl)-phenyl]-cyclobutyl}-1,2,4-oxadiazol-5-yl)-2-methyl-phenol |

TABLE I-continued

| Example | Structure | Name |
|---|---|---|
| 100 | 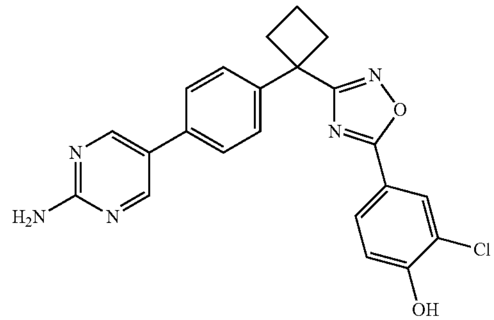 [SMILES: Nc1ncc(-c2ccc(C3(c4noc(-c5ccc(O)c(Cl)c5)n4)CCC3)cc2)cn1] | 4-(3-{1-[4-(2-Amino-pyrimidin-5-yl)-phenyl]-cyclobutyl}-1,2,4-oxadiazol-5-yl)-2-chloro-phenol |
| 101 | 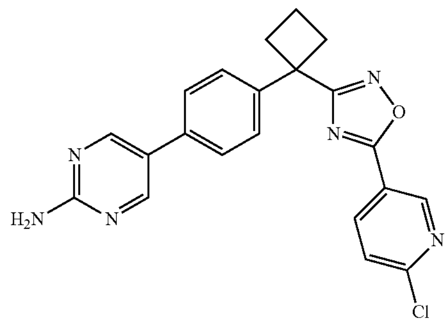 [SMILES: Nc1ncc(-c2ccc(C3(c4noc(-c5ccc(Cl)nc5)n4)CCC3)cc2)cn1] | 5-(4-{1-[5-(6-Chloro-pyridin-3-yl)-1,2,4-oxadiazol-3-yl]-cyclobutyl}-phenyl)-pyrimidin-2-ylamine |
| 102 | Chiral | {(R)-1-[5-(3-{1-[4-(2-Amino-pyrimidin-5-yl)-phenyl]-cyclobutyl}-1,2,4-oxadiazol-5-yl)-pyridin-2-yl]-pyrrolidin-2-yl}-methanol |
| 103 | Chiral | (R)-1-[5-(3-{1-[4-(2-Amino-pyrimidin-5-yl)-phenyl]-cyclobutyl}-1,2,4-oxadiazol-5-yl)-pyridin-2-yl]-pyrrolidin-3-ol |

TABLE I-continued

| Example | Structure | Name |
|---|---|---|
| 104 | 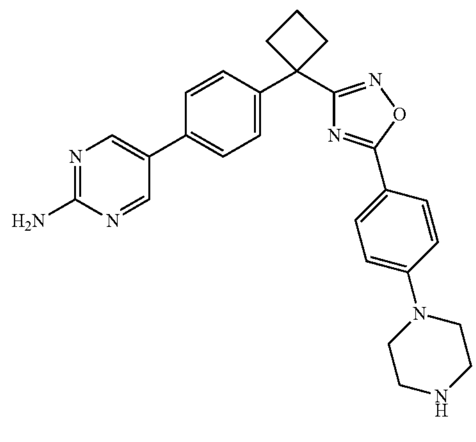 [SMILES: Nc1ncc(-c2ccc(C3(c4noc(-c5ccc(N6CCNCC6)cc5)n4)CCC3)cc2)cn1] | 5-(4-{1-[5-(4-Piperazin-1-yl-phenyl)-1,2,4-oxadiazol-3-yl]-cyclobutyl}-phenyl)-pyrimidin-2-ylamine |
| 105 | Chiral | (S)-1-[5-(3-{1-[4-(2-Amino-pyrimidin-5-yl)-phenyl]-cyclobutyl}-1,2,4-oxadiazol-5-yl)-pyridin-2-yl]-pyrrolidin-3-ol |
| 106 | 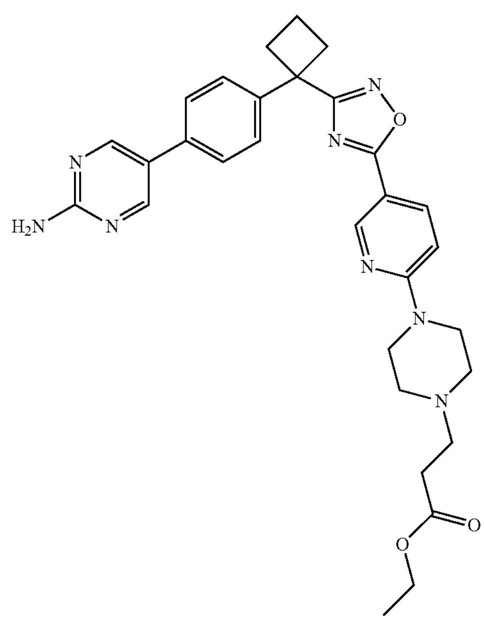 [SMILES: CCOC(=O)CCN1CCN(c2ccc(-c3nc(C4(c5ccc(-c6cnc(N)nc6)cc5)CCC4)no3)cn2)CC1] | 3-{4-[5-(3-{1-[4-(2-Amino-pyrimidin-5-yl)-phenyl]-cyclobutyl}-1,2,4-oxadiazol-5-yl)-pyridin-2-yl]-piperazin-1-yl}-propionic acid ethyl ester |

TABLE I-continued

| Example | Structure | Name |
|---|---|---|
| 107 | 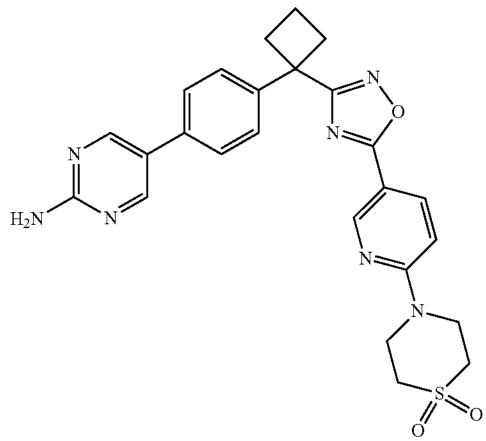 [SMILES: Nc1ncc(-c2ccc(C3(c4noc(-c5ccc(N6CCS(=O)(=O)CC6)nc5)n4)CCC3)cc2)cn1] | 5-[4-(1-{5-[6-(1,1-Dioxo-1λ$^6$-thiomorpholin-4-yl)-pyridin-3-yl]-1,2,4-oxadiazol-3-yl}-cyclobutyl)-phenyl]-pyrimidin-2-ylamine |
| 108 | 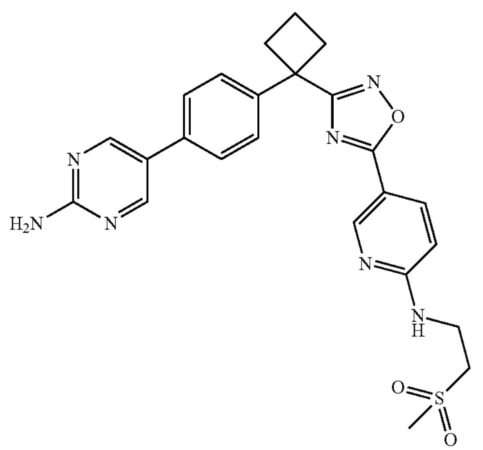 [SMILES: CS(=O)(=O)CCNc1ccc(-c2nc(C3(c4ccc(-c5cnc(N)nc5)cc4)CCC3)no2)cn1] | 5-[4-(1-{5-[6-(2-Methanesulfonyl-ethylamino)-pyridin-3-yl]-1,2,4-oxadiazol-3-yl}-cyclobutyl)-phenyl]-pyrimidin-2-ylamine |
| 109 | 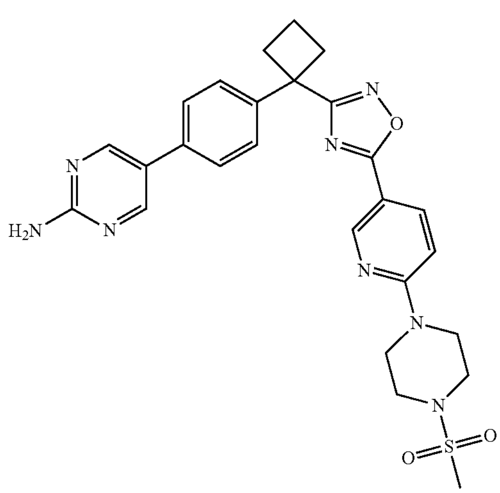 [SMILES: CS(=O)(=O)N1CCN(c2ccc(-c3nc(C4(c5ccc(-c6cnc(N)nc6)cc5)CCC4)no3)cn2)CC1] | 5-[4-(1-{5-[6-(4-Methanesulfonyl-piperazin-1-yl)-pyridin-3-yl]-1,2,4-oxadiazol-3-yl}-cyclobutyl)-phenyl]-pyrimidin-2-ylamine |

TABLE I-continued

| Example | Structure | Name |
|---|---|---|
| 110 | 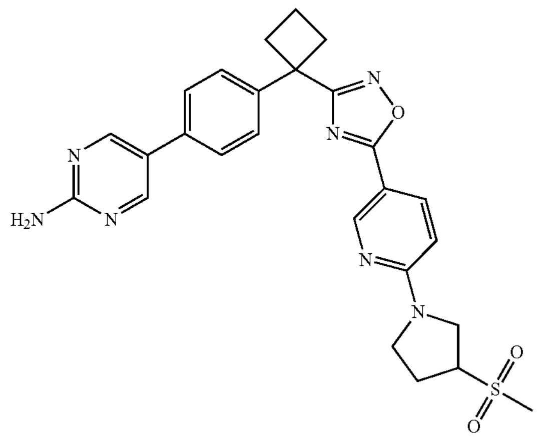 [SMILES: CS(=O)(=O)C1CCN(c2ccc(-c3nc(C4(c5ccc(-c6cnc(N)nc6)cc5)CCC4)no3)cn2)C1] | 5-[4-(1-{5-[6-(3-Methanesulfonyl-pyrrolidin-1-yl)-pyridin-3-yl]-1,2,4-oxadiazol-3-yl}-cyclobutyl)-phenyl]-pyrimidin-2-ylamine |
| 111 | 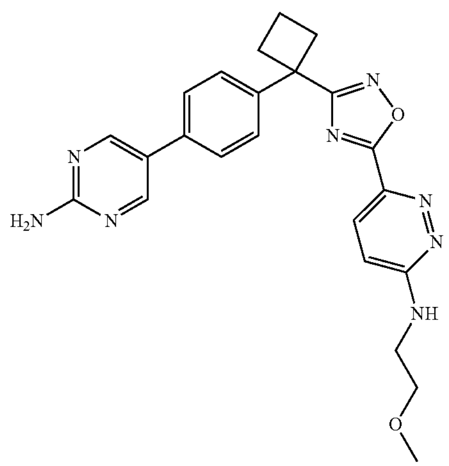 [SMILES: COCCNc1ccc(-c2nc(C3(c4ccc(-c5cnc(N)nc5)cc4)CCC3)no2)nn1] | [6-(3-{1-[4-(2-Amino-pyrimidin-5-yl)-phenyl]-cyclobutyl}-1,2,4-oxadiazol-5-yl)-pyridazin-3-yl]-(2-methoxy-ethyl)-amine |
| 112 | 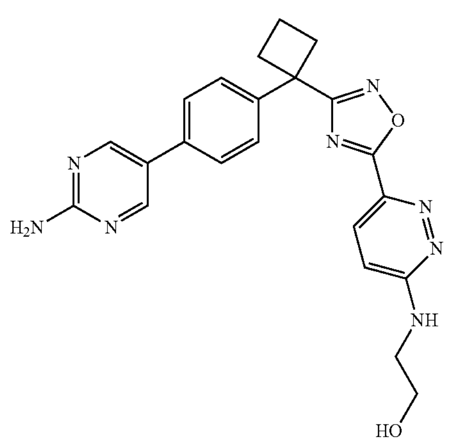 [SMILES: Nc1ncc(-c2ccc(C3(c4noc(-c5ccc(NCCO)nn5)n4)CCC3)cc2)cn1] | 2-[6-(3-{1-[4-(2-Amino-pyrimidin-5-yl)-phenyl]-cyclobutyl}-1,2,4-oxadiazol-5-yl)-pyridazin-3-ylamino]-ethanol |

TABLE I-continued

| Example | Structure | Name |
|---|---|---|
| 113 | 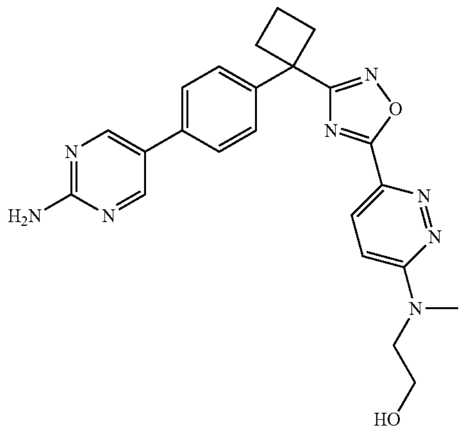 [SMILES: CN(CCO)c1ccc(-c2nc(C3(c4ccc(-c5cnc(N)nc5)cc4)CCC3)no2)nn1] | 2-{[6-(3-{1-[4-(2-Amino-pyrimidin-5-yl)-phenyl]-cyclobutyl}-1,2,4-oxadiazol-5-yl)-pyridazin-3-yl]-methyl-amino}-ethanol |
| 114 | 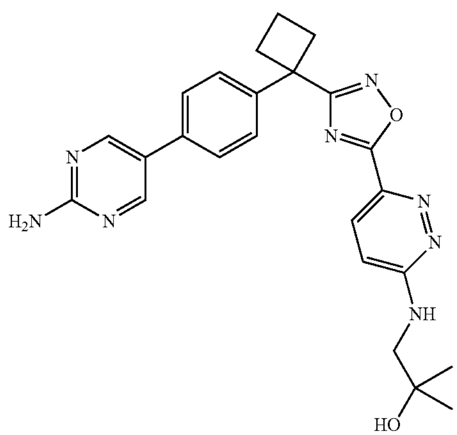 [SMILES: CC(C)(O)CNc1ccc(-c2nc(C3(c4ccc(-c5cnc(N)nc5)cc4)CCC3)no2)nn1] | 1-[6-(3-{1-[4-(2-Amino-pyrimidin-5-yl)-phenyl]-cyclobutyl}-1,2,4-oxadiazol-5-yl)-pyridazin-3-ylamino]-2-methyl-propan-2-ol |
| 115 | 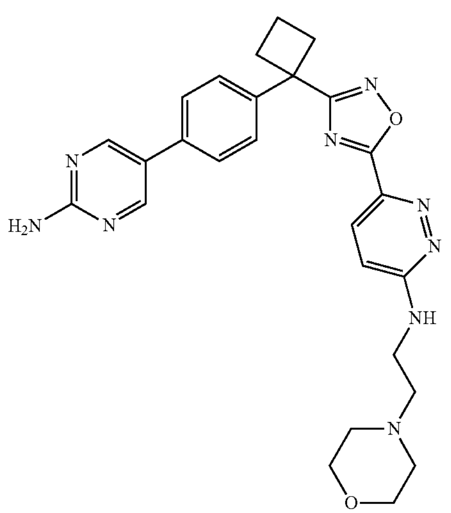 [SMILES: Nc1ncc(-c2ccc(C3(c4noc(-c5ccc(NCCN6CCOCC6)nn5)n4)CCC3)cc2)cn1] | [6-(3-{1-[4-(2-Amino-pyrimidin-5-yl)-phenyl]-cyclobutyl}-1,2,4-oxadiazol-5-yl)-pyridazin-3-yl]-(2-morpholin-4-yl-ethyl)-amine |

TABLE I-continued

| Example | Structure | Name |
|---|---|---|
| 116 | 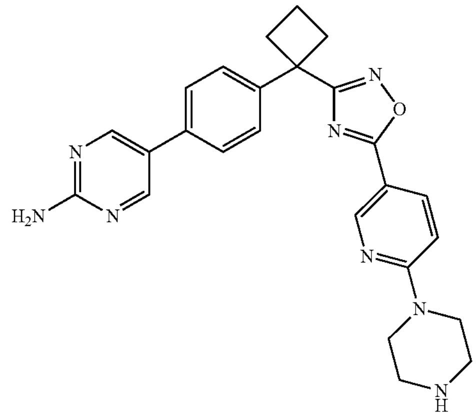 [SMILES: Nc1ncc(-c2ccc(C3(c4noc(-c5ccc(N6CCNCC6)nc5)n4)CCC3)cc2)cn1] | 5-(4-{1-[5-(6-Piperazin-1-yl-pyridin-3-yl)-1,2,4-oxadiazol-3-yl]-cyclobutyl}-phenyl)-pyrimidin-2-ylamine |
| 117 | 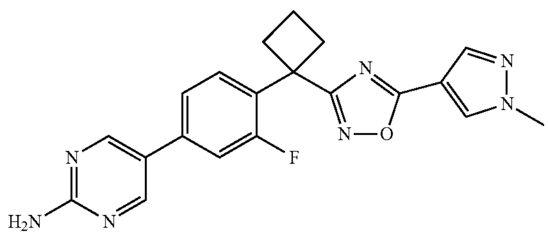 [SMILES: Cn1cc(-c2nc(C3(c4ccc(-c5cnc(N)nc5)cc4F)CCC3)no2)cn1] | 5-(3-Fluoro-4-{1-[5-(1-methyl-1H-pyrazol-4-yl)-1,2,4-oxadiazol-3-yl]-cyclobutyl}-phenyl)-pyrimidin-2-ylamine |
| 118 | 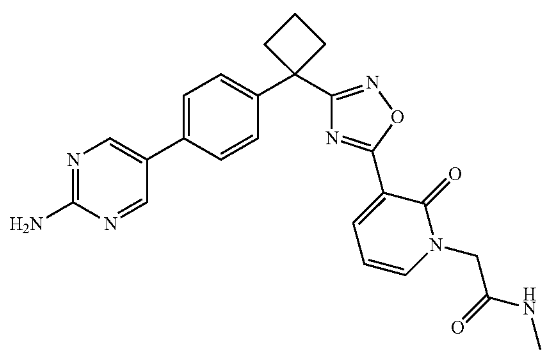 [SMILES: CNC(=O)Cn1cccc(-c2nc(C3(c4ccc(-c5cnc(N)nc5)cc4)CCC3)no2)c1=O] | 2-[3-(3-{1-[4-(2-Amino-pyrimidin-5-yl)-phenyl]-cyclobutyl}-1,2,4-oxadiazol-5-yl)-2-oxo-2H-pyridin-1-yl]-N-methyl-acetamide |
| 119 | 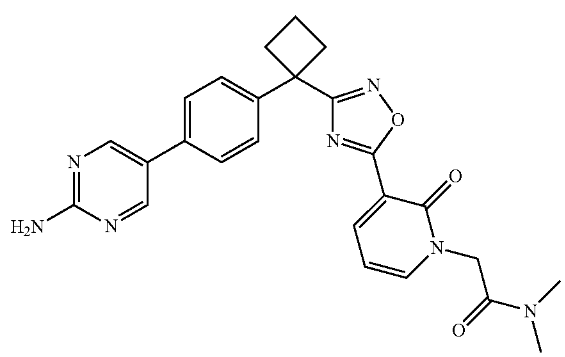 [SMILES: CN(C)C(=O)Cn1cccc(-c2nc(C3(c4ccc(-c5cnc(N)nc5)cc4)CCC3)no2)c1=O] | 2-[3-(3-{1-[4-(2-Amino-pyrimidin-5-yl)-phenyl]-cyclobutyl}-1,2,4-oxadiazol-5-yl)-2-oxo-2H-pyridin-1-yl]-N,N-dimethyl-acetamide |

TABLE I-continued

| Example | Structure | Name |
|---|---|---|
| 120 | 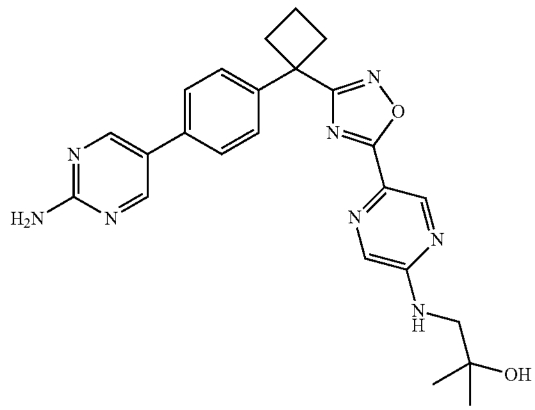 [SMILES: CC(C)(O)CNc1cnc(-c2nc(C3(c4ccc(-c5cnc(N)nc5)cc4)CCC3)no2)cn1] | 1-[5-(3-{1-[4-(2-Amino-pyrimidin-5-yl)-phenyl]-cyclobutyl}-1,2,4-oxadiazol-5-yl)-pyrazin-2-ylamino]-2-methyl-propan-2-ol |
| 121 | 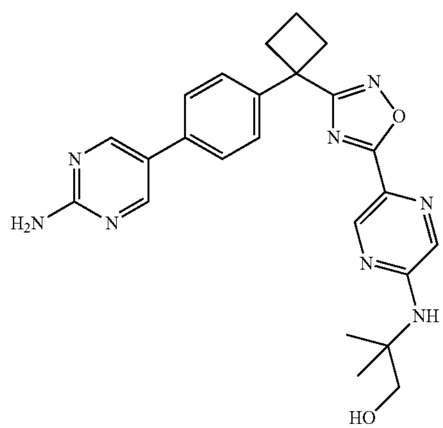 [SMILES: CC(C)(CO)Nc1cnc(-c2nc(C3(c4ccc(-c5cnc(N)nc5)cc4)CCC3)no2)cn1] | 2-[5-(3-{1-[4-(2-Amino-pyrimidin-5-yl)-phenyl]-cyclobutyl}-1,2,4-oxadiazol-5-yl)-pyrazin-2-ylamino]-2-methyl-propan-1-ol |
| 122 | 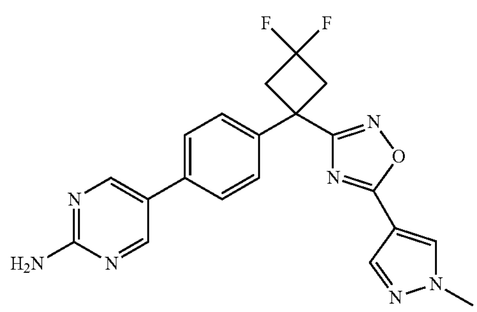 [SMILES: Cn1cc(-c2nc(C3(c4ccc(-c5cnc(N)nc5)cc4)CC(F)(F)C3)no2)cn1] | 5-(4-{3,3-Difluoro-1-[5-(1-methyl-1H-pyrazol-4-yl)-1,2,4-oxadiazol-3-yl]-cyclobutyl}-phenyl)-pyrimidin-2-ylamine |
| 123 | 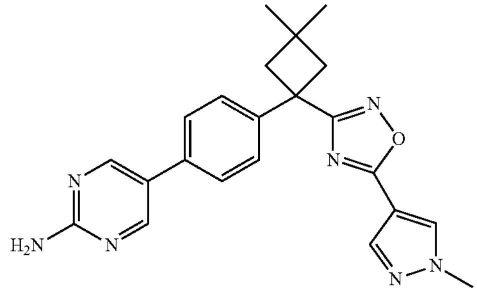 [SMILES: Cn1cc(-c2nc(C3(c4ccc(-c5cnc(N)nc5)cc4)CC(C)(C)C3)no2)cn1] | 5-(4-{3,3-Dimethyl-1-[5-(1-methyl-1H-pyrazol-4-yl)-1,2,4-oxadiazol-3-yl]-cyclobutyl}-phenyl)-pyrimidin-2-ylamine |

TABLE I-continued

| Example | Structure | Name |
|---|---|---|
| 124 | 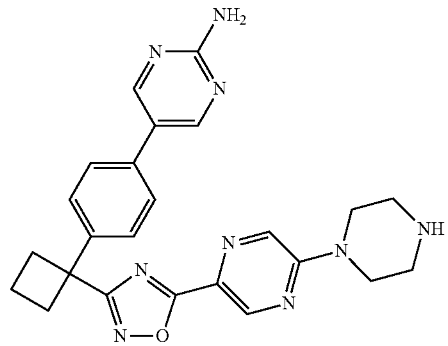 [SMILES: Nc1ncc(-c2ccc(C3(c4noc(-c5cnc(N6CCNCC6)cn5)n4)CCC3)cc2)cn1] | 5-(4-{1-[5-(3,4,5,6-Tetrahydro-1H-1,2'-bipyrazinyl-5'-yl)-1,2,4-oxadiazol-3-yl]-cyclobutyl}-phenyl)-pyrimidin-2-ylamine |
| 125 | Chiral | (R)-5'-(3-{1-[4-(2-Amino-pyrimidin-5-yl)-phenyl]-cyclobutyl}-1,2,4-oxadiazol-5-yl)-3,4,5,6-tetrahydro-2H-1,2'-bipyrazinyl-3-carboxylic acid methyl ester |
| 126 | Chiral | (S)-5'-(3-{1-[4-(2-Amino-pyrimidin-5-yl)-phenyl]-cyclobutyl}-1,2,4-oxadiazol-5-yl)-3,4,5,6-tetrahydro-2H-1,2'-bipyrazinyl-3-carboxylic acid methyl ester |
| 127 | 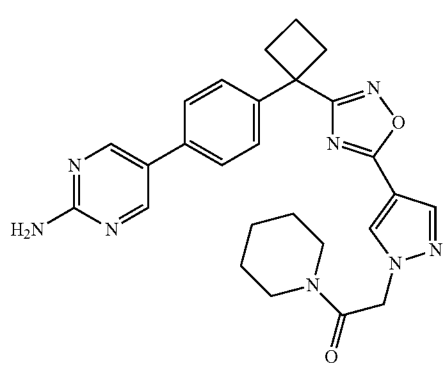 [SMILES: Nc1ncc(-c2ccc(C3(c4noc(-c5cnn(CC(=O)N6CCCCC6)c5)n4)CCC3)cc2)cn1] | 2-[4-(3-{1-[4-(2-Amino-pyrimidin-5-yl)-phenyl]-cyclobutyl}-1,2,4-oxadiazol-5-yl)-pyrazol-1-yl]-1-piperidin-1-yl-ethanone |

TABLE I-continued

| Example | Structure | Name |
|---|---|---|
| 128 | 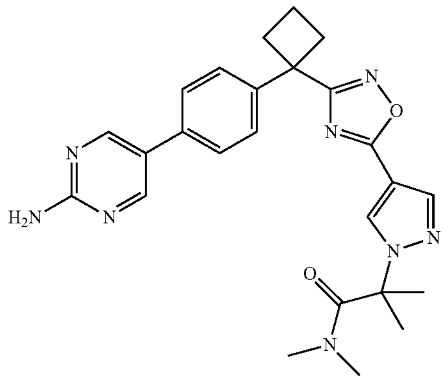 [SMILES: CN(C)C(=O)C(C)(C)n1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-1,2,4-oxadiazol-5-yl)-pyrazol-1-yl]-N,N-dimethyl-isobutyramide |
| 129 | 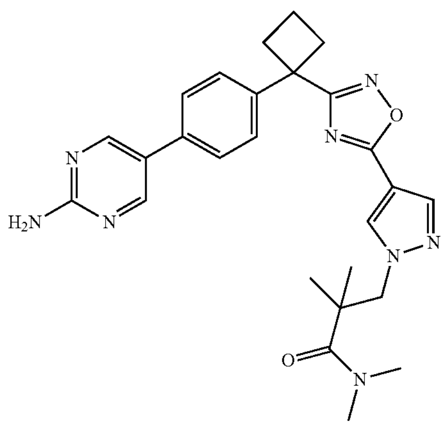 [SMILES: CN(C)C(=O)C(C)(C)Cn1cc(-c2nc(C3(c4ccc(-c5cnc(N)nc5)cc4)CCC3)no2)cn1] | 3-[4-(3-{1-[4-(2-Amino-pyrimidin-5-yl)-phenyl]-cyclobutyl}-1,2,4-oxadiazol-5-yl)-pyrazol-1-yl]-2,2,N,N-tetramethyl-propionamide |
| 130 | 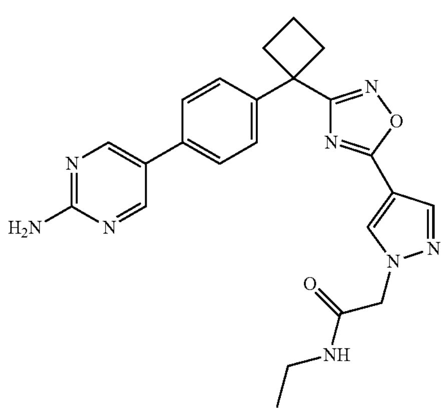 [SMILES: CCNC(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-1,2,4-oxadiazol-5-yl)-pyrazol-1-yl]-N-ethyl-acetamide |

TABLE I-continued

| Example | Structure | Name |
|---|---|---|
| 131 | 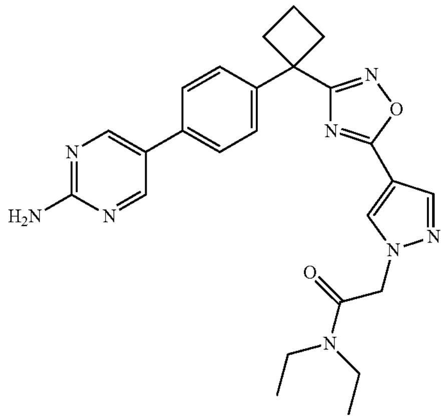 [SMILES: CCN(CC)C(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl]-1,2,4-oxadiazol-5-yl)-pyrazol-1-yl]-N,N-diethyl-acetamide |
| 132 | 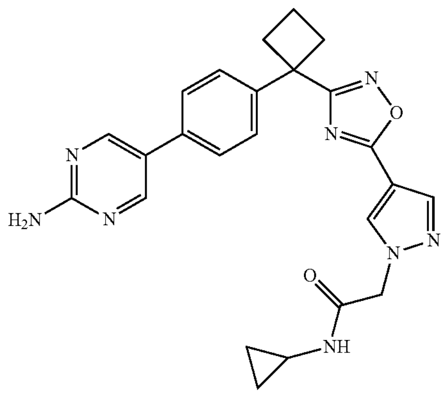 [SMILES: Nc1ncc(-c2ccc(C3(c4noc(-c5cnn(CC(=O)NC6CC6)c5)n4)CCC3)cc2)cn1] | 2-[4-(3-{1-[4-(2-Amino-pyrimidin-5-yl)-phenyl]-cyclobutyl}-1,2,4-oxadiazol-5-yl)-pyrazol-1-yl]-N-cyclopropyl-acetamide |
| 133 | 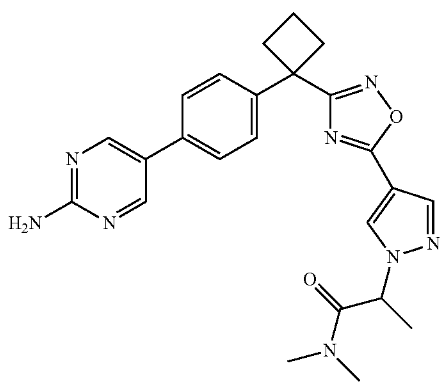 [SMILES: CC(C(=O)N(C)C)n1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-1,2,4-oxadiazol-5-yl)-pyrazol-1-yl]-N,N-dimethyl-propionamide |
| 134 | 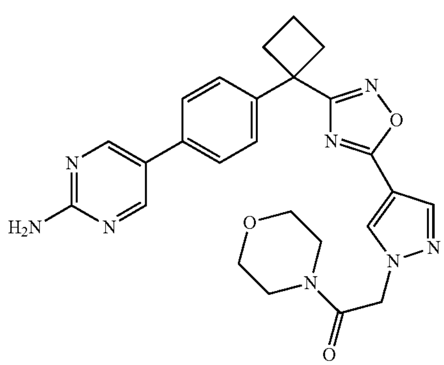 [SMILES: Nc1ncc(-c2ccc(C3(c4noc(-c5cnn(CC(=O)N6CCOCC6)c5)n4)CCC3)cc2)cn1] | 2-[4-(3-{1-[4-(2-Amino-pyrimidin-5-yl)-phenyl]-cyclobutyl}-1,2,4-oxadiazol-5-yl)-pyrazol-1-yl]-1-morpholin-4-yl-ethanone |

TABLE I-continued

| Example | Structure | Name |
|---|---|---|
| 135 | 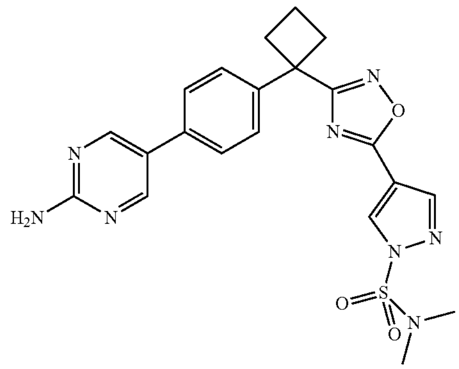 [SMILES: CN(C)S(=O)(=O)n1cc(-c2nc(C3(c4ccc(-c5cnc(N)nc5)cc4)CCC3)no2)cn1] | 4-(3-{1-[4-(2-Amino-pyrimidin-5-yl)-phenyl]-cyclobutyl}-1,2,4-oxadiazol-5-yl)-pyrazole-1-sulfonic acid dimethylamide |
| 136 | 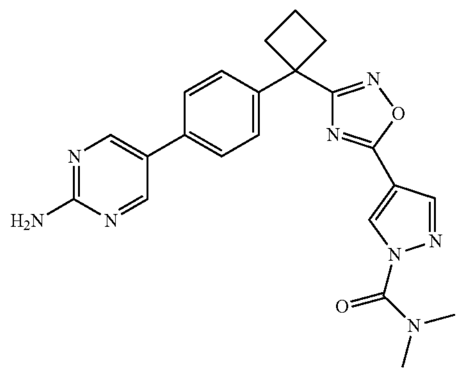 [SMILES: CN(C)C(=O)n1cc(-c2nc(C3(c4ccc(-c5cnc(N)nc5)cc4)CCC3)no2)cn1] | 4-(3-{1-[4-(2-Amino-pyrimidin-5-yl)-phenyl]-cyclobutyl}-1,2,4-oxadiazol-5-yl)-pyrazole-1-carboxylic acid dimethylamide |
| 137 | 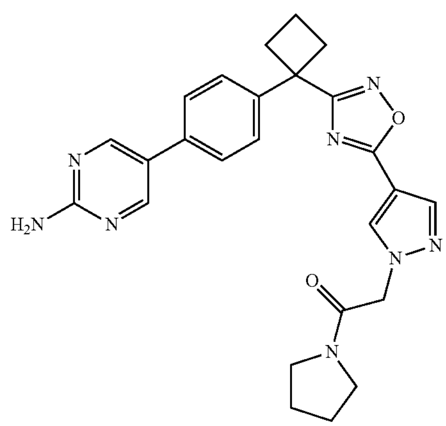 [SMILES: Nc1ncc(-c2ccc(C3(c4noc(-c5cnn(CC(=O)N6CCCC6)c5)n4)CCC3)cc2)cn1] | 2-[4-(3-{1-[4-(2-Amino-pyrimidin-5-yl)-phenyl]-cyclobutyl}-1,2,4-oxadiazol-5-yl)-pyrazol-1-yl]-1-pyrrolidin-1-yl-ethanone |
| 138 | 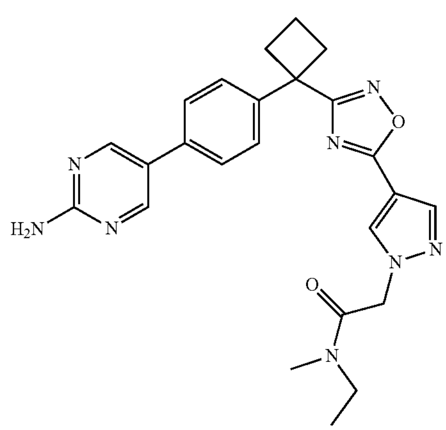 [SMILES: CCN(C)C(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-1,2,4-oxadiazol-5-yl)-pyrazol-1-yl]-N-ethyl-N-methyl-acetamide |

TABLE I-continued

| Example | Structure | Name |
|---|---|---|
| 139 | 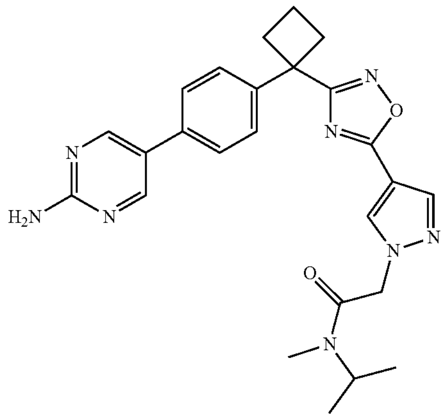 [SMILES: CC(C)N(C)C(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-1,2,4-oxadiazol-5-yl)-pyrazol-1-yl]-N-isopropyl-N-methyl-acetamide |
| 140 | 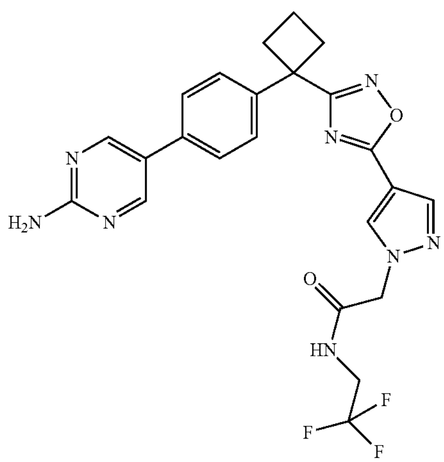 [SMILES: Nc1ncc(-c2ccc(C3(c4noc(-c5cnn(CC(=O)NCC(F)(F)F)c5)n4)CCC3)cc2)cn1] | 2-[4-(3-{1-[4-(2-Amino-pyrimidin-5-yl)-phenyl]-cyclobutyl}-1,2,4-oxadiazol-5-yl)-pyrazol-yl]-N-(2,2,2-trifluoro-ethyl)-acetamide |
| 141 | 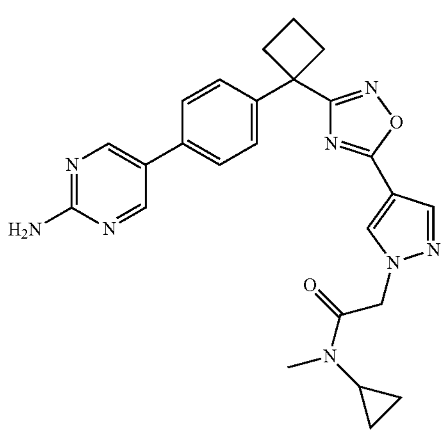 [SMILES: CN(C(=O)Cn1cc(-c2nc(C3(c4ccc(-c5cnc(N)nc5)cc4)CCC3)no2)cn1)C1CC1] | 2-[4-(3-{1-[4-(2-Amino-pyrimidin-5-yl)-phenyl]-cyclobutyl]-1,2,4-oxadiazol-5-yl)-pyrazol-1-yl]-N-cyclopropyl-N-methyl-acetamide |

TABLE I-continued

| Example | Structure | Name |
|---|---|---|
| 142 | 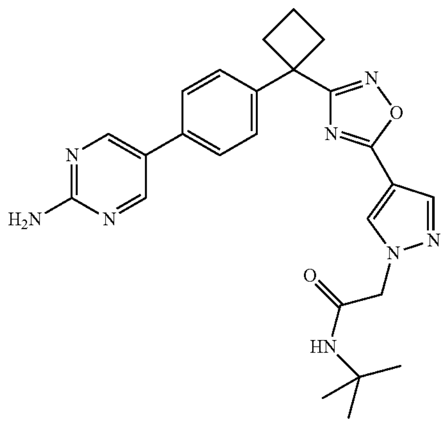 [SMILES: CC(C)(C)NC(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-1,2,4-oxadiazol-5-yl)-pyrazol-1-yl]-N-tert-butyl-acetamide |
| 143 | 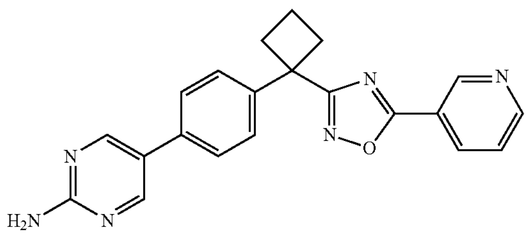 | 5-{4-[1-(5-Pyridin-3-yl-1,2,4-oxadiazol-3-yl)-cyclobutyl]-phenyl}-pyrimidin-2-ylamine |
| 144 | 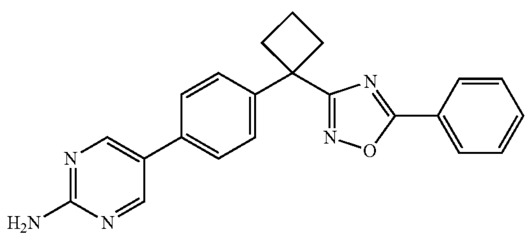 [SMILES: Nc1ncc(-c2ccc(C3(c4noc(-c5ccccc5)n4)CCC3)cc2)cn1] | 5-{4-[1-(5-Phenyl-1,2,4-oxadiazol-3-yl)-cyclobutyl]-phenyl}-pyrimidin-2-ylamine |
| 145 | 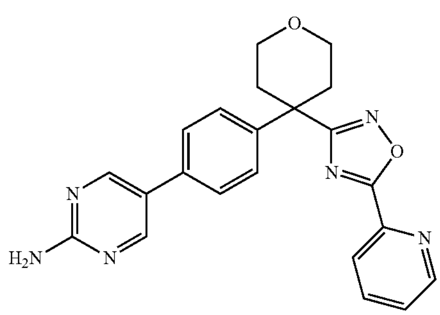 [SMILES: Nc1ncc(-c2ccc(C3(c4noc(-c5ccccn5)n4)CCOCC3)cc2)cn1] | 5-{4-[4-(5-Pyridin-2-yl-1,2,4-oxadiazol-3-yl)-tetrahydro-pyran-4-yl]-phenyl}-pyrimidin-2-ylamine |
| 146 | 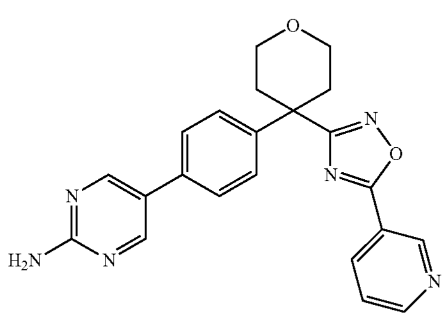 [SMILES: Nc1ncc(-c2ccc(C3(c4noc(-c5cccnc5)n4)CCOCC3)cc2)cn1] | 5-{4-[4-(5-Pyridin-3-yl-1,2,4-oxadiazol-3-yl)-tetrahydro-pyran-4-yl]-phenyl}-pyrimidin-2-ylamine |

TABLE I-continued

| Example | Structure | Name |
|---|---|---|
| 147 | 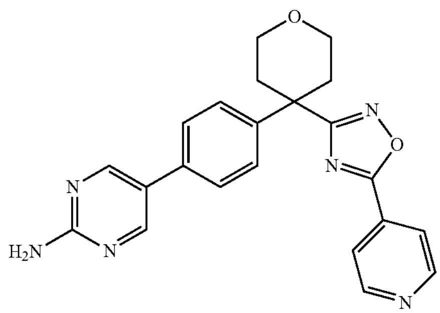 [SMILES: Nc1ncc(-c2ccc(C3(c4noc(-c5ccncc5)n4)CCOCC3)cc2)cn1] | 5-{4-[4-(5-Pyridin-4-yl-1,2,4-oxadiazol-3-yl)-tetrahydro-pyran-4-yl]-phenyl}-pyrimidin-2-ylamine |
| 148 | 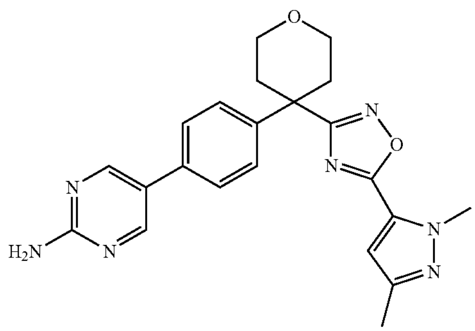 [SMILES: Cc1cc(-c2nc(C3(c4ccc(-c5cnc(N)nc5)cc4)CCOCC3)no2)n(C)n1] | 5-(4-{4-[5-(2,5-Dimethyl-2H-pyrazol-3-yl)-1,2,4-oxadiazol-3-yl]-tetrahydro-pyran-4-yl}-phenyl)-pyrimidin-2-ylamine |
| 149 | 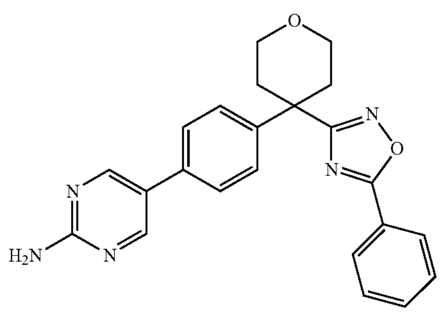 [SMILES: Nc1ncc(-c2ccc(C3(c4noc(-c5ccccc5)n4)CCOCC3)cc2)cn1] | 5-{4-[4-(5-Phenyl-1,2,4-oxadiazol-3-yl)-tetrahydro-pyran-yl]-phenyl}-pyrimidin-2-ylamine |
| 150 | 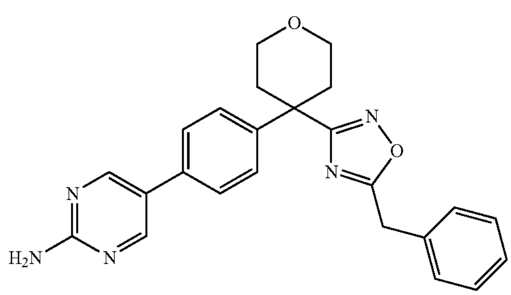 [SMILES: Nc1ncc(-c2ccc(C3(c4noc(Cc5ccccc5)n4)CCOCC3)cc2)cn1] | 5-{4-[4-(5-Benzyl-1,2,4-oxadiazol-3-yl)-tetrahydro-pyran-4-yl]-phenyl}-pyrimidin-2-ylamine |
| 151 | 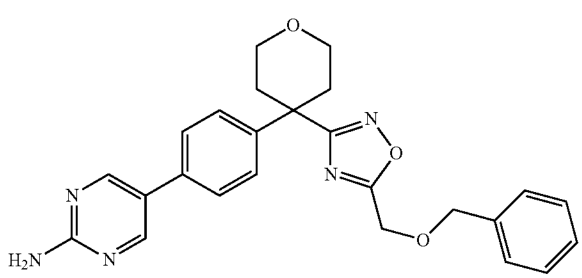 [SMILES: Nc1ncc(-c2ccc(C3(c4noc(COCc5ccccc5)n4)CCOCC3)cc2)cn1] | 5-{4-[4-(5-Benzyloxymethyl-1,2,4-oxadiazol-3-yl)-tetrahydro-pyran-4-yl]-phenyl}-pyrimidin-2-ylamine |

TABLE I-continued

| Example | Structure | Name |
|---|---|---|
| 152 | 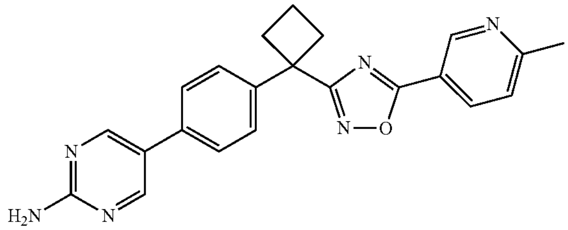 [SMILES: Cc1ccc(-c2nc(C3(c4ccc(-c5cnc(N)nc5)cc4)CCC3)no2)cn1] | 5-(4-{1-[5-(6-Methyl-pyridin-3-yl)-1,2,4-oxadiazol-3-yl]-cyclobutyl}-phenyl)-pyrimidin-2-ylamine |
| 153 | 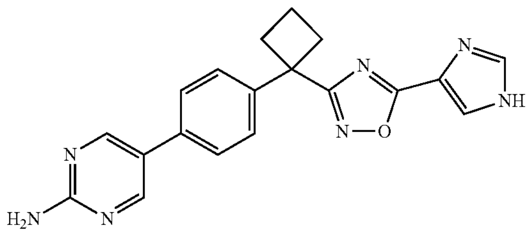 [SMILES: Nc1ncc(-c2ccc(C3(c4noc(-c5c[nH]cn5)n4)CCC3)cc2)cn1] | 5-(4-{1-[5-(1H-Imidazol-4-yl)-1,2,4-oxadiazol-3-yl]-cyclobutyl}-phenyl)-pyrimidin-2-ylamine |
| 154 | 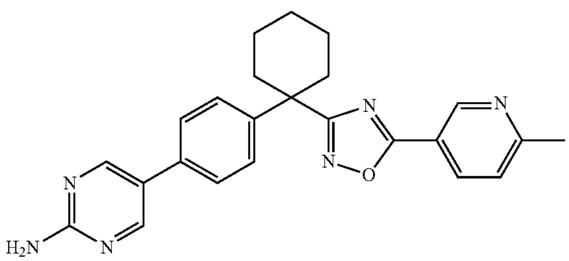 [SMILES: Cc1ccc(-c2nc(C3(c4ccc(-c5cnc(N)nc5)cc4)CCCCC3)no2)cn1] | 5-(4-{1-[5-(6-Methyl-pyridin-3-yl)-1,2,4-oxadiazol-3-yl]-cyclohexyl}-phenyl)-pyrimidin-2-ylamine |
| 155 | 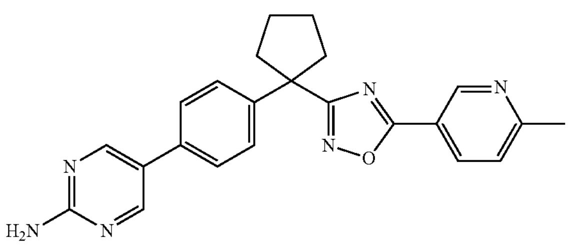 [SMILES: Cc1ccc(-c2nc(C3(c4ccc(-c5cnc(N)nc5)cc4)CCCC3)no2)cn1] | 5-(4-{1-[5-(6-Methyl-pyridin-3-yl)-1,2,4-oxadiazol-3-yl]-cyclopentyl}-phenyl)-pyrimidin-2-ylamine |
| 156 | 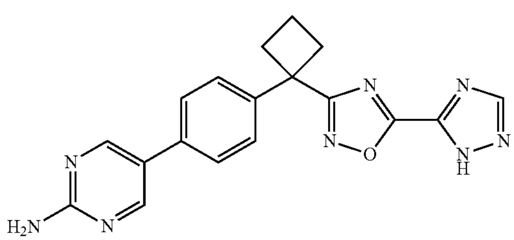 [SMILES: Nc1ncc(-c2ccc(C3(c4noc(-c5ncn[nH]5)n4)CCC3)cc2)cn1] | 5-(4-{1-[5-(2H-1,2,4-Triazol-3-yl)-1,2,4-oxadiazol-3-yl]-cyclobutyl}-phenyl)-pyrimidin-2-ylamine |
| 157 | 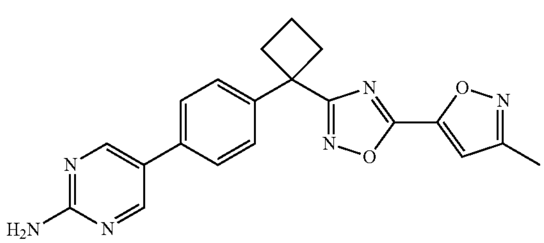 | 5-(4-{1-[5-(3-Methyl-isoxazol-5-yl)-1,2,4-]oxadiazol-3-yl]-cyclobutyl}-phenyl)-pyrimidin-2-ylamine |

TABLE I-continued

| Example | Structure | Name |
|---|---|---|
| 158 | 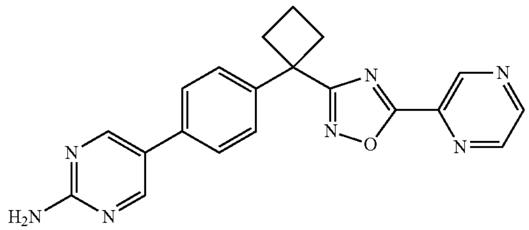 | 5-{4-[1-(5-Pyrazin-2-yl-1,2,4-oxadiazol-3-yl)-cyclobutyl]-phenyl}-pyrimidin-2-ylamine |
| 159 | 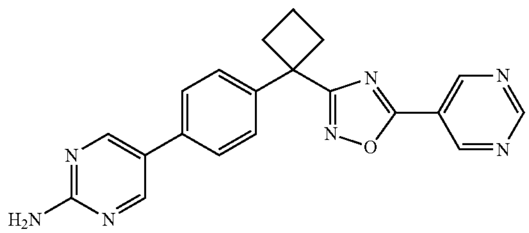 [SMILES: Nc1ncc(-c2ccc(C3(c4noc(-c5cncnc5)n4)CCC3)cc2)cn1] | 5-{4-[1-(5-Pyrimidin-5-yl-1,2,4-oxadiazol-3-yl)-cyclobutyl]-phenyl}-pyrimidin-2-ylamine |
| 160 | 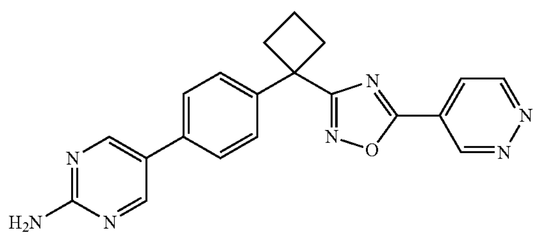 [SMILES: Nc1ncc(-c2ccc(C3(c4noc(-c5ccnnc5)n4)CCC3)cc2)cn1] | 5-{4-[1-(5-Pyridazin-4-yl-1,2,4-oxadiazol-3-yl)-cyclobutyl]-phenyl}-pyrimidin-2-ylamine |
| 161 | 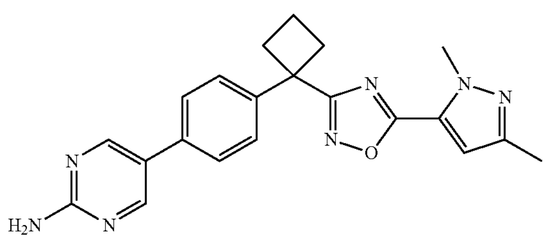 [SMILES: Cc1cc(-c2nc(C3(c4ccc(-c5cnc(N)nc5)cc4)CCC3)no2)n(C)n1] | 5-(4-{1-[5-(2,5-Dimethyl-2H-pyrazol-3-yl)-1,2,4-oxadiazol-3-yl]-cyclobutyl}-phenyl)-pyrimidin-2-ylamine |
| 162 | 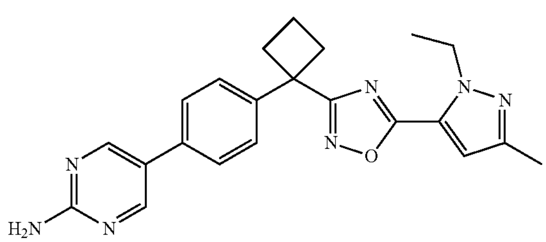 [SMILES: CCn1nc(C)cc1-c1nc(C2(c3ccc(-c4cnc(N)nc4)cc3)CCC2)no1] | 5-(4-{1-[5-(2-Ethyl-5-methyl-2H-pyrazol-3-yl)-1,2,4-oxadiazol-3-yl]-cyclobutyl}-phenyl)-pyrimidin-2-ylamine |
| 163 | 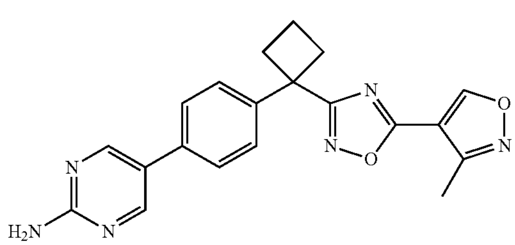 [SMILES: Cc1nocc1-c1nc(C2(c3ccc(-c4cnc(N)nc4)cc3)CCC2)no1] | 5-(4-{1-[5-(3-Methyl-isoxazol-4-yl)-1,2,4-oxadiazol-3-yl]-cyclobutyl}-phenyl)-pyrimidin-2-ylamine |

TABLE I-continued

| Example | Structure | Name |
|---|---|---|
| 164 | 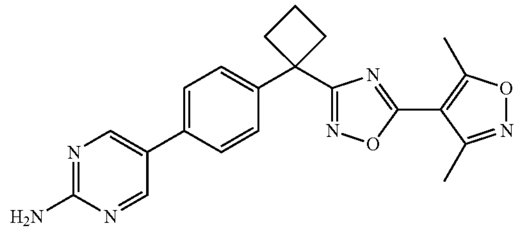 | 5-(4-{1-[5-(3,5-Dimethyl-isoxazol-4-yl)-1,2,4-oxadiazol-3-yl]-cyclobutyl}-phenyl)-pyrimidin-2-ylamine |
| 165 | 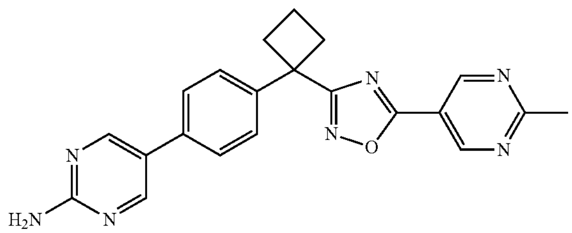 [SMILES: Cc1ncc(-c2nc(C3(c4ccc(-c5cnc(N)nc5)cc4)CCC3)no2)cn1] | 5-(4-{1-[5-(2-Methyl-pyrimidin-5-yl)-1,2,4-oxadiazol-3-yl]-cyclobutyl}-phenyl)-pyrimidin-2-ylamine |
| 166 | 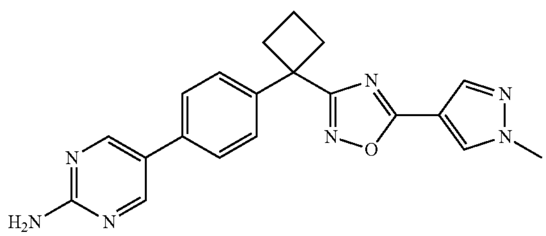 [SMILES: Cn1cc(-c2nc(C3(c4ccc(-c5cnc(N)nc5)cc4)CCC3)no2)cn1] | 5-(4-{1-[5-(1-Methyl-1H-pyrazol-4-yl)-1,2,4-oxadiazol-3-yl]-cyclobutyl}-phenyl)-pyrimidin-2-ylamine |
| 167 | 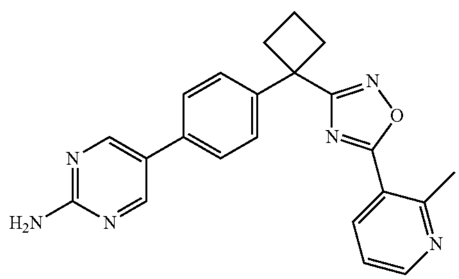 [SMILES: Cc1ncccc1-c1nc(C2(c3ccc(-c4cnc(N)nc4)cc3)CCC2)no1] | 5-(4-{1-[5-(2-Methyl-pyridin-3-yl)-1,2,4-oxadiazol-3-yl]-cyclobutyl}-phenyl)-pyrimidin-2-ylamine |
| 168 | 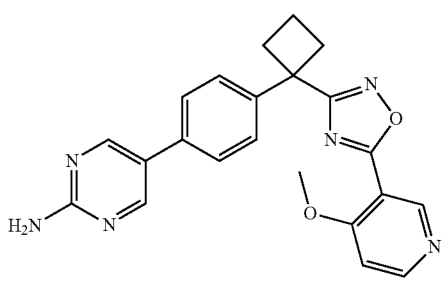 [SMILES: COc1ccncc1-c1nc(C2(c3ccc(-c4cnc(N)nc4)cc3)CCC2)no1] | 5-(4-{1-[5-(4-Methoxy-pyridin-3-yl)-1,2,4-oxadiazol-3-yl]-cyclobutyl}-phenyl)-pyrimidin-2-ylamine |
| 169 | 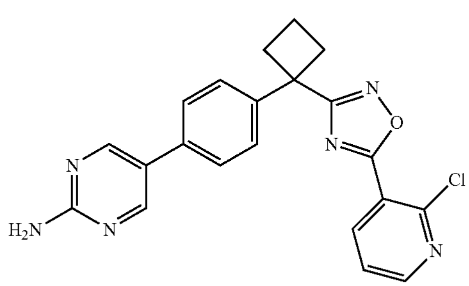 [SMILES: Nc1ncc(-c2ccc(C3(c4noc(-c5cccnc5Cl)n4)CCC3)cc2)cn1] | 5-(4-{1-[5-(2-Chloro-pyridin-3-yl)-1,2,4-oxadiazol-3-yl]-cyclobutyl}-phenyl)-pyrimidin-2-ylamine |

TABLE I-continued

| Example | Structure | Name |
|---|---|---|
| 170 | 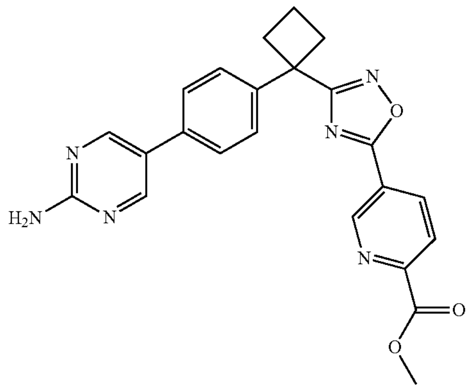 [SMILES: COC(=O)c1ccc(-c2nc(C3(c4ccc(-c5cnc(N)nc5)cc4)CCC3)no2)cn1] | 5-(3-{1-[4-(2-Amino-pyrimidin-5-yl)-phenyl]-cyclobutyl}-1,2,4-oxadiazol-5-yl)-pyridine-2-carboxylic acid methyl ester |
| 171 | 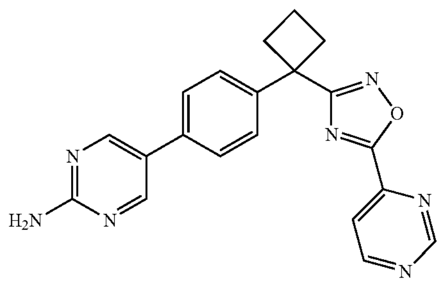 [SMILES: Nc1ncc(-c2ccc(C3(c4noc(-c5ccncn5)n4)CCC3)cc2)cn1] | 5-{4-[1-(5-Pyrimidin-4-yl-1,2,4-oxadiazol-3-yl)-cyclobutyl]-phenyl}-pyrimidin-2-ylamine |
| 172 | 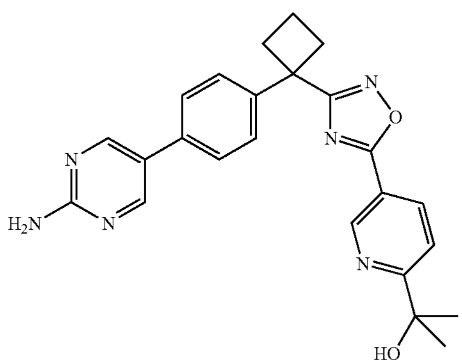 [SMILES: CC(C)(O)c1ccc(-c2nc(C3(c4ccc(-c5cnc(N)nc5)cc4)CCC3)no2)cn1] | 2-[5-(3-{1-[4-(2-Amino-pyrimidin-5-yl)-phenyl]-cyclobutyl}-1,2,4-oxadiazol-5-yl)-pyridin-2-yl]-propan-2-ol |
| 173 | 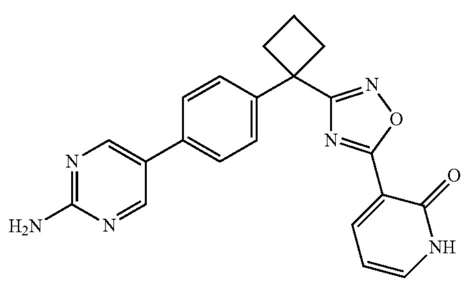 [SMILES: Nc1ncc(-c2ccc(C3(c4noc(-c5ccc[nH]c5=O)n4)CCC3)cc2)cn1] | 3-(3-{1-[4-(2-Amino-pyrimidin-5-yl)-phenyl]-cyclobutyl}-1,2,4-oxadiazol-5-yl)-1H-pyridin-2-one |
| 174 | 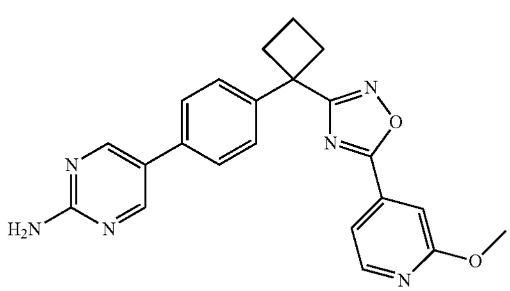 [SMILES: COc1cc(-c2nc(C3(c4ccc(-c5cnc(N)nc5)cc4)CCC3)no2)ccn1] | 5-(4-{1-[5-(2-Methoxy-pyridin-4-yl)-1,2,4-oxadiazol-3-yl]-cyclobutyl}-phenyl)-pyrimidin-2-ylamine |

TABLE I-continued

| Example | Structure | Name |
|---|---|---|
| 175 | 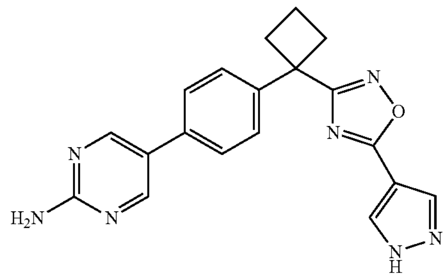 [SMILES: Nc1ncc(-c2ccc(C3(c4noc(-c5cn[nH]c5)n4)CCC3)cc2)cn1] | 5-(4-{1-[5-(1H-Pyrazol-4-yl)-1,2,4-oxadiazol-3-yl]-cyclobutyl}-phenyl)-pyrimidin-2-ylamine |
| 176 | 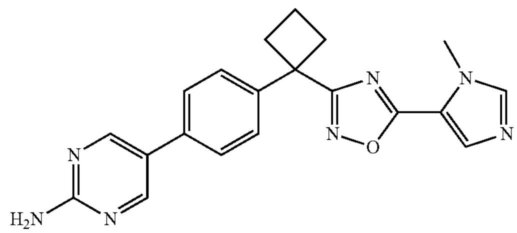 [SMILES: Cn1cncc1-c1nc(C2(c3ccc(-c4cnc(N)nc4)cc3)CCC2)no1] | 5-(4-{1-[5-(3-Methyl-3H-imidazol-4-yl)-1,2,4-oxadiazol-3-yl]-cyclobutyl}-phenyl)-pyrimidin-2-ylamine |
| 177 | 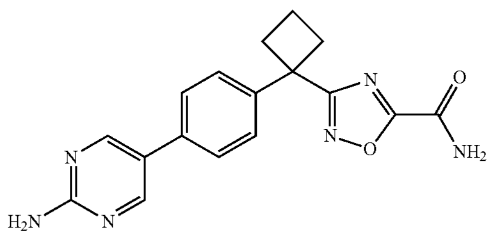 [SMILES: NC(=O)c1nc(C2(c3ccc(-c4cnc(N)nc4)cc3)CCC2)no1] | 3-{1-[4-(2-Amino-pyrimidin-5-yl)-phenyl]-cyclobutyl}-1,2,4-oxadiazole-5-carboxylic acid amide |
| 178 | 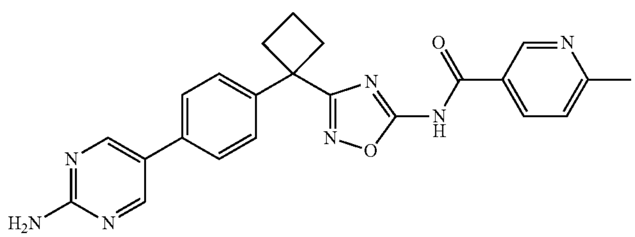 [SMILES: Cc1ccc(C(=O)Nc2nc(C3(c4ccc(-c5cnc(N)nc5)cc4)CCC3)no2)cn1] | N-(3-{1-[4-(2-Amino-pyrimidin-5-yl)-phenyl]-cyclobutyl}-1,2,4-oxadiazol-5-yl)-6-methyl-nicotinamide |
| 179 | 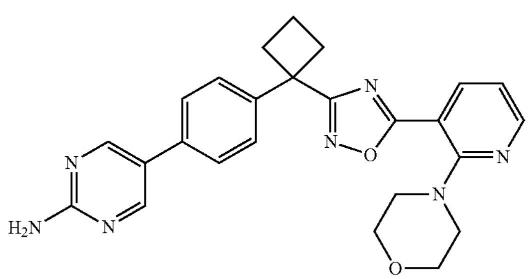 [SMILES: Nc1ncc(-c2ccc(C3(c4noc(-c5cccnc5N5CCOCC5)n4)CCC3)cc2)cn1] | 5-(4-{1-[5-(2-Morpholin-4-yl-pyridin-3-yl)-1,2,4-oxadiazol-3-yl]-cyclobutyl}-phenyl)-pyrimidin-2-ylamine |
| 180 | 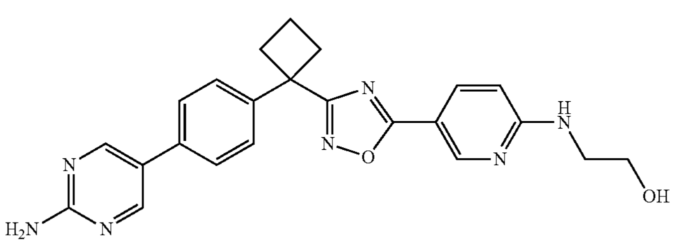 [SMILES: Nc1ncc(-c2ccc(C3(c4noc(-c5ccc(NCCO)nc5)n4)CCC3)cc2)cn1] | 2-[5-(3-{1-[4-(2-Amino-pyrimidin-5-yl)-phenyl]-cyclobutyl}-1,2,4-oxadiazol-5-yl)-pyridin-2-ylamino]-ethanol |

TABLE I-continued

| Example | Structure | Name |
|---|---|---|
| 181 | 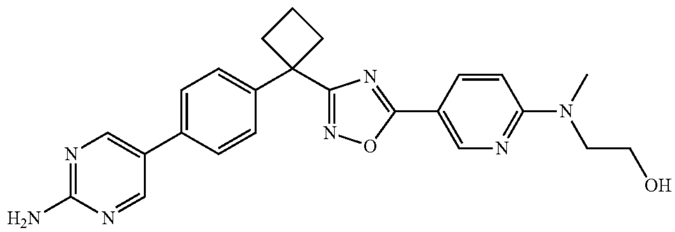 [SMILES: CN(CCO)c1ccc(-c2nc(C3(c4ccc(-c5cnc(N)nc5)cc4)CCC3)no2)cn1] | 2-{[5-(3-{1-[4-(2-Amino-pyrimidin-5-yl)-phenyl]-cyclobutyl}-1,2,4-oxadiazol-5-yl)-pyridin-2-yl]-methyl-amino}-ethanol |
| 182 | 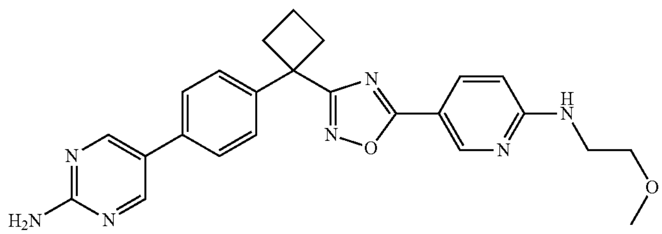 | 5-[4-(1-{5-[6-(2-Methoxy-ethylamino)-pyridin-3-yl]-1,2,4-oxadiazol-3-yl}-cyclobutyl)-phenyl]-pyrimidin-2-ylamine |
| 183 | 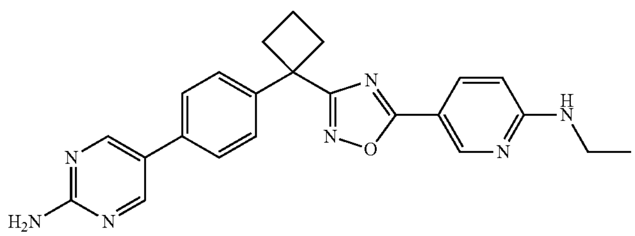 [SMILES: CCNc1ccc(-c2nc(C3(c4ccc(-c5cnc(N)nc5)cc4)CCC3)no2)cn1] | 5-(4-{1-[5-(6-Ethylamino-pyridin-3-yl)-1,2,4-oxadiazol-3-yl]-cyclobutyl}-phenyl)-pyrimidin-2-ylamine |
| 184 | 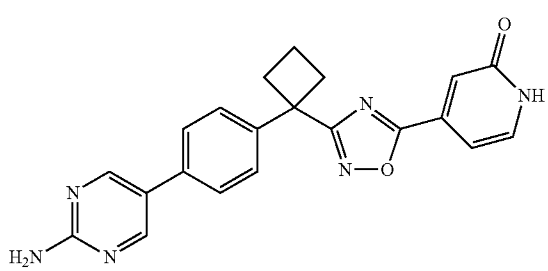 [SMILES: Nc1ncc(-c2ccc(C3(c4noc(-c5cc[nH]c(=O)c5)n4)CCC3)cc2)cn1] | 4-(3-{1-[4-(2-Amino-pyrimidin-5-yl)-phenyl]-cyclobutyl}-1,2,4-oxadiazol-5-yl)-1H-pyridin-2-one |
| 185 | 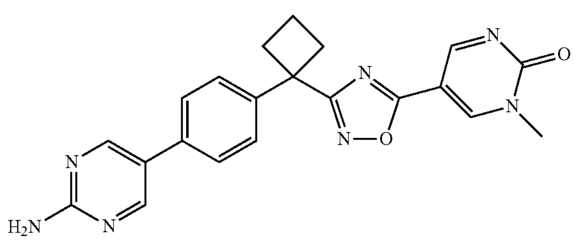 [SMILES: Cn1cc(-c2nc(C3(c4ccc(-c5cnc(N)nc5)cc4)CCC3)no2)cnc1=O] | 5-(3-{1-[4-(2-Amino-pyrimidin-5-yl)-phenyl]-cyclobutyl}-1,2,4-oxadiazol-5-yl)-1-methyl-1H-pyrimidin-2-one |
| 186 | 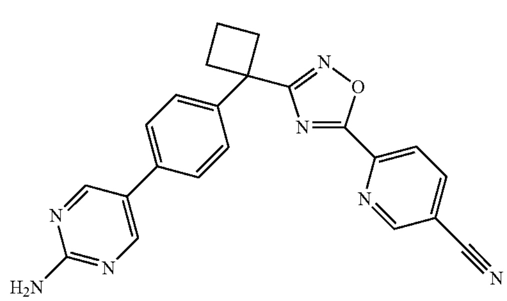 [SMILES: N#Cc1ccc(-c2nc(C3(c4ccc(-c5cnc(N)nc5)cc4)CCC3)no2)nc1] | 6-(3-{1-[4-(2-Amino-pyrimidin-5-yl)-phenyl]-cyclobutyl}-1,2,4-oxadiazol-5-yl)-nicotinonitrile |

TABLE I-continued

| Example | Structure | Name |
|---|---|---|
| 187 | 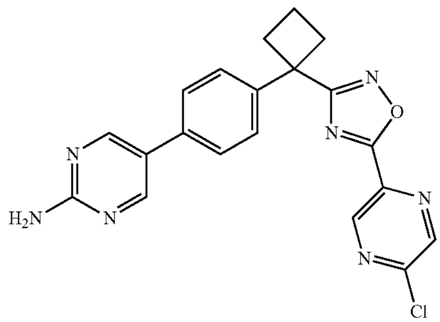 [SMILES: Nc1ncc(-c2ccc(C3(c4noc(-c5cnc(Cl)cn5)n4)CCC3)cc2)cn1] | 5-(4-{1-[5-(5-Chloro-pyrazin-2-yl)-1,2,4-oxadiazol-3-yl]-cyclobutyl}-phenyl)-pyrimidin-2-ylamine |
| 188 | 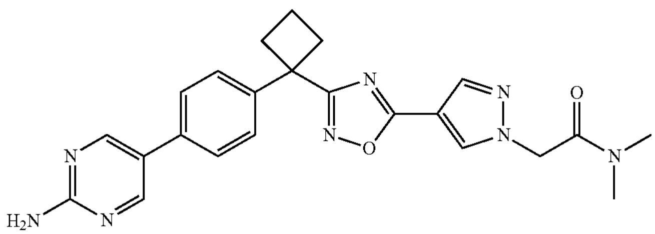 | 2-[4-(3-{1-[4-(2-Amino-pyrimidin-5-yl)-phenyl]-cyclobutyl}-1,2,4-oxadiazol-5-yl)-pyrazol-1-yl]-N,N-dimethyl-acetamide |
| 189 | 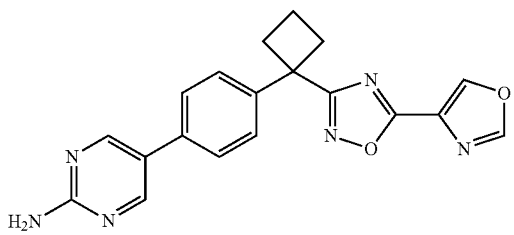 | 5-{4-[1-(5-Oxazol-4-yl-1,2,4-oxadiazol-3-yl)-cyclobutyl]-phenyl}-pyrimidin-2-ylamine |
| 190 | 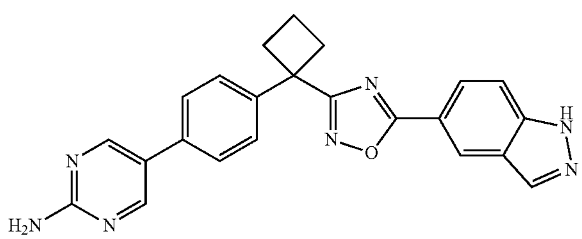 [SMILES: Nc1ncc(-c2ccc(C3(c4noc(-c5ccc6[nH]ncc6c5)n4)CCC3)cc2)cn1] | 5-(4-{1-[5-(1H-Indazol-5-yl)-1,2,4-oxadiazol-3-yl]-cyclobutyl}-phenyl)-pyrimidin-2-ylamine |
| 191 | 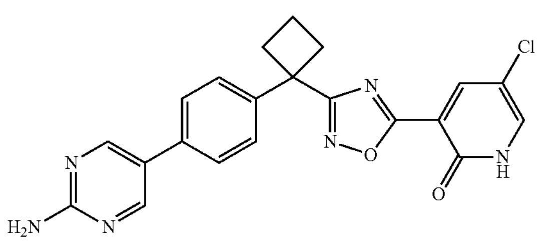 [SMILES: Nc1ncc(-c2ccc(C3(c4noc(-c5cc(Cl)c[nH]c5=O)n4)CCC3)cc2)cn1] | 3-(3-{1-[4-(2-Amino-pyrimidin-5-yl)-phenyl]-cyclobutyl}-1,2,4-oxadiazol-5-yl)-5-chloro-1H-pyridin-2-one |
| 192 | 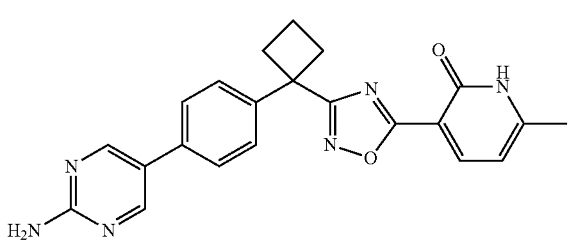 [SMILES: Cc1ccc(-c2nc(C3(c4ccc(-c5cnc(N)nc5)cc4)CCC3)no2)c(=O)[nH]1] | 3-(3-{1-[4-(2-Amino-pyrimidin-5-yl)-phenyl]-cyclobutyl}-1,2,4-oxadiazol-5-yl)-6-methyl-1H-pyridin-2-one |

TABLE I-continued

| Example | Structure | Name |
|---|---|---|
| 193 | 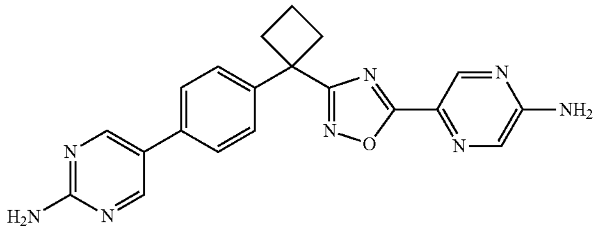 | 5-(4-{1-[5-(5-Amino-pyrazin-2-yl)-1,2,4-oxadiazol-3-yl]-cyclobutyl}-phenyl)-pyrimidin-2-ylamine |
| 194 | 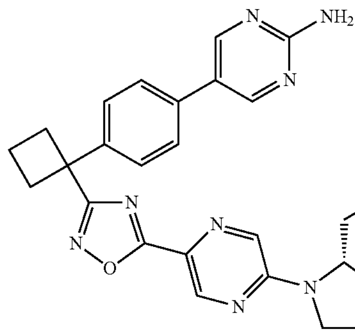 | {(S)-1-[5-(3-{1-[4-(2-Amino-pyrimidin-5-yl)-phenyl]-cyclobutyl}-1,2,4-oxadiazol-5-yl)-pyrazin-2-yl]-pyrrolidin-2-yl}-methanol |
| 195 | 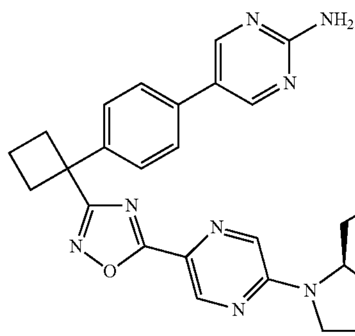 | {(R)-1-[5-(3-{1-[4-(2-Amino-pyrimidin-5-yl)-phenyl]-cyclobutyl}-1,2,4-oxadiazol-5-yl)-pyrazin-2-yl]-pyrrolidin-2-yl}-methanol |
| 196 | 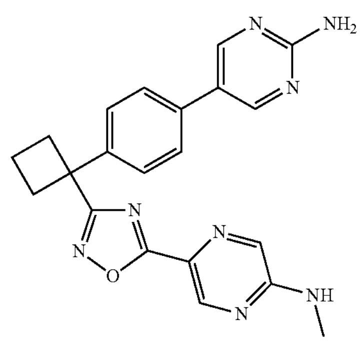 [SMILES: CNc1cnc(-c2nc(C3(c4ccc(-c5cnc(N)nc5)cc4)CCC3)no2)cn1] | 5-(4-{1-[5-(5-Methylamino-pyrazin-2-yl)-1,2,4-oxadiazol-3-yl]-cyclobutyl}-phenyl)-pyrimidin-2-ylamine |
| 197 | 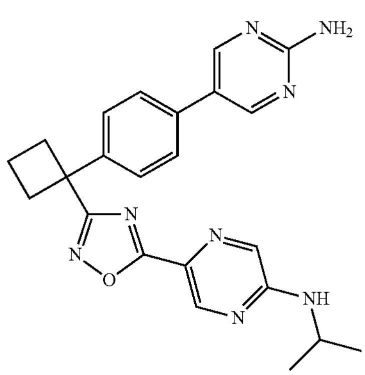 [SMILES: CC(C)Nc1cnc(-c2nc(C3(c4ccc(-c5cnc(N)nc5)cc4)CCC3)no2)cn1] | 5-(4-{1-[5-(5-Isopropylamino-pyrazin-2-yl)-1,2,4-oxadiazol-3-yl]-cyclobutyl}-phenyl)-pyrimidin-2-ylamine |

TABLE I-continued

| Example | Structure | Name |
|---|---|---|
| 198 | 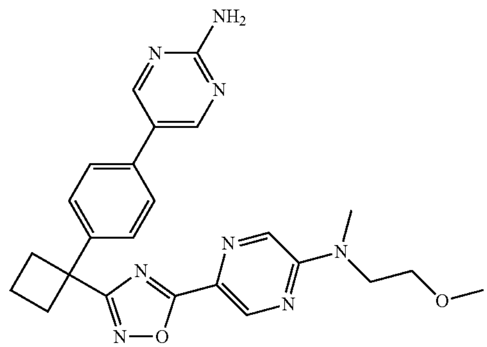 [SMILES: COCCN(C)c1cnc(-c2nc(C3(c4ccc(-c5cnc(N)nc5)cc4)CCC3)no2)cn1] | 5-{4-[1-(5-{5-[(2-Methoxy-ethyl)-methyl-amino]-pyrazin-2-yl}-1,2,4-oxadiazol-3-yl)-cyclobutyl]-phenyl}-pyrimidin-2-ylamine |
| 199 | 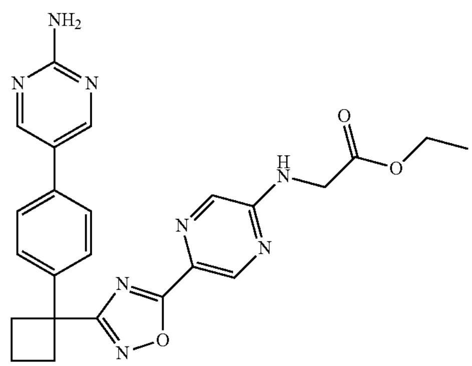 [SMILES: CCOC(=O)CNc1cnc(-c2nc(C3(c4ccc(-c5cnc(N)nc5)cc4)CCC3)no2)cn1] | [5-(3-{1-[4-(2-Amino-pyrimidin-5-yl)-phenyl]-cyclobutyl}-1,2,4-oxadiazol-5-yl)-pyrazin-2-ylamino]-acetic acid ethyl ester |
| 200 | 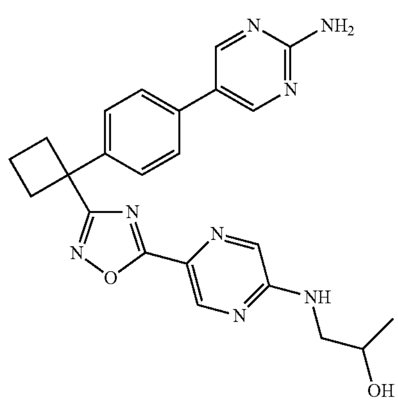 [SMILES: CC(O)CNc1cnc(-c2nc(C3(c4ccc(-c5cnc(N)nc5)cc4)CCC3)no2)cn1] | 1-[5-(3-{1-[4-(2-Amino-pyrimidin-5-yl)-phenyl]-cyclobutyl}-1,2,4-oxadiazol-5-yl)-pyrazin-2-ylamino]-propan-2-ol |
| 201 | 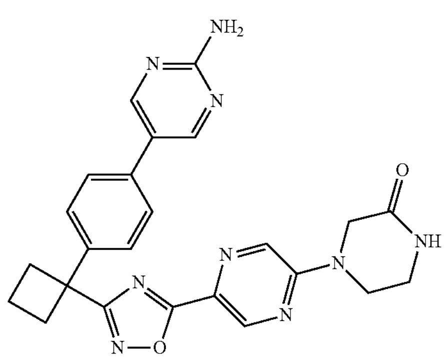 [SMILES: Nc1ncc(-c2ccc(C3(c4noc(-c5cnc(N6CCNC(=O)C6)cn5)n4)CCC3)cc2)cn1] | 5'-(3-{1-[4-(2-Amino-pyrimidin-5-yl)-phenyl]-cyclobutyl}-1,2,4-oxadiazol-5-yl)-5,6-dihydro-4H-1,2'-bipyrazinyl-3-one |

TABLE I-continued

| Example | Structure | Name |
|---|---|---|
| 202 | 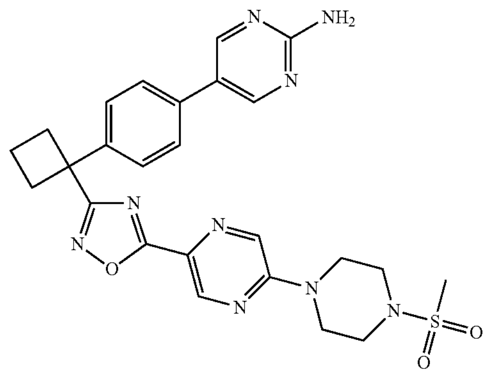 [SMILES: CS(=O)(=O)N1CCN(c2cnc(-c3nc(C4(c5ccc(-c6cnc(N)nc6)cc5)CCC4)no3)cn2)CC1] | 5-(4-{1-[5-(4-Methanesulfonyl-3,4,5,6-tetrahydro-2H-1,2'-bipyrazinyl-5'-yl)-1,2,4-oxadiazol-3-yl]-cyclobutyl}-phenyl)-pyrimidin-2-ylamine |
| 203 | 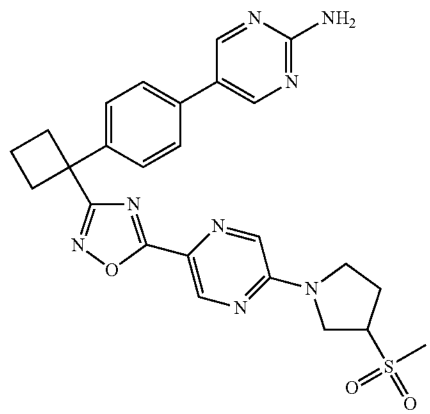 [SMILES: CS(=O)(=O)C1CCN(c2cnc(-c3nc(C4(c5ccc(-c6cnc(N)nc6)cc5)CCC4)no3)cn2)C1] | 5-[4-(1-{5-[5-(3-Methanesulfonyl-pyrrolidin-1-yl)-pyrazin-2-yl]-1,2,4-oxadiazol-3-yl}-cyclobutyl)-phenyl]-pyrimidin-2-ylamine |
| 204 | 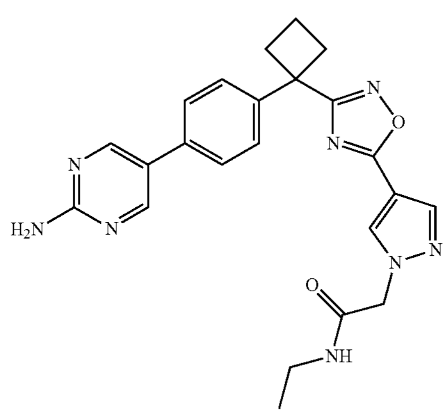 [SMILES: CCNC(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-[1,2,4]oxadiazol-5-yl)-pyrazol-1-yl]-N-ethyl-acetamide |
| 205 | 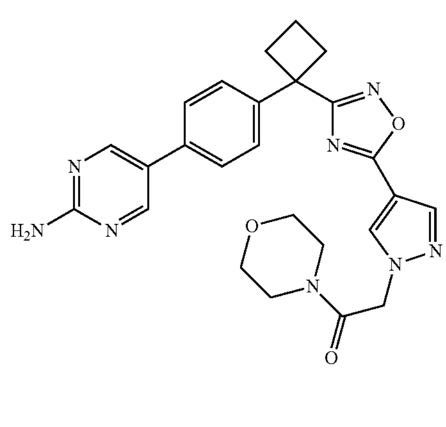 [SMILES: Nc1ncc(-c2ccc(C3(c4noc(-c5cnn(CC(=O)N6CCOCC6)c5)n4)CCC3)cc2)cn1] | 2-[4-(3-{1-[4-(2-Amino-pyrimidin-5-yl)-phenyl]-cyclobutyl}-[1,2,4]oxadiazol-5-yl)-pyrazol-1-yl]-1-morpholin-4-yl-ethanone |

TABLE I-continued

| Example | Structure | Name |
|---|---|---|
| 206 | 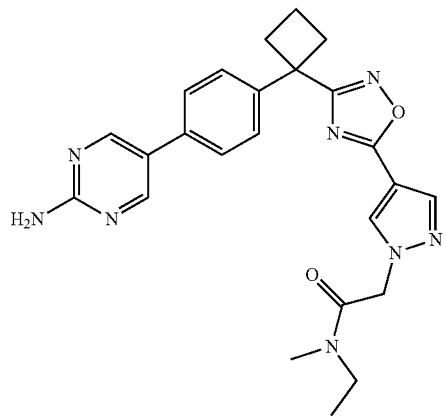 [SMILES: CCN(C)C(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-[1,2,4]oxadiazol-5-yl)-pyrazol-1-yl]-N-ethyl-N-methyl-acetamide |
| 207 | 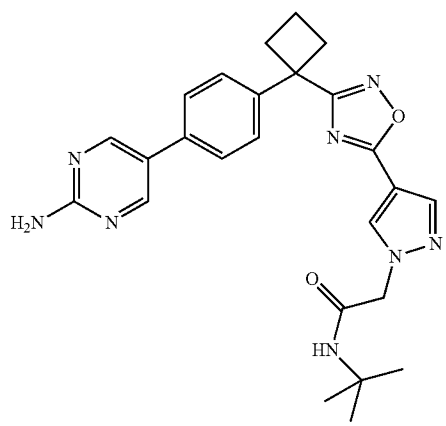 [SMILES: CC(C)(C)NC(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-[1,2,4]oxadiazol-5-yl)-pyrazol-1-yl]-N-tert-butyl-acetamide |
| 208 | 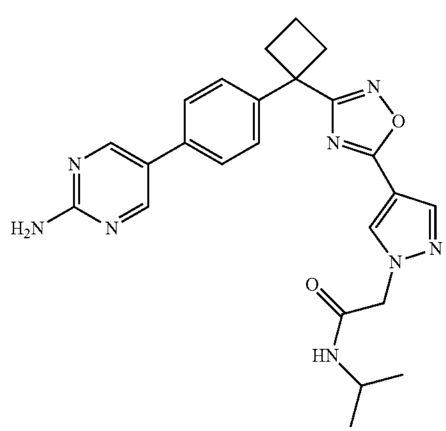 [SMILES: CC(C)NC(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-[1,2,4]oxadiazol-5-yl)-pyrazol-1-yl]-N-isopropyl-acetamide |

TABLE I-continued

| Example | Structure | Name |
|---|---|---|
| 209 | 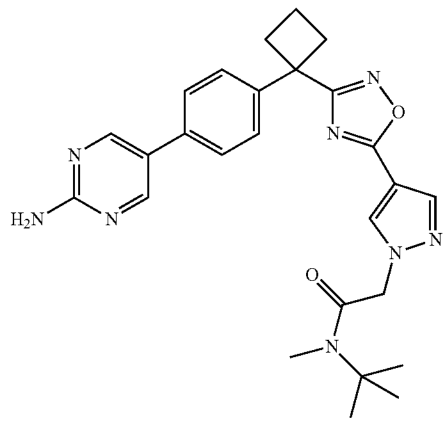 [SMILES: CN(C(=O)Cn1cc(-c2nc(C3(c4ccc(-c5cnc(N)nc5)cc4)CCC3)no2)cn1)C(C)(C)C] | 2-[4-(3-{1-[4-(2-Amino-pyrimidin-5-yl)-phenyl]-cyclobutyl}-[1,2,4]oxadiazol-5-yl)-pyrazol-1-yl]-N-tert-butyl-N-methyl-acetamide |
| 210 | 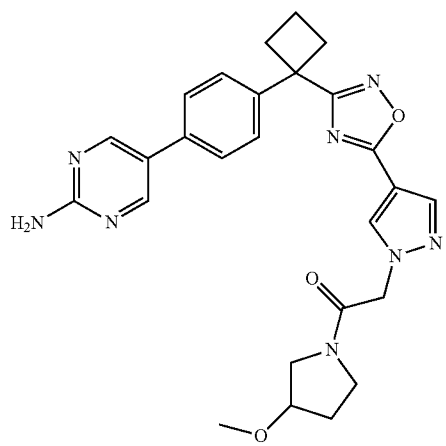 [SMILES: COC1CCN(C(=O)Cn2cc(-c3nc(C4(c5ccc(-c6cnc(N)nc6)cc5)CCC4)no3)cn2)C1] | 2-[4-(3-{1-[4-(2-Amino-pyrimidin-5-yl)-phenyl]-cyclobutyl}-[1,2,4]oxadiazol-5-yl)-pyrazol-1-yl]-1-(3-methoxy-pyrrolidin-1-yl)-ethanone |
| 211 | 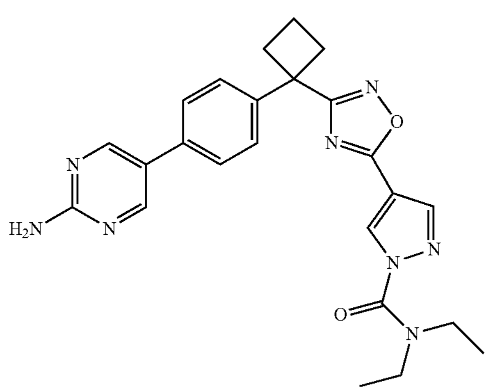 [SMILES: CCN(CC)C(=O)n1cc(-c2nc(C3(c4ccc(-c5cnc(N)nc5)cc4)CCC3)no2)cn1] | 4-(3-{1-[4-(2-Amino-pyrimidin-5-yl)-phenyl]-cyclobutyl}-[1,2,4]oxadiazol-5-yl)-pyrazole-1-carboxylic acid diethylamide |

TABLE I-continued

| Example | Structure | Name |
|---|---|---|
| 212 | 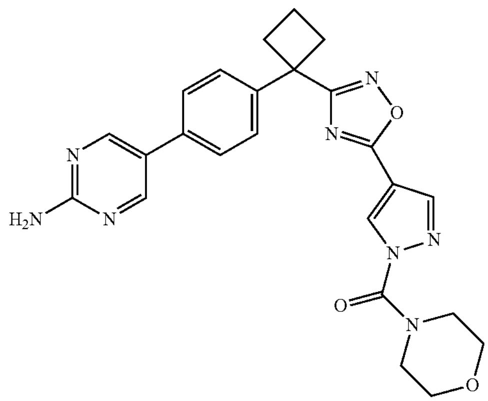 [SMILES: Nc1ncc(-c2ccc(C3(c4noc(-c5cnn(C(=O)N6CCOCC6)c5)n4)CCC3)cc2)cn1] | [4-(3-{1-[4-(2-Amino-pyrimidin-5-yl)-phenyl]-cyclobutyl}-[1,2,4]oxadiazol-5-yl)-pyrazol-1-yl]-morpholin-4-yl-methanone |
| 213 | 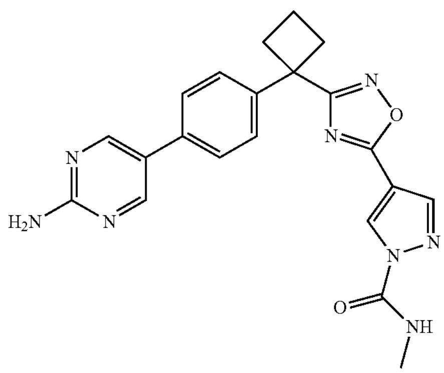 [SMILES: CNC(=O)n1cc(-c2nc(C3(c4ccc(-c5cnc(N)nc5)cc4)CCC3)no2)cn1] | 4-(3-{1-[4-(2-Amino-pyrimidin-5-yl)-phenyl]-cyclobutyl}-[1,2,4]oxadiazol-5-yl)-pyrazole-1-carboxylic acid methylamide |
| 214 | 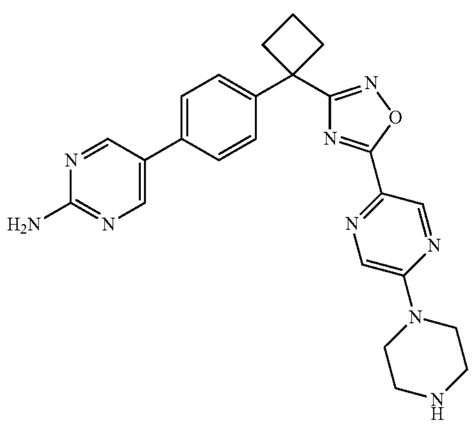 [SMILES: Nc1ncc(-c2ccc(C3(c4noc(-c5cnc(N6CCNCC6)cn5)n4)CCC3)cc2)cn1] | 5-(4-{1-[5-(3,4,5,6-Tetrahydro-2H-[1,2']bipyrazinyl-5'-yl)-[1,2,4]oxadiazol-3-yl]-cyclobutyl}-phenyl)-pyrimidin-2-ylamine |
| 215 | 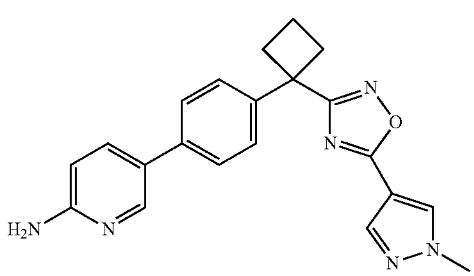 [SMILES: Cn1cc(-c2nc(C3(c4ccc(-c5ccc(N)nc5)cc4)CCC3)no2)cn1] | 5-(4-{1-[5-(1-Methyl-1H-pyrazol-4-yl)-[1,2,4]oxadiazol-3-yl]-cyclobutyl}-phenyl)-pyridin-2-ylamine |

TABLE I-continued

| Example | Structure | Name |
|---|---|---|
| 216 | 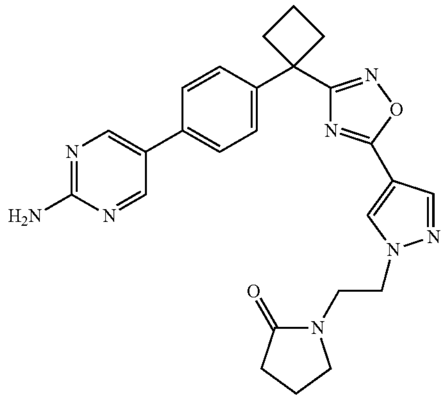 [SMILES: Nc1ncc(-c2ccc(C3(c4noc(-c5cnn(CCN6CCCC6=O)c5)n4)CCC3)cc2)cn1] | 1-{2-[4-(3-{1-[4-(2-Amino-pyrimidin-5-yl)-phenyl]-cyclobutyl}-[1,2,4]oxadiazol-5-yl)-pyrazol-1-yl]-ethyl}-pyrrolidin-2-one |
| 217 | 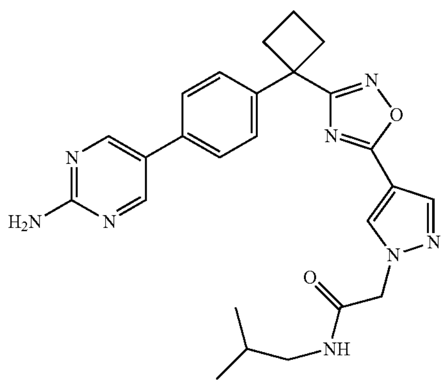 [SMILES: CC(C)CNC(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-[1,2,4]oxadiazol-5-yl)-pyrazol-1-yl]-N-isobutyl-acetamide |
| 218 | 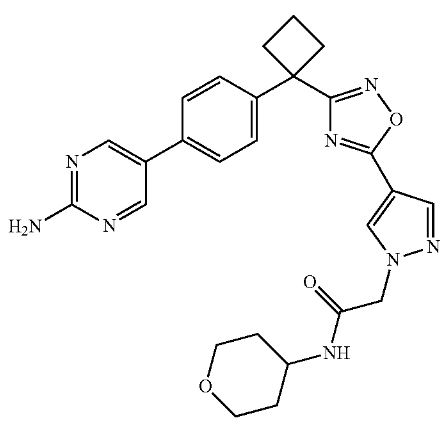 [SMILES: Nc1ncc(-c2ccc(C3(c4noc(-c5cnn(CC(=O)NC6CCOCC6)c5)n4)CCC3)cc2)cn1] | 2-[4-(3-{1-[4-(2-Amino-pyrimidin-5-yl)-phenyl]-cyclobutyl}-[1,2,4]oxadiazol-5-yl)-pyrazol-1-yl]-N-(tetrahydro-pyran-4-yl)-acetamide |

TABLE I-continued

| Example | Structure | Name |
|---|---|---|
| 219 | 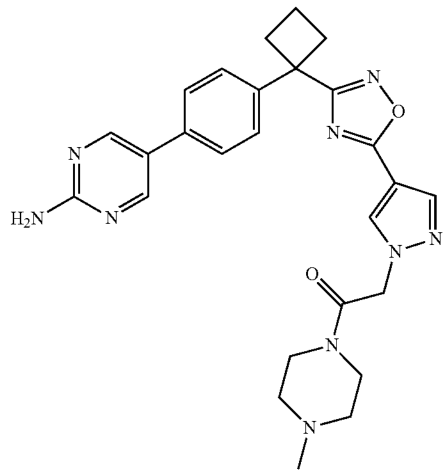 [SMILES: CN1CCN(C(=O)Cn2cc(-c3nc(C4(c5ccc(-c6cnc(N)nc6)cc5)CCC4)no3)cn2)CC1] | 2-[4-(3-{1-[4-(2-Amino-pyrimidin-5-yl)-phenyl]-cyclobutyl}-[1,2,4]oxadiazol-5-yl)-pyrazol-1-yl]-1-(4-methyl-piperazin-1-yl)-ethanone |
| 220 | 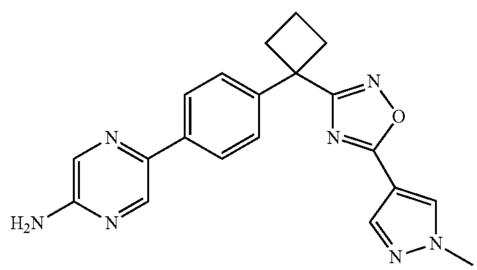 [SMILES: Cn1cc(-c2nc(C3(c4ccc(-c5cnc(N)cn5)cc4)CCC3)no2)cn1] | 5-(4-{1-[5-(1-Methyl-1H-pyrazol-4-yl)-[1,2,4]oxadiazol-3-yl]-cyclobutyl}-phenyl)-pyrazin-2-ylamine |
| 221 | 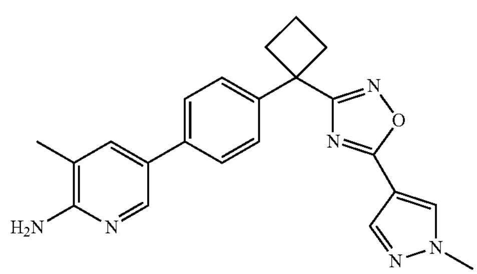 [SMILES: Cc1cc(-c2ccc(C3(c4noc(-c5cnn(C)c5)n4)CCC3)cc2)cnc1N] | 3-Methyl-5-(4-{1-[5-(1-methyl-1H-pyrazol-4-yl)-[1,2,4]oxadiazol-3-yl]-cyclobutyl}-phenyl)-pyridin-2-ylamine |
| 222 | 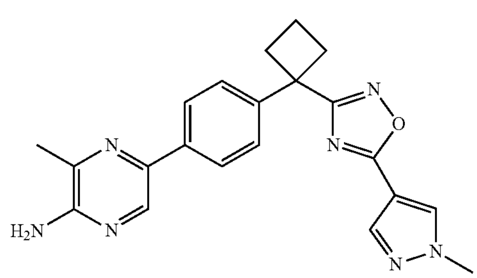 [SMILES: Cc1nc(-c2ccc(C3(c4noc(-c5cnn(C)c5)n4)CCC3)cc2)cnc1N] | 3-Methyl-5-(4-{1-[5-(1-methyl-1H-pyrazol-4-yl)-[1,2,4]oxadiazol-3-yl]-cyclobutyl}-phenyl)-pyrazin-2-ylamine |

TABLE I-continued

| Example | Structure | Name |
|---|---|---|
| 223 | 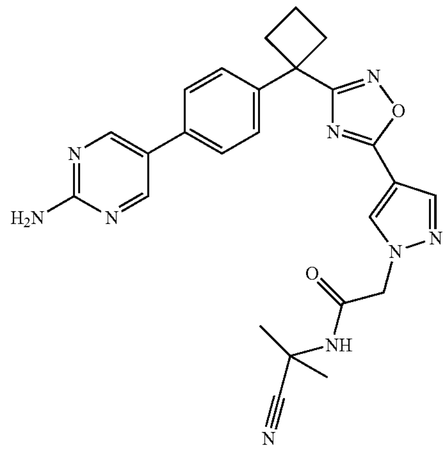 [SMILES: CC(C)(C#N)NC(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-[1,2,4]oxadiazol-5-yl)-pyrazol-1-yl]-N-(cyano-dimethyl-methyl)-acetamide |
| 224 | 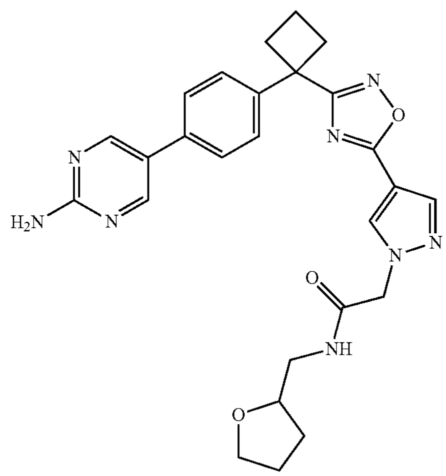 [SMILES: Nc1ncc(-c2ccc(C3(c4noc(-c5cnn(CC(=O)NCC6CCCO6)c5)n4)CCC3)cc2)cn1] | 2-[4-(3-{1-[4-(2-Amino-pyrimidin-5-yl)-phenyl]-cyclobutyl}-[1,2,4]oxadiazol-5-yl)-pyrazol-1-yl]-N-(tetrahydro-furan-2-ylmethyl)-acetamide |
| 225 | 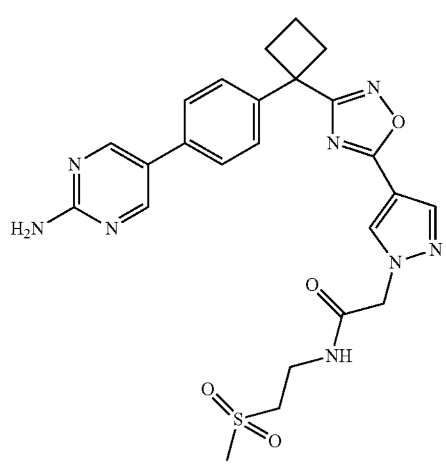 [SMILES: CS(=O)(=O)CCNC(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-[1,2,4]oxadiazol-5-yl)-pyrazol-1-yl]-N-(2-methanesulfonyl-ethyl)-acetamide |

TABLE I-continued

| Example | Structure | Name |
|---|---|---|
| 226 | 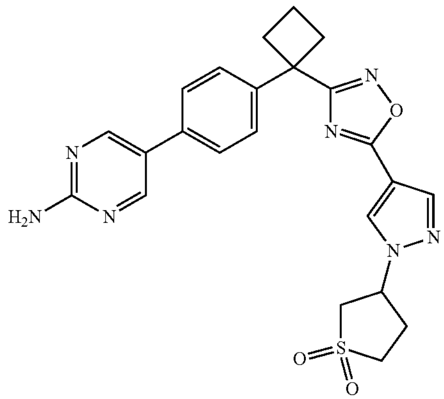 [SMILES: Nc1ncc(-c2ccc(C3(c4noc(-c5cnn(C6CCS(=O)(=O)C6)c5)n4)CCC3)cc2)cn1] | 5-[4-(1-{5-[1-(1,1-Dioxo-tetrahydro-1lambda6-thiophen-3-yl)-1H-pyrazol-4-yl]-[1,2,4]oxadiazol-3-yl}-cyclobutyl)-phenyl]-pyrimidin-2-ylamine |
| 227 | 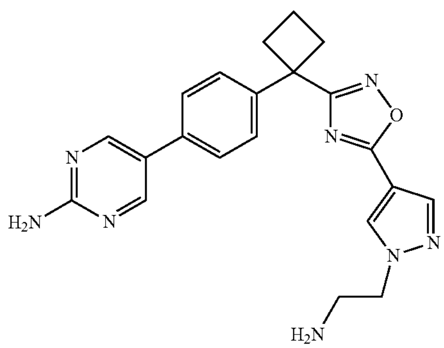 [SMILES: NCCn1cc(-c2nc(C3(c4ccc(-c5cnc(N)nc5)cc4)CCC3)no2)cn1] | 5-[4-(1-{5-[1-(2-Amino-ethyl)-1H-pyrazol-4-yl]-[1,2,4]oxadiazol-3-yl}-cyclobutyl)-phenyl]-pyrimidin-2-ylamine |
| 228 | 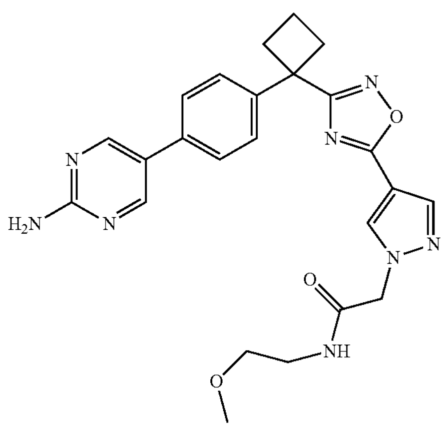 [SMILES: COCCNC(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-[1,2,4]oxadiazol-5-yl)-pyrazol-1-yl]-N-(2-methoxy-ethyl)-acetamide |
| 229 | 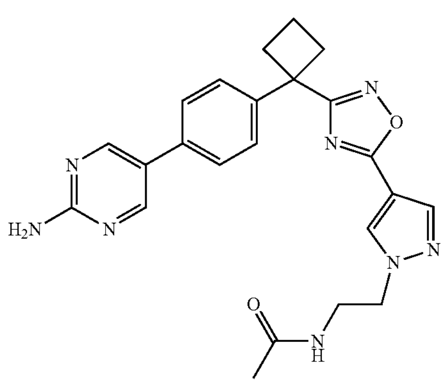 [SMILES: CC(=O)NCCn1cc(-c2nc(C3(c4ccc(-c5cnc(N)nc5)cc4)CCC3)no2)cn1] | N-{2-[4-(3-{1-[4-(2-Amino-pyrimidin-5-yl)-phenyl]-cyclobutyl}-[1,2,4]oxadiazol-5-yl)-pyrazol-1-yl]-ethyl}-acetamide |

TABLE I-continued

| Example | Structure | Name |
|---|---|---|
| 230 | 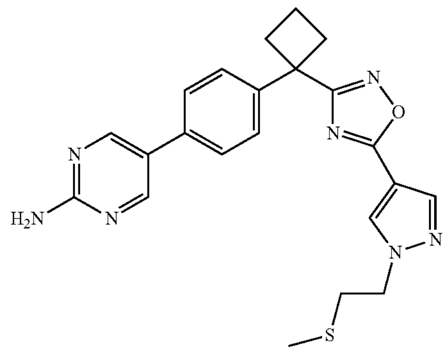 [SMILES: CSCCn1cc(-c2nc(C3(c4ccc(-c5cnc(N)nc5)cc4)CCC3)no2)cn1] | 5-[4-(1-{5-[1-(2-Methylsulfanyl-ethyl)-1H-pyrazol-4-yl]-[1,2,4]oxadiazol-3-yl}-cyclobutyl)-phenyl]-pyrimidin-2-ylamine |
| 231 | 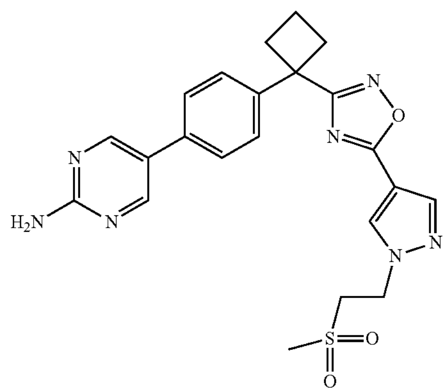 [SMILES: CS(=O)(=O)CCn1cc(-c2nc(C3(c4ccc(-c5cnc(N)nc5)cc4)CCC3)no2)cn1] | 5-[4-(1-{5-[1-(2-Methanesulfonyl-ethyl)-1H-pyrazol-4-yl]-[1,2,4]oxadiazol-3-yl}-cyclobutyl)-phenyl]-pyrimidin-2-ylamine |
| 232 | 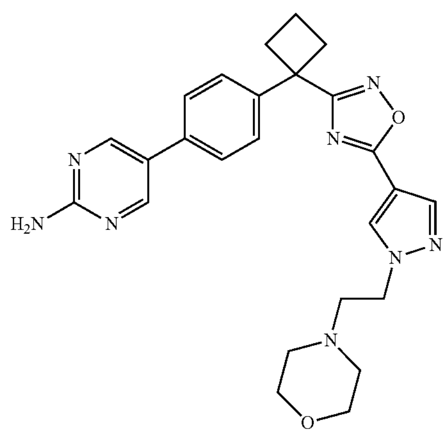 [SMILES: Nc1ncc(-c2ccc(C3(c4noc(-c5cnn(CCN6CCOCC6)c5)n4)CCC3)cc2)cn1] | 5-[4-(1-{5-[1-(2-Morpholin-4-yl-ethyl)-1H-pyrazol-4-yl]-[1,2,4]oxadiazol-3-yl}-cyclobutyl)-phenyl]-pyrimidin-2-ylamine |
| 233 | 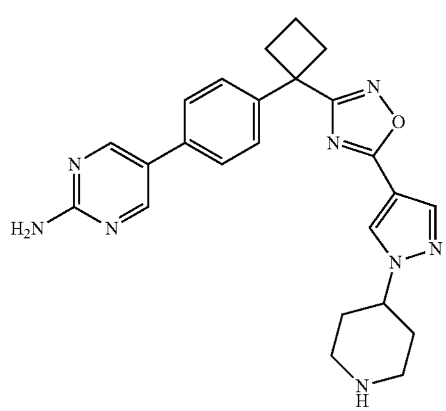 [SMILES: Nc1ncc(-c2ccc(C3(c4noc(-c5cnn(C6CCNCC6)c5)n4)CCC3)cc2)cn1] | 5-(4-{1-[5-(1-Piperidin-4-yl-1H-pyrazol-4-yl)-[1,2,4]oxadiazol-3-yl]-cyclobutyl}-phenyl)-pyrimidin-2-ylamine |

TABLE I-continued

| Example | Structure | Name |
|---|---|---|
| 234 | 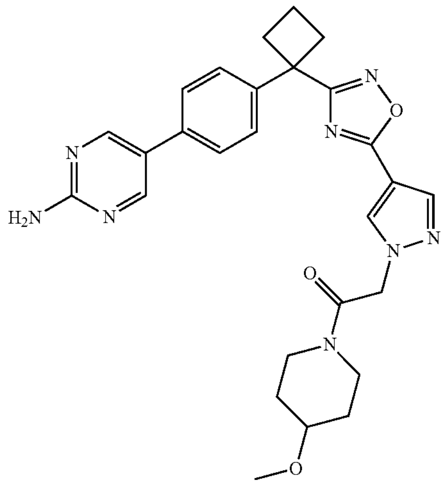 [SMILES: COC1CCN(C(=O)Cn2cc(-c3nc(C4(c5ccc(-c6cnc(N)nc6)cc5)CCC4)no3)cn2)CC1] | 2-[4-(3-{1-[4-(2-Amino-pyrimidin-5-yl)-phenyl]-cyclobutyl}-[1,2,4]oxadiazol-5-yl)-pyrazol-1-yl]-1-(4-methoxy-piperidin-1-yl)-ethanone |
| 235 | 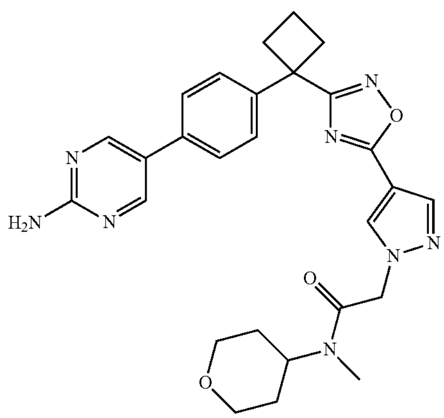 [SMILES: CN(C(=O)Cn1cc(-c2nc(C3(c4ccc(-c5cnc(N)nc5)cc4)CCC3)no2)cn1)C1CCOCC1] | 2-[4-(3-{1-[4-(2-Amino-pyrimidin-5-yl)-phenyl]-cyclobutyl}-[1,2,4]oxadiazol-5-yl)-pyrazol-1-yl]-N-methyl-N-(tetrahydro-pyran-4-yl)-acetamide |
| 236 | 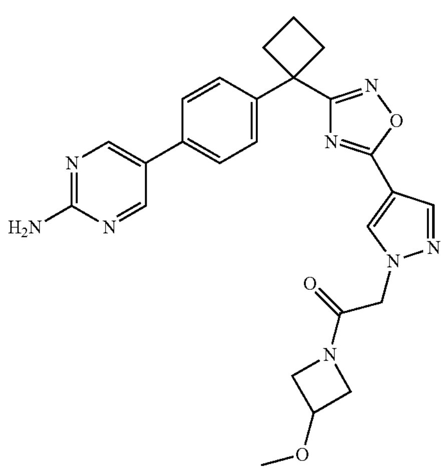 [SMILES: COC1CN(C(=O)Cn2cc(-c3nc(C4(c5ccc(-c6cnc(N)nc6)cc5)CCC4)no3)cn2)C1] | 2-[4-(3-{1-[4-(2-Amino-pyrimidin-5-yl)-phenyl]-cyclobutyl}-[1,2,4]oxadiazol-5-yl)-pyrazol-1-yl]-1-(3-methoxy-azetidin-1-yl)-ethanone |

TABLE I-continued

| Example | Structure | Name |
|---|---|---|
| 237 | 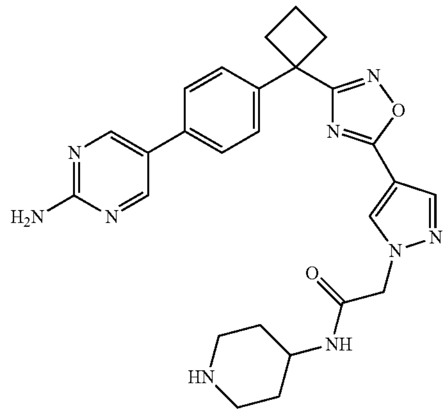 [SMILES: Nc1ncc(-c2ccc(C3(c4noc(-c5cnn(CC(=O)NC6CCNCC6)c5)n4)CCC3)cc2)cn1] | 2-[4-(3-{1-[4-(2-Amino-pyrimidin-5-yl)-phenyl]-cyclobutyl}-[1,2,4]oxadiazol-5-yl)-pyrazol-1-yl]-N-piperidin-4-yl-acetamide |
| 238 | 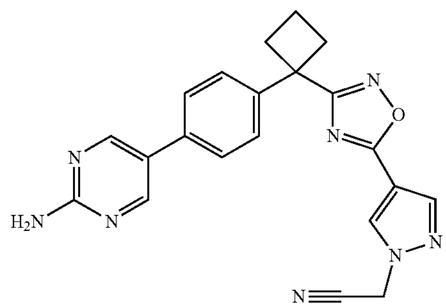 [SMILES: N#CCn1cc(-c2nc(C3(c4ccc(-c5cnc(N)nc5)cc4)CCC3)no2)cn1] | [4-(3-{1-[4-(2-Amino-pyrimidin-5-yl)-phenyl]-cyclobutyl}-[1,2,4]oxadiazol-5-yl)-pyrazol-1-yl]-acetonitrile |
| 239 | 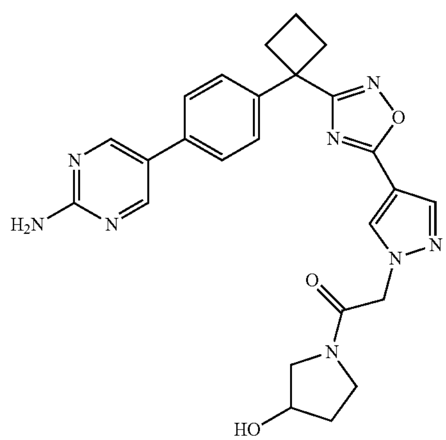 [SMILES: Nc1ncc(-c2ccc(C3(c4noc(-c5cnn(CC(=O)N6CCC(O)C6)c5)n4)CCC3)cc2)cn1] | 2-[4-(3-{1-[4-(2-Amino-pyrimidin-5-yl)-phenyl]-cyclobutyl}-[1,2,4]oxadiazol-5-yl)-pyrazol-1-yl]-1-(3-hydroxy-pyrrolidin-1-yl)-ethanone |
| 240 | 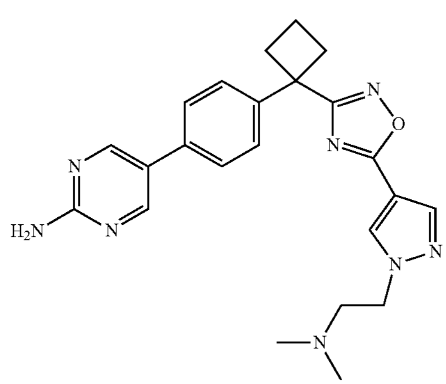 [SMILES: CN(C)CCn1cc(-c2nc(C3(c4ccc(-c5cnc(N)nc5)cc4)CCC3)no2)cn1] | 5-[4-(1-{5-[1-(2-Dimethylamino-ethyl)-1H-pyrazol-4-yl]-[1,2,4]oxadiazol-3-yl}-cyclobutyl)-phenyl]-pyrimidin-2-ylamine |

TABLE I-continued

| Example | Structure | Name |
|---|---|---|
| 241 | 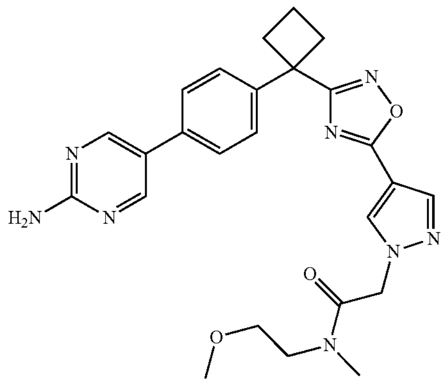 [SMILES: COCCN(C)C(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-[1,2,4]oxadiazol-5-yl)-pyrazol-1-yl]-N-(2-methoxy-ethyl)-N-methyl-acetamide |
| 242 | 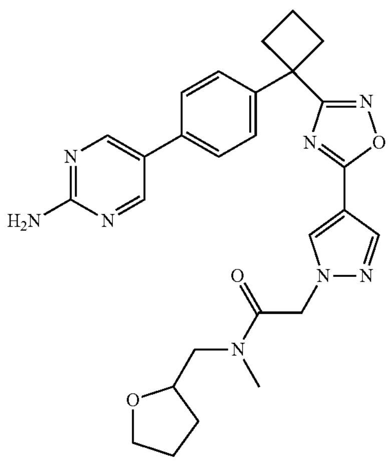 [SMILES: CN(CC1CCCO1)C(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-[1,2,4]oxadiazol-5-yl)-pyrazol-1-yl]-N-methyl-N-(tetrahydro-furan-2-ylmethyl)-acetamide |
| 243 | 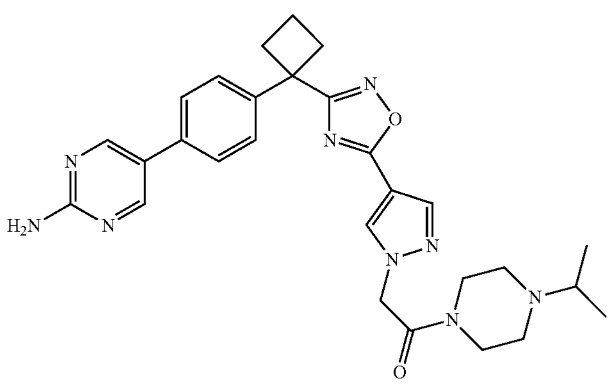 [SMILES: CC(C)N1CCN(C(=O)Cn2cc(-c3nc(C4(c5ccc(-c6cnc(N)nc6)cc5)CCC4)no3)cn2)CC1] | 2-[4-(3-{1-[4-(2-Amino-pyrimidin-5-yl)-phenyl]-cyclobutyl}-[1,2,4]oxadiazol-5-yl)-pyrazol-1-yl]-1-(4-isopropyl-piperazin-1-yl)-ethanone |

TABLE I-continued

| Example | Structure | Name |
|---|---|---|
| 244 | 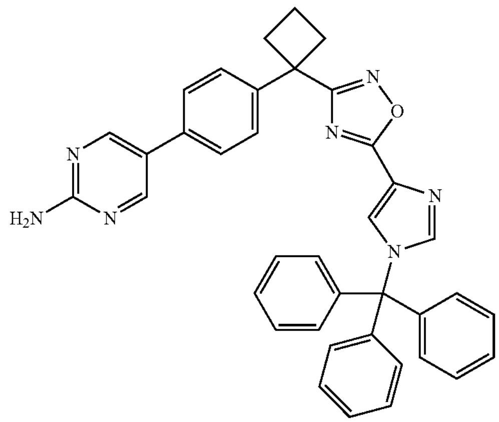 [SMILES: Nc1ncc(-c2ccc(C3(c4noc(-c5cn(C(c6ccccc6)(c6ccccc6)c6ccccc6)cn5)n4)CCC3)cc2)cn1] | 5-(4-{1-[5-(1-Trityl-1H-imidazol-4-yl)-[1,2,4]oxadiazol-3-yl]-cyclobutyl}-phenyl)-pyrimidin-2-ylamine |
| 245 | 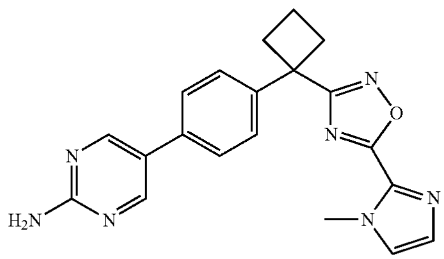 [SMILES: Cn1ccnc1-c1nc(C2(c3ccc(-c4cnc(N)nc4)cc3)CCC2)no1] | 5-(4-{1-[5-(1-Methyl-1H-imidazol-2-yl)-[1,2,4]oxadiazol-3-yl]-cyclobutyl}-phenyl)-pyrimidin-2-ylamine |
| 246 | 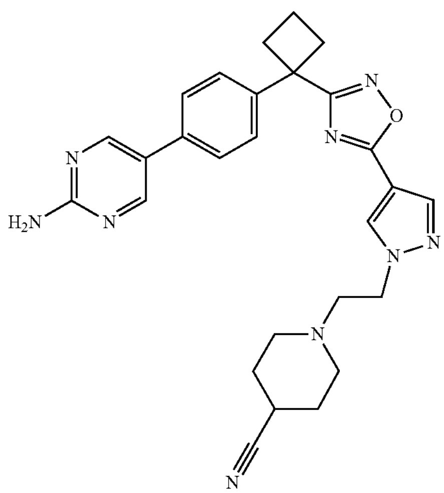 [SMILES: N#CC1CCN(CCn2cc(-c3nc(C4(c5ccc(-c6cnc(N)nc6)cc5)CCC4)no3)cn2)CC1] | 1-{2-[4-(3-{1-[4-(2-Amino-pyrimidin-5-yl)-phenyl]-cyclobutyl}-[1,2,4]oxadiazol-5-yl)-pyrazol-1-yl]-ethyl}-piperidine-4-carbonitrile |
| 247 | 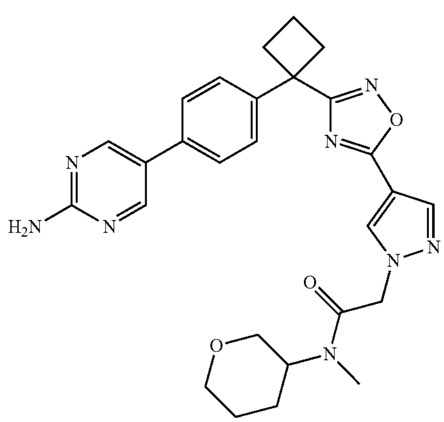 [SMILES: CN(C(=O)Cn1cc(-c2nc(C3(c4ccc(-c5cnc(N)nc5)cc4)CCC3)no2)cn1)C1CCCOC1] | 2-[4-(3-{1-[4-(2-Amino-pyrimidin-5-yl)-phenyl]-cyclobutyl}-[1,2,4]oxadiazol-5-yl)-pyrazol-1-yl]-N-methyl-N-(tetrahydro-pyran-3-yl)-acetamide |

TABLE I-continued

| Example | Structure | Name |
|---|---|---|
| 248 | 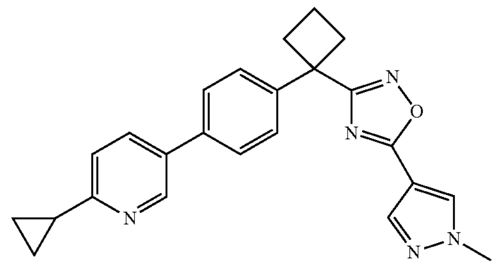 [SMILES: Cn1cc(-c2nc(C3(c4ccc(-c5ccc(C6CC6)nc5)cc4)CCC3)no2)cn1] | 2-Cyclopropyl-5-(4-{1-[5-(1-methyl-1H-pyrazol-4-yl)-[1,2,4]oxadiazol-3-yl]-cyclobutyl}-phenyl)-pyridine |
| 249 | 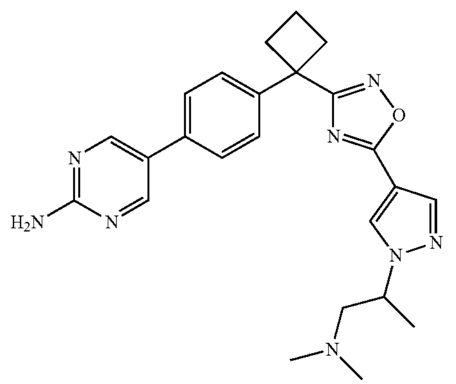 [SMILES: CC(CN(C)C)n1cc(-c2nc(C3(c4ccc(-c5cnc(N)nc5)cc4)CCC3)no2)cn1] | 5-[4-(1-{5-[1-(2-Dimethylamino-1-methyl-ethyl)-1H-pyrazol-4-yl]-[1,2,4]oxadiazol-3-yl}-cyclobutyl)-phenyl]-pyrimidin-2-ylamine |
| 250 | 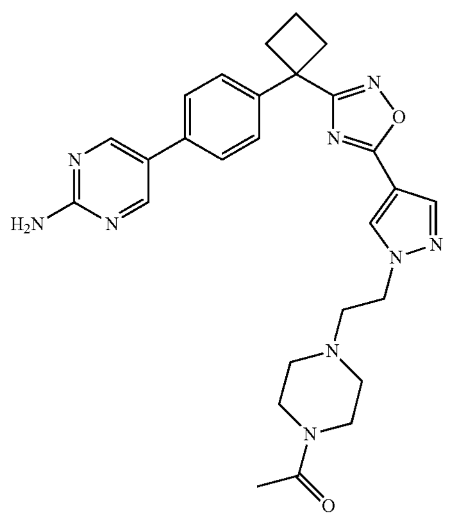 [SMILES: CC(=O)N1CCN(CCn2cc(-c3nc(C4(c5ccc(-c6cnc(N)nc6)cc5)CCC4)no3)cn2)CC1] | 1-(4-{2-[4-(3-{1-[4-(2-Amino-pyrimidin-5-yl)-phenyl]-cyclobutyl}-[1,2,4]oxadiazol-5-yl)-pyrazol-1-yl]-ethyl}-piperazin-1-yl)-ethanone |
| 251 | 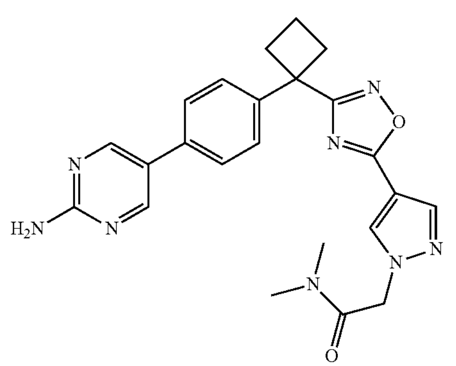 [SMILES: CN(C)C(=O)Cn1cc(-c2nc(C3(c4ccc(-c5cnc(N)nc5)cc4)CCC3)no2)cn1] | 2-[4-(3-{1-[4-(2-Amino-pyrimidin-5-yl)-phenyl]-cyclobutyl}-[1,2,4]oxadiazol-5-yl)-imidazol-1-yl]-N,N-dimethyl-acetamide |

TABLE I-continued

| Example | Structure | Name |
|---|---|---|
| 252 | 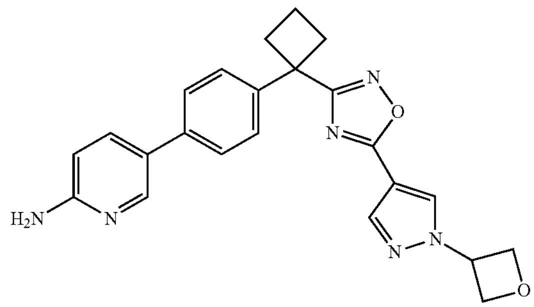 [SMILES: Nc1ccc(-c2ccc(C3(c4noc(-c5cnn(C6COC6)c5)n4)CCC3)cc2)cn1] | 5-(4-{1-[5-(1-Oxetan-3-yl-1H-pyrazol-4-yl)-[1,2,4]oxadiazol-3-yl]-cyclobutyl}-phenyl)-pyridin-2-ylamine |
| 253 | 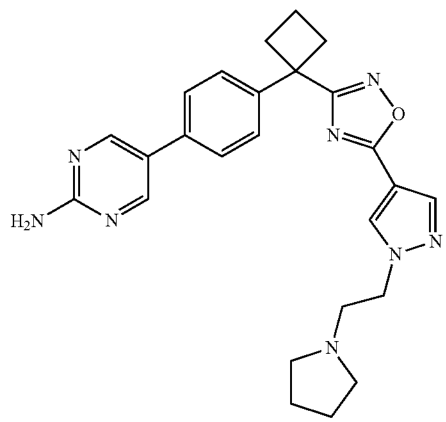 [SMILES: Nc1ncc(-c2ccc(C3(c4noc(-c5cnn(CCN6CCCC6)c5)n4)CCC3)cc2)cn1] | 5-[4-(1-{5-[1-(2-Pyrrolidin-1-yl-ethyl)-1H-pyrazol-4-yl]-[1,2,4]oxadiazol-3-yl}-cyclobutyl)-phenyl]-pyrimidin-2-ylamine |
| 254 | 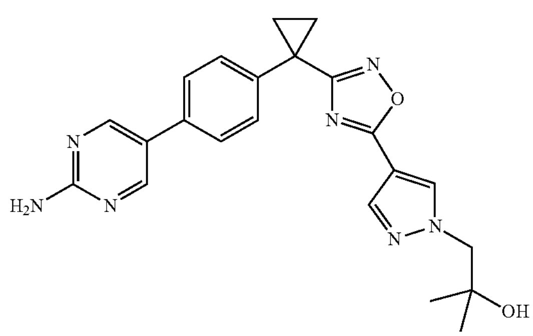 [SMILES: CC(C)(O)Cn1cc(-c2nc(C3(c4ccc(-c5cnc(N)nc5)cc4)CC3)no2)cn1] | 1-[4-(3-{1-[4-(2-Amino-pyrimidin-5-yl)-phenyl]-cyclopropyl}-[1,2,4]oxadiazol-5-yl)-pyrazol-1-yl]-2-methyl-propan-2-ol |
| 255 | 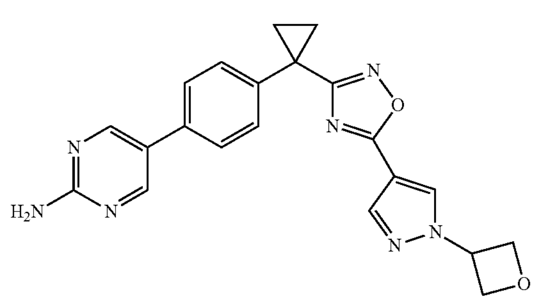 [SMILES: Nc1ncc(-c2ccc(C3(c4noc(-c5cnn(C6COC6)c5)n4)CC3)cc2)cn1] | 5-(4-{1-[5-(1-Oxetan-3-yl-1H-pyrazol-4-yl)-[1,2,4]oxadiazol-3-yl]-cyclopropyl}-phenyl)-pyrimidin-2-ylamine |

TABLE I-continued

| Example | Structure | Name |
|---|---|---|
| 256 | 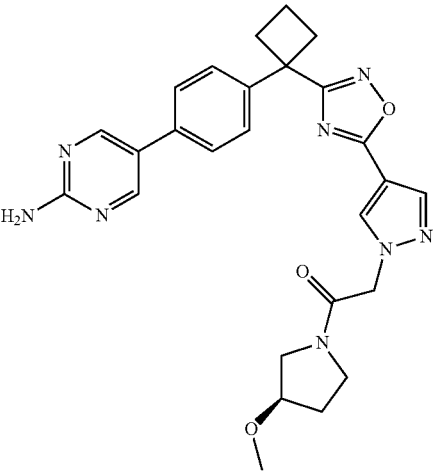 [SMILES: CO[C@@H]1CCN(C(=O)Cn2cc(-c3nc(C4(c5ccc(-c6cnc(N)nc6)cc5)CCC4)no3)cn2)C1] | 2-[4-(3-{1-[4-(2-Amino-pyrimidin-5-yl)-phenyl]-cyclobutyl}-[1,2,4]oxadiazol-5-yl)-pyrazol-1-yl]-1-((R)-3-methoxy-pyrrolidin-1-yl)-ethanone |
| 257 | 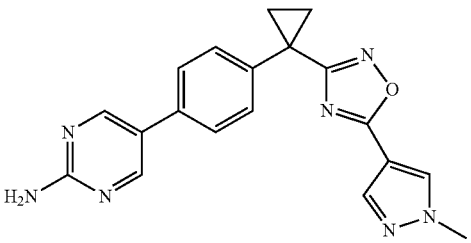 [SMILES: Cn1cc(-c2nc(C3(c4ccc(-c5cnc(N)nc5)cc4)CC3)no2)cn1] | 5-(4-{1-[5-(1-Methyl-1H-pyrazol-4-yl)-[1,2,4]oxadiazol-3-yl]-cyclopropyl}-phenyl)-pyrimidin-2-ylamine |
| 258 | 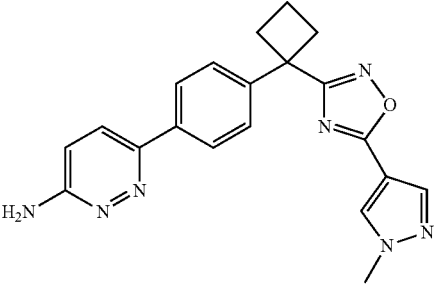 [SMILES: Cn1cc(-c2nc(C3(c4ccc(-c5ccc(N)nn5)cc4)CCC3)no2)cn1] | 6-(4-{1-[5-(1-Methyl-1H-pyrazol-4-yl)-[1,2,4]oxadiazol-3-yl]-cyclobutyl}-phenyl)-pyridazin-3-ylamine |
| 259 | 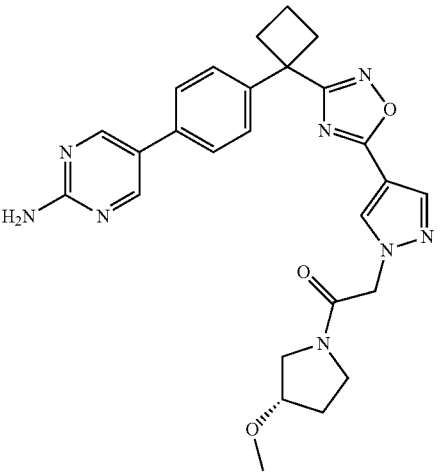 [SMILES: CO[C@H]1CCN(C(=O)Cn2cc(-c3nc(C4(c5ccc(-c6cnc(N)nc6)cc5)CCC4)no3)cn2)C1] | 2-[4-(3-{1-[4-(2-Amino-pyrimidin-5-yl)-phenyl]-cyclobutyl}-[1,2,4]oxadiazol-5-yl)-pyrazol-1-yl]-1-((S)-3-methoxy-pyrrolidin-1-yl)-ethanone |

TABLE I-continued

| Example | Structure | Name |
|---|---|---|
| 260 | | |
| 261 | 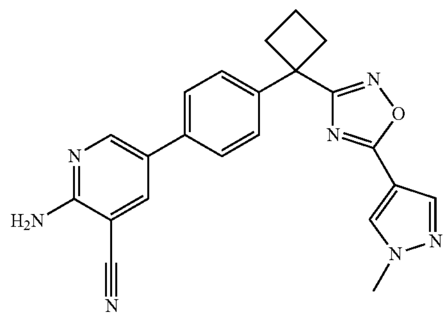 [SMILES: Cn1cc(-c2nc(C3(c4ccc(-c5cnc(N)c(C#N)c5)cc4)CCC3)no2)cn1] | 2-Amino-5-(4-{1-[5-(1-methyl-1H-pyrazol-4-yl)-[1,2,4]oxadiazol-3-yl]-cyclobutyl}-phenyl)-nicotinonitrile |
| 262 | 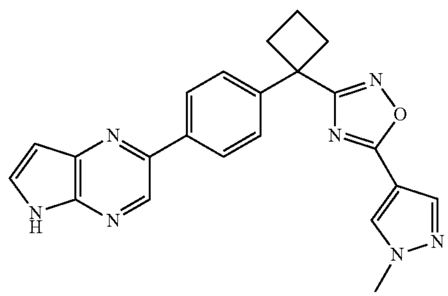 [SMILES: Cn1cc(-c2nc(C3(c4ccc(-c5cnc6[nH]ccc6n5)cc4)CCC3)no2)cn1] | 2-(4-{1-[5-(1-Methyl-1H-pyrazol-4-yl)-[1,2,4]oxadiazol-3-yl]-cyclobutyl}-phenyl)-5H-pyrrolo[2,3-b]pyrazine |
| 263 | 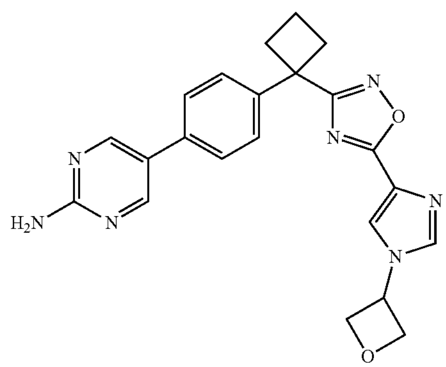 [SMILES: Nc1ncc(-c2ccc(C3(c4noc(-c5cn(C6COC6)cn5)n4)CCC3)cc2)cn1] | 5-(4-{1-[5-(1-Oxetan-3-yl-1H-imidazol-4-yl)-[1,2,4]oxadiazol-3-yl]-cyclobutyl}-phenyl)-pyrimidin-2-ylamine |
| 264 | 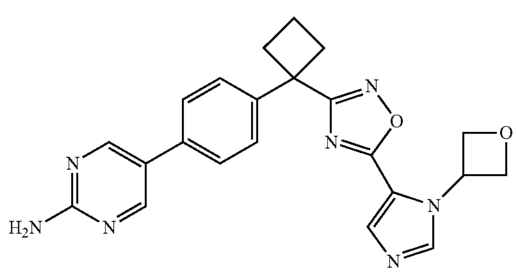 [SMILES: Nc1ncc(-c2ccc(C3(c4noc(-c5cncn5C5COC5)n4)CCC3)cc2)cn1] | 5-(4-{1-[5-(3-Oxetan-3-yl-3H-imidazol-4-yl)-[1,2,4]oxadiazol-3-yl]-cyclobutyl}-phenyl)-pyrimidin-2-ylamine |
| 265 | 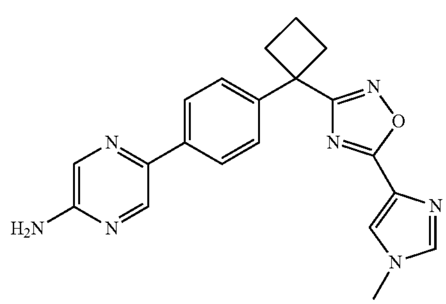 [SMILES: Cn1cnc(-c2nc(C3(c4ccc(-c5cnc(N)cn5)cc4)CCC3)no2)c1] | 5-(4-{1-[5-(1-Methyl-1H-imidazol-4-yl)-[1,2,4]oxadiazol-3-yl]-cyclobutyl}-phenyl)-pyrazin-2-ylamine |

TABLE I-continued
| Example | Structure | Name |
|---|---|---|
| 266 | 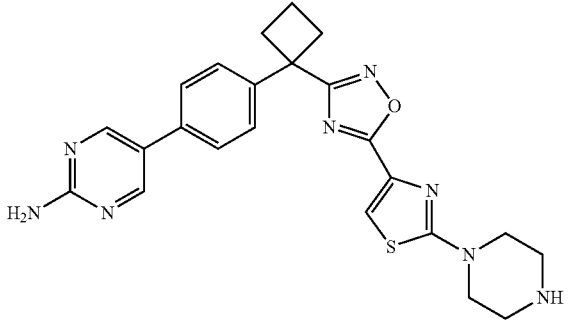 [SMILES: Nc1ncc(-c2ccc(C3(c4noc(-c5csc(N6CCNCC6)n5)n4)CCC3)cc2)cn1] | 5-(4-{1-[5-(2-Piperazin-1-yl-thiazol-4-yl)-[1,2,4]oxadiazol-3-yl]-cyclobutyl}-phenyl)-pyrimidin-2-ylamine |
| 267 | 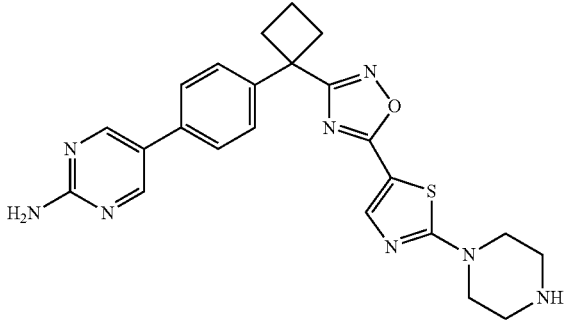 [SMILES: Nc1ncc(-c2ccc(C3(c4noc(-c5cnc(N6CCNCC6)s5)n4)CCC3)cc2)cn1] | 5-(4-{1-[5-(2-Piperazin-1-yl-thiazol-5-yl)-[1,2,4]oxadiazol-3-yl]-cyclobutyl}-phenyl)-pyrimidin-2-ylamine |
| 268 | 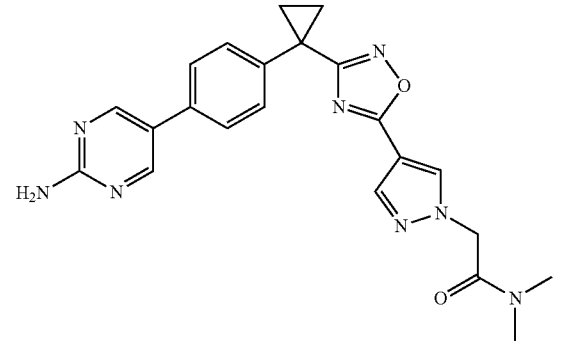 [SMILES: CN(C)C(=O)Cn1cc(-c2nc(C3(c4ccc(-c5cnc(N)nc5)cc4)CC3)no2)cn1] | 2-[4-(3-{1-[4-(2-Amino-pyrimidin-5-yl)-phenyl]-cyclopropyl}-[1,2,4]oxadiazol-5-yl)-pyrazol-1-yl]-N,N-dimethyl-acetamide |
| 269 | 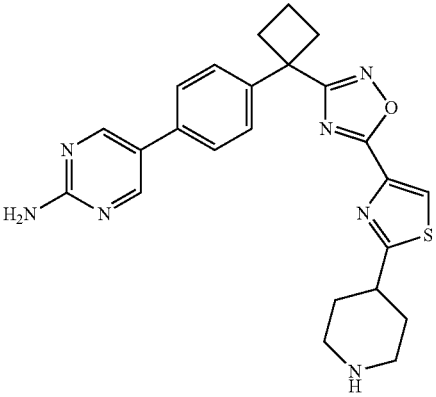 [SMILES: Nc1ncc(-c2ccc(C3(c4noc(-c5csc(C6CCNCC6)n5)n4)CCC3)cc2)cn1] | 5-(4-{1-[5-(2-Piperidin-4-yl-thiazol-4-yl)-[1,2,4]oxadiazol-3-yl]-cyclobutyl}-phenyl)-pyrimidin-2-ylamine |

TABLE I-continued

| Example | Structure | Name |
|---|---|---|
| 270 | 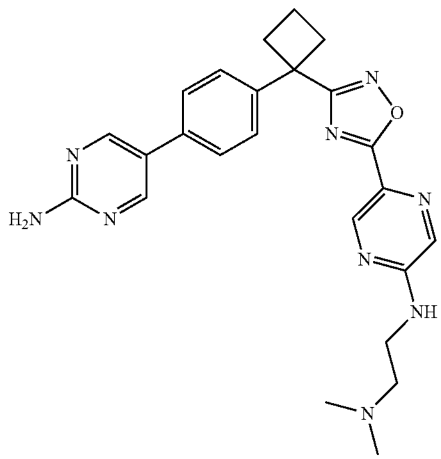 [SMILES: CN(C)CCNc1cnc(-c2nc(C3(c4ccc(-c5cnc(N)nc5)cc4)CCC3)no2)cn1] | N-[5-(3-{1-[4-(2-Amino-pyrimidin-5-yl)-phenyl]-cyclobutyl}-[1,2,4]oxadiazol-5-yl)-pyrazin-2-yl]-N',N'-dimethyl-ethane-1,2-diamine |
| 271 | 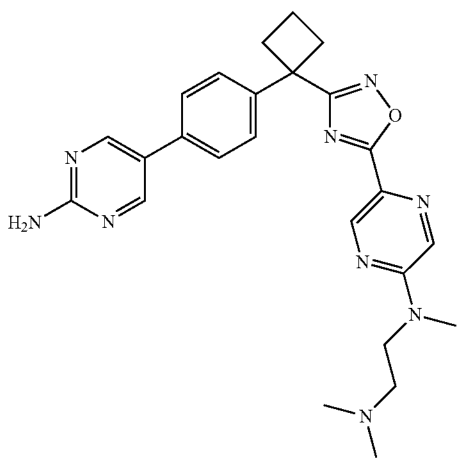 [SMILES: CN(C)CCN(C)c1cnc(-c2nc(C3(c4ccc(-c5cnc(N)nc5)cc4)CCC3)no2)cn1] | N-[5-(3-{1-[4-(2-Amino-pyrimidin-5-yl)-phenyl]-cyclobutyl}-[1,2,4]oxadiazol-5-yl)-pyrazin-2-yl]-N,N',N'-trimethyl-ethane-1,2-diamine |
| 272 | 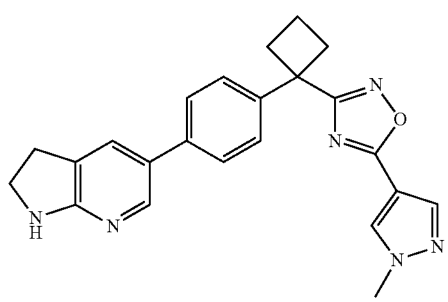 [SMILES: Cn1cc(-c2nc(C3(c4ccc(-c5cnc6c(c5)CCN6)cc4)CCC3)no2)cn1] | 5-(4-{1-[5-(1-Methyl-1H-pyrazol-4-yl)-[1,2,4]oxadiazol-3-yl]-cyclobutyl}-phenyl)-2,3-dihydro-1H-pyrrolo[2,3-b]pyridine |
| 273 | 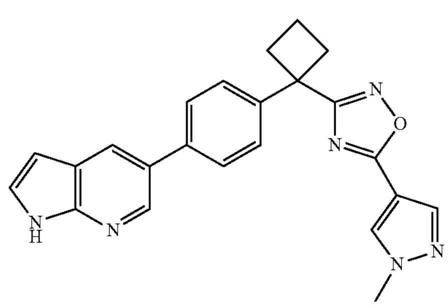 [SMILES: Cn1cc(-c2nc(C3(c4ccc(-c5cnc6[nH]ccc6c5)cc4)CCC3)no2)cn1] | 5-(4-{1-[5-(1-Methyl-1H-pyrazol-4-yl)-[1,2,4]oxadiazol-3-yl]-cyclobutyl}-phenyl)-1H-pyrrolo[2,3-b]pyridine |

TABLE I-continued

| Example | Structure | Name |
|---|---|---|
| 274 | 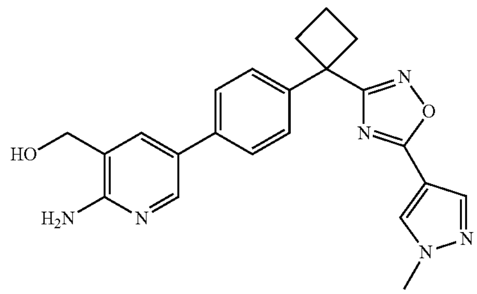 [SMILES: Cn1cc(-c2nc(C3(c4ccc(-c5cnc(N)c(CO)c5)cc4)CCC3)no2)cn1] | [2-Amino-5-(4-{1-[5-(1-methyl-1H-pyrazol-4-yl)-[1,2,4]oxadiazol-3-yl]-cyclobutyl}-phenyl)-pyridin-3-yl]-methanol |
| 275 | 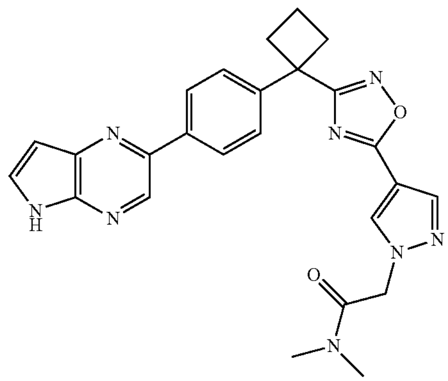 [SMILES: CN(C)C(=O)Cn1cc(-c2nc(C3(c4ccc(-c5cnc6[nH]ccc6n5)cc4)CCC3)no2)cn1] | N,N-Dimethyl-2-[4-(3-{1-[4-(5H-pyrrolo[2,3-b]pyrazin-2-yl)-phenyl]-cyclobutyl}-[1,2,4]oxadiazol-5-yl)-pyrazol-1-yl]-acetamide |
| 276 | 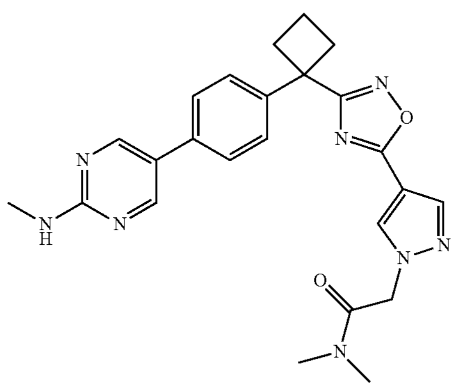 [SMILES: CNc1ncc(-c2ccc(C3(c4noc(-c5cnn(CC(=O)N(C)C)c5)n4)CCC3)cc2)cn1] | N,N-Dimethyl-2-[4-(3-{1-[4-(2-methylamino-pyrimidin-5-yl)-phenyl]-cyclobutyl}-[1,2,4]oxadiazol-5-yl)-pyrazol-1-yl]-acetamide |
| 277 | 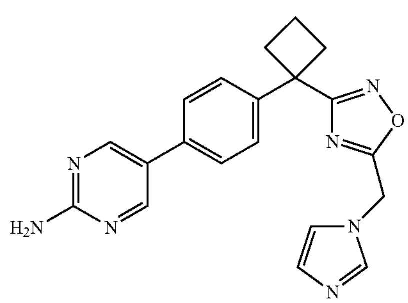 [SMILES: Nc1ncc(-c2ccc(C3(c4noc(Cn5ccnc5)n4)CCC3)cc2)cn1] | 5-{4-[1-(5-Imidazol-1-ylmethyl-[1,2,4]oxadiazol-3-yl)-cyclobutyl]-phenyl}-pyrimidin-2-ylamine |

TABLE I-continued

| Example | Structure | Name |
|---|---|---|
| 278 | 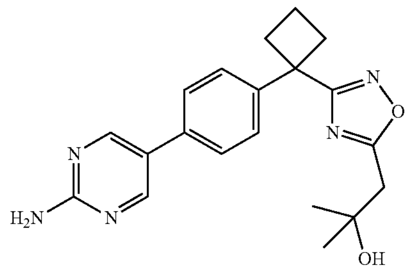 [SMILES: CC(C)(O)Cc1nc(C2(c3ccc(-c4cnc(N)nc4)cc3)CCC2)no1] | 1-(3-{1-[4-(2-Amino-pyrimidin-5-yl)-phenyl]-cyclobutyl}-[1,2,4]oxadiazol-5-yl)-2-methyl-propan-2-ol |
| 279 | 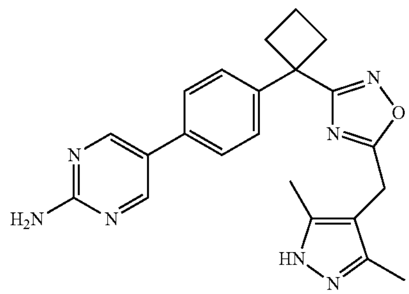 [SMILES: Cc1n[nH]c(C)c1Cc1nc(C2(c3ccc(-c4cnc(N)nc4)cc3)CCC2)no1] | 5-(4-{1-[5-(3,5-Dimethyl-1H-pyrazol-4-ylmethyl)-[1,2,4]oxadiazol-3-yl]-cyclobutyl}-phenyl)-pyrimidin-2-ylamine |
| 280 | 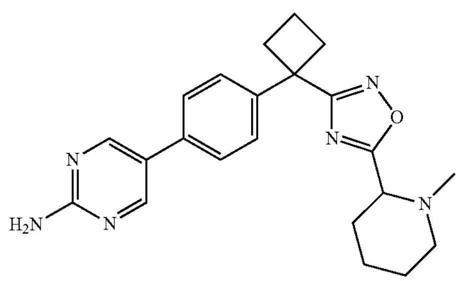 [SMILES: CN1CCCCC1c1nc(C2(c3ccc(-c4cnc(N)nc4)cc3)CCC2)no1] | 5-(4-{1-[5-(1-Methyl-piperidin-2-yl)-[1,2,4]oxadiazol-3-yl]-cyclobutyl}-phenyl)-pyrimidin-2-ylamine |
| 281 | 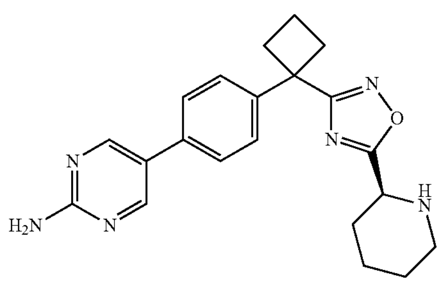 [SMILES: Nc1ncc(-c2ccc(C3(c4noc([C@@H]5CCCCN5)n4)CCC3)cc2)cn1] | 5-{4-[1-((S)-5-Piperidin-2-yl-[1,2,4]oxadiazol-3-yl)-cyclobutyl]-phenyl}-pyrimidin-2-ylamine |
| 282 | 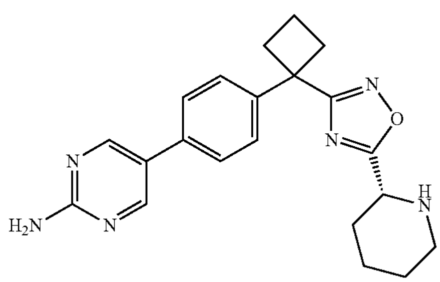 [SMILES: Nc1ncc(-c2ccc(C3(c4noc([C@H]5CCCCN5)n4)CCC3)cc2)cn1] | 5-{4-[1-((R)-5-Piperidin-2-yl-[1,2,4]oxadiazol-3-yl)-cyclobutyl]-phenyl}-pyrimidin-2-ylamine |

TABLE I-continued

| Example | Structure | Name |
| --- | --- | --- |
| 283 | 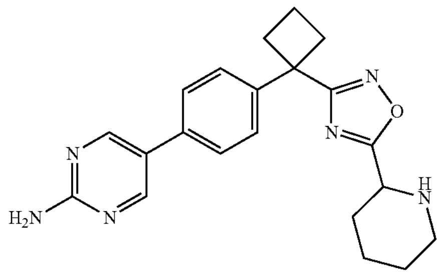 [SMILES: Nc1ncc(-c2ccc(C3(c4noc(C5CCCCN5)n4)CCC3)cc2)cn1] | 5-{4-[1-(5-Piperidin-2-yl-[1,2,4]oxadiazol-3-yl)-cyclobutyl]-phenyl}-pyrimidin-2-ylamine |
| 284 | 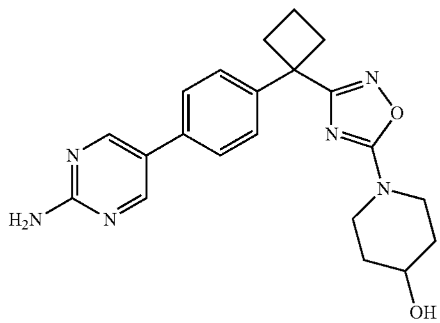 [SMILES: Nc1ncc(-c2ccc(C3(c4noc(N5CCC(O)CC5)n4)CCC3)cc2)cn1] | 1-(3-{1-[4-(2-Amino-pyrimidin-5-yl)-phenyl]-cyclobutyl}-[1,2,4]oxadiazol-5-yl)-piperidin-4-ol |
| 285 | 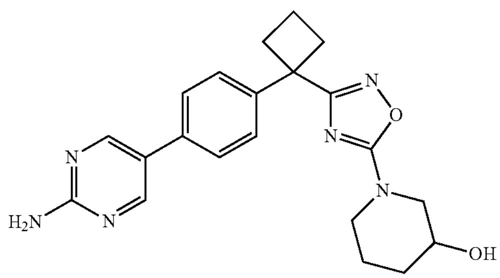 [SMILES: Nc1ncc(-c2ccc(C3(c4noc(N5CCCC(O)C5)n4)CCC3)cc2)cn1] | 1-(3-{1-[4-(2-Amino-pyrimidin-5-yl)-phenyl]-cyclobutyl}-[1,2,4]oxadiazol-5-yl)-piperidin-3-ol |
| 286 | 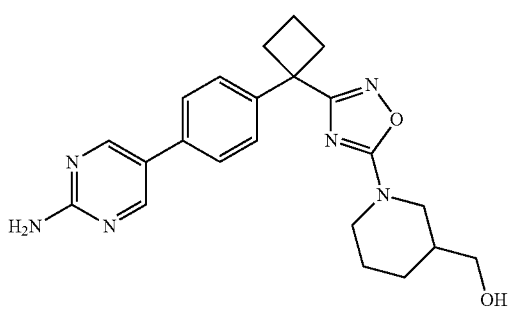 [SMILES: Nc1ncc(-c2ccc(C3(c4noc(N5CCCC(CO)C5)n4)CCC3)cc2)cn1] | [1-(3-{1-[4-(2-Amino-pyrimidin-5-yl)-phenyl]-cyclobutyl}-[1,2,4]oxadiazol-5-yl)-piperidin-3-yl]-methanol |
| 287 | 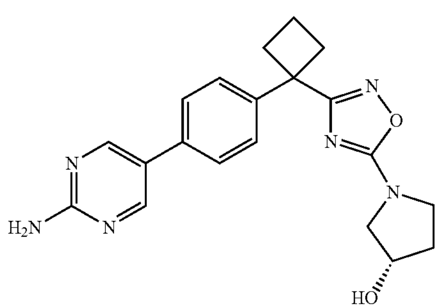 [SMILES: Nc1ncc(-c2ccc(C3(c4noc(N5CC[C@H](O)C5)n4)CCC3)cc2)cn1] | (S)-1-(3-{1-[4-(2-Amino-pyrimidin-5-yl)-phenyl]-cyclobutyl}-[1,2,4]oxadiazol-5-yl)-pyrrolidin-3-ol |

TABLE I-continued

| Example | Structure | Name |
|---|---|---|
| 288 | 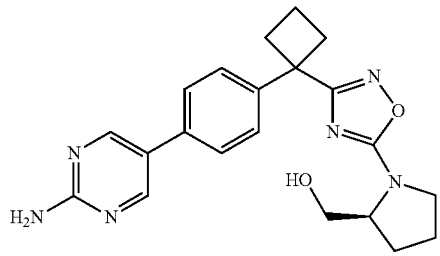 [SMILES: Nc1ncc(-c2ccc(C3(c4noc(N5CCC[C@H]5CO)n4)CCC3)cc2)cn1] | [(S)-1-(3-{1-[4-(2-Amino-pyrimidin-5-yl)-phenyl]-cyclobutyl}-[1,2,4]oxadiazol-5-yl)-pyrrolidin-2-yl]-methanol |
| 289 | 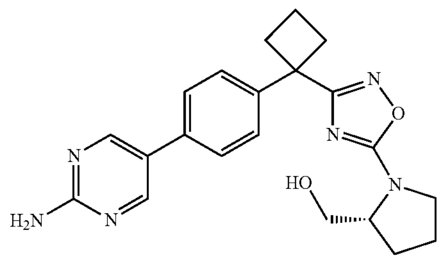 [SMILES: Nc1ncc(-c2ccc(C3(c4noc(N5CCC[C@@H]5CO)n4)CCC3)cc2)cn1] | [(R)-1-(3-{1-[4-(2-Amino-pyrimidin-5-yl)-phenyl]-cyclobutyl}-[1,2,4]oxadiazol-5-yl)-pyrrolidin-2-yl]-methanol |
| 290 | 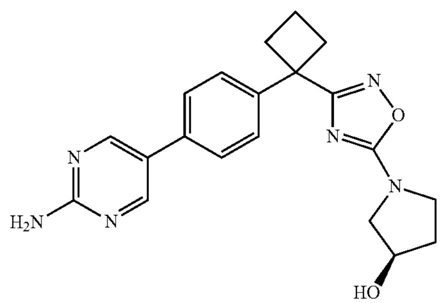 [SMILES: Nc1ncc(-c2ccc(C3(c4noc(N5CC[C@@H](O)C5)n4)CCC3)cc2)cn1] | (R)-1-(3-{1-[4-(2-Amino-pyrimidin-5-yl)-phenyl]-cyclobutyl}-[1,2,4]oxadiazol-5-yl)-pyrrolidin-3-ol |
| 291 | 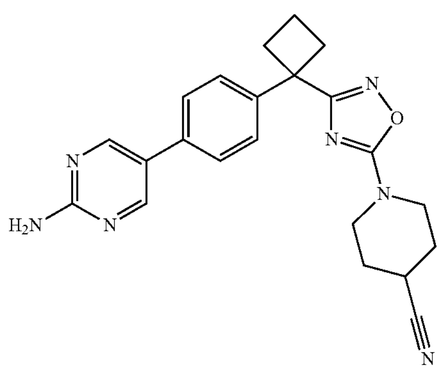 [SMILES: N#CC1CCN(c2nc(C3(c4ccc(-c5cnc(N)nc5)cc4)CCC3)no2)CC1] | 1-(3-{1-[4-(2-Amino-pyrimidin-5-yl)-phenyl]-cyclobutyl}-[1,2,4]oxadiazol-5-yl)-piperidine-4-carbonitrile |
| 292 | 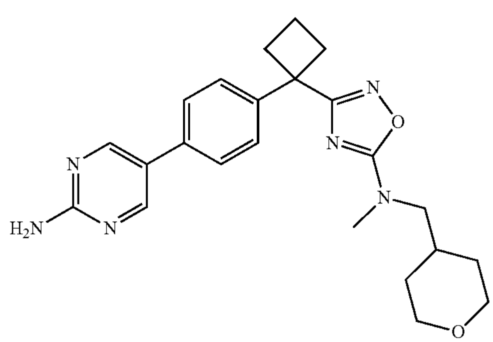 [SMILES: CN(CC1CCOCC1)c1nc(C2(c3ccc(-c4cnc(N)nc4)cc3)CCC2)no1] | 5-[4-(1-{5-[Methyl-(tetrahydro-pyran-4-ylmethyl)-amino]-[1,2,4]oxadiazol-3-yl}-cyclobutyl)-phenyl]-pyrimidin-2-ylamine |

TABLE I-continued

| Example | Structure | Name |
|---|---|---|
| 293 | 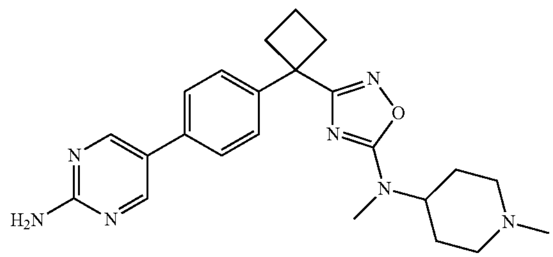 [SMILES: CN1CCC(N(C)c2nc(C3(c4ccc(-c5cnc(N)nc5)cc4)CCC3)no2)CC1] | 5-[4-(1-{5-[Methyl-(1-methyl-piperidin-4-yl)-amino]-[1,2,4]oxadiazol-3-yl}-cyclobutyl)-phenyl]-pyrimidin-2-ylamine |
| 294 | 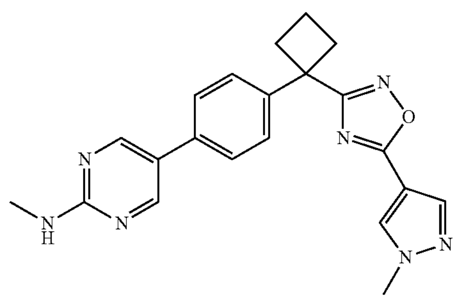 [SMILES: CNc1ncc(-c2ccc(C3(c4noc(-c5cnn(C)c5)n4)CCC3)cc2)cn1] | Methyl-[5-(4-{1-[5-(1-methyl-1H-pyrazol-4-yl)-[1,2,4]oxadiazol-3-yl]-cyclobutyl}-phenyl)-pyrimidin-2-yl]-amine |
| 295 | 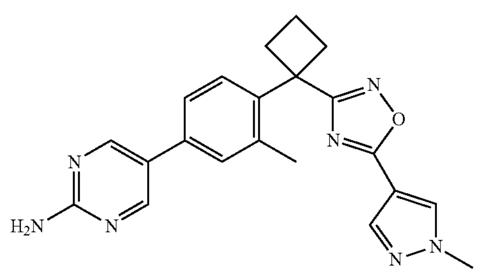 [SMILES: Cc1cc(-c2cnc(N)nc2)ccc1C1(c2noc(-c3cnn(C)c3)n2)CCC1] | 5-(3-Methyl-4-{1-[5-(1-methyl-1H-pyrazol-4-yl)-[1,2,4]oxadiazol-3-yl]-cyclobutyl}-phenyl)-pyrimidin-2-ylamine |
| 296 | 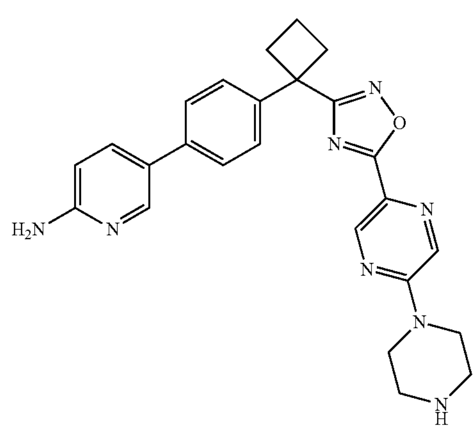 [SMILES: Nc1ccc(-c2ccc(C3(c4noc(-c5cnc(N6CCNCC6)cn5)n4)CCC3)cc2)cn1] | 5-(4-{1-[5-(3,4,5,6-Tetrahydro-2H-[1,2']bipyrazinyl-5'-yl)-[1,2,4]oxadiazol-3-yl]-cyclobutyl}-phenyl)-pyridin-2-ylamine |

TABLE I-continued

| Example | Structure | Name |
|---|---|---|
| 297 | 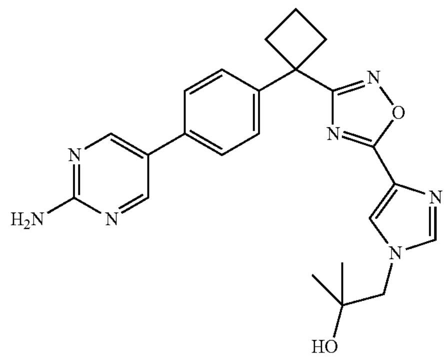 [SMILES: CC(C)(O)Cn1cnc(-c2nc(C3(c4ccc(-c5cnc(N)nc5)cc4)CCC3)no2)c1] | 1-[4-(3-{1-[4-(2-Amino-pyrimidin-5-yl)-phenyl]-cyclobutyl}-[1,2,4]oxadiazol-5-yl)-imidazol-1-yl]-2-methyl-propan-2-ol |
| 298 | 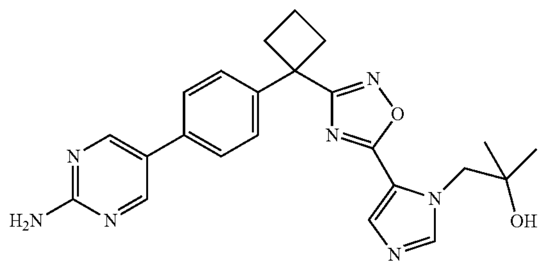 [SMILES: CC(C)(O)Cn1cncc1-c1nc(C2(c3ccc(-c4cnc(N)nc4)cc3)CCC2)no1] | 1-[5-(3-{1-[4-(2-Amino-pyrimidin-5-yl)-phenyl]-cyclobutyl}-[1,2,4]oxadiazol-5-yl)-imidazol-1-yl]-2-methyl-propan-2-ol |
| 299 | 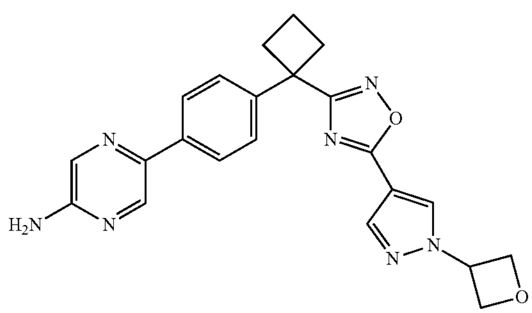 [SMILES: Nc1cnc(-c2ccc(C3(c4noc(-c5cnn(C6COC6)c5)n4)CCC3)cc2)cn1] | 5-(4-{1-[5-(1-Oxetan-3-yl-1H-pyrazol-4-yl)-[1,2,4]oxadiazol-3-yl]-cyclobutyl}-phenyl)-pyrazin-2-ylamine; compound with trifluoro-acetic acid |
| 300 | 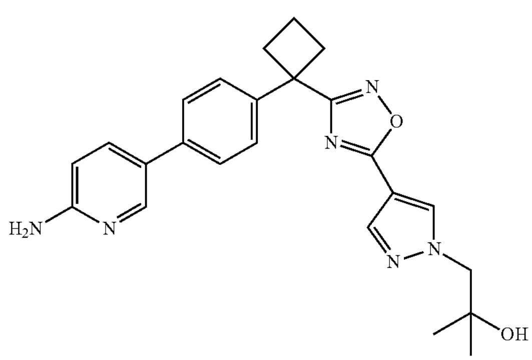 [SMILES: CC(C)(O)Cn1cc(-c2nc(C3(c4ccc(-c5ccc(N)nc5)cc4)CCC3)no2)cn1] | 1-[4-(3-{1-[4-(6-Amino-pyridin-3-yl)-phenyl]-cyclobutyl}-[1,2,4]oxadiazol-5-yl)-pyrazol-1-yl]-2-methyl-propan-2-ol |

TABLE I-continued

| Example | Structure | Name |
|---|---|---|
| 301 | 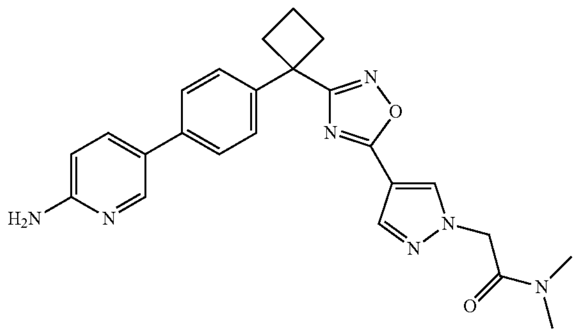 [SMILES: CN(C)C(=O)Cn1cc(-c2nc(C3(c4ccc(-c5ccc(N)nc5)cc4)CCC3)no2)cn1] | 2-[4-(3-{1-[4-(6-Amino-pyridin-3-yl)-phenyl]-cyclobutyl}-[1,2,4]oxadiazol-5-yl)-pyrazol-1-yl]-N,N-dimethyl-acetamide |
| 302 4 | | 5-(4-{1-[5-(3,4,5,6-Tetrahydro-2H-[1,2']bipyrazinyl-5'-yl)-[1,2,4]oxadiazol-3-yl]-cyclobutyl}-phenyl)-pyrazin-2-ylamine |
| 303 | 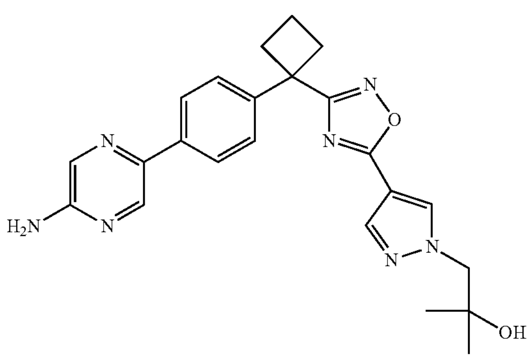 [SMILES: CC(C)(O)Cn1cc(-c2nc(C3(c4ccc(-c5cnc(N)cn5)cc4)CCC3)no2)cn1] | 1-[4-(3-{1-[4-(5-Amino-pyrazin-2-yl)-phenyl]-cyclobutyl}-[1,2,4]oxadiazol-5-yl)-pyrazol-1-yl]-2-methyl-propan-2-ol |
| 304 | 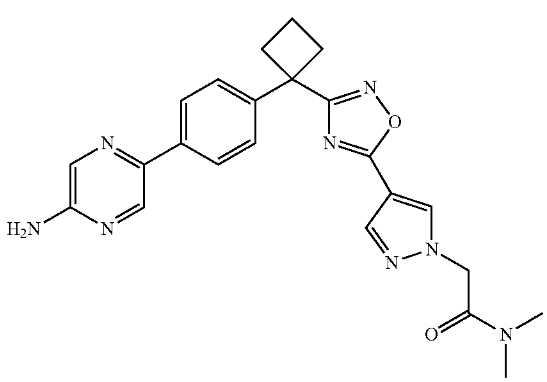 [SMILES: CN(C)C(=O)Cn1cc(-c2nc(C3(c4ccc(-c5cnc(N)cn5)cc4)CCC3)no2)cn1] | 2-[4-(3-{1-[4-(5-Amino-pyrazin-2-yl)-phenyl]-cyclobutyl}-[1,2,4]oxadiazol-5-yl)-pyrazol-1-yl]-N,N-dimethyl-acetamide |

TABLE I-continued

| Example | Structure | Name |
| --- | --- | --- |
| 305 | 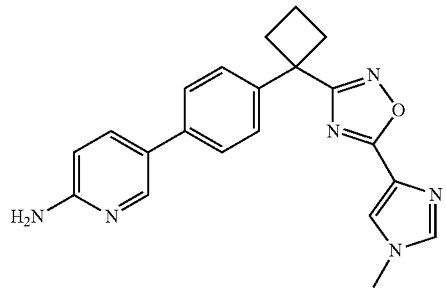 [SMILES: Cn1cnc(-c2nc(C3(c4ccc(-c5ccc(N)nc5)cc4)CCC3)no2)c1] | 5-(4-{1-[5-(1-Methyl-1H-imidazol-4-yl)-[1,2,4]oxadiazol-3-yl]-cyclobutyl}-phenyl)-pyridin-2-ylamine |
| 306 | 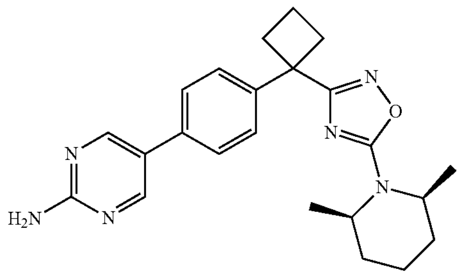 [SMILES: C[C@@H]1CCC[C@H](C)N1c1nc(C2(c3ccc(-c4cnc(N)nc4)cc3)CCC2)no1] | 5-(4-{1-[5-(cis-2,6-Dimethyl-piperidin-1-yl)-[1,2,4]oxadiazol-3-yl]-cyclobutyl}-phenyl)-pyrimidin-2-ylamine |
| 307 | 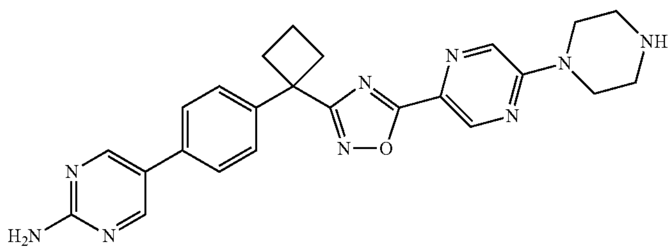 [SMILES: Nc1ncc(-c2ccc(C3(c4noc(-c5cnc(N6CCNCC6)cn5)n4)CCC3)cc2)cn1] | 5-(4-{1-[5-(3,4,5,6-Tetrahydro-2H-1,2'-bipyrazinyl-5'-yl)-1,2,4-oxadiazol-3-yl]-cyclobutyl}-phenyl)-pyrimidin-2-ylamine |
| 308 | 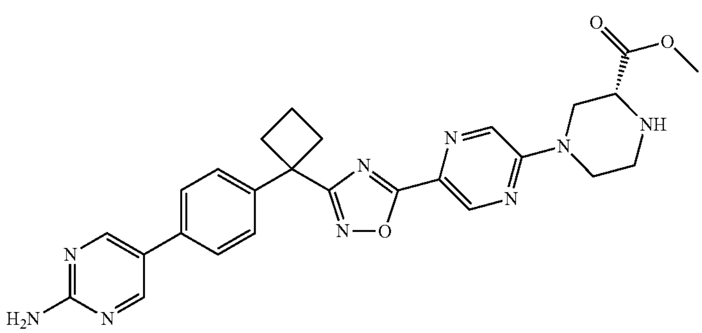 [SMILES: COC(=O)[C@H]1CN(c2cnc(-c3nc(C4(c5ccc(-c6cnc(N)nc6)cc5)CCC4)no3)cn2)CCN1] | (R)-5'-(3-{1-[4-(2-Amino-pyrimidin-5-yl)-phenyl]-cyclobutyl}-1,2,4-oxadiazol-5-yl)-3,4,5,6-tetrahydro-2H-1,2'-bipyrazinyl-3-carboxylic acid methyl ester |
| 309 | 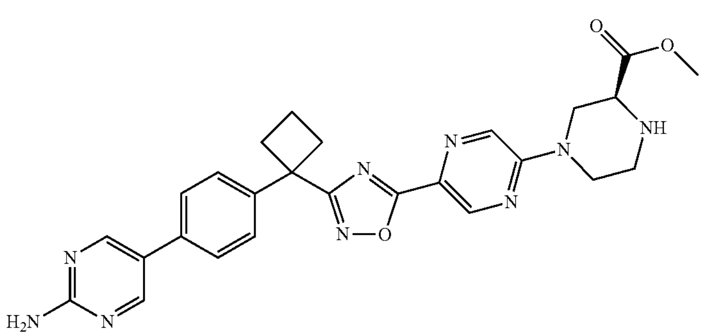 [SMILES: COC(=O)[C@@H]1CN(c2cnc(-c3nc(C4(c5ccc(-c6cnc(N)nc6)cc5)CCC4)no3)cn2)CCN1] | (S)-5'-(3-{1-[4-(2-Amino-pyrimidin-5-yl)-phenyl]-cyclobutyl}-1,2,4-oxadiazol-5-yl)-3,4,5,6-tetrahydro-2H-1,2'-bipyrazinyl-3-carboxylic acid methyl ester |

In one embodiment, the invention relates to any of the compounds depicted in Table I above and the pharmaceutically acceptable salt thereof.

Representative compounds of the invention show activity in the FLAP binding assay and in the human whole blood $LTB_4$ production inhibition assay, described in the assessment of biological properties section, as shown in Table II.

TABLE II

| Example | FLAP SPA $IC_{50}$ (nM) | hWB $LTB_4$ $IC_{50}$ (nM) |
|---|---|---|
| 1 | 8.4 | 330 |
| 2 | 2.2 | 100 |
| 3 | 5.6 | 350 |
| 4 | 4.6 | 720 |
| 5 | 2.4 | >5000 |
| 6 | 1.1 | 150 |
| 7 | 2.4 | 50 |
| 8 | 8.5 | 400 |
| 9 | 7.0 | 2000 |
| 10 | 2.1 | 290 |
| 11 | 120 | 1300 |
| 12 | 8.3 | 470 |
| 13 | 170 | >5000 |
| 14 | 57 | >5000 |
| 15 | 20 | 440 |
| 16 | 3.3 | >5000 |
| 17 | 2.1 | 180 |
| 18 | 2.9 | 300 |
| 19 | 11 | 1400 |
| 20 | 1.9 | 63 |
| 21 | 3.1 | 160 |
| 22 | 2.6 | 140 |
| 23 | 4.2 | 73 |
| 24 | 11 | 460 |
| 25 | 21 | 690 |
| 26 | 160 | 1600 |
| 27 | 340 | >5000 |
| 28 | 4.3 | 320 |
| 29 | 6.9 | 190 |
| 30 | 6.5 | 230 |
| 31 | 3 | 1300 |
| 32 | 4.6 | 77 |
| 33 | 4.0 | 550 |
| 34 | 7.7 | 780 |
| 35 | 3.6 | 600 |
| 36 | 4.3 | 260 |
| 37 | 3.7 | 340 |
| 38 | 2.4 | >5000 |
| 39 | 12 | 800 |
| 40 | 4.7 | 2100 |
| 41 | 8.1 | 930 |
| 42 | 8.4 | 690 |
| 43 | 3.2 | 230 |
| 44 | 3.1 | 75 |
| 45 | 7.9 | 950 |
| 46 | 7.5 | 1500 |
| 47 | 15 | 2400 |
| 48 | 2.5 | 430 |
| 49 | 3.7 | 660 |
| 50 | 4.4 | 490 |
| 51 | 7.0 | 1000 |
| 52 | 4.3 | 780 |
| 53 | 6.2 | 580 |
| 54 | 15 | 1200 |
| 55 | 13 | 1100 |
| 56 | 8.4 | 990 |
| 57 | 1.8 | 45 |
| 58 | 2.0 | >5000 |
| 59 | 5.1 | 130 |
| 60 | 4.7 | 150 |
| 61 | 1.5 | 53 |
| 62 | 1.3 | 13 |
| 63 | 1.0 | 25 |
| 64 | 7.7 | 310 |
| 65 | 5.9 | 97 |
| 66 | 8.4 | 120 |
| 67 | 12 | 290 |
| 68 | 1.1 | 130 |
| 69 | 2.4 | 65 |
| 70 | 3.0 | 220 |
| 71 | 2.4 | 200 |
| 72 | 1.9 | 18 |
| 73 | 6.8 | 450 |
| 74 | 71 | 520 |
| 75 | 3.5 | 190 |
| 76 | 3.9 | 190 |
| 77 | 2.6 | 160 |
| 78 | 8.8 | 160 |
| 79 | 3.5 | 69 |
| 80 | 6.5 | 390 |
| 81 | 6.4 | 130 |
| 82 | 3.1 | 99 |
| 83 | 4.0 | 110 |
| 84 | 4.0 | 160 |
| 85 | 1.3 | 71 |
| 86 | 1.2 | 79 |
| 87 | 4.5 | 150 |
| 88 | 6.3 | 160 |
| 89 | 1.9 | 43 |
| 90 | 3.4 | 210 |
| 91 | 3.7 | 151 |
| 92 | 4.9 | 150 |
| 93 | 2.4 | 160 |
| 94 | 6.1 | 560 |
| 95 | 3.2 | 130 |
| 96 | 13 | 2700 |
| 97 | 2.9 | 92 |
| 98 | 2.3 | 110 |
| 99 | 2.0 | 150 |
| 100 | 2.1 | 170 |
| 101 | 3.3 | 250 |
| 102 | 2.5 | 180 |
| 103 | 1.3 | 63 |
| 104 | 1.3 | 99 |
| 105 | 1.9 | 78 |
| 106 | 2.7 | 130 |
| 107 | 1.4 | 98 |
| 108 | 1.3 | 110 |
| 109 | 1.3 | 98 |
| 110 | 0.92 | 110 |
| 111 | 1.2 | 32 |
| 112 | 1.4 | 760 |
| 113 | 1.6 | 100 |
| 114 | 2.6 | 290 |
| 115 | 3.3 | 140 |
| 116 | 1.8 | 150 |
| 117 | 2.6 | 140 |
| 118 | 21 | 1700 |
| 119 | 40 | 790 |
| 120 | 9.1 | 740 |
| 121 | 4.9 | 450 |
| 122 | 14 | 360 |
| 123 | 35 | 1500 |
| 124 | 3.5 | >5000 |
| 125 | 5.0 | >5000 |
| 126 | 5.7 | >5000 |
| 127 | 3.2 | 120 |
| 128 | 6.7 | 180 |
| 129 | 3.9 | 140 |
| 130 | 1.5 | 75 |
| 131 | 3.9 | 88 |
| 132 | 2.8 | 69 |
| 133 | 4.3 | 72 |
| 134 | 5.8 | 120 |
| 135 | 10.4 | 190 |
| 136 | 1.5 | 66 |
| 137 | 7.7 | 170 |
| 138 | 2.8 | 38 |
| 139 | 2.6 | 95 |
| 140 | 4.4 | 68 |
| 141 | 0.9 | 43 |
| 142 | 1.1 | 40 |
| 143 | 2.2 | 250 |
| 144 | 1.4 | 470 |

TABLE II-continued

| Example | FLAP SPA IC$_{50}$ (nM) | hWB LTB$_4$ IC$_{50}$ (nM) |
|---|---|---|
| 145 | 78 | >5000 |
| 146 | 27 | 840 |
| 147 | 33 | 1700 |
| 148 | 46 | 3300 |
| 149 | 15 | >5000 |
| 150 | 180 | >5000 |
| 151 | 210 | >5000 |
| 152 | 3.5 | 210 |
| 153 | 2.5 | 270 |
| 154 | 1.7 | 810 |
| 155 | 2.8 | 400 |
| 156 | 13 | >5000 |
| 157 | 4.1 | 690 |
| 158 | 5.7 | 360 |
| 159 | 6.0 | 340 |
| 160 | 6.2 | 240 |
| 161 | 6.6 | 860 |
| 162 | 6.4 | 1000 |
| 163 | 4.0 | 450 |
| 164 | 5.5 | 570 |
| 165 | 6.0 | 450 |
| 166 | 1.9 | 45 |
| 167 | 5.1 | 660 |
| 168 | 5.5 | 230 |
| 169 | 2.1 | 130 |
| 170 | 2.9 | 390 |
| 171 | 14 | 820 |
| 172 | 4.3 | 260 |
| 173 | 2.9 | >5000 |
| 174 | 5.3 | 510 |
| 175 | 2.3 | 110 |
| 176 | 5.6 | 410 |
| 177 | 98 | 1300 |
| 178 | 61 | >5000 |
| 179 | 12 | 1400 |
| 180 | 0.85 | 73 |
| 181 | 1.2 | 62 |
| 182 | 1.1 | 40 |
| 183 | 0.88 | 53 |
| 184 | 2.6 | 140 |
| 185 | 7.3 | 230 |
| 186 | 12 | 710 |
| 187 | 8.4 | 3400 |
| 188 | 6.2 | 81 |
| 189 | 8.1 | 310 |
| 190 | 1.2 | 27 |
| 191 | 2.6 | >5000 |
| 192 | 1.7 | >5000 |
| 193 | 1.6 | 45 |
| 194 | 3.0 | 85 |
| 195 | 2.9 | 140 |
| 196 | 2.1 | 24 |
| 197 | 1.5 | 48 |
| 198 | 2.0 | 57 |
| 199 | 1.0 | 42 |
| 200 | 1.5 | 67 |
| 201 | 2.3 | 400 |
| 202 | 2.6 | 70 |
| 203 | 1.9 | 130 |
| 204 | 4.5 | 75 |
| 205 | 5.8 | 120 |
| 206 | 4.3 | 38 |
| 207 | 2.7 | 40 |
| 208 | 2.8 | 52 |
| 209 | 1.0 | 27 |
| 210 | 4.6 | 110 |
| 211 | 3.0 | 89 |
| 212 | 2.2 | 22 |
| 213 | 0.85 | 110 |
| 214 | 4.0 | 150 |
| 215 | 2.1 | 26 |
| 216 | 1.3 | 59 |
| 217 | 3.4 | 81 |
| 218 | 1.2 | 160 |
| 219 | 3.1 | 140 |
| 220 | 0.7 | 16 |
| 221 | 1.9 | 47 |
| 222 | 2.2 | 44 |
| 223 | 1.8 | 460 |
| 224 | 2.8 | 64 |
| 225 | 0.89 | >5000 |
| 226 | 1.2 | 45 |
| 227 | 2.6 | 240 |
| 228 | 3.3 | 160 |
| 229 | 6.0 | 410 |
| 230 | 1.3 | 64 |
| 231 | 2.3 | 61 |
| 232 | 1.8 | 26 |
| 233 | 9.8 | 700 |
| 234 | 3.5 | 82 |
| 235 | 1.7 | 67 |
| 236 | 5.6 | 230 |
| 237 | 2.0 | >5000 |
| 238 | 1.0 | 37 |
| 239 | 6.2 | 2500 |
| 240 | 3.6 | 47 |
| 241 | 3.5 | 140 |
| 242 | 5.4 | 120 |
| 243 | 8.5 | 200 |
| 244 | 250 | >5000 |
| 245 | 38 | 1700 |
| 246 | 8.1 | 79 |
| 247 | 8.2 | 88 |
| 248 | 730 | >5000 |
| 249 | 7.8 | 69 |
| 250 | 8.6 | 220 |
| 251 | 36 | 2200 |
| 252 | 5.3 | 34 |
| 253 | 8.1 | 75 |
| 254 | 190 | 4700 |
| 255 | 150 | 1900 |
| 256 | 22 | 220 |
| 257 | 100 | 2200 |
| 258 | 73 | 610 |
| 259 | 16 | 210 |
| 260 | 76 | 2000 |
| 261 | 9.3 | 240 |
| 262 | 2.4 | 27 |
| 263 | 16 | 190 |
| 264 | 8.3 | 280 |
| 265 | 6.2 | 55 |
| 266 | 6.5 | 160 |
| 267 | 4.0 | 60 |
| 268 | 670 | >5000 |
| 269 | 5.6 | 320 |
| 270 | 5.4 | 46 |
| 271 | 5.3 | 44 |
| 272 | 3.8 | 79 |
| 273 | 3.9 | 79 |
| 274 | 8.8 | 220 |
| 275 | 2.8 | 140 |
| 276 | 7.0 | 110 |
| 277 | 260 | 2800 |
| 278 | 78 | 1700 |
| 279 | 29 | >5000 |
| 280 | 17 | 1400 |
| 281 | 62 | 1400 |
| 282 | 26 | 1100 |
| 283 | 60 | 1400 |
| 284 | 18 | 120 |
| 285 | 22 | 330 |
| 286 | 14 | 200 |
| 287 | 36 | 200 |
| 288 | 26 | 310 |
| 289 | 31 | 500 |
| 290 | 35 | 230 |
| 291 | 19 | 210 |
| 292 | 22 | 330 |
| 293 | 150 | 750 |
| 294 | 4.4 | 35 |
| 295 | 12 | 100 |
| 296 | 2.1 | 230 |
| 297 | 46 | 520 |
| 298 | 16 | 510 |

TABLE II-continued

| Example | FLAP SPA IC$_{50}$ (nM) | hWB LTB$_4$ IC$_{50}$ (nM) |
|---|---|---|
| 299 | 2.9 | 24 |
| 300 | 8.4 | 89 |
| 301 | 6.0 | 140 |
| 302 | 2.6 | 150 |
| 303 | 7.3 | 31 |
| 304 | 10 | 65 |
| 305 | 15 | 120 |
| 306 | 12 | 580 |
| 307 | 3.5 | 150 |
| 308 | 5.0 | 480 |
| 309 | 5.7 | 760 |

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g. $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-6}$alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylhio" refer to alkyl groups linked to a second group via an oxygen or sulfur atom. "Alkanoyl" refers to an alkyl group linked to a carbonyl group (C═O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain.

Such groups can be substituted as herein above described by groups such as oxo to result in definitions such as but not limited to: alkoxycarbonyl, acyl, amido and thioxo. As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term $C_{1-3}$ hydroxy also means $C_{1-3}$alkylhydroxy or $C_{1-3}$alkyl-OH.

The term "$C_{3-10}$ carbocycle" or $C_{3-10}$ cycloalkyl refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ carbocycle may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo [2.2.2]heptanyl, [2.2.1]heptanyl bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "$C_{6-10}$ aryl" or "aryl" refers to aromatic hydrocarbon rings containing from six to ten carbon ring atoms. The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "5 to 11-membered heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, tetrahydropyranyl, oxetanyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

The term "5 to 11-membered heteroaryl" shall be understood to mean an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl, pyrazolopyrimidinyl, imidazopyridinyl, pyrrolopyridinyl, dihydropyrrolopyridinyl, pyrrolopyrimidinyl, pyrrolopyridazinyl, pyrrolopyrazinyl pyrazolopyridinyl, pyrazolopyrimidinyl, indazolyl and benzothiazolyl. It will be further understood that any of the above heteroaryl rings may be partially hydrogenated.

It will be understood that one to three carbon ring moieties in the each of the $C_{3-10}$ carbocyclic rings, the 5 to 11-membered heterocyclic rings, the nonaromatic portion of the bicyclic aryl rings, and the nonaromatic portion of the bicyclic heteroaryl rings can independently be replaced with a carbonyl, thiocarbonyl, or iminyl moiety, i.e., —C(=O)—, —C(=S)— and —C(=NR$^8$)—, respectively, where R$^8$ is as defined above.

The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C$_1$-C$_4$ alkyl)$_4$$^+$salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention also provides processes for making compounds of Formula (I). In all Schemes, unless specified otherwise, R$^1$, R$^2$, R$^3$, R$^4$ and R$^5$ in the Formulas below shall have the meaning of R$^1$, R$^2$, R$^3$, R$^4$ and R$^5$ in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the Schemes below, are either commercially available or easily prepared from commercially available materials by those skilled in the art.

The compounds of Formula (I) may be synthesized according to Scheme 1:

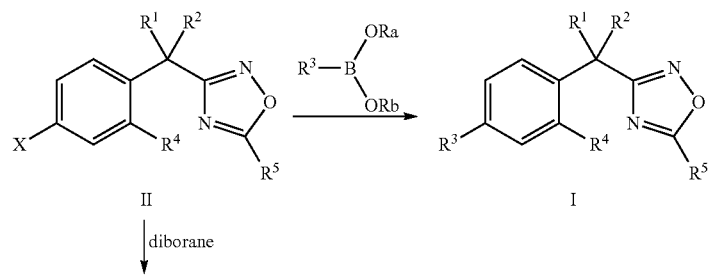

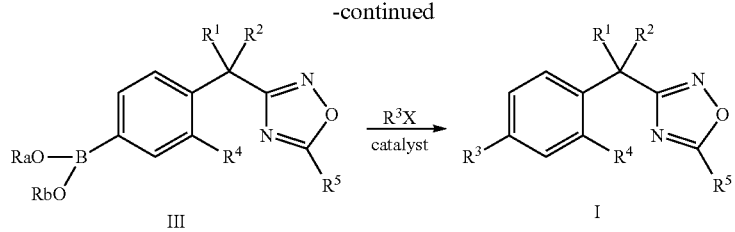

As illustrated in scheme 1, reaction of a compound of formula II with a boronic acid or the corresponding boronic acid ester shown in the above scheme, in a suitable solvent, in the presence of a suitable a suitable catalyst, provides a compound of formula (I). Ra and Rb are hydrogen or Ra and Rb together with the oxygen atoms to which they are attached form a 5-6 membered ring optionally substituted with 2-4 methyl groups.

Alternatively, reaction of a compound of formula II with a diborane, under standard reaction conditions, provides a compound of formula III. Coupling the intermediate of formula III with a halide or triflate $R^3X$, in a suitable solvent, in the presence of a suitable catalyst, provides a compound of formula (I). X is chloro, bromo, triflate, or iodo. A compound of formula (I) may also be prepared by reacting a compound of formula (II) with a halide of formula $R^3X$, wherein X is a halogen atom, in a suitable solvent, in the presence of a suitable palladium catalyst and hexamethylstannane.

The compounds of Formula (I) may be prepared according to Scheme 2:

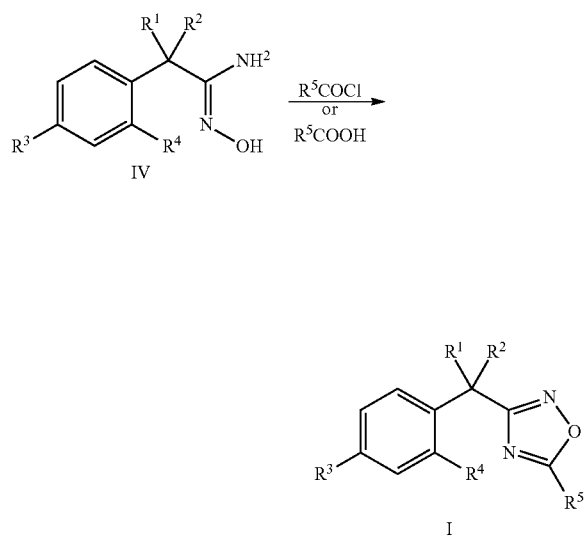

As illustrated in scheme 2, reaction of a compound of formula IV with an acid chloride $R^5COCl$, in a suitable solvent, in the presence of a suitable base, provides a compound of formula (I).

Alternatively, reaction of a compound of formula IV with an acid $R^5COOH$, in a suitable solvent, in the presence of carbonyl diimidazole, or other suitable amide coupling reagent, provides a compound of formula (I).

The intermediate of formula II may be synthesized as outlined in Scheme 3:

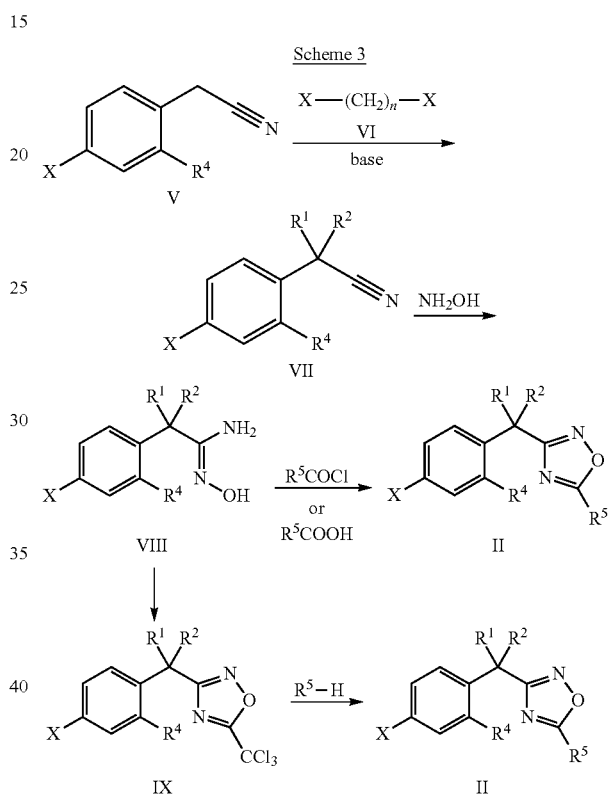

As illustrated in scheme 3, reaction of a nitrile of formula V with a dihalide VI wherein one of the carbon atoms in the alkyl chain may be optionally substituted with O, S or N, in a suitable solvent, in the presence of a suitable base such as sodium hydride, provides a substituted nitrile of formula VII. $R^1$ and $R^2$ together with the carbon atom to which they are attached form a $C_{3-8}$ carbocyclic or heterocyclic ring. X is chloro, bromo, or iodo. Reaction of the compound of formula VII with hydroxylamine, under standard reaction conditions, provides a compound of formula VIII. Reaction of the compound of formula VIII with an acid chloride $R^5COCl$, in a suitable solvent, in the presence of a suitable base, provides a compound of formula II. Alternatively, reaction of a compound of formula VIII with an acid $R^5COOH$, in a suitable solvent, in the presence of carbonyl diimidazole, or other suitable amide coupling reagent, provides a compound of formula II.

Intermediate of formula VIII may also be converted to the trichloromethyl intermediate of formula IX by standard procedures. Reaction of the intermediate IX with $R^5H$ when $R^5H$ contains a primary or secondary amino group, in a suitable solvent provides an intermediate of formula II The intermediate of formula II may also be synthesized as shown in Scheme 4:

Scheme 4

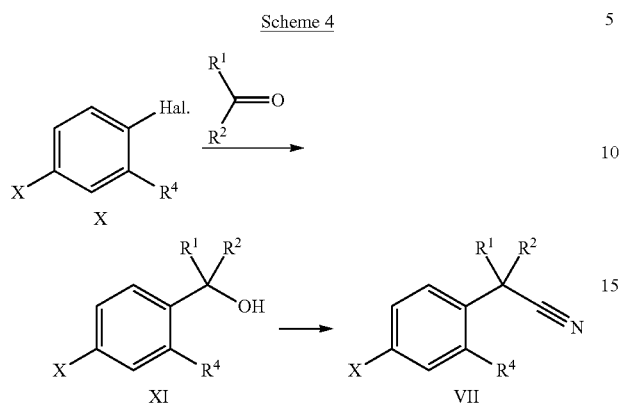

As shown in scheme 4, when X=H, reaction of a compound of formula X with a carbonyl compound, in a suitable solvent, provides a hydroxy compound of formula XI. Conversion of the hydroxyl group in compound of formula XI to a cyano group, using standard procedures, provides a compound of formula VII. The compound of formula VII is converted to the intermediate of formula II by the reactions shown in scheme 3.

The intermediate of formula IV may be synthesized according to Scheme 5:

Scheme 5

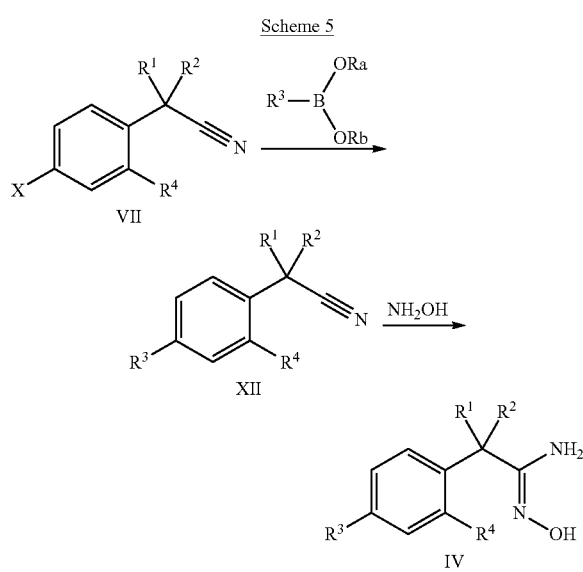

As illustrated above in scheme 5, reaction of a nitrile of formula VII with a boronic acid or the corresponding boronic acid ester shown in the above scheme, in a suitable solvent, in the presence of a suitable catalyst, provides a compound of formula XII. Ra and Rb are hydrogen or Ra and Rb together with the oxygen atoms to which they are attached form a 5-6 membered ring optionally substituted with 2-4 methyl groups. Reaction of a compound of formula XI with hydroxylamine, under standard reaction conditions, provides a compound of formula IV.

Further modification of the initial product of Formula (I), by methods known in the art and illustrated in the Examples below, may be used to prepare additional compounds of this invention.

SYNTHETIC EXAMPLES

Preparation of Intermediates

Nitrile Intermediate

Synthesis of
1-(4-bromo-phenyl)-cyclobutanecarbonitrile
(Intermediate I-1.1)

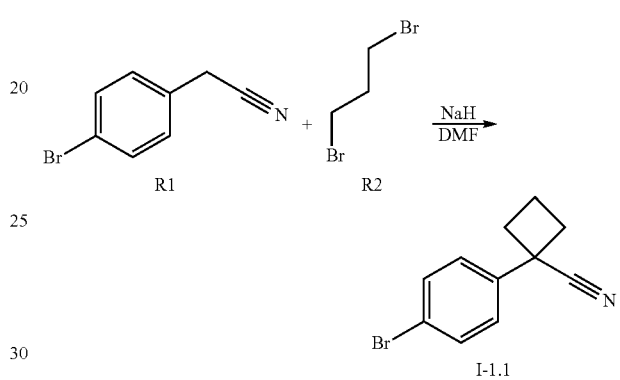

R1 (10 g, 51.009 mmol) is dissolved in DMF (50 mL) and cooled to 0° C. NaH (4.451 g, 102 mmol, 55% in oil) is added slowly and the mixture stirred for 30 minutes. To this R2 (20.593 g, 102 mmol) is added slowly and stirred for 2 h at 0° C. The mixture is quenched with chilled water and extracted with Et$_2$O. The organic layers are combined, washed with brine, dried over anhydrous Na$_2$SO$_4$, filtered and concentrated in vacuo. Purification is done by silica flash column to afford title compound (10 g) as a liquid; m/z 236/238 [M, M+2]

The following compounds are synthesized in a similar fashion from the appropriate reagents:

Intermediate I-1.4 is made using THF/DMSO (1:1) as the solvent and half the concentration.

TABLE 1

Nitrile intermediates

| Intermediate | Structure | m/z |
|---|---|---|
| I-1.2 | 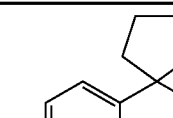 | no ionization |
| I-1.3 | 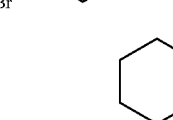 | no ionization |

TABLE 1-continued

Nitrile intermediates

| Intermediate | Structure | m/z |
|---|---|---|
| I-1.4 | 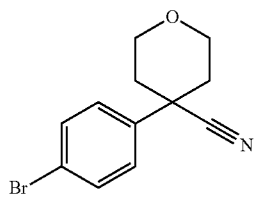 [SMILES: N#CC1(c2ccc(Br)cc2)CCOCC1] | 266.5/268.5 |
| I-1.5 | 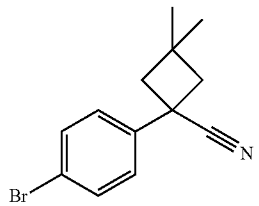 | no ionization |
| I-1.6 | 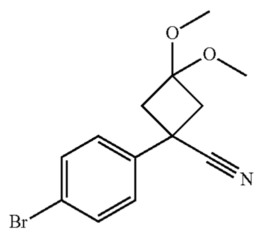 [SMILES: COC1(OC)CC(C#N)(c2ccc(Br)cc2)C1] | 296/298 |
| I-1.7 | 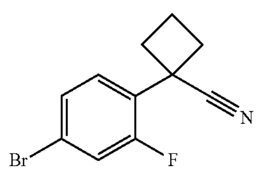 [SMILES: N#CC1(c2ccc(Br)cc2F)CCC1] | no ionization |

Synthesis of 1-(4-bromo-phenyl)-3,3-difluoro-cyclobutanecarbonitrile (Intermediate I-1.9)

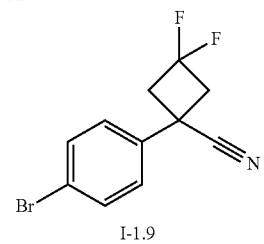

Step 1: Synthesis of 1-(4-bromo-phenyl)-3-oxo-cyclobutanecarbonitrile (I-1.8)

I-1.6 (0.6 g, 2.127 mmol) is dissolved in acetone (5 mL) and 6M HCl (3 mL) is added. The mixture is heated at 90° C. for 5 hours. The mixture is concentrated in vacuo and diluted with EtOAc/saturated aqueous NaHCO₃. The organic phase is separated, washed with brine, dried over Na₂SO₄, filtered and concentrated in vacuo. The crude material is purified by flash chromatography (SiO₂, 0-20% EtOAc/heptanes) to afford title compound (0.426 g) as an oil. Title compound does not ionize.

Step 2: Synthesis of 1-(4-bromo-phenyl)-3,3-difluoro-cyclobutanecarbonitrile (I-1.9)

I-1.8 (0.426 g, 1.699 mmol) is dissolved in DCM (10 mL) and cooled to −10° C. DAST (0.6 mL, 4.578 mmol) is added and the mixture is warmed to room temperature and stirred overnight. The mixture is diluted with DCM and quenched with saturated aqueous NaHCO₃ slowly. The organic layer is separated, washed with brine, dried over Na₂SO₄, filtered and concentrated in vacuo. The crude is purified by flash chromatography (SiO₂, 0-15% EtOAc/heptanes) to afford title compound (0.385 g) as an oil. Title compound does not ionize.

Synthesis of I-1-[4-(2-amino-pyrimidin-5-yl)-phenyl]-cyclobutanecarbonitrile (Intermediate I-1.10)

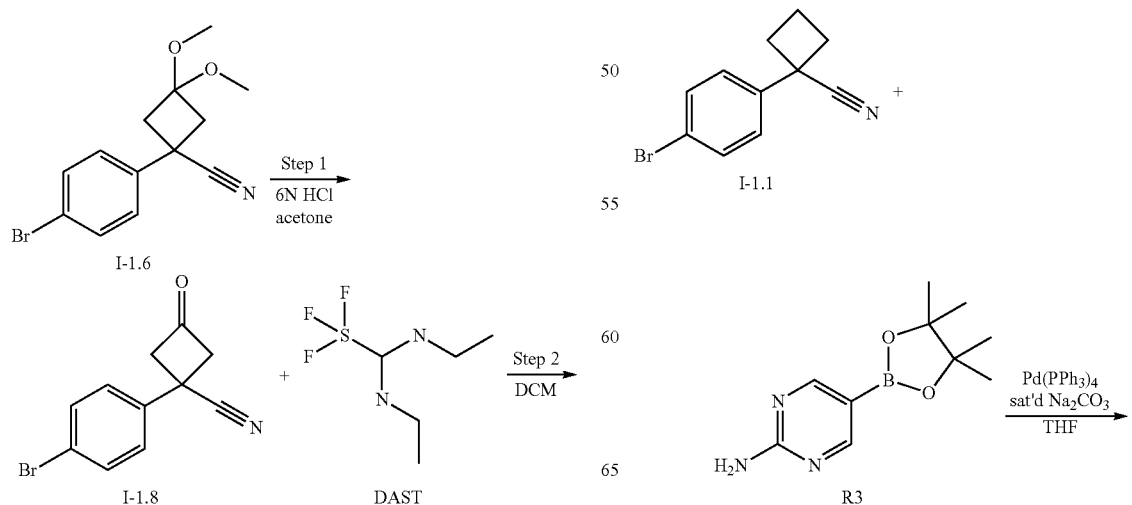

-continued

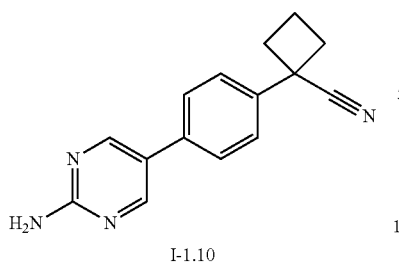

I-1.10

To a suspension of I-1.1 (10 g, 42.353 mmol) and R3 (11.235 g, 50.824 mmol) in THF (100 mL) is added Pd(PPh$_3$)$_4$ (4.894 g, 4.235 mmol) and saturated aqueous Na$_2$CO$_3$. The mixture is heated to reflux overnight. The reaction is concentrated in vacuo and purified by flash chromatography (SiO$_2$, 0-3% MeOH/DCM) to afford title compound (10.2 g); m/z 251 [M+H].

The following compounds are synthesized in similar fashion from the appropriate reagents:

TABLE 2

Nitrile intermediates

| Intermediate | Structure | m/z |
|---|---|---|
| I-1.11 | 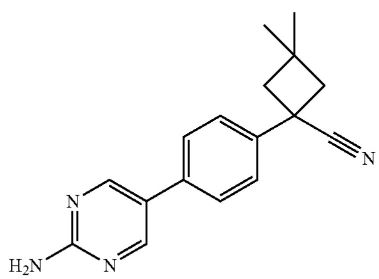 [SMILES: CC1(C)CC(C#N)(c2ccc(-c3cnc(N)nc3)cc2)C1] | 312.4 |
| I-1.12 | 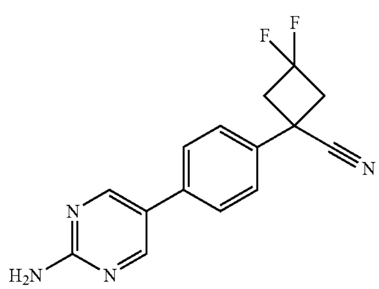 [SMILES: N#CC1(c2ccc(-c3cnc(N)nc3)cc2)CC(F)(F)C1] | 320.3 |
| I-1.13 | 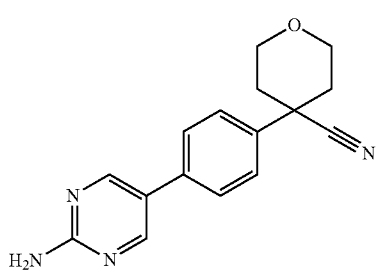 [SMILES: N#CC1(c2ccc(-c3cnc(N)nc3)cc2)CCOCC1] | 281.5 |

Synthesis of 1-[4-(2-amino-pyrimidin-5-yl)-phenyl]-cyclopropanecarbonitrile

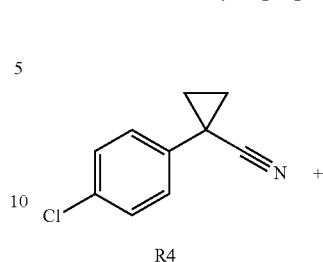

I-1.14

In a vial is added R4 (500 mg, 2.815 mmol), R3 (653 mg, 2.956 mmol), K$_3$PO$_4$ (945 mg, 4.45 mmol) and Pd$_2$(dba)$_3$ (128 mg, 0.14 mmol). The vial is evacuated and back filled with N$_2$ three times. 1,4-Dioxane (10 mL, degassed with N$_2$) is added to the vial followed by the addition of water (3.4 mL). The vial is evacuated and purged with N2 and then heated at 70° C. for 18 hours. After this time, the reaction mixture is filtered and the solid is washed with methanol (MeOH), dichloromethane (DCM) and ethyl acetate (EtOAc). The filtrate is concentrated in vacuo. The resulting mixture is diluted with water and extracted with EtOAc twice. The organics are combined, washed with brine, dried over Na$_2$SO$_4$, filtered and concentrated in vacuo. The crude residue is purified by flash chromatography (SiO$_2$, 1.2-10% MeOH/DCM) to afford the title compound (604 mg) as a solid; m/z 237.1 [M+1].

Carboxamidine Intermediate

Synthesis of 1-(4-bromo-phenyl)-N-hydroxy-cyclobutanecarboxamidine (Intermediate I-2.1)

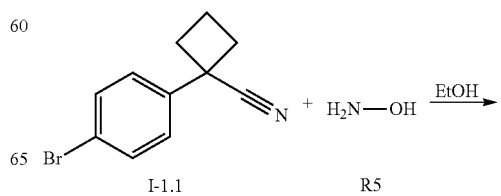

I-1.1     R5

-continued

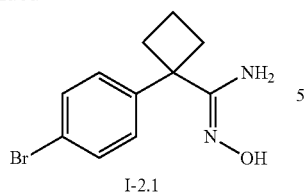
I-2.1

I-1.1 (10 g, 42.353 mmol), R5 (200 mL, 50% wt solution in water), and ethanol (EtOH) (200 mL) are heated at 80° C. overnight. The mixture is cooled and concentrated in vacuo to aqueous which is extracted with DCM. The combined organics are dried over $Na_2SO_4$, filtered and concentrated in vacuo to afford title compound (10.68 g) as an oil; m/z 269/271 [M, M+2].

The following compounds are synthesized in similar fashion from the appropriate reagents:

TABLE 3

Carboxamidine intermediates

| Intermediate | Structure | m/z |
|---|---|---|
| I-2.2 | 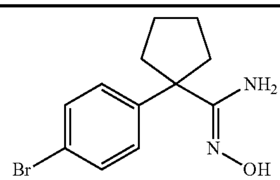 | 283/285 |
| I-2.3 | 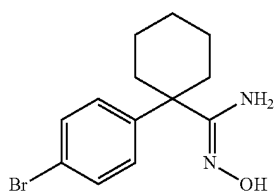 [SMILES: N/C(=N\O)C1(c2ccc(Br)cc2)CCCCC1] | 297/299 |
| I-2.4 | 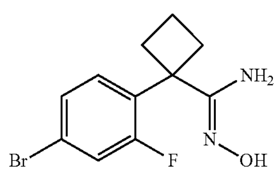 [SMILES: N/C(=N\O)C1(c2ccc(Br)cc2F)CCC1] | 287/289 |

Synthesis of I-1-[4-(2-amino-pyrimidin-5-yl)-phenyl]-N-hydroxy-cyclobutanecarboxamidine (Intermediate I-2.5)

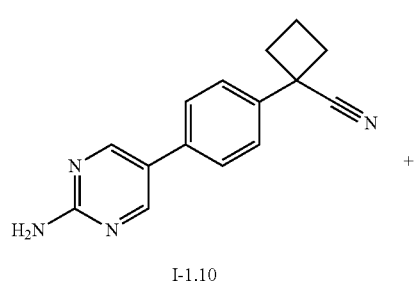
I-1.10

-continued $H_2N$—OH ⟶

R5

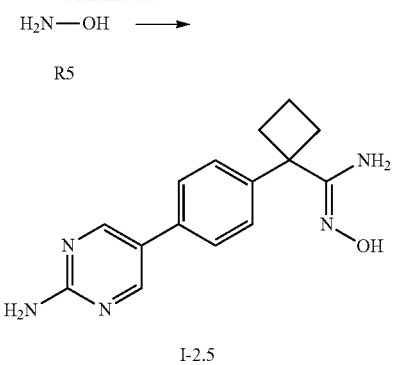
I-2.5

Synthesis same as described for intermediate I-2.1; m/z 284 [M+H]

The following compounds are synthesized in similar fashion from the appropriate reagents:

TABLE 4

Carboxamidine intermediates

| Intermediate | Structure | m/z |
|---|---|---|
| I-2.6 | 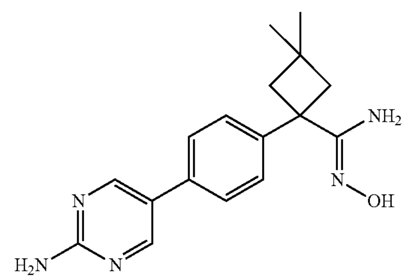 [SMILES: CC1(C)CC(/C(N)=N/O)(c2ccc(-c3cnc(N)nc3)cc2)C1] | 312.36 |
| I-2.7 | 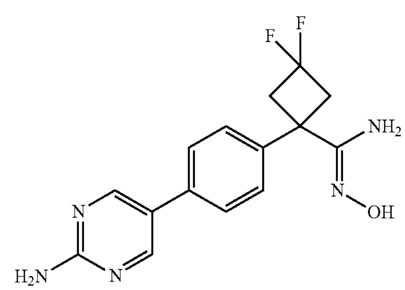 [SMILES: N/C(=N\O)C1(c2ccc(-c3cnc(N)nc3)cc2)CC(F)(F)C1] | 320.3 |
| I-2.8 | 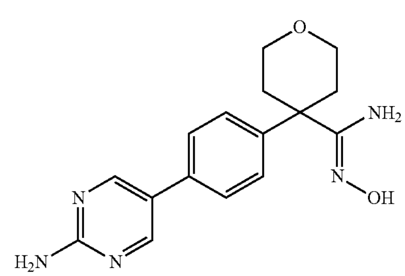 [SMILES: N/C(=N\O)C1(c2ccc(-c3cnc(N)nc3)cc2)CCOCC1] | no data |

TABLE 4-continued

Carboxamidine intermediates

| Intermediate | Structure | m/z |
|---|---|---|
| I-2.9 | 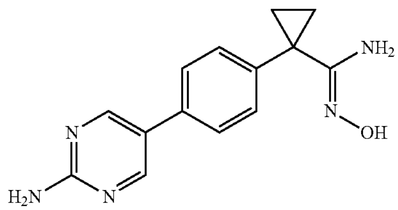 [SMILES: N/C(=N\O)C1(c2ccc(-c3cnc(N)nc3)cc2)CC1] | 270.16 |

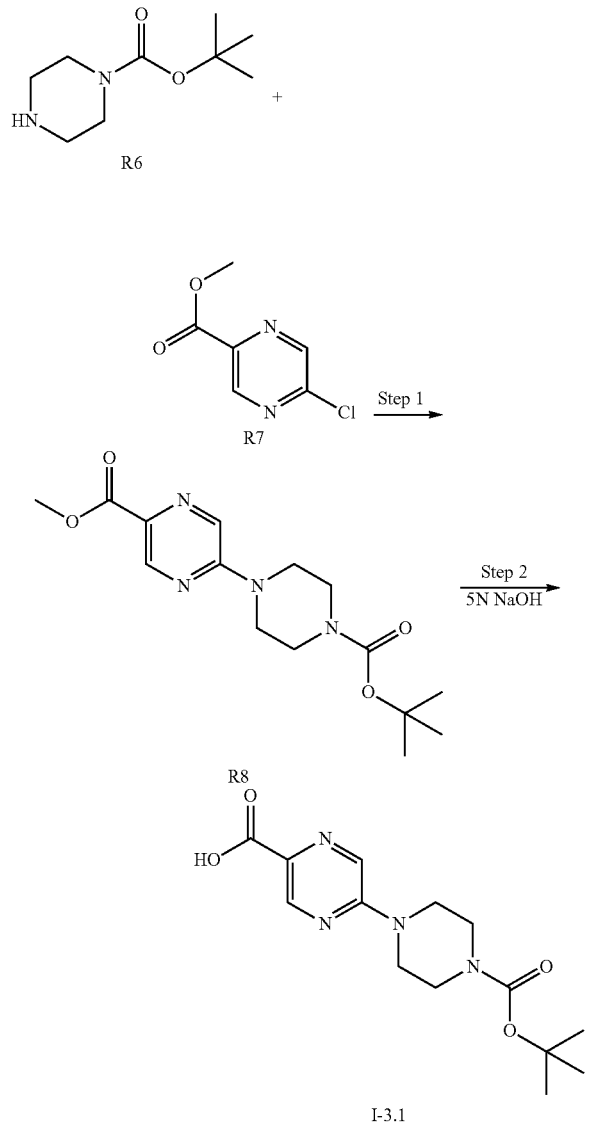

Carboxylic Acid Intermediates

Synthesis of 2,3,5,6-Tetrahydro-[1,2']bipyrazinyl-4,5'-dicarboxylic acid 4-tert-butyl ester (Intermediate I-3.1)

Step 1: Synthesis of 2,3,5,6-Tetrahydro-[1,2']bipyrazinyl-4,5'-dicarboxylic acid 4-tert-butyl ester 5'-methyl ester (R8)

A 250 ml RB flask is charged with R7 (2.8 g, 16.11 mmol) in 60 mL of NMP. R6 (3.0 g, 16.11 mmol) is added followed by triethylamine (2.7 ml, 19.33 mmol). The reaction is warmed to 60° C. under nitrogen and stirred overnight. After 18 h, the reaction is cooled to room temperature, poured into ice water and the resulting solid R8 is isolated by filtration and used without further purification. (5.0 g)

Step 2: Synthesis of 2,3,5,6-Tetrahydro-[1,2']bipyrazinyl-4,5'-dicarboxylic acid 4-tert-butyl ester R8 (5.0 g, 15.51 mmol) is treated with ethanol (150 ml) and 5N NaOH at room temperature. The mixture becomes homogenous before a persisting precipitate forms. At this time water is added (200 ml) and the resulting solid mass is broken up using a spatula. The reaction is stirred for 4 h and treated with water. The mixture is acidified using acetic acid (AcOH) and the product is extracted into DCM (2×). The combined organics are dried (MgSO4), filtered and concentrated to give the title compound. (4.3 g)

Synthesis of 4-(4-Carboxy-thiazol-2-yl)-piperidine-1-carboxylic acid tert-butyl ester (Intermediate I-3.2)

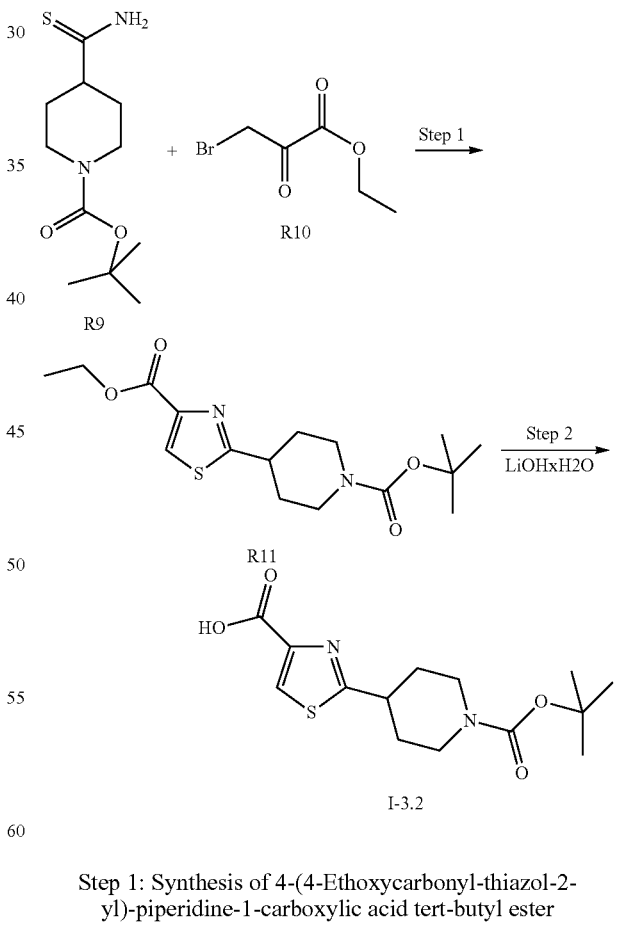

Step 1: Synthesis of 4-(4-Ethoxycarbonyl-thiazol-2-yl)-piperidine-1-carboxylic acid tert-butyl ester (R11)

A solution of R9 (1.0 g, 4.09 mmol) in dimethylformamide (DMF) (5 ml) is cooled to 0° C. under nitrogen. To this mixture is added R10 (0.63 ml, 4.50 mmol) as a DMF solution (5 ml, dropwise addition). Upon complete addition, the reaction is allowed to gradually warm to ambient temperature and stirred over night. After this time the reaction is treated with triethylamine (1 ml, dropwise) and stirred for 10 minutes. The reaction is then poured into water and the product is extracted into EtOAc (3×). The combined organics are dried (MgSO4), filtered and concentrated. The remaining residue is purified via column chromatography (25 g silica gel, 5-50% EtOAc/heptane) to afford R11. (1.0 g)

Step 2: Synthesis of 4-(4-Carboxy-thiazol-2-yl)-piperidine-1-carboxylic acid tert-butyl ester (Intermediate I-3.2)

To a stirred solution of R11 (0.50 g, 1.47 mmol) in THF (15 ml) is added lithium hydroxide monohydrate (93 mg, 2.20 mmol). Enough water is added so as to dissolve the lithium hydroxide (~1.5 ml). The reaction is stirred at room temperature for 5 h and then acidified using AcOH. The reaction is poured into water and the product is extracted into EtOAc (3×). The combined organics are dried (MgSO4), filtered and concentrated to afford the title compound which is used without further purification. (400 mg)

Aryl Bromide Intermediate Method I-A

Synthesis of 3-[1-(4-bromo-phenyl)-cyclobutyl]-5-(1-ethyl-5-methyl-1H-pyrazol-4-yl)-1,2,4-oxadiazole (Intermediate I-4.1)

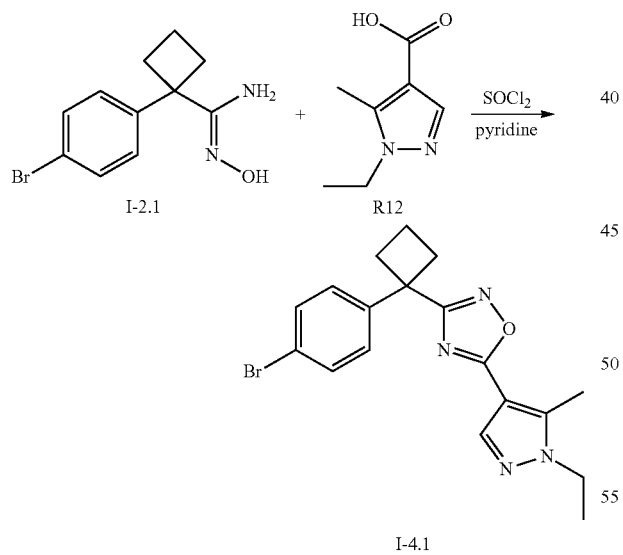

I-4.1

R12 (0.12 g, 0.78 mmol) is dissolved in pyridine (2 mL) and SOCl$_2$ (0.065 mL, 0.892 mmol) is added and the mixture is stirred for 30 minutes. I-2.1 (0.2 g, 0.743 mmol) is added and the mixture stirred at room temperature for 15 minutes and 110° C. overnight. The mixture is concentrated in vacuo, dissolved in DCM, washed with saturated aqueous NaHCO$_3$, dried over Na$_2$SO$_4$, filtered and concentrated in vacuo to afford title compound (0.24 g); m/z 387/389 [M, M+2].

Intermediates listed with Method I-A in Table 5 are synthesized in similar fashion from the appropriate reagents.

Aryl Bromide Intermediate Method I-B

Synthesis of 5-{3-[1-(4-bromo-phenyl)-cyclobutyl]-1,2,4-oxadiazol-5-yl}-pyridin-2-ylamine (Intermediate I-4.2)

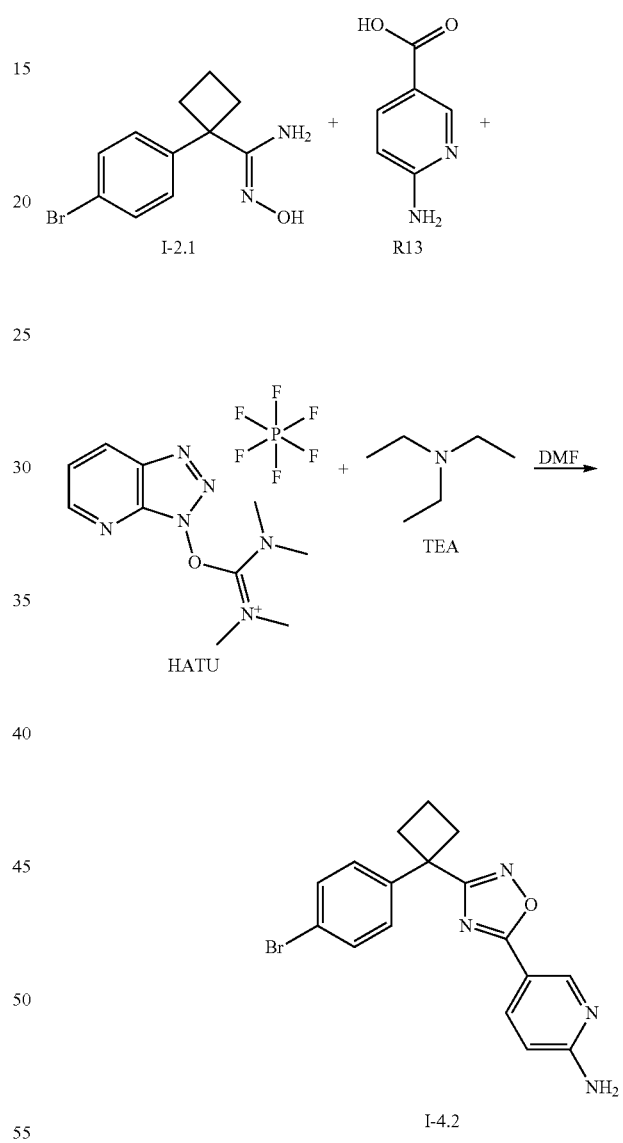

R13 (0.102 g, 0.743 mmol) is dissolved in DMF (2 mL) then HATU (0.282 g, 0.743 mmol) and TEA (0.103 mL, 0.743 mmol) are added. The mixture is stirred at room temperature for 5 minutes, I-2.1 (0.2 g, 0.743 mmol) is added and the mixture stirred 2 h at room temperature and then 90° C. overnight. The mixture is concentrated in vacuo, partitioned between EtOAc and water, organics separated and dried over MgSO$_4$, filtered and concentrated in vacuo. The residue is purified by flash chromatography (SiO$_2$, 0-3% MeOH/DCM) to afford the title compound (0.222 g); m/z 373 [M+2]

Intermediates listed with Method I-B in Table 5 are synthesized in similar fashion from the appropriate reagents.

Aryl Bromide Intermediate Method I-C

Synthesis of 2-{3-[1-(4-bromo-phenyl)-cyclobutyl]-1,2,4-oxadiazol-5-yl}-pyrazine (Intermediate I-4.3)

I-2.1 (0.2 g, 0.743 mmol) is dissolved in pyridine (2 mL) and R14 (0.105 g, 0.743 mmol) is added. The mixture is heated at 110° C. overnight, then concentrated in vacuo, redissolved in DCM and washed with saturated aqueous NaHCO₃. The organics are dried over Na₂SO₄, filtered and concentrated in vacuo to afford title compound (0.234 g); m/z 358 [M+1].

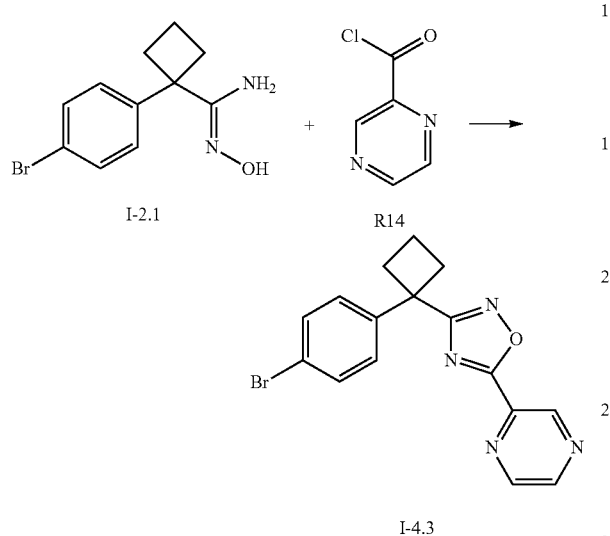

Intermediates listed with Method I-C in Table 5 are synthesized in similar fashion from the appropriate reagents.

Aryl Bromide Intermediate Method I-D

Synthesis of {{3-[1-(4-bromo-phenyl)-cyclobutyl]-1,2,4-oxadiazol-5-yl}-pyrrolidin-1-yl-methanone (Intermediate I-6.20)

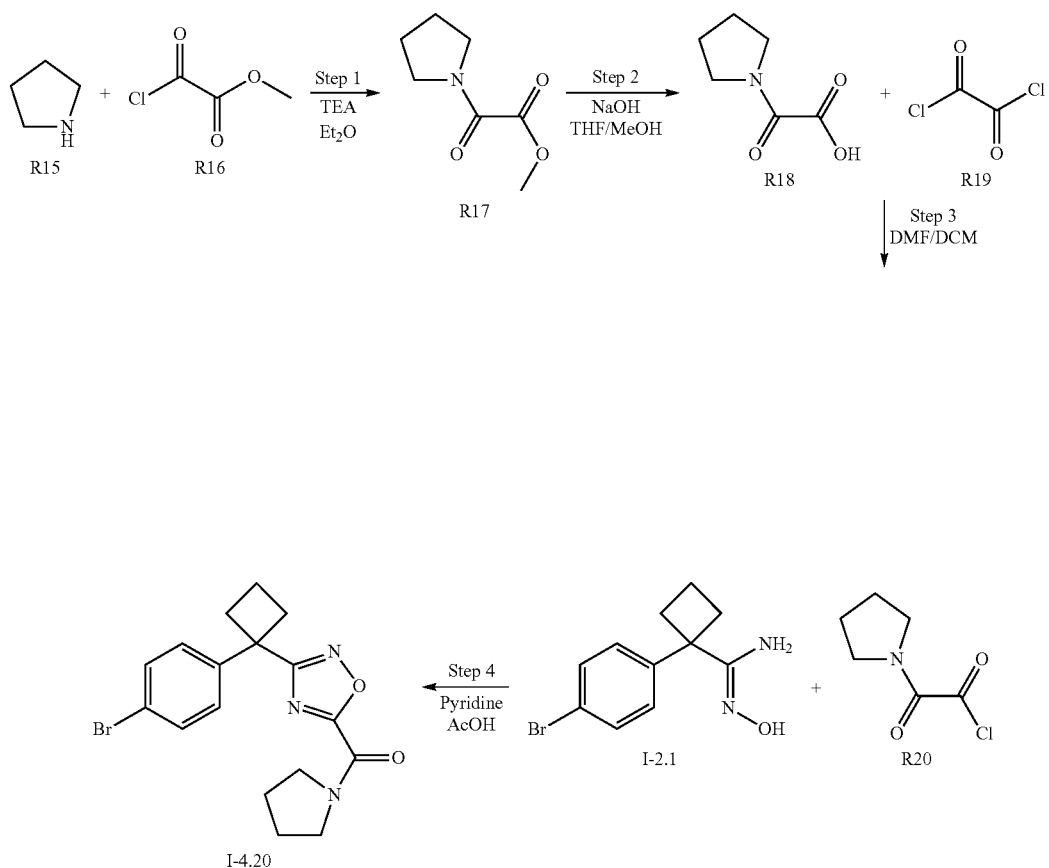

Step 1: Synthesis of oxo-pyrrolidin-1-yl-acetic acid methyl ester (R17)

R15 (0.7 mL, 8.464 mmol) and TEA (1.175 mL, 8.464 mmol) are dissolved in diethyl ether (Et$_2$O) (15 mL) at 0° C. and a solution of R16 (0.702 mL, 7.618 mmol) in Et$_2$O (5 mL) is added slowly. The mixture is slowly warmed to room temperature over 2 h. The mixture is filtered and the filtrate is concentrated in vacuo to afford title compound (2 g); m/z 158 [M+1].

Step 2: Synthesis of oxo-pyrrolidin-1-yl-acetic acid (R18)

R17 (2 g, 12.725 mmol) is dissolved in tetrahydrofuran (THF) (15 mL) and MeOH (15 mL) and 2M NaOH (12.73 mL, 25.451 mmol) is added. The mixture is stirred at room temperature for 2 h and then concentrated in vacuo. The crude is acidified to pH4-5 using 2M HCl and extracted with EtOAc, Et$_2$O, and tert-butylmethyl ether (TBME). The mixture is acidified to pH 1 and extracted with DCM. The organics are combined to afford title compound (0.823 g); m/z 144 [M+1].

Step 3: Synthesis of oxo-pyrrolidin-1-yl-acetyl chloride (R20)

R18 (0.2 g, 1.397 mmol) is dissolved in DCM (10 mL) and R19 (0.118 mL, 1.397 mmol) is added dropwise followed by DMF (0.050 mL). The mixture is stirred at room temperature for 1 h and then concentrated in vacuo to afford title compound (0.250 g); m/z 199 [M+1].

Step 4: Synthesis of {3-[1-(4-bromo-phenyl)-cyclobutyl]-1,2,4-oxadiazol-5-yl}-pyrrolidin-1-yl-methanone (Intermediate I-4.20)

R20 (0.126 g, 0.780 mmol) is dissolved in pyridine (2 mL) and I-2.1 (0.2 g, 0.743 mmol) is added. The mixture is stirred until homogeneous and then heated to 50° C. for 17 h. The crude is concentrated in vacuo, dissolved in DCM and washed with saturated aqueous NaHCO$_3$. The organic is concentrated in vacuo and purified by flash chromatography to afford title compound (0.168 g); m/z 376/378 [M, M+2].

Note: The reaction is also performed in acetic acid (AcOH) (2 mL) instead of pyridine with reaction time of 2 h.

Intermediates listed with Method I-D in Table 5 are synthesized in similar fashion from the appropriate reagents.

Aryl Bromide Intermediate Method I-E

Synthesis of 3-[1-(4-bromo-phenyl)-cyclobutyl]-5-pyrrolidin-1-yl-1,2,4-oxadiazole (Intermediate I-4.21)

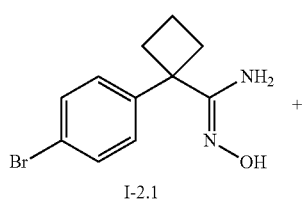

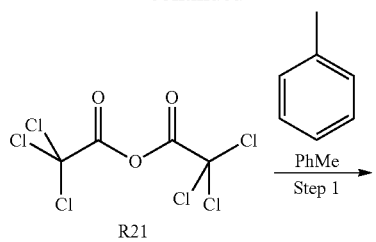

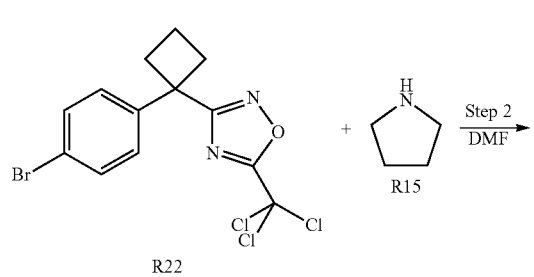

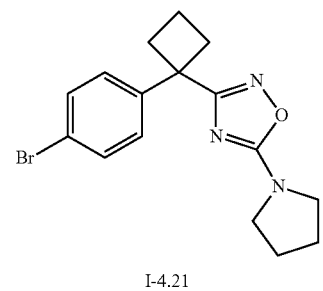

I-4.21

Step 1: Synthesis of 3-[1-(4-bromo-phenyl)-cyclobutyl]-5-trichloromethyl-1,2,4-oxadiazole (R19)

I-2.1 (0.5 g, 1.858 mmol) is dissolved in toluene (30 mL) and R21 (0.407 mL, 2.229 mmol) is added. The mixture is heated at 110° C. for 2 h, cooled to room temperature and washed with water followed by saturated aqueous NaHCO$_3$. The organic is concentrated in vacuo to afford title compound (0.8 g); m/z 396 [M]

Step 2: Synthesis of 3-[1-(4-bromo-phenyl)-cyclobutyl]-5-pyrrolidin-1-yl-1,2,4-oxadiazole (Intermediate I-4.21)

To a stirred solution of R15 (0.044 mL, 0.530 mmol) in DMF (2 mL), is added R22 (0.2 g, 0.504 mmol) and the mixture is stirred at room temperature for 30 minutes. Water is added and the solution is extracted with EtOAc. The organics are combined and concentrated in vacuo to afford title compound (0.080 g); m/z 348/350 [M, M+2].

Intermediates listed with Method I-E in Table 5 are synthesized in similar fashion from the appropriate reagents.

Aryl Bromide Intermediate Method I-F

Synthesis of 3-[1-(4-bromo-phenyl)-cyclobutyl]-cyclopenta-1,3-dienecarboxylic acid dimethylamide (Intermediate I-6.23)

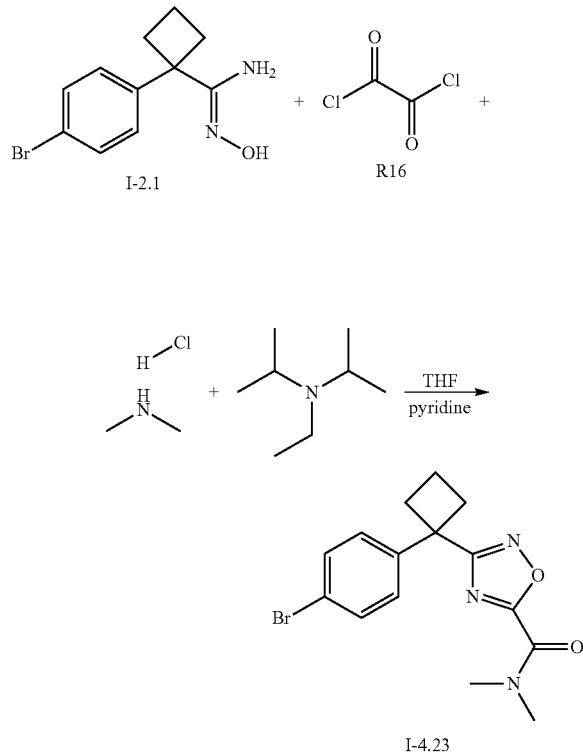

To a solution of R16 (0.208 mL, 2.452 mmol) and R20 (0.2 g, 2.452 mmol) in THF (20 mL) is added DIEA (0.849 mL, 4.905 mmol) at 0° C. and stirred for 30 minutes. This solution is added to I-2.1 (0.3 g, 1.115 mmol) in pyridine (5 mL) and stirred for 30 minutes then heated at 50° C. overnight. The mixture is purified by flash chromatography to afford title compound (0.240 g); m/z 351 [M+1].

Intermediates listed with Method I-F in Table 5 are synthesized in similar fashion from the appropriate reagents.

Synthesis of 5-{3-[1-(4-bromo-phenyl)-cyclobutyl]-1,2,4-oxadiazol-5-yl}-pyridine-2-carboxylic acid (Intermediate I-4.25)

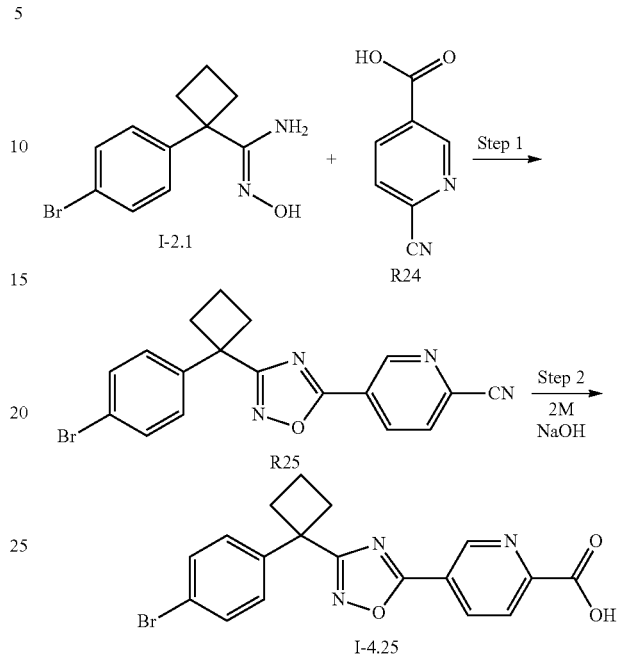

Step 1: Synthesis of 5-{3-[1-(4-bromo-phenyl)-cyclobutyl]-1,2,4-oxadiazol-5-yl}-pyridine-2-carbonitrile (R25)

R25 is prepared according to General Intermediate method I-B; m/z 381/383

Step 2: Synthesis of 5-{3-[1-(4-bromo-phenyl)-cyclobutyl]-1,2,4-oxadiazol-5-yl}-pyridine-2-carboxylic acid (Intermediate I-4.25)

To a solution of R25 (1.4 g, 3.67 mmol) in ethanol (70 mL) is added 2M aqueous NaOH (9.2 mL, 18.3 mmol). The mixture is stirred at 80° C. for 4 h and then concentrated in vacuo before acidification to pH 5-6 with 1 M aqueous HCl. The precipitate formed is collection by filtration. The filtrate is extracted with EtOAc, dried over $Na_2SO_4$, filtered and concentrated in vacuo to give a solid which is combined with the precipitate isolated to give the title reagent (1.1 g); m/z 400/402 ($M^+$+1)

Synthesis of 1-{3-[1-(4-bromo-phenyl)-cyclobutyl]-1,2,4-oxadiazol-5-yl}-pyrrolidin-2-one (Intermediate I-4.26)

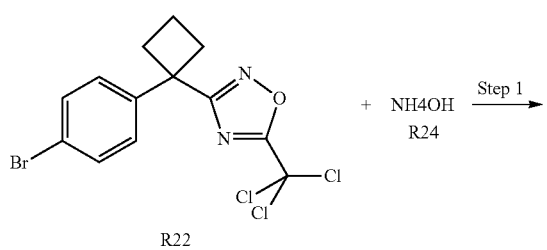

-continued

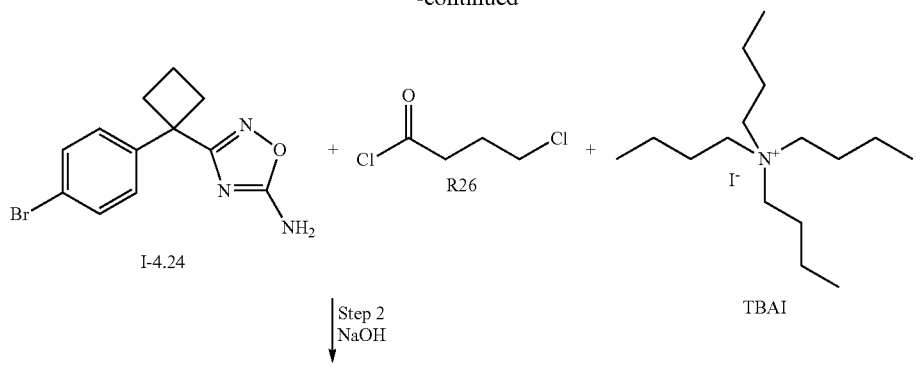

↓ Step 2
  NaOH

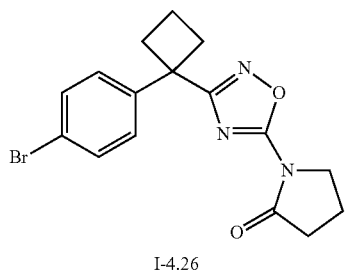

I-4.26

Step 1: Synthesis of 3-[1-(4-bromo-phenyl)-cyclobutyl]-1,2,4-oxadiazol-5-ylamine (Intermediate I-4.24)

Synthesis of Intermediate I-4.24 employs conditions found in intermediate method I-E Step 2: Synthesis of 1-{3-[1-(4-bromo-phenyl)-cyclobutyl]-1,2,4-oxadiazol-5-yl}-pyrrolidin-2-one (I-4.26)

I-4.24-(0.15 g, 0.510 mmol) is dissolved in THF (5 mL) and cooled to 0° C. before adding TEA (0.11 mL, 0.76 mmol) and then R26 (0.06 mL, 0.56 mmol). The mixture slowly warms to room temperature over an hour. NaOH solution (1 mL, 50% w/v) and TBAI (0.0094 g, 0.03 mmol) are added and the mixture is stirred at room temperature overnight. Additional R26 is added and the mixture heated to 50° C. for 8 h before diluting with water and extracting with EtOAc. The organics are dried over $Na_2SO_4$, filtered and concentrated in vacuo to afford title compound (0.155 g); m/z 362/364 [M, M+2].

Synthesis of N-{3-[1-(4-bromo-phenyl)-cyclobutyl]-1,2,4-oxadiazol-5-yl}-methanesulfonamide (Intermediate I-4.28)

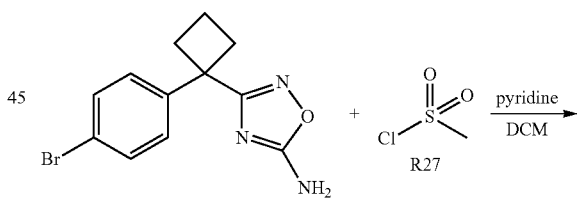

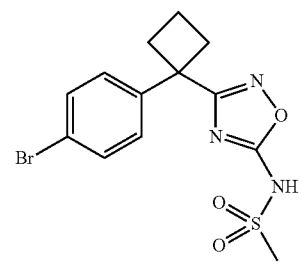

I-4.28

To a solution of I-4.24 (0.2 g, 0.68 mmol) in DCM (5 mL) at 0° C. is added pyridine (0.06 mL, 0.75 mmol) followed by dropwise addition of R27 (0.06 mL, 0.75 mmol). After further addition of R27 and heating to 50° C. for 8 h, the mixture is diluted with water. Saturated aqueous $NaHCO_3$ is added and the product is extracted into DCM. The organics are dried with $Na_2SO_4$, filtered and concentrated in vacuo. The residue is purified by flash chromatography ($SiO_2$, 30% EtOAc/heptane and 10% methanol/DCM) to give the title compound (100 mg); m/z 372/374 [M, M+2].

Aryl Bromide Intermediate Method I-G

Synthesis of 5-{3-[1-(4-bromo-phenyl)-cyclobutyl]-1,2,4-oxadiazol-5-yl}-1-methyl-1H-pyrazin-2-one (Intermediate I-4.32)

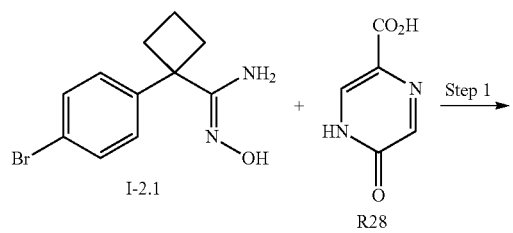

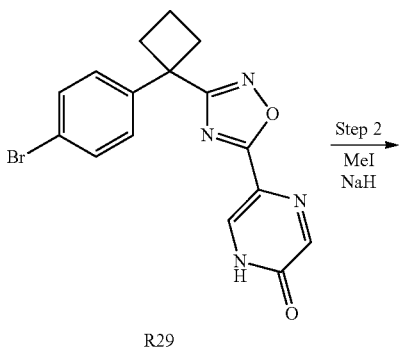

Step 1: Synthesis of 5-{3-[1-(4-bromo-phenyl)-cyclobutyl]-1,2,4-oxadiazol-5-yl}-1H-pyrazin-2-one (R29)

Synthesis of R29 employs conditions used for intermediate method I-B using the appropriate reagents.

Step 1: Synthesis of 55-{3-[1-(4-bromo-phenyl)-cyclobutyl]-1,2,4-oxadiazol-5-yl}-1-methyl-1H-pyrazin-2-one (I-4.32)

To a solution of R29 (0.091 g, 0.247 mmol) in DMF (1 mL), is added NaH (60% in oil suspension, 0.011 g, 0.268 mmol) under $N_2$ followed by methyl iodide (MeI) (0.016 mL, 0.256 mmol). After stifling at room temperature for 18 h, the reaction mixture is partitioned between EtOAc and saturated aqueous $NaHCO_3$. The organics are washed with brine, dried over $Na_2SO_4$, filtered and concentrated in vacuo. The residue is purified by flash chromatography ($SiO_2$, 10%-20% EtOAc/heptanes) to give the title intermediate (0.100 g); m/z 387/389 [M+1].

Intermediates listed with Method I-G in Table 5 are synthesized in similar fashion from the appropriate reagents.

Aryl Bromide Intermediate Method I-H

Synthesis of 3-[1-(4-bromo-phenyl)-cyclobutyl]-5-[1-(2-methoxy-ethyl)-1H-pyrazol-4-yl]-1,2,4-oxadiazole (Intermediate I-4.40)

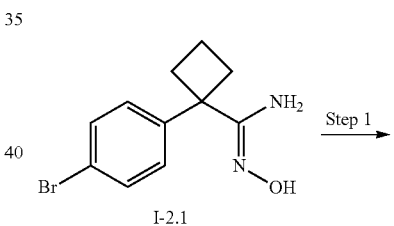

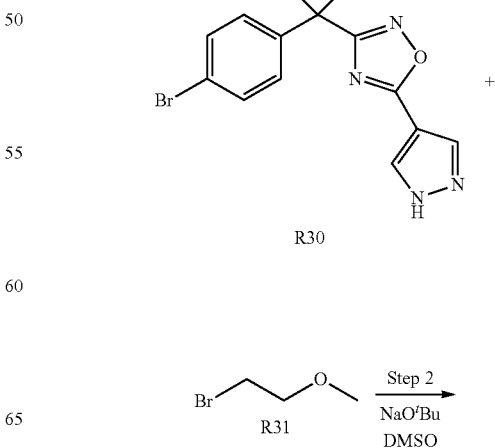

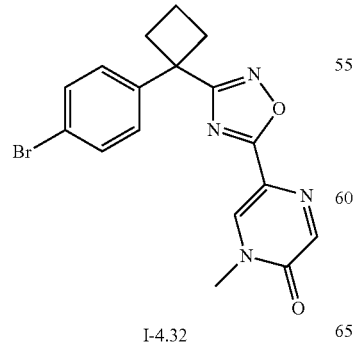

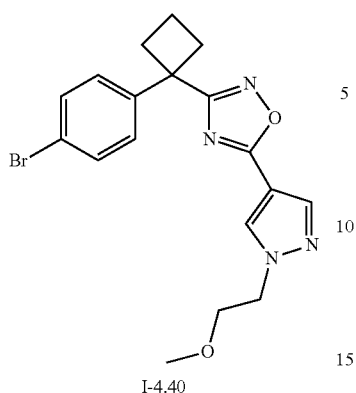

I-4.40

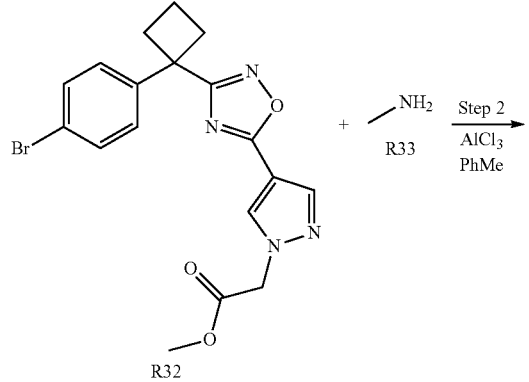

Step 1: Synthesis of 3-[1-(4-bromo-phenyl)-cyclobutyl]-5-(1H-pyrazol-4-yl)-1,2,4-oxadiazole (R30)

Synthesis employs intermediate method I-B from the appropriate reagents; m/z 345/347 [M, M+2].

Step 2: Synthesis of 3-[1-(4-bromo-phenyl)-cyclobutyl]-5-[1-(2-methoxy-ethyl)-1H-pyrazol-4-yl]-1,2,4-oxadiazole (Intermediate I-4.40)

R30 (0.4 g, 0.382 mmol) is dissolved in dimethyl sulfoxide (DMSO) (10 mL) and sodium tert-butoxide (NaO$^t$Bu) (0.074 g, 0.765 mmol) and R31 (0.029 g, 0.210 mmol) are added.

The reaction is stirred at room temperature for 2 h, water is added (10 mL) and the solution is neutralized with 1N HCl. The solution is extracted with EtOAc (2×10 mL) and the organics are combined, dried over Na$_2$SO$_4$, filtered and concentrated in vacuo. The residue is purified by flash chromatography (SiO$_2$, 30-50% EtOAc/heptanes) to afford title compound (0.180 g); m/z 403/405 [M, M+2].

Intermediates listed with Method I-H in Table 5 are synthesized in similar fashion from the appropriate reagents. Intermediates listed with Method I-H* in Table 5 are synthesized in similar fashion using KO$^t$Bu and the appropriate reagents.

Synthesis of 2-(4-{3-[1-(4-bromo-phenyl)-cyclobutyl]-1,2,4-oxadiazol-5-yl}-pyrazol-1-yl)-N-methyl-acetamide (Intermediate I-4.47)

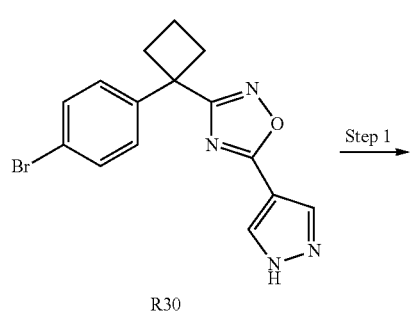

R30

Step 1: Synthesis of (4-{3-[1-(4-bromo-phenyl)-cyclobutyl]-1,2,4-oxadiazol-5-yl}-pyrazol-1-yl)-acetic acid methyl ester (R32)

Step 1 employs intermediate method I-H from the appropriate reagents. m/z 417 [M].

Step 2: Synthesis of 2-(4-{3-[1-(4-bromo-phenyl)-cyclobutyl]-1,2,4-oxadiazol-5-yl}-pyrazol-1-yl)-N-methyl-acetamide (Intermediate I-4.47)

R32 (0.542 mL, 2M in THF, 1.086 mmol) is dissolved in PhMe (3 mL) and AlCl$_3$ (0.542 mL, 2M in toluene, 1.086 mmoL) is added. The mixture is stirred for 30 minutes, R32 (0.151 g, 0.362 mmol) is added and the reaction heated at 100° C. for 1 h. The mixture is cooled to room temperature and carefully quenched with water (~1 mL). The mixture is

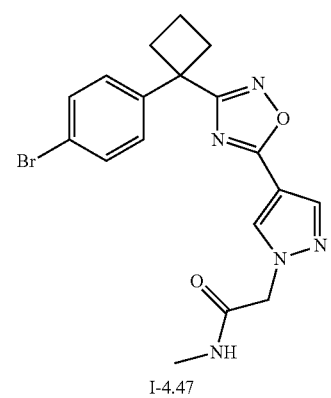

I-4.47 filtered, rinsed with toluene and DCM and the filtrate concentrated in vacuo to afford the title compound (0.102 g); m/z 417 [M+1].

Aryl Bromide Intermediate Method I-I

Synthesis of 2-(4-{3-[1-(4-bromo-phenyl)-cyclobutyl]-1,2,4-oxadiazol-5-yl}-pyrazol-1-yl)-propan-1-ol (Intermediate I-4.48)

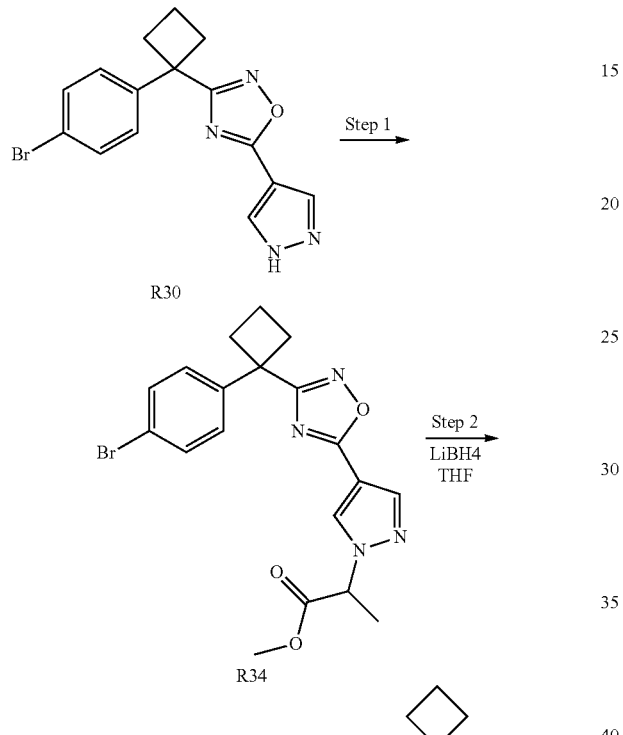

Step 1: Synthesis of 2-(4-{3-[1-(4-bromo-phenyl)-cyclobutyl]-1,2,4-oxadiazol-5-yl}-pyrazol-1-yl)-propionic acid ethyl ester (R34)

Step 1 employs intermediate method I-H from the appropriate reagents; m/z 446 [M].

Step 2: Synthesis of 2-(4-{3-[1-(4-bromo-phenyl)-cyclobutyl]-1,2,4-oxadiazol-5-yl}-pyrazol-1-yl)-propan-1-ol (Intermediate I-4.48)

R34 (0.1 g, 0.225 mmol) is dissolved in THF (2 mL), cooled to 0° C., and LiBH$_4$ (0.010 g, 0.449 mmol) is added. The reaction is stirred at room temperature for 3 h, and concentrated in vacuo. The residue is quenched with saturated aqueous NH$_4$Cl and extracted with DCM. The organics are dried over Na$_2$SO$_4$, filtered and concentrated in vacuo to afford title compound (0.076 g); m/z 404 [M+1].

Intermediates listed with Method I-I in Table 5 are synthesized in similar fashion from the appropriate reagents.

Aryl Bromide Intermediate Method I-J

Synthesis of 3-[1-(4-bromo-phenyl)-cyclobutyl]-5-(1-ethyl-1H-pyrazol-4-yl)-1,2,4-oxadiazole (Intermediate I-4.50)

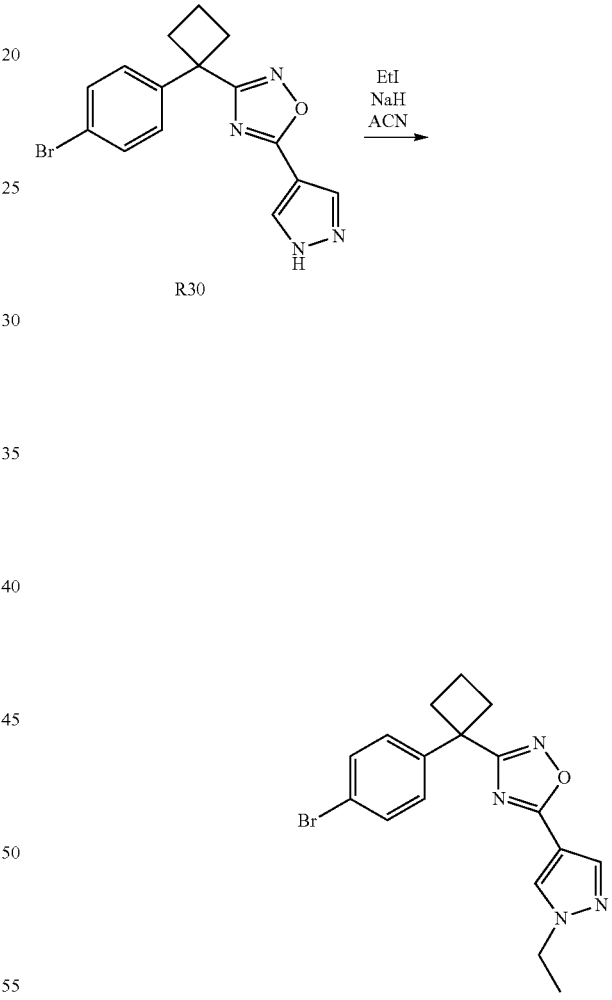

NaH (0.014 g, 60% dispersion in mineral oil, 0.359 mmol) is added to R30 (0.118 g, 0.342 mmol) in acetonitrile (ACN) (2 mL) at 0° C. The mixture is stirred for 30 minutes and ethyl iodide (EtI) (0.030 mL, 0.376 mmol) is added. The reaction is stirred for 2 h, then quenched with MeOH (~1 mL) and concentrated in vacuo. The residue is dissolved in DCM, washed with saturated aqueous NaHCO$_3$, dried over Na$_2$SO$_4$, filtered and concentrated in vacuo to afford title compound (0.105 g); m/z 374 [M+1].

Intermediates listed with Method I-J in Table 5 are synthesized in similar fashion from the appropriate reagents.

Aryl Bromide Intermediate Method I-K

Synthesis of N-{3-[1-(4-bromo-phenyl)-cyclobutyl]-1,2,4-oxadiazol-5-yl}-6-methyl-nicotinamide (Intermediate I-4.54)

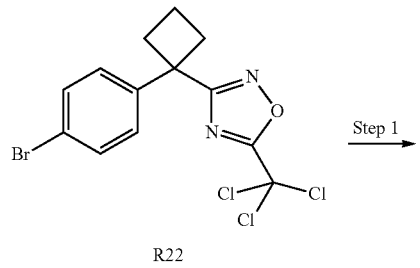

R22

Step 1

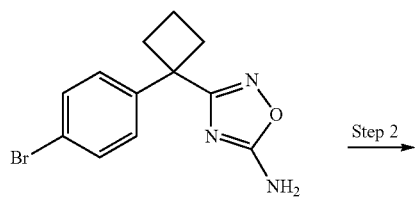

I-4.24

Step 2

Step 1: Synthesis of N-{3-[1-(4-bromo-phenyl)-cyclobutyl]-1,2,4-oxadiazol-5-yl}-6-methyl-nicotinamide (Intermediate I-4.24))

Synthesis of I-4.24 employs the conditions used in intermediate method I-E from the appropriate reagents.

Step 2: Synthesis of N-{3-[1-(4-bromo-phenyl)-cyclobutyl]-1,2,4-oxadiazol-5-yl}-6-methyl-nicotinamide (Intermediate I-4.54)

Synthesis of I-4.54 employs the conditions used in intermediate method I-C from the appropriate reagents.

Aryl Bromide Intermediate Method I-L

Synthesis of 5-{3-[1-(4-bromo-phenyl)-cyclobutyl]-1,2,4-oxadiazol-5-yl}-1-methyl-1H-pyrimidin-2-one (Intermediate I-4.55)

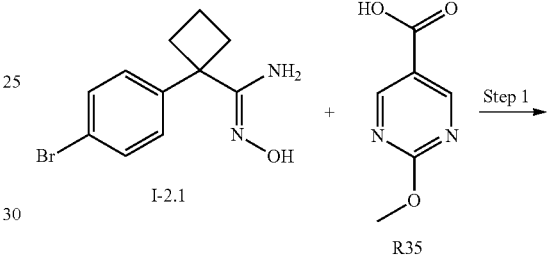

I-2.1        R35

Step 1

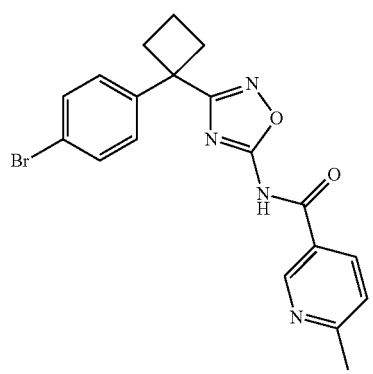

I-4.54

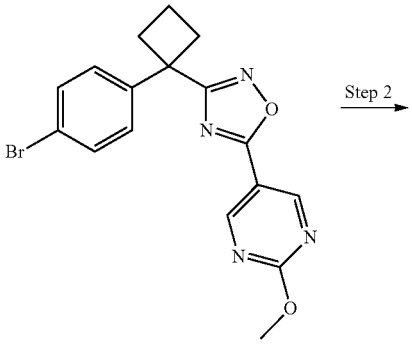

R36

Step 2

-continued

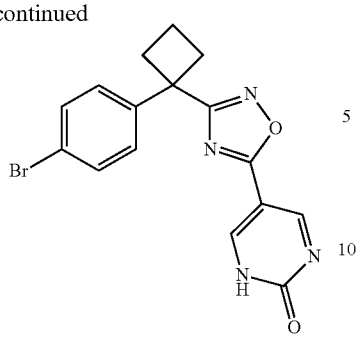

R37

| Step 3

The mixture is cooled and diluted with water (5 mL) and filtered to afford title compound (0.173 g) which is further washed with water and dried under vacuum; m/z 374 [M+1].

Step 3: Synthesis of 5-{3-[1-(4-bromo-phenyl)-cyclobutyl]-1,2,4-oxadiazol-5-yl}-1-methyl-1H-pyrimidin-2-one (Intermediate I-4.55)

Synthesis of I-6.53 employs conditions used in intermediate method I-G from the appropriate reagents; m/z 388 [M+1].

Aryl Bromide Intermediate Method I-M

Synthesis of 3-[1-(4-Bromo-phenyl)-cyclobutyl]-5-(1-methyl-1H-pyrazol-4-yl)-[1,2,4]oxadiazole (Intermediate I-4.56)

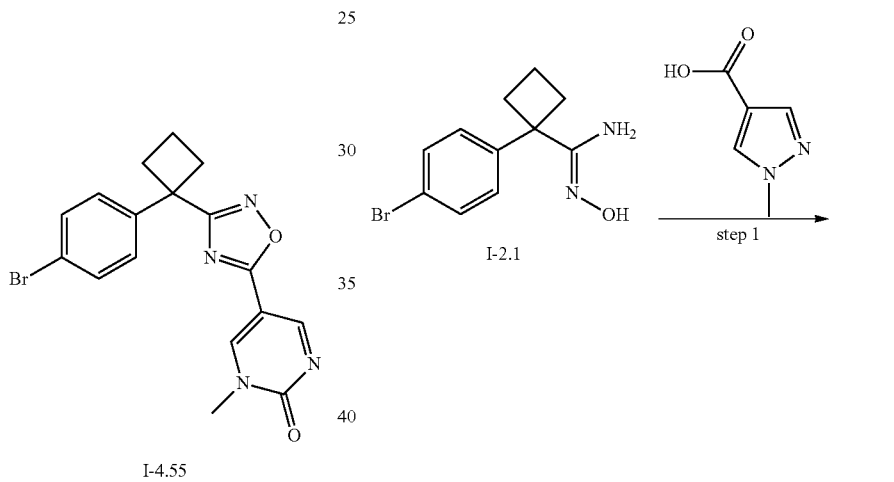

I-4.55

Step 1: Synthesis of 5-{3-[1-(4-bromo-phenyl)-cyclobutyl]-1,2,4-oxadiazol-5-yl}-2-methoxy-pyrimidine (R36)

Synthesis of R36 employs conditions used in intermediate method I-B from the appropriate reagents; m/z 388 [M+1].

Step 2: Synthesis of 5-{3-[1-(4-bromo-phenyl)-cyclobutyl]-1,2,4-oxadiazol-5-yl}-1H-pyrimidin-2-one (R37)

R36 (0.184 g, 0.476 mmol) and pyridine hydrochloride (0.220 g, 1.903 mmol) are heated at 165° C. for 15 minutes.

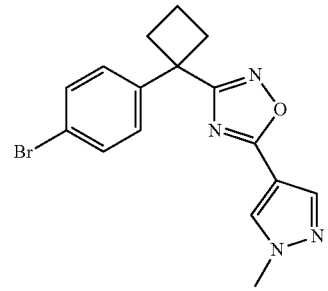

I-4.56

To a microwave reactor was added 1-methyl-1H-pyrazole-4-carboxylic acid (258 mg, 2.04 mmol) in THF (10 ml), followed by the addition of 1,1'-carbonyldiimidazole (331 mg, 2.04 mmol). The reaction mixture was stirred at 50° C. for 30 minutes, followed by the addition of I-2.1 (500 mg, 1.86 mmol). The reaction mixture was reacted in microwave reactor at 150° C. for 1 hour. The reaction mixture was diluted with EtOAc, washed with water, brine, dried over Na₂SO₄, filtered, and concentrated. The residue was purified by flash chromatography (SiO₂, 0-50% EtOAc/heptane) to afford title compound (484 mg); m/z 359,361 [M, M+2]

TABLE 5

Aryl bromide intermediates

| Intermediate | Structure | Method | m/z |
|---|---|---|---|
| I-6.4 | 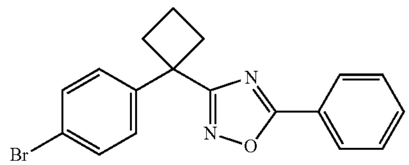 [SMILES: Brc1ccc(C2(c3noc(-c4ccccc4)n3)CCC2)cc1] | I-C | 355/357 |
| I-6.5 | 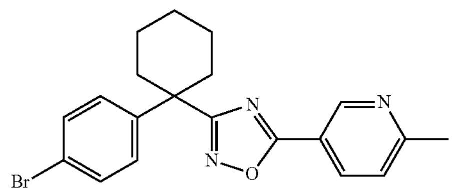 [SMILES: Cc1ccc(-c2nc(C3(c4ccc(Br)cc4)CCCCC3)no2)cn1] | I-A | 398/400 |
| I-6.6 | 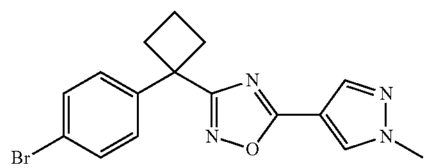 [SMILES: Cn1cc(-c2nc(C3(c4ccc(Br)cc4)CCC3)no2)cn1] | I-A | 359/361 |
| I-6.7 | 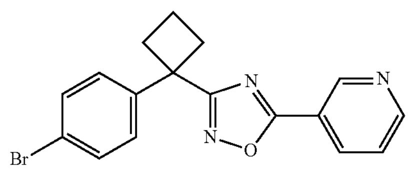 [SMILES: Brc1ccc(C2(c3noc(-c4cccnc4)n3)CCC2)cc1] | I-C | 356/358 |
| I-6.8 | 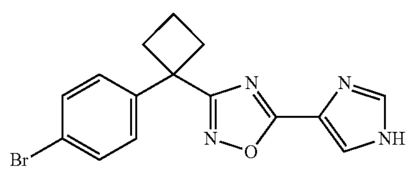 [SMILES: Brc1ccc(C2(c3noc(-c4c[nH]cn4)n3)CCC2)cc1] | I-A | 345/347 |
| I-6.9 | 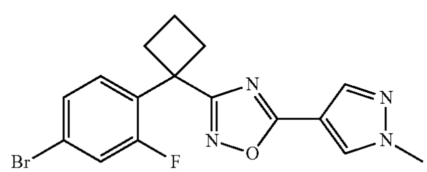 [SMILES: Cn1cc(-c2nc(C3(c4ccc(Br)cc4F)CCC3)no2)cn1] | I-A | 377/379 |
| I-6.10 | 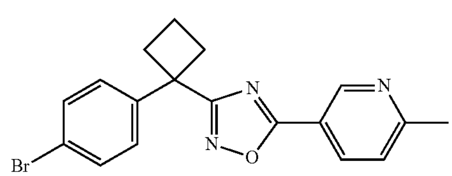 [SMILES: Cc1ccc(-c2nc(C3(c4ccc(Br)cc4)CCC3)no2)cn1] | I-A | 370/372 |

TABLE 5-continued
Aryl bromide intermediates
| Intermediate | Structure | Method | m/z |
|---|---|---|---|
| I-6.11 | 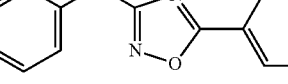 | I-C | 384/386 |
| I-6.12 | 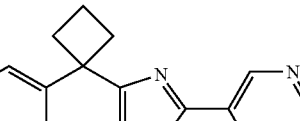 | I-A | 372/374 |
| I-6.13 | 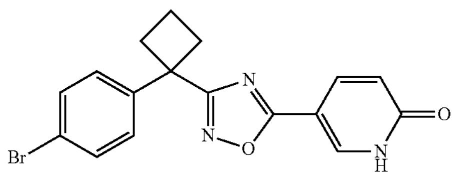 [SMILES: O=c1ccc(-c2nc(C3(c4ccc(Br)cc4)CCC3)no2)c[nH]1] | I-B | 372/374 |
| I-6.14 | 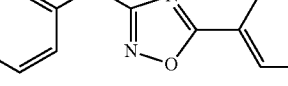 | I-A | 386/388 |
| I-6.15 | 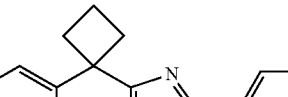 | I-A | 357/359 |
| I-6.16 | 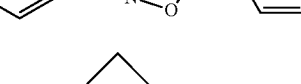 | I-A | 371/373 |
| I-6.17 | 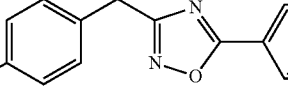 | I-A | 357/359 |
| I-6.18 | 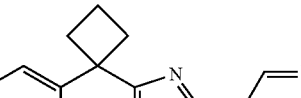 | I-A | 387/389 |
| I-6.19 | 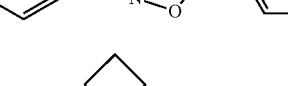 | I-A | 373/375 |

TABLE 5-continued

Aryl bromide intermediates

| Intermediate | Structure | Method | m/z |
| --- | --- | --- | --- |
| I-6.22 | 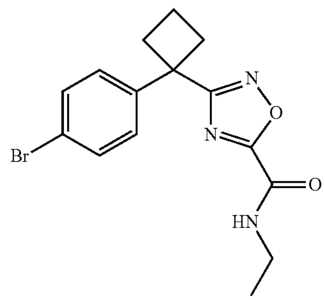 [SMILES: CCNC(=O)c1nc(C2(c3ccc(Br)cc3)CCC2)no1] | I-D | 351 |
| I-6.24 | 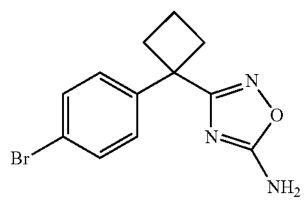 [SMILES: Nc1nc(C2(c3ccc(Br)cc3)CCC2)no1] | I-E | 294/296 |
| I-6.27 | 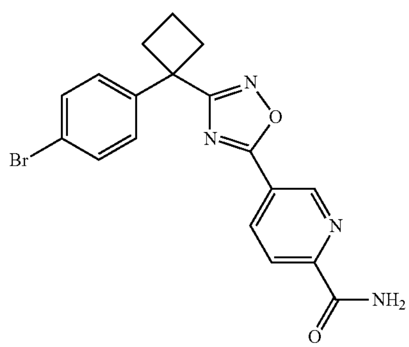 [SMILES: NC(=O)c1ccc(-c2nc(C3(c4ccc(Br)cc4)CCC3)no2)cn1] | I-F | 503/505 |
| I-6.29 | 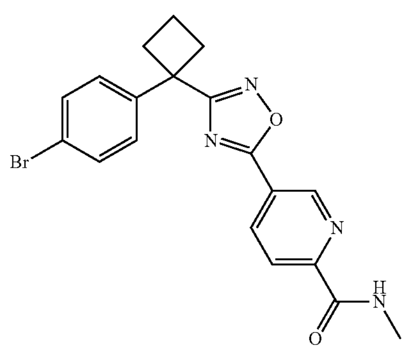 [SMILES: CNC(=O)c1ccc(-c2nc(C3(c4ccc(Br)cc4)CCC3)no2)cn1] | I-F | 413/415 |
| I-6.30 | 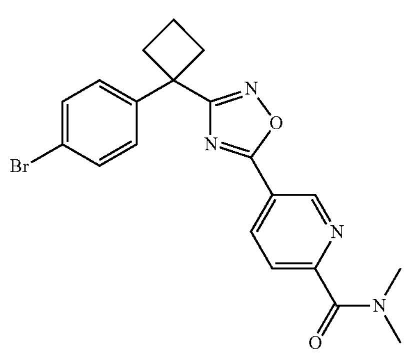 [SMILES: CN(C)C(=O)c1ccc(-c2nc(C3(c4ccc(Br)cc4)CCC3)no2)cn1] | I-F | 427/429 |

TABLE 5-continued
| Aryl bromide intermediates | | | |
|---|---|---|---|
| Intermediate | Structure | Method | m/z |
| I-6.31 | 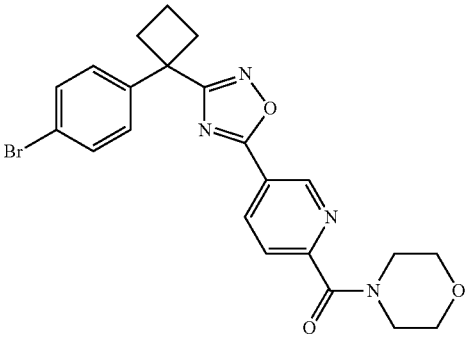 [SMILES: O=C(c1ccc(-c2nc(C3(c4ccc(Br)cc4)CCC3)no2)cn1)N1CCOCC1] | I-F | 469/471 |
| I-6.33 | 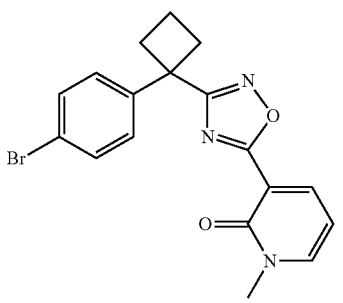 [SMILES: Cn1cccc(-c2nc(C3(c4ccc(Br)cc4)CCC3)no2)c1=O] | I-G | 386/388 |
| I-6.34 | 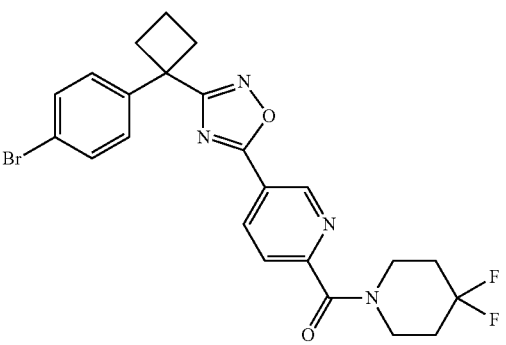 [SMILES: O=C(c1ccc(-c2nc(C3(c4ccc(Br)cc4)CCC3)no2)cn1)N1CCC(F)(F)CC1] | I-F | 503/505 |
| I-6.35 | 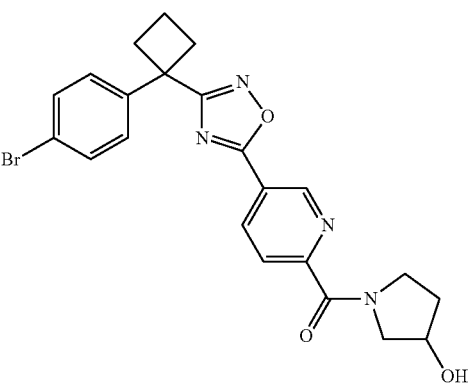 [SMILES: O=C(c1ccc(-c2nc(C3(c4ccc(Br)cc4)CCC3)no2)cn1)N1CCC(O)C1] | I-F | 469/471 |

TABLE 5-continued

Aryl bromide intermediates

| Intermediate | Structure | Method | m/z |
|---|---|---|---|
| I-6.36 | 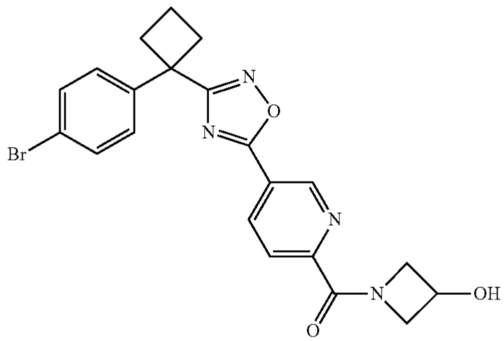 [SMILES: O=C(c1ccc(-c2nc(C3(c4ccc(Br)cc4)CCC3)no2)cn1)N1CC(O)C1] | I-F | 455/457 |
| I-6.37 | 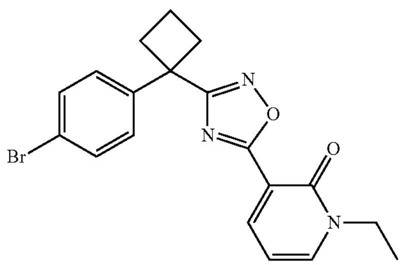 [SMILES: CCn1cccc(-c2nc(C3(c4ccc(Br)cc4)CCC3)no2)c1=O] | I-G | 400/402 |
| I-6.38 | 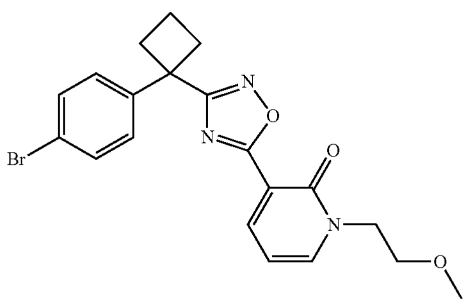 [SMILES: COCCn1cccc(-c2nc(C3(c4ccc(Br)cc4)CCC3)no2)c1=O] | I-G | 430/432 |
| I-6.39 | 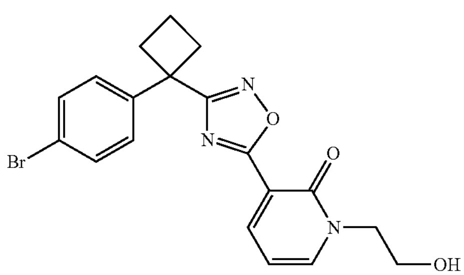 [SMILES: O=c1c(-c2nc(C3(c4ccc(Br)cc4)CCC3)no2)cccn1CCO] | I-G | 416/418 |
| I-6.41 | 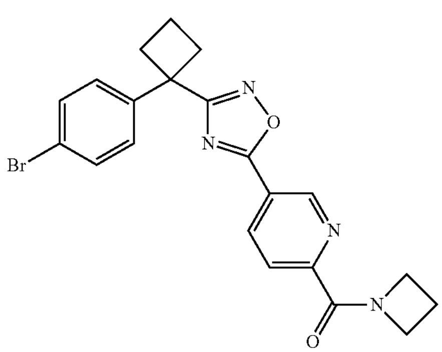 [SMILES: O=C(c1ccc(-c2nc(C3(c4ccc(Br)cc4)CCC3)no2)cn1)N1CCC1] | I-F | 439/441 |

TABLE 5-continued

Aryl bromide intermediates

| Intermediate | Structure | Method | m/z |
|---|---|---|---|
| I-6.42 | 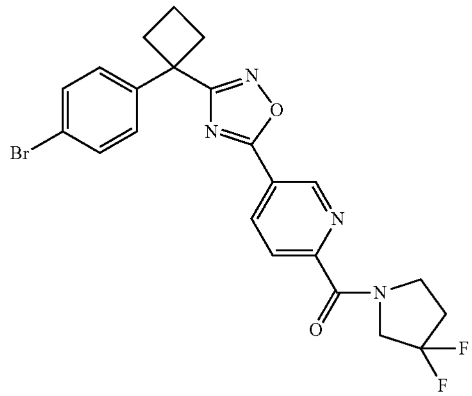 [SMILES: O=C(c1ccc(-c2nc(C3(c4ccc(Br)cc4)CCC3)no2)cn1)N1CCC(F)(F)C1] | I-F | 489/491 |
| I-6.43 | 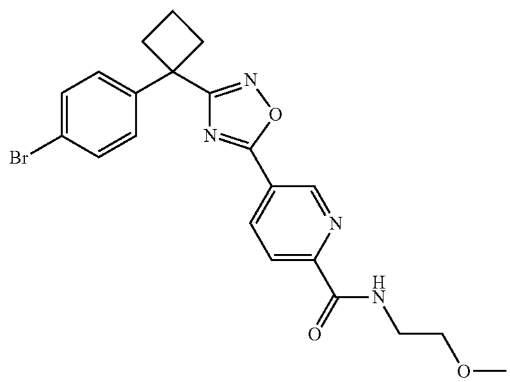 [SMILES: COCCNC(=O)c1ccc(-c2nc(C3(c4ccc(Br)cc4)CCC3)no2)cn1] | I-F | 457/459 |
| I-6.44 | 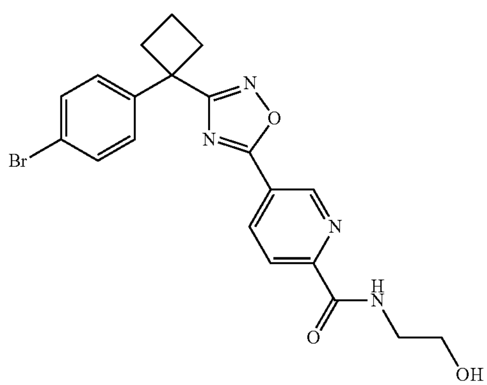 [SMILES: O=C(NCCO)c1ccc(-c2nc(C3(c4ccc(Br)cc4)CCC3)no2)cn1] | I-F | 443/445 |
| I-6.45 | 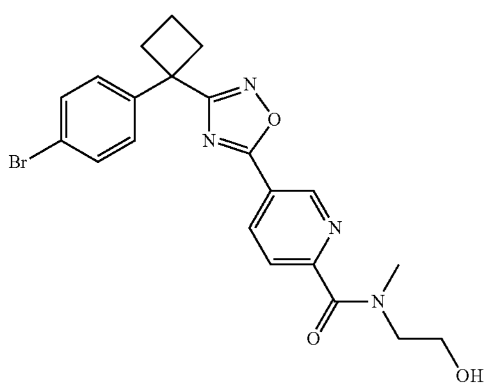 [SMILES: CN(CCO)C(=O)c1ccc(-c2nc(C3(c4ccc(Br)cc4)CCC3)no2)cn1] | I-F | 457/459 |

TABLE 5-continued

| Aryl bromide intermediates | | | |
|---|---|---|---|
| Intermediate | Structure | Method | m/z |
| I-6.46 | | I-H | 418 |
| I-6.49 | | I-H | 404 |
| I-6.51 | | I-I | 418 |
| I-6.52 | | I-J | 404 |

TABLE 5-continued

| Aryl bromide intermediates | | | |
|---|---|---|---|
| Intermediate | Structure | Method | m/z |
| I-6.53 | | I-H | 402 |
| I-4.57 | | I-M | 430/432 |
| I-4.58 | | I-M | 359/361 |
| I-4.59 | | I-M | 543 |

Pinacolboronate Intermediates

Synthesis of 5-(1-Methyl-1H-pyrazol-4-yl)-3-{1-[4-(4,4,5,5-tetramethyl-[1,3,2]dioxaborolan-2-yl)-phenyl]-cyclobutyl}-[1,2,4]oxadiazole (Intermediate I-5.1)

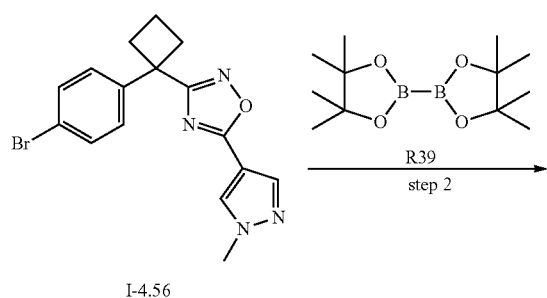

I-4.56

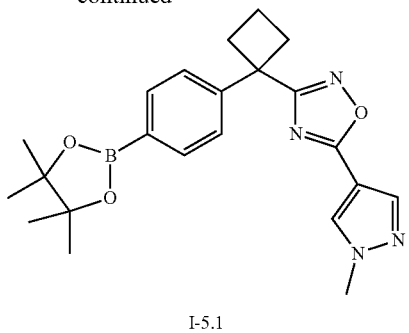

I-5.1

To a sealed vial was added I-4.56 (324 mg, 0.9 mmol), R39 (275 mg, 1.08 mmol), potassium acetate (354 mg, 3.6 mmol) and 1,1'-bis(diphenylphosphino) ferrocenedichloropalladium(II) dichloromethane ($PdCl_2$(dppf)) (74 mg, 0.09 mmol) in 1,4-dioxane (5 ml). The reaction mixture was stirred under argon at 100° C. for 4 hours. The reaction mixture was diluted with EtOAc and washed with water. The organic layer was separated, washed with brine, dried over $Na_2SO_4$, filtered and concentrated. The residue was purified by flash chromatography ($SiO_2$, 0-50% EtOAc/heptane) to afford the title compound (301 mg); m/z 407 [M+1]

Pinacol Boronates in Table 6 are Synthesized in a Similar Fashion from the Appropriate Reagents.

TABLE 6

| Reagent | Pinacolboronate intermediates Structure | m/z |
|---|---|---|
| I-5.2 | 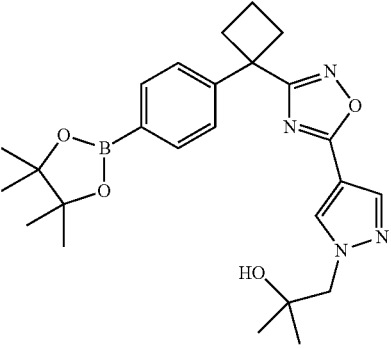 [SMILES: CC(C)(O)Cn1cc(-c2nc(C3(c4ccc(B5OC(C)(C)C(C)(C)O5)cc4)CCC3)no2)cn1] | 465 |
| I-5.3 | 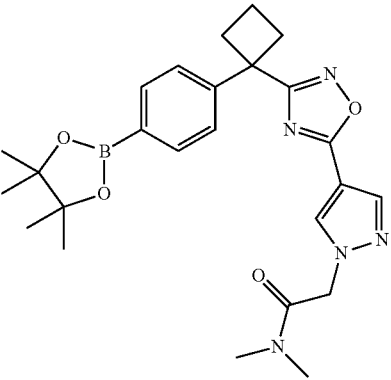 [SMILES: CN(C)C(=O)Cn1cc(-c2nc(C3(c4ccc(B5OC(C)(C)C(C)(C)O5)cc4)CCC3)no2)cn1] | 478 |

TABLE 6-continued
Pinacolboronate intermediates
| Reagent | Structure | m/z |
|---------|-----------|-----|
| I-5.4 | 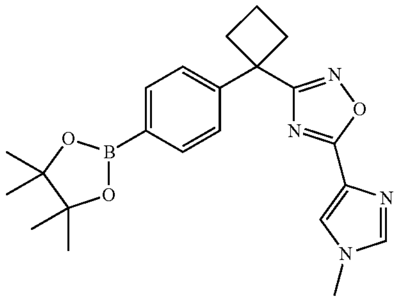 [SMILES: Cn1cnc(-c2nc(C3(c4ccc(B5OC(C)(C)C(C)(C)O5)cc4)CCC3)no2)c1] | 407 |
| I-5.5 | 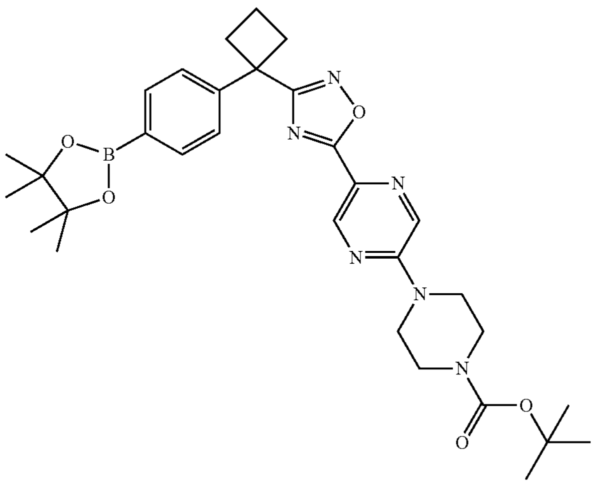 [SMILES: CC(C)(C)OC(=O)N1CCN(c2cnc(-c3nc(C4(c5ccc(B6OC(C)(C)C(C)(C)O6)cc5)CCC4)no3)cn2)CC1] | |
| I-5.6 | 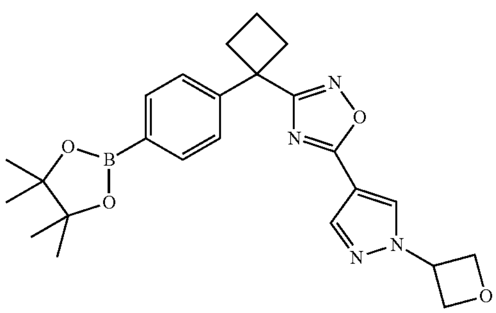 [SMILES: CC1(C)OB(c2ccc(C3(c4noc(-c5cnn(C6COC6)c5)n4)CCC3)cc2)OC1(C)C] | 449 |
Acid Chloride Intermediates
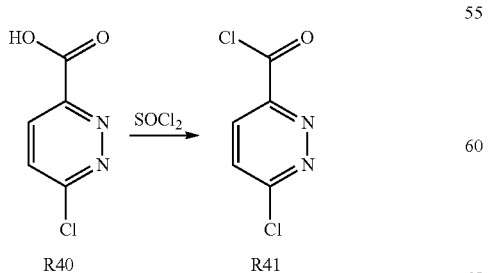

Synthesis of 6-chloro-pyridazine-3-carbonyl chloride

R40 (0.2 g, 1.261 mmol) is heated in SOCl$_2$ (2 mL) for 1 h at reflux. The mixture is concentrated in vacuo to afford title compound which is used crude in subsequent reactions.

Synthesis of 2-methyl-nicotinoyl chloride

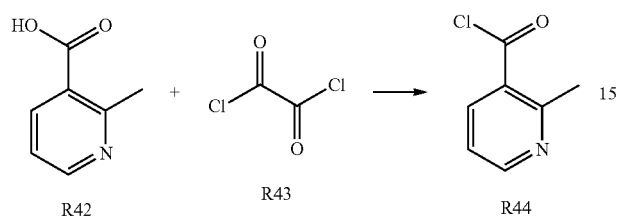

To R42 (0.2 g, 1.1458 mmol) in DCM (5 mL) is added R43 (0.875 mL, 2 M in DCM, 1.75 mmol) followed by a drop of DMF. The reaction mixture is stirred for 30 minutes at room temperature, concentrated in vacuo, and used crude in subsequent reactions. Acid chlorides in Table 7 are made in a similar fashion from the appropriate reagents.

TABLE 7

Acid chloride intermediates

| Reagent | Structure |
|---------|-----------|
| R45 | 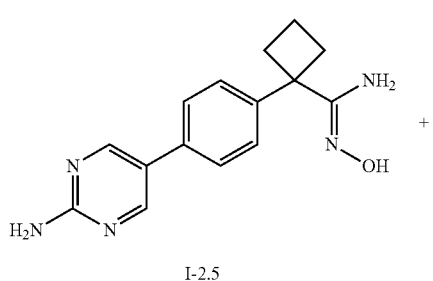 |

Method 1

Synthesis of 5-{4-[1-(5-m-tolyl-1,2,4-oxadiazol-3-yl)-cyclobutyl]-phenyl}-pyrimidin-2-ylamine (Example 34 in Table 8)

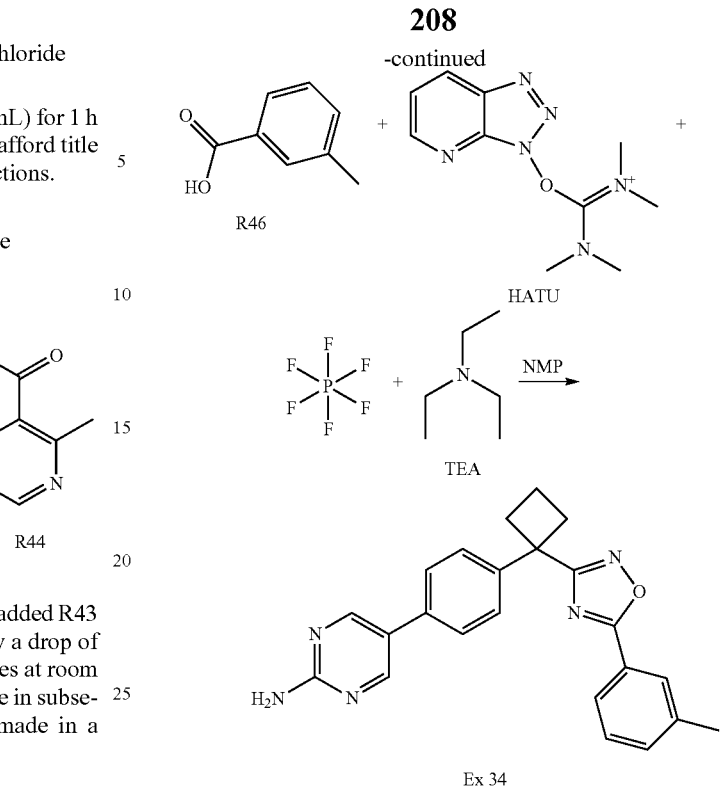

To a solution of R46 (0.05 g, 0.367 mmoL), HATU (0.279 g, 0.734 mmol) and triethylamine (TEA) (0.205 mL, 1.469 mmol) in N-methylpyrrolidinone (NMP) (3 mL) which is prestirred for 5 minutes is added I-2.5 (0.104 g, 0.367 mmol) and the reaction is heated at 80° C. overnight. The reaction is cooled and purified by flash chromatography (SiO$_2$, 0-10% MeOH/DCM) to afford title compound (0.006 g); m/z 384.2 [M+H].

Compounds in Table 8 listed with Method 1 are synthesized in a similar fashion.

Method 2

Synthesis of 5-(4-{1-[5-(2-methyl-2H-pyrazol-3-yl)-1,2,4-oxadiazol-3-yl]-cyclobutyl}-phenyl)-pyrimidin-2-ylamine (Example 57 in Table 8)

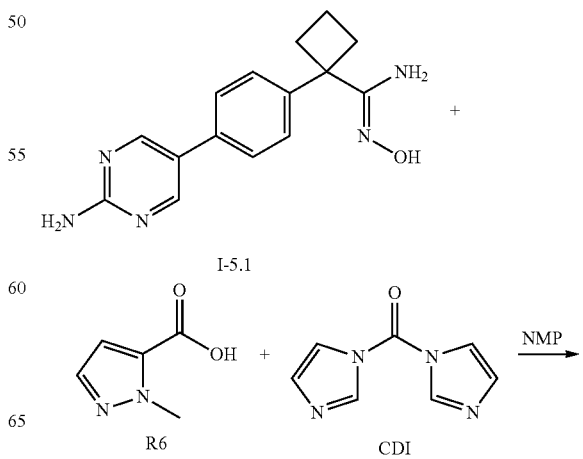

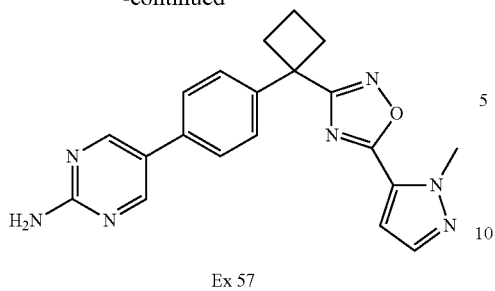

Ex 57

To a solution of R47 (0.098 g, 0.776 mmol) in NMP (0.8 mL) is added CDI (0.126 g, 0.776 mmol) and the mixture is heated at 50° C. for 20 minutes. I-2.5 (0.2 g, 0.706 mmol) is added and the mixture is heated at 120° C. for 2 h. The mixture is cooled and 10 volumes of water is added. The resulting solid is filtered, slurried in MeOH (4 mL) at 70° C. for 1 h, cooled and filtered to afford title compound (0.115 g) as a solid; m/z 374.5 [M+H].

Compounds in Table 8 listed with Method 2 are synthesized in a similar fashion.

Method 3

Synthesis of 5-(4-{1-[5-(1-ethyl-5-methyl-1H-pyrazol-4-yl)-1,2,4-oxadiazol-3-yl]-cyclobutyl}-phenyl)-pyrimidin-2-ylamine (Example 2 in Table 8)

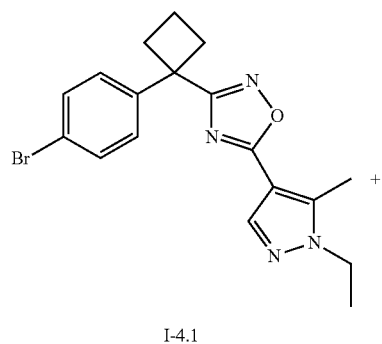

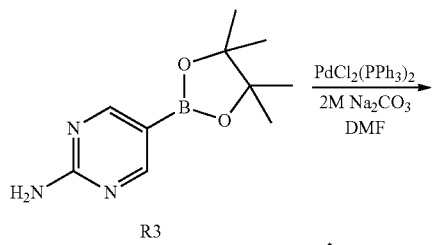

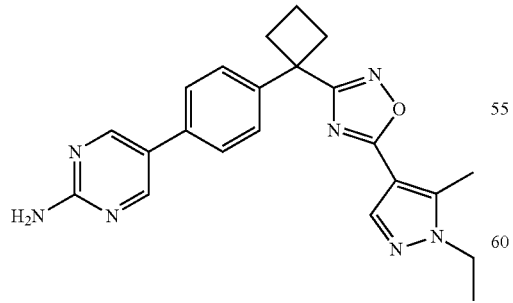

Ex 2

I-4.1 (0.24 g, 0.620 mmol), R3 (0.164 g, 0.744 mmol), bis(triphenylphosphino)dichloropalldium(II) (PdCl₂ (PPh₃)₂) (0.043 g, 0.062 mmol), and 2M Na₂CO₃ (0.619 mL, 1.239 mmol) is dissolved in DMF (2 mL). The mixture is heated at 80° C. until completion, then filtered through a PTFE frit and concentrated in vacuo. The residue is dissolved in DCM, washed with saturated aqueous NaHCO₃, dried over Na₂SO₄, filtered and concentrated in vacuo. The crude material is purified by preparative HPLC to afford title compound (0.111 g); m/z 402 [M+1].

Compounds in Table 8 listed with Method 3 are synthesized in a similar fashion.

Method 4

Synthesis of 5-{4-[1-(5-pyridin-3-yl-1,2,4-oxadiazol-3-yl)-cyclobutyl]-phenyl}-pyrimidin-2-ylamine (Example 143 in Table 8)

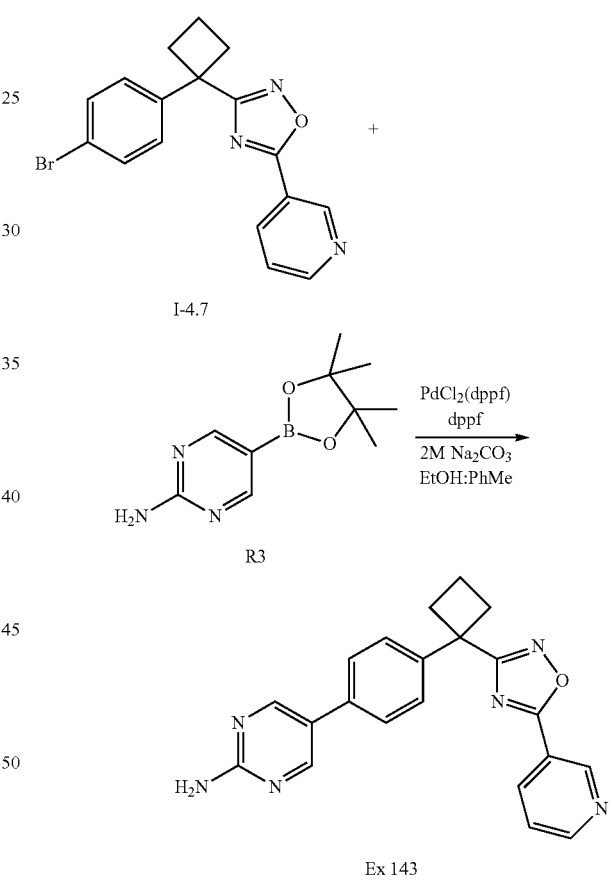

To a suspension mixture of I-4.7 (0.13 g, 0.37 mmol), R3 (0.061 g, 0.44 mmol) and 2M Na₂CO₃ (0.55 mL, 1.1 mmol) in EtOH:PhMe (4:1, 3 mL) in a pressure tube is added PdCl₂ (dppf) (0.03 g, 0.04 mmol) and diphenylphosphinoferrocene (dppf) (0.02 g, 0.04 mmol). The reaction mixture is stirred at 90° C. for 2 h. The reaction mixture is filtered through a pad of Celite®, washed with EtOAc and DCM. The collected filtrate is concentrated in vacuo. Purification by preparative HPLC gives the title compound (0.017 g); m/z 371.1 [M+1].

Compounds in Table 8 listed with Method 4 are synthesized in a similar fashion.

Method 5

Synthesis of [5-(3-{1-[4-(2-amino-pyrimidin-5-yl)-phenyl]-cyclobutyl}-1,2,4-oxadiazol-5-yl)-pyridin-2-yl]-(4,4-difluoro-piperidin-1-yl)-methanone (Example 59 in Table 8)

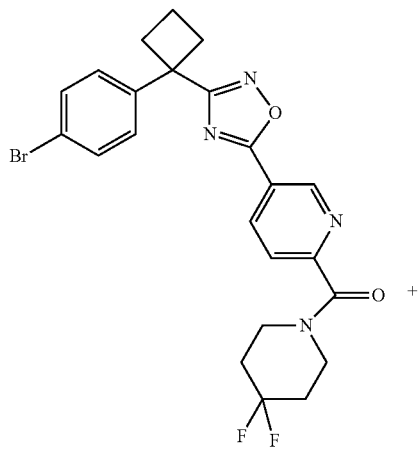

I-4.34-(0.16 g, 0.318 mmol), R3 (0.046 g, 0.334 mmol), PdCl$_2$(PPh$_3$)$_2$ (0.011 g, 0.016 mmol), and 2M Na$_2$CO$_3$ (0.636 mL, 1.272 mmol) is dissolved in DMF (3 mL) and MeOH (0.5 mL). The mixture is heated at 100° C. for 1 h, then concentrated in vacuo. The residue is dissolved in EtOAc, washed with saturated aqueous NaHCO$_3$, dried over Na$_2$SO$_4$, filtered and concentrated in vacuo. The crude material is purified by preparative HPLC to afford title compound (0.052 g); m/z 518 [M+1].

Compounds in Table 8 listed with Method 5 are synthesized in a similar fashion.

Method 6

Synthesis of 5-(4-{1-[5-(5-chloro-pyrazin-2-yl)-1,2,4-oxadiazol-3-yl]-cyclobutyl}-phenyl)-pyrimidin-2-ylamine (Example 187 in Table 8)

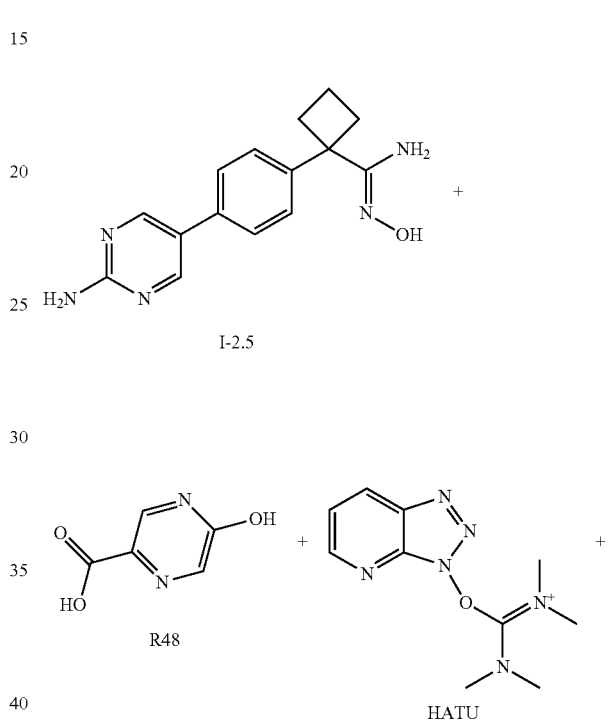

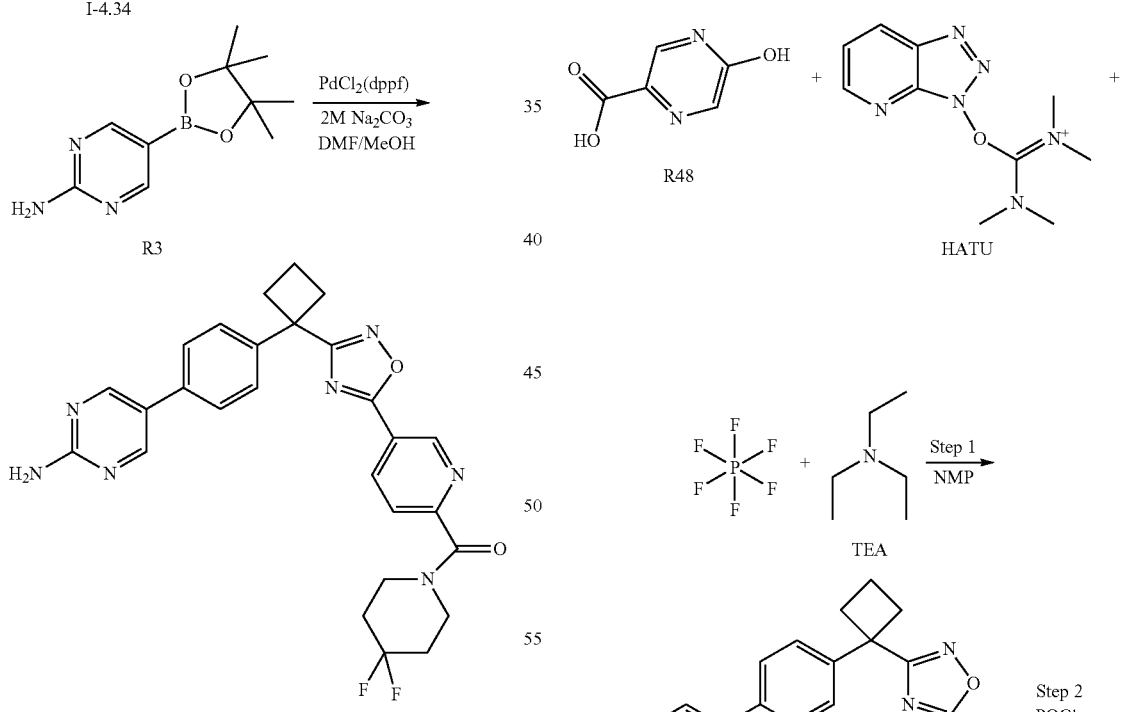

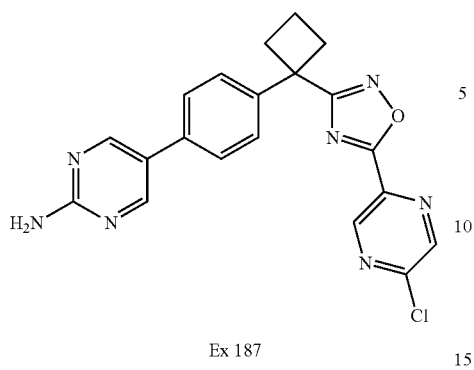

Ex 187

Step 1: Synthesis of 5-(3-{1-[4-(2-amino-pyrimidin-5-yl)-phenyl]-cyclobutyl}-1,2,4-oxadiazol-5-yl)-pyrazin-2-ol (R49)

Conditions described in Method 1 are employed; m/z 388 [M+1].

Step 2: Synthesis of 5-(4-{1-[5-(5-chloro-pyrazin-2-yl)-1,2,4-oxadiazol-3-yl]-cyclobutyl}-phenyl)-pyrimidin-2-ylamine (Example 187)

POCl$_3$ (3 mL) is added to R49 (0.1 g, 0.155 mmol) and the mixture heated at 50° C. for 3 h. The POCl$_3$ is removed in vacuo and the residue purified by chromatography to afford title compound (0.012 g); m/z 406.2 [M+1].

Compounds in Table 8 listed with Method 6 are synthesized in a similar fashion.

Method 7

Synthesis of 2-{[5-(3-{1-[4-(2-amino-pyrimidin-5-yl)-phenyl]-cyclobutyl}-1,2,4-oxadiazol-5-yl)-pyrazin-2-yl]-methyl-amino}-ethanol (Example 61 in Table 8)

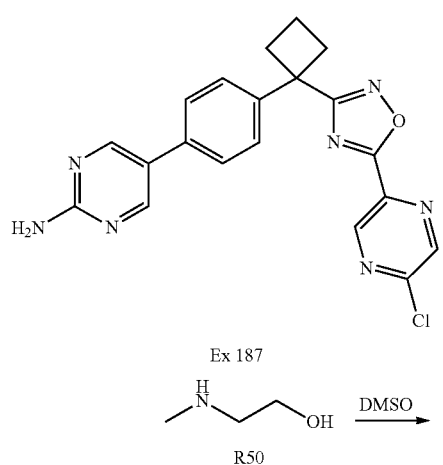

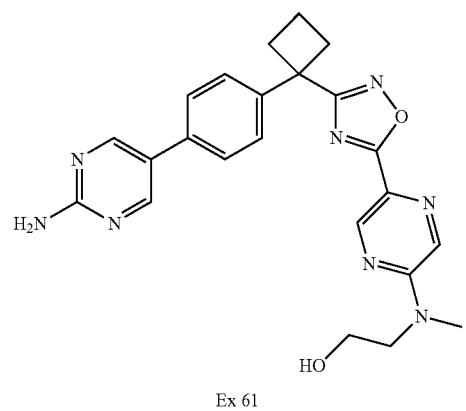

Ex 61

Example 187 (0.256 g, 0.448 mmoL) is dissolved in DMSO (3 mL) and R50 (0.107 mL, 1.344 mmol) is added. The mixture is stirred at room temperature for 1 h, then purified directly by preparative HPLC to give title compound (0.055 g); m/z 445 [M+1].

Compounds in Table 8 listed with Method 7 are synthesized in a similar fashion. Examples 180-182 employ DMF as the solvent, Example 183 employs THF as solvent and 10 eq. of amine, Example 193 is neat, and Examples 194-203 and 307-309 employ NMP as solvent, 3 eq. diisopropylethylamine (DIEA), and are heated at 120° C. for 3 days.

Method 8

Synthesis of 2-(3-{1-[4-(2-amino-pyrimidin-5-yl)-phenyl]-cyclobutyl}-1,2,4-oxadiazol-5-ylamino)-ethanol (Example 74 in Table 8)

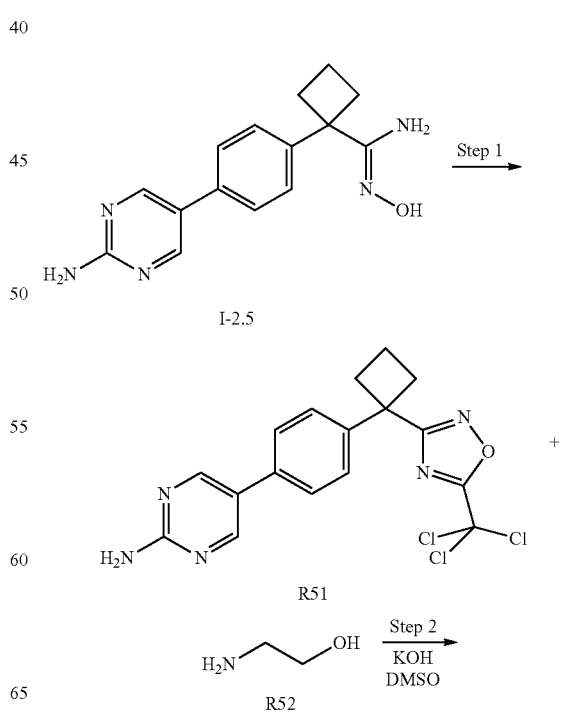

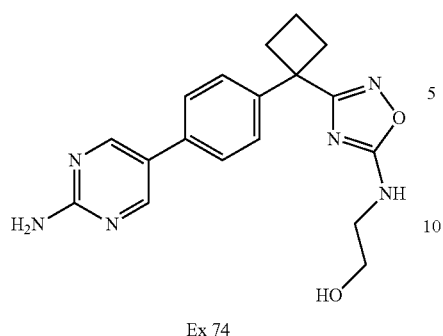

Ex 74

Step 1: Synthesis of 5-{4-[1-(5-trichloromethyl-1,2,4-oxadiazol-3-yl)-cyclobutyl]-phenyl}-pyrimidin-2-ylamine (R51)

Conditions employed in Intermediate Method I-E Step 1 using the appropriate reagents are used; m/z 411 [M+1].

Step 2: Synthesis of 2-(3-{1-[4-(2-amino-pyrimidin-5-yl)-phenyl]-cyclobutyl}-1,2,4-oxadiazol-5-ylamino)-ethanol (Example 74)

R51 (0.1 g, 0.243 mmol) is added to a solution of R52 (0.022 mL, 0.365 mmol) and KOH (0.020 g, 0.365 mmol) in DMSO (1.5 mL) and stirred at room temperature for 3 h. The mixture is purified by preparative HPLC to afford title compound (0.05 g); m/z 353 [M+1].

Compounds in Table 8 listed with Method 8 are synthesized in a similar fashion.

Method 9

Synthesis of 2-{[4-(3-{1-[4-(2-amino-pyrimidin-5-yl)-phenyl]-cyclobutyl}-1,2,4-oxadiazol-5-yl)-pyridin-2-yl]-methyl-amino}-ethanol (Example 94 in Table 8)

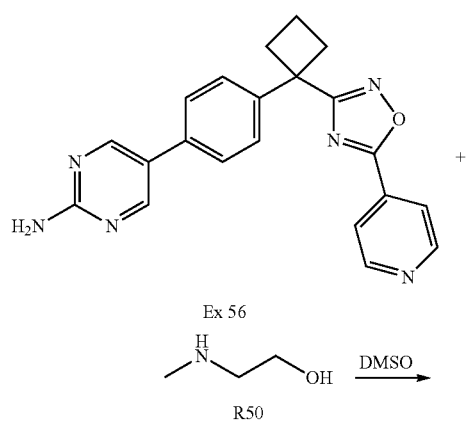

Ex 56

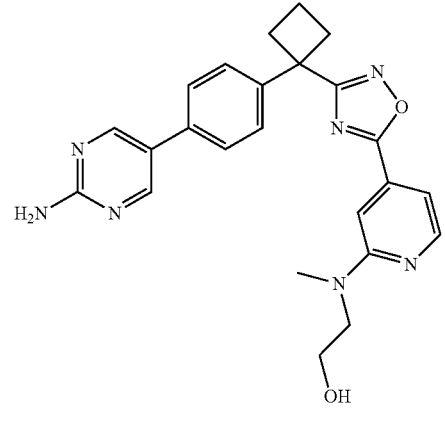

Ex 94

Synthesis similar to Method 7 except THF is used as the solvent; m/z 440.2 [M+1]

Compounds in Table 8 listed with Method 9 are synthesized in a similar fashion. Examples 107-108 employ 1 mL of NMP as a cosolvent. Examples 109, 110, and 121 employ NMP as a solvent instead of THF.

Method 10

Synthesis of 5-{4-[1-(5-piperazin-1-yl-1,2,4-oxadiazol-3-yl)-cyclobutyl]-phenyl}-pyrimidin-2-ylamine (Example 104 in Table 8)

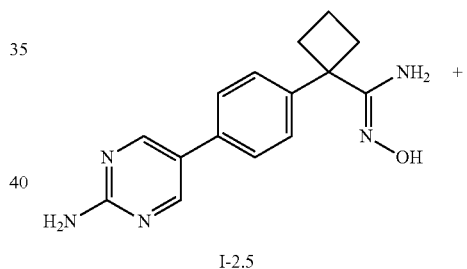

I-2.5

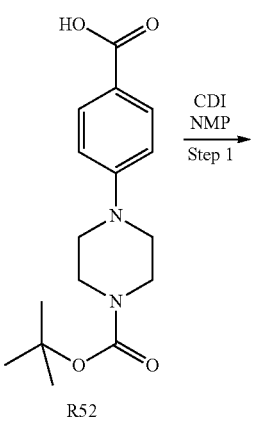

R52

-continued

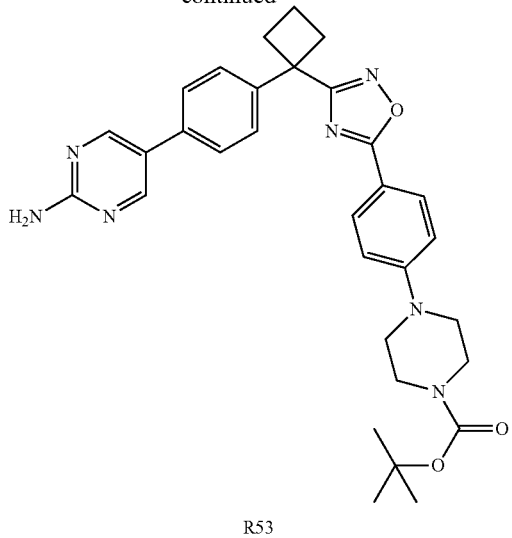

R53

| Step 2
| 4N HCl
▼

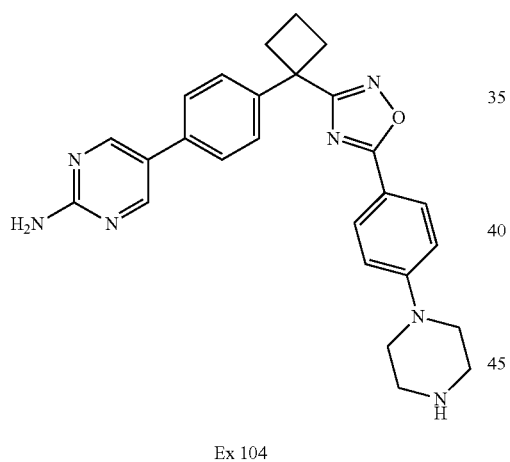

Ex 104

Step 1: Synthesis of 4-(3-{1-[4-(2-amino-pyrimidin-5-yl)-phenyl]-cyclobutyl}-1,2,4-oxadiazol-5-yl)-piperazine-1-carboxylic acid tert-butyl ester (R52)

Synthesis is similar to conditions used in Method 2.

Step 2: Synthesis of 5-{4-[1-(5-piperazin-1-yl-1,2,4-oxadiazol-3-yl)-cyclobutyl]-phenyl}-pyrimidin-2-ylamine (Example 104)

R53 (0.049 g, 0.089 mmol) is dissolved in 4M HCl in dioxane (0.221 mL, 0.885 mmol) and the mixture is stirred at room temperature overnight. The mixture is concentrated in vacuo, sonicated in MeOH and filtered to afford title compound (0.008 g); m/z 454.2 [M+1].

Compounds in Table 8 listed with Method 10 are synthesized in a similar fashion.

Method 11

Synthesis of [6-(3-{1-[4-(2-amino-pyrimidin-5-yl)-phenyl]-cyclobutyl}-1,2,4-oxadiazol-5-yl)-pyridazin-3-yl]-(2-methoxy-ethyl)-amine (Example 111 in Table 8)

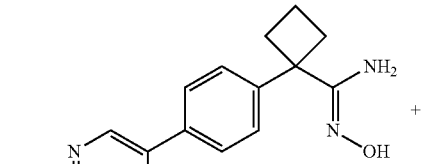

I-2.5

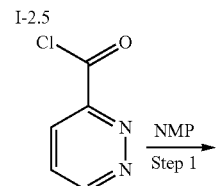

R54

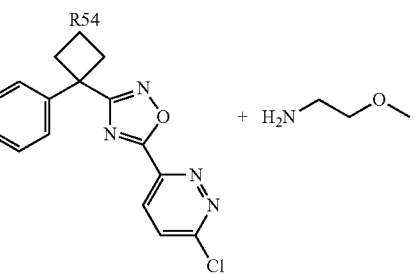

R55                                                           R56

| Step 2
▼

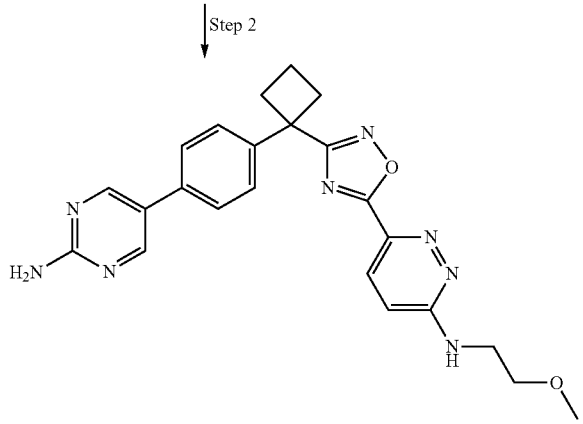

Ex 111

Step 1: Synthesis of 5-(4-{1-[5-(6-chloro-pyridazin-3-yl)-1,2,4-oxadiazol-3-yl]-cyclobutyl}-phenyl)-pyrimidin-2-ylamine (R55)

R54 (0.223 g, 1.261 mmol) and I-2.5 (0.356 g, 1.256 mmol) are stirred in NMP (1.3 mL) for 20 minutes then heated at 70° C. for 2 h. Water is added and the material is filtered to afford title compound (0.311 g).

Step 2: Synthesis of [6-(3-{1-[4-(2-amino-pyrimidin-5-yl)-phenyl]-cyclobutyl}-1,2,4-oxadiazol-5-yl)-pyridazin-3-yl]-(2-methoxy-ethyl)-amine (Example 111)

R55 (0.067 g, 0.165 mmoL) and R56 (0.5 mL) are heated in at 70° C. for 30 minutes then concentrated in vacuo and purified by preparative HPLC to afford title compound (0.022 g); m/z 445.6 [M+1].

Compounds in Table 7 listed with Method 11 are synthesized in a similar fashion.

Compounds 271 and 272 are carried out with DMSO as solvent at 115° C.

Method 12

Synthesis of 5-(4-{1-[5-(6-piperazin-1-yl-pyridin-3-yl)-1,2,4-oxadiazol-3-yl]-cyclobutyl}-phenyl)-pyrimidin-2-ylamine (Example 116 in Table 8)

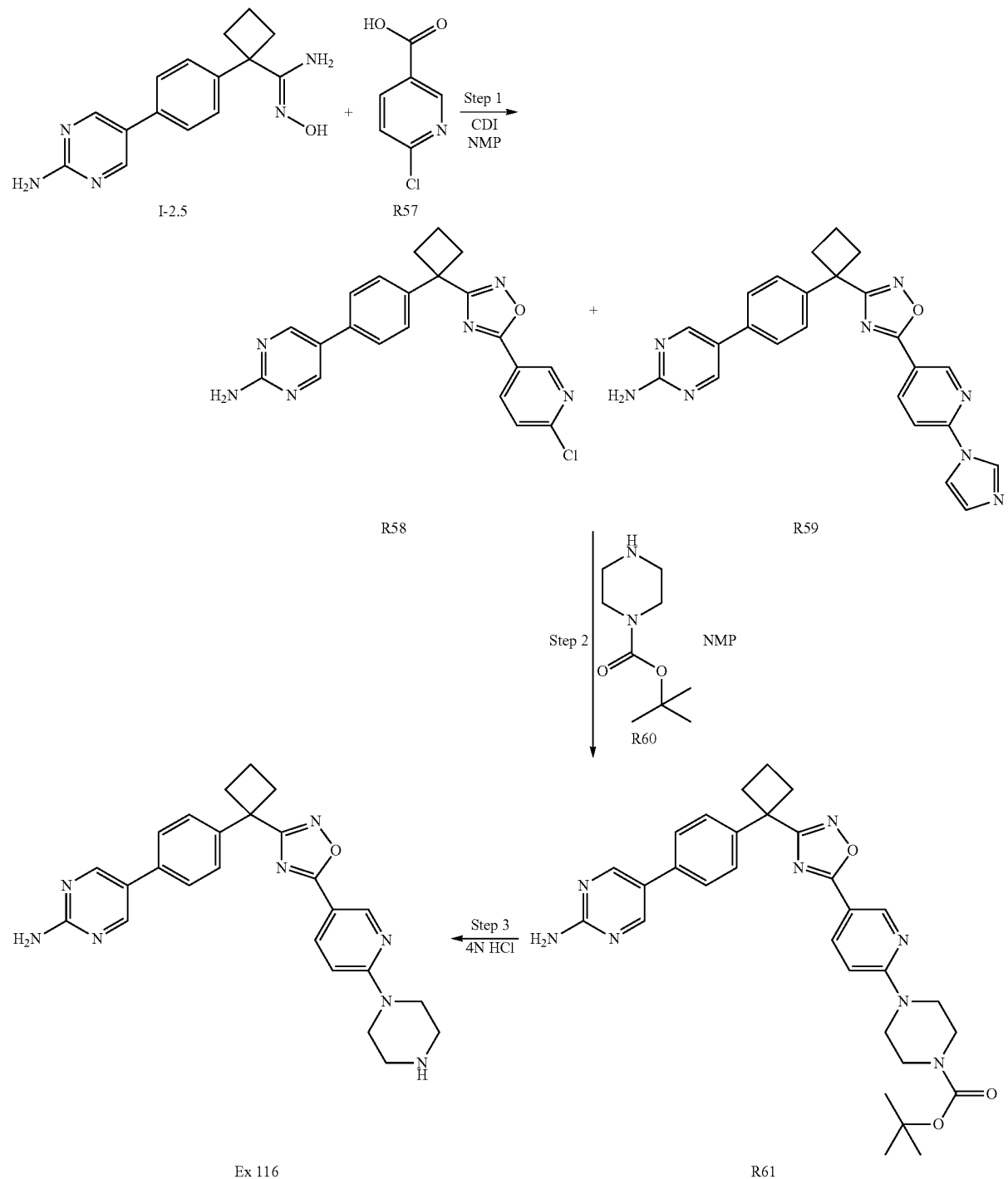

Step 1: Synthesis of 5-(4-{1-[5-(6-chloro-pyridin-3-yl)-1,2,4-oxadiazol-3-yl]-cyclobutyl}-phenyl)-pyrimidin-2-ylamine (R58) and 5-(4-{1-[5-(6-Imidazol-1-yl-pyridin-3-yl)-1,2,4-oxadiazol-3-yl]-cyclobutyl}-phenyl)-pyrimidin-2-ylamine (R59)

Synthesis employs similar conditions described in Method 1 to afford both R58 and R59 which can be used as a mixture in the subsequent reaction Step 2: Synthesis of 4-[5-(3-{1-[4-(2-amino-pyrimidin-5-yl)-phenyl]-cyclobutyl}-1,2,4-oxadiazol-5-yl)-pyridin-2-yl]-piperazine-1-carboxylic acid tert-butyl ester (R61)

The mixture of R58 and R59 (0.2 g, 0.494 mmol) and R60 (0.276 g, 1.482 mmol) are refluxed in NMP (3 mL) overnight.

The mixture is then cooled and diluted with water and filtered to afford title compound (0.027 g) as a solid.

Step 3: Synthesis of 5-(4-{1-[5-(6-piperazin-1-yl-pyridin-3-yl)-1,2,4-oxadiazol-3-yl]-cyclobutyl}-phenyl)-pyrimidin-2-ylamine (Example 116)

Synthesis employs similar condition described in Method 10, Step 2 using the appropriate reagents; m/z 455.4 [M+1]. Compounds in Table 8 listed with Method 12 are synthesized in a similar fashion.

Method 13

Synthesis of 2-[3-(3-{1-[4-(2-amino-pyrimidin-5-yl)-phenyl]-cyclobutyl}-1,2,4-oxadiazol-5-yl)-2-oxo-2H-pyridin-1-yl]-N-methyl-acetamide (Example 118 in Table 8)

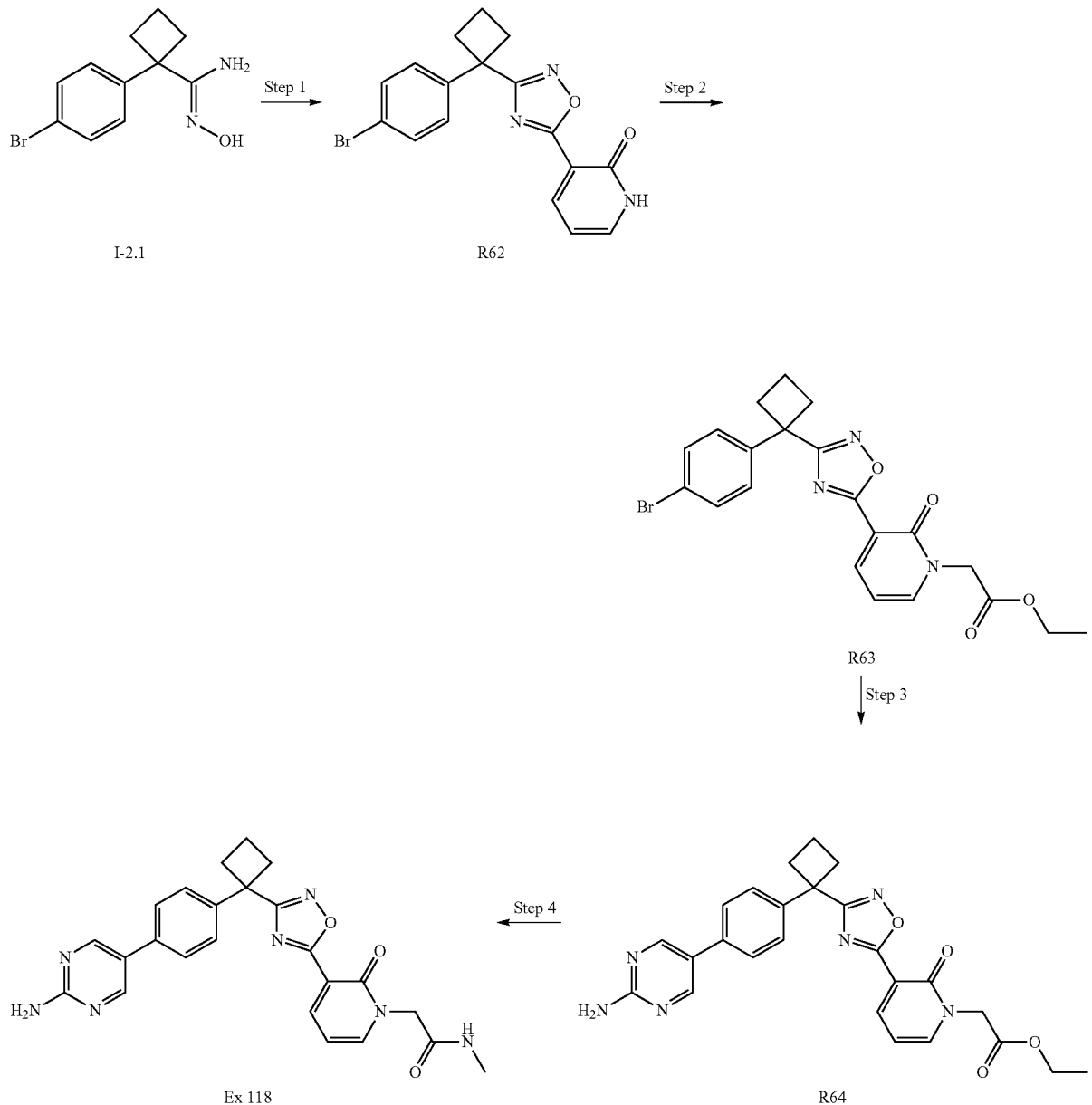

Step 1: Synthesis of 3-{3-[1-(4-bromo-phenyl)-cyclobutyl}-1,2,4-oxadiazol-5-yl]-1H-pyridin-2-one (R62)

Synthesis employed is similar to that used in intermediate method I-B using the appropriate reagents; m/z 373 [M+1].

Step 2: Synthesis of (3-{3-[1-(4-bromo-phenyl)-cyclobutyl}-1,2,4-oxadiazol-5-yl]-2-oxo-2H-pyridin-1-yl)-acetic acid ethyl ester (R63)

Synthesis employed is similar to that used in intermediate method I-H* using the appropriate reagents; m/z 459 [M+1].

Step 3: Synthesis of [3-(3-{1-[4-(2-amino-pyrimidin-5-yl)-phenyl]-cyclobutyl}-1,2,4-oxadiazol-5-yl)-2-oxo-2H-pyridin-1-yl]-acetic acid ethyl ester (R64)

Synthesis employed is similar to that used in Method 3 using the appropriate reagents; m/z 473 [M+1].

Step 4: Synthesis of 2-[3-(3-{1-[4-(2-amino-pyrimidin-5-yl)-phenyl]-cyclobutyl}-1,2,4-oxadiazol-5-yl)-2-oxo-2H-pyridin-1-yl]-N-methyl-acetamide (Example 118)

Synthesis employed is similar to that used in the synthesis of Intermediate I-6.46 step 2 using the appropriate reagents; m/z 458 [M+1].

Compounds in Table 8 listed with Method 13 are synthesized in a similar fashion.

Method 14

Synthesis of 2-[4-(3-{1-[4-(2-amino-pyrimidin-5-yl)-phenyl]-cyclobutyl}-1,2,4-oxadiazol-5-yl)-pyrazol-1-yl]-N,N-dimethyl-acetamide (Example 188 in Table 8)

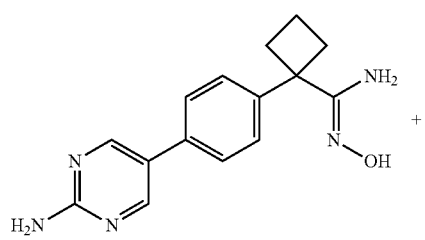

I-2.5

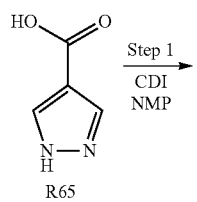

R65

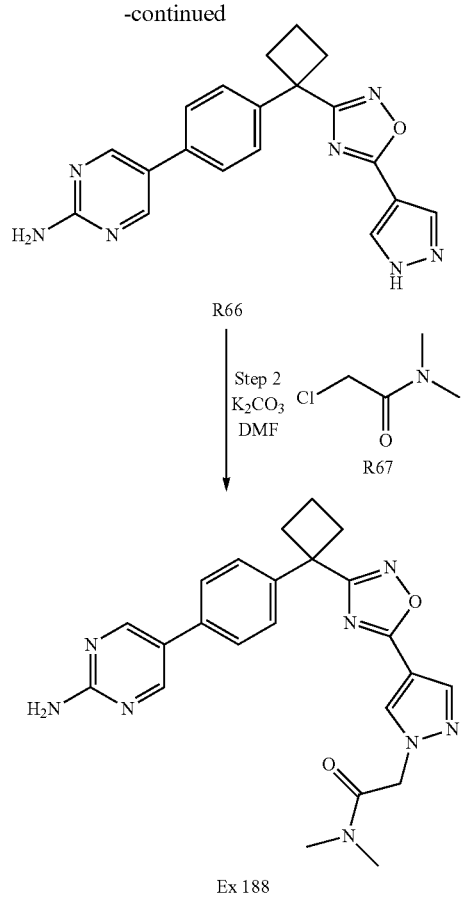

R66

Ex 188

Step 1: Synthesis of 5-(4-{1-[5-(1H-pyrazol-4-yl)-1,2,4-oxadiazol-3-yl]-cyclobutyl}-phenyl)-pyrimidin-2-ylamine (R66)

R65 (8.703 g, 77.648 mmol) and CDI (12.591 g, 77.648 mmol) are stirred at 50° C. in NMP (80 mL) for 30 minutes. I-2.5 (20 g, 70.589 mmol) is added and the mixture heated at 130° C. for 2 h. The reaction is cooled to room temperature and 1 L of distilled water is added and allowed to stir for 48 h. The water is decanted to afford title compound as an oil (24.566 g); m/z 360.4 [M+1].

Step 2: Synthesis of 2-[4-(3-{1-[4-(2-amino-pyrimidin-5-yl)-phenyl]-cyclobutyl}-1,2,4-oxadiazol-5-yl)-pyrazol-1-yl]-N,N-dimethyl-acetamide (Example 188)

R66 (1 g, 2.783 mmol) is dissolved in DMF (5 mL) then $K_2CO_3$ (0.385 g, 2.783 mmol) and R67 (0.286 mL, 2.783 mmoL) are added. The mixture is stirred at room temperature overnight, diluted with water and extracted with EtOAc. The combined organics are washed sequentially with water and brine, dried over $Na_2SO_4$, filtered and concentrated in vacuo. The residue is purified by flash chromatography ($SiO_2$, 5% MeOH/DCM) to afford title compound (0.519 g); m/z 445.4 [M+1].

Compounds in Table 8 listed with Method 14 are synthesized in a similar fashion.

Method 15

Synthesis of 2-[4-(3-{1-[4-(2-amino-pyrimidin-5-yl)-phenyl]-cyclobutyl}-1,2,4-oxadiazol-5-yl)-pyrazol-1-yl]-N,N-dimethyl-isobutyramide (Example 128 in Table 8)

Step 2: Synthesis of 2-[4-(3-{1-[4-(2-amino-pyrimidin-5-yl)-phenyl]-cyclobutyl}-1,2,4-oxadiazol-5-yl)-pyrazol-1-yl]-2-methyl-propionic acid (R70)

R69 (0.129 g, 0.272 mmol) is dissolved in THF/water/MeOH (1/0.5/0.2 mL) and LiOH (0.034 g, 0.817 mmol) is added. The reaction is stirred at 40° C. for 1 h, diluted with 1N

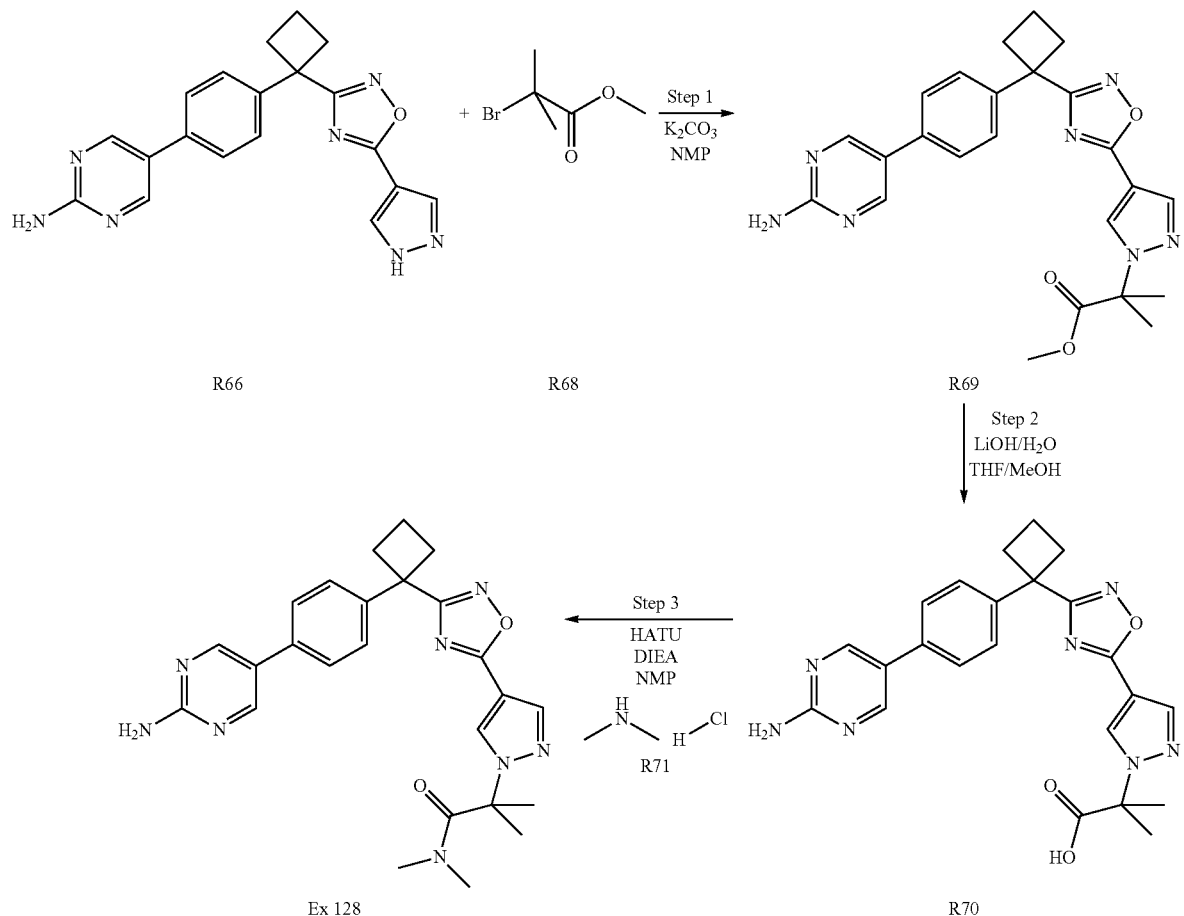

Step 1: Synthesis of 2-[4-(3-{1-[4-(2-amino-pyrimidin-5-yl)-phenyl]-cyclobutyl}-1,2,4-oxadiazol-5-yl)-pyrazol-1-yl]-2-methyl-propionic acid methyl ester (R69)

R66 (0.1 g, 0.278 mmoL) and $K_2CO_3$ (0.042 g, 0.306 mmol) are combined in NMP (2 mL) and R68 (0.108 g, 0.557 mmol) is added. The reaction is stirred for 4 h at 50° C., diluted with water, and extracted with EtOAc. The combined organics are washed with water, then brine, dried over $Na_2SO_4$, filtered and concentrated in vacuo to afford title compound (0.012 g); m/z 474.3 [M+1]

Example 129 employs $Cs_2CO_3$ instead of $K_2CO_3$.

HCl and extracted with EtOAc. The combined organics are washed with brine, dried over $Na_2SO_4$, filtered and concentrated in vacuo to afford title compound (0.087 g); m/z 446.2 [M+1]

Step 3: Synthesis of 2-[4-(3-{1-[4-(2-amino-pyrimidin-5-yl)-phenyl]-cyclobutyl}-1,2,4-oxadiazol-5-yl)-pyrazol-1-yl]-N,N-dimethyl-isobutyramide (Example 128)

R70 (0.087 g, 0.195 mmol) is dissolved in NMP (2 mL) and HATU (0.089 g, 0.234 mmol) is added. The mixture stirs for 15 minutes before adding DIEA (0.102 mL, 0.586 mmol) and R71 (0.024 g, 0.293 mmoL) then stirred for 2 h. The reaction is purified directly by preparative HPLC to afford title compound (0.072 g); m/z 473.3 [M+1].

Compounds in Table 8 listed with Method 15 are synthesized in a similar fashion.

Method 16

Synthesis of 5-(4-{1-[5-(1-methanesulfonyl-1H-pyrazol-4-yl)-1,2,4-oxadiazol-3-yl]-cyclobutyl}-phenyl)-pyrimidin-2-ylamine (Example 135 in Table 8)

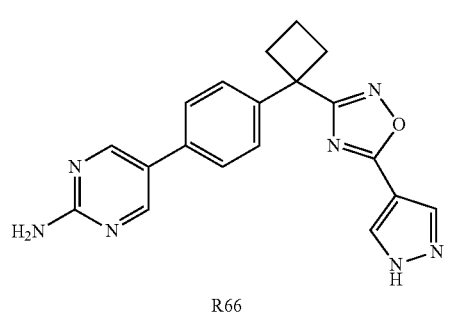

R66

+

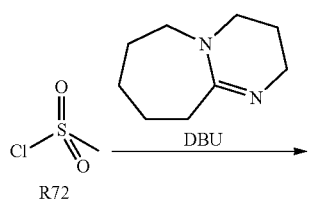

R72

DBU →

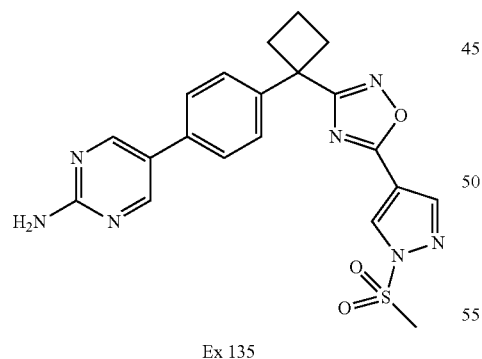

Ex 135

R66 (0.065 g, 0.181 mmol) is dissolved in THF (2 mL) and treated with DBU (0.033 mL, 0.226 mmol). R72 (0.029 mL, 0.271 mmol) is added dropwise and the reaction is stirred 1 h at room temperature. Added a small amount of DMAP (<10 mg) and an additional 1 eq of R72 and DBU and stirred an additional hour. Concentrated in vacuo and redissolved in 1 mL ACN/water and quenched with a few drops ammonia in MeOH. Filtered and purified by reverse phase preparative HPLC to afford title compound (0.045 g); m/z 467.3 [M+1].

Compounds in Table 8 listed with Method 16 are synthesized in a similar fashion.

Method 17

Synthesis of 5-{4-[4-(5-pyridin-2-yl-1,2,4-oxadiazol-3-yl)-tetrahydro-pyran-4-yl]-phenyl}-pyrimidin-2-ylamine (Example 145 in Table 8)

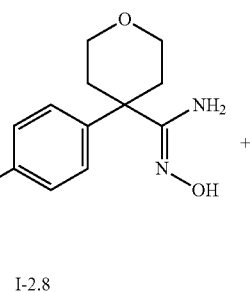

I-2.8

+

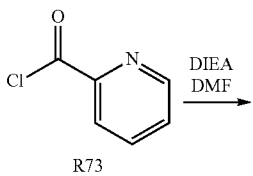

R73

DIEA
DMF →

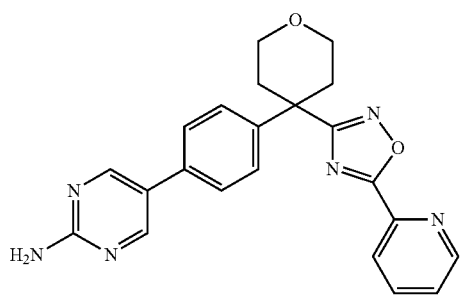

Ex 145

I-2.8 (0.1 g, 0.319 mmoL) is dissolved in DMF (1 mL) then DIEA (0.3 ml, 1.625 mmol) and R73 (0.071 g, 0.5 mmol) are added and the mixture is heated at 120° C. for 2 h. The solvent is removed in vacuo and the residue purified by flash chromatography (SiO$_2$, 0-60% EtOAc/heptanes then 0-5% MeOH/DCM) to afford title compound (0.052 g); m/z 401.6 [M+1].

Compounds in Table 8 listed with Method 17 are synthesized in a similar fashion. Example 167 and 169 employ NMP as a solvent.

Method 18

Synthesis of 2-(5-{3-[1-(4'-amino-biphenyl-4-yl)-cyclobutyl]-1,2,4-oxadiazol-5-yl}-pyridin-2-yl)-propan-2-ol (Example 172 in Table 8)

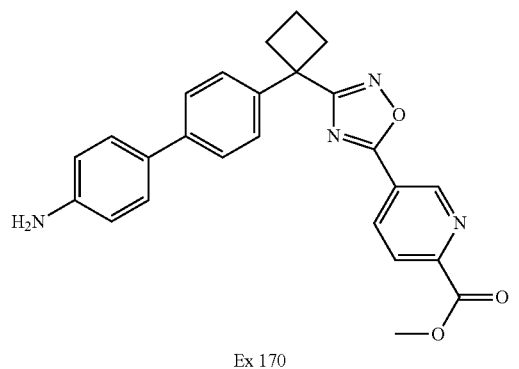

Ex 170   +

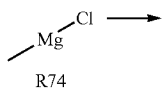

R74

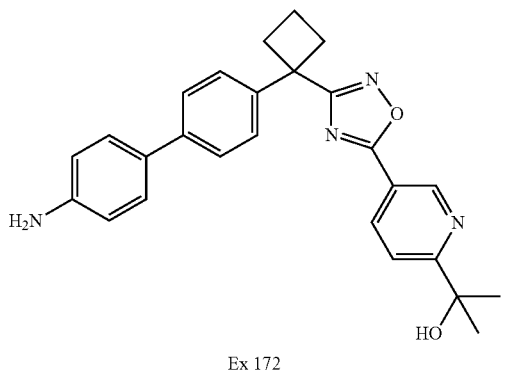

Ex 172

Ex 170 (0.3 g, 0.7 mmol) is dissolved in THF (5 mL) and R74 (2.334 mL, 3M, 7.002 mmol) is added. The mixture is stirred for 2 h, then treated with water, and extracted with DCM. The combined organics are washed with brine, dried over MgSO$_4$, filtered and concentrated in vacuo. The residue is purified by reverse phase preparative HPLC to afford title compound (0.020 g); m/z 429.2 [M+1].

Compounds in Table 8 listed with Method 18 are synthesized in a similar fashion.

Method 19

Synthesis of 3-(3-{1-[4-(2-amino-pyrimidin-5-yl)-phenyl]-cyclobutyl}-1,2,4-oxadiazol-5-yl)-1H-pyridin-2-one (Example 173 in Table 8)

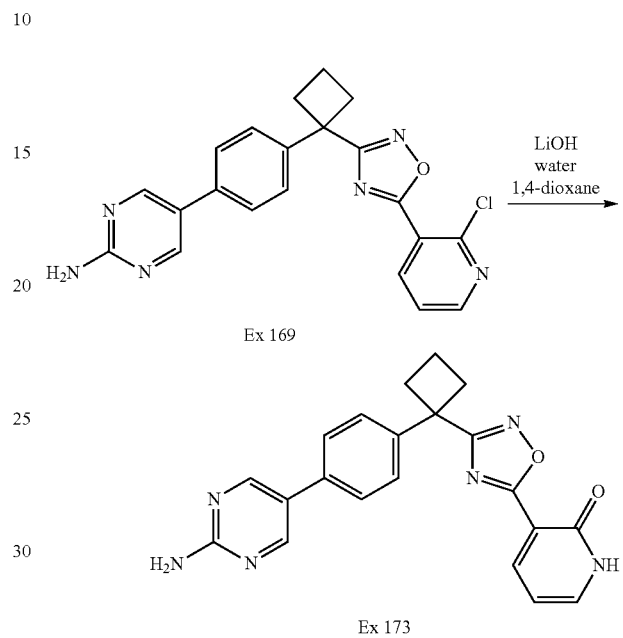

Ex 169 (0.1 g, 0.247 mmol) is dissolved in 1,4-dioxane (4 mL), LiOH (1 mL, 10% solution in water) is added and the reaction stirred at 70° C. overnight. Additional LiOH is added (2 mL of the 10% solution in water is added and several hours later 30 mg LiOH and 3 mL water) and the reaction is heated overnight, cooled to room temperature, and concentrated in vacuo. The residue is purified by flash chromatography (SiO$_2$, 0-10% MeOH/DCM) to afford title compound (0.020 g); m/z 387.2 [M+1].

Compounds in Table 8 listed with Method 19 are synthesized in a similar fashion.

Method 20

Synthesis of 5-(3-{1-[4-(2-amino-pyrimidin-5-yl)-phenyl]-cyclobutyl}-1,2,4-oxadiazol-5-yl)-pyrazine-2-carboxylic acid methyl ester (Example 1 in Table 8)

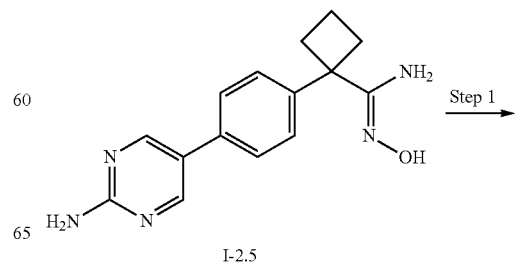

I-2.5

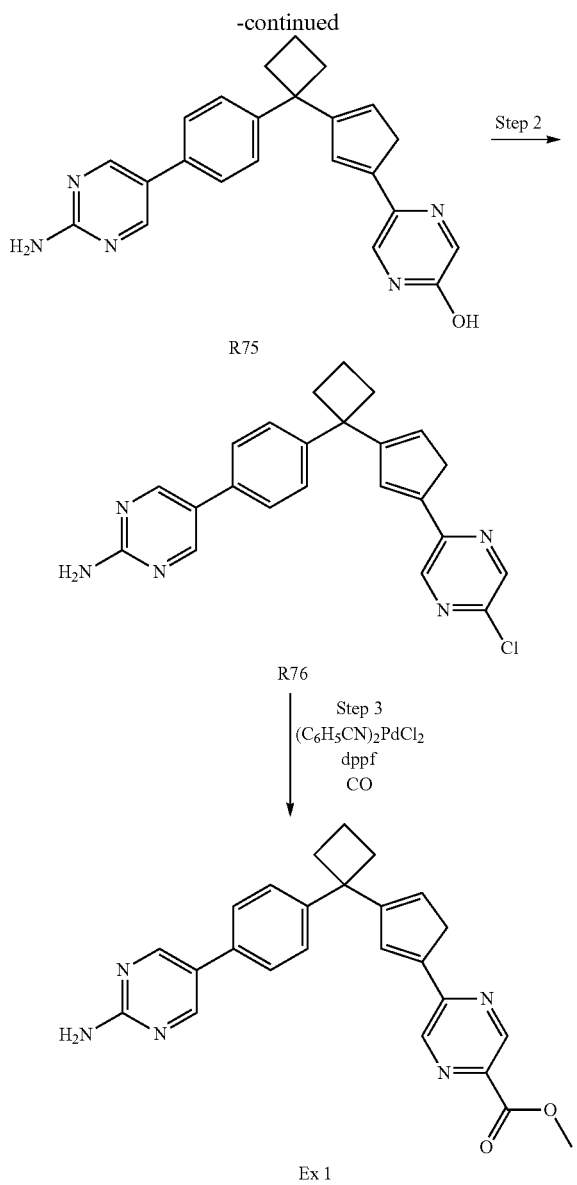

R75

R76

Step 3
(C₆H₅CN)₂PdCl₂
dppf
CO

Ex 1

Step 1: Synthesis of 5-(3-{1-[4-(2-amino-pyrimidin-5-yl)-phenyl]-cyclobutyl}-1,2,4-oxadiazol-5-yl)-pyrazin-2-ol (R75)

Synthesis of R75 employs conditions used in Method 2 from the appropriate reagents; m/z 388.2 [M+1].

Step 2: Synthesis of 5-(4-{1-[5-(5-chloro-pyrazin-2-yl)-1,2,4-oxadiazol-3-yl]-cyclobutyl}-phenyl)-pyrimidin-2-ylamine (R76)

Synthesis of R76 employs conditions used in Example 6, step 2 from the appropriate reagents; m/z 406.2/408.2 [M+1, M+3 3:1]

Step 3: Synthesis of 5-(3-{1-[4-(2-amino-pyrimidin-5-yl)-phenyl]-cyclobutyl}-1,2,4-oxadiazol-5-yl)-pyrazine-2-carboxylic acid methyl ester (Example 1)

R76 (3 g, 7.392 mmol), bis(benzonitrile)palladium (II) chloride (C₆H₅CN)₂PdCl₂, 0.008 g, 0.020 mmol), dppf (0.546 g, 0.986 mmol), anhydrous triethylamine (12.8 mL, 98.56 mmol), methanol (200 mL) and DMF (200 mL) are saturated with carbon monoxide and then heated at 65° C. in an autoclave vessel under 20 psi CO atmosphere. After 5 h, the reaction is cooled to room temperature, filtered through Celite® bed, and the filter cake is rinsed with EtOAc. The organic layer is washed with chilled brine, dried over Na₂SO₄, filtered and concentrated in vacuo. The residue is purified by preparative HPLC to afford title compound (0.06 g); m/z 430.5 [M+1].

Compounds in Table 8 listed with Method 20 are synthesized in a similar fashion.

Method 21

Synthesis of 5-(4-{1-[5-(3-Oxetan-3-yl-3H-imidazol-4-yl)-[1,2,4]oxadiazol-3-yl]-cyclobutyl}-phenyl)-pyrimidin-2-ylamine (Example 264) and 5-(4-{1-[5-(1-Oxetan-3-yl-1H-imidazol-4-yl)-[1,2,4]oxadiazol-3-yl]-cyclobutyl}-phenyl)-pyrimidin-2-ylamine (Example 265)

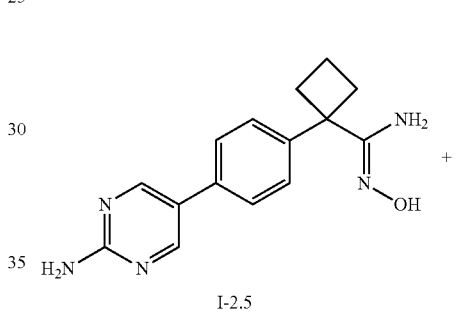

I-2.5

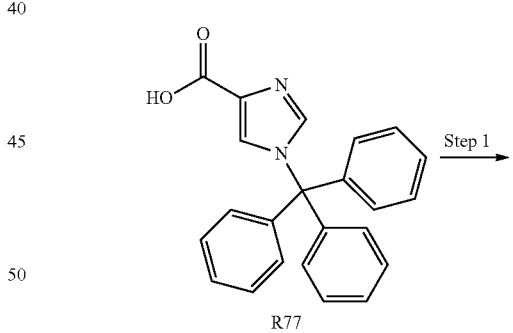

R77

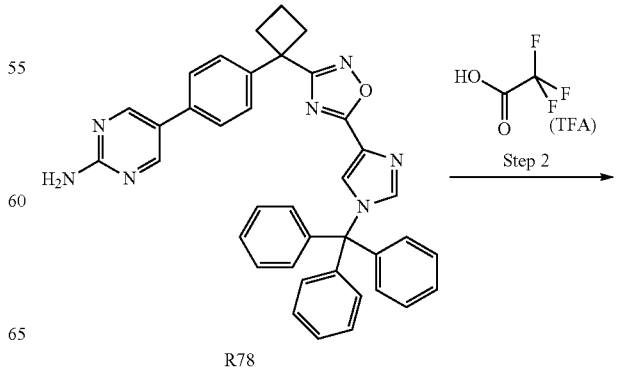

R78

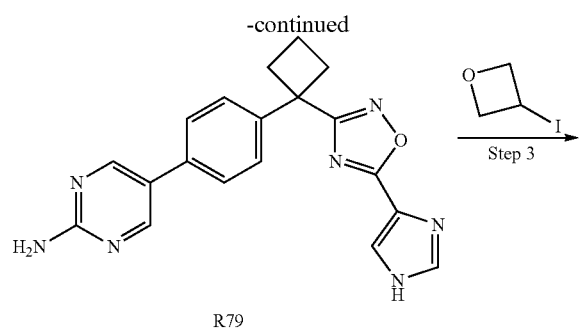

Step 1: Synthesis of 5-(4-{1-[5-(1-Trityl-1H-imidazol-4-yl)-[1,2,4]oxadiazol-3-yl]-cyclobutyl}-phenyl)-pyrimidin-2-ylamine (R78)

To a suspension of R77 (750 mg, 2.1 mmol) in THF (10 mL) is added 1,1'-carbonyldiimidazole (343 mg, 2.1 mmol) at room temperature. The mixture is stirred at 50° C. for 30 minutes. A suspension of I-2.5 (400 mg, 1.4 mmol) in THF (5 mL) is added to the above mixture and the resulting mixture is heated at 130° C. in a microwave reactor for 2 hours. The mixture is cooled down and is concentrated under vacuum. The residue is extracted with $H_2O$ (10 mL) and EtOAc (20 mL). The combined organic layers are dried with $MgSO_4$ and is filtered. The filtrate is concentrated and the residue is purified by silica gel flash chromatography with 10% MeOH in $CH_2Cl_2$ as the eluent to afford R68 (760 mg) m/z: 602 [M+1]

Step 2: Synthesis of 5-(4-{1-[5-(1H-Imidazol-4-yl)-[1,2,4]oxadiazol-3-yl]-cyclobutyl}-phenyl)-pyrimidin-2-ylamine. (R79)

To a solution of R78 (760 mg, 1.2 mmol) in $CH_2Cl_2$ (20 mL) is added TFA (0.5 mL, 6.3 mmol) at room temperature. The solution is stirred at the same temperature for 24 hours. The solution is concentrated under vacuum to afford R79 (350 mg); m/z: 360 [M+1].

Step 3: Syntheses of 5-(4-{1-[5-(3-Oxetan-3-yl-3H-imidazol-4-yl)-[1,2,4]oxadiazol-3-yl]-cyclobutyl}-phenyl)-pyrimidin-2-ylamine (Example 264) and 5-(4-{1-[5-(1-Oxetan-3-yl-1H-imidazol-4-yl)-[1,2,4]oxadiazol-3-yl]-cyclobutyl}-phenyl)-pyrimidin-2-ylamine (Example 265)

To a round bottom flask is added R79 (375 mg, 1.0 mmol), 3-iodooxetane (384 mg, 2.0 mmol) and $K_2CO_3$ (433 mg, 3.1 mmol) in DMF (10 mL). The reaction mixture is stirred at 80° C. for 12 hours. The reaction is cooled to room temperature and water (10 mL) is added. The solution is extracted with EtOAc (20 mL) and $H_2O$ (10 mL). The combined organic layer is dried with $MgSO_4$ and is filtered. The filtrate is concentrated and the residue is purified by silica gel flash column chromatography with 10% MeOH in TBME as the eluent to afford the title compounds (264: 35 mg; 265: 25 mg). 264: m/z 416 [M+H]. 265: m/z 416 [M+H].

Compounds in Table 8 listed with Method 21 are synthesized in a similar fashion.

Method 22

Synthesis of 5-(4-{1-[5-(3,4,5,6-Tetrahydro-2H-[1,2']bipyrazinyl-5'-yl)-[1,2,4]oxadiazol-3-yl]-cyclobutyl}-phenyl)-pyrimidin-2-ylamine (Example 214)

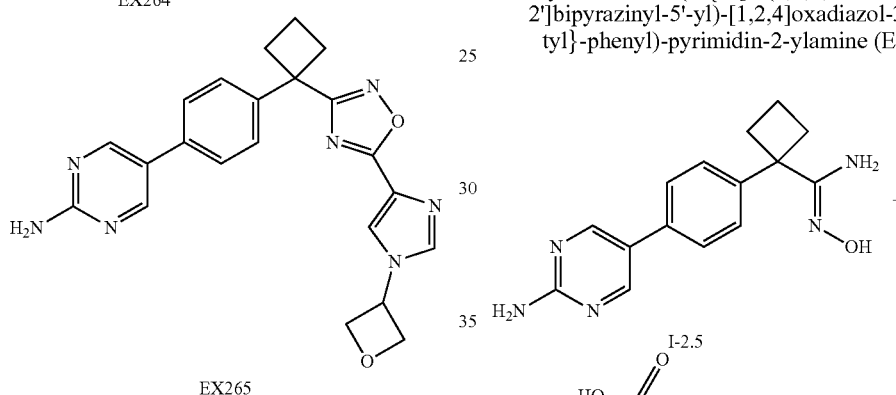

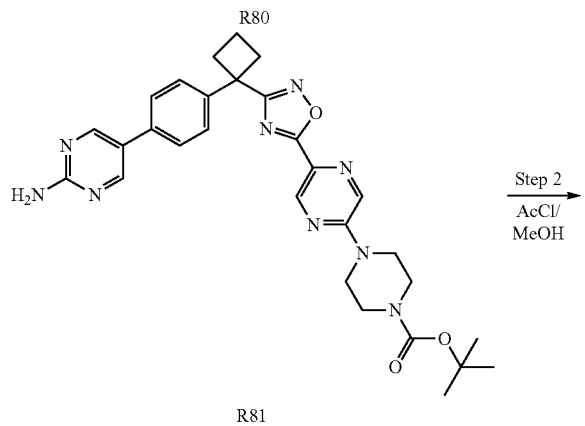

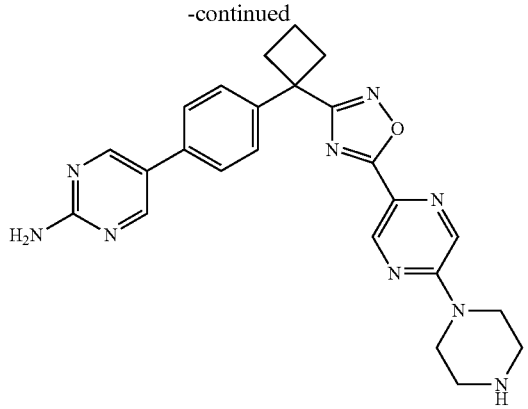

Example 214

Step 1: Synthesis of 5'-(3-{1-[4-(2-Amino-pyrimidin-5-yl)-phenyl]-cyclobutyl}-[1,2,4]oxadiazol-5-yl)-2,3,5,6-tetrahydro-[1,2']bipyrazinyl-4-carboxylic acid tert-butyl ester (R81)

To a suspension of R80 (490 mg, 1.59 mmol) in dioxane (10 ml) is added CDI (260 mg, 1.59 mmol) at room temperature. The mixture is stirred at 50° C. for 30 minutes. After this time I-2.5 (300 mg, 1.06 mmol) is added and the resulting mixture is heated at 80° C. for 18 hours. After this time the reaction appears complete and is cooled and poured into NaHCO₃ (sat.) and EtOAc. The layers are separated and the aqueous phase is extracted with EtOAc (2×). The combined organics are dried (MgSO4), filtered and concentrated to give the crude product which is purified via flash chromatography (25 g silica gel, 0-8% MeOH/DCM). Product-containing fractions are combined and concentrated to give R81. (210 mg)

Step 2: Synthesis of 5-(4-{1-[5-(3,4,5,6-Tetrahydro-2H-[1,2']bipyrazinyl-5'-yl)-[1,2,4]oxadiazol-3-yl]-cyclobutyl}-phenyl)-pyrimidin-2-ylamine (Example 214)

To a stirred suspension of R81 (210 mg, 0.38 mmol) in methanol (15 ml) is added acetyl chloride (0.50 ml, 7.00 mmol) in a dropwise manner. The resulting mixture is stirred at room temperature over night. After this time the reaction is basified with 2N ammonia in MeOH and concentrated. The remaining crude is purified via flash chromatography (10 g silica gel, 0-10% MeOH/DCM) to afford the title compound (32 mg) m/z 456.3 [M+1]

Compounds in Table 8 listed with Method 22 are synthesized in a similar fashion. For examples 282-284 THF was used in place of dioxane as the solvent in step 1.

Method 23

Synthesis of 5-(4-{1-[5-(2-piperazin-1-yl-thiazol-4-yl)-[1,2,4]oxadiazol-3-yl]-cyclobutyl}-phenyl)-pyrimidin-2-ylamine (Example 267)

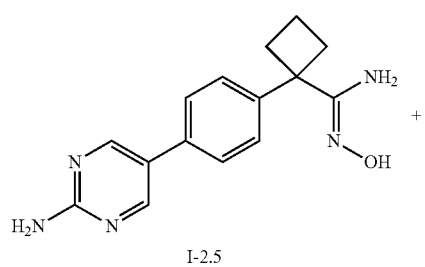

I-2.5

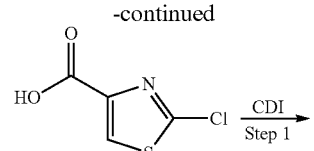

R82

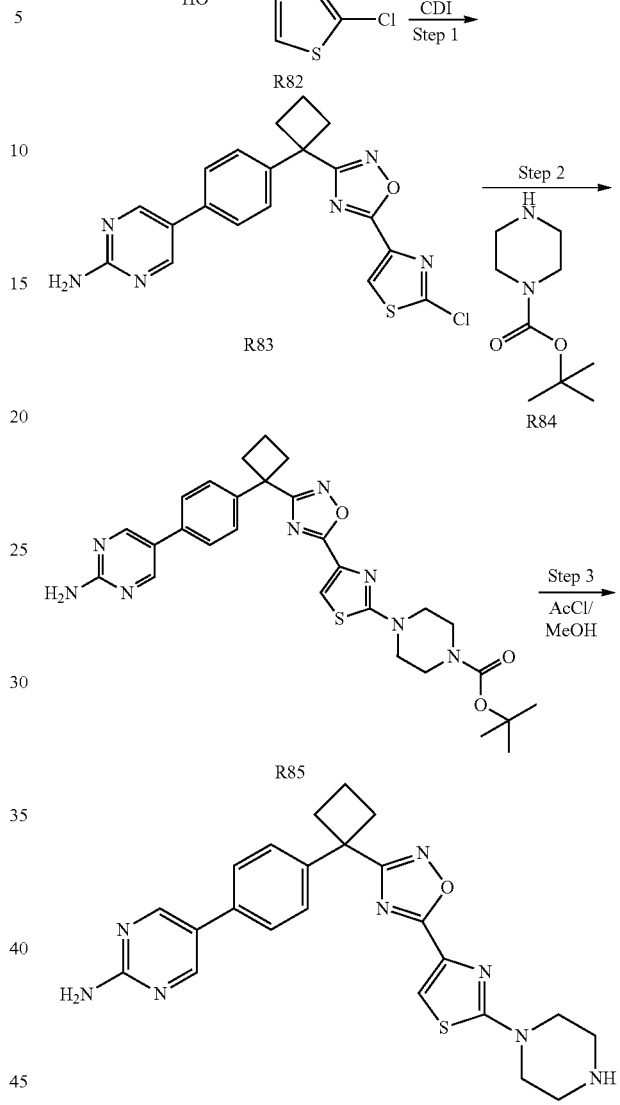

Example 267

Step 1: Synthesis of 5-(4-{1-[5-(2-Chloro-thiazol-4-yl)-[1,2,4]oxadiazol-3-yl]-cyclobutyl}-phenyl)-pyrimidin-2-ylamine (R83)

To a suspension of R82 (173 mg, 1.06 mmol) in THF (5 ml) is added CDI (72 mg, 1.06 mmol) at room temperature. The mixture is stirred at 50° C. for 30 minutes. After this time I-2.5 (200 mg, 0.71 mmol) is added and the resulting mixture is heated 80° C. for 3 hours. The mixture is cooled to ambient temperature and treated with AcOH (0.5 ml). After warming to 80° C. the reaction is stirred over night. Upon cooling to room temperature the reaction is poured into water and EtOAc. The layers are separated and the aqueous phase is extracted with EtOAc. The combined organics are dried (MgSO4), filtered and concentrated to give the crude which is purified via column chromatography (25 g silica gel, 0-8% MeOH/DCM). Product-containing fractions are concentrated to give R83 (120 mg) m/z 411.1

Step 2: Synthesis of 4-[4-(3-{1-[4-(2-Amino-pyrimidin-5-yl)-phenyl]-cyclobutyl}-[1,2,4]oxadiazol-5-yl)-thiazol-2-yl]-piperazine-1-carboxylic acid tert-butyl ester (R85)

To a solution of R83 (120 mg, 0.29 mmol) in NMP (4 ml) is added R84 (82 mg, 0.44 mmol) and potassium carbonate (101 mg, 0.73 mmol). The vessel is capped and warmed to 80° C. over night. After this time the reaction is cooled to ambient temperature and poured into water and EtOAc. The layers are separated and the aqueous phase is extracted with EtOAc (2×). The combined organics are dried (MgSO4), filtered and concentrated. The remaining residue is purified via flash chromatography (10 g silica gel, 0-5% MeOH/DCM) and the product-containing fractions are combined and concentrated to give R85 (70 mg).

Step 3: Synthesis of 5-(4-{1-[5-(2-piperazin-1-yl-thiazol-4-yl)-[1,2,4]oxadiazol-3-yl]-cyclobutyl}-phenyl)-pyrimidin-2-ylamine (Example 267)

To a stirred suspension of R85d (70 mg, 0.12 mmol) in methanol (5 ml) is added acetyl chloride (0.20 ml, 2.80 mmol) in a dropwise manner. The resulting solution is stirred at ambient temperature over night. After this time the reaction is basified using 7N ammonia (in methanol) and concentrated. The remaining solids are diluted with 10% MeOH/DCM and filtered. The solids are washed with DCM and the combined filtrates are concentrated. The crude product is purified via column chromatography (15 g Amine column, 0-8% MeOH/DCM) to afford the title compound (35 mg) m/z 461.4 [M+1]

Compounds in Table 8 listed with Method 23 are synthesized in a similar fashion.

Method 24

Synthesis of 5-(4-{1-[5-(2-Piperidin-4-yl-thiazol-4-yl)-[1,2,4]oxadiazol-3-yl]-cyclobutyl}-phenyl)-pyrimidin-2-ylamine (Example 270)

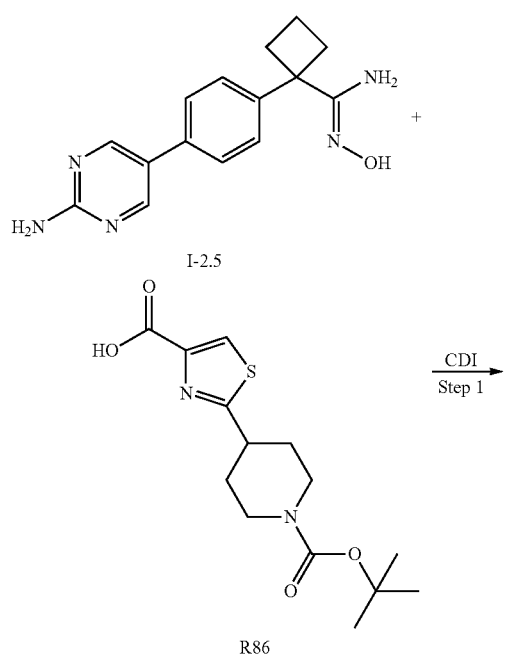

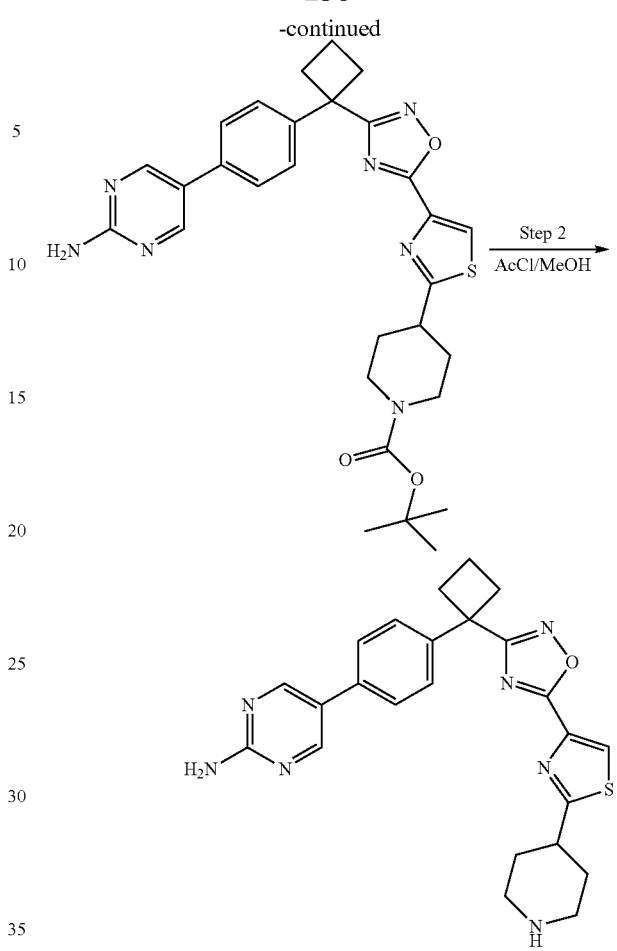

Example 270

Step 1: Synthesis of 4-[4-(3-{1-[4-(2-Amino-pyrimidin-5-yl)-phenyl]-cyclobutyl}-[1,2,4]oxadiazol-5-yl)-thiazol-2-yl]-piperidine-1-carboxylic acid tert-butyl ester (R87)

To a suspension of R86 (400 mg, 1.28 mmol) in THF (10 ml) is added CDI (208 mg, 1.28 mmol) at room temperature. The mixture is stirred at 50° C. for 30 minutes. After this time I-2.5 (300 mg, 1.06 mmol) is added and the resulting mixture is heated at 80° C. for 3 hours. After this time the reaction is cooled to room temperature and treated with AcOH (1 ml). The reaction is warmed to 80° C. for 16 h and cooled to room temperature. The reaction is poured into water and EtOAc. The layers are separated and the aqueous phase is extracted with EtOAc (1×). The combined organics are dried (MgSO4), filtered and concentrated. The crude is purified via column chromatography (25 g silica gel, 0-5% MeOH/DCM) to afford R87 (450 mg) which is used without further purification.

Step 2: Synthesis of 5-(4-{1-[5-(2-Piperidin-4-yl-thiazol-4-yl)-[1,2,4]oxadiazol-3-yl]-cyclobutyl}-phenyl)-pyrimidin-2-ylamine (Example 270)

To a stirred solution of R87 (450 mg, 0.80 mmol) in methanol (25 ml) is added acetyl chloride (1.5 ml, 21.0 mmol, dropwise). The resulting mixture is stirred at room temperature over night. After this time the reaction is basified using 2N ammonia (in methanol) and concentrated. The remaining solid is purified via flash chromatography (15 g amine column, 5-10% MeOH/DCM) to give the title compound (150 mg) m/z 460.4 [M+1]

Method 25

Synthesis of 1-(3-{1-[4-(2-Amino-pyrimidin-5-yl)-phenyl]-cyclobutyl}-[1,2,4]oxadiazol-5-yl)-2-methyl-propan-2-ol (Example 279)

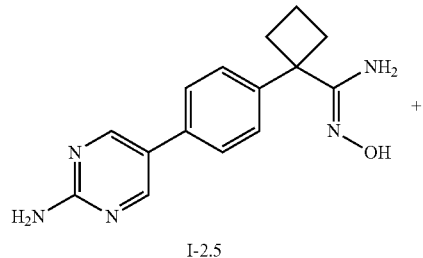

I-2.5

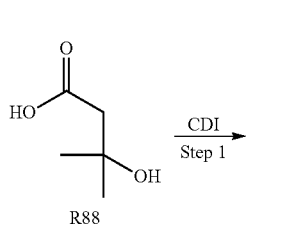

R88

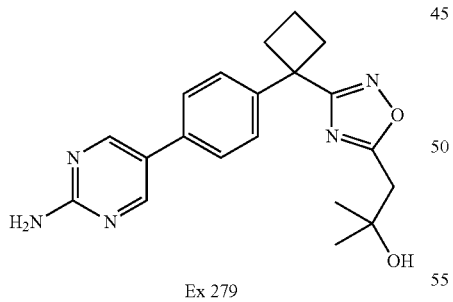

Ex 279

To a suspension of R88 (125 mg, 1.06 mmol) in THF (10 ml) is added CDI (172 mg, 1.06 mmol) at room temperature. The mixture is stirred at 50° C. for 30 minutes. After this time I-2.5 (200 mg, 0.71 mmol) is added and the resulting mixture is heated at 80° C. for 20 hours. After this time the reaction is cooled to ambient temperature and treated with AcOH (1 ml). The reaction is warmed to 80° C. and stirred for 6 h. The mixture is cooled to ambient temperature and stirred overnight. The reaction is concentrated and the remaining residue is purified via column chromatography (25 g silica gel, 0-5% MeOH/DCM). Product-containing fractions are combined and concentrated to afford the title compound (100 mg). m/z 366.4 [M+1]

Method 26

Synthesis of 5-(4-{1-[5-(1-Methyl-piperidin-2-yl)-[1,2,4]oxadiazol-3-yl]-cyclobutyl}-phenyl)-pyrimidin-2-ylamine (Example 281)

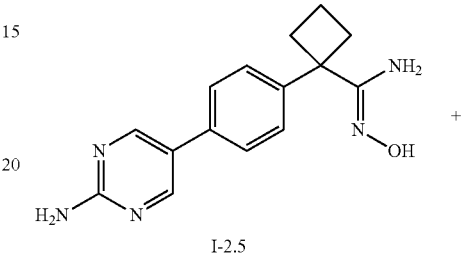

I-2.5

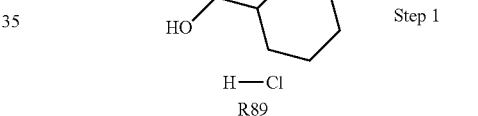

R89

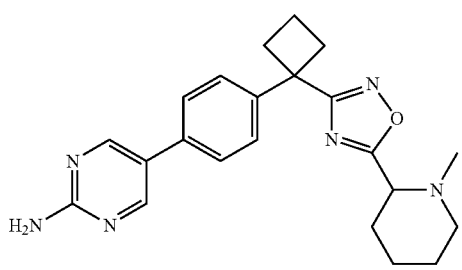

Ex 281

To a suspension of R89 (190 mg, 1.06 mmol) in dioxane (10 ml) is added DIEA (0.18 ml, 1.06 mmol) and CDI (172 mg, 1.06 mmol) at room temperature. The mixture is stirred at 50° C. for 30 minutes. After this time I-2.5 (200 mg, 0.71 mmol) is added and the resulting mixture is heated at 100° C. for 20 hours. After this time the reaction is concentrated and the remaining residue is purified via column chromatography (25 g silica gel, 0-5% MeOH/DCM). The product-containing fractions are combined and concentrated to give the title compound (140 mg) m/z 391.4 [M+1]

Method 27 Synthesis of 5-(4-{1-[5-(3,4,5,6-Tetrahydro-2H-[1,2']bipyrazinyl-5'-yl)-[1,2,4]oxadiazol-3-yl]-cyclobutyl}-phenyl)-pyridin-2-ylamine (Example 297)

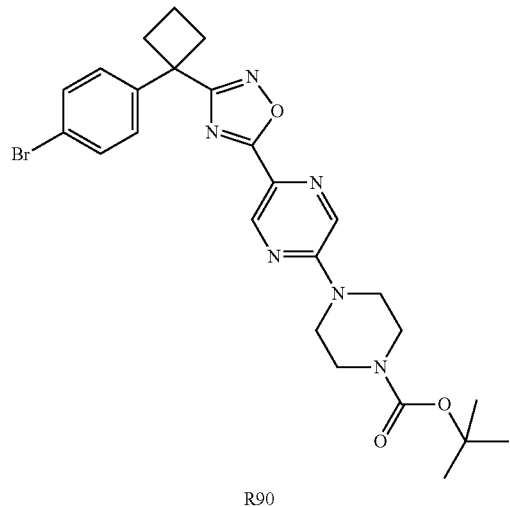

R90

+

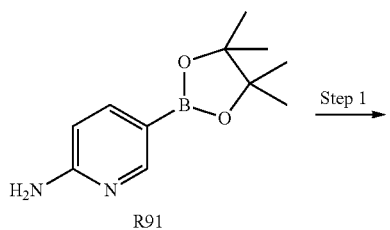

R91

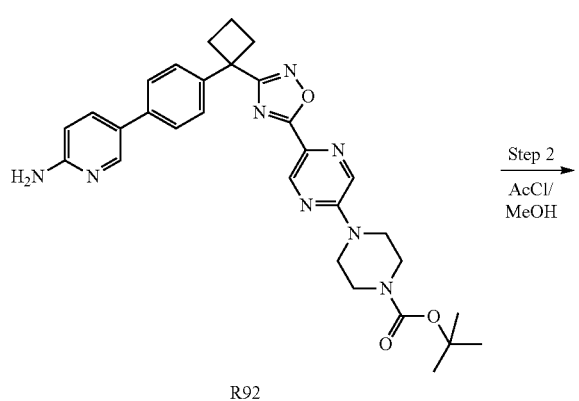

R92

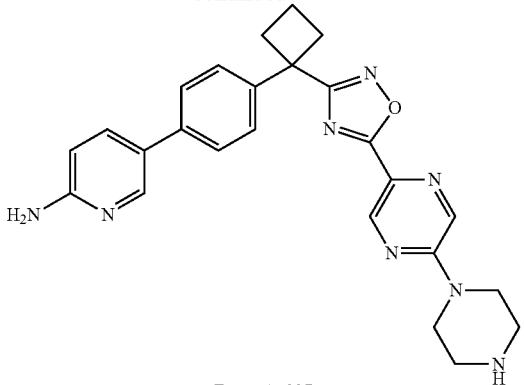

Example 297

Step 1: Synthesis of 5'-(3-{1-[4-(6-Amino-pyridin-3-yl)-phenyl]-cyclobutyl}-[1,2,4]oxadiazol-5-yl)-2,3,5,6-tetrahydro-[1,2']bipyrazinyl-4-carboxylic acid tert-butyl ester (R92)

In a 100 ml flask is added R90 (600 mg, 1.11 mmol) in DMF (25 ml), followed by the addition of R91 (268 mg, 1.22 mmol), tetrakis(triphenylphosphine)palladium(0) (128 mg, 0.11 mmol) and aq. 2M $Na_2CO_3$ (2.22 ml, 4.43 mmol). The reaction mixture is stirred at 100° C. for 16 hours after which time it is poured into brine and extracted with EtOAc (3×). The combined organic fractions are dried (MgSO4), filtered, then concentrated in vacuo to give the crude material. Purification via column chromatography (50 g silica gel, 0-10% MeOH/DCM) afforded R92 (155 mg).

Step 2: Synthesis of 5-(4-{1-[5-(3,4,5,6-Tetrahydro-2H-[1,2']bipyrazinyl-5'-yl)-[1,2,4]oxadiazol-3-yl]-cyclobutyl}-phenyl)-pyridin-2-ylamine (Example 297)

In a 20 ml scintillation vial is added methanol (10 ml) followed by acetyl chloride (1 ml, 14.01 mmol, dropwise). Upon complete addition, R92 (150 mg, 0.27 mmol) is added as a methanol suspension (5 ml). After stifling at ambient temperature over night the reaction is concentrated. The remaining residue is diluted with $NaHCO_3$ (sat.) and DCM. The layers are separated and the aqueous phase is extracted twice more with DCM. The combined organics are dried (MgSO4), filtered and concentrated. The crude is purified via column chromatography (10 g silica gel, 0-10% MeOH/DCM) to give the title compound (50 mg) m/z 455.4 [M+1]

Method 28
Synthesis of 5-(4-{1-[5-(3,4,5,6-Tetrahydro-2H-[1,2']bipyrazinyl-5'-yl)-[1,2,4]oxadiazol-3-yl]-cyclobutyl}-phenyl)-pyrazin-2-ylamine (Example 303)
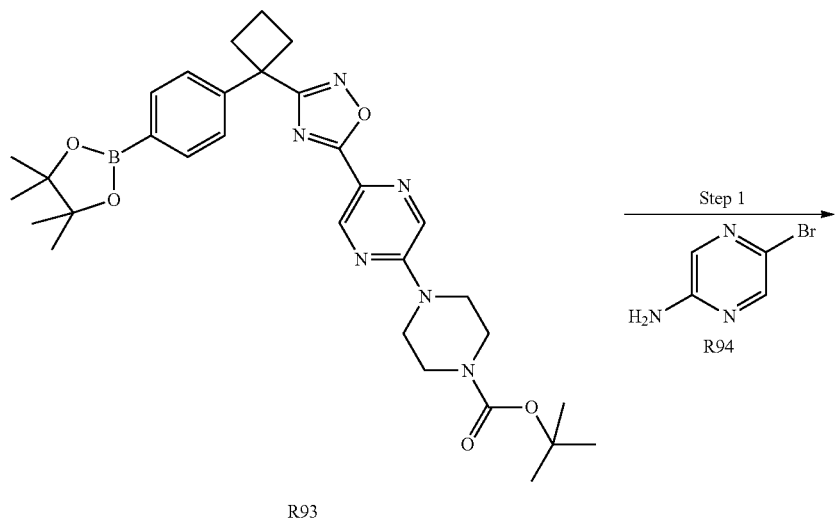
R93
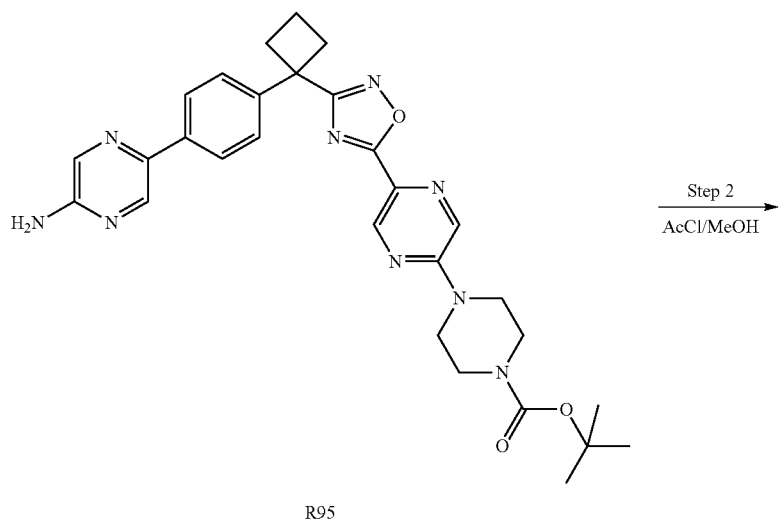
R95
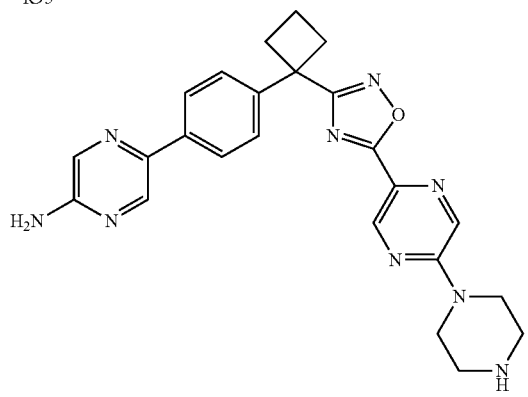
Example 303

Step 1: Synthesis of 5'-(3-{1-[4-(5-Amino-pyrazin-2-yl)-phenyl]-cyclobutyl}-[1,2,4]oxadiazol-5-yl)-2,3,5,6-tetrahydro-[1,2']bipyrazinyl-4-carboxylic acid tert-butyl ester (R95)

In a microwave reaction vessel is added R93 (600 mg, 1.02 mmol) in DMF (15 ml) followed by the addition of R94 (177 mg, 1.02 mmol), tetrakis(triphenylphosphine)palladium(0) (118 mg, 0.10 mmol) and 2M aq. Na$_2$CO$_3$ (2.04 ml, 4.08 mmol). The reaction mixture is capped and stirred at 85° C. for 16 hours. Upon cooling to ambient temperature the reaction mixture is poured into brine and extracted with EtOAc (3×). The combined organic fractions are dried with magnesium sulfate, filtered, and concentrated in vacuo to give the crude product. Purification via flash chromatography (25 g silica gel, 0-8% MeOH/DCM) afforded R95. (550 mg)

Step 2: Synthesis of 5-(4-{1-[5-(3,4,5,6-Tetrahydro-2H-[1,2']bipyrazinyl-5'-yl)-[1,2,4]oxadiazol-3-yl]-cyclobutyl}-phenyl)-pyrazin-2-ylamine (Example 303)

To a suspension of R95 (600 mg, 1.08 mmol) in methanol (10 ml) is added acetyl chloride (1.0 ml, 14.01 mmol) in a dropwise manner. The resulting mixture is stirred at room temperature over night. After this time the reaction is basified using 7N ammonia in methanol and concentrated. The remaining crude is purified via flash chromatography (25 g silica gel, 0-10% MeOH/DCM, with 0.5% NH4OH) to give the title compound (20 mg) m/z 456.3 [M+1]

Method 29

Synthesis of: 5-(4-{1-[5-(1-Oxetan-3-yl-1H-pyrazol-4-yl)-[1,2,4]oxadiazol-3-yl]-cyclobutyl}-phenyl)-pyridin-2-ylamine (Example 252)

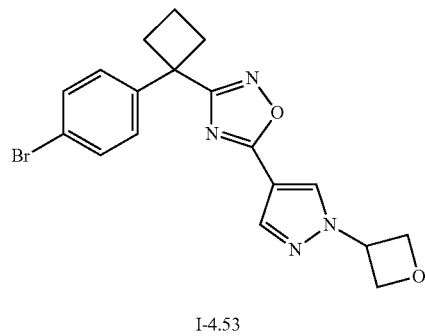

I-4.53

+

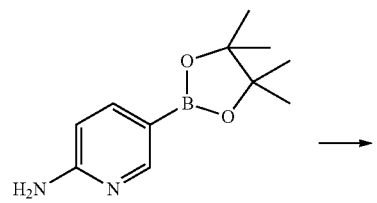

R91

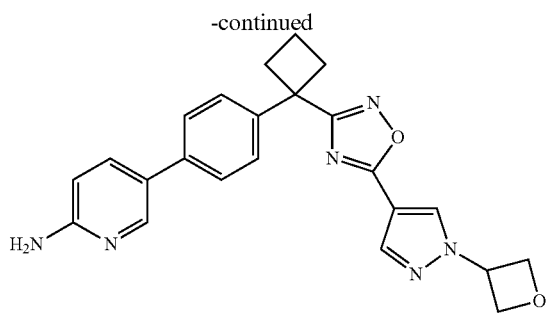

Example 252

To a solution of I-4.53 (125 mg, 0.312 mmol) in 3 ml of DMF was added R91 (82 mg, 0.374 mmol), tetrakis(triphenylphosphine)palladium(0) (36 mg, 0.031 mmol) and aq. Na$_2$CO$_3$ (0.623 mL, 1.246 mmol). The reaction mixture was stirred at 80° C. for 16 hours. The reaction mixture was allowed to cool to room temperature, poured into brine, and extracted with EtOAc. The combined organic fractions were dried sodium sulfate, filtered and concentrated in vacuo. The residue was purified by flash chromatography (SiO$_2$, 0-5% MeOH/DCM) which yields the title compound (50 mg) as a white solid; m/z 416 [M+1].

Method 30

Synthesis of 5-(4-{1-[5-(1-Oxetan-3-yl-1H-pyrazol-4-yl)-[1,2,4]oxadiazol-3-yl]-cyclobutyl}-phenyl)-pyrazin-2-ylamine (Example 300)

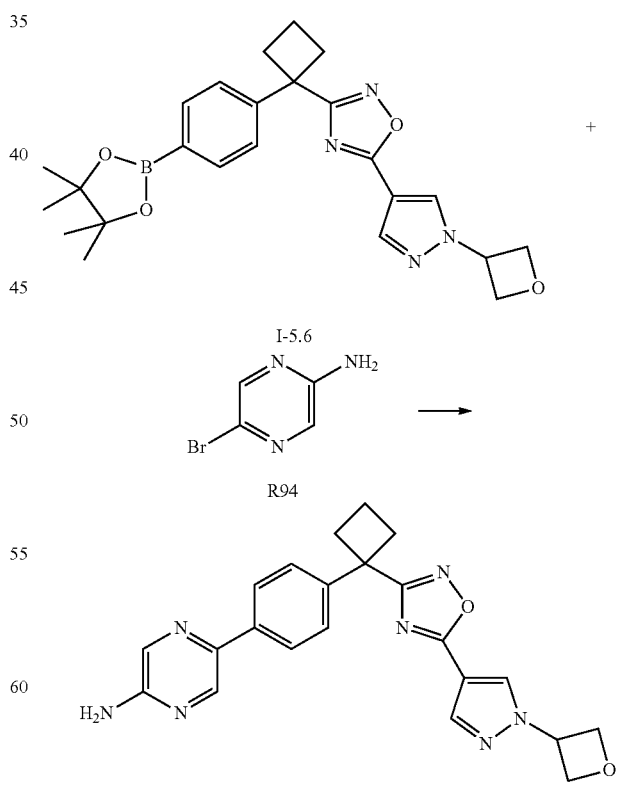

Example 300

To a solution of I-5.6 (363 mg, 0.810 mmol) 3 ml of DMF, followed by the addition of R94 (211 mg, 1.215 mmol), tetrakis(triphenylphosphine)palladium(0) (94 mg, 0.081 mmol) and aq. Na$_2$CO$_3$ (1.619 mL, 3.240 mmol) and stirred at 80° C. for 16 hours. The reaction mixture was poured into water and brine, and product was extracted with EtOAc. The combined organic fractions were dried with sodium sulfate, filtered, and concentrated in vacuo. This is purified by flash chromatography (SiO$_2$, 0-10% MeOH/DCM) followed by purification by preparative HPLC which yields the title compound (116 mgs) as a solid; m/z 416 [M+1].

Method 31

Synthesis of 5-(4-{1-[5-(1-Methyl-1H-pyrazol-4-yl)-[1,2,4]oxadiazol-3-yl]-cyclobutyl}-phenyl)-pyridin-2-ylamine (Example 215)

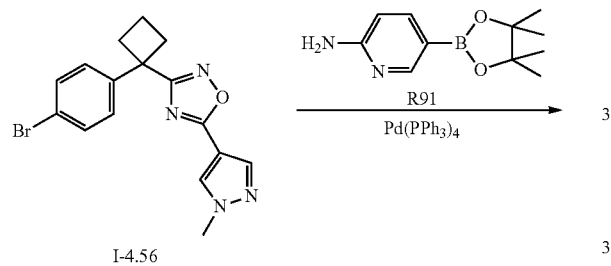

Example 215

To a microwave vial was added I-4.56 (80 mg, 0.223 mmol) in DMF (2.5 ml), followed by the addition of R91 (54 mg, 0.245 mmol), tetrakis(triphenylphosphine)palladium(0) (26 mg, 0.022 mmol) and 2M aq. Na$_2$CO$_3$ (0.35 ml, 0.7 mmol). The reaction mixture was stirred in microwave reactor at 130° C. for 1 hour. The reaction mixture was diluted with EtOAc, washed with water, brine, dried over Na$_2$SO$_4$, filtered and concentrated. The residue was purified by flash chromatography (SiO$_2$, 0-5% MeOH/CH$_2$Cl$_2$) to afford the title compound (33 mg); m/z 373 [M+1].

Compounds in Table 8 listed with method 31 are synthesized in a similar fashion.

Method 32

Synthesis of 5-(4-{1-[5-(1-Methyl-1H-pyrazol-4-yl)-[1,2,4]oxadiazol-3-yl]-cyclobutyl}-phenyl)-pyrazin-2-ylamine (Example 220)

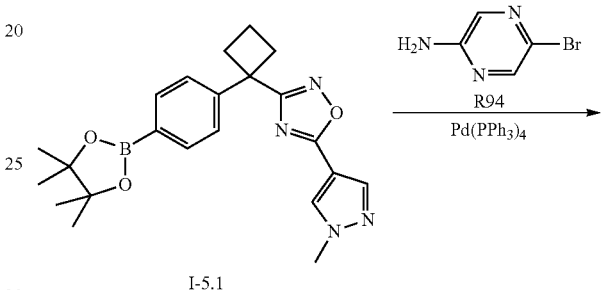

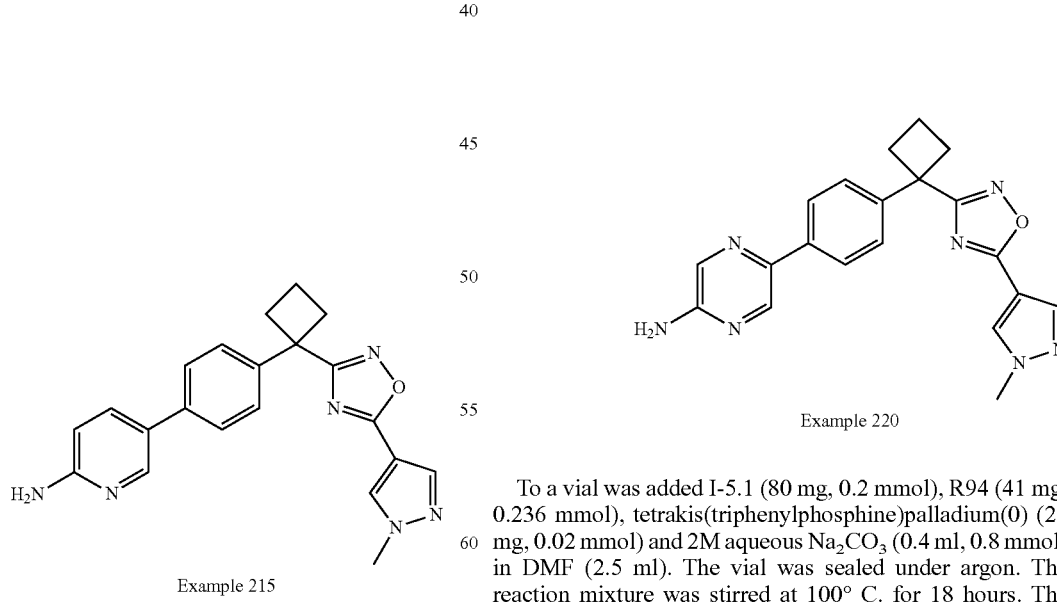

Example 220

To a vial was added I-5.1 (80 mg, 0.2 mmol), R94 (41 mg, 0.236 mmol), tetrakis(triphenylphosphine)palladium(0) (23 mg, 0.02 mmol) and 2M aqueous Na$_2$CO$_3$ (0.4 ml, 0.8 mmol) in DMF (2.5 ml). The vial was sealed under argon. The reaction mixture was stirred at 100° C. for 18 hours. The reaction mixture was diluted with EtOAc, washed with water. The organic layer was separated, washed with brine, dried over Na$_2$SO$_4$, filtered and concentrated. The residue was purified by flash chromatography (SiO$_2$, 0-5% MeOH/CH$_2$Cl$_2$) to afford title compound (44 mg); m/z 374 [M+1]

Compounds in Table 8 listed with method 32 are synthesized in a similar fashion.

Method 33

Synthesis of 2-[4-(3-{1-[4-(2-Amino-pyrimidin-5-yl)-phenyl]-cyclobutyl}-[1,2,4]oxadiazol-5-yl)-pyrazol-1-yl]-1-morpholin-4-yl-ethanone (Example 205)

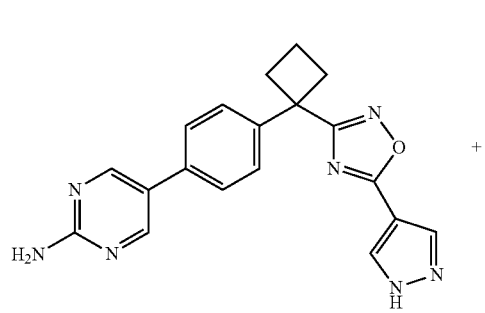

R79

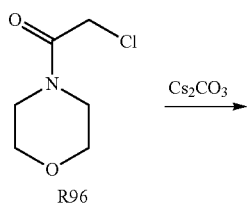

R96

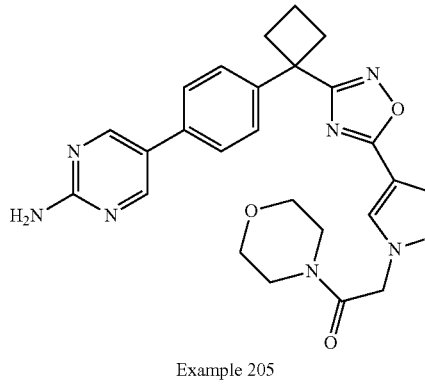

Example 205

R79 (75 mg, 0.209 mmol) is treated with DMF (1.5 mL), R96 (51.2 mg, 0.313 mmol), and Cs$_2$CO$_3$ (153 mg, 0.470 mmol) and the resulting mixture is stirred for 2 hours. The reaction is purified by reverse-phase preparative HPLC to give Example 205 (47.0 mg); m/z 487.4 [M+1].

Compounds in Table 8 listed with Method 33 are synthesized in a similar fashion.

Example 226 is carried out at 70° C.

Example 230, 232, 238, 240 are carried out at 60° C.

Example 246 is carried out at 60° C. for 3 hours.

Example 249 is carried out at 60° C. overnight.

Example 250 is carried out at 60° C. for 5 hours.

Example 253 required a second addition of alkylating reagent and base after 1 hour.

Method 34

Preparation of 5-[4-(1-{5-[1-(2-Amino-ethyl)-1H-pyrazol-4-yl]-[1,2,4]oxadiazol-3-yl}-cyclobutyl)-phenyl]-pyrimidin-2-ylamine (Example 227)

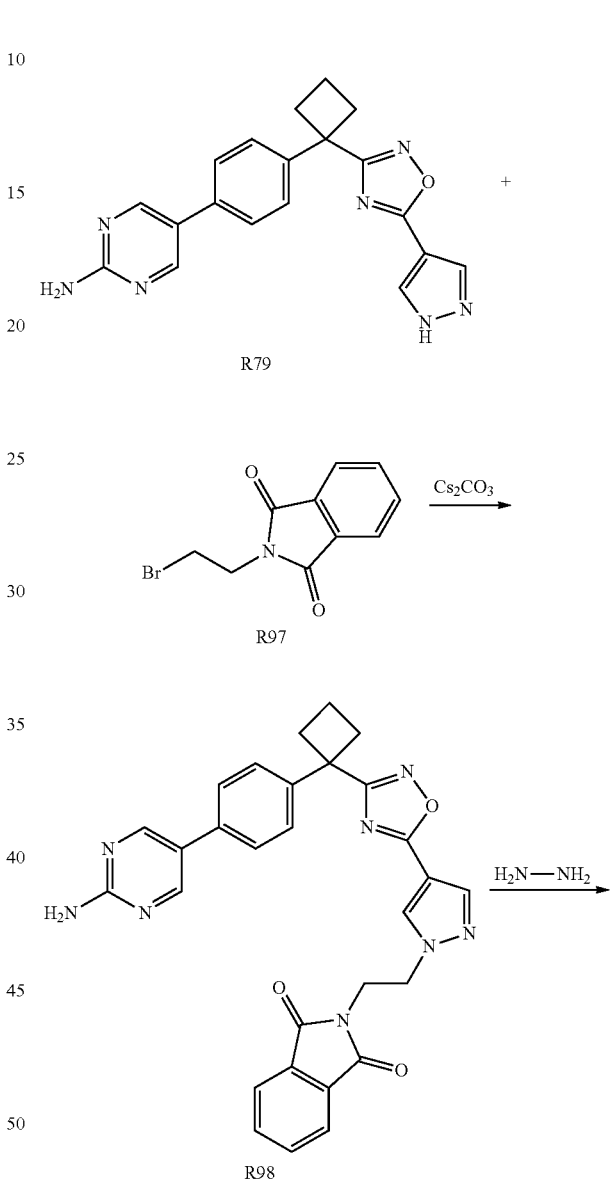

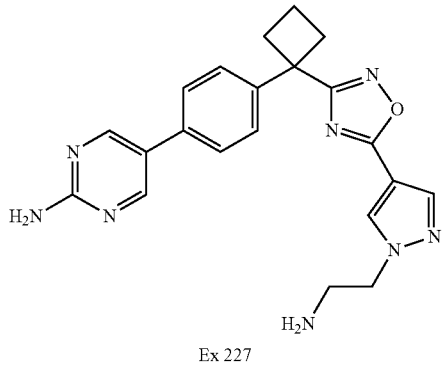

Ex 227

Step 1: Synthesis of 2-{2-[4-(3-{1-[4-(2-Amino-pyrimidin-5-yl)-phenyl]-cyclobutyl}-[1,2,4]oxadiazol-5-yl)-pyrazol-1-yl]ethyl}-isoindole-1,3-dione (R98)

R79 (200 mg, 0.557 mmol) is treated with DMF (5.0 mL), R97 (212 mg, 0.835 mmol), $Cs_2CO_3$ (408 mg, 1.25 mmol) and the resulting mixture is stirred for 3 hours. The mixture is then diluted with EtOAc and water and the phases are separated. The organic phase is washed with water and brine, dried over $Na_2SO_4$, filtered, and concentrated in vacuo. The resulting residue is purified by flash chromatography eluting 0-10% MeOH/DCM to afford R98 (224 mg); m/z 533.4 [M+1].

Step 2: Synthesis of 5-[4-(1-{5-[1-(2-Amino-ethyl)-1H-pyrazol-4-yl]-[1,2,4]oxadiazol-3-yl}-cyclobutyl)-phenyl]-pyrimidin-2-ylamine (Example 227)

R98 (224 mg, 0.421 mmol) is treated with ethanol (5.00 mL) and hydrazine hydrate (179 μL, 3.68 mmol) and the resulting mixture is heated at 50° C. for 2 hours. The reaction is filtered and the filtrate concentrated in vacuo. The residue is partitioned between ethyl acetate and water, and the phases separated. The aqueous phase is rendered basic by addition of solid $Na_2CO_3$ and extracted with ethyl acetate. The combined organic phases are dried over $Na_2SO_4$, filtered, and concentrated in vacuo. The residue is purified by reverse-phase preparative HPLC to give Example 227 (199.0 mg); m/z 403.3 [M+1].

Method 35

Preparation of N-{2-[4-(3-{1-[4-(2-Amino-pyrimidin-5-yl)-phenyl]-cyclobutyl}-[1,2,4]oxadiazol-5-yl)-pyrazol-1-yl]-ethyl}-acetamide (Example 229)

Example 227 (70.0 mg, 0.136 mmol) is treated with DCM (1.0 mL), DIEA (60.0 mL, 0.339 mmol), and AcCl (13.3 mg, 0.169 mmol) and the resulting mixture is stirred for 1 hour. The reaction was treated with 0.5 mL ethanol and concentrated in vacuo. The residue was purified directly by reverse-phase preparative HPLC to give example 229 (19.5 mg); m/z 445.4 [M+1].

Method 36

Preparation of 5-[4-(1-{5-[1-(2-Methanesulfonyl-ethyl)-1H-pyrazol-4-yl]-[1,2,4]oxadiazol-3-yl}-cyclobutyl)-phenyl]-pyrimidin-2-ylamine (Example 231)

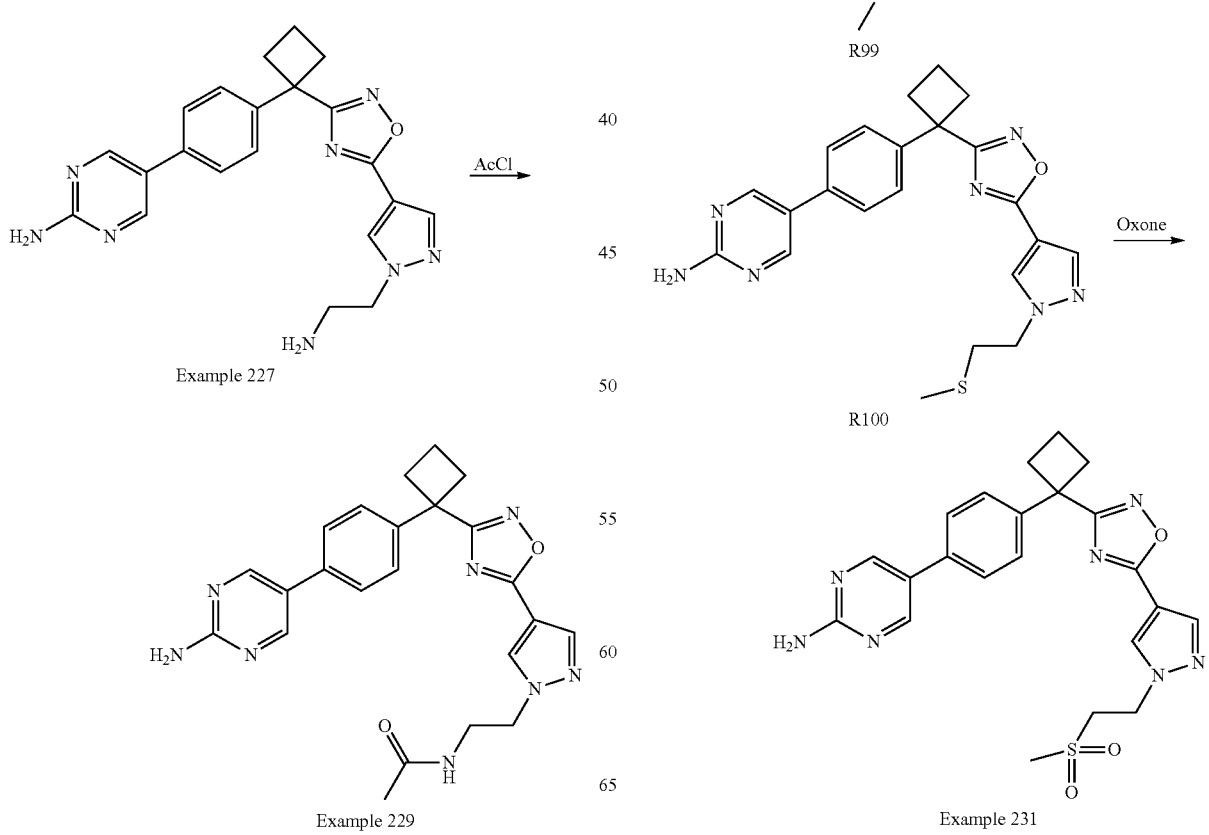

253

Step 1: Synthesis of 5-[4-(1-{5-[1-(2-Methylsulfanyl-ethyl)-1H-pyrazol-4-yl]-[1,2,4]oxadiazol-3-yl}-cyclobutyl)-phenyl]-pyrimidin-2-ylaine (R100)

Synthesized according to method 34 step 1 using R99 in place of R97 to afford R100 (77.6 mg).

Step 2: Synthesis of 5-[4-(1-{5-[1-(2-Methanesulfonyl-ethyl)-1H-pyrazol-4-yl]-[1,2,4]oxadiazol-3-yl}-cyclobutyl)-phenyl]-pyrimidin-2-ylamine (Example 231)

R100 (60.0 mg, 0.138 mmol) is treated with methanol (3.0 mL), water (1.0 mL), and oxone (340 mg, 0.554 mmol) and the resulting mixture is stirred 3 hours. The reaction mixture was filtered through a syringe filter and rinsed through with 1 mL of DMF. The resulting filtrate was concentrated in vacuo and purified directly by reverse-phase preparative HPLC to give Example 231 (19.5 mg); m/z 466.4 [M+1].

Method 37

Preparation of 2-[4-(3-{1-[4-(2-Amino-pyrimidin-5-yl)-phenyl]-cyclobutyl}-[1,2,4]oxadiazol-5-yl)-pyrazol-1-yl]-1-(3-hydroxy-pyrrolidin-1-yl)-ethanone (Example 239)

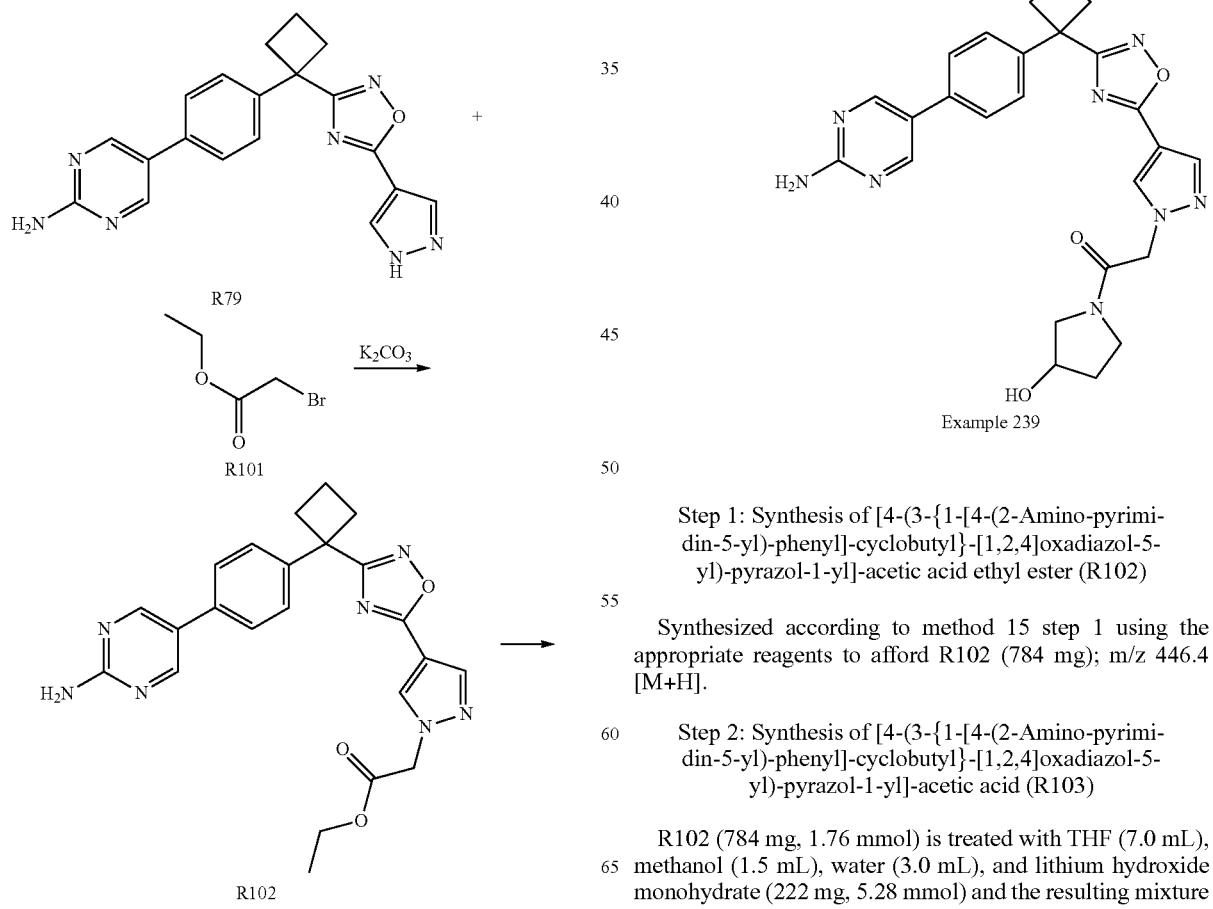

Step 1: Synthesis of [4-(3-{1-[4-(2-Amino-pyrimidin-5-yl)-phenyl]-cyclobutyl}-[1,2,4]oxadiazol-5-yl)-pyrazol-1-yl]-acetic acid ethyl ester (R102)

Synthesized according to method 15 step 1 using the appropriate reagents to afford R102 (784 mg); m/z 446.4 [M+H].

Step 2: Synthesis of [4-(3-{1-[4-(2-Amino-pyrimidin-5-yl)-phenyl]-cyclobutyl}-[1,2,4]oxadiazol-5-yl)-pyrazol-1-yl]-acetic acid (R103)

R102 (784 mg, 1.76 mmol) is treated with THF (7.0 mL), methanol (1.5 mL), water (3.0 mL), and lithium hydroxide monohydrate (222 mg, 5.28 mmol) and the resulting mixture is stirred at 40° C. for 1.5 hours. The mixture is then treated with 1N hydrochloric acid (5.28 mL, 5.28 mmol) and concentrated in vacuo to afford R103 (960 mg).

Step 3: Synthesis of 2-[4-(3-{1-[4-(2-Amino-pyrimidin-5-yl)-phenyl]-cyclobutyl}-[1,2,4]oxadiazol-5-yl)-pyrazol-1-yl]-1-[3-(tetrahydro-pyran-2-yloxy)-pyrrolidin-1-yl]-ethanone (R105)

Synthesized according to method 15 step 3 using the appropriate reagents to afford R105 (65.0 mg); m/z 571.4 [M+H].

Step 4: Synthesis of 2-[4-(3-{1-[4-(2-Amino-pyrimidin-5-yl)-phenyl]-cyclobutyl}-[1,2,4]oxadiazol-5-yl)-pyrazol-1-yl]-1-(3-hydroxy-pyrrolidin-1-yl)-ethanone (Example 41)

R105 (65.0 mg, 0.114 mmol) is treated with ethanol (1.5 mL) and p-toluenesulfonic acid (5.7 mg, 0.20 mmol) and the resulting mixture is stirred at 60° C. for 2.5 hours. The reaction was cooled to room temperature and filtered. The resulting solid was purified by reverse-phase preparative HPLC eluting 10-90% acetonitrile/water/0.1% formic acid to give Example 239 (22.0 mg); m/z 487.4 [M+1].

Method 38

Synthesis of 2-[4-(3-{1-[4-(2-amino-pyrimidin-5-yl)-phenyl]-cyclopropyl}-[1,2,4]oxadiazol-5-yl)-pyrazol-1-yl]-N,N-dimethyl-acetamide (Example 269)

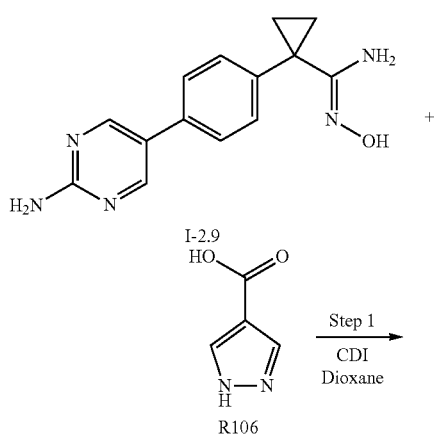

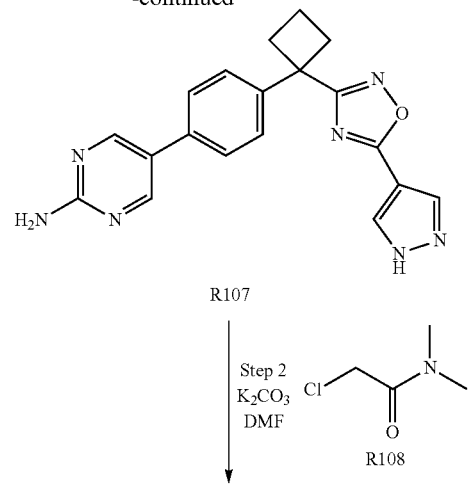

R107

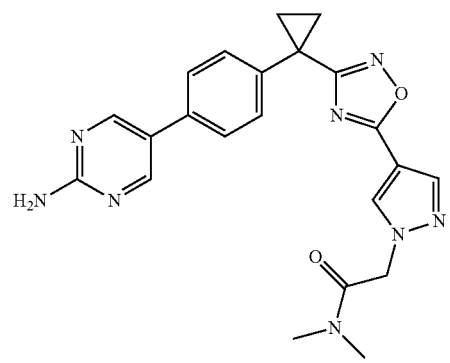

Example 269

Step 1: Synthesis of 5-(4-{1-[5-(1H-pyrazol-4-yl)-[1,2,4]oxadiazol-3-yl]-cyclobutyl}-phenyl)-pyrimidin-2-ylamine (R107)

R108 (213 mg, 1.903 mmol) and CDI (309 mg, 1.903 mmol) in 1,4-dioxane (4 mL) are stirred at 55° C. for 1 hour. I-2.9 (466 mg, 1.73 mmol) is added and the mixture is heated at 120° C. for 18 hours. After this time, the reaction mixture is concentrated in vacuo and the resulting residue is suspended in the mixture of DCM and MeOH then filtered to afford the title compound (429 mg); m/z 346.4 [M+1].

Step 2: Synthesis of 2-[4-(3-{1-[4-(2-amino-pyrimidin-5-yl)-phenyl]-cyclopropyl}-[1,2,4]oxadiazol-5-yl)-pyrazol-1-yl]-N,N-dimethyl-acetamide (Example 269)

Synthesis is similar to conditions used in Method 14 Step 2 using the appropriate reagents; m/z 431.4 [M+1].

Compounds in Table 8 listed with Method 38 are synthesized in a similar fashion.

Method 39

Synthesis of 1-(3-{1-[4-(2-amino-pyrimidin-5-yl)-phenyl]-cyclobutyl}-[1,2,4]oxadiazol-5-yl)-piperidin-4-ol (Example 285)

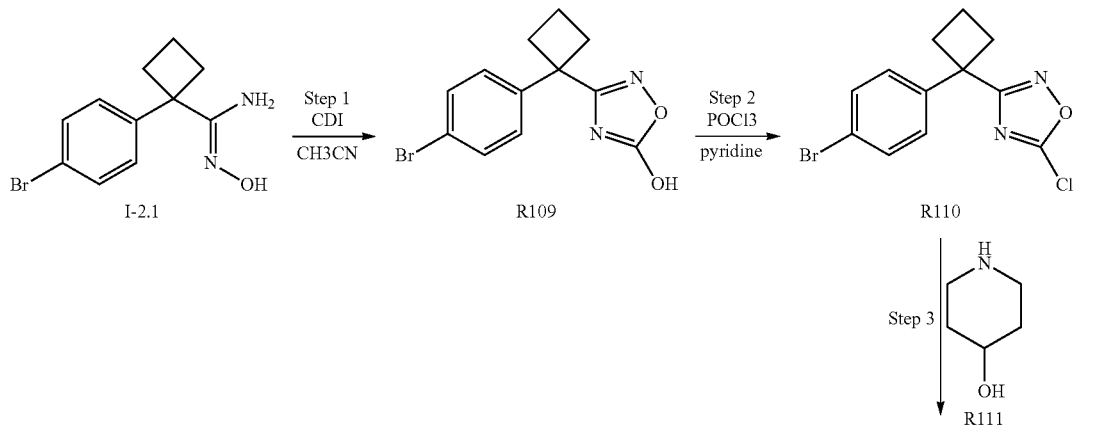

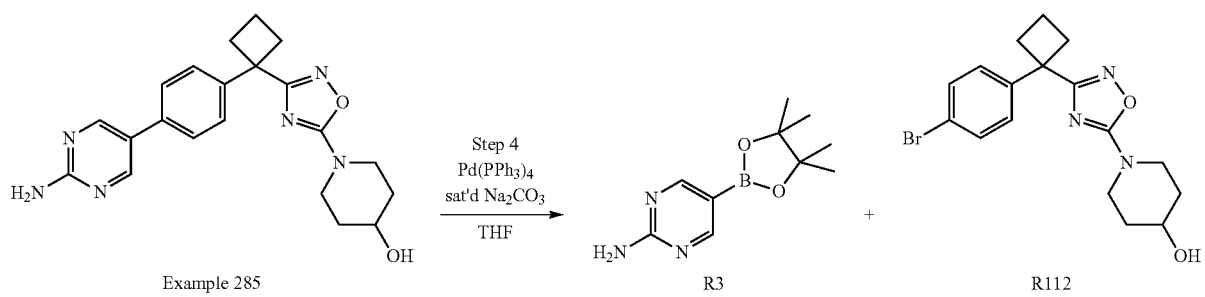

Step 1: Synthesis of 3-[1-(4-bromo-phenyl)-cyclobutyl]-[1,2,4]oxadiazol-5-ol (R109)

To a solution of I-2.1 (7 g, 26.009 mmol) in CH$_3$CN (140 mL) is added CDI (10.543 g, 65.023 mmol) in a pressure flask. The reaction mixture is stirred at 75° C. for 24 hours. After this time, the reaction mixture is concentrated in vacuo and the resulting residue is quenched 1N HCl aqueous solution and extracted with EA twice. The organics are combined and washed with brine, dried over Na$_2$SO$_4$, filtered and concentrated in vacuo to afford the title compound (7.629 g); m/z 295.2/297.2 [M/M+2].

Step 2: Synthesis of 3-[1-(4-bromo-phenyl)-cyclobutyl]-5-chloro-[1,2,4]oxadiazole (R110)

To a solution of R109 (500 mg, 1.694 mmol) in pyridine (1.618 mL, 20 mmol) is added POCl$_3$ (1.551 mL, 16.94 mmol) in a pressure flask. The reaction mixture is stirred at 90° C. for 18 hours. After this time, the reaction mixture is poured into ice water and extracted with EA twice. The organics are combined and washed with brine, dried over Na$_2$SO$_4$, filtered and concentrated in vacuo. The crude is purified by flash chromatography (SiO$_2$, 5-40% EA/Heptane) to afford the title compound (316 mg); no ionization.

Step 3: Synthesis of 1-{3-[1-(4-bromo-phenyl)-cyclobutyl]-[1,2,4]oxadiazol-5-yl}-piperidin-4-ol (R112)

To a solution of R110 (94.3 mg, 0.301 mmol) in DMSO (1 mL) is added R111 (36.5 mg, 0.361 mmol) and DIEA (0.131 mL, 0.75 mmol). The reaction mixture is stirred at room temperature for 1 hour. After this time, the reaction mixture is quenched with water and extracted with EA twice. The organics are combined and washed with brine, dried over Na$_2$SO$_4$, filtered and concentrated in vacuo to afford the title compound (114 mg); m/z 378.2/380.2 [M/M+2].

Step 4: Synthesis of 1-(3-{1-[4-(2-amino-pyrimidin-5-yl)-phenyl]-cyclobutyl}-[1,2,4]oxadiazol-5-yl)-piperidin-4-ol (Example 285)

To a mixture of R3 (79.8 mg, 0.361 mmol) and Pd(PPh$_3$)$_4$ (34.8 mg, 0.03 mmol) in a microwave vial is added the THF (1 mL) solution of R112 (114 mg, 0.301 mmol) and saturated Na$_2$CO$_3$ aqueous solution (0.5 mL). The reaction mixture is purged with argon and then heated in microwave oven at 110° C. for 45 minutes. After this time, the reaction mixture is quenched with water and extracted with EA twice. The organics are combined and washed with brine, dried over Na$_2$SO$_4$, filtered and concentrated in vacuo. The crude is purified by flash chromatography (SiO$_2$, 1.2-10% MeOH/DCM) to afford the title compound (36 mg); m/z 393.25 [M+1].

Compounds in Table 8 listed with Method 39 are synthesized in a similar fashion.

Method 40

Synthesis of 2-Cyclopropyl-5-(4-{1-[5-(1-methyl-1H-pyrazol-4-yl)-[1,2,4]oxadiazol-3-yl]-cyclobutyl}-phenyl)-pyridine (Example 248)

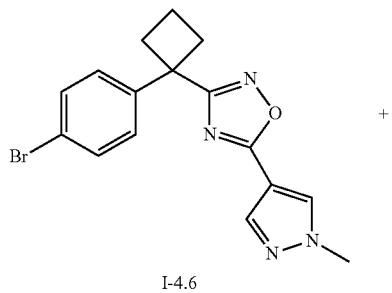

I-4.6

+

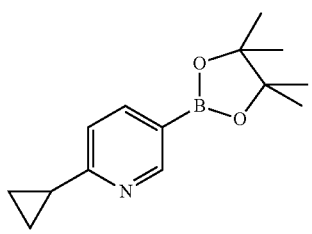

R113

$\xrightarrow{\text{PdCl}_2(\text{dppf})}{\text{KOAc, Dioxane}}$

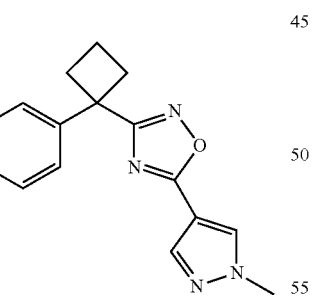

Ex 248

I-4.6 (50 mg, 0.139 mmol), R113 (68 mg, 0.278 mmol), PdCl$_2$(dppf) (11 mg, 0.014 mmol), potassium acetate (55 mg, 0.556 mmol) and 1,4-dioxane (1 mL, degassed) are mixed in a vial and the reaction mixture is heated at 100° C. for 64 hours. After this time, the reaction mixture is cooled to room temperature and filtered through celite and the filtrate is concentrated in vacuo. Purification by preparative HPLC gives the title compound which is free based by dissolving in EA and washing with saturated NaHCO$_3$ aqueous solution. The organics are combined and concentrated to give the title compound (8 mg); m/z 398.4 [M+1].

Method 41

Synthesis of 6-(4-{1-[5-(1-Methyl-1H-pyrazol-4-yl)-[1,2,4]oxadiazol-3-yl]-cyclobutyl}-phenyl)-pyridazin-3-ylamine (Example 258)

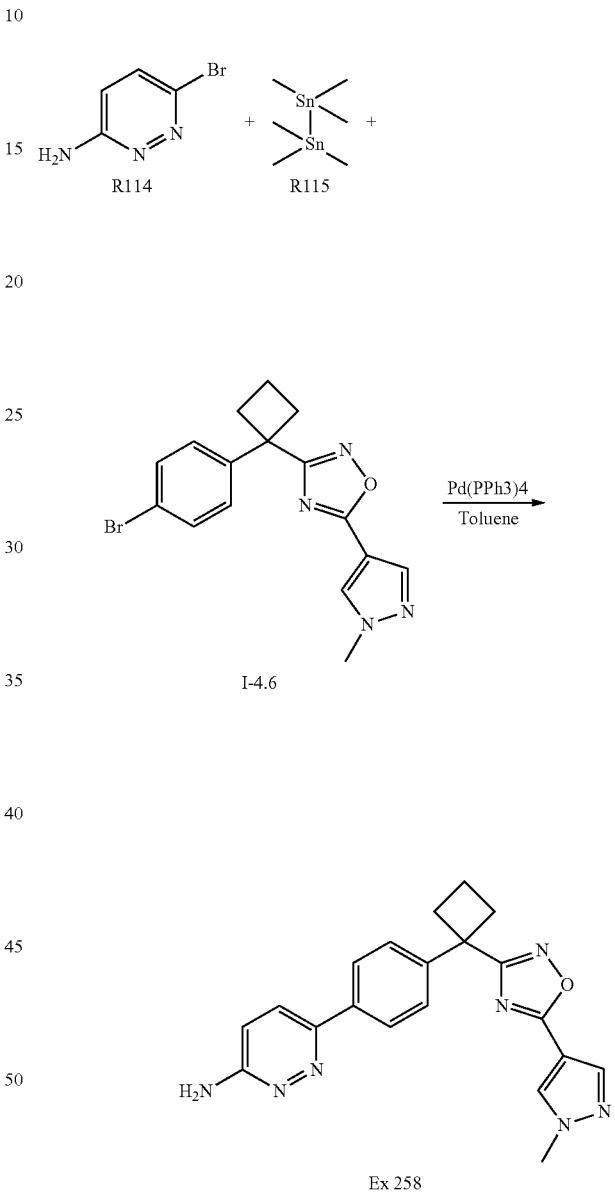

A reaction vessel is charged with I-4.6 (200 mg, 0.557 mmol) and R115 (0.127 mL, 0.613 mmol) and diluted with degassed toluene (3 mL). Pd(PPh$_3$)$_4$ (64 mg, 0.056 mmol) is added and the vessel is purged with argon. The vessel is sealed and heated at 115° C. for 1 hour. The vessel is cooled and R114 (116 mg, 0.668 mmol) is added along with more Pd(PPh$_3$)$_4$ (64 mg, 0.056 mmol). The vessel is purged with argon, capped and heated at 115° C. for 18 hours. The mixture is cooled and concentrated in vacuo. Purification by preparative HPLC then prep-TLC (10% MeOH/DCM) gives the title compound (9 mg); m/z 374.4 [M+1].

Compounds in Table 8 listed with Method 41 are synthesized in a similar fashion.

Method 42

Synthesis of Methyl-[5-(4-{1-[5-(1-methyl-1H-pyrazol-4-yl)-[1,2,4]oxadiazol-3-yl]-cyclobutyl}-phenyl)-pyrimidin-2-yl]-amine (Example 295)

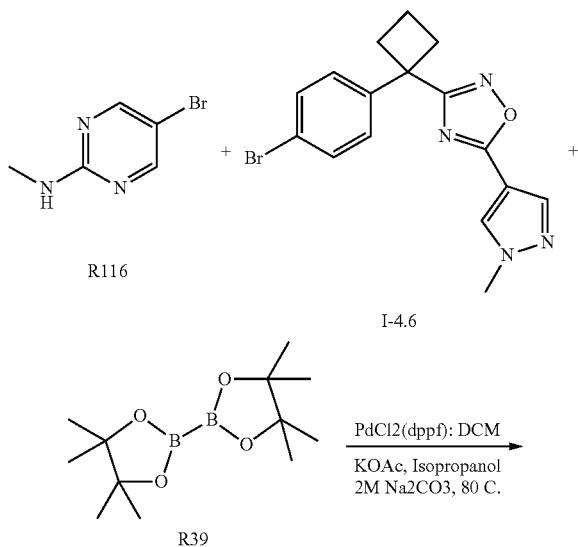

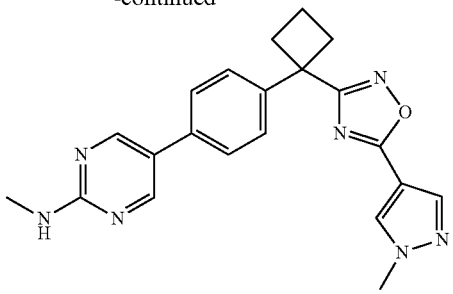

Example 295

R116 (39 mg, 0.209 mmol) and R39 (69 mg, 0.272 mmol) are added to a vial and degassed isopropanol (1 mL) is added. PdCl$_2$(dppf):DCM (17 mg, 0.021 mmol) and potassium acetate (62 mg, 0.627 mmol) are added and the mixture is heated for 1 hour at 80° C. After this time, the reaction mixture is cooled and I-6.6 (75 mg, 0.209 mmol) and 2M Na$_2$CO$_3$ aqueous solution (0.418 mL, 0.836 mmol) are added and it is heated at 80° C. for 18 hours. After this time, the mixture is cooled and concentrated in vacuo. Purification by preparative HPLC gives the title compound which is free based by dissolving in EA and washed with saturated NaHCO$_3$ aqueous solution. The organics are combined and concentrated to give the title compound (8 mg); m/z 388.4 [M+1].

Compounds in Table 8 listed with Method 42 are synthesized in a similar fashion (Ex 104).

TABLE 8

| Example | Structure | Method | Retention time | m/z | LC MS method |
|---|---|---|---|---|---|
| 1 | 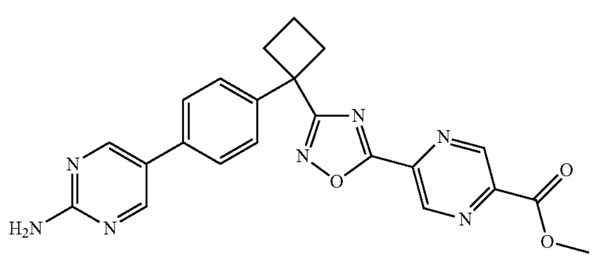 [SMILES: COC(=O)c1cnc(-c2nc(C3(c4ccc(-c5cnc(N)nc5)cc4)CCC3)no2)cn1] | 20 | 5.65 | 430.5 | A |
| 2 | 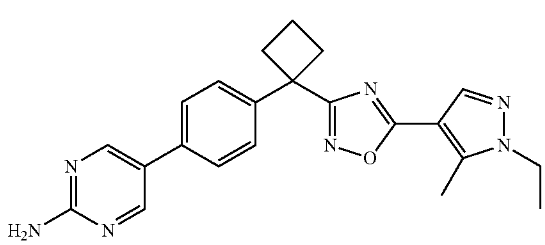 [SMILES: CCn1ncc(-c2nc(C3(c4ccc(-c5cnc(N)nc5)cc4)CCC3)no2)c1C] | 3 | 4.12 | 402.4 | B |

TABLE 8-continued

| | Final compounds | | | | |
|---|---|---|---|---|---|
| Example | Structure | Method | Retention time | m/z | LC MS method |
| 3 | | 3 | 3.6 | 401.2 | B |
| 4 | | 1 | 3.63 | 386.2 | B |
| 5 | | 1 | 3.65 | 374.2 | B |
| 6 | | 1 | 3.65 | 374.2 | B |
| 7 | | 1 | 3.62 | 389.3 | B |
| 8 | | 1 | 3.52 | 372.2 | B |

TABLE 8-continued

Final compounds

| Example | Structure | Method | Retention time | m/z | LC MS method |
|---|---|---|---|---|---|
| 9 | 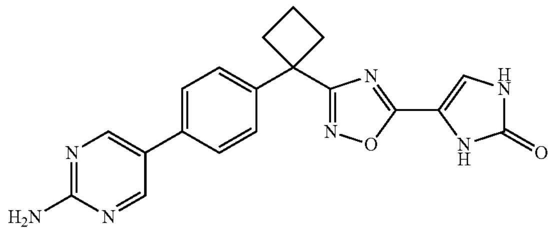 [SMILES: Nc1ncc(-c2ccc(C3(c4noc(-c5c[nH]c(=O)[nH]5)n4)CCC3)cc2)cn1] | 1 | 3.16 | 376.2 | B |
| 10 | 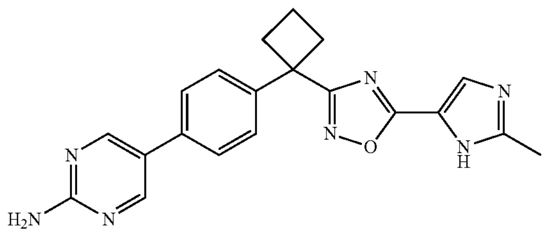 [SMILES: Cc1ncc(-c2nc(C3(c4ccc(-c5cnc(N)nc5)cc4)CCC3)no2)[nH]1] | 1 | 3.09 | 374.2 | B |
| 11 | 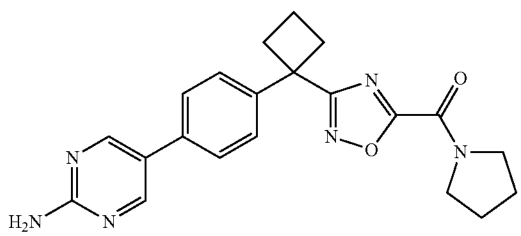 [SMILES: Nc1ncc(-c2ccc(C3(c4noc(C(=O)N5CCCC5)n4)CCC3)cc2)cn1] | 3 | 3.91 | 391 | C |
| 12 | 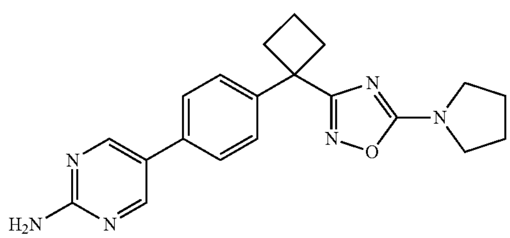 [SMILES: Nc1ncc(-c2ccc(C3(c4noc(N5CCCC5)n4)CCC3)cc2)cn1] | 3 | 3.83 | 363.3 | B |
| 13 | 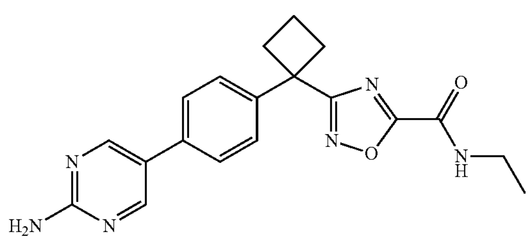 [SMILES: CCNC(=O)c1nc(C2(c3ccc(-c4cnc(N)nc4)cc3)CCC2)no1] | 3 | 3.9 | 365.2 | B |
| 14 | 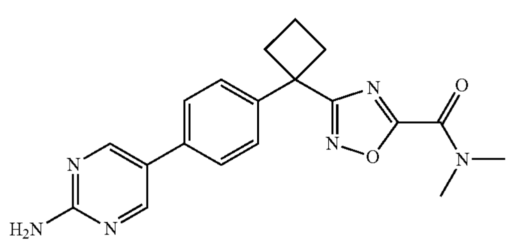 [SMILES: CN(C)C(=O)c1nc(C2(c3ccc(-c4cnc(N)nc4)cc3)CCC2)no1] | 3 | 3.63 | 365.3 | B |

TABLE 8-continued

| Final compounds | | | | | |
|---|---|---|---|---|---|
| Example | Structure | Method | Retention time | m/z | LC MS method |
| 15 | | 3 | 3.1 | 309.2 | B |
| 16 | | 1 | 3.28 | 388.3 | B |
| 17 | | 3 | 3.7 | 414.2 | B |
| 18 | | 3 | 3.6 | 387.2 | B |
| 19 | | 1 | 3.77 | 387.2 | B |
| 20 | | 3 | 3.39 | 386.2 | B |

TABLE 8-continued

| Example | Structure | Method | Retention time | m/z | LC MS method |
|---|---|---|---|---|---|
| 21 | 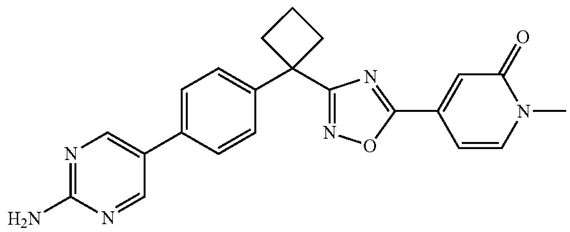 [SMILES: Cn1ccc(-c2nc(C3(c4ccc(-c5cnc(N)nc5)cc4)CCC3)no2)cc1=O] | 1 | 3.7 | 401.2 | B |
| 22 | 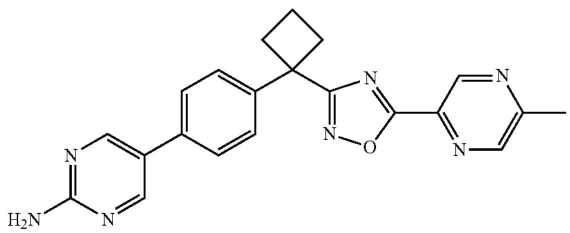 | 1 | 3.99 | 386.2 | B |
| 23 | 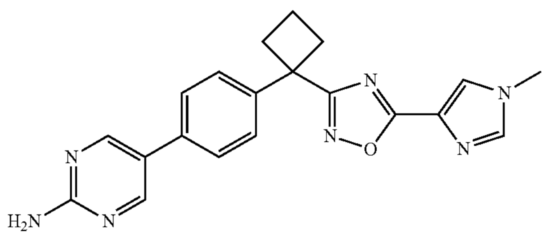 [SMILES: Cn1cnc(-c2nc(C3(c4ccc(-c5cnc(N)nc5)cc4)CCC3)no2)c1] | 1 | 3.46 | 374.2 | B |
| 24 | 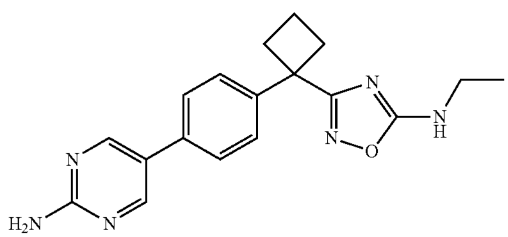 [SMILES: CCNc1nc(C2(c3ccc(-c4cnc(N)nc4)cc3)CCC2)no1] | 1 | 3.66 | 337.2 | B |
| 25 | 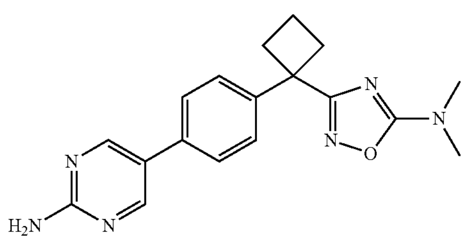 [SMILES: CN(C)c1nc(C2(c3ccc(-c4cnc(N)nc4)cc3)CCC2)no1] | 1 | 3.7 | 337.2 | B |
| 26 | 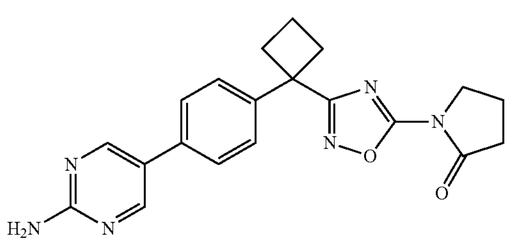 [SMILES: Nc1ncc(-c2ccc(C3(c4noc(N5CCCC5=O)n4)CCC3)cc2)cn1] | 3 | 3.67 | 377.2 | B |

TABLE 8-continued

Final compounds

| Example | Structure | Method | Retention time | m/z | LC MS method |
|---|---|---|---|---|---|
| 27 | 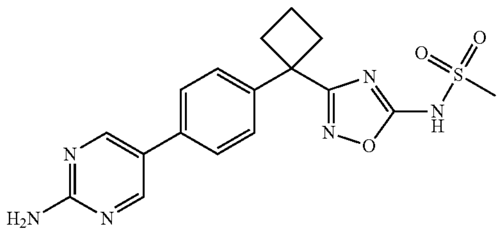 [SMILES: CS(=O)(=O)Nc1nc(C2(c3ccc(-c4cnc(N)nc4)cc3)CCC2)no1] | 3 | 3.14 | 387.2 | B |
| 28 | 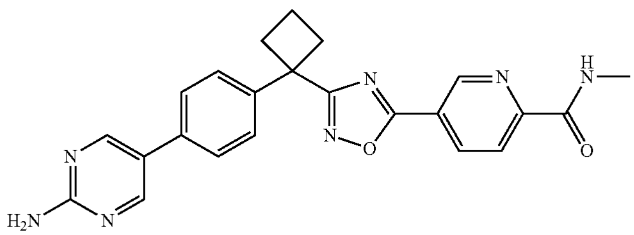 [SMILES: CNC(=O)c1ccc(-c2nc(C3(c4ccc(-c5cnc(N)nc5)cc4)CCC3)no2)cn1] | 3 | 3.97 | 428.3 | B |
| 29 | 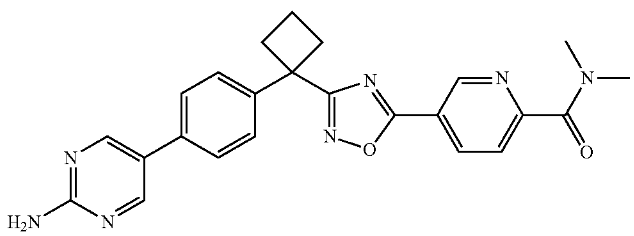 [SMILES: CN(C)C(=O)c1ccc(-c2nc(C3(c4ccc(-c5cnc(N)nc5)cc4)CCC3)no2)cn1] | 3 | 3.80 | 442.3 | B |
| 30 | 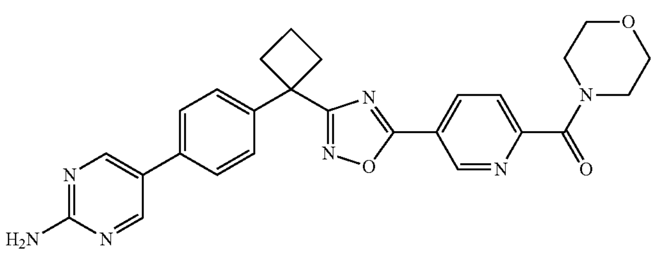 [SMILES: Nc1ncc(-c2ccc(C3(c4noc(-c5ccc(C(=O)N6CCOCC6)nc5)n4)CCC3)cc2)cn1] | 3 | 3.79 | 484.3 | B |
| 31 | 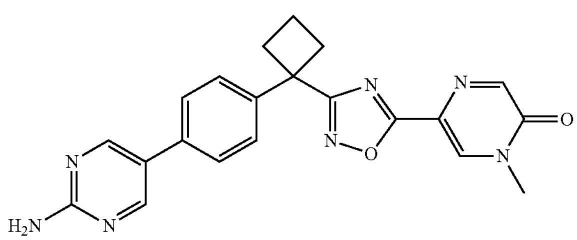 [SMILES: Cn1cc(-c2nc(C3(c4ccc(-c5cnc(N)nc5)cc4)CCC3)no2)ncc1=O] | 3 | 3.54 | 402.2 | B |
| 32 | 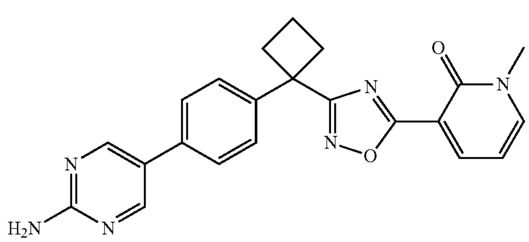 [SMILES: Cn1cccc(-c2nc(C3(c4ccc(-c5cnc(N)nc5)cc4)CCC3)no2)c1=O] | 3 | 3.53 | 401.4 | B |

TABLE 8-continued
Final compounds
| Example | Structure | Method | Retention time | m/z | LC MS method |
|---|---|---|---|---|---|
| 33 | 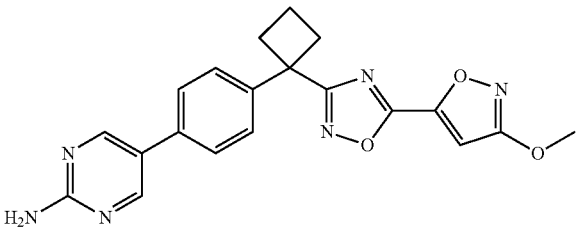 [SMILES: COc1cc(-c2nc(C3(c4ccc(-c5cnc(N)nc5)cc4)CCC3)no2)on1] | 2 | 4.28 | 391.2 | C |
| 34 | 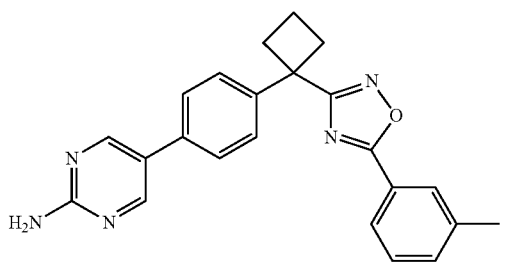 [SMILES: Cc1cccc(-c2nc(C3(c4ccc(-c5cnc(N)nc5)cc4)CCC3)no2)c1] | 1 | 2.72 | 384.2 | D |
| 35 | 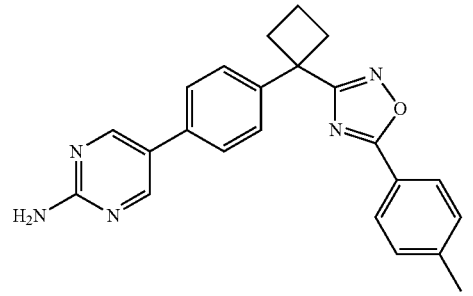 [SMILES: Cc1ccc(-c2nc(C3(c4ccc(-c5cnc(N)nc5)cc4)CCC3)no2)cc1] | 1 | 2.67 | 384.1 | D |
| 36 | 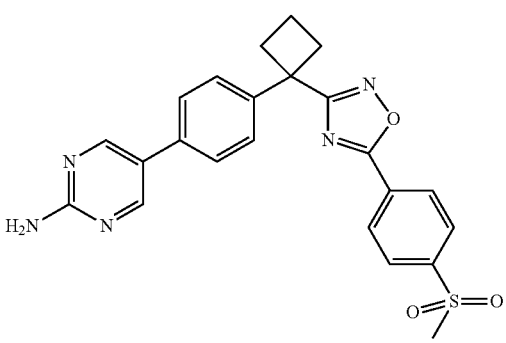 [SMILES: CS(=O)(=O)c1ccc(-c2nc(C3(c4ccc(-c5cnc(N)nc5)cc4)CCC3)no2)cc1] | 1 | 1.94 | 447.9 | D |
| 37 | 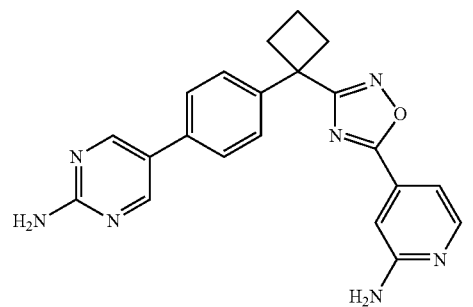 [SMILES: Nc1cc(-c2nc(C3(c4ccc(-c5cnc(N)nc5)cc4)CCC3)no2)ccn1] | 1 | 1.73 | 386.2 | E |

TABLE 8-continued

Final compounds

| Example | Structure | Method | Retention time | m/z | LC MS method |
|---|---|---|---|---|---|
| 38 | 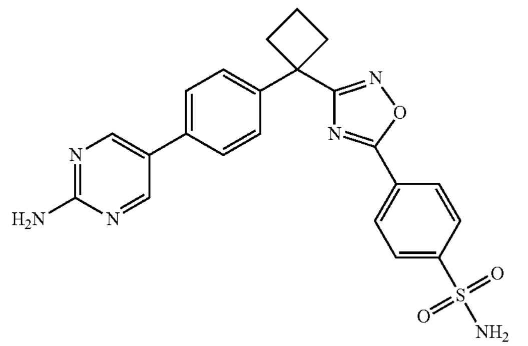 [SMILES: Nc1ncc(-c2ccc(C3(c4noc(-c5ccc(S(N)(=O)=O)cc5)n4)CCC3)cc2)cn1] | 1 | 2.29 | 449.2 | E |
| 39 | 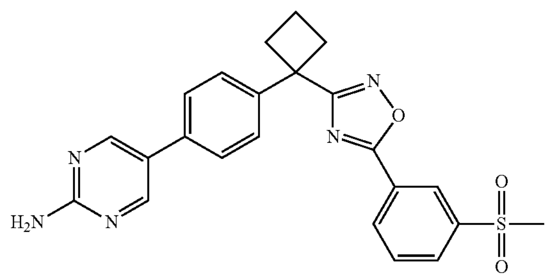 [SMILES: CS(=O)(=O)c1cccc(-c2nc(C3(c4ccc(-c5cnc(N)nc5)cc4)CCC3)no2)c1] | 1 | 2.48 | 448.2 | E |
| 40 | 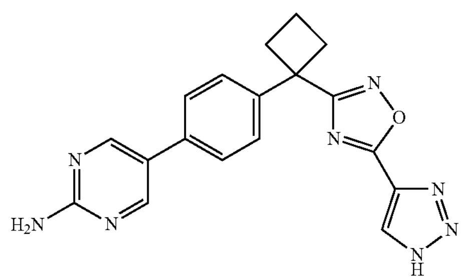 [SMILES: Nc1ncc(-c2ccc(C3(c4noc(-c5c[nH]nn5)n4)CCC3)cc2)cn1] | 1 | 4.88 | 361.6 | D |
| 41 | 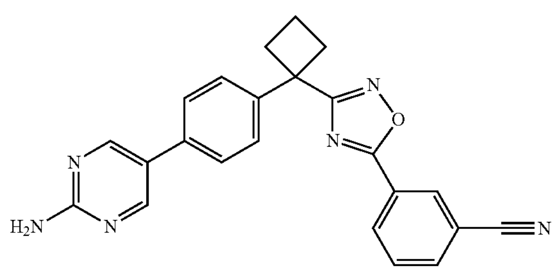 [SMILES: N#Cc1cccc(-c2nc(C3(c4ccc(-c5cnc(N)nc5)cc4)CCC3)no2)c1] | 1 | 2.78 | 395.2 | E |
| 42 | 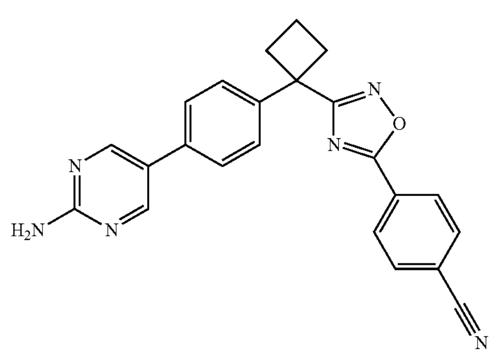 [SMILES: N#Cc1ccc(-c2nc(C3(c4ccc(-c5cnc(N)nc5)cc4)CCC3)no2)cc1] | 1 | 2.26 | 395.0 | E |

TABLE 8-continued

Final compounds

| Example | Structure | Method | Retention time | m/z | LC MS method |
|---|---|---|---|---|---|
| 43 | 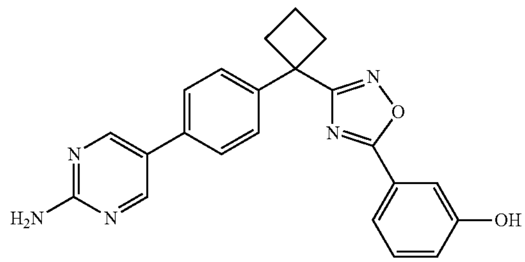 [SMILES: Nc1ncc(-c2ccc(C3(c4noc(-c5cccc(O)c5)n4)CCC3)cc2)cn1] | 1 | 2.48 | 386.2 | E |
| 44 | 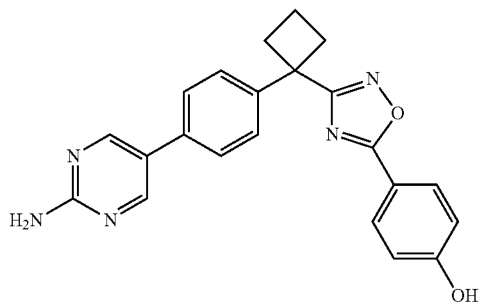 [SMILES: Nc1ncc(-c2ccc(C3(c4noc(-c5ccc(O)cc5)n4)CCC3)cc2)cn1] | 1 | 2.44 | 386.2 | E |
| 45 | 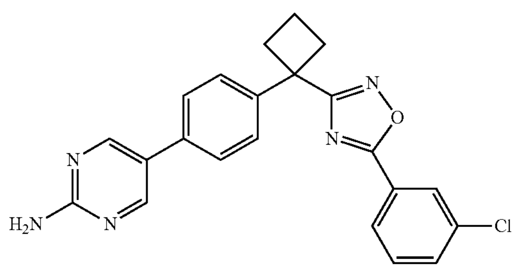 [SMILES: Nc1ncc(-c2ccc(C3(c4noc(-c5cccc(Cl)c5)n4)CCC3)cc2)cn1] | 1 | 3.26 | 404.2 | E |
| 46 | 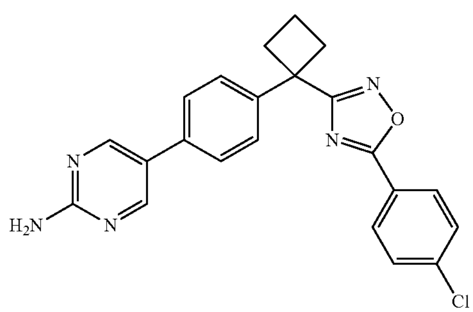 [SMILES: Nc1ncc(-c2ccc(C3(c4noc(-c5ccc(Cl)cc5)n4)CCC3)cc2)cn1] | 1 | 3.26 | 404.2 | E |
| 47 | 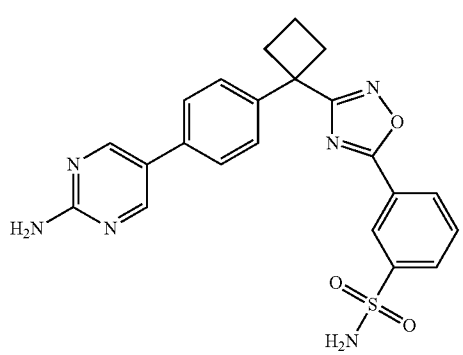 [SMILES: Nc1ncc(-c2ccc(C3(c4noc(-c5cccc(S(N)(=O)=O)c5)n4)CCC3)cc2)cn1] | 1 | 2.29 | 449.2 | E |

TABLE 8-continued

Final compounds

| Example | Structure | Method | Retention time | m/z | LC MS method |
|---|---|---|---|---|---|
| 48 | 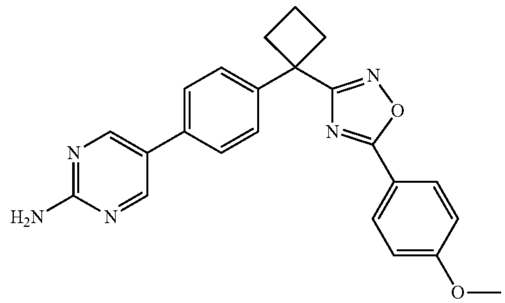 [SMILES: COc1ccc(-c2nc(C3(c4ccc(-c5cnc(N)nc5)cc4)CCC3)no2)cc1] | 1 | 2.87 | 400.2 | E |
| 49 | 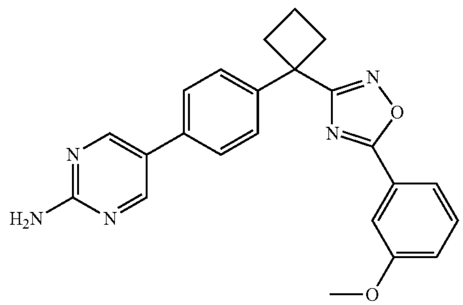 [SMILES: COc1cccc(-c2nc(C3(c4ccc(-c5cnc(N)nc5)cc4)CCC3)no2)c1] | 1 | 2.92 | 400.2 | E |
| 50 | 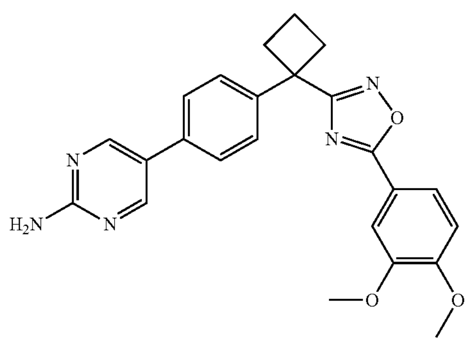 [SMILES: COc1ccc(-c2nc(C3(c4ccc(-c5cnc(N)nc5)cc4)CCC3)no2)cc1OC] | 1 | 2.7 | 430.2 | E |
| 51 | 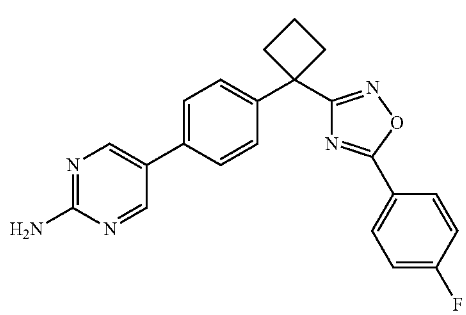 [SMILES: Nc1ncc(-c2ccc(C3(c4noc(-c5ccc(F)cc5)n4)CCC3)cc2)cn1] | 1 | 2.91 | 388.2 | D |

TABLE 8-continued
Final compounds
| Example | Structure | Method | Retention time | m/z | LC MS method |
|---|---|---|---|---|---|
| 52 | 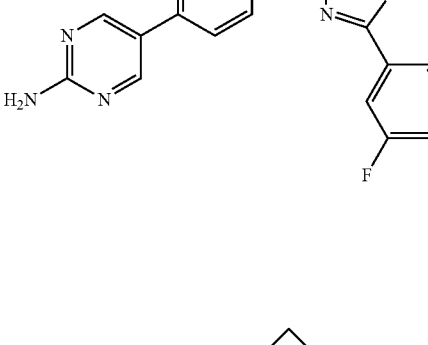 | 1 | 2.95 | 388.2 | D |
| 53 | 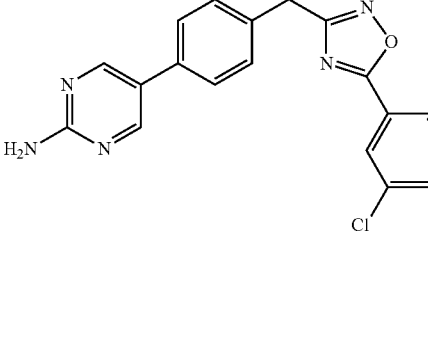 | 1 | 3.39 | 418.2 | D |
| 54 | 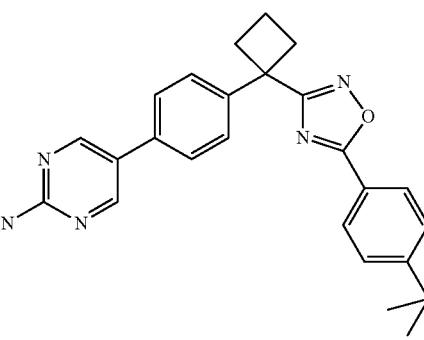 | 1 | 3.61 | 426.2 | D |
| 55 | 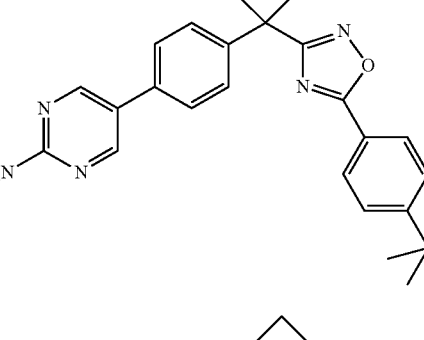 | 1 | 3.45 | 438.2 | D |

TABLE 8-continued

Final compounds

| Example | Structure | Method | Retention time | m/z | LC MS method |
|---|---|---|---|---|---|
| 56 | 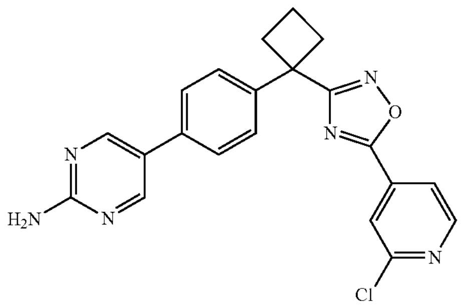 [SMILES: Nc1ncc(-c2ccc(C3(c4noc(-c5ccnc(Cl)c5)n4)CCC3)cc2)cn1] | 1 | 2.76 | 405.2 | D |
| 57 | 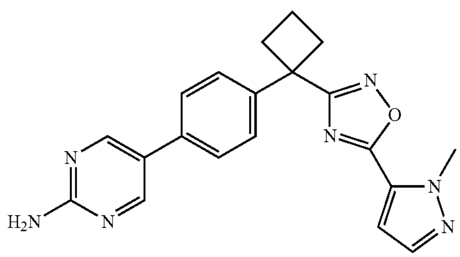 [SMILES: Cn1nccc1-c1nc(C2(c3ccc(-c4cnc(N)nc4)cc3)CCC2)no1] | 2 | 5.21 | 374.6 | F |
| 58 | 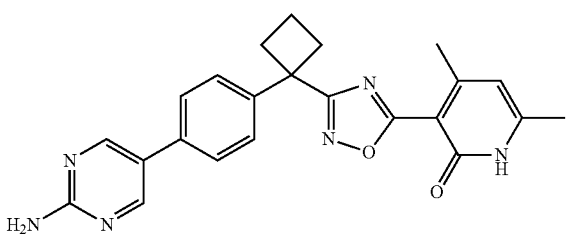 [SMILES: Cc1cc(C)c(-c2nc(C3(c4ccc(-c5cnc(N)nc5)cc4)CCC3)no2)c(=O)[nH]1] | 1 | 3.48 | 415.3 | B |
| 59 | 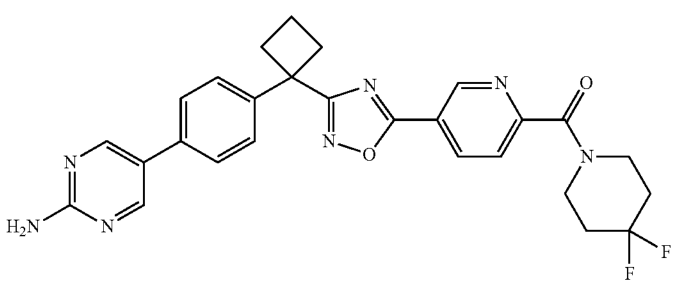 [SMILES: Nc1ncc(-c2ccc(C3(c4noc(-c5ccc(C(=O)N6CCC(F)(F)CC6)nc5)n4)CCC3)cc2)cn1] | 5 | 4.23 | 518.3 | B |
| 60 | 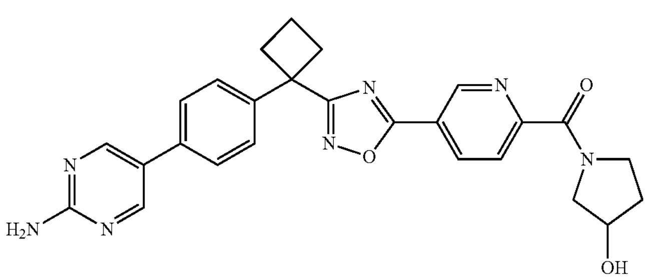 [SMILES: Nc1ncc(-c2ccc(C3(c4noc(-c5ccc(C(=O)N6CCC(O)C6)nc5)n4)CCC3)cc2)cn1] | 5 | 3.46 | 484.4 | B |

TABLE 8-continued

| Example | Structure | Method | Retention time | m/z | LC MS method |
|---|---|---|---|---|---|
| 61 | 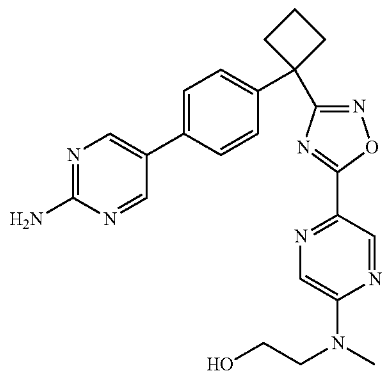 [SMILES: CN(CCO)c1cnc(-c2nc(C3(c4ccc(-c5cnc(N)nc5)cc4)CCC3)no2)cn1] | 7 | 3.57 | 445.3 | B |
| 62 | 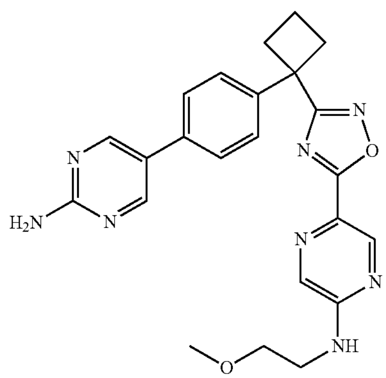 [SMILES: COCCNc1cnc(-c2nc(C3(c4ccc(-c5cnc(N)nc5)cc4)CCC3)no2)cn1] | 7 | 3.79 | 445.3 | B |
| 63 | 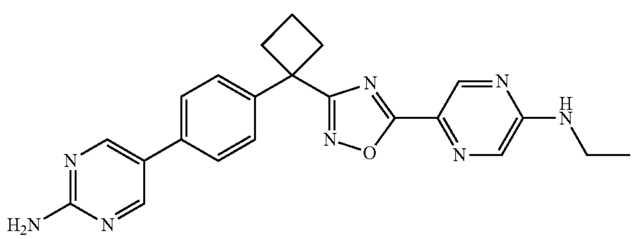 [SMILES: CCNc1cnc(-c2nc(C3(c4ccc(-c5cnc(N)nc5)cc4)CCC3)no2)cn1] | 7 | 3.92 | 415.4 | B |
| 64 | 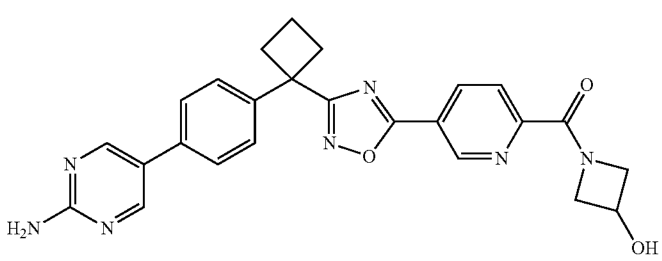 [SMILES: Nc1ncc(-c2ccc(C3(c4noc(-c5ccc(C(=O)N6CC(O)C6)nc5)n4)CCC3)cc2)cn1] | 5 | 3.52 | 470.4 | B |
| 65 | 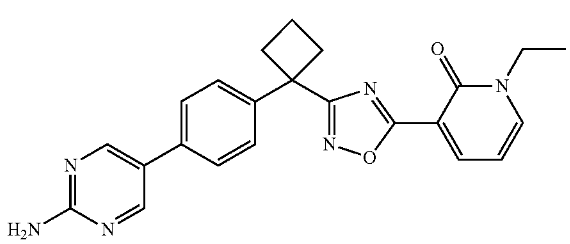 [SMILES: CCn1cccc(-c2nc(C3(c4ccc(-c5cnc(N)nc5)cc4)CCC3)no2)c1=O] | 3 | 3.6 | 415.3 | B |

TABLE 8-continued

Final compounds

| Example | Structure | Method | Retention time | m/z | LC MS method |
|---|---|---|---|---|---|
| 66 | 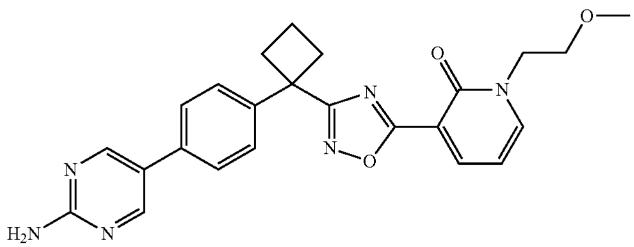 [SMILES: COCCn1cccc(-c2nc(C3(c4ccc(-c5cnc(N)nc5)cc4)CCC3)no2)c1=O] | 3 | 3.6 | 445.3 | B |
| 67 | 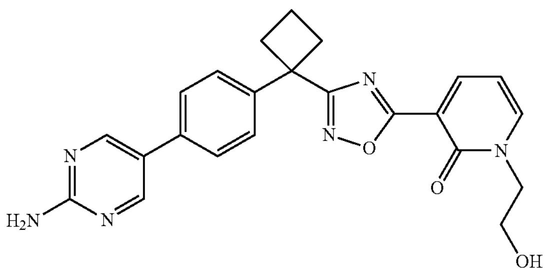 [SMILES: Nc1ncc(-c2ccc(C3(c4noc(-c5cccn(CCO)c5=O)n4)CCC3)cc2)cn1] | 3 | 3.34 | 431.4 | B |
| 68 | 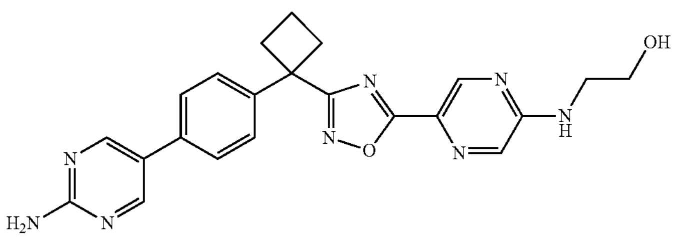 [SMILES: Nc1ncc(-c2ccc(C3(c4noc(-c5cnc(NCCO)cn5)n4)CCC3)cc2)cn1] | 7 | 3.39 | 431.3 | B |
| 69 | 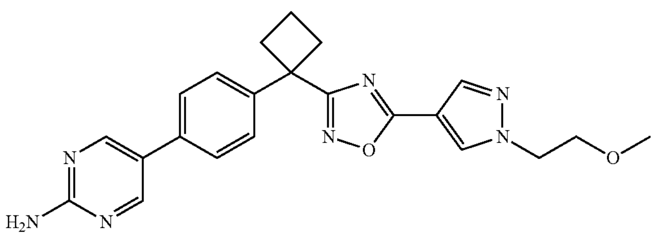 [SMILES: COCCn1cc(-c2nc(C3(c4ccc(-c5cnc(N)nc5)cc4)CCC3)no2)cn1] | 3 | 3.78 | 418.3 | B |
| 70 | 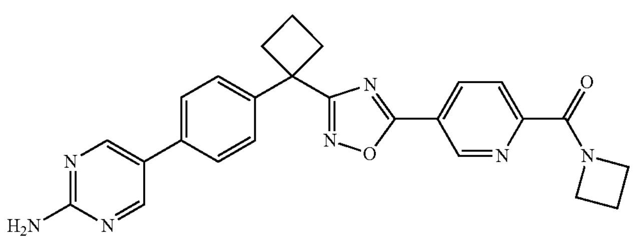 [SMILES: Nc1ncc(-c2ccc(C3(c4noc(-c5ccc(C(=O)N6CCC6)nc5)n4)CCC3)cc2)cn1] | 3 | 4.06 | 454.3 | B |
| 71 | 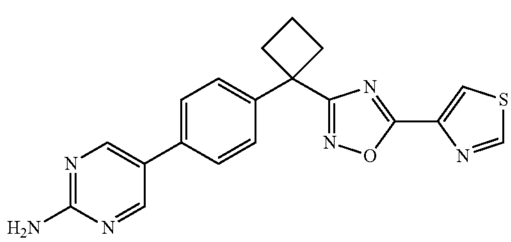 [SMILES: Nc1ncc(-c2ccc(C3(c4noc(-c5cscn5)n4)CCC3)cc2)cn1] | 1 | 3.77 | 377.2 | B |

TABLE 8-continued

Final compounds

| Example | Structure | Method | Retention time | m/z | LC MS method |
|---|---|---|---|---|---|
| 72 | 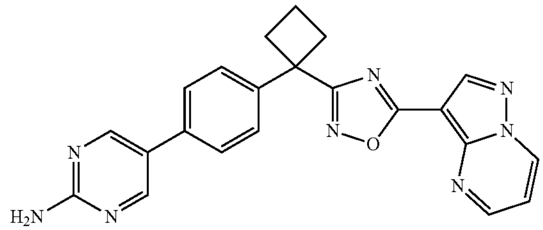 | 1 | 3.63 | 411.3 | B |
| 73 | 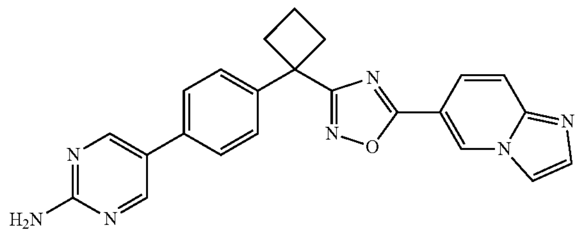 [SMILES: Nc1ncc(-c2ccc(C3(c4noc(-c5ccc6nccn6c5)n4)CCC3)cc2)cn1] | 1 | 3.06 | 410.3 | B |
| 74 | 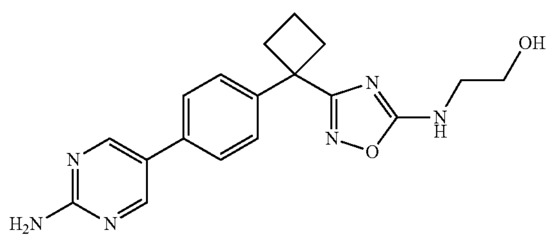 [SMILES: Nc1ncc(-c2ccc(C3(c4noc(NCCO)n4)CCC3)cc2)cn1] | 8 | 3.06 | 353.2 | B |
| 75 | 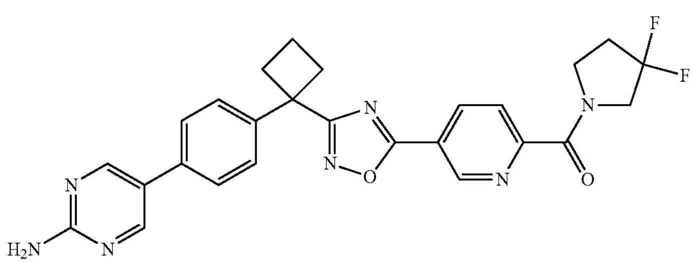 [SMILES: Nc1ncc(-c2ccc(C3(c4noc(-c5ccc(C(=O)N6CCC(F)(F)C6)nc5)n4)CCC3)cc2)cn1] | 3 | 4.47 | 504.4 | B |
| 76 | 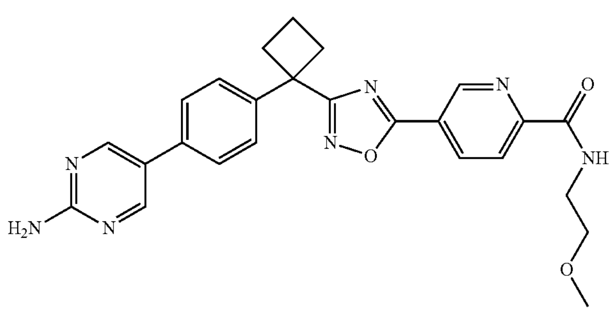 [SMILES: COCCNC(=O)c1ccc(-c2nc(C3(c4ccc(-c5cnc(N)nc5)cc4)CCC3)no2)cn1] | 3 | 4.16 | 472.4 | B |
| 77 | 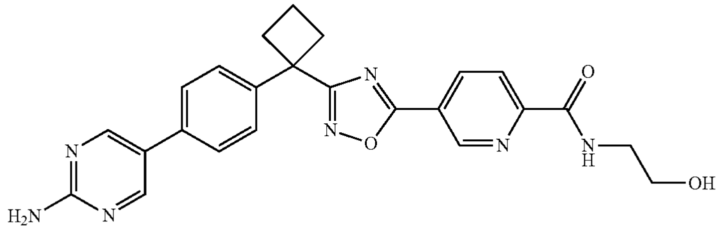 [SMILES: Nc1ncc(-c2ccc(C3(c4noc(-c5ccc(C(=O)NCCO)nc5)n4)CCC3)cc2)cn1] | 3 | 3.66 | 458.3 | B |

TABLE 8-continued

Final compounds

| Example | Structure | Method | Retention time | m/z | LC MS method |
|---|---|---|---|---|---|
| 78 | 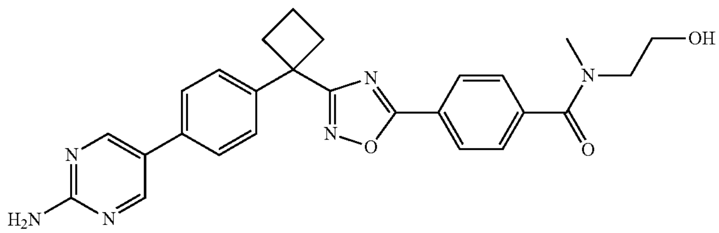 [SMILES: CN(CCO)C(=O)c1ccc(-c2nc(C3(c4ccc(-c5cnc(N)nc5)cc4)CCC3)no2)cc1] | 3 | 3.52 | 472.4 | B |
| 79 | 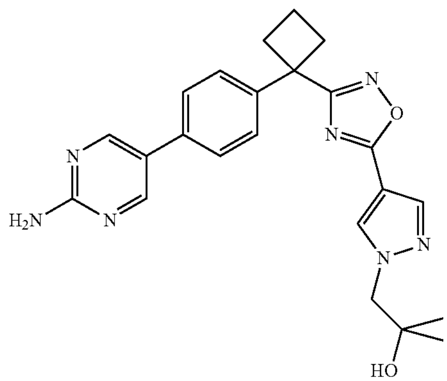 [SMILES: CC(C)(O)Cn1cc(-c2nc(C3(c4ccc(-c5cnc(N)nc5)cc4)CCC3)no2)cn1] | 3 | 3.65 | 432.4 | B |
| 80 | 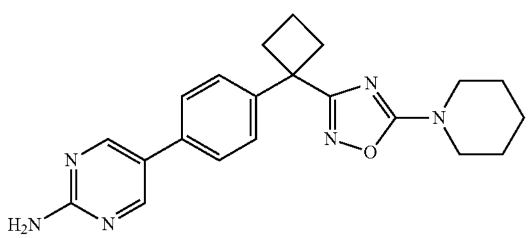 [SMILES: Nc1ncc(-c2ccc(C3(c4noc(N5CCCCC5)n4)CCC3)cc2)cn1] | 8 | 4.25 | 377.3 | B |
| 81 | 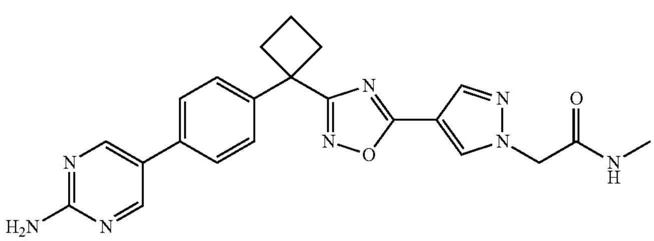 [SMILES: CNC(=O)Cn1cc(-c2nc(C3(c4ccc(-c5cnc(N)nc5)cc4)CCC3)no2)cn1] | 3 | 3.36 | 431.5 | B |
| 82 | 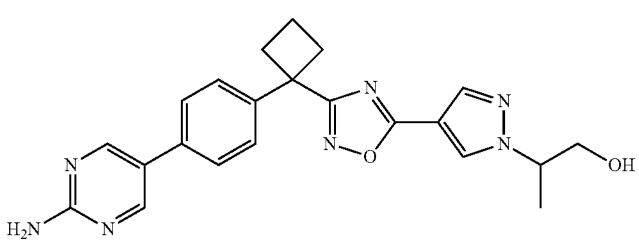 [SMILES: CC(CO)n1cc(-c2nc(C3(c4ccc(-c5cnc(N)nc5)cc4)CCC3)no2)cn1] | 3 | 3.54 | 418.5 | B |

TABLE 8-continued
Final compounds
| Example | Structure | Method | Retention time | m/z | LC MS method |
|---|---|---|---|---|---|
| 83 | 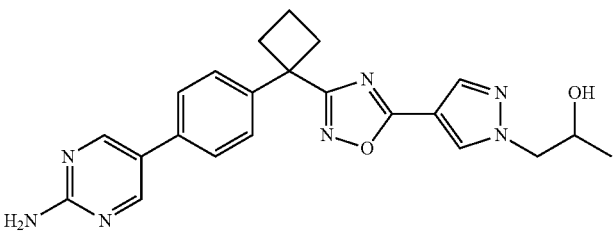 [SMILES: CC(O)Cn1cc(-c2nc(C3(c4ccc(-c5cnc(N)nc5)cc4)CCC3)no2)cn1] | 3 | 3.51 | 418.5 | B |
| 84 | 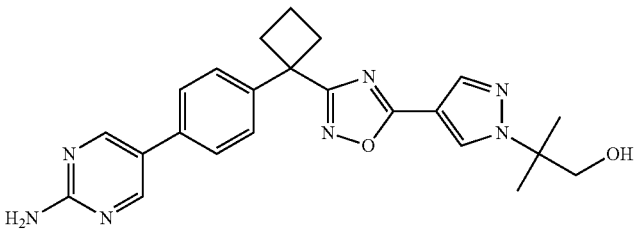 [SMILES: CC(C)(CO)n1cc(-c2nc(C3(c4ccc(-c5cnc(N)nc5)cc4)CCC3)no2)cn1] | 3 | 3.73 | 432.5 | B |
| 85 | 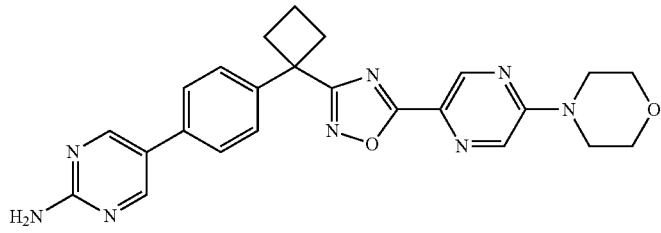 [SMILES: Nc1ncc(-c2ccc(C3(c4noc(-c5cnc(N6CCOCC6)cn5)n4)CCC3)cc2)cn1] | 7 | 3.99 | 457.5 | B |
| 86 | 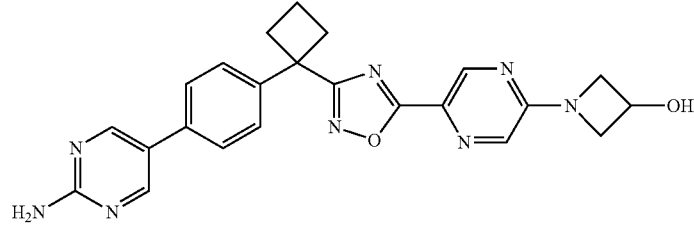 [SMILES: Nc1ncc(-c2ccc(C3(c4noc(-c5cnc(N6CC(O)C6)cn5)n4)CCC3)cc2)cn1] | 7 | 3.47 | 443.3 | B |
| 87 | 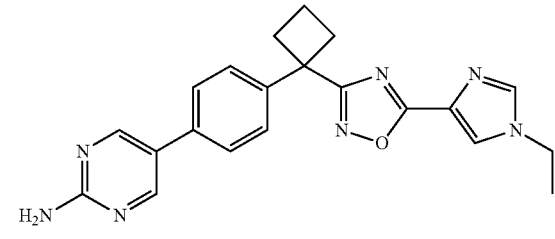 [SMILES: CCn1cnc(-c2nc(C3(c4ccc(-c5cnc(N)nc5)cc4)CCC3)no2)c1] | 3 | 3.54 | 388.3 | B |
| 88 | 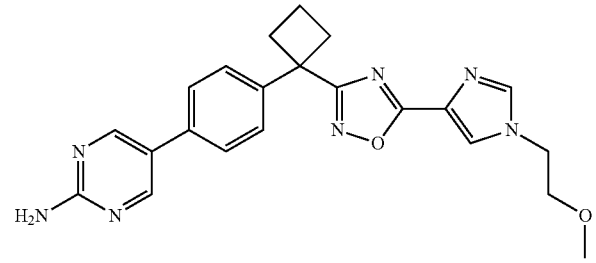 [SMILES: COCCn1cnc(-c2nc(C3(c4ccc(-c5cnc(N)nc5)cc4)CCC3)no2)c1] | 3 | 3.49 | 418.3 | B |

TABLE 8-continued

Final compounds

| Example | Structure | Method | Retention time | m/z | LC MS method |
|---------|-----------|--------|----------------|-----|--------------|
| 89 | 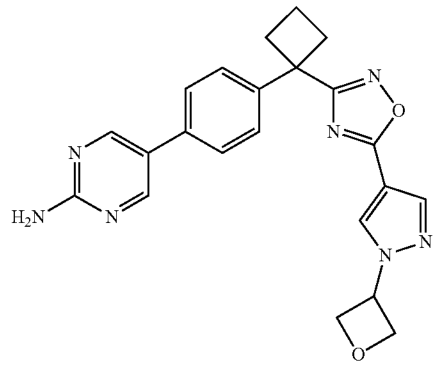 [SMILES: Nc1ncc(-c2ccc(C3(c4noc(-c5cnn(C6COC6)c5)n4)CCC3)cc2)cn1] | 3 | 3.66 | 416.3 | B |
| 90 | 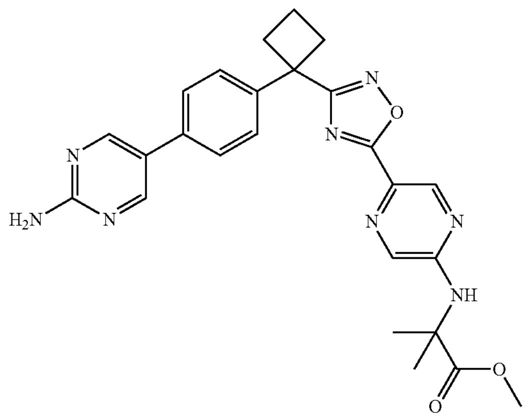 [SMILES: COC(=O)C(C)(C)Nc1cnc(-c2nc(C3(c4ccc(-c5cnc(N)nc5)cc4)CCC3)no2)cn1] | 7 | 4.12 | 487.3 | B |
| 91 | 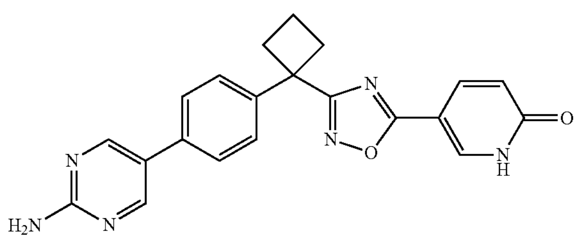 [SMILES: Nc1ncc(-c2ccc(C3(c4noc(-c5ccc(=O)[nH]c5)n4)CCC3)cc2)cn1] | 3 | 3.46 | 387.3 | B |
| 92 | 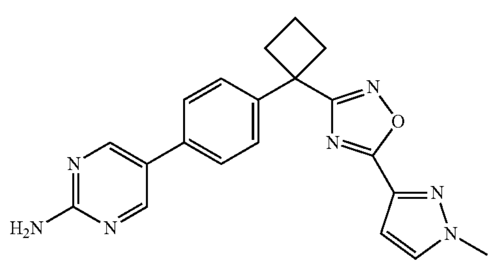 [SMILES: Cn1ccc(-c2nc(C3(c4ccc(-c5cnc(N)nc5)cc4)CCC3)no2)n1] | 2 | 5.36 | 374.6 | F |
| 93 | 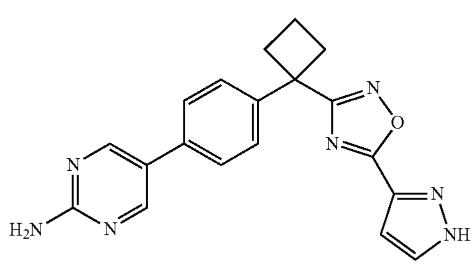 [SMILES: Nc1ncc(-c2ccc(C3(c4noc(-c5cc[nH]n5)n4)CCC3)cc2)cn1] | 2 | 5 | 360.6 | F |

TABLE 8-continued

Final compounds

| Example | Structure | Method | Retention time | m/z | LC MS method |
|---|---|---|---|---|---|
| 94 | 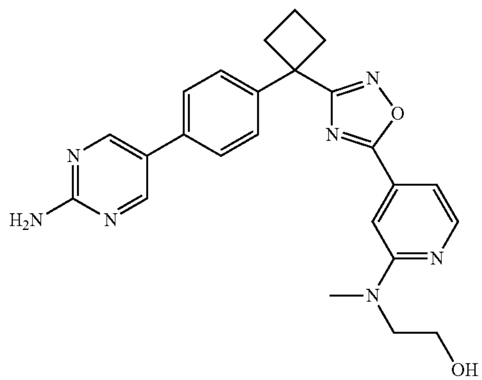 [SMILES: CN(CCO)c1cc(-c2nc(C3(c4ccc(-c5cnc(N)nc5)cc4)CCC3)no2)ccn1] | 9 | 1.97 | 440.2 | D |
| 95 | 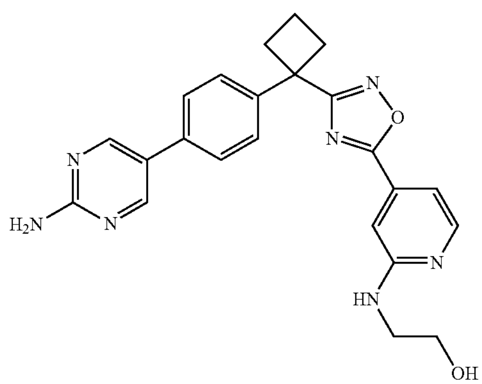 [SMILES: Nc1ncc(-c2ccc(C3(c4noc(-c5ccnc(NCCO)c5)n4)CCC3)cc2)cn1] | 9 | 1.21 | 430.3 | G |
| 96 | 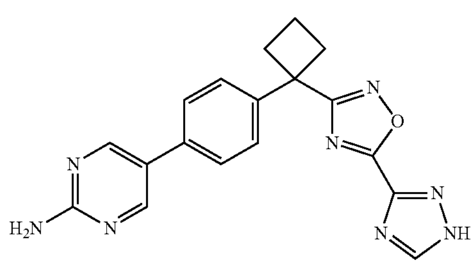 [SMILES: Nc1ncc(-c2ccc(C3(c4noc(-c5nc[nH]n5)n4)CCC3)cc2)cn1] | 2 | 4.6 | 361.6 | F |
| 97 | 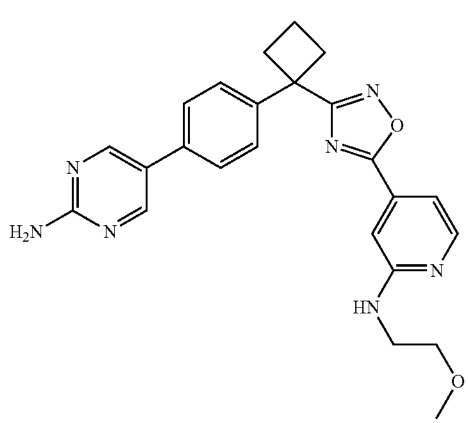 [SMILES: COCCNc1cc(-c2nc(C3(c4ccc(-c5cnc(N)nc5)cc4)CCC3)no2)ccn1] | 9 | 2.15 | 444.2 | D |

TABLE 8-continued

Final compounds

| Example | Structure | Method | Retention time | m/z | LC MS method |
|---|---|---|---|---|---|
| 98 | 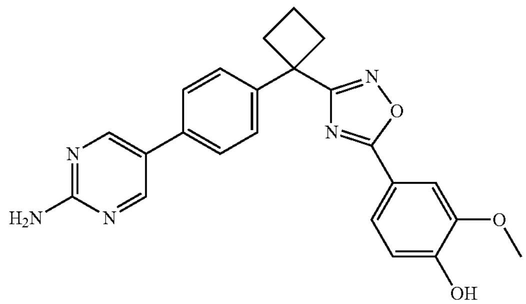 [SMILES: COc1cc(-c2nc(C3(c4ccc(-c5cnc(N)nc5)cc4)CCC3)no2)ccc1O] | 2 | 2.49 | 416.2 | D |
| 99 | 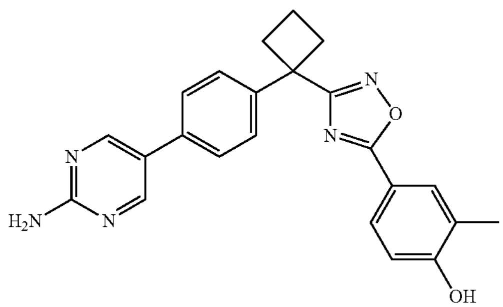 [SMILES: Cc1cc(-c2nc(C3(c4ccc(-c5cnc(N)nc5)cc4)CCC3)no2)ccc1O] | 2 | 2.63 | 400.2 | D |
| 100 | 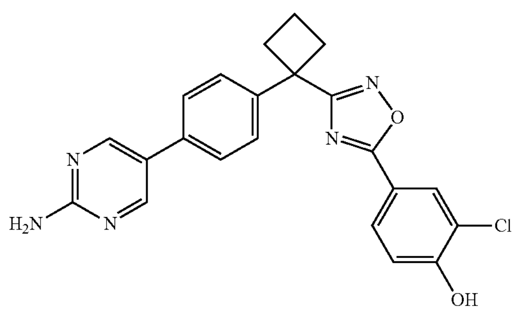 [SMILES: Nc1ncc(-c2ccc(C3(c4noc(-c5ccc(O)c(Cl)c5)n4)CCC3)cc2)cn1] | 2 | 2.7 | 420.2 | D |
| 101 | 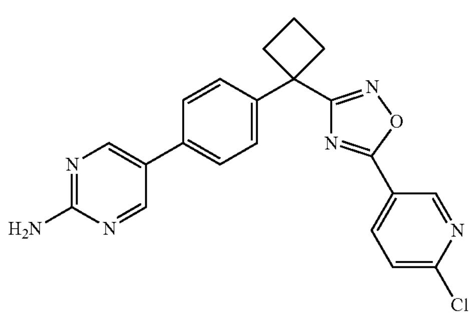 [SMILES: Nc1ncc(-c2ccc(C3(c4noc(-c5ccc(Cl)nc5)n4)CCC3)cc2)cn1] | 2 | 1.53 | 405.2 | H |

TABLE 8-continued
Final compounds
| Example | Structure | Method | Retention time | m/z | LC MS method |
|---|---|---|---|---|---|
| 102 | 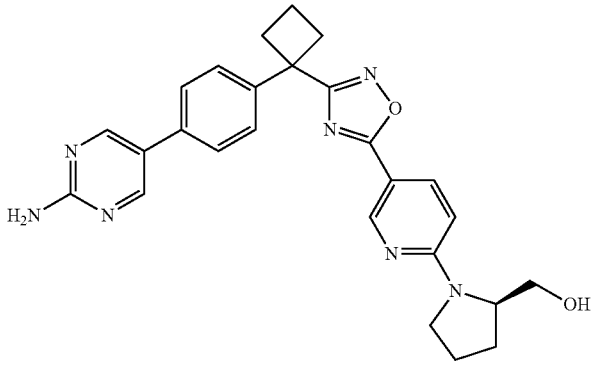 [SMILES: Nc1ncc(-c2ccc(C3(c4noc(-c5ccc(N6CCC[C@@H]6CO)nc5)n4)CCC3)cc2)cn1] | 9 | 2.35 | 470.2 | D |
| 103 | 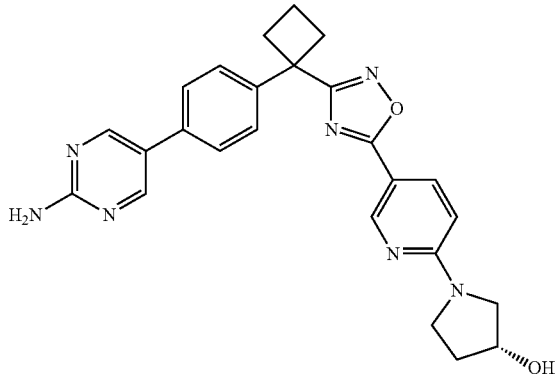 [SMILES: Nc1ncc(-c2ccc(C3(c4noc(-c5ccc(N6CC[C@@H](O)C6)nc5)n4)CCC3)cc2)cn1] | 9 | 2.07 | 456.2 | D |
| 104 | 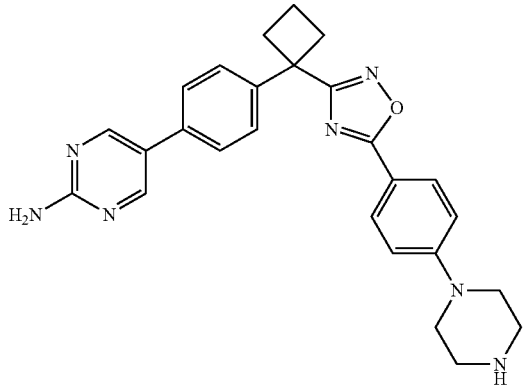 [SMILES: Nc1ncc(-c2ccc(C3(c4noc(-c5ccc(N6CCNCC6)cc5)n4)CCC3)cc2)cn1] | 10 | 1.67 | 454.2 | D |
| 105 | 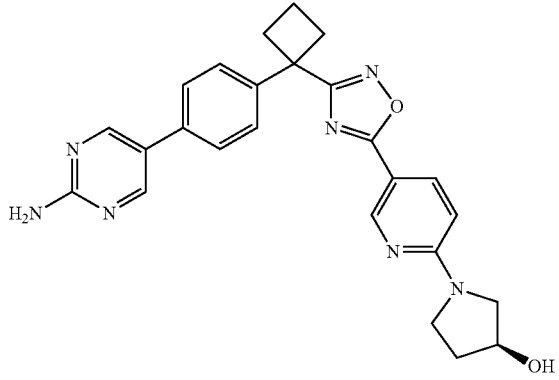 [SMILES: Nc1ncc(-c2ccc(C3(c4noc(-c5ccc(N6CC[C@H](O)C6)nc5)n4)CCC3)cc2)cn1] | 9 | 2.08 | 456.2 | D |

TABLE 8-continued
Final compounds
| Example | Structure | Method | Retention time | m/z | LC MS method |
|---|---|---|---|---|---|
| 106 | 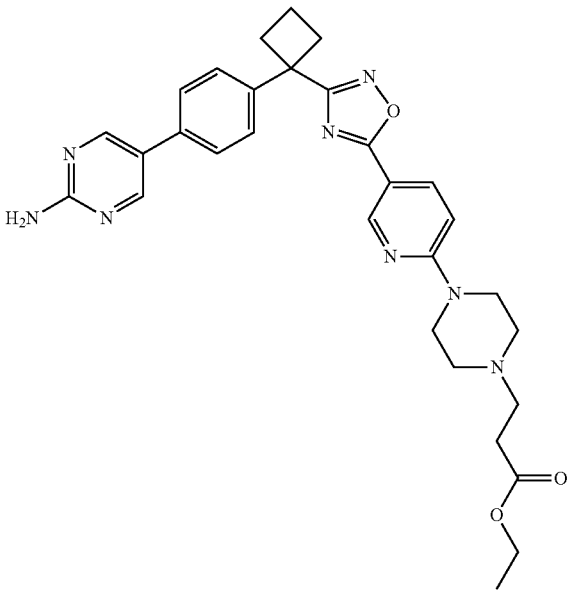 [SMILES: CCOC(=O)CCN1CCN(c2ccc(-c3nc(C4(c5ccc(-c6cnc(N)nc6)cc5)CCC4)no3)cn2)CC1] | 9 | 1.91 | 555.2 | D |
| 107 | 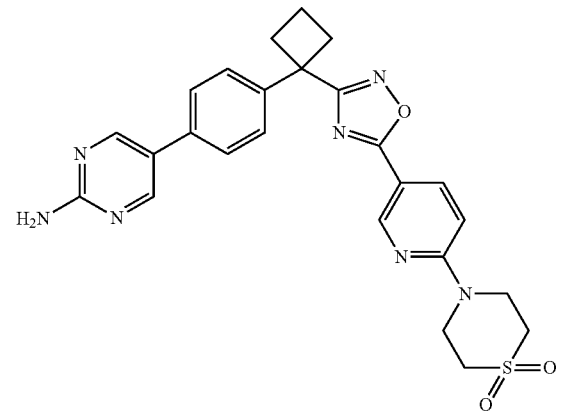 [SMILES: Nc1ncc(-c2ccc(C3(c4noc(-c5ccc(N6CCS(=O)(=O)CC6)nc5)n4)CCC3)cc2)cn1] | 9 | 2.34 | 504.2 | D |
| 108 | 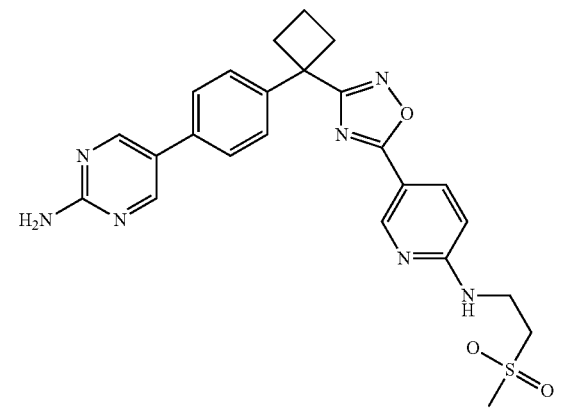 | 9 | 2.14 | 492.2 | D |

TABLE 8-continued

Final compounds

| Example | Structure | Method | Retention time | m/z | LC MS method |
|---|---|---|---|---|---|
| 109 | 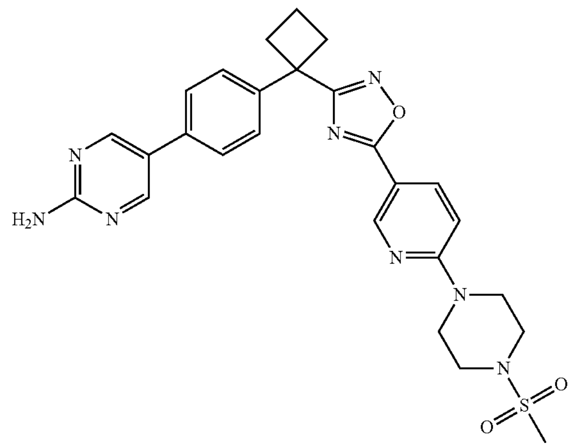 [SMILES: CS(=O)(=O)N1CCN(c2ccc(-c3nc(C4(c5ccc(-c6cnc(N)nc6)cc5)CCC4)no3)cn2)CC1] | 9 | 2.55 | 533.2 | D |
| 110 | 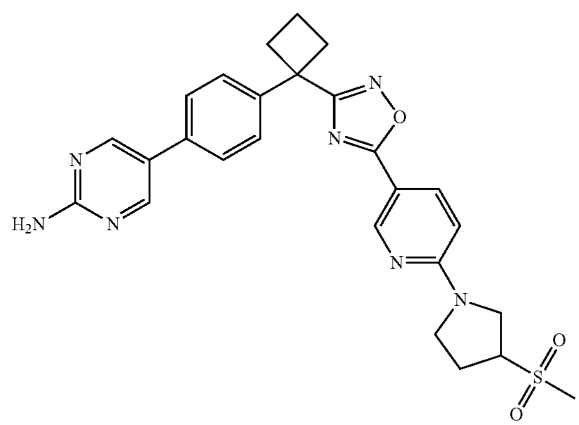 [SMILES: CS(=O)(=O)C1CCN(c2ccc(-c3nc(C4(c5ccc(-c6cnc(N)nc6)cc5)CCC4)no3)cn2)C1] | 9 | 2.26 | 518.2 | D |
| 111 | 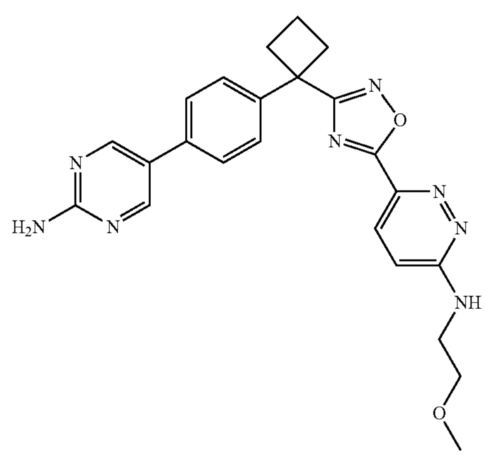 [SMILES: COCCNc1ccc(-c2nc(C3(c4ccc(-c5cnc(N)nc5)cc4)CCC3)no2)nn1] | 11 | 5.04 | 445.6 | D |

TABLE 8-continued

Final compounds

| Example | Structure | Method | Retention time | m/z | LC MS method |
|---|---|---|---|---|---|
| 112 | 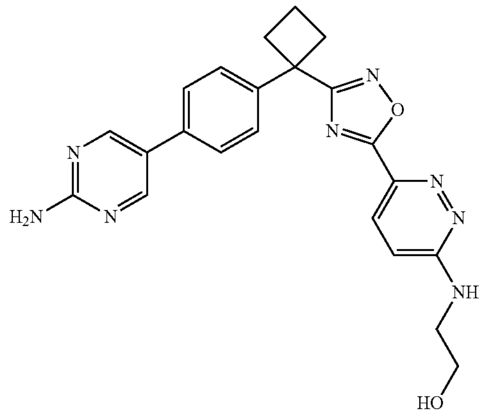 [SMILES: Nc1ncc(-c2ccc(C3(c4noc(-c5ccc(NCCO)nn5)n4)CCC3)cc2)cn1] | 11 | 4.54 | 431.6 | D |
| 113 | 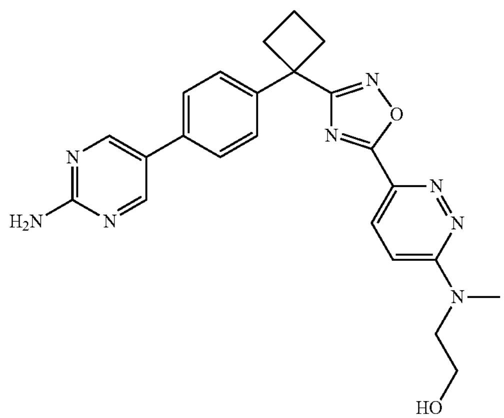 [SMILES: CN(CCO)c1ccc(-c2nc(C3(c4ccc(-c5cnc(N)nc5)cc4)CCC3)no2)nn1] | 11 | 4.78 | 445.6 | D |
| 114 | 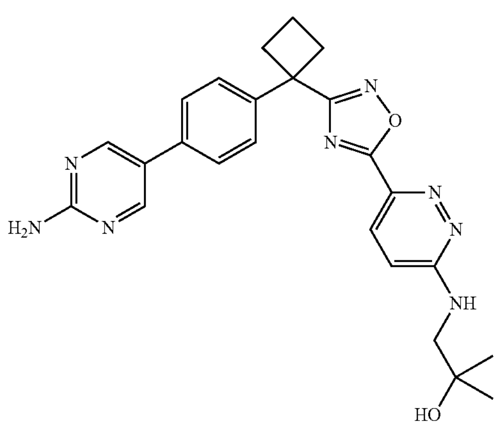 [SMILES: CC(C)(O)CNc1ccc(-c2nc(C3(c4ccc(-c5cnc(N)nc5)cc4)CCC3)no2)nn1] | 11 | 4.87 | 459.6 | D |

TABLE 8-continued

Final compounds

| Example | Structure | Method | Retention time | m/z | LC MS method |
|---------|-----------|--------|----------------|-----|--------------|
| 115 | 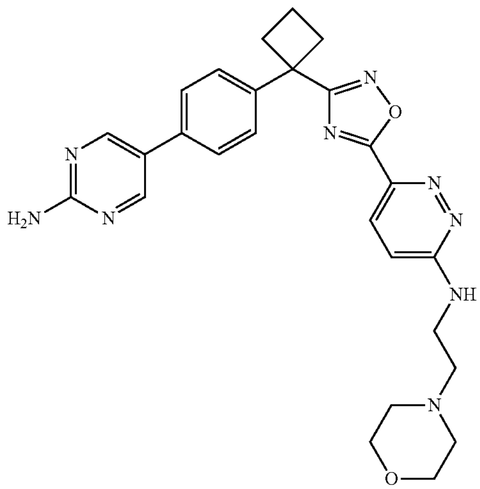 [SMILES: Nc1ncc(-c2ccc(C3(c4noc(-c5ccc(NCCN6CCOCC6)nn5)n4)CCC3)cc2)cn1] | 11 | 4.03 | 500.6 | D |
| 116 | 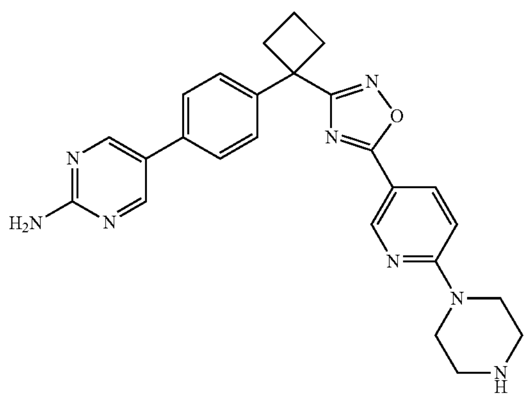 [SMILES: Nc1ncc(-c2ccc(C3(c4noc(-c5ccc(N6CCNCC6)nc5)n4)CCC3)cc2)cn1] | 12 | 1.91 | 455.4 | D |
| 117 | 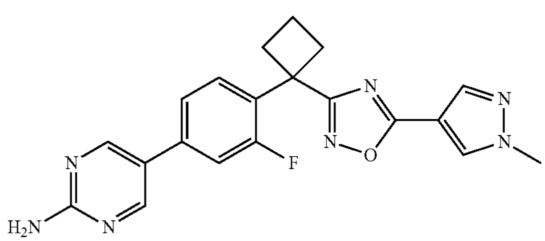 [SMILES: Cn1cc(-c2nc(C3(c4ccc(-c5cnc(N)nc5)cc4F)CCC3)no2)cn1] | 3 | 3.9 | 392.3 | D |
| 118 | 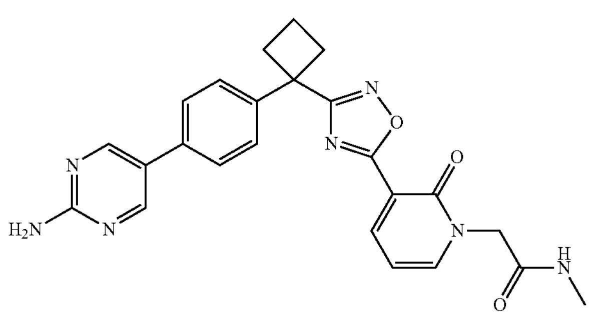 [SMILES: CNC(=O)Cn1cccc(-c2nc(C3(c4ccc(-c5cnc(N)nc5)cc4)CCC3)no2)c1=O] | 13 | 3.32 | 458.4 | D |

TABLE 8-continued

Final compounds

| Example | Structure | Method | Retention time | m/z | LC MS method |
|---|---|---|---|---|---|
| 119 | 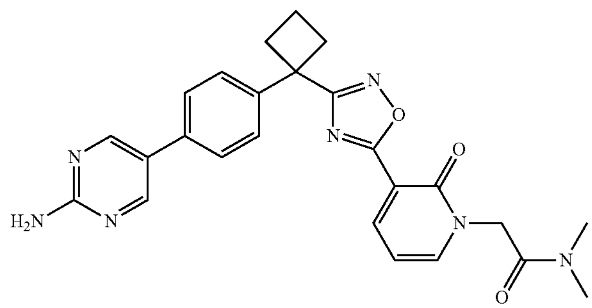 [SMILES: CN(C)C(=O)Cn1cccc(-c2nc(C3(c4ccc(-c5cnc(N)nc5)cc4)CCC3)no2)c1=O] | 13 | 3.44 | 472.4 | D |
| 120 | 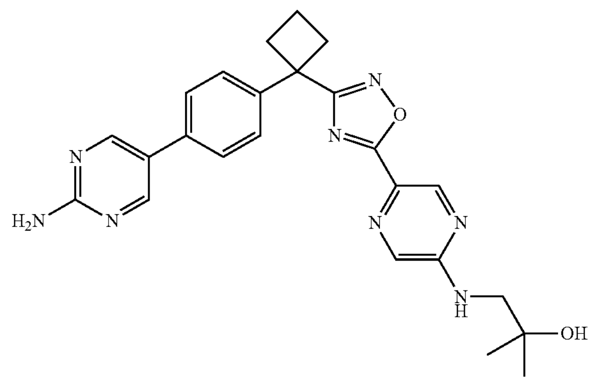 [SMILES: CC(C)(O)CNc1cnc(-c2nc(C3(c4ccc(-c5cnc(N)nc5)cc4)CCC3)no2)cn1] | 7 | 3.76 | 459.4 | D |
| 121 | 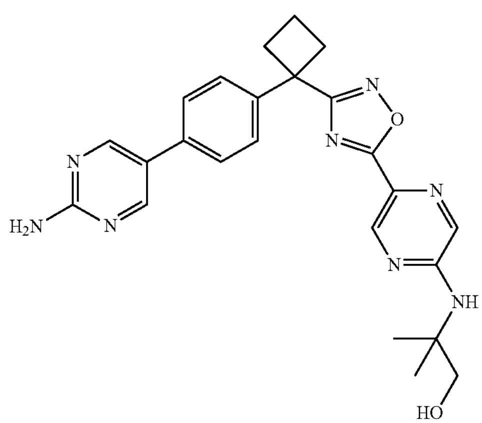 [SMILES: CC(C)(CO)Nc1cnc(-c2nc(C3(c4ccc(-c5cnc(N)nc5)cc4)CCC3)no2)cn1] | 9 | 1.24 | 459 | E |
| 122 | 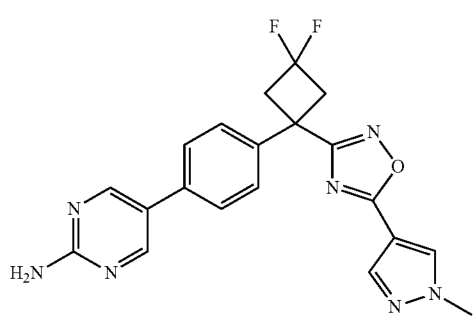 [SMILES: Cn1cc(-c2nc(C3(c4ccc(-c5cnc(N)nc5)cc4)CC(F)(F)C3)no2)cn1] | 2 | 1.41 | 410.4 | I |

TABLE 8-continued

Final compounds

| Example | Structure | Method | Retention time | m/z | LC MS method |
|---------|-----------|--------|----------------|-----|--------------|
| 123 | 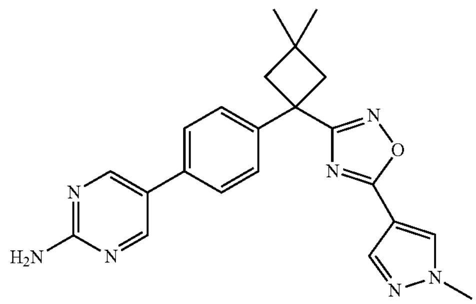 [SMILES: Cn1cc(-c2nc(C3(c4ccc(-c5cnc(N)nc5)cc4)CC(C)(C)C3)no2)cn1] | 2 | 1.57 | 402.4 | I |
| 124 | 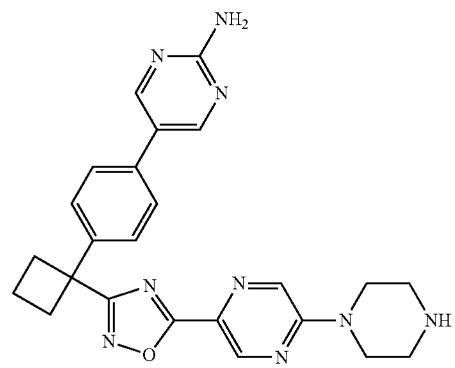 [SMILES: Nc1ncc(-c2ccc(C3(c4noc(-c5cnc(N6CCNCC6)cn5)n4)CCC3)cc2)cn1] | 7 | 0.64 | 456.2 | J |
| 125 | 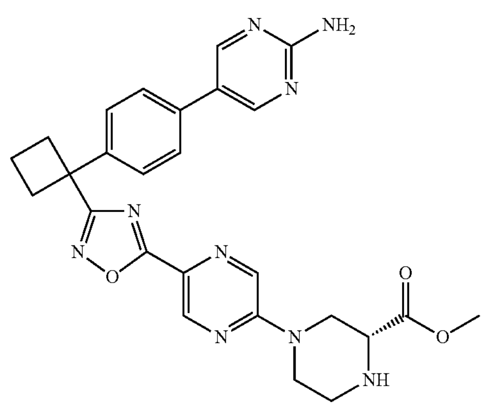 [SMILES: COC(=O)[C@H]1CN(c2cnc(-c3nc(C4(c5ccc(-c6cnc(N)nc6)cc5)CCC4)no3)cn2)CCN1] | 7 | 0.71 | 514.1 | J |
| 126 | 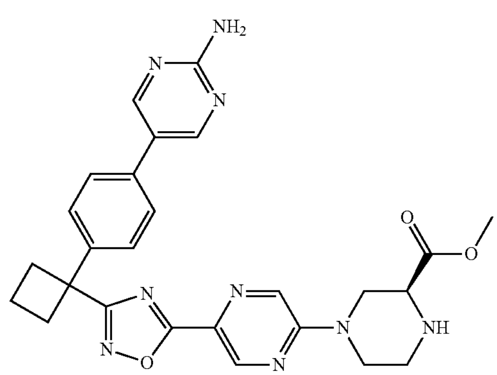 [SMILES: COC(=O)[C@@H]1CN(c2cnc(-c3nc(C4(c5ccc(-c6cnc(N)nc6)cc5)CCC4)no3)cn2)CCN1] | 7 | 0.71 | 514.1 | J |

TABLE 8-continued

Final compounds

| Example | Structure | Method | Retention time | m/z | LC MS method |
|---------|-----------|--------|----------------|-----|--------------|
| 127 | 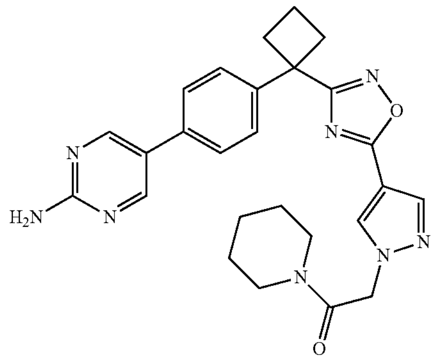 | 14 | 0.84 | 485.3 | J |
| 128 | 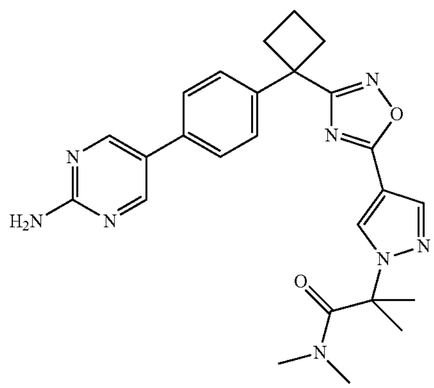 [SMILES: CN(C)C(=O)C(C)(C)n1cc(-c2nc(C3(c4ccc(-c5cnc(N)nc5)cc4)CCC3)no2)cn1] | 15 | 0.85 | 473.3 | J |
| 129 | 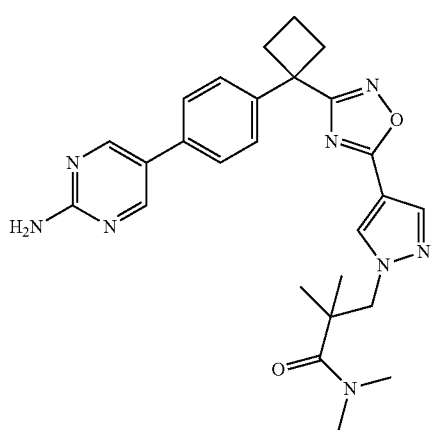 [SMILES: CN(C)C(=O)C(C)(C)Cn1cc(-c2nc(C3(c4ccc(-c5cnc(N)nc5)cc4)CCC3)no2)cn1] | 15 | 0.87 | 487.3 | J |

TABLE 8-continued

Final compounds

| Example | Structure | Method | Retention time | m/z | LC MS method |
|---------|-----------|--------|----------------|-----|--------------|
| 130 | 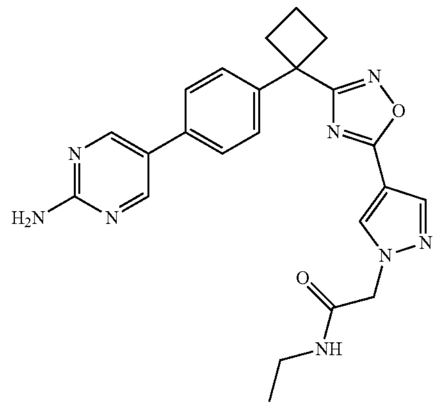 [SMILES: CCNC(=O)Cn1cc(-c2nc(C3(c4ccc(-c5cnc(N)nc5)cc4)CCC3)no2)cn1] | 15 | 0.73 | 445.2 | J |
| 131 | 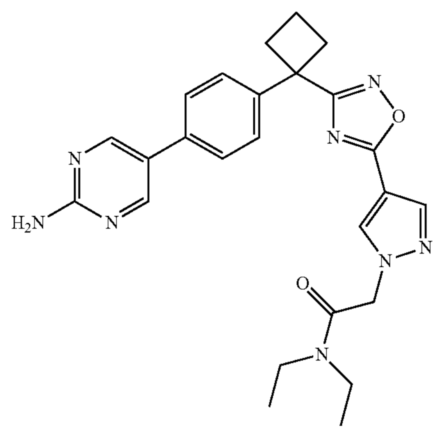 [SMILES: CCN(CC)C(=O)Cn1cc(-c2nc(C3(c4ccc(-c5cnc(N)nc5)cc4)CCC3)no2)cn1] | 15 | 0.83 | 473.3 | J |
| 132 | 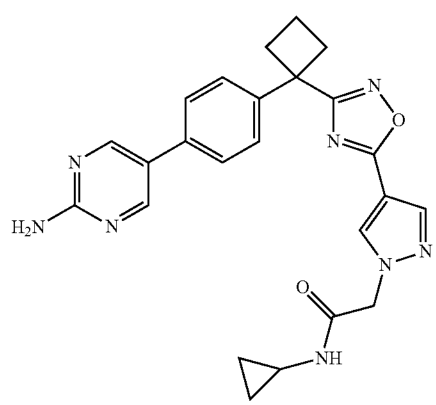 [SMILES: Nc1ncc(-c2ccc(C3(c4noc(-c5cnn(CC(=O)NC6CC6)c5)n4)CCC3)cc2)cn1] | 15 | 0.73 | 457.2 | J |

TABLE 8-continued
Final compounds
| Example | Structure | Method | Retention time | m/z | LC MS method |
|---------|-----------|--------|----------------|-----|--------------|
| 133 | 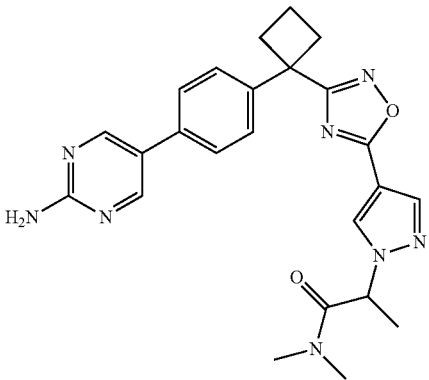 [SMILES: CC(C(=O)N(C)C)n1cc(-c2nc(C3(c4ccc(-c5cnc(N)nc5)cc4)CCC3)no2)cn1] | 15 | 0.78 | 460.3 | J |
| 134 | 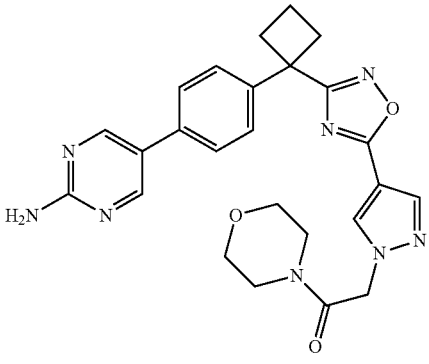 [SMILES: Nc1ncc(-c2ccc(C3(c4noc(-c5cnn(CC(=O)N6CCOCC6)c5)n4)CCC3)cc2)cn1] | 14 | 0.73 | 487.3 | J |
| 135 | 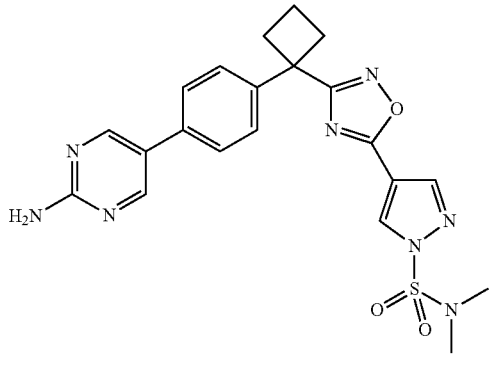 [SMILES: CN(C)S(=O)(=O)n1cc(-c2nc(C3(c4ccc(-c5cnc(N)nc5)cc4)CCC3)no2)cn1] | 16 | 6.21 | 467.3 | F |
| 136 | 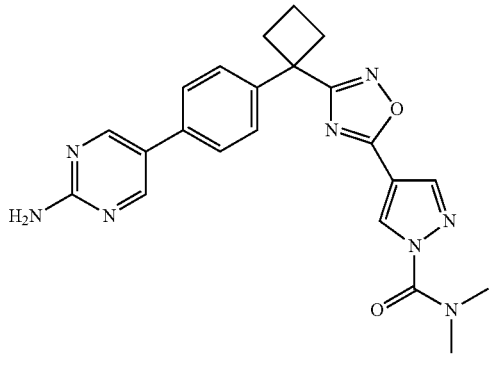 [SMILES: CN(C)C(=O)n1cc(-c2nc(C3(c4ccc(-c5cnc(N)nc5)cc4)CCC3)no2)cn1] | 16 | 5.59 | 431.3 | F |

TABLE 8-continued
Final compounds
| Example | Structure | Method | Retention time | m/z | LC MS method |
|---|---|---|---|---|---|
| 137 | 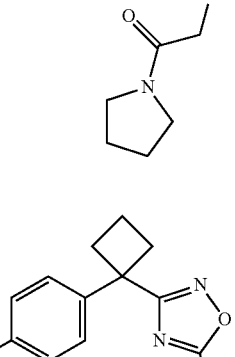 | 15 | 1.35 | 471.4 | H |
| 138 | 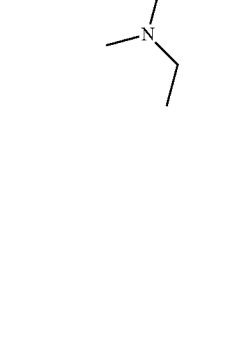 | 15 | 1.35 | 459.4 | H |
| 139 | 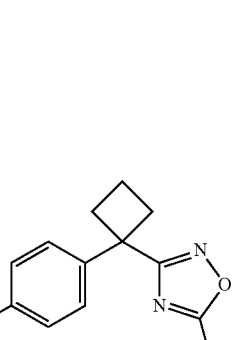 | 15 | 1.39 | 473.4 | H |

TABLE 8-continued

Final compounds

| Example | Structure | Method | Retention time | m/z | LC MS method |
|---|---|---|---|---|---|
| 140 | 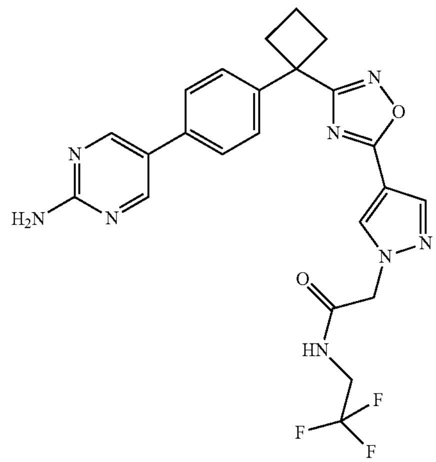 [SMILES: Nc1ncc(-c2ccc(C3(c4noc(-c5cnn(CC(=O)NCC(F)(F)F)c5)n4)CCC3)cc2)cn1] | 15 | 1.38 | 499.2 | H |
| 141 | 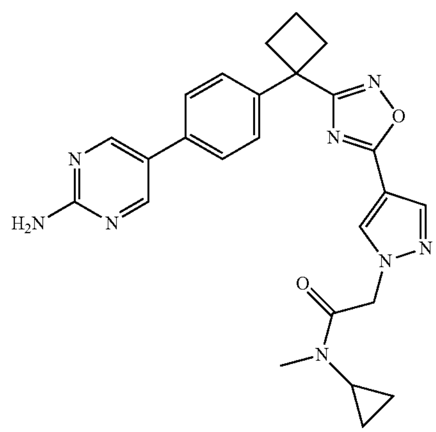 [SMILES: CN(C(=O)Cn1cc(-c2nc(C3(c4ccc(-c5cnc(N)nc5)cc4)CCC3)no2)cn1)C1CC1] | 15 | 1.38 | 471.6 | H |
| 142 | 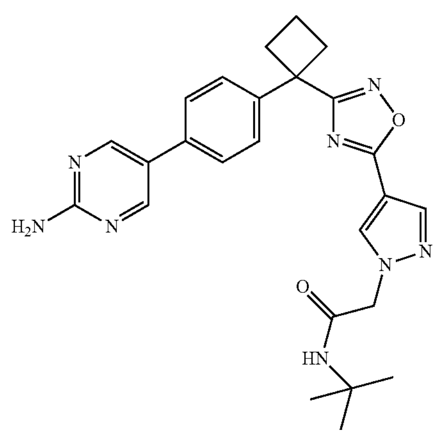 [SMILES: CC(C)(C)NC(=O)Cn1cc(-c2nc(C3(c4ccc(-c5cnc(N)nc5)cc4)CCC3)no2)cn1] | 15 | 1.42 | 473.4 | H |
| 143 | 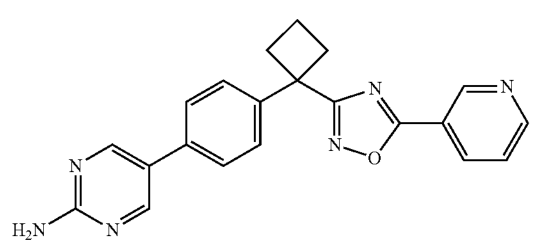 [SMILES: Nc1ncc(-c2ccc(C3(c4noc(-c5cccnc5)n4)CCC3)cc2)cn1] | 4 | 3.92 | 371.1 | B |

TABLE 8-continued

| Example | Structure | Method | Retention time | m/z | LC MS method |
|---|---|---|---|---|---|
| 144 | 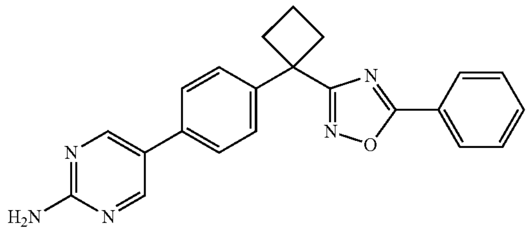 [SMILES: Nc1ncc(-c2ccc(C3(c4noc(-c5ccccc5)n4)CCC3)cc2)cn1] | 4 | 4.36 | 370.1 | B |
| 145 | 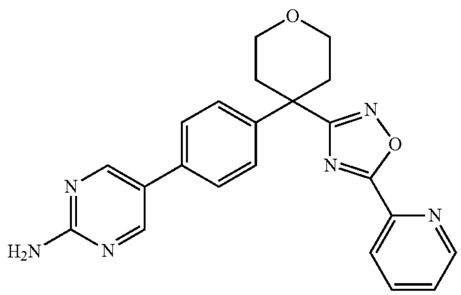 [SMILES: Nc1ncc(-c2ccc(C3(c4noc(-c5ccccn5)n4)CCOCC3)cc2)cn1] | 17 | 6.23 | 401.6 | A |
| 146 | 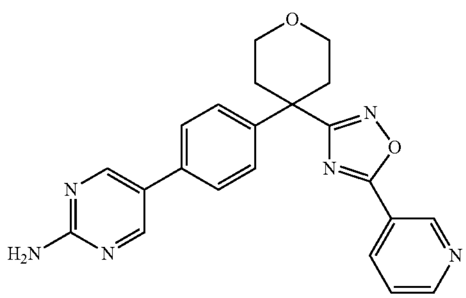 [SMILES: Nc1ncc(-c2ccc(C3(c4noc(-c5cccnc5)n4)CCOCC3)cc2)cn1] | 17 | 6.25 | 401.6 | A |
| 147 | 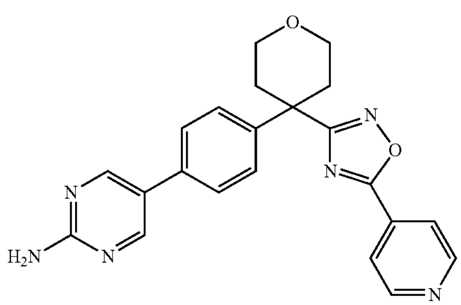 [SMILES: Nc1ncc(-c2ccc(C3(c4noc(-c5ccncc5)n4)CCOCC3)cc2)cn1] | 17 | 6.27 | 401.6 | A |
| 148 | 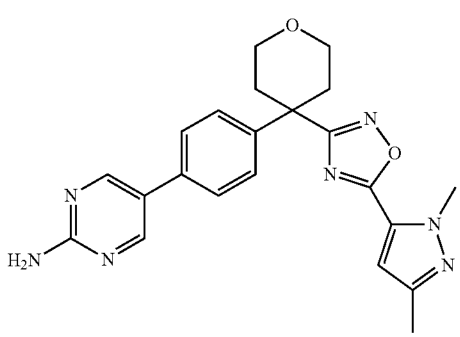 [SMILES: Cc1cc(-c2nc(C3(c4ccc(-c5cnc(N)nc5)cc4)CCOCC3)no2)n(C)n1] | 17 | 6.67 | 418.6 | A |

TABLE 8-continued

Final compounds

| Example | Structure | Method | Retention time | m/z | LC MS method |
|---------|-----------|--------|----------------|------|--------------|
| 149 | 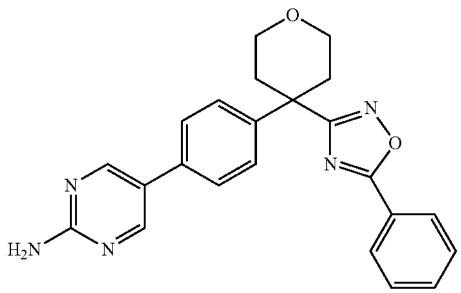 [SMILES: Nc1ncc(-c2ccc(C3(c4noc(-c5ccccc5)n4)CCOCC3)cc2)cn1] | 17 | 7.17 | 400.6 | A |
| 150 | 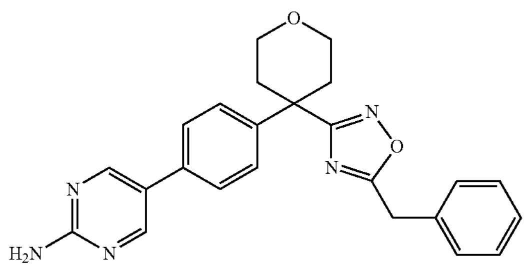 [SMILES: Nc1ncc(-c2ccc(C3(c4noc(Cc5ccccc5)n4)CCOCC3)cc2)cn1] | 17 | 7.88 | 532.5 | A |
| 151 | 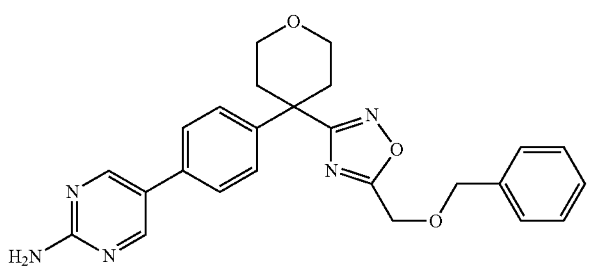 [SMILES: Nc1ncc(-c2ccc(C3(c4noc(COCc5ccccc5)n4)CCOCC3)cc2)cn1] | 17 | 8.23 | 444.5 | A |
| 152 | 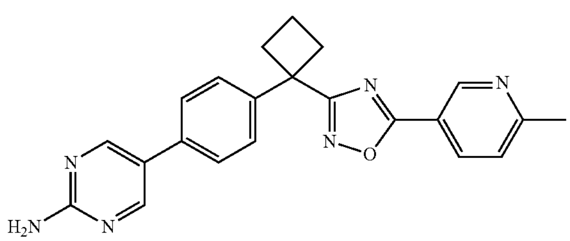 [SMILES: Cc1ccc(-c2nc(C3(c4ccc(-c5cnc(N)nc5)cc4)CCC3)no2)cn1] | 3 | 4.08 | 385.1 | A |
| 153 | 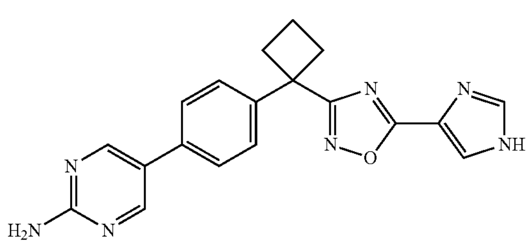 [SMILES: Nc1ncc(-c2ccc(C3(c4noc(-c5c[nH]cn5)n4)CCC3)cc2)cn1] | 3 | 3.26 | 360.1 | A |

TABLE 8-continued

| Example | Structure | Method | Retention time | m/z | LC MS method |
|---|---|---|---|---|---|
| 154 | 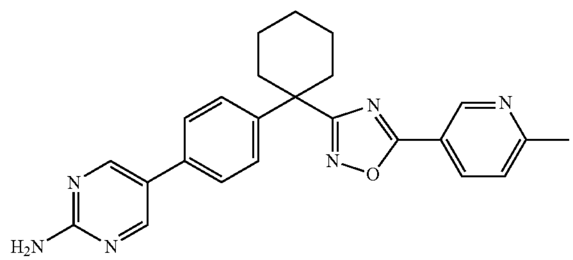 [SMILES: Cc1ccc(-c2nc(C3(c4ccc(-c5cnc(N)nc5)cc4)CCCCC3)no2)cn1] | 3 | 4.55 | 413.1 | A |
| 155 | 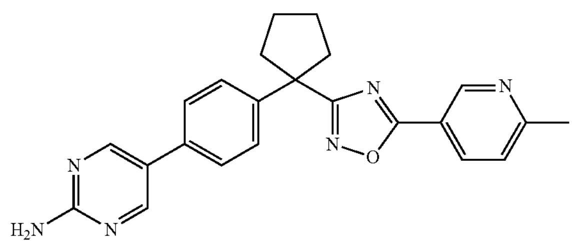 [SMILES: Cc1ccc(-c2nc(C3(c4ccc(-c5cnc(N)nc5)cc4)CCCC3)no2)cn1] | 3 | 4.29 | 399.1 | A |
| 156 | 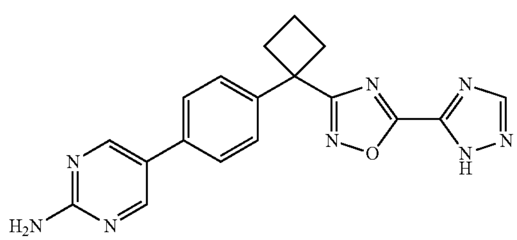 [SMILES: Nc1ncc(-c2ccc(C3(c4noc(-c5ncn[nH]5)n4)CCC3)cc2)cn1] | 1 | 3.28 | 361.2 | A |
| 157 | 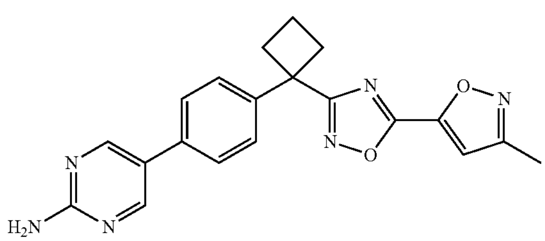 [SMILES: Cc1cc(-c2nc(C3(c4ccc(-c5cnc(N)nc5)cc4)CCC3)no2)on1] | 2 | 4.12 | 375.1 | A |
| 158 | 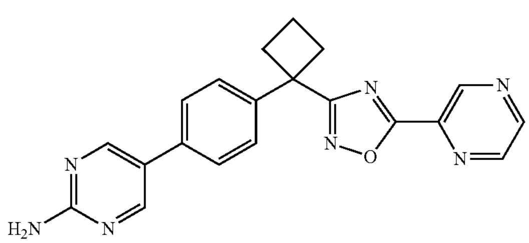 [SMILES: Nc1ncc(-c2ccc(C3(c4noc(-c5cnccn5)n4)CCC3)cc2)cn1] | 3 | 3.73 | 372.1 | A |
| 159 | 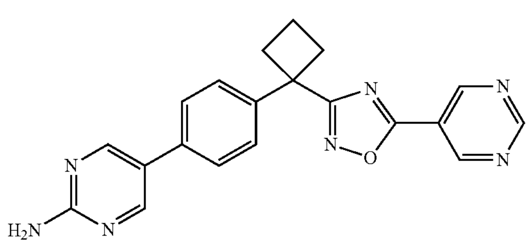 [SMILES: Nc1ncc(-c2ccc(C3(c4noc(-c5cncnc5)n4)CCC3)cc2)cn1] | 3 | 3.71 | 372.1 | A |

TABLE 8-continued

Final compounds

| Example | Structure | Method | Retention time | m/z | LC MS method |
|---|---|---|---|---|---|
| 160 | 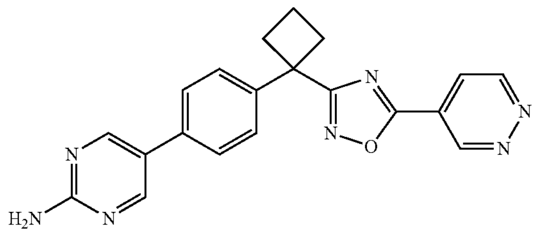 [SMILES: Nc1ncc(-c2ccc(C3(c4noc(-c5ccnnc5)n4)CCC3)cc2)cn1] | 3 | 3.58 | 372.1 | A |
| 161 | 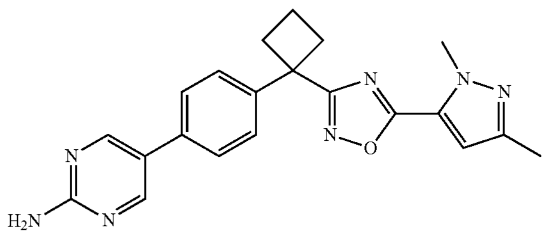 [SMILES: Cc1cc(-c2nc(C3(c4ccc(-c5cnc(N)nc5)cc4)CCC3)no2)n(C)n1] | 3 | 4.26 | 388.2 | A |
| 162 | 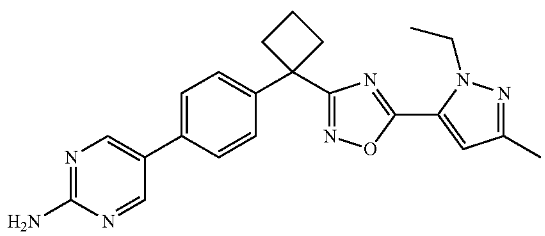 [SMILES: CCn1nc(C)cc1-c1nc(C2(c3ccc(-c4cnc(N)nc4)cc3)CCC2)no1] | 3 | 4.53 | 402.2 | A |
| 163 | 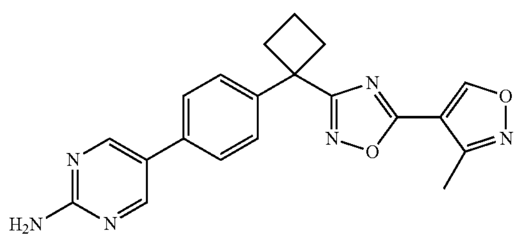 | 2 | 4.13 | 375.3 | A |
| 164 | 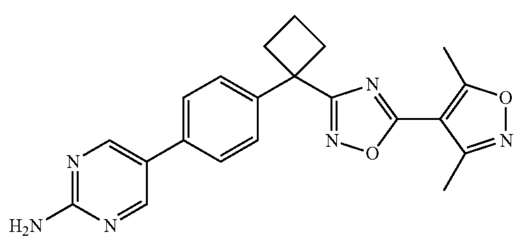 [SMILES: Cc1noc(C)c1-c1nc(C2(c3ccc(-c4cnc(N)nc4)cc3)CCC2)no1] | 2 | 4.41 | 389.3 | A |
| 165 | 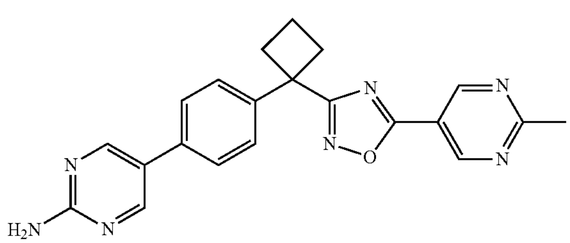 [SMILES: Cc1ncc(-c2nc(C3(c4ccc(-c5cnc(N)nc5)cc4)CCC3)no2)cn1] | 3 | 3.81 | 386.4 | A |

TABLE 8-continued

Final compounds

| Example | Structure | Method | Retention time | m/z | LC MS method |
|---|---|---|---|---|---|
| 166 | 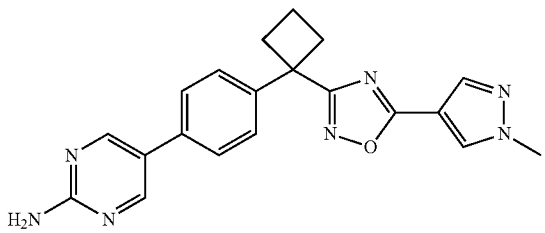 | 3 | 3.9 | 374.4 | A |
| 167 | 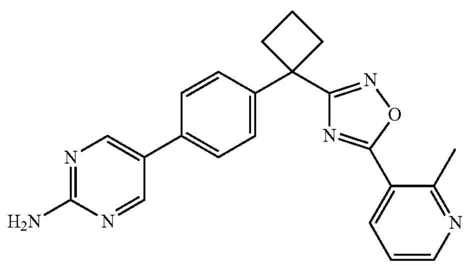 [SMILES: Cc1ncccc1-c1nc(C2(c3ccc(-c4cnc(N)nc4)cc3)CCC2)no1] | 17 | 2.66 | 385.2 | D |
| 168 | 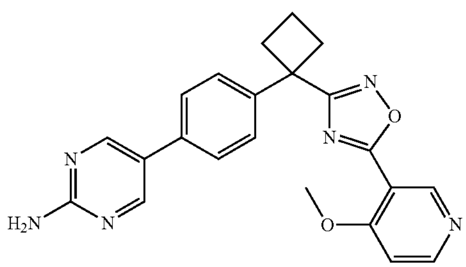 [SMILES: COc1ccncc1-c1nc(C2(c3ccc(-c4cnc(N)nc4)cc3)CCC2)no1] | 1 | 2.12 | 401.2 | D |
| 169 | 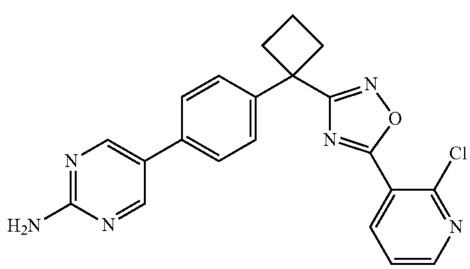 [SMILES: Nc1ncc(-c2ccc(C3(c4noc(-c5cccnc5Cl)n4)CCC3)cc2)cn1] | 17 | 2.65 | 405.2 | D |
| 170 | 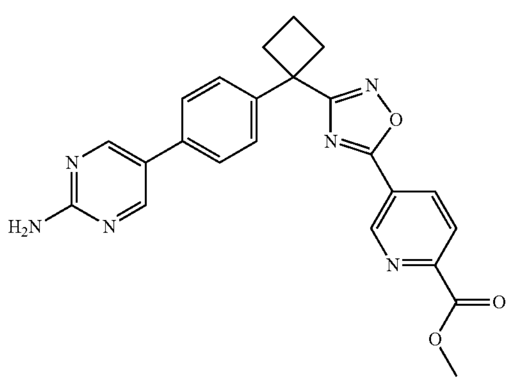 [SMILES: COC(=O)c1ccc(-c2nc(C3(c4ccc(-c5cnc(N)nc5)cc4)CCC3)no2)cn1] | 1 | 2.57 | 429.2 | D |

TABLE 8-continued

Final compounds

| Example | Structure | Method | Retention time | m/z | LC MS method |
|---|---|---|---|---|---|
| 171 | 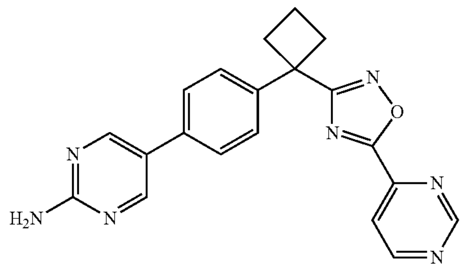 [SMILES: Nc1ncc(-c2ccc(C3(c4noc(-c5ccncn5)n4)CCC3)cc2)cn1] | 1 | 3.66 | 372.2 | B |
| 172 | 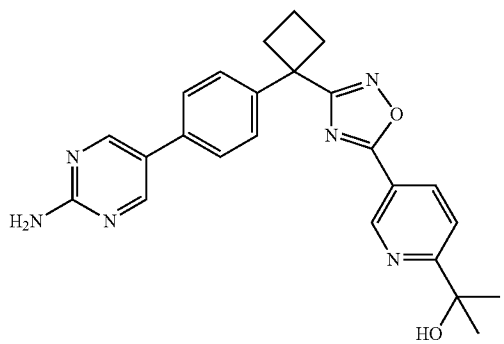 [SMILES: CC(C)(O)c1ccc(-c2nc(C3(c4ccc(-c5cnc(N)nc5)cc4)CCC3)no2)cn1] | 18 | 2.53 | 429.2 | D |
| 173 | 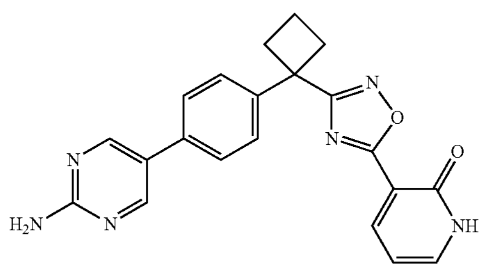 [SMILES: Nc1ncc(-c2ccc(C3(c4noc(-c5ccc[nH]c5=O)n4)CCC3)cc2)cn1] | 19 | 1.91 | 387.2 | D |
| 174 | 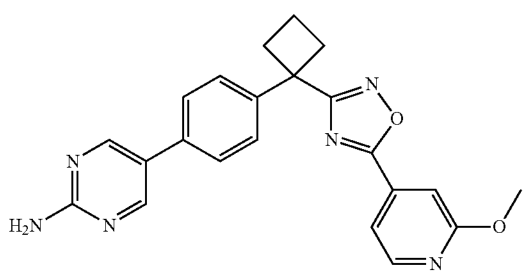 [SMILES: COc1cc(-c2nc(C3(c4ccc(-c5cnc(N)nc5)cc4)CCC3)no2)ccn1] | 1 | 2.86 | 401.2 | D |
| 175 | 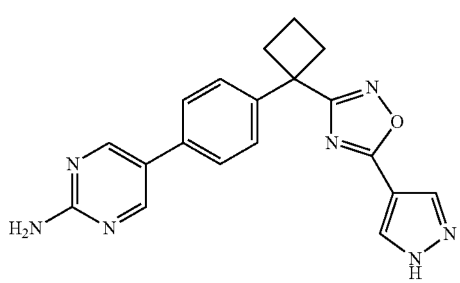 | 1 | 1.32 | 360.5 | I |

TABLE 8-continued

Final compounds

| Example | Structure | Method | Retention time | m/z | LC MS method |
|---|---|---|---|---|---|
| 176 | 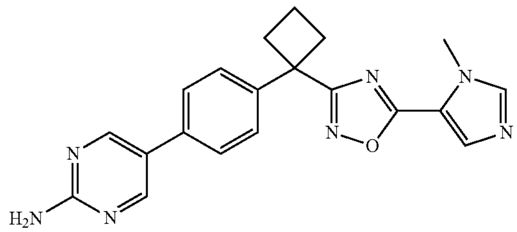 [SMILES: Cn1cncc1-c1nc(C2(c3ccc(-c4cnc(N)nc4)cc3)CCC2)no1] | 1 | 3.46 | 374.3 | B |
| 177 | 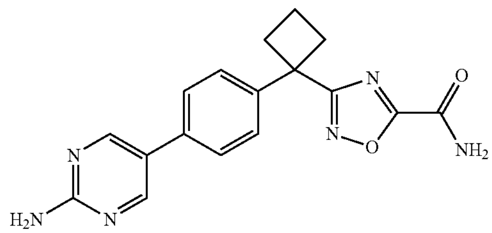 [SMILES: NC(=O)c1nc(C2(c3ccc(-c4cnc(N)nc4)cc3)CCC2)no1] | 1 | 3.7 | 337.2 | B |
| 178 | 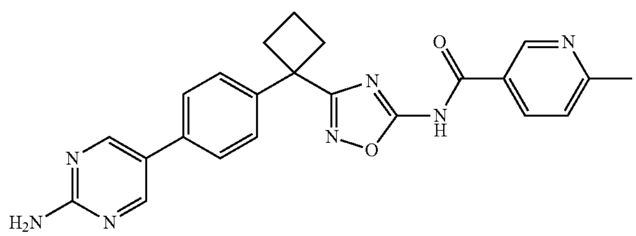 [SMILES: Cc1ccc(C(=O)Nc2nc(C3(c4ccc(-c5cnc(N)nc5)cc4)CCC3)no2)cn1] | 3 | 3.33 | 428.2 | B |
| 179 | 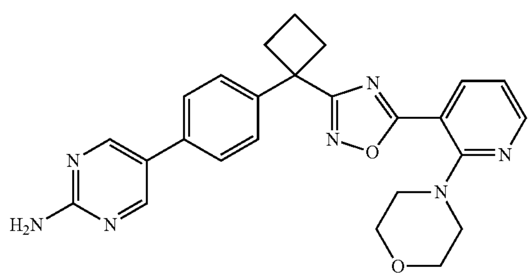 [SMILES: Nc1ncc(-c2ccc(C3(c4noc(-c5cccnc5N5CCOCC5)n4)CCC3)cc2)cn1] | 1 | 2.08 | 456 | C |
| 180 | 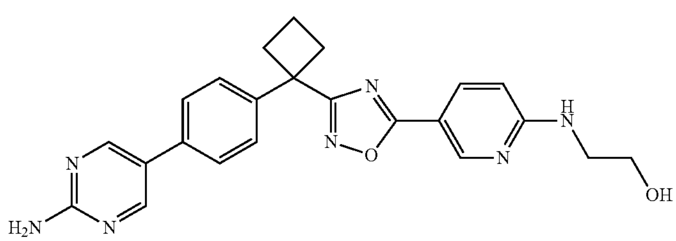 | 7 | 3.38 | 430.3 | B |
| 181 | 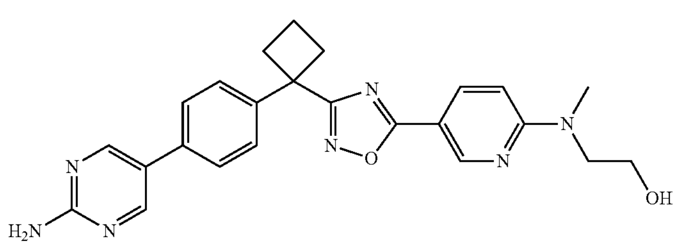 [SMILES: CN(CCO)c1ccc(-c2nc(C3(c4ccc(-c5cnc(N)nc5)cc4)CCC3)no2)cn1] | 7 | 3.73 | 444.3 | B |

TABLE 8-continued

Final compounds

| Example | Structure | Method | Retention time | m/z | LC MS method |
|---|---|---|---|---|---|
| 182 | 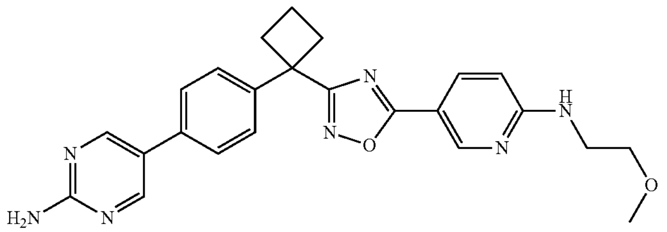 [SMILES: COCCNc1ccc(-c2nc(C3(c4ccc(-c5cnc(N)nc5)cc4)CCC3)no2)cn1] | 7 | 3.82 | 444.3 | B |
| 183 | 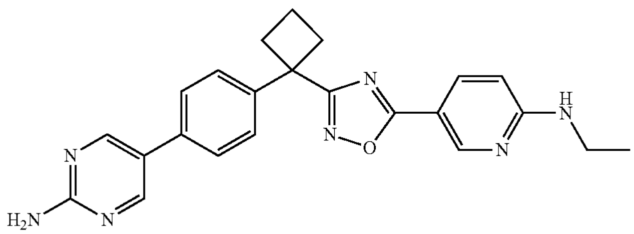 | 7 | 3.78 | 414.3 | B |
| 184 | 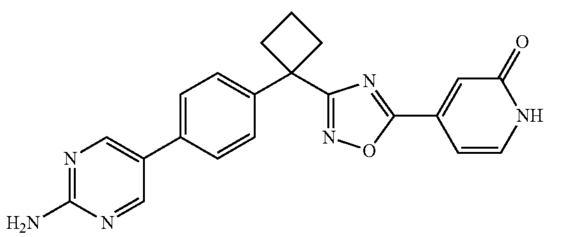 [SMILES: Nc1ncc(-c2ccc(C3(c4noc(-c5cc[nH]c(=O)c5)n4)CCC3)cc2)cn1] | 1 | 3.42 | 387.3 | B |
| 185 | 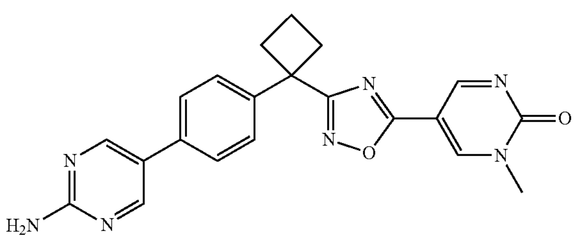 [SMILES: Cn1cc(-c2nc(C3(c4ccc(-c5cnc(N)nc5)cc4)CCC3)no2)cnc1=O] | 3 | 3.29 | 402.2 | B |
| 186 | 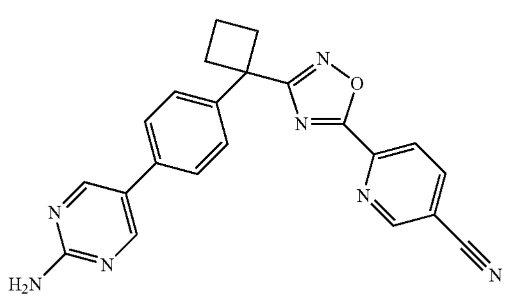 [SMILES: N#Cc1ccc(-c2nc(C3(c4ccc(-c5cnc(N)nc5)cc4)CCC3)no2)nc1] | 1 | 3.9 | 396.1 | B |

TABLE 8-continued

Final compounds

| Example | Structure | Method | Retention time | m/z | LC MS method |
|---|---|---|---|---|---|
| 187 | 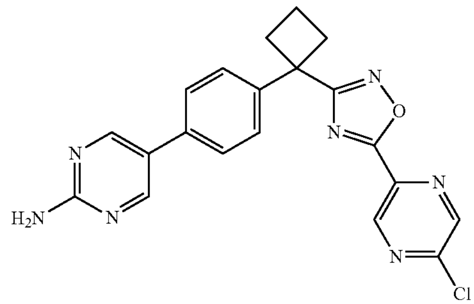 [SMILES: Nc1ncc(-c2ccc(C3(c4noc(-c5cnc(Cl)cn5)n4)CCC3)cc2)cn1] | 6 | 4.24 | 406.2 | B |
| 188 | 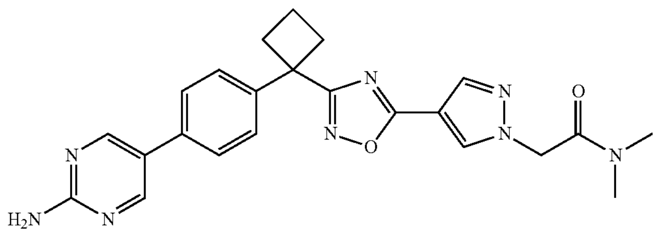 [SMILES: CN(C)C(=O)Cn1cc(-c2nc(C3(c4ccc(-c5cnc(N)nc5)cc4)CCC3)no2)cn1] | 14 | 1.13 | 445.4 | E |
| 189 | 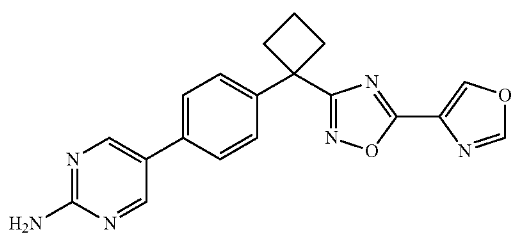 | 1 | 3.65 | 361.2 | B |
| 190 | 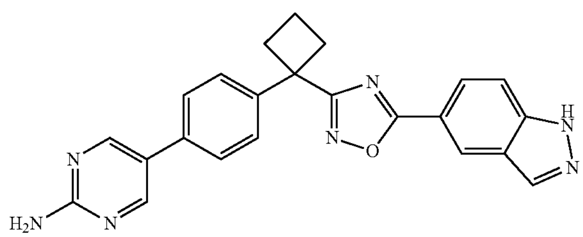 [SMILES: Nc1ncc(-c2ccc(C3(c4noc(-c5ccc6[nH]ncc6c5)n4)CCC3)cc2)cn1] | 1 | 4.09 | 410.2 | B |
| 191 | 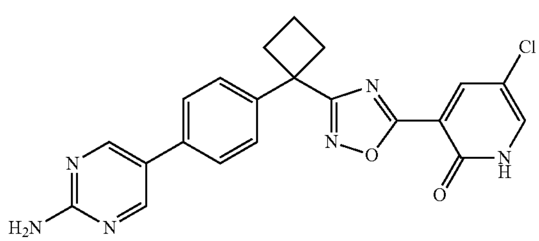 [SMILES: Nc1ncc(-c2ccc(C3(c4noc(-c5cc(Cl)c[nH]c5=O)n4)CCC3)cc2)cn1] | 1 | 3.61 | 421.2 | B |
| 192 | 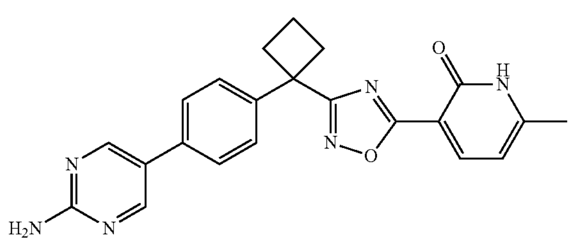 [SMILES: Cc1ccc(-c2nc(C3(c4ccc(-c5cnc(N)nc5)cc4)CCC3)no2)c(=O)[nH]1] | 1 | 3.33 | 401.4 | B |

TABLE 8-continued

Final compounds

| Example | Structure | | Method | Retention time | m/z | LC MS method |
|---|---|---|---|---|---|---|
| 193 | 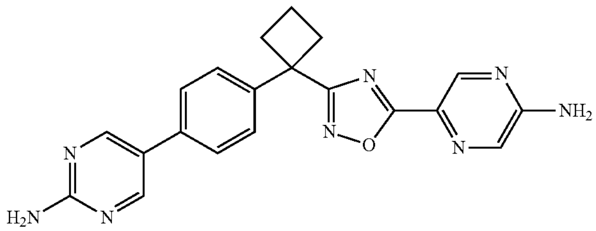 | | 3 | 3.45 | 387.3 | B |
| 194 | 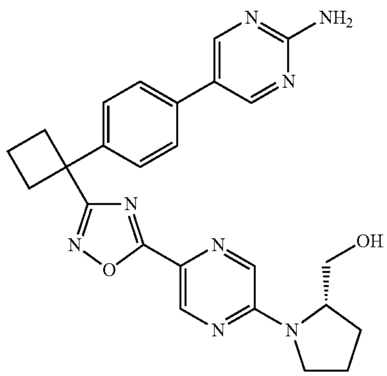 | Chiral | 7 | 0.89 | 471.2 | J |
| 195 | 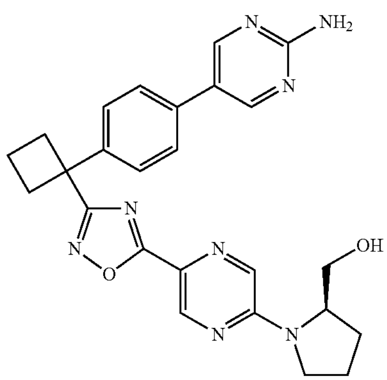 | Chiral | 7 | 0.89 | 471.2 | J |
| 196 | 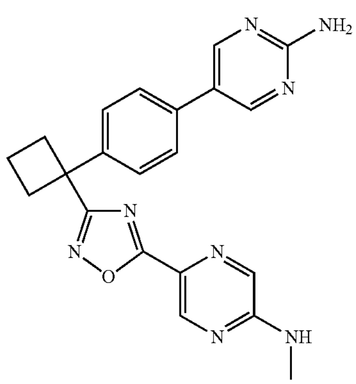 [SMILES: CNc1cnc(-c2nc(C3(c4ccc(-c5cnc(N)nc5)cc4)CCC3)no2)cn1] | | 7 | 0.86 | 401.2 | J |

TABLE 8-continued
Final compounds
| Example | Structure | Method | Retention time | m/z | LC MS method |
|---|---|---|---|---|---|
| 197 | 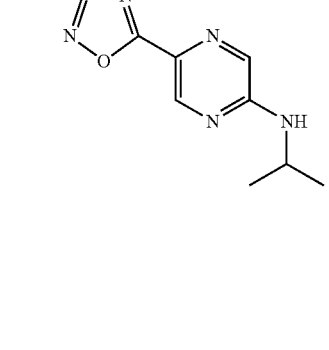 | 7 | 1.01 | 429.2 | J |
| 198 | 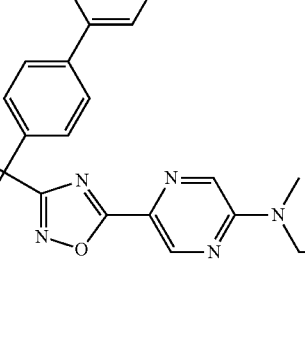 | 7 | 0.99 | 459.2 | J |
| 199 | 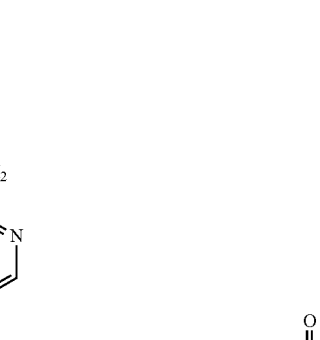 | 7 | 0.95 | 473.2 | J |

TABLE 8-continued
Final compounds
| Example | Structure | Method | Retention time | m/z | LC MS method |
|---|---|---|---|---|---|
| 200 | 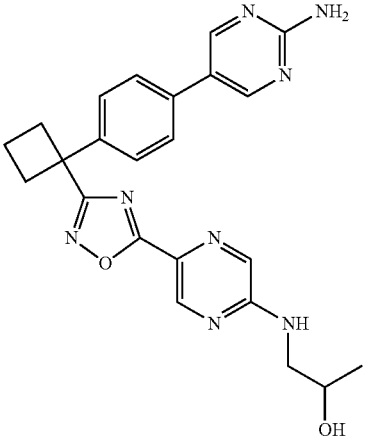 [SMILES: CC(O)CNc1cnc(-c2nc(C3(c4ccc(-c5cnc(N)nc5)cc4)CCC3)no2)cn1] | 7 | 0.82 | 445.2 | J |
| 201 | 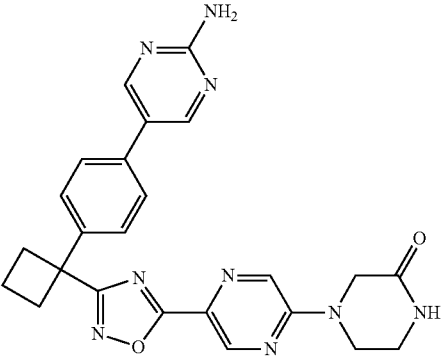 [SMILES: Nc1ncc(-c2ccc(C3(c4noc(-c5cnc(N6CCNC(=O)C6)cn5)n4)CCC3)cc2)cn1] | 7 | 0.79 | 470.2 | J |
| 202 | 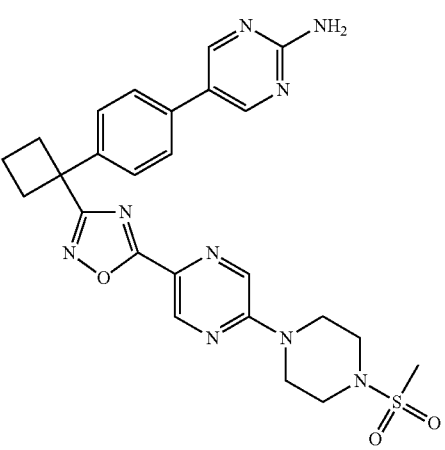 [SMILES: CS(=O)(=O)N1CCN(c2cnc(-c3nc(C4(c5ccc(-c6cnc(N)nc6)cc5)CCC4)no3)cn2)CC1] | 7 | 0.92 | 534.2 | J |

TABLE 8-continued

Final compounds

| Example | Structure | Method | Retention time | m/z | LC MS method |
|---|---|---|---|---|---|
| 203 | 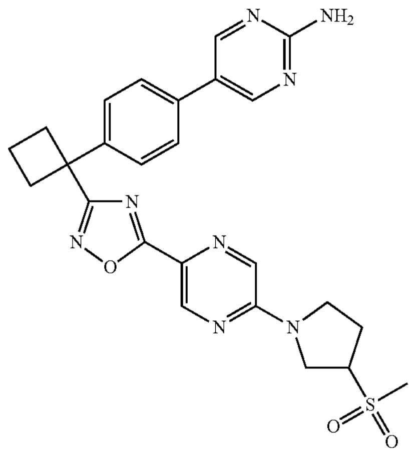 [SMILES: CS(=O)(=O)C1CCN(c2cnc(-c3nc(C4(c5ccc(-c6cnc(N)nc6)cc5)CCC4)no3)cn2)C1] | 7 | 0.84 | 519.2 | J |
| 204 | 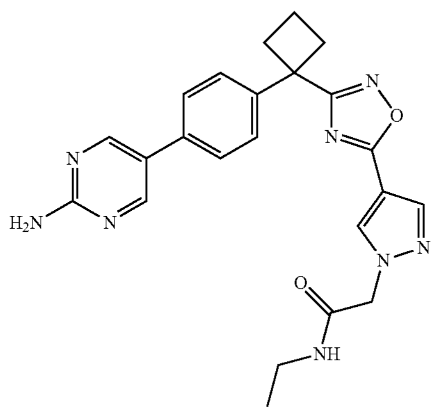 [SMILES: CCNC(=O)Cn1cc(-c2nc(C3(c4ccc(-c5cnc(N)nc5)cc4)CCC3)no2)cn1] | 15 | 1.33 | 445.4 | I |
| 205 | 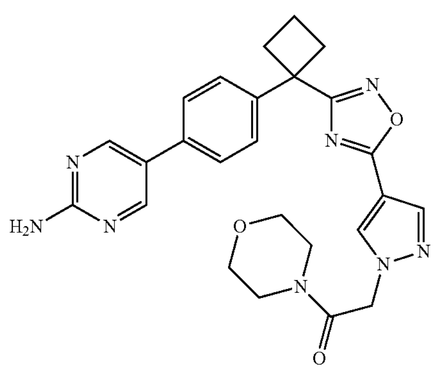 [SMILES: Nc1ncc(-c2ccc(C3(c4noc(-c5cnn(CC(=O)N6CCOCC6)c5)n4)CCC3)cc2)cn1] | 33 | 1.13 | 487.4 | K |

TABLE 8-continued

Final compounds

| Example | Structure | Method | Retention time | m/z | LC MS method |
|---|---|---|---|---|---|
| 206 | 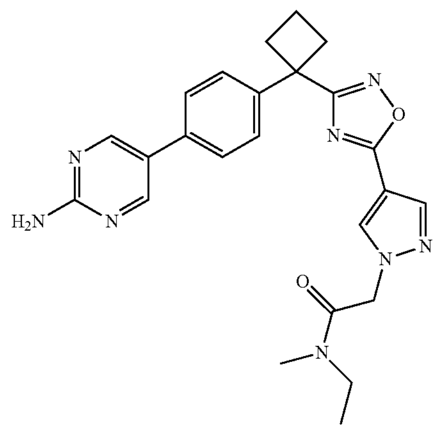 [SMILES: CCN(C)C(=O)Cn1cc(-c2nc(C3(c4ccc(-c5cnc(N)nc5)cc4)CCC3)no2)cn1] | 15 | 1.16 | 459.4 | K |
| 207 | 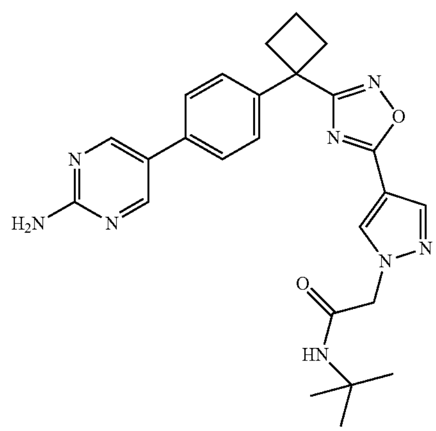 [SMILES: CC(C)(C)NC(=O)Cn1cc(-c2nc(C3(c4ccc(-c5cnc(N)nc5)cc4)CCC3)no2)cn1] | 15 | 1.25 | 473.4 | K |
| 208 | 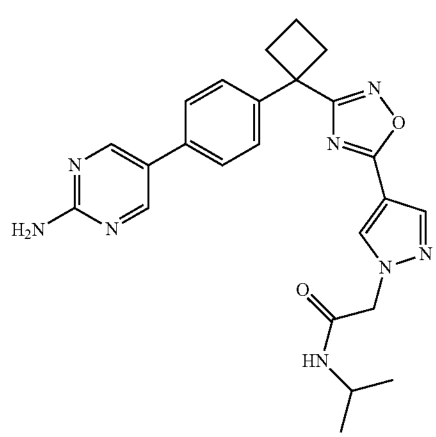 [SMILES: CC(C)NC(=O)Cn1cc(-c2nc(C3(c4ccc(-c5cnc(N)nc5)cc4)CCC3)no2)cn1] | 15 | 1.35 | 459.4 | K |

TABLE 8-continued

Final compounds

| Example | Structure | Method | Retention time | m/z | LC MS method |
|---|---|---|---|---|---|
| 209 | 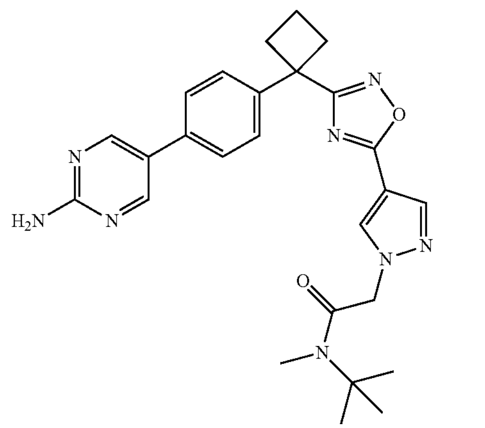 [SMILES: CN(C(=O)Cn1cc(-c2nc(C3(c4ccc(-c5cnc(N)nc5)cc4)CCC3)no2)cn1)C(C)(C)C] | 15 | 1.46 | 487.4 | K |
| 210 | 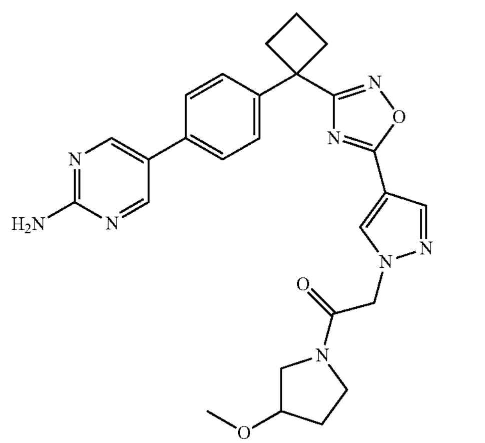 [SMILES: COC1CCN(C(=O)Cn2cc(-c3nc(C4(c5ccc(-c6cnc(N)nc6)cc5)CCC4)no3)cn2)C1] | 15 | 1.33 | 501.4 | K |
| 211 | 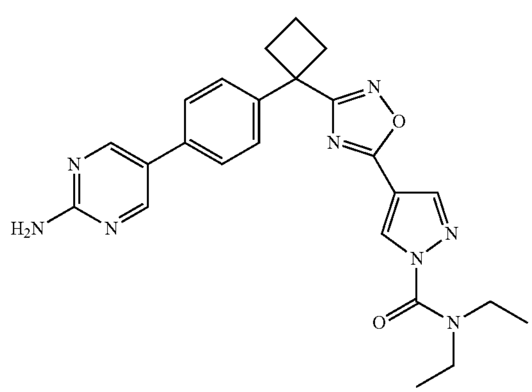 [SMILES: CCN(CC)C(=O)n1cc(-c2nc(C3(c4ccc(-c5cnc(N)nc5)cc4)CCC3)no2)cn1] | 16 | 1.42 | 459.4 | K |

TABLE 8-continued

Final compounds

| Example | Structure | Method | Retention time | m/z | LC MS method |
|---|---|---|---|---|---|
| 212 | 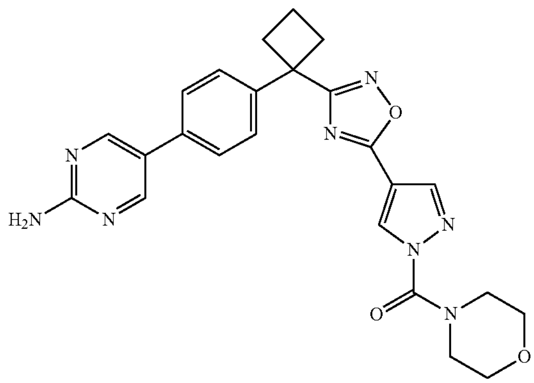 [SMILES: Nc1ncc(-c2ccc(C3(c4noc(-c5cnn(C(=O)N6CCOCC6)c5)n4)CCC3)cc2)cn1] | 16 | 1.26 | 473.4 | K |
| 213 | 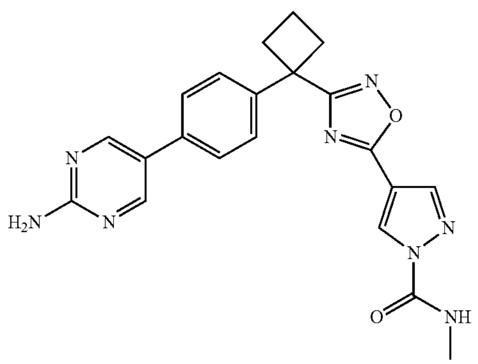 [SMILES: CNC(=O)n1cc(-c2nc(C3(c4ccc(-c5cnc(N)nc5)cc4)CCC3)no2)cn1] | 16 | 1.23 | 417.4 | K |
| 214 | 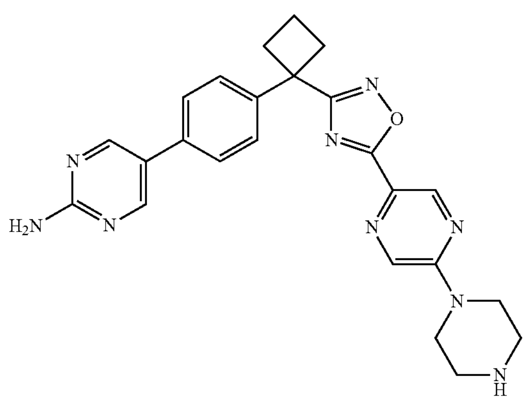 [SMILES: Nc1ncc(-c2ccc(C3(c4noc(-c5cnc(N6CCNCC6)cn5)n4)CCC3)cc2)cn1] | 22 | 0.55 | 456.3 | J |
| 215 | 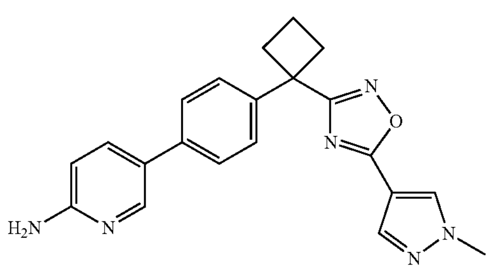 [SMILES: Cn1cc(-c2nc(C3(c4ccc(-c5ccc(N)nc5)cc4)CCC3)no2)cn1] | 31 | 4.24 | 373.3 | F |

TABLE 8-continued

Final compounds

| Example | Structure | Method | Retention time | m/z | LC MS method |
|---|---|---|---|---|---|
| 216 | 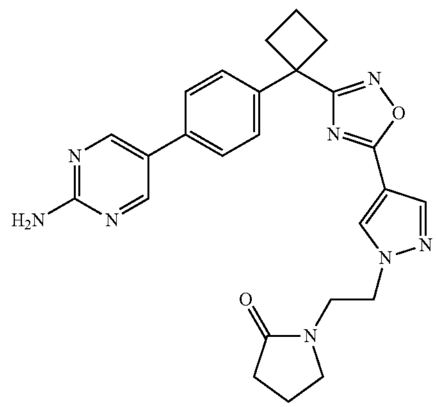 [SMILES: Nc1ncc(-c2ccc(C3(c4noc(-c5cnn(CCN6CCCC6=O)c5)n4)CCC3)cc2)cn1] | 33 | 1.33 | 471.5 | I |
| 217 | 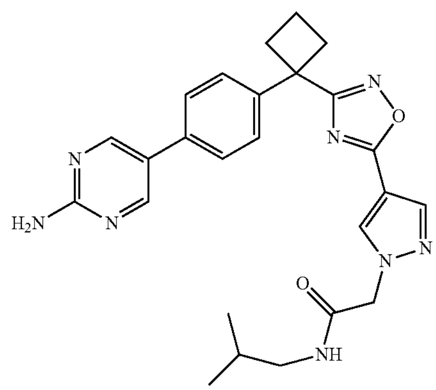 [SMILES: CC(C)CNC(=O)Cn1cc(-c2nc(C3(c4ccc(-c5cnc(N)nc5)cc4)CCC3)no2)cn1] | 15 | 1.24 | 473.4 | K |
| 218 | 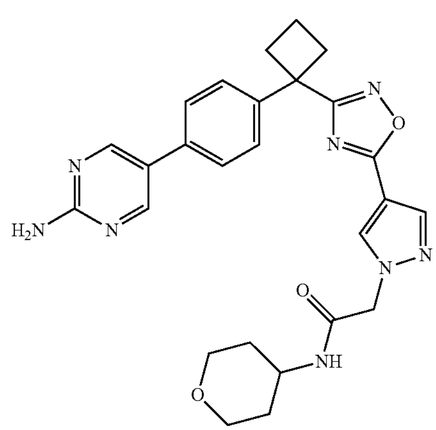 [SMILES: Nc1ncc(-c2ccc(C3(c4noc(-c5cnn(CC(=O)NC6CCOCC6)c5)n4)CCC3)cc2)cn1] | 15 | 1.13 | 499.2 | K |

TABLE 8-continued

Final compounds

| Example | Structure | Method | Retention time | m/z | LC MS method |
|---|---|---|---|---|---|
| 219 | 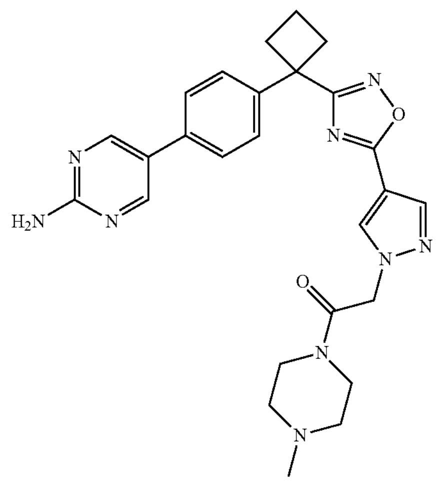 [SMILES: CN1CCN(C(=O)Cn2cc(-c3nc(C4(c5ccc(-c6cnc(N)nc6)cc5)CCC4)no3)cn2)CC1] | 15 | 0.97 | 500.4 | K |
| 220 | 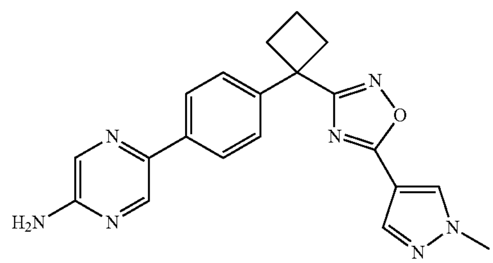 [SMILES: Cn1cc(-c2nc(C3(c4ccc(-c5cnc(N)cn5)cc4)CCC3)no2)cn1] | 32 | 5.41 | 374.4 | F |
| 221 | 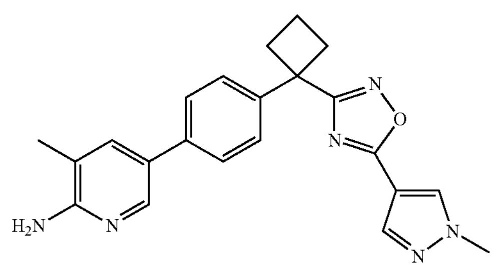 [SMILES: Cc1cc(-c2ccc(C3(c4noc(-c5cnn(C)c5)n4)CCC3)cc2)cnc1N] | 32 | 4.44 | 387.4 | F |
| 222 | 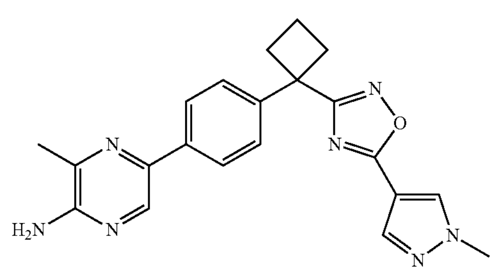 [SMILES: Cc1nc(-c2ccc(C3(c4noc(-c5cnn(C)c5)n4)CCC3)cc2)cnc1N] | 32 | 1.48 | 388.4 | J |

TABLE 8-continued

Final compounds

| Example | Structure | Method | Retention time | m/z | LC MS method |
|---|---|---|---|---|---|
| 223 | 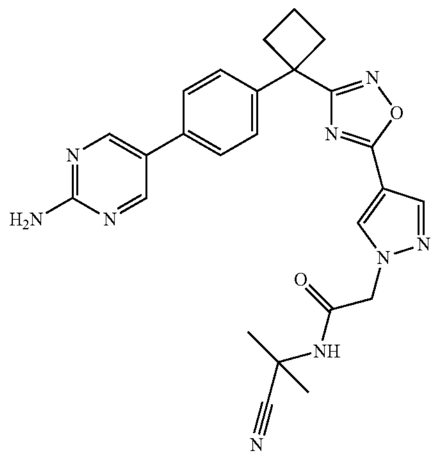 [SMILES: CC(C)(C#N)NC(=O)Cn1cc(-c2nc(C3(c4ccc(-c5cnc(N)nc5)cc4)CCC3)no2)cn1] | 15 | 0.83 | 482.5 | I |
| 224 | 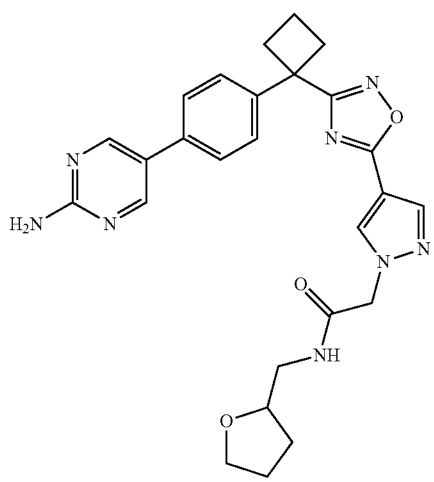 [SMILES: Nc1ncc(-c2ccc(C3(c4noc(-c5cnn(CC(=O)NCC6CCCO6)c5)n4)CCC3)cc2)cn1] | 15 | 0.81 | 501.35 | I |
| 225 | 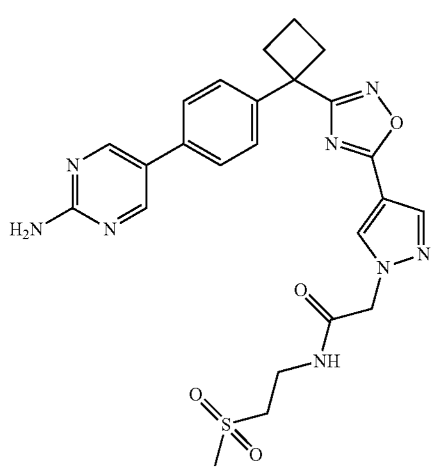 [SMILES: CS(=O)(=O)CCNC(=O)Cn1cc(-c2nc(C3(c4ccc(-c5cnc(N)nc5)cc4)CCC3)no2)cn1] | 15 | 0.73 | 523.3 | I |

TABLE 8-continued

Final compounds

| Example | Structure | Method | Retention time | m/z | LC MS method |
|---|---|---|---|---|---|
| 226 | 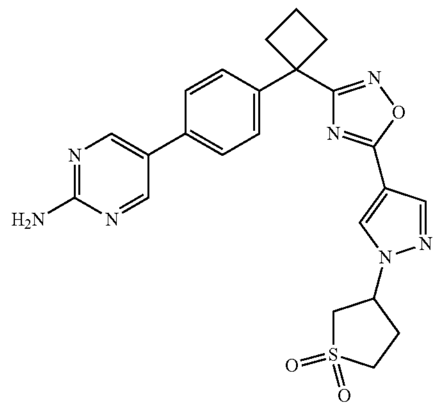 [SMILES: Nc1ncc(-c2ccc(C3(c4noc(-c5cnn(C6CCS(=O)(=O)C6)c5)n4)CCC3)cc2)cn1] | 33 | 0.83 | 478.3 | I |
| 227 | 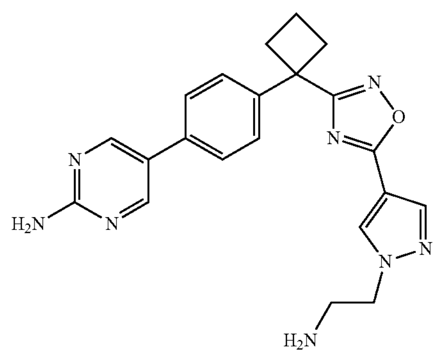 [SMILES: NCCn1cc(-c2nc(C3(c4ccc(-c5cnc(N)nc5)cc4)CCC3)no2)cn1] | 34 | 1.1 | 403.3 | I |
| 228 | 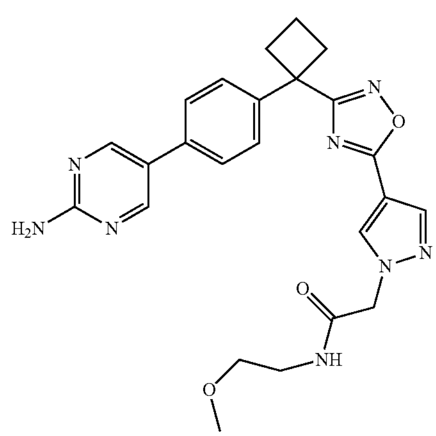 [SMILES: COCCNC(=O)Cn1cc(-c2nc(C3(c4ccc(-c5cnc(N)nc5)cc4)CCC3)no2)cn1] | 15 | 0.74 | 475.3 | J |

TABLE 8-continued

Final compounds

| Example | Structure | Method | Retention time | m/z | LC MS method |
|---|---|---|---|---|---|
| 229 | 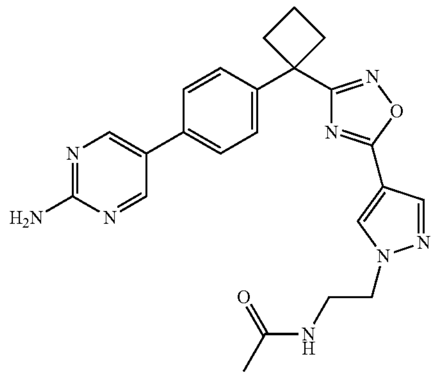 [SMILES: CC(=O)NCCn1cc(-c2nc(C3(c4ccc(-c5cnc(N)nc5)cc4)CCC3)no2)cn1] | 35 | 1.1 | 445.4 | K |
| 230 | 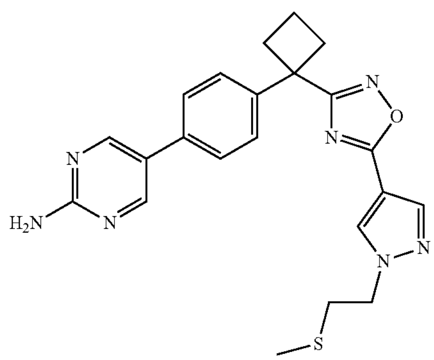 [SMILES: CSCCn1cc(-c2nc(C3(c4ccc(-c5cnc(N)nc5)cc4)CCC3)no2)cn1] | 33 | 1.3 | 434.4 | K |
| 231 | 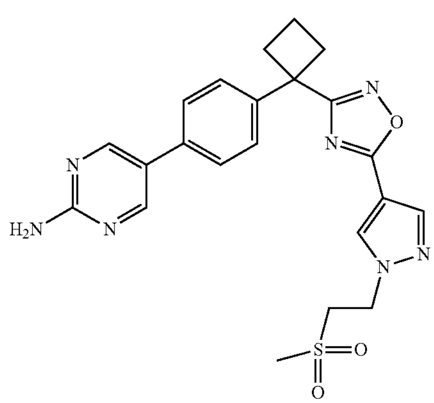 [SMILES: CS(=O)(=O)CCn1cc(-c2nc(C3(c4ccc(-c5cnc(N)nc5)cc4)CCC3)no2)cn1] | 36 | 1.36 | 466.4 | I |

TABLE 8-continued

Final compounds

| Example | Structure | Method | Retention time | m/z | LC MS method |
|---------|-----------|--------|----------------|-----|--------------|
| 232 | 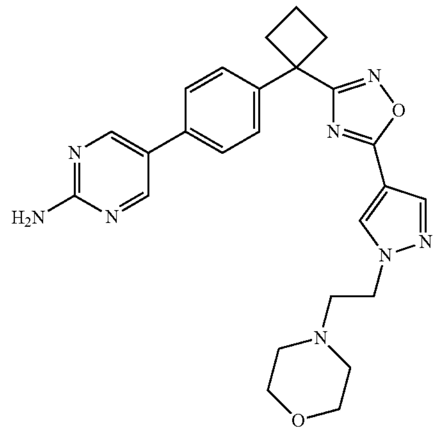 [SMILES: Nc1ncc(-c2ccc(C3(c4noc(-c5cnn(CCN6CCOCC6)c5)n4)CCC3)cc2)cn1] | 33 | 1.17 | 473.5 | I |
| 233 | 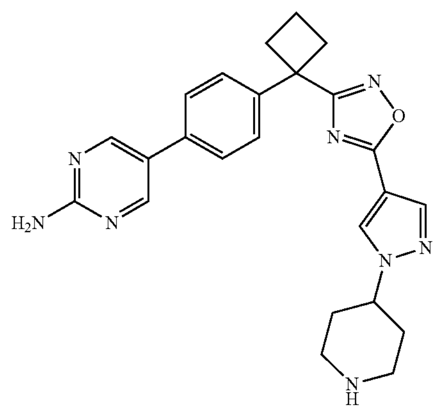 [SMILES: Nc1ncc(-c2ccc(C3(c4noc(-c5cnn(C6CCNCC6)c5)n4)CCC3)cc2)cn1] | 10 | 0.99 | 443.4 | K |
| 234 | 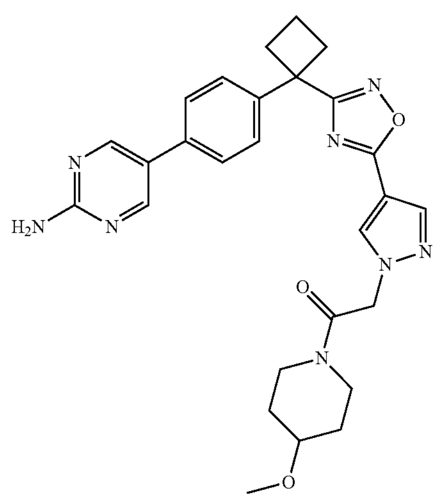 [SMILES: COC1CCN(C(=O)Cn2cc(-c3nc(C4(c5ccc(-c6cnc(N)nc6)cc5)CCC4)no3)cn2)CC1] | 15 | 1.18 | 515.4 | K |

TABLE 8-continued

Final compounds

| Example | Structure | Method | Retention time | m/z | LC MS method |
|---|---|---|---|---|---|
| 235 | 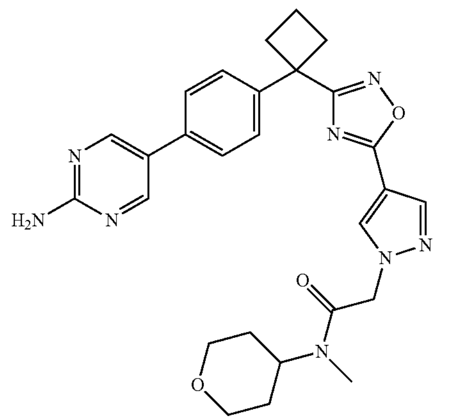 [SMILES: CN(C(=O)Cn1cc(-c2nc(C3(c4ccc(-c5cnc(N)nc5)cc4)CCC3)no2)cn1)C1CCOCC1] | 15 | 1.18 | 515.4 | K |
| 236 | 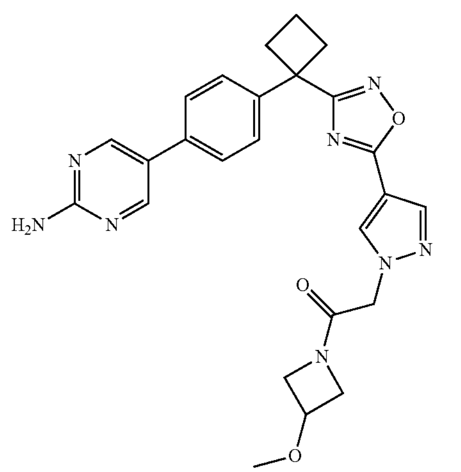 [SMILES: COC1CN(C(=O)Cn2cc(-c3nc(C4(c5ccc(-c6cnc(N)nc6)cc5)CCC4)no3)cn2)C1] | 15 | 1.12 | 487.4 | K |
| 237 | 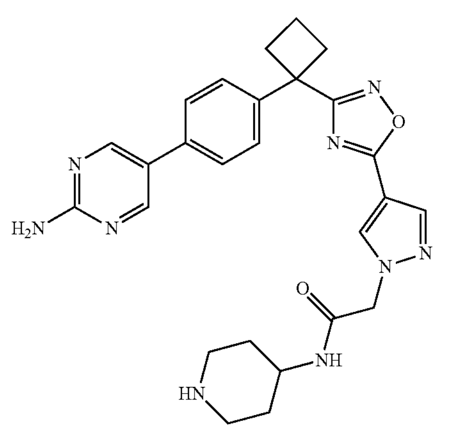 [SMILES: Nc1ncc(-c2ccc(C3(c4noc(-c5cnn(CC(=O)NC6CCNCC6)c5)n4)CCC3)cc2)cn1] | 10 | 0.97 | 500.4 | K |

TABLE 8-continued
Final compounds
| Example | Structure | Method | Retention time | m/z | LC MS method |
|---|---|---|---|---|---|
| 238 | 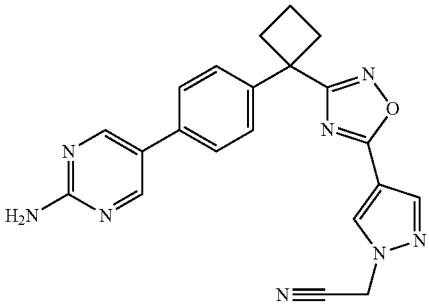 [SMILES: N#CCn1cc(-c2nc(C3(c4ccc(-c5cnc(N)nc5)cc4)CCC3)no2)cn1] | 33 | 1.18 | 399.4 | K |
| 239 | 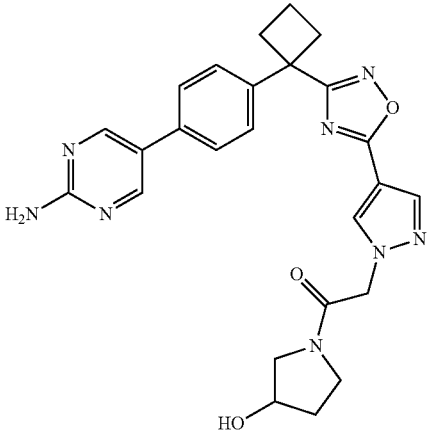 [SMILES: Nc1ncc(-c2ccc(C3(c4noc(-c5cnn(CC(=O)N6CCC(O)C6)c5)n4)CCC3)cc2)cn1] | 37 | 1.05 | 487.4 | K |
| 240 | 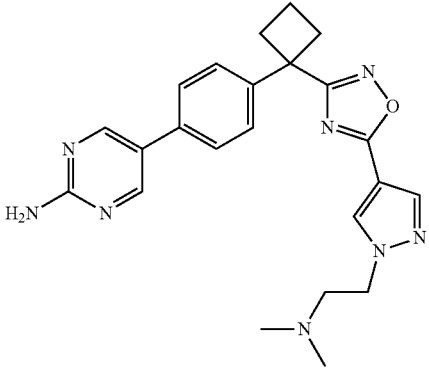 [SMILES: CN(C)CCn1cc(-c2nc(C3(c4ccc(-c5cnc(N)nc5)cc4)CCC3)no2)cn1] | 33 | 0.95 | 431.4 | K |
| 241 | 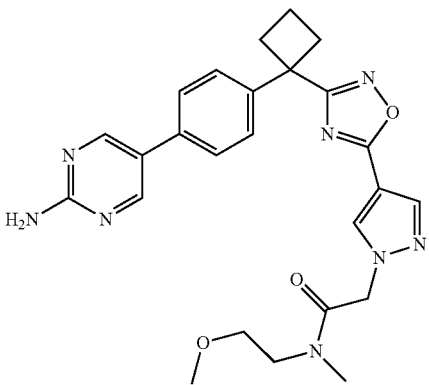 [SMILES: COCCN(C)C(=O)Cn1cc(-c2nc(C3(c4ccc(-c5cnc(N)nc5)cc4)CCC3)no2)cn1] | 15 | 1.16 | 489.4 | K |

TABLE 8-continued

Final compounds

| Example | Structure | Method | Retention time | m/z | LC MS method |
|---|---|---|---|---|---|
| 242 | 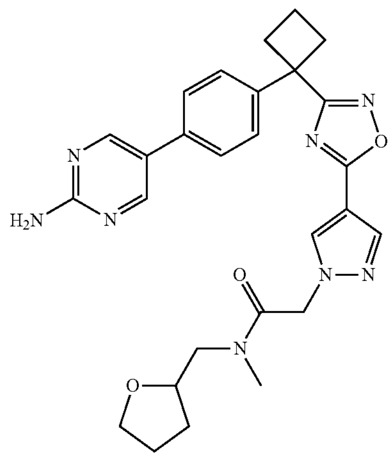 [SMILES: CN(CC1CCCO1)C(=O)Cn1cc(-c2nc(C3(c4ccc(-c5cnc(N)nc5)cc4)CCC3)no2)cn1] | 15 | 1.21 | 515.4 | K |
| 243 | 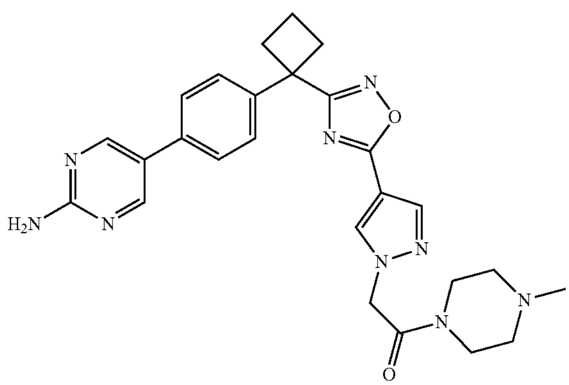 [SMILES: CN1CCN(C(=O)Cn2cc(-c3nc(C4(c5ccc(-c6cnc(N)nc6)cc5)CCC4)no3)cn2)CC1] | 15 | 1.02 | 528.4 | K |
| 244 | 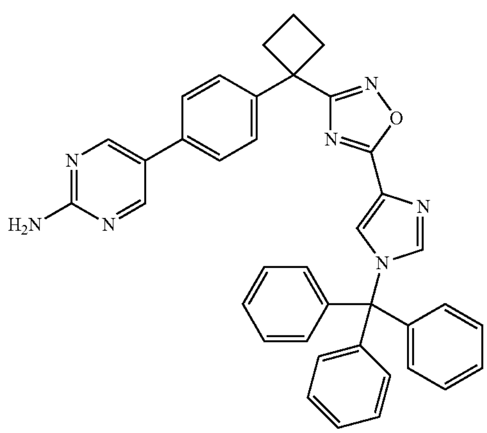 [SMILES: Nc1ncc(-c2ccc(C3(c4noc(-c5cn(C(c6ccccc6)(c6ccccc6)c6ccccc6)cn5)n4)CCC3)cc2)cn1] | 2 | 1.71 | 360.4 | I |
| 245 | 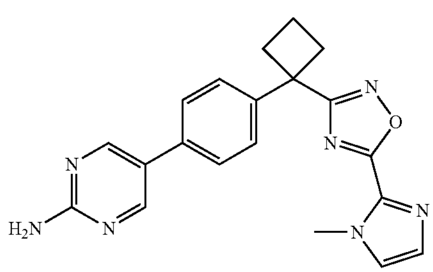 [SMILES: Cn1ccnc1-c1nc(C2(c3ccc(-c4cnc(N)nc4)cc3)CCC2)no1] | 2 | 1.36 | 374.4 | I |

TABLE 8-continued

Final compounds

| Example | Structure | Method | Retention time | m/z | LC MS method |
|---------|-----------|--------|----------------|-----|--------------|
| 246 | 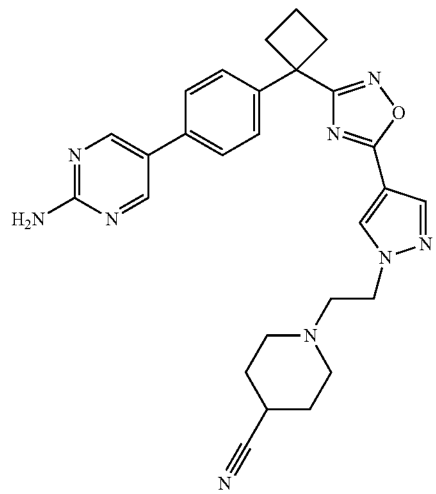 [SMILES: N#CC1CCN(CCn2cc(-c3nc(C4(c5ccc(-c6cnc(N)nc6)cc5)CCC4)no3)cn2)CC1] | 33 | 1.04 | 496.4 | K |
| 247 | 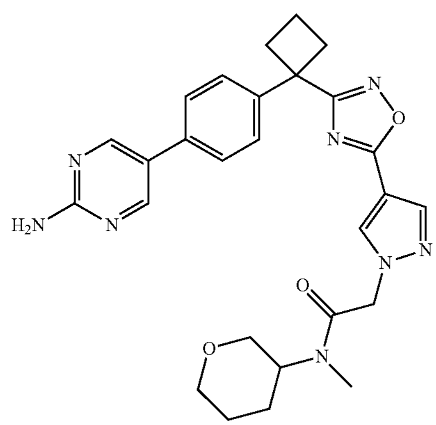 [SMILES: CN(C(=O)Cn1cc(-c2nc(C3(c4ccc(-c5cnc(N)nc5)cc4)CCC3)no2)cn1)C1CCCOC1] | 15 | 1.18 | 515.4 | K |
| 248 | 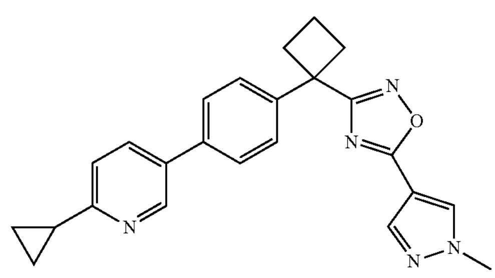 [SMILES: Cn1cc(-c2nc(C3(c4ccc(-c5ccc(C6CC6)nc5)cc4)CCC3)no2)cn1] | 40 | 1.32 | 398.4 | E |

TABLE 8-continued

Final compounds

| Example | Structure | Method | Retention time | m/z | LC MS method |
|---------|-----------|--------|----------------|-----|--------------|
| 249 | 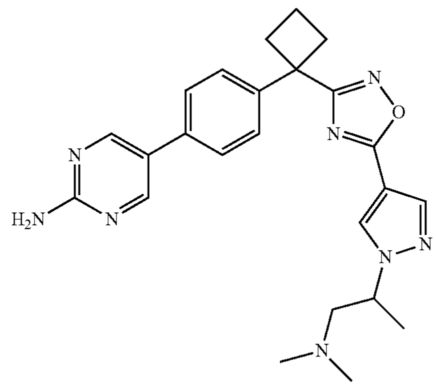 [SMILES: CC(CN(C)C)n1cc(-c2nc(C3(c4ccc(-c5cnc(N)nc5)cc4)CCC3)no2)cn1] | 33 | 1.02 | 445.4 | K |
| 250 | 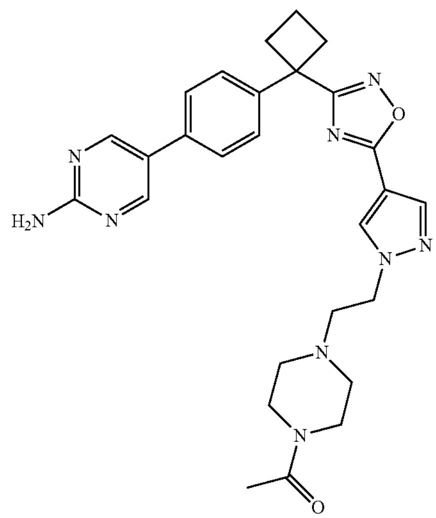 [SMILES: CC(=O)N1CCN(CCn2cc(-c3nc(C4(c5ccc(-c6cnc(N)nc6)cc5)CCC4)no3)cn2)CC1] | 33 | 1.01 | 514.4 | K |
| 251 | 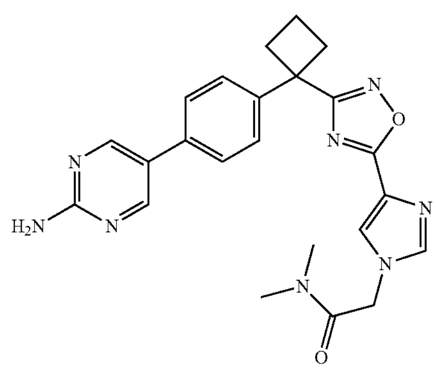 [SMILES: CN(C)C(=O)Cn1cnc(-c2nc(C3(c4ccc(-c5cnc(N)nc5)cc4)CCC3)no2)c1] | 21 | 1.24 | 445.4 | I |
| 252 | 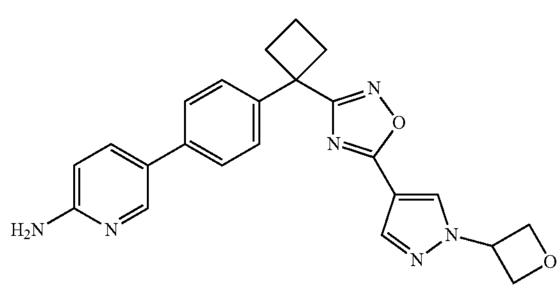 [SMILES: Nc1ccc(-c2ccc(C3(c4noc(-c5cnn(C6COC6)c5)n4)CCC3)cc2)cn1] | 29 | 0.61 | 416.4 | J |

TABLE 8-continued

Final compounds

| Example | Structure | Method | Retention time | m/z | LC MS method |
|---|---|---|---|---|---|
| 253 | 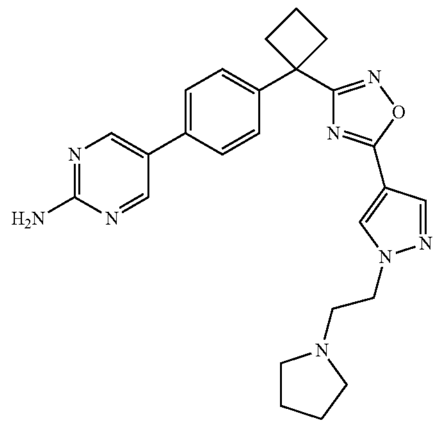 [SMILES: Nc1ncc(-c2ccc(C3(c4noc(-c5cnn(CCN6CCCC6)c5)n4)CCC3)cc2)cn1] | 33 | 1.01 | 457.4 | K |
| 254 | 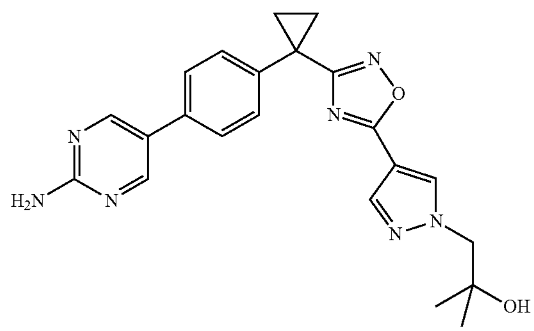 [SMILES: CC(C)(O)Cn1cc(-c2nc(C3(c4ccc(-c5cnc(N)nc5)cc4)CC3)no2)cn1] | 38 | 1.32 | 418.4 | K |
| 255 | 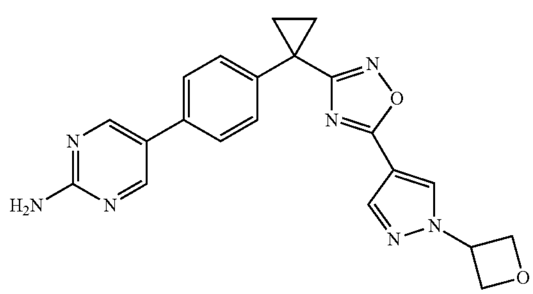 [SMILES: Nc1ncc(-c2ccc(C3(c4noc(-c5cnn(C6COC6)c5)n4)CC3)cc2)cn1] | 38 | 1.32 | 402.4 | K |
| 256 | 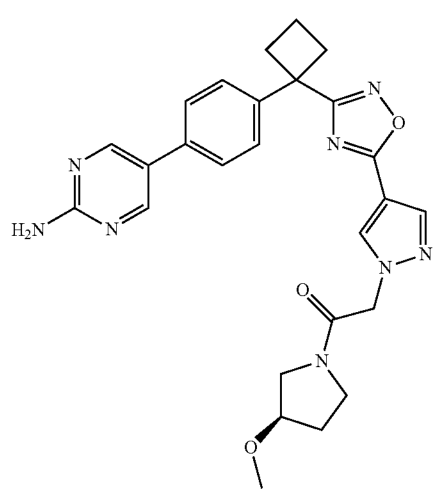 [SMILES: CO[C@@H]1CCN(C(=O)Cn2cc(-c3nc(C4(c5ccc(-c6cnc(N)nc6)cc5)CCC4)no3)cn2)C1] | 15 | 1.17 | 501.4 | K |

TABLE 8-continued
Final compounds
| Example | Structure | Method | Retention time | m/z | LC MS method |
|---------|-----------|--------|----------------|-----|--------------|
| 257 | 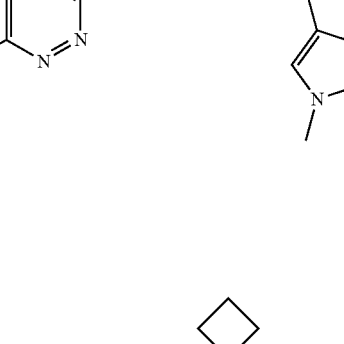 | 38 | 1.33 | 360.4 | K |
| 258 | 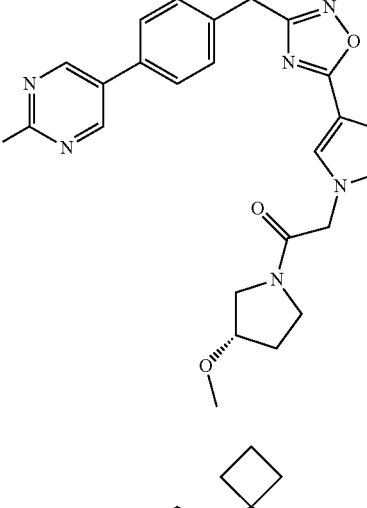 | 41 | 0.98 | 374.4 | E |
| 259 | 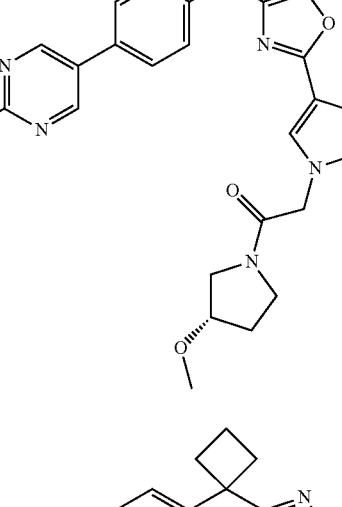 | 15 | 1.15 | 501.4 | K |
| 260 | 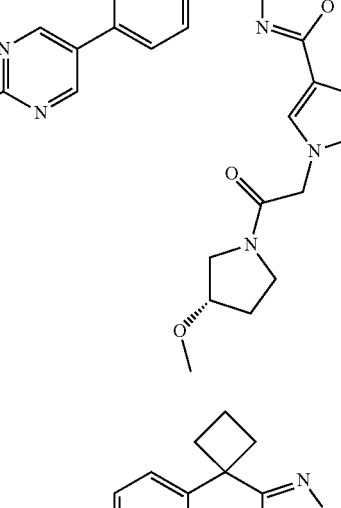 | 4 | 1.39 | 397.4 | K |

TABLE 8-continued

Final compounds

| Example | Structure | Method | Retention time | m/z | LC MS method |
|---|---|---|---|---|---|
| 261 | 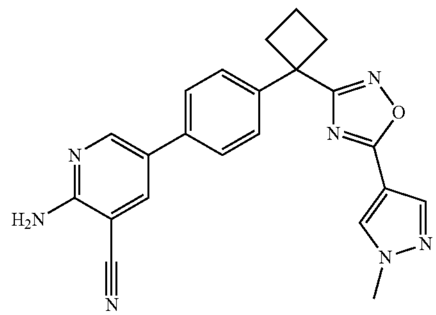 [SMILES: Cn1cc(-c2nc(C3(c4ccc(-c5cnc(N)c(C#N)c5)cc4)CCC3)no2)cn1] | 4 | 1.32 | 398.4 | K |
| 262 | 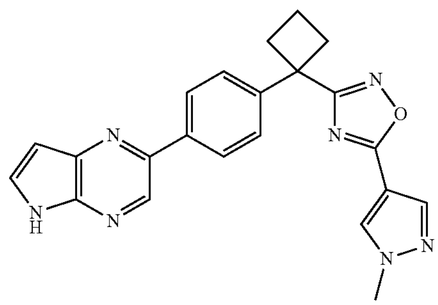 [SMILES: Cn1cc(-c2nc(C3(c4ccc(-c5cnc6[nH]ccc6n5)cc4)CCC3)no2)cn1] | 41 | 1.29 | 398.4 | E |
| 263 | 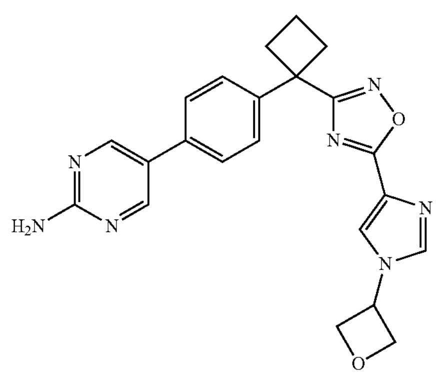 [SMILES: Nc1ncc(-c2ccc(C3(c4noc(-c5cn(C6COC6)cn5)n4)CCC3)cc2)cn1] | 21 | 0.67 | 416.31 | J |
| 264 | 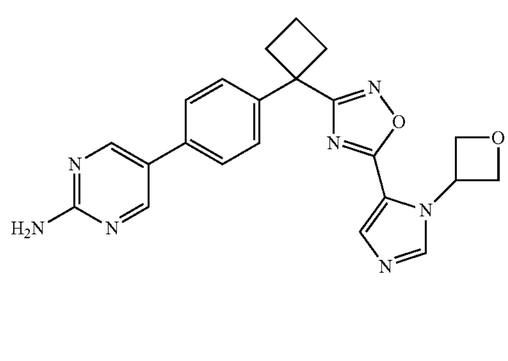 [SMILES: Nc1ncc(-c2ccc(C3(c4noc(-c5cncn5C5COC5)n4)CCC3)cc2)cn1] | 21 | 0.72 | 416.29 | J |

TABLE 8-continued

Final compounds

| Example | Structure | Method | Retention time | m/z | LC MS method |
|---|---|---|---|---|---|
| 265 | 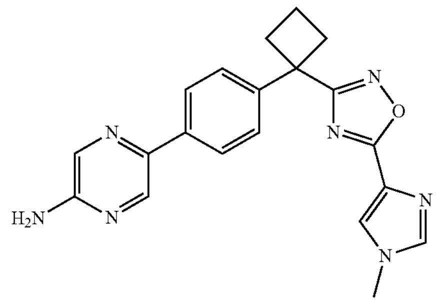 [SMILES: Cn1cnc(-c2nc(C3(c4ccc(-c5cnc(N)cn5)cc4)CCC3)no2)c1] | 32 | 0.71 | 374.2 | J |
| 266 | 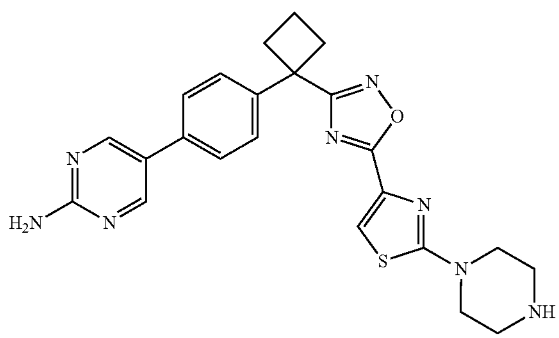 [SMILES: Nc1ncc(-c2ccc(C3(c4noc(-c5csc(N6CCNCC6)n5)n4)CCC3)cc2)cn1] | 23 | 1 | 461.4 | E |
| 267 | 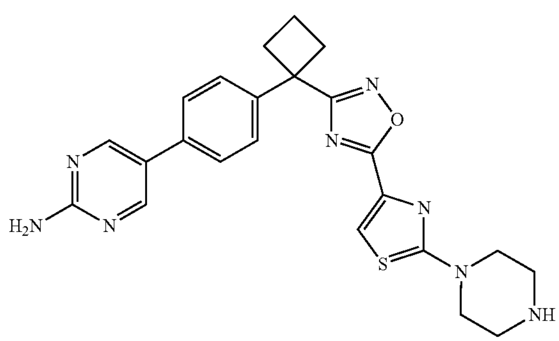 | 23 | 0.99 | 461.4 | E |
| 268 | 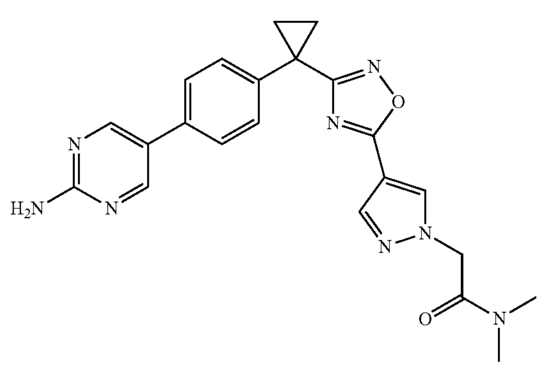 [SMILES: CN(C)C(=O)Cn1cc(-c2nc(C3(c4ccc(-c5cnc(N)nc5)cc4)CC3)no2)cn1] | 38 | 1.26 | 431.4 | K |

TABLE 8-continued

Final compounds

| Example | Structure | Method | Retention time | m/z | LC MS method |
|---|---|---|---|---|---|
| 269 | 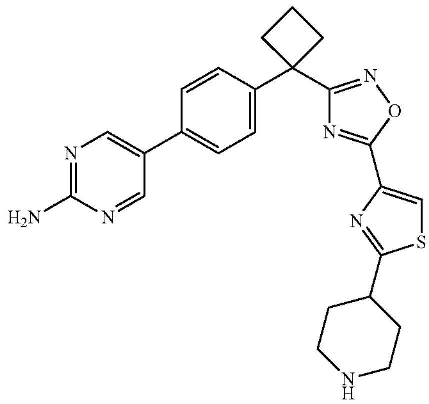 [SMILES: Nc1ncc(-c2ccc(C3(c4noc(-c5csc(C6CCNCC6)n5)n4)CCC3)cc2)cn1] | 24 | 1.04 | 460.4 | E |
| 270 | 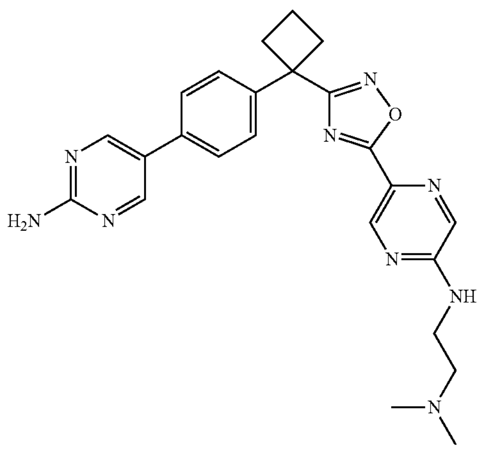 [SMILES: CN(C)CCNc1cnc(-c2nc(C3(c4ccc(-c5cnc(N)nc5)cc4)CCC3)no2)cn1] | 11 DMSO/ 115 | 1.03 | 458.4 | E |
| 271 | 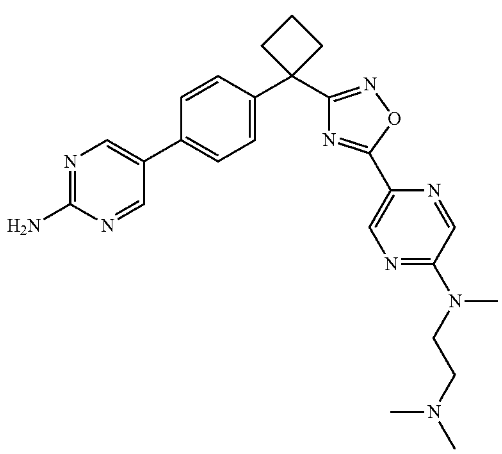 [SMILES: CN(C)CCN(C)c1cnc(-c2nc(C3(c4ccc(-c5cnc(N)nc5)cc4)CCC3)no2)cn1] | 11 DMSO/ 115 | 0.99 | 472.4 | E |

TABLE 8-continued

Final compounds

| Example | Structure | Method | Retention time | m/z | LC MS method |
|---|---|---|---|---|---|
| 272 | 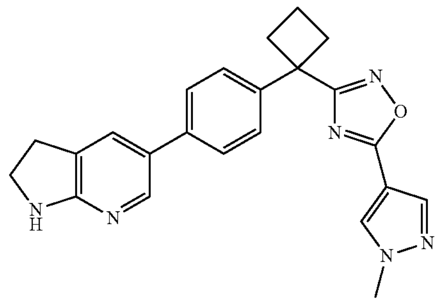 [SMILES: Cn1cc(-c2nc(C3(c4ccc(-c5cnc6c(c5)CCN6)cc4)CCC3)no2)cn1] | 41 | 1.07 | 399.4 | E |
| 273 | 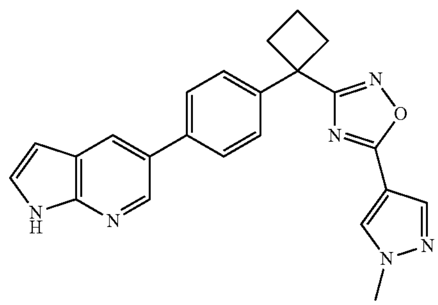 [SMILES: Cn1cc(-c2nc(C3(c4ccc(-c5cnc6[nH]ccc6c5)cc4)CCC3)no2)cn1] | 41 | 1.34 | 397.4 | E |
| 274 | 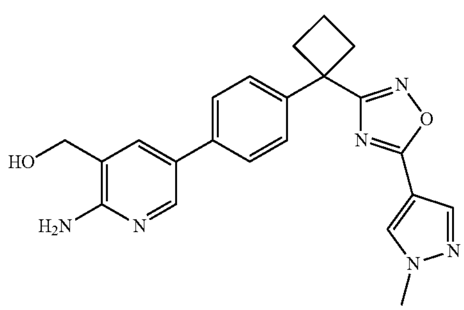 [SMILES: Cn1cc(-c2nc(C3(c4ccc(-c5cnc(N)c(CO)c5)cc4)CCC3)no2)cn1] | 41 | 1.01 | 403.4 | E |
| 275 | 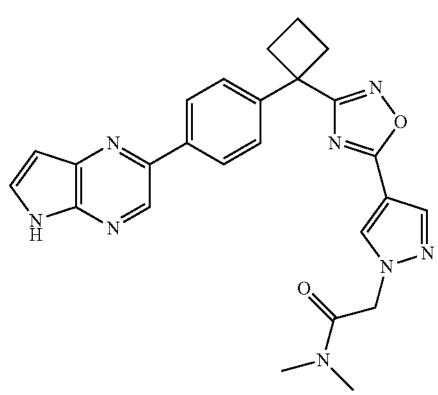 [SMILES: CN(C)C(=O)Cn1cc(-c2nc(C3(c4ccc(-c5cnc6[nH]ccc6n5)cc4)CCC3)no2)cn1] | 41 | 1.21 | 469.4 | E |

TABLE 8-continued

Final compounds

| Example | Structure | Method | Retention time | m/z | LC MS method |
|---|---|---|---|---|---|
| 276 | 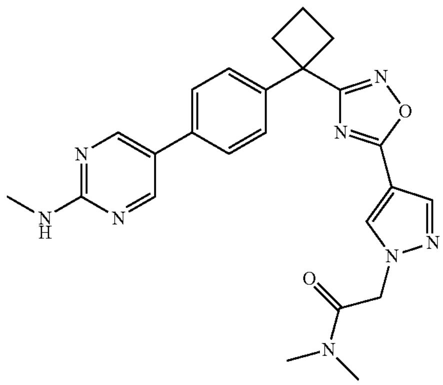 [SMILES: CNc1ncc(-c2ccc(C3(c4noc(-c5cnn(CC(=O)N(C)C)c5)n4)CCC3)cc2)cn1] | 41 | 1.21 | 459.4 | E |
| 277 | 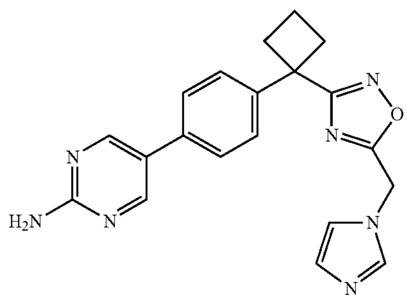 [SMILES: Nc1ncc(-c2ccc(C3(c4noc(Cn5ccnc5)n4)CCC3)cc2)cn1] | 2 | 0.51 | 374.18 | J |
| 278 | 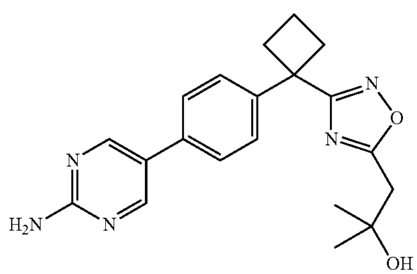 [SMILES: CC(C)(O)Cc1nc(C2(c3ccc(-c4cnc(N)nc4)cc3)CCC2)no1] | 25 | 0.73 | 366.4 | J |
| 279 | 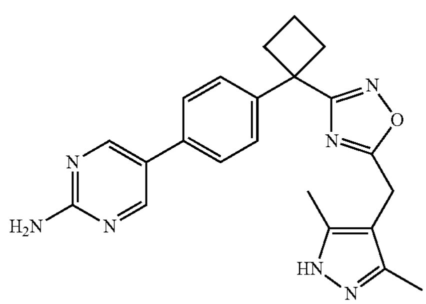 [SMILES: Cc1n[nH]c(C)c1Cc1nc(C2(c3ccc(-c4cnc(N)nc4)cc3)CCC2)no1] | 2 | 1.32 | 402.4 | I |
| 280 | 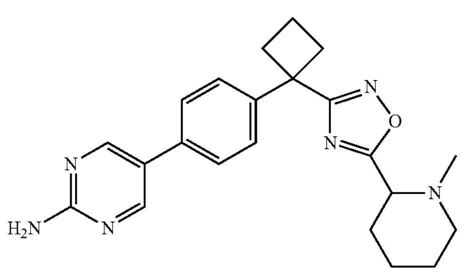 [SMILES: CN1CCCCC1c1nc(C2(c3ccc(-c4cnc(N)nc4)cc3)CCC2)no1] | 26 | 0.96 | 391.4 | E |

TABLE 8-continued
| Example | Structure | Method | Retention time | m/z | LC MS method |
|---|---|---|---|---|---|
| 281 | 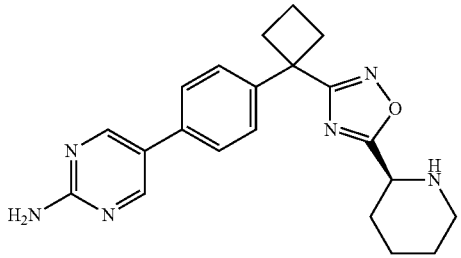 [SMILES: Nc1ncc(-c2ccc(C3(c4noc([C@@H]5CCCCN5)n4)CCC3)cc2)cn1] | 22 | 0.88 | 377.4 | E |
| 282 | 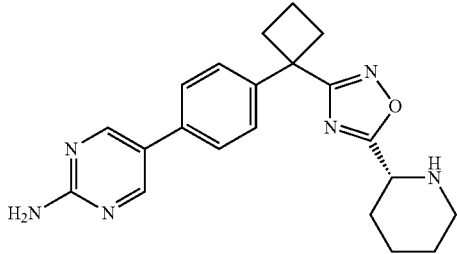 [SMILES: Nc1ncc(-c2ccc(C3(c4noc([C@H]5CCCCN5)n4)CCC3)cc2)cn1] | 22 | 0.89 | 377.4 | E |
| 283 | 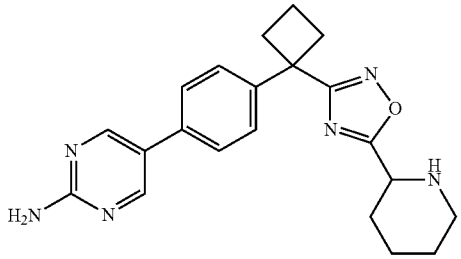 [SMILES: Nc1ncc(-c2ccc(C3(c4noc(C5CCCCN5)n4)CCC3)cc2)cn1] | 22 | 0.89 | 377.4 | E |
| 284 | 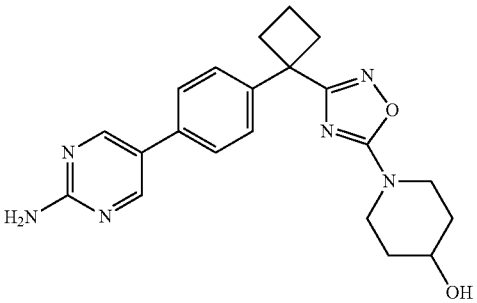 [SMILES: Nc1ncc(-c2ccc(C3(c4noc(N5CCC(O)CC5)n4)CCC3)cc2)cn1] | 39 | 0.66 | 393.3 | J |
| 285 | 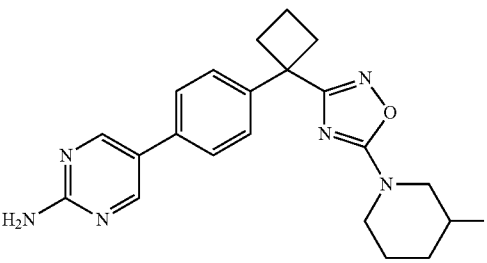 | 39 | 0.68 | 393.2 | J |

TABLE 8-continued

Final compounds

| Example | Structure | Method | Retention time | m/z | LC MS method |
|---------|-----------|--------|----------------|-----|--------------|
| 286 | 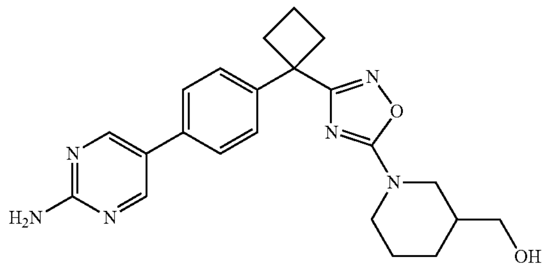 [SMILES: Nc1ncc(-c2ccc(C3(c4noc(N5CCCC(CO)C5)n4)CCC3)cc2)cn1] | 39 | 0.73 | 407.3 | J |
| 287 | 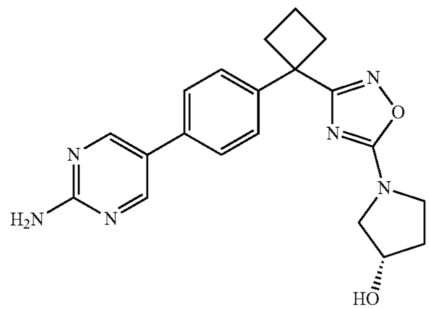 [SMILES: Nc1ncc(-c2ccc(C3(c4noc(N5CC[C@H](O)C5)n4)CCC3)cc2)cn1] | 39 | 1.22 | 379.4 | K |
| 288 | 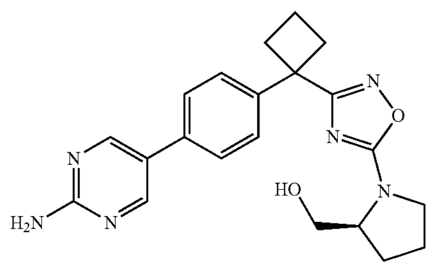 [SMILES: Nc1ncc(-c2ccc(C3(c4noc(N5CCC[C@H]5CO)n4)CCC3)cc2)cn1] | 39 | 1.3 | 393.4 | K |
| 289 | 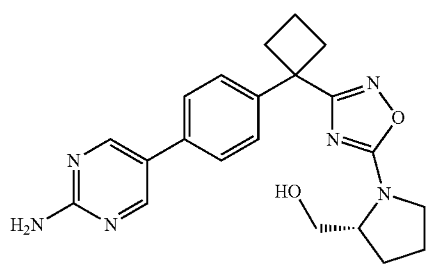 [SMILES: Nc1ncc(-c2ccc(C3(c4noc(N5CCC[C@@H]5CO)n4)CCC3)cc2)cn1] | 39 | 0.75 | 393.2 | J |
| 290 | 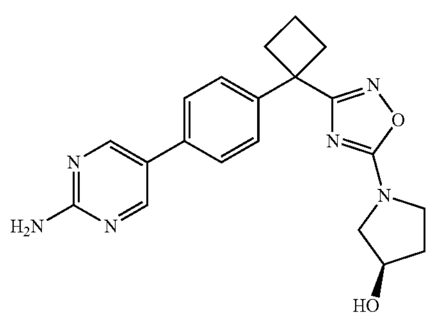 [SMILES: Nc1ncc(-c2ccc(C3(c4noc(N5CC[C@@H](O)C5)n4)CCC3)cc2)cn1] | 39 | 0.66 | 379.2 | J |

TABLE 8-continued

Final compounds

| Example | Structure | Method | Retention time | m/z | LC MS method |
|---|---|---|---|---|---|
| 291 | 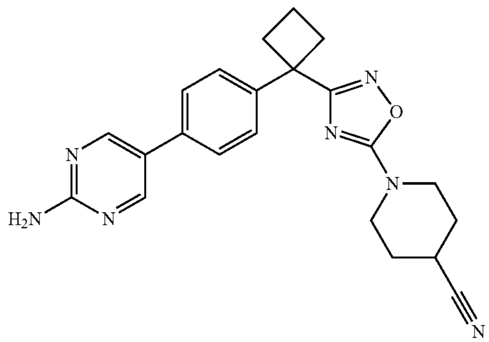 [SMILES: N#CC1CCN(c2nc(C3(c4ccc(-c5cnc(N)nc5)cc4)CCC3)no2)CC1] | 39 | 0.83 | 402.2 | J |
| 292 | 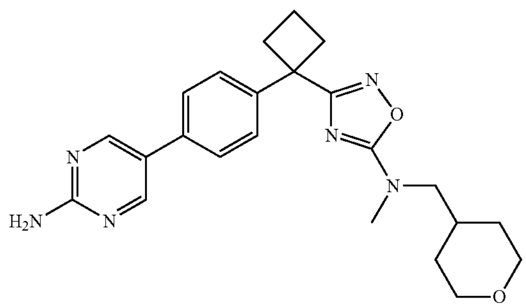 [SMILES: CN(CC1CCOCC1)c1nc(C2(c3ccc(-c4cnc(N)nc4)cc3)CCC2)no1] | 39 | 0.87 | 421.3 | J |
| 293 | 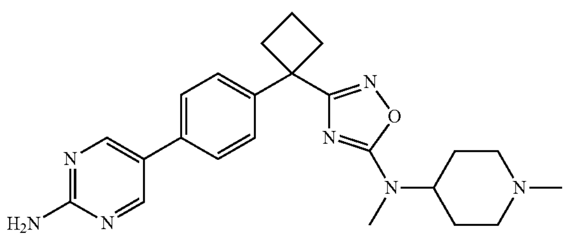 [SMILES: CN1CCC(N(C)c2nc(C3(c4ccc(-c5cnc(N)nc5)cc4)CCC3)no2)CC1] | 39 | 1.09 | 420.4 | K |
| 294 | 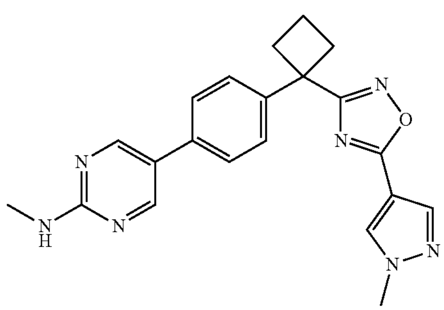 [SMILES: CNc1ncc(-c2ccc(C3(c4noc(-c5cnn(C)c5)n4)CCC3)cc2)cn1] | 42 | 1.29 | 388.4 | E |
| 295 | 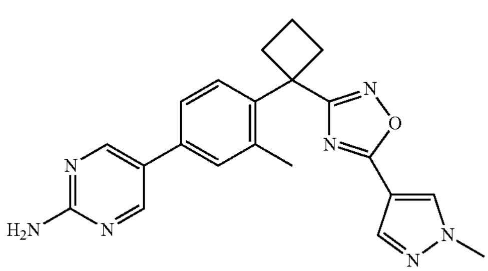 [SMILES: Cc1cc(-c2cnc(N)nc2)ccc1C1(c2noc(-c3cnn(C)c3)n2)CCC1] | 2 | 1.25 | 388.4 | E |

TABLE 8-continued

Final compounds

| Example | Structure | Method | Retention time | m/z | LC MS method |
|---|---|---|---|---|---|
| 296 | 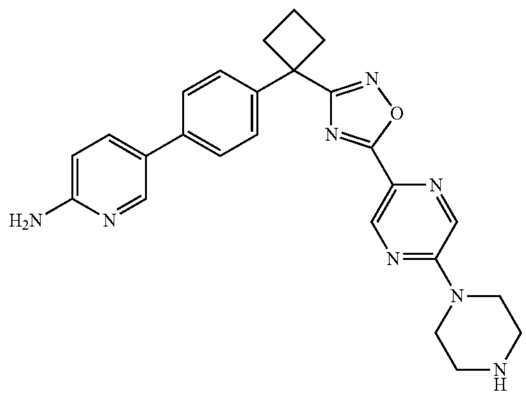 [SMILES: Nc1ccc(-c2ccc(C3(c4noc(-c5cnc(N6CCNCC6)cn5)n4)CCC3)cc2)cn1] | 27 | 0.94 | 455.4 | E |
| 297 | 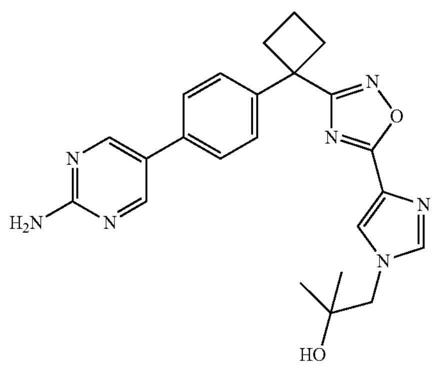 [SMILES: CC(C)(O)Cn1cnc(-c2nc(C3(c4ccc(-c5cnc(N)nc5)cc4)CCC3)no2)c1] | 21 | 0.65 | 432.31 | J |
| 298 | 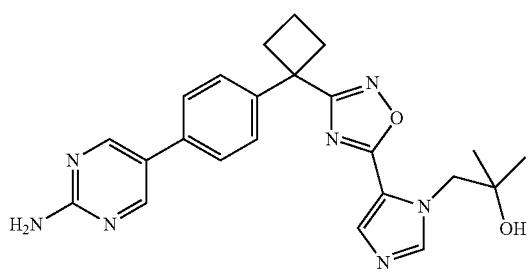 [SMILES: CC(C)(O)Cn1cncc1-c1nc(C2(c3ccc(-c4cnc(N)nc4)cc3)CCC2)no1] | 21 | 0.67 | 432.29 | J |
| 299 | 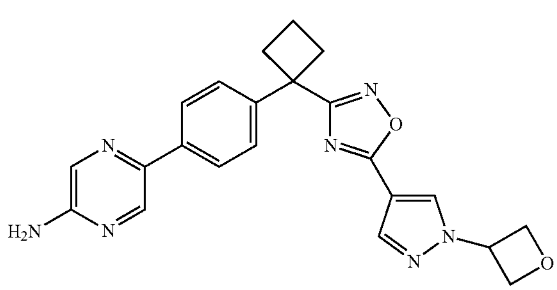 [SMILES: Nc1cnc(-c2ccc(C3(c4noc(-c5cnn(C6COC6)c5)n4)CCC3)cc2)cn1] | 30 | 0.78 | 416.3 | J |

TABLE 8-continued

| | Final compounds | | | | |
|---|---|---|---|---|---|
| Example | Structure | Method | Retention time | m/z | LC MS method |
| 300 | | 31 | 0.69 | 431.3 | J |
| 301 | | 31 | 0.63 | 444.3 | J |
| 302 | | 28 | 1.79 | 456.3 | G |
| 303 | | 32 | 0.81 | 432.3 | J |

TABLE 8-continued

Final compounds

| Example | Structure | Method | Retention time | m/z | LC MS method |
|---|---|---|---|---|---|
| 304 | 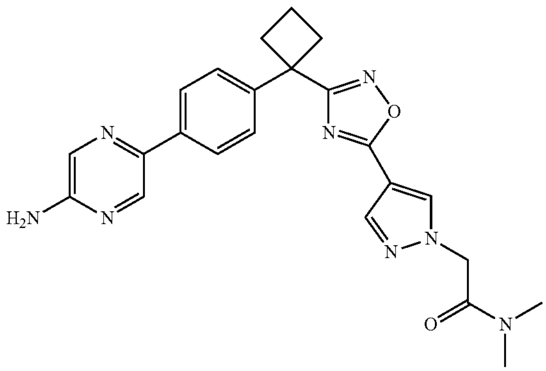 [SMILES: CN(C)C(=O)Cn1cc(-c2nc(C3(c4ccc(-c5cnc(N)cn5)cc4)CCC3)no2)cn1] | 32 | 0.74 | 445.3 | J |
| 305 | 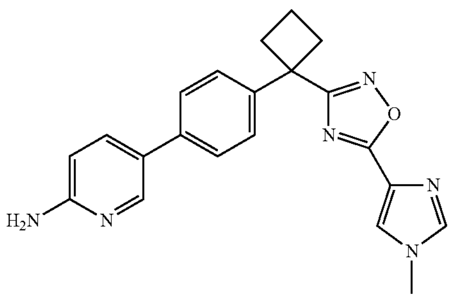 [SMILES: Cn1cnc(-c2nc(C3(c4ccc(-c5ccc(N)nc5)cc4)CCC3)no2)c1] | 31 | 0.59 | 373.2 | J |
| 306 | 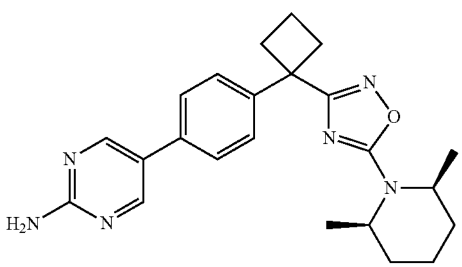 [SMILES: C[C@@H]1CCC[C@H](C)N1c1nc(C2(c3ccc(-c4cnc(N)nc4)cc3)CCC2)no1] | 39 | 1.08 | 405.3 | J |
| 307 | 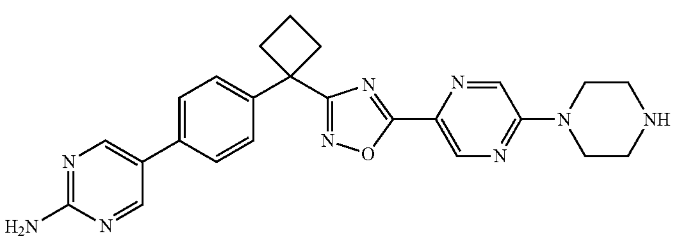 [SMILES: Nc1ncc(-c2ccc(C3(c4noc(-c5cnc(N6CCNCC6)cn5)n4)CCC3)cc2)cn1] | 7 | 0.64 | 456.2 | J |
| 308 | 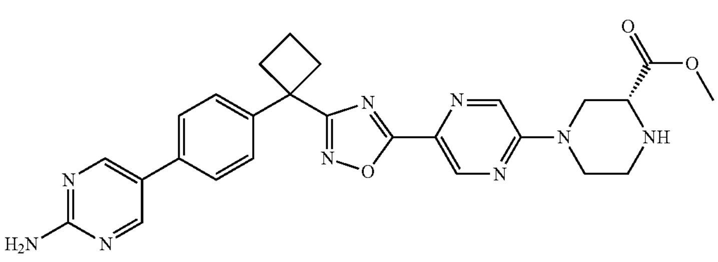 [SMILES: COC(=O)[C@H]1CN(c2cnc(-c3nc(C4(c5ccc(-c6cnc(N)nc6)cc5)CCC4)no3)cn2)CCN1] | 7 | 0.71 | 514.1 | J |

TABLE 8-continued

Final compounds

| Example | Structure | Method | Retention time | m/z | LC MS method |
|---|---|---|---|---|---|
| 309 | 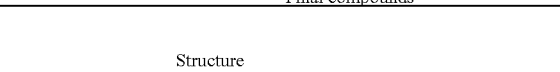 | 7 | 0.71 | 514.1 | J |

Analytical Methods

LC-MS Method A

| | |
|---|---|
| Column | Agilent Zorbax Eclipse XDB-C8 |
| | 5 μm, 4.6 × 150 mm |
| | Ambient temperature |
| Mobile phase | A = Formic acid (aq) 0.1% |
| | B = Formic acid (acetonitrile) 0.1% |
| Flow rate | 1.5 ml/min |
| Injection volume | 7 ul |
| Detector | 200-600 nm (nominal) |
| Gradient | |

| Time (mins) | % B |
|---|---|
| 0 | 1 |
| 2 | 20 |
| 7 | 95 |
| 9 | 95 |
| 9.3 | 1 |
| 10 | 1 |

LC-MS Method B

| | |
|---|---|
| Column | Waters Atlantis dC18 |
| | 100 × 2.1 mm, 3 μm column |
| | 40° C. |
| Mobile phase | A - 0.1% Formic acid (water) |
| | B - 0.1% Formic acid (acetonitrile) |
| Flow rate | 0.6 ml/min |
| Injection volume | 3 μl |
| Detector | 215 nm (nominal) |
| Gradient | |

| Time (mins) | % B |
|---|---|
| 0 | 5 |
| 5 | 100 |
| 5.4 | 100 |
| 5.42 | 5 |

LC-MS Method C

| | |
|---|---|
| Column | Atlantis dC18 |
| | 2.1 × 50 mm, 3 μm |
| Mobile phase | A = Formic acid (aq) 0.1% |
| | B = Formic acid (acetonitrile) 0.1% |
| Flow rate | 1 ml/min |
| Injection volume | 3 μl |
| Detector | 215 nm (nominal) |
| Gradient | |

| Time (mins) | % B |
|---|---|
| 0 | 5 |
| 2.5 | 100 |
| 2.7 | 100 |
| 2.71 | 5 |
| 3 | 5 |

LC-MS Method D

| | |
|---|---|
| Column | Agilent SB-C18 |
| | 1.8 μm, 3 × 50 mm |
| | Ambient temperature |
| Mobile phase | A = Formic acid (aq) 0.1% |
| | B = Formic acid (acetonitrile) 0.1% |
| Flow rate | 1.5 ml/min |
| Injection volume | 3 μL |
| Detector | 220 and 254 nm |
| Gradient | |

| Time (mins) | % B |
|---|---|
| 0 | 5 |
| 3.8 | 90 |
| 4.5 | 100 |

LC-MS Method E

| | |
|---|---|
| Column | Agilent SB-C18 |
| | 1.8 μm, 3 × 50 mm column |
| | Ambient temperature |
| Mobile phase | A = Formic acid (aq) 0.1% |
| | B = Formic acid (acetonitrile) 0.1% |
| Flow rate | 1.5 ml/min |
| Injection volume | 3 μL |
| Detector | 220 and 254 nm |
| Gradient | |

| Time (mins) | % B |
|---|---|
| 0 | 12 |
| 0.25 | 30 |
| 0.3 | 40 |
| 1.19 | 95 |
| 1.75 | 100 |

LC-MS Method F

| | |
|---|---|
| Column | Agilent Zorbax Eclipse XDB-C8 |
| | 5 μm, 4.6 × 150 mm |
| | Ambient temperature |
| Mobile phase | A = Formic acid (aq) 0.1% |
| | B = Formic acid (acetonitrile) 0.1% |
| Flow rate | 1.5 ml/min |
| Injection volume | 7 μL |
| Detector | 200-600 nm |

-continued

| Gradient | Time (mins) | % B |
|---|---|---|
| | 0 | 5 |
| | 7 | 95 |
| | 9 | 95 |
| | 9.3 | 5 |
| | 10 | 5 |

LC-MS Method G

| Column | Waters BEH C18 |
|---|---|
| | 1.7 μm, 2.1 × 50 mm |
| | Ambient temperature |
| Mobile phase | A = Formic acid (aq) 0.1% |
| | B = Formic acid (acetonitrile) 0.1% |
| Flow rate | 0.8 ml/min |
| Injection volume | 1 μL |
| Detector | 210-400 nm |

| Gradient | Time (mins) | % B |
|---|---|---|
| | 0 | 10 |
| | 4.5 | 95 |
| | 4.58 | 95 |

LC-MS Method H

| Column | Agilent SB-C18 |
|---|---|
| | 1.8 μm, 3 × 50 mm |
| | Ambient temperature |
| Mobile phase | A = Formic acid (aq) 0.1% |
| | B = Formic acid (acetonitrile) 0.1% |
| Flow rate | 1.5 ml/min |
| Injection volume | 3 μL |
| Detector | 220 and 254 nm |

| Gradient | Time (mins) | % B |
|---|---|---|
| | 0 | 5 |
| | 0.25 | 50 |
| | 0.3 | 70 |
| | 1.3 | 90 |
| | 1.7 | 100 |

LC-MS Method I

| Column | Agilent Zorbax XDB-C8 |
|---|---|
| | 5 μm, 4.6 × 150 mm |
| | Ambient temperature |
| Mobile phase | A = Formic acid (aq) 0.1% |
| | B = Formic acid (acetonitrile) 0.1% |
| Flow rate | 1.5 ml/min |
| Injection volume | 7 μL |
| Detector | 200-600 nm |

| Gradient | Time (mins) | % B |
|---|---|---|
| | 0 | 5 |
| | 1.7 | 95 |
| | 2 | 95 |
| | 2.1 | 5 |
| | 2.3 | 5 |

LC-MS Method J

| Column | Waters BEH C18 |
|---|---|
| | 1.7 μm, 2.1 × 50 mm |
| | Ambient temperature |

-continued

| Mobile phase | A = Formic acid (aq) 0.1% |
|---|---|
| | B = Formic acid (acetonitrile) 0.1% |
| Flow rate | 0.8 ml/min |
| Injection volume | 1 μL |
| Detector | 210-400 nm |

| Gradient | Time (mins) | % B |
|---|---|---|
| | 0 | 10 |
| | 1.19 | 95 |
| | 1.7 | 95 |

LC-MS Method K

| Column | Agilent SB-AQ |
|---|---|
| | 1.8 μm, 3 × 50 mm |
| | Ambient temperature |
| Mobile phase | A = Formic acid (aq) 0.1% |
| | B = Formic acid (acetonitrile) 0.1% |
| Flow rate | 1.5 ml/min |
| Injection volume | 3 μL |
| Detector | 220 and 254 nm |

| Gradient | Time (mins) | % B |
|---|---|---|
| | 0 | 5 |
| | 0.25 | 50 |
| | 0.3 | 70 |
| | 1.3 | 90 |
| | 1.7 | 100 |

Assessment of Biological Properties

1. Binding Assay

Compounds are assessed for the ability to bind to FLAP in a binding assay that measures compound-specific displacement of an iodinated ($^{125}$I) FLAP inhibitor via a Scintillation Proximity Assay format (adapted from S. Charleson et al., Mol. Pharmacol., 1992, 41, 873-879).

Cell pellets produced from sf9 insect cells expressing recombinant human FLAP protein are resuspended in buffer A [15 mM Tris-HCl (pH 7.5), 2 mM MgCl$_2$, 0.3 mM EDTA, 1 mM PMSF]. The cells are lysed with a Dounce homogenizer and the material is centrifuged at 10,000×g for 10 minutes. The supernatant is then collected and centrifuged at 100,000×g for 60 minutes. To prepare membrane protein for an assay, an aliquot of the 100,000×g pellet is resuspended in 1 ml of buffer A, Dounce homogenized, and finally subjected to polytron mixing (30 seconds). Membrane protein (25 μl, 5 μg) is mixed with WGA SPA beads (Amersham) and stirred for 1 h. To an assay plate (Perkin Elmer FlexiPlate) is added 25 μl of test compound prepared in Binding buffer [100 mM Tris (pH 7.5), 140 mM NaCl, 5% glycerol, 2 mM EDTA, 0.5 mM TCEP, 0.05% Tween 20], 25 μl of [$^{125}$I]L-691,831 (an iodinated analog of MK-591, Charleson et al. Mol. Pharmacol., 41, 873-879, 1992) and finally 50 μl of the bead/protein mixture. (final concentrations: beads, 200 μg/well; protein, 5 μg/well; [$^{125}$I] probe, 0 08 nM/well (17 nCi/well). The plates are shaken for 2 h before reading on a Microbeta plate reader. Non-specific binding is determined by the addition of 10 μM cold L-691,831 compound.

In general, the preferred potency range (IC$_{50}$) of compounds in the above assay is between 0.1 nM to 10 μM, the more preferred potency range is 0.1 nM to 1 μM, and the most preferred potency range is 0.1 nM to 100 nM.

2. Whole Blood Assay

Compounds are additionally tested in a human whole blood assay to determine their ability to inhibit the synthesis of LTB$_4$ in a cellular system. Compounds are combined with heparinized human whole blood and incubated for 15 minutes at 37° C. Calcimycin (20 μM final, prepared in phosphate-buffered saline, pH 7.4) is then added and the mixture is incubated for another 30 minutes at 37° C. The samples are centrifuged for 5 min at low speed (1500×g) and the plasma layer is removed. Plasma $LTB_4$ concentrations are then measured using an antibody-based homogenous time-resolved fluorescence method (CisBio, Bedford, Mass.).

In general, the preferred potency range ($IC_{50}$) of compounds in the above assay is between 10 nM to 10 μM, the more preferred potency range is 10 nM to 1 μM, and the most preferred potency range is 10 nM to 100 nM.

Method of Use

The compounds of the invention are effective inhibitors of 5-lipoxygenase activating protein (FLAP) and thus inhibit leukotriene production. Therefore, in one embodiment of the invention, there is provided methods of treating leukotriene-mediated disorders using compounds of the invention. In another embodiment, there is provided methods of treating cardiovascular, inflammatory, allergic, pulmonary and fibrotic diseases, renal diseases and cancer using compounds of the invention.

Without wishing to be bound by theory, by inhibiting the activity of FLAP, the compounds of the invention block the production of LTs resulting from the oxidation of arachidonic acid by 5-LO and subsequent metabolism. Thus, the inhibition of FLAP activity is an attractive means for preventing and treating a variety of diseases mediated by LTs. These include:
Cardiovascular diseases including atherosclerosis, myocardial infarction, stroke, aortic aneurysm, sickle cell crisis, ischemia-reperfusion injury, pulmonary arterial hypertension and sepsis;
Allergic diseases including asthma, allergic rhinitis, rhinosinusitis, atopic dermatitis and urticaria;
Fibrotic diseases including airway remodeling in asthma, idiopathic pulmonary fibrosis, scleroderma, asbestosis;
Pulmonary syndromes including adult respiratory distress syndrome, viral bronchiolitis, obstructive sleep apnea, chronic obstructive pulmonary disease, cystic fibrosis, and bronchopulmonary dysplasia;
Inflammatory diseases including rheumatoid arthritis, osteoarthritis, gout, glomerulonephritis, interstitial cystitis, psoriasis, multiple sclerosis, inflammatory bowel disease systemic lupus erythematosus, transplant rejection, inflammatory and allergic ocular diseases;
Cancer including solid tumors, leukemias and lymphomas; and
Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound of Formula I:

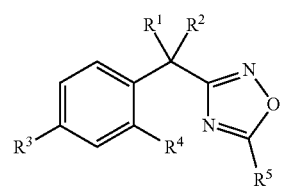

wherein:
$R^1$ and $R^2$ together with the carbon atom to which they are attached form a $C_{3-10}$ carbocyclic ring or a 5-11 membered heterocyclic ring, wherein each carbocycle or heterocycle is optionally independently substituted with one to two groups selected from $C_{1-6}$ alkyl and halogen;

R³ is 5-11 membered heteroaryl ring containing one to three heteroatoms selected from nitrogen, oxygen and sulfur, wherein each R³ is optionally independently substituted with one to three groups selected from $C_{1-5}$ alkyl, $C_{3-6}$ carbocycle, cyano, $C_{1-5}$ alkoxy, $C_{1-3}$ hydroxy, amino, $C_{1-3}$ alkylamino and $C_{1-3}$ dialkylamino;

R⁴ is hydrogen, halogen, $C_{1-3}$ alkyl or nitrile;

R⁵ is $C_{1-6}$ alkyl, $C_{3-10}$ carbocycle, 5-11 membered heterocycle, aryl, 5-11 membered heteroaryl, —C(O)—R⁶ or —NR⁷R⁸, wherein each R⁵ is optionally independently substituted with one to three groups selected from R⁹, R¹⁰ and R¹¹;

R⁶ is $C_{3-8}$ heterocycle, amino, $C_{1-3}$ alkylamino, $C_{1-3}$ dialkylamino, —NH-5-6 membered heteroaryl or —NH-5-6 membered heterocycle, each optionally independently substituted with one to three groups selected from R⁹, R¹⁰ and R¹¹;

R⁷ and R⁸ are each independently hydrogen, 5-6 membered heterocyclic ring optionally substituted with one to three methyl groups, —S(O)$_n$$C_{1-6}$alkyl or $C_{1-6}$ alkyl which is optionally substituted with 5-6 membered heterocycle;

R⁹, R¹⁰ and R¹¹ are independently selected from
(a) —H,
(b) —OH,
(c) halogen,
(d) —CN,
(e) —CF₃,
(f) $C_{1-6}$alkyl optionally substituted with one to three —OH, CN, —N(R¹²)(R¹³), aryl, —O—$C_{1-2}$ alkyl-aryl, 3-6 membered heterocycle, —C(O)-3-6 membered heterocycle, $C_{1-6}$alkoxy, —S(O)$_n$$C_{1-6}$alkyl or —C(O)N(R¹²)(R¹³),
(g) $C_{1-6}$alkoxy,
(h) —N(R¹²)(R¹³),
(i) —S(O)$_n$$C_{1-6}$alkyl,
(j) —CO₂R¹²,
(k) —C(O)N(R¹²)(R¹³),
(l) —S(O)₂N(R¹²)(R¹³),
(m) a 3-10 membered heterocyclic group optionally substituted with one to three groups selected from $C_{1-6}$alkyl, $C_{1-6}$alkylhydroxy, $C_{1-6}$alkyl-CO₂R¹², —S(O)$_n$$C_{1-6}$alkyl, oxo and —CO₂R¹²,
(n') oxo,
(o) —C(O)—$C_{1-3}$ alkyl,
(p) —C(O)-3-6 membered heterocycle optionally substituted with one to three groups selected from halogen hydroxy and $C_{1-6}$alkoxy,
(q) 5-6 membered heteroaryl ring optionally substituted with one to three —$C_{1-4}$alkyl groups,
(r) aryl;

R¹² and R¹³ are each independently selected from —H, —$C_{1-6}$alkyl, —C(O)—$C_{1-6}$ alkyl and a 3-6 membered heterocyclic group, each of which is optionally independently substituted with one to three —OH, $C_{1-6}$ alkyl, $C_{1-6}$alkoxy, —C(O)N(R¹⁴)(R¹⁵), —N(R¹⁴)(R¹⁵), —S(O)$_n$$C_{1-6}$alkyl, CN, $C_{3-10}$ carbocycle, —CO₂R¹², CF₃, 3-6 membered heterocycle, halogen; or R¹² and R¹³ together with the nitrogen atom to which they are attached form a heterocyclyl ring optionally substituted with one to three —OH, CN, $C_{1-6}$alkyl, $C_{1-6}$alkoxy, —C(O)—$C_{1-3}$alkyl or oxo;

R¹⁴ and R¹⁵ are each independently selected from —H and —$C_{1-6}$alkyl;

n is 0, 1 or 2;

or a pharmaceutically acceptable salt thereof.

2. A compound according to claim 1, wherein:

R¹ and R² together with the carbon atom to which they are attached is cyclopropyl, cyclobutyl, cyclopentyl, cyclohexyl, cycloheptyl, cyclooctyl, 2.2.1 bicycloheptyl, oxetanyl, tetrahydrofuranyl, tetrahydropyranyl, pyrrolidinyl, piperidinyl, tetrahydrothienyl, wherein each carbocycle or heterocycle is optionally independently substituted with one to two groups selected from $C_{1-6}$ alkyl and halogen;

R³ is pyridinyl, pyrimidinyl, pyrazinyl, pyridazinyl, pyrrolyl, imidazolyl, thienyl, furanyl, thiazolyl, indolyl, pyrrolopyridinyl, pyrrolopyrimidinyl, pyrrolopyrazinyl, dihydropyrrolopyridinyl or pyrrolopyridazinyl wherein each R³ is optionally independently substituted with one to three groups selected from $C_{1-3}$ alkyl, $C_{3-6}$ carbocycle, cyano, $C_{1-3}$ alkoxy, $C_{1-3}$ hydroxy, amino, $C_{1-3}$ alkylamino and $C_{1-3}$ dialkylamino;

R⁴ is hydrogen, halogen, methyl or ethyl;

R⁵ is methyl, ethyl, propyl, isopropyl, butyl, isobutyl, tert. butyl, pentyl, hexyl, cyclopropyl, cyclobutyl, cyclopentyl, cyclohexyl, cycloheptyl, cyclooctyl, phenyl, piperidinyl, piperazinyl, morpholinyl, thiomorpholinyl, pyrrolidinyl, tetrahydropyranyl, pyrrolyl, thienyl, furanyl, thiazolyl, oxazolyl, isoxazolyl, pyrazolyl, imidazolyl, triazolyl, pyridinyl, pyrimidinyl, pyrazinyl, pyridazinyl, quinolinyl, isoquinolinyl, indolyl, pyrrolopyridinyl, pyrrolopyrimidinyl, pyrazolopyrimidinyl, imidazopyridinyl, indazolyl, —C(O)—R⁶, hydroxy or —NR⁷R⁸, wherein each R⁵ is optionally independently substituted with one to three groups selected from R⁹, R¹⁰ and R¹¹;

R⁶ is azetidinyl, pyrrolidinyl, piperidinyl, piperazinyl, tetrahydropyranyl, morpholinyl, thiomorpholinyl, amino, $C_{1-3}$ alkylamino, $C_{1-3}$ dialkylamino, —NH-pyridinyl or —NH-5-6 membered heterocycle, each optionally independently substituted with one to three groups selected from R⁹, R¹⁰ and R¹¹;

R⁷ and R⁸ are each independently hydrogen, 5-6 membered heterocyclic ring optionally substituted with one to three methyl groups, $C_{1-5}$ alkyl which is optionally substituted with 5-6 membered heterocycle; or —S(O)$_n$$C_{1-6}$alkyl;

R⁹, R¹⁰ and R¹¹ are independently selected from
(a) —H,
(b) —OH,
(c) halogen,
(d) —CN,
(e) —CF₃,
(f) $C_{1-6}$alkyl optionally substituted with one to three —OH, CN, —N(R¹²)(R¹³), phenyl, benzyl, phenethyl, azetidinyl, pyrrolidinyl, piperidinyl, piperazinyl, morpholinyl, —C(O)-3-6 membered heterocycle, $C_{1-6}$alkoxy, —S(O)$_n$$C_{1-6}$alkyl or —C(O)N(R¹²)(R¹³),
(g) $C_{1-6}$alkoxy,
(h) —N(R¹²)(R¹³),
(i) —S(O)$_n$$C_{1-6}$alkyl,
(j) —CO₂R¹²,
(k) —C(O)N(R¹²)(R¹³),
(l) —S(O)₂N(R¹²)(R¹³),
(m) oxetanyl, tetrahydrofuranyl, tetrahydropyranyl, tetrahydrothienyl, azetidinyl, pyrrolidinyl, piperidinyl, piperazinyl, morpholinyl or thiomorpholinyl, optionally substituted with one to three groups selected from $C_{1-6}$ alkyl, $C_{1-6}$alkylhydroxy, $C_{1-6}$ alkyl-CO₂R¹², —S(O)$_n$$C_{1-6}$alkyl, oxo and —CO₂R¹²,
(n') oxo,
(o) —C(O)—$C_{1-3}$ alkyl, (p) —C(O)-3-6 membered heterocycle optionally substituted with one to three groups selected from halogen hydroxy and $C_{1-6}$alkoxy, (q) imidazolyl, pyrazolyl, thiazolyl, furanyl, pyridinyl, pyrimidinyl, pyridazinyl each optionally substituted with one to three —$C_{1-4}$alkyl groups, (r) phenyl;

$R^{12}$ and $R^{13}$ are each independently selected from —H, —$C_{1-6}$alkyl, —C(O)—$C_{1-6}$ alkyl and a 3-6 membered heterocyclic group, each of which is optionally independently substituted with one to three —OH, $C_{1-6}$ alkyl, $C_{1-6}$alkoxy, —C(O)N($R^{14}$)($R^{15}$), —N($R^{14}$)($R^{15}$), —S(O)$_n$$C_{1-6}$alkyl, CN, cyclopropyl, cyclobutyl, cyclopentyl, cyclohexyl, —CO$_2$$R^{12}$, CF$_3$, 3-6 membered heterocycle, halogen; or $R^{12}$ and $R^{13}$ together with the nitrogen atom to which they are attached form a heterocyclyl ring optionally substituted with one to three —OH, CN, $C_{1-6}$alkyl, $C_{1-6}$alkoxy, —C(O)—$C_{1-3}$alkyl or oxo;

$R^{14}$ and $R^{15}$ are each independently selected from —H and —$C_{1-6}$alkyl;

n is 0 or 2;

or a pharmaceutically acceptable salt thereof.

3. A compound according to claim 1, wherein:

$R^1$ and $R^2$ together with the carbon atom to which they are attached is cyclopropyl, cyclobutyl, cyclopentyl, cyclohexyl, 2.2.1 bicycloheptyl or tetrahydropyranyl wherein each carbocycle or heterocycle is optionally independently substituted with one to two groups selected from $C_{1-3}$ alkyl and halogen;

or a pharmaceutically acceptable salt thereof.

4. A compound according to claim 1, wherein:

$R^3$ is pyridinyl, pyrimidinyl, pyrazinyl, pyrrolopyrazinyl, dihydropyrrolopyridinyl, pyrrolopyridinyl or pyridazinyl, wherein each $R^3$ is optionally independently substituted with one to three groups selected from $C_{1-3}$ alkyl, cyclopropyl, cyclobutyl, cyano, $C_{1-3}$ alkoxy, $C_{1-3}$ hydroxy, amino, $C_{1-3}$ alkylamino and $C_{1-3}$ dialkylamino;

or a pharmaceutically acceptable salt thereof.

5. A compound according to claim 1, wherein:

$R^5$ is methyl, ethyl, propyl, isopropyl, butyl, isobutyl, tert. butyl, pentyl, hexyl, phenyl, piperidinyl, piperazinyl, morpholinyl, thiomorpholinyl, pyrrolidinyl, furanyl, thiazolyl, oxazolyl, isoxazolyl, pyrazolyl, imidazolyl, triazolyl, pyridinyl, pyrimidinyl, pyrazinyl, pyridazinyl, quinolinyl, isoquinolinyl, indolyl, pyrrolopyridinyl, pyrrolopyrimidinyl, pyrazolopyrimidinyl, imidazopyridinyl, indazolyl, —C(O)—$R^6$, hydroxy or —N$R^7$$R^8$, wherein each $R^5$ is optionally independently substituted with one to three groups selected from $R^9$, $R^{10}$ and $R^{11}$;

$R^6$ is azetidinyl, pyrrolidinyl, piperidinyl, piperazinyl, morpholinyl, amino, —NH-pyridinyl optionally substituted with a methyl group, $C_{1-3}$ alkylamino or $C_{1-3}$ dialkylamino;

$R^7$ and $R^8$ are each independently hydrogen, 5-6 membered heterocyclic ring optionally substituted with one to three methyl groups, $C_{1-5}$ alkyl which is optionally substituted with 5-6 membered heterocycle; or $R^7$ and $R^8$ are each independently —S(O)$_n$$C_{1-6}$alkyl;

$R^9$, $R^{10}$ and $R^{11}$ are independently selected from (a) —H, (b) —OH, (c) halogen, (d) —CN, (e) —CF$_3$, (f) $C_{1-6}$alkyl optionally substituted with one to three —OH, CN, —N($R^{12}$)($R^{13}$), phenyl, benzyl, azetidinyl, pyrrolidinyl, piperidinyl, piperazinyl, morpholinyl, —C(O)-piperidine, —C(O)-pyrrolidine, —C(O)-morpholine, $C_{1-6}$alkoxy, —S(O)$_n$$C_{1-3}$alkyl or —C(O)N($R^{12}$)($R^{13}$), (g) $C_{1-6}$alkoxy, (h) —N($R^{12}$)($R^{13}$), (i) —S(O)$_2$$C_{1-6}$alkyl, (j) —CO$_2$$R^{12}$, (k) —C(O)N($R^{12}$)($R^{13}$), (l) —S(O)$_2$N($R^{12}$)($R^{13}$), (m) oxetanyl, tetrahydrofuranyl, tetrahydropyranyl, tetrahydrothienyl, azetidinyl, pyrrolidinyl, piperidinyl, piperazinyl, morpholinyl or thiomorpholinyl, optionally substituted with one to three groups selected from $C_{1-6}$ alkyl, $C_{1-6}$ alkylhydroxy, $C_{1-6}$ alkyl-CO$_2$$R^{12}$, —S(O)$_2$$C_{1-6}$alkyl, oxo and —CO$_2$$R^{12}$, (n') oxo, (o) —C(O)—$C_{1-3}$ alkyl, (p) —C(O)-azetidine, —C(O)-piperidine, —C(O)-pyrrolidine or —C(O)-morpholine optionally substituted with one to three groups selected from halogen, hydroxy and $C_{1-6}$alkoxy, (q) imidazolyl, pyrazolyl, thiazolyl, furanyl, pyridinyl, pyrimidinyl, pyridazinyl each optionally substituted with one to three —$C_{1-4}$alkyl groups, (r) phenyl;

$R^{12}$ and $R^{13}$ are each independently selected from —H, —$C_{1-6}$alkyl, —C(O)—$C_{1-6}$ alkyl, morpholinyl, piperidinyl, piperizinyl and tetrahydropyranyl, each of which is optionally independently substituted with one to three —OH, $C_{1-6}$ alkyl, $C_{1-6}$alkoxy, —C(O)N($R^{14}$)($R^{15}$), —N($R^{14}$)($R^{15}$), —S(O)$_2$$Cl_{1-6}$alkyl, CN, cyclopropyl, cyclobutyl, cyclopentyl, cyclohexyl, —CO$_2$$R^{12}$, CF$_3$, morpholinyl, piperidinyl, piperizinyl, tetrahydrofuranyl, tetrahydropyranyl; or $R^{12}$ and $R^{13}$ together with the nitrogen atom to which they are attached form a 5-6 membered heterocyclyl ring optionally substituted with one to three —OH, CN, $C_{1-6}$alkyl, $C_{1-6}$alkoxy, —C(O)—$C_{1-3}$alkyl or oxo;

$R^{14}$ and $R^{15}$ are each independently selected from —H and —$C_{1-4}$alkyl;

or a pharmaceutically acceptable salt thereof.

6. A compound according to claim 1, wherein:

$R^1$ and $R^2$ together with the carbon atom to which they are attached is cyclopropyl, cyclobutyl, cyclopentyl, cyclohexyl, 2.2.1 bicycloheptyl or tetrahydropyranyl wherein each carbocycle or heterocycle is optionally independently substituted with one to two groups selected from methyl, ethyl and fluoro;

$R^3$ is pyridinyl, pyrimidinyl, pyrazinyl, pyrrolopyrazinyl, dihydropyrrolopyridinyl, pyrrolopyridinyl or pyridazinyl, wherein each $R^3$ is optionally independently substituted with one to two amino, —NHCH$_3$, —CH$_2$—OH, cyclopropyl group, cyano or one to two methyl groups;

$R^4$ is hydrogen, methyl or fluoro;

$R^5$ is methyl, ethyl, phenyl, piperidinyl, piperazinyl, pyrrolidinyl, thiazolyl, oxazolyl, isoxazolyl, pyrazolyl, imidazolyl, triazolyl, pyridinyl, pyrimidinyl, pyrazinyl, pyridazinyl, pyrazolopyrimidinyl, imidazopyridinyl, indazolyl, —C(O)—$R^6$, hydroxy or —N$R^7$$R^8$, wherein each $R^5$ is optionally independently substituted with one to three groups selected from $R^9$, $R^{10}$ and $R^{11}$;

$R^6$ is azetidinyl, pyrrolidinyl, piperidinyl, piperazinyl, morpholinyl, amino, —NH-pyridinyl optionally substituted with a methyl group, $C_{1-3}$ alkylamino or $C_{1-3}$ dialkylamino;

R⁷ and R⁸ are each independently hydrogen, piperidinyl optionally substituted with methyl, $C_{1-3}$ alkyl which is optionally substituted with tetrahydropyranyl ring; or
R⁷ and R⁸ are each independently —S(O)₂C₁₋₆alkyl;
R⁹, R¹⁰ and R¹¹ are independently selected from
(a) —H,
(b) —OH,
(c) halogen,
(d) —CN,
(e) —CF₃,
(f) $C_{1-6}$alkyl optionally substituted with one to three —OH, CN, —N(R¹²)(R¹³), phenyl, benzyl, azetidinyl, pyrrolidinyl, piperidinyl, piperazinyl, morpholinyl, —C(O)-piperidine, —C(O)-pyrrolidine, —C(O)-morpholine, $C_{1-6}$alkoxy, —S(O)ₙC₁₋₃alkyl or —C(O)N(R¹²)(R¹³),
(g) $C_{1-6}$alkoxy,
(h) —N(R¹²)(R¹³),
(i) —S(O)₂C₁₋₆alkyl,
(j) —CO₂R¹²,
(k) —C(O)N(R¹²)(R¹³),
(l) —S(O)₂N(R¹²)(R¹³),
(m) oxetanyl, tetrahydrofuranyl, tetrahydropyranyl, tetrahydrothienyl, azetidinyl, pyrrolidinyl, piperidinyl, piperazinyl, morpholinyl or thiomorpholinyl, optionally substituted with one to three groups selected from $C_{1-6}$ alkyl, $C_{1-6}$ alkylhydroxy, $C_{1-6}$ alkyl-CO₂R¹², —S(O)₂C₁₋₆alkyl, oxo and —CO₂R¹²,
(n') oxo,
(o) —C(O)—$C_{1-3}$ alkyl,
(p) —C(O)-azetidine, —C(O)-piperidine, —C(O)-pyrrolidine or —C(O)-morpholine optionally substituted with one to three groups selected from halogen, hydroxy and $C_{1-6}$alkoxy,
(q) imidazolyl, pyrazolyl, thiazolyl optionally substituted with one to three methyl groups,
(r) phenyl;
R¹² and R¹³ are each independently selected from —H, tetrahydropyranyl, piperidinyl, —C(O)methyl, and —$C_{1-6}$alkyl, wherein the alkyl group is optionally independently substituted with one to three —OH, $C_{1-6}$alkoxy, —C(O)N(R¹⁴)(R¹⁵), —N(R¹⁴)(R¹⁵), —S(O)₂C₁₋₆alkyl, cyclopropyl, morpholinyl, tetrahydrofuranyl, tetrahydropyranyl, —CO₂R¹², CN or halogen; or
R¹² and R¹³ together with the nitrogen atom to which they are attached form a pyrrolidinyl, piperidinyl, piperazinyl or morpholinyl ring optionally substituted with one to three —OH, CN, $C_{1-3}$alkyl, $C_{1-3}$alkoxy, —C(O)—$C_{1-3}$ alkyl or oxo;
R¹⁴ and R¹⁵ are each independently selected from —H and —$C_{1-4}$alkyl;
or a pharmaceutically acceptable salt thereof.

7. A compound according to claim 6, wherein:
R¹ and R² together with the carbon atom to which they are attached is cyclobutyl, cyclopentyl, cyclohexyl or 2.2.1 bicycloheptyl wherein each carbocycle is optionally independently substituted with one to two groups selected from methyl and fluoro;
or a pharmaceutically acceptable salt thereof.

8. A compound according to claim 6, wherein:
R¹ and R² together with the carbon atom to which they are attached is tetrahydropyranyl;
or a pharmaceutically acceptable salt thereof.

9. A compound according to claim 6, wherein:
R³ is selected from

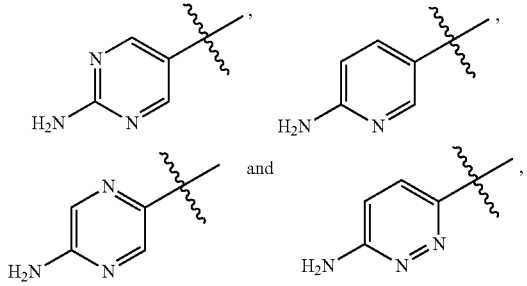

or a pharmaceutically acceptable salt thereof.

10. A compound according to claim 6, wherein:
R⁵ is selected from imidazolyl, pyrazolyl, triazolyl, thiazolyl, oxazolyl, pyrazolopyrimidinyl, imidazopyridinyl, indazolyl, pyridinyl, pyrimidinyl, pyrazinyl, pyridazinyl, pyrrolidinyl, piperidinyl and phenyl, wherein each R⁵ is optionally independently substituted with one to three groups selected from R⁹, R¹⁰ and R¹¹;
or a pharmaceutically acceptable salt thereof.

11. A compound according to claim 6, wherein:
R⁵ is selected from —C(O)—R⁶ and —NR⁷R⁸, wherein each R⁵ is optionally independently substituted with one to three groups selected from R⁹, R¹⁰ and R¹¹;
or a pharmaceutically acceptable salt thereof.

12. A compound according to claim 6, wherein:
R¹ and R² together with the carbon atom to which they are attached is cyclobutyl, cyclopentyl, cyclohexyl or tetrahydropyranyl wherein each carbocycle or is optionally independently substituted with one to two groups selected from methyl and fluoro;
R³ is selected from

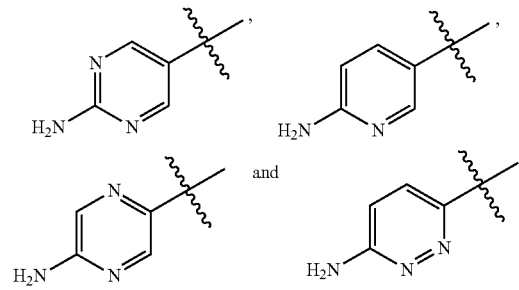

R⁴ is hydrogen or fluoro;
R⁵ is selected from imidazolyl, pyrazolyl, triazolyl, thiazolyl, oxazolyl, pyrazolopyrimidinyl, imidazopyridinyl, indazolyl, pyridinyl, pyrimidinyl, pyrazinyl, pyridazinyl, pyrrolidinyl, piperidinyl and phenyl, wherein each R⁵ is optionally independently substituted with one to three groups selected from R⁹, R¹⁰ and R¹¹;
or a pharmaceutically acceptable salt thereof.

13. A compound according to claim 6, wherein:
R¹ and R² together with the carbon atom to which they are attached is cyclobutyl, cyclopentyl, cyclohexyl or tetrahydropyranyl wherein each carbocycle or is optionally independently substituted with one to two groups selected from methyl and fluoro;

R³ is selected from
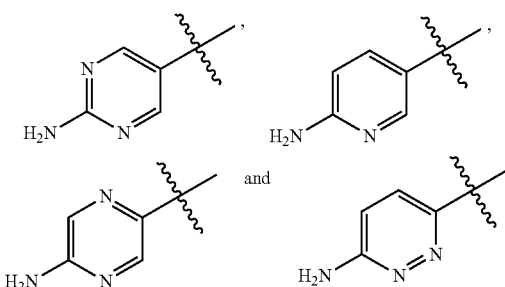
R⁴ is hydrogen or fluoro;
R⁵ is selected from —C(O)—R⁶ and —NR⁷R⁸, wherein each R⁵ is optionally independently substituted with one to three groups selected from R⁹, R¹⁰ and R¹¹;
or a pharmaceutically acceptable salt thereof.
14. A compound selected from a group consisting of:
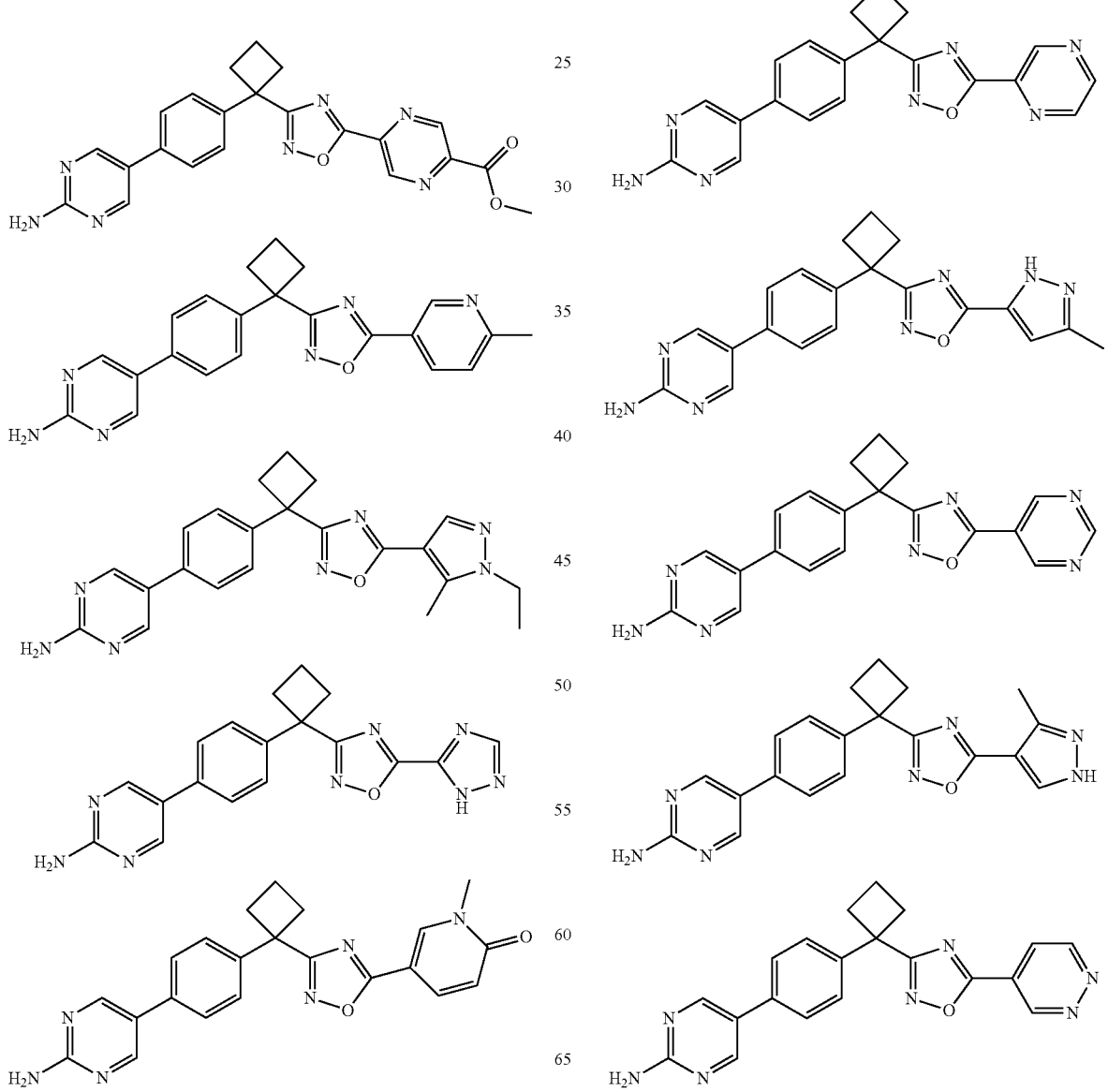

419
-continued
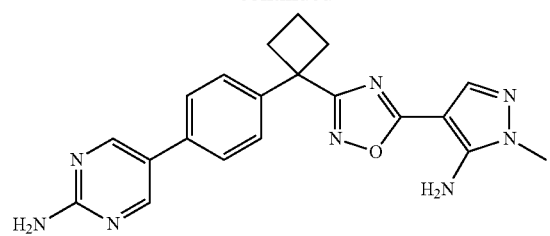
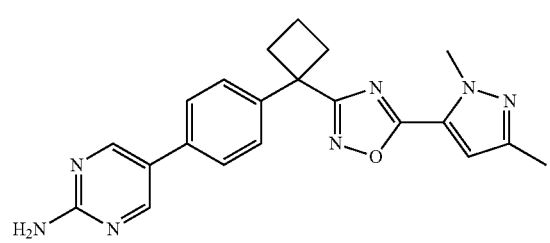
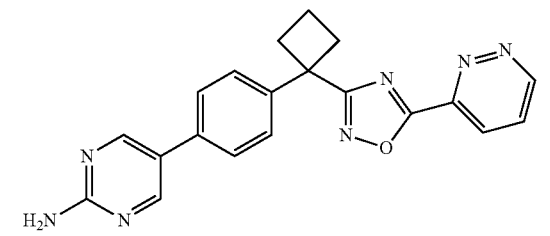
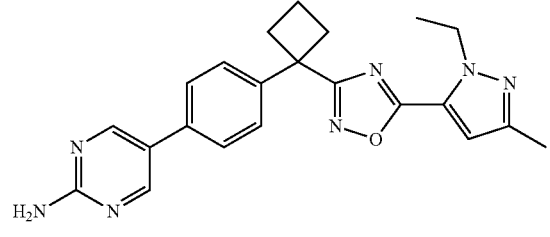
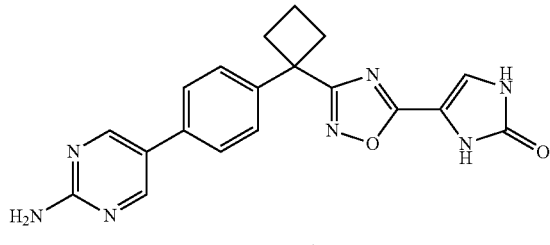
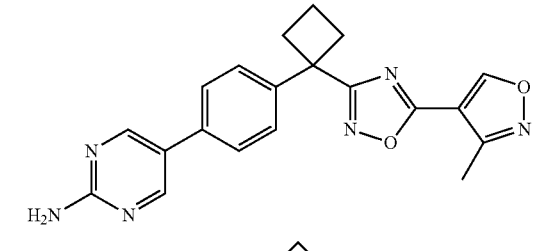
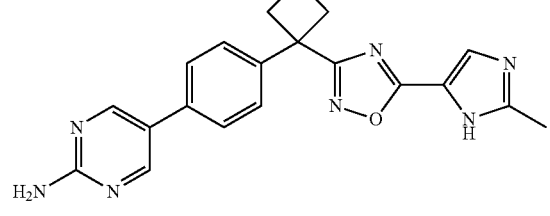
420
-continued
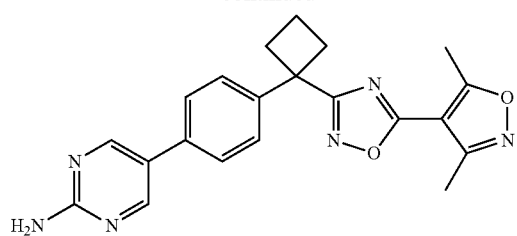
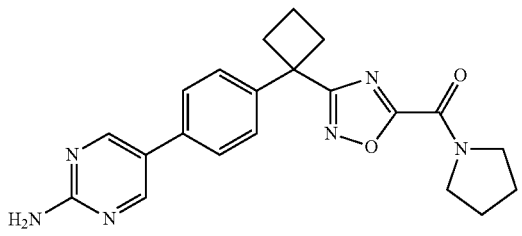
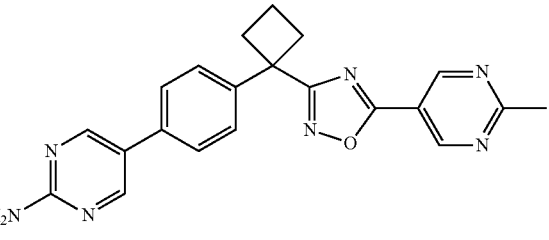
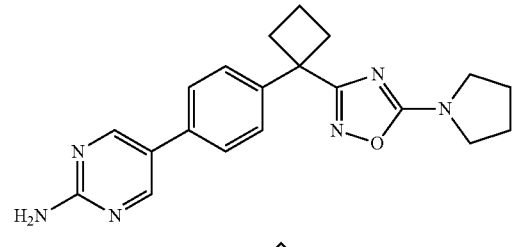
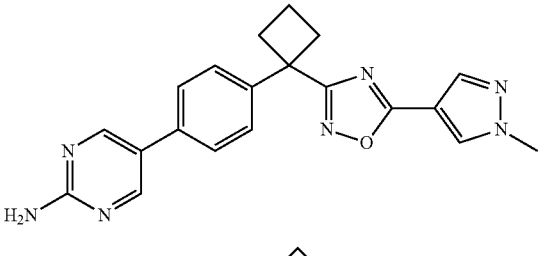
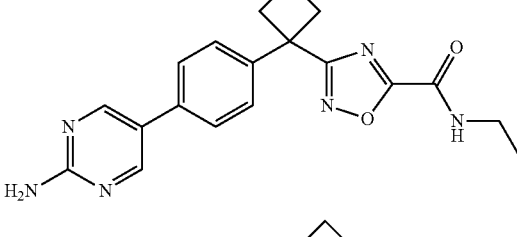
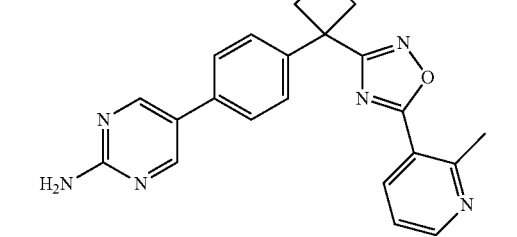

421
-continued
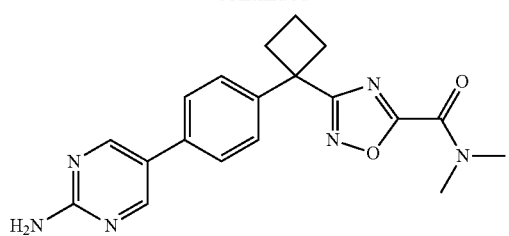
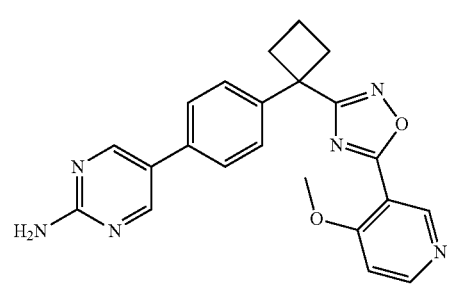
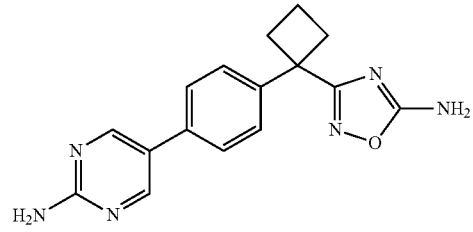
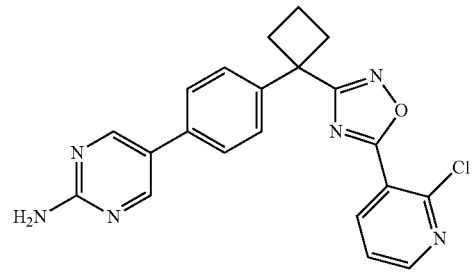
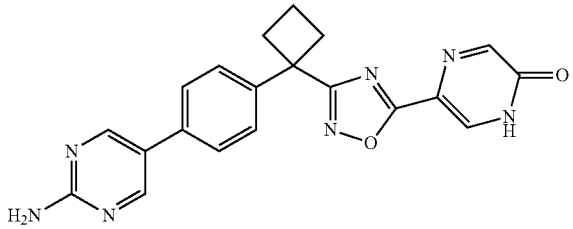
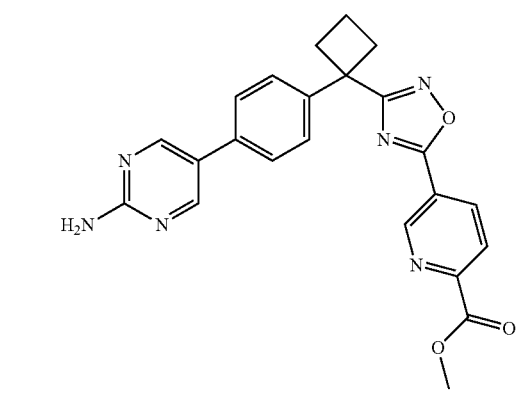
422
-continued
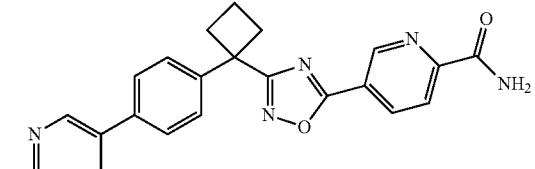
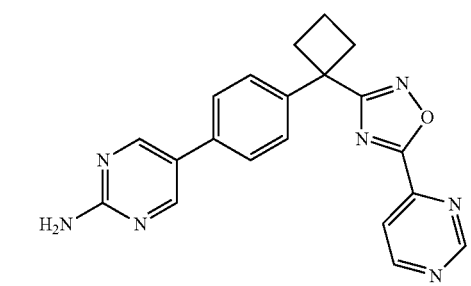
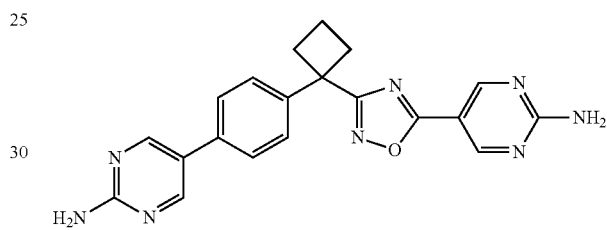
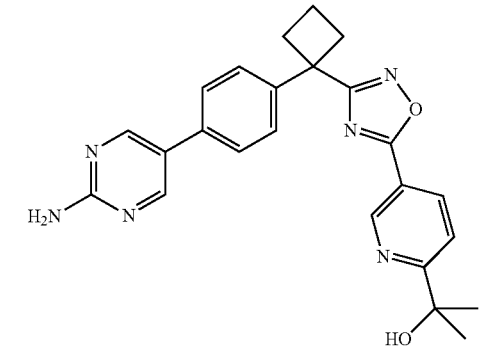
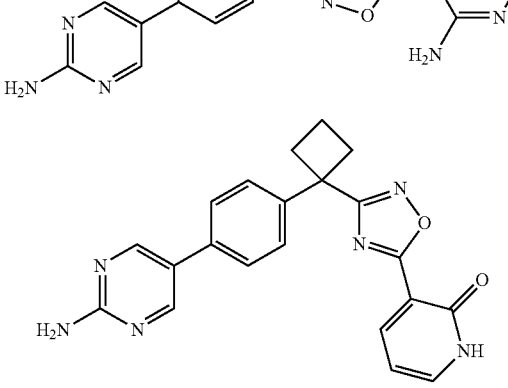

423
-continued
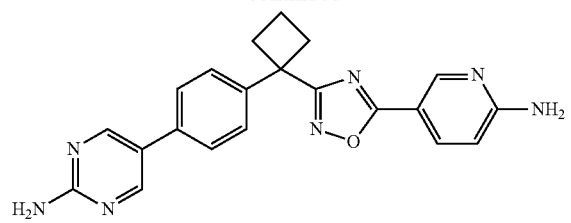
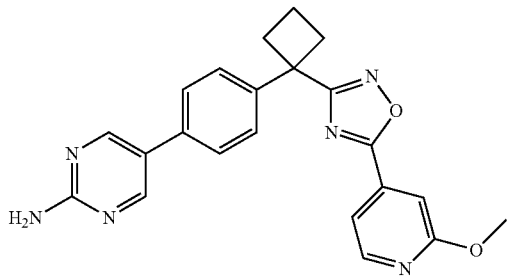
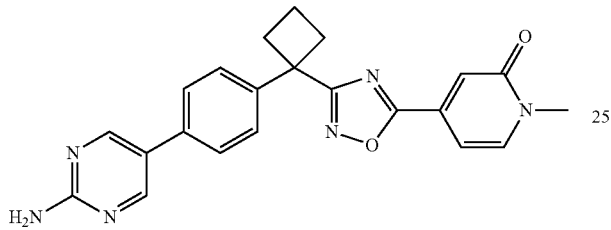
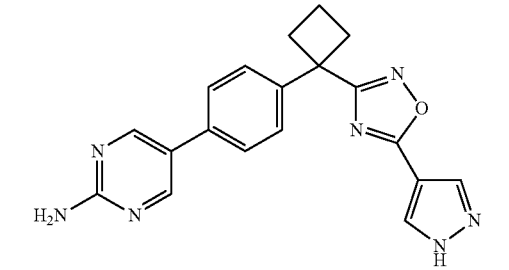
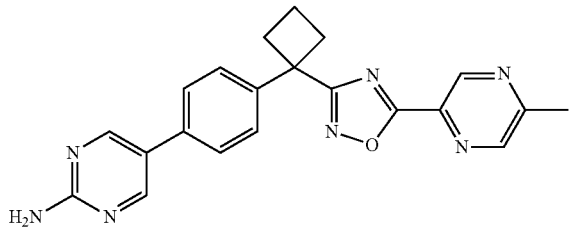
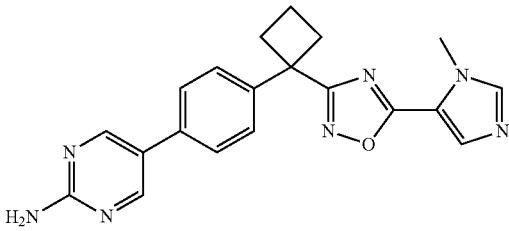
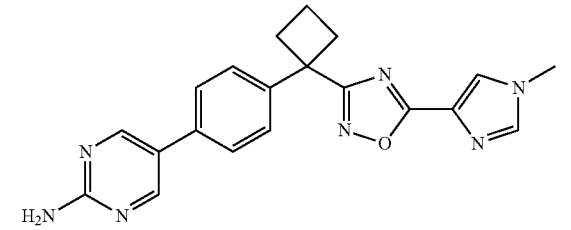
424
-continued
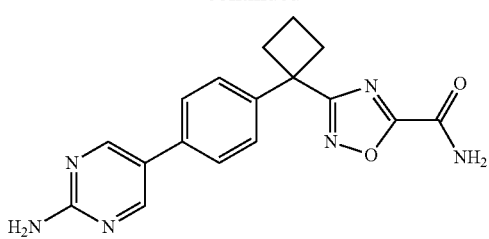
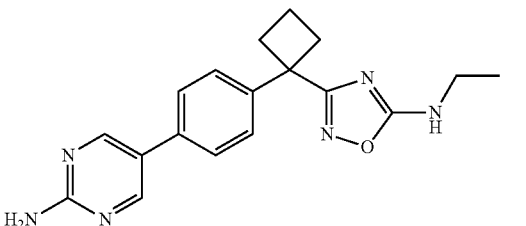
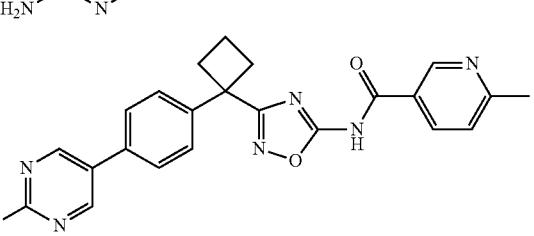
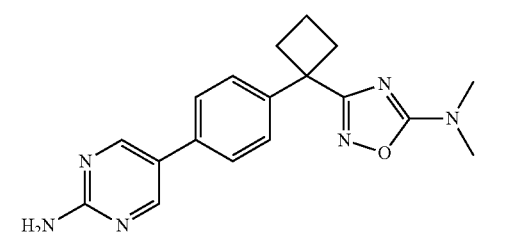
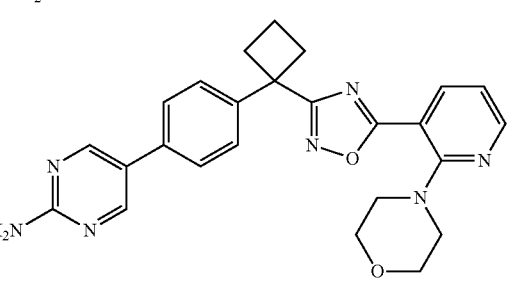
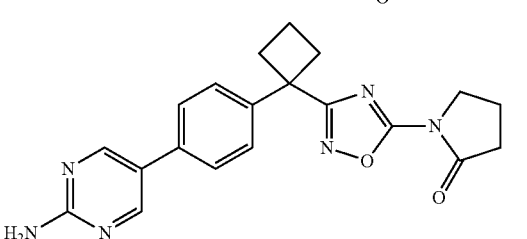
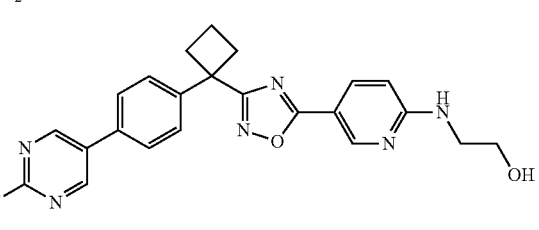

425
-continued
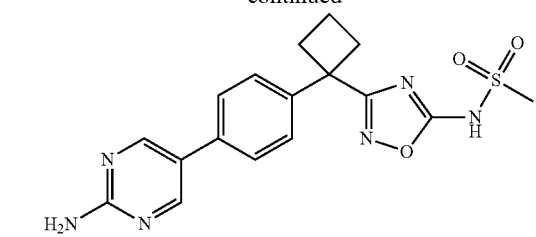
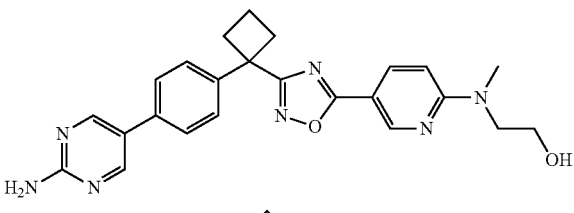
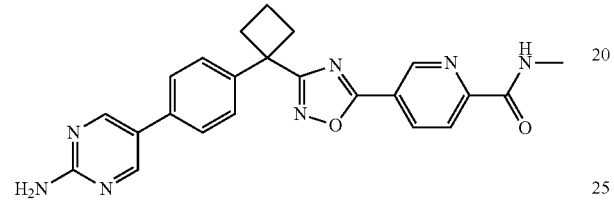
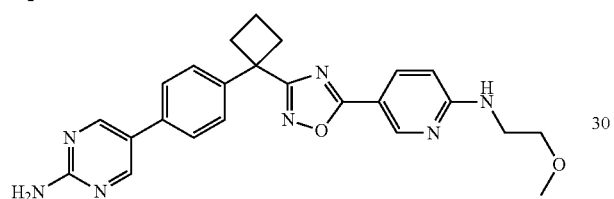
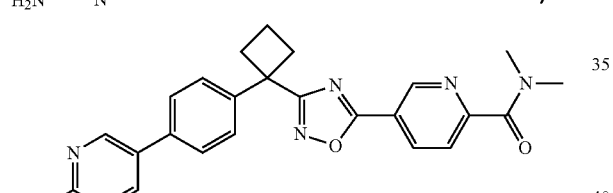
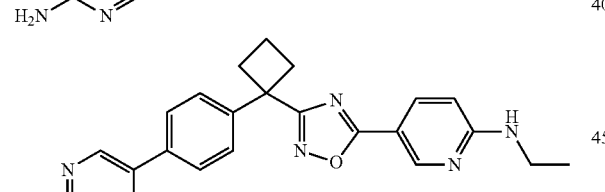
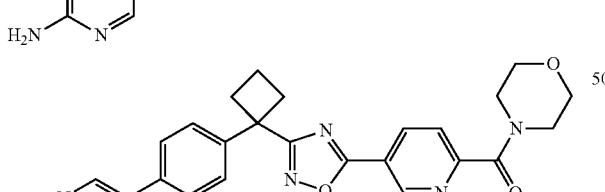
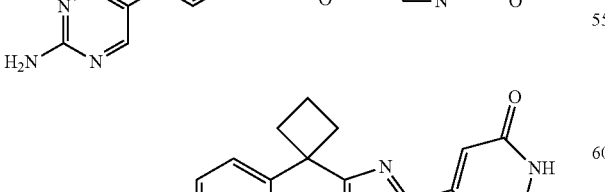
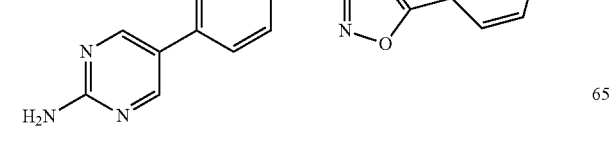
426
-continued
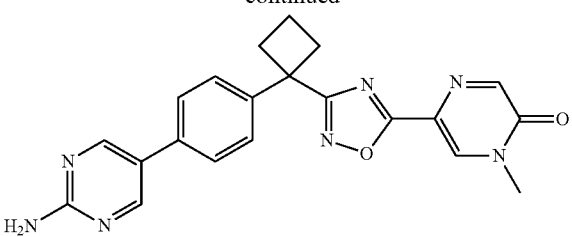
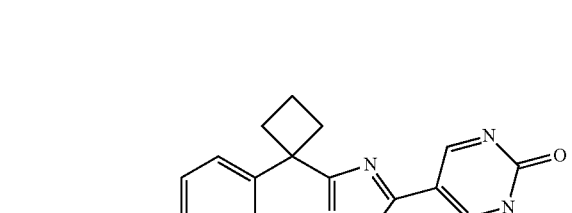
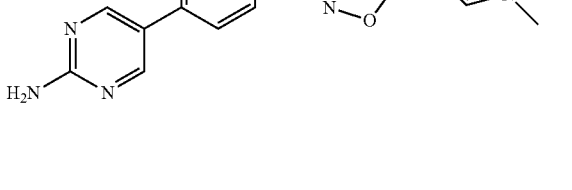
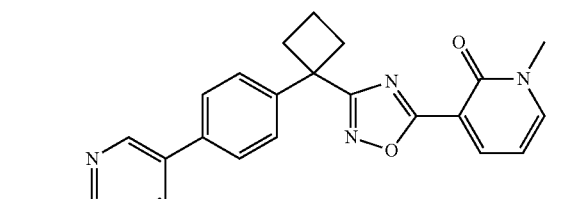
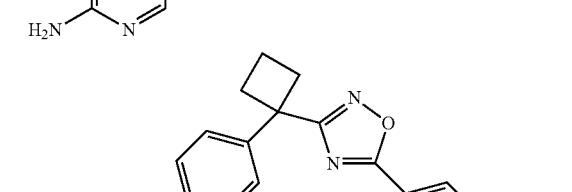
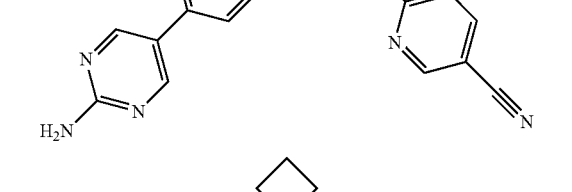
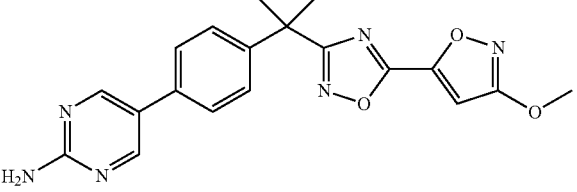
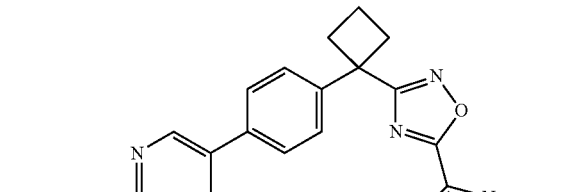

427
-continued
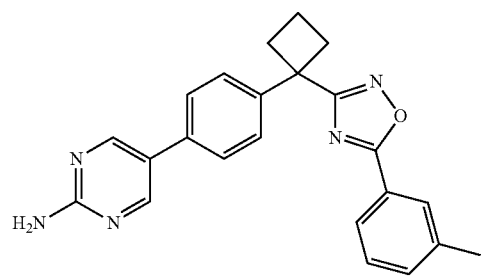
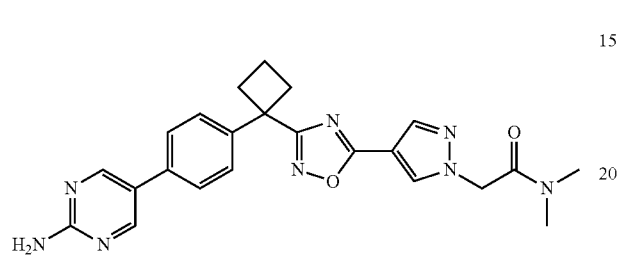
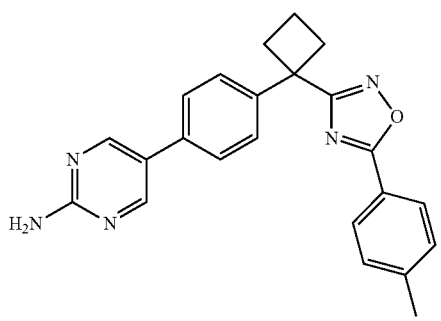
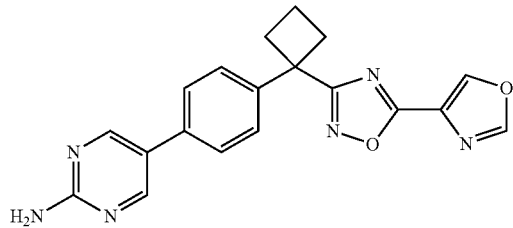
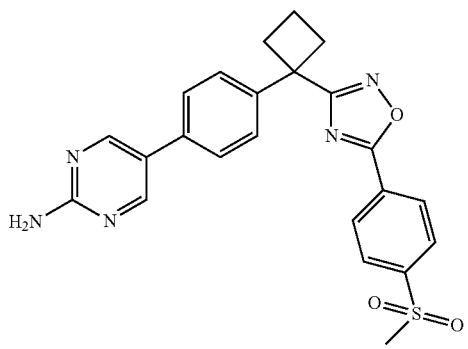
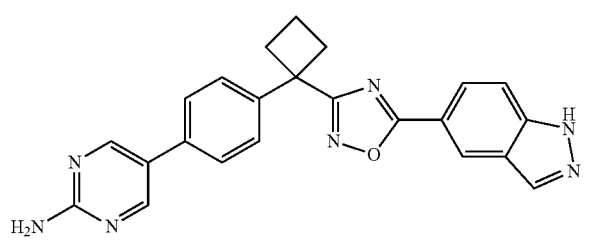
428
-continued
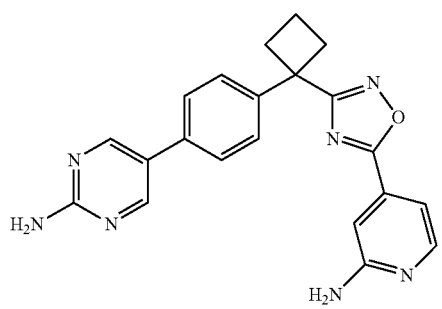
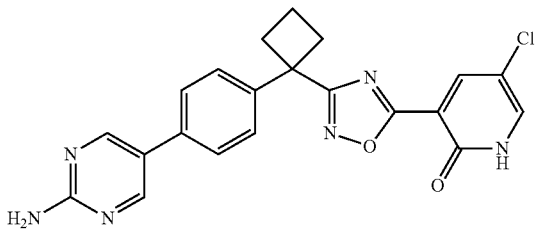
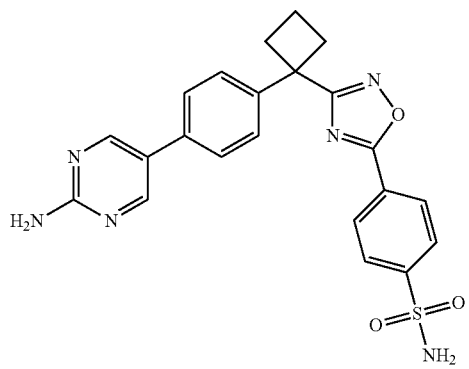
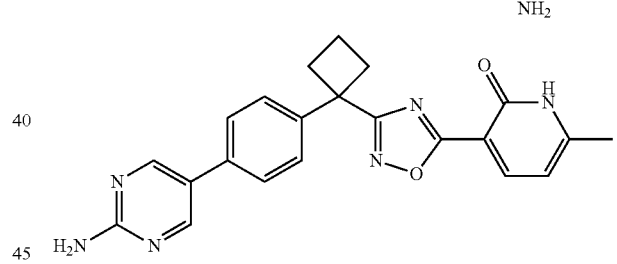
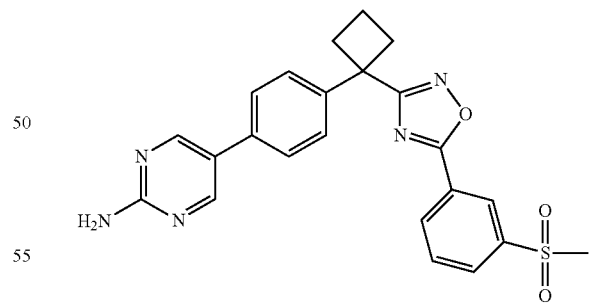

429
-continued
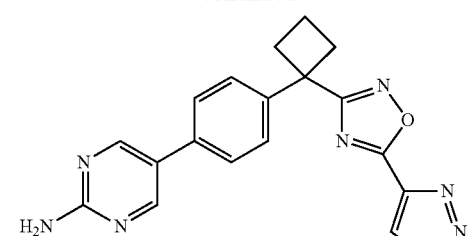
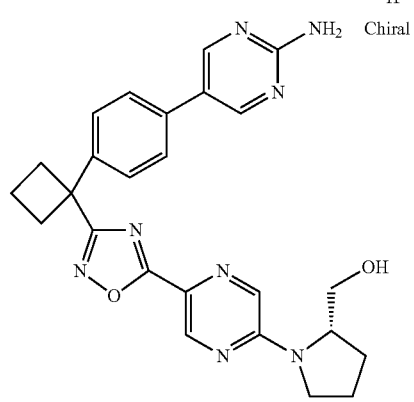
Chiral
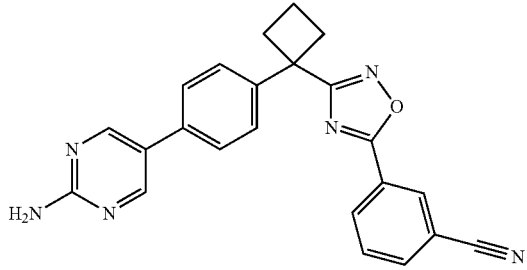
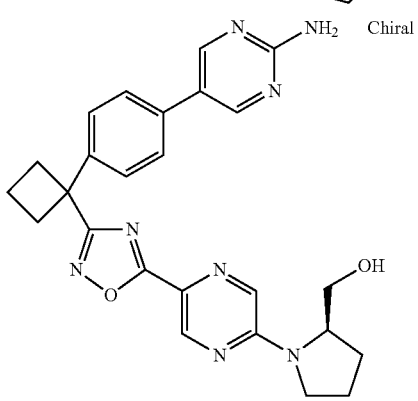
Chiral
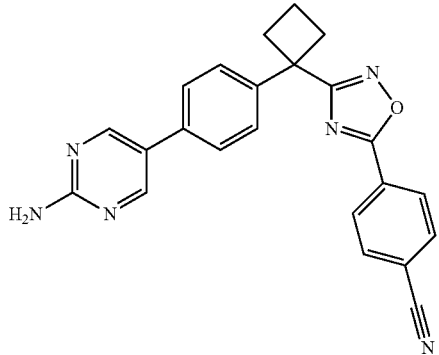
430
-continued
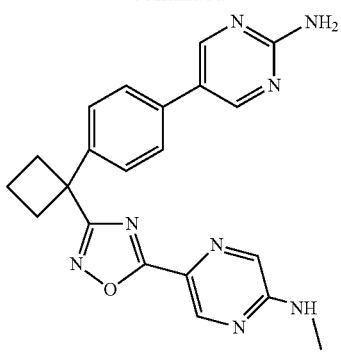
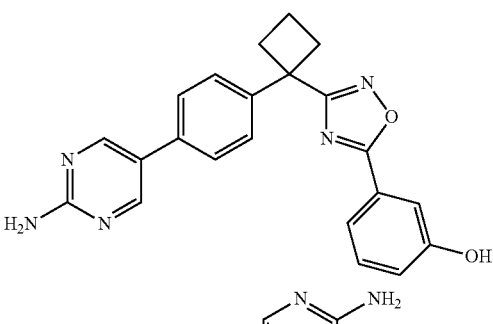
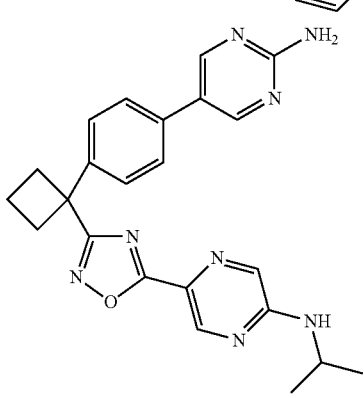
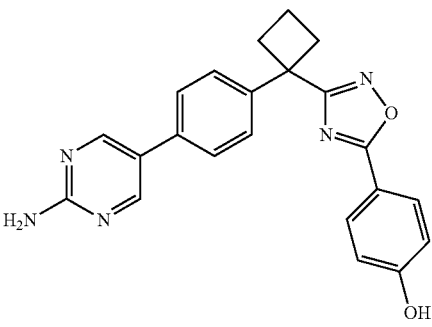
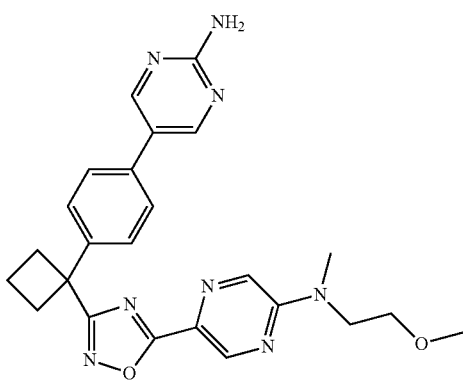

| 431 | 432 |
|---|---|
| -continued | -continued |
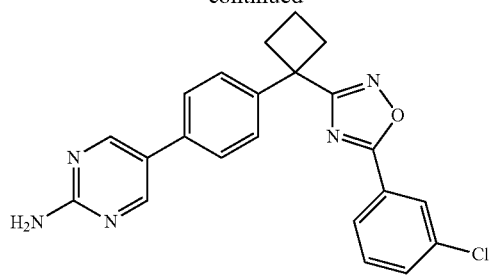
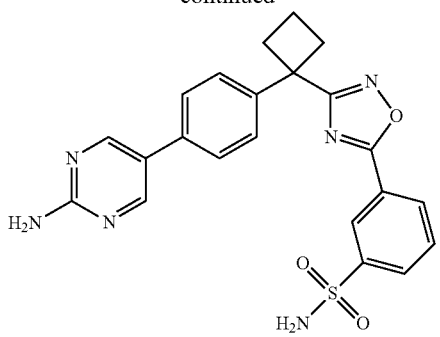
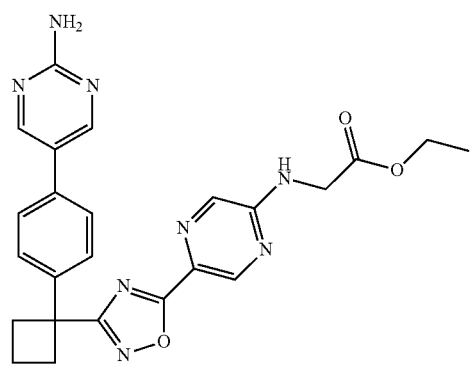
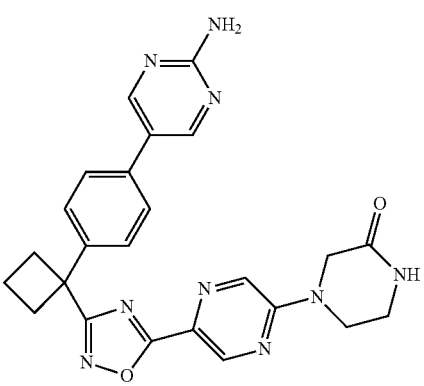
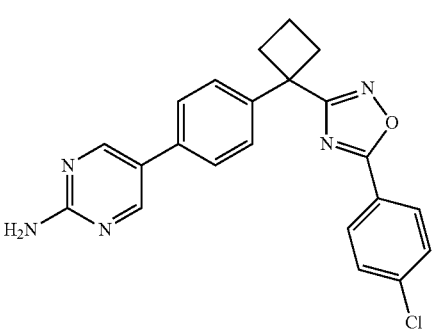
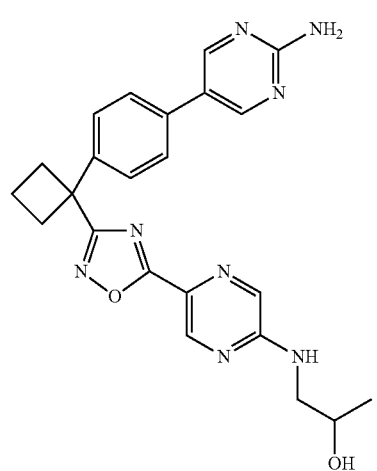

433
-continued
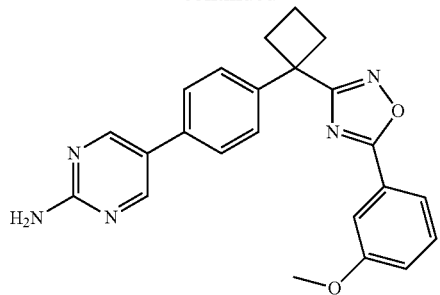
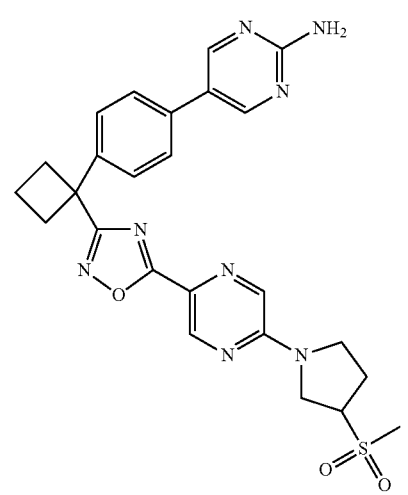
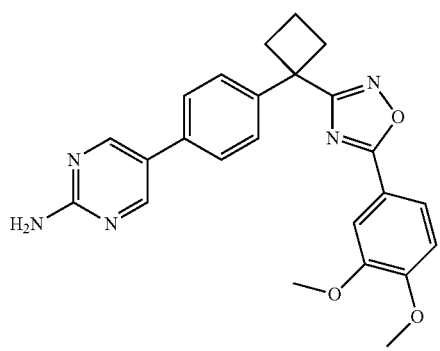
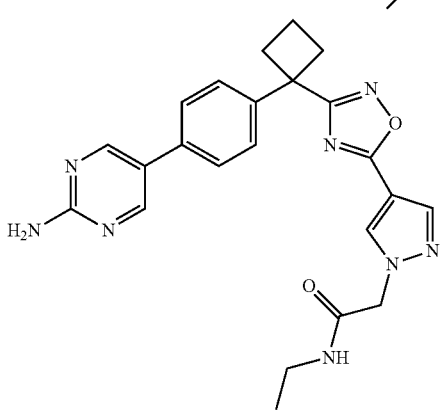
434
-continued
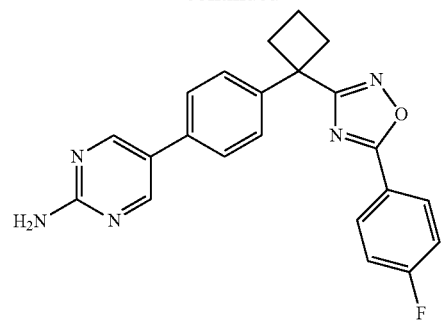
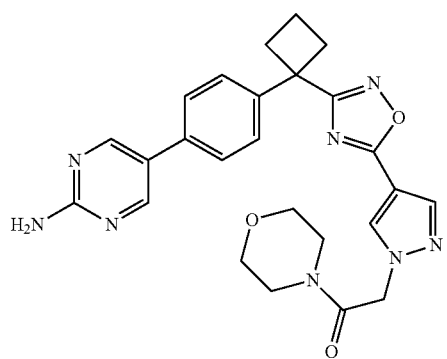
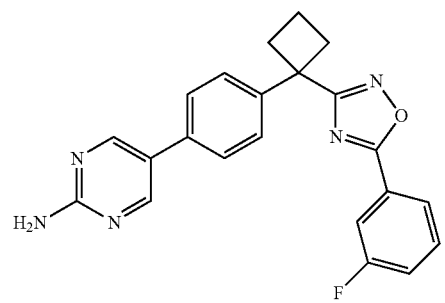
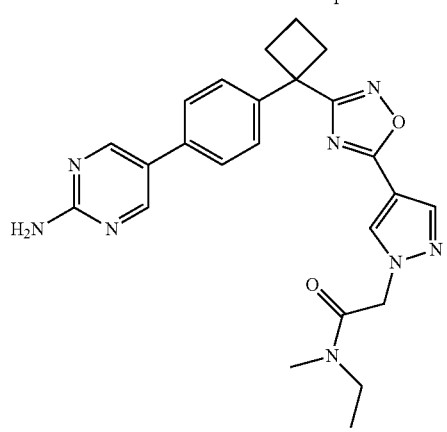
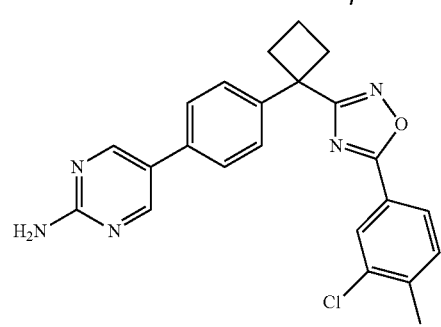

435
-continued
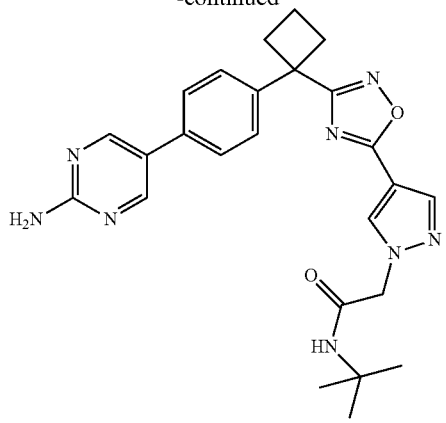
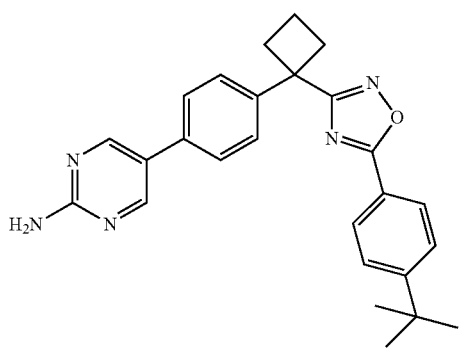
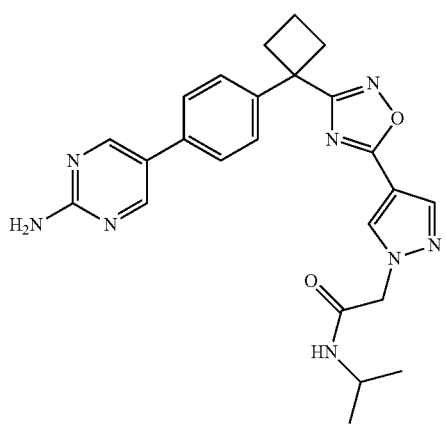
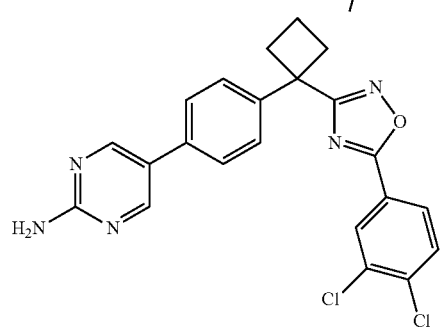
436
-continued
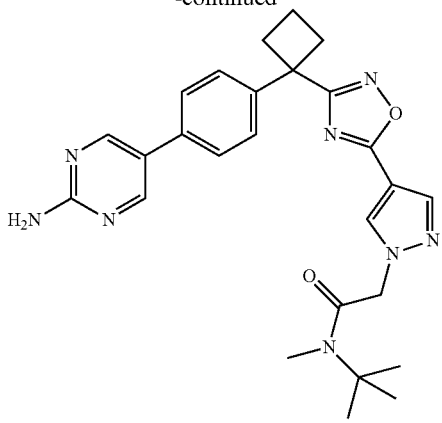
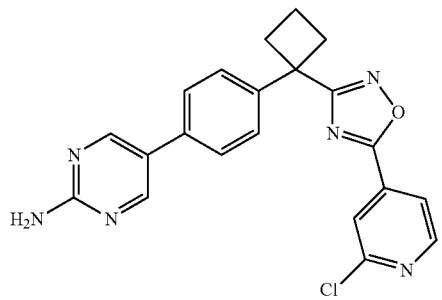
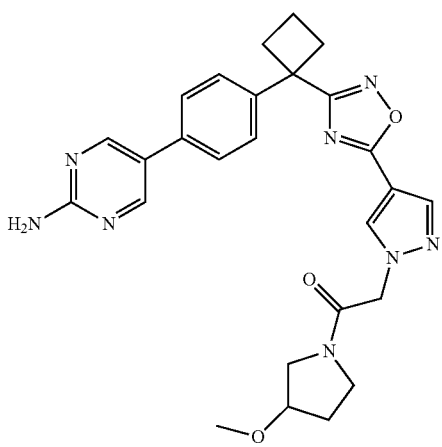
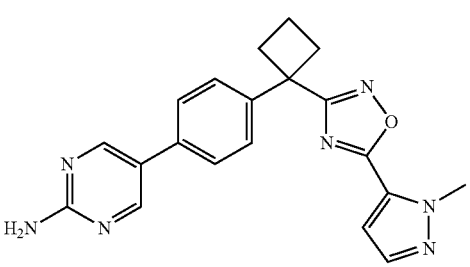

437
-continued
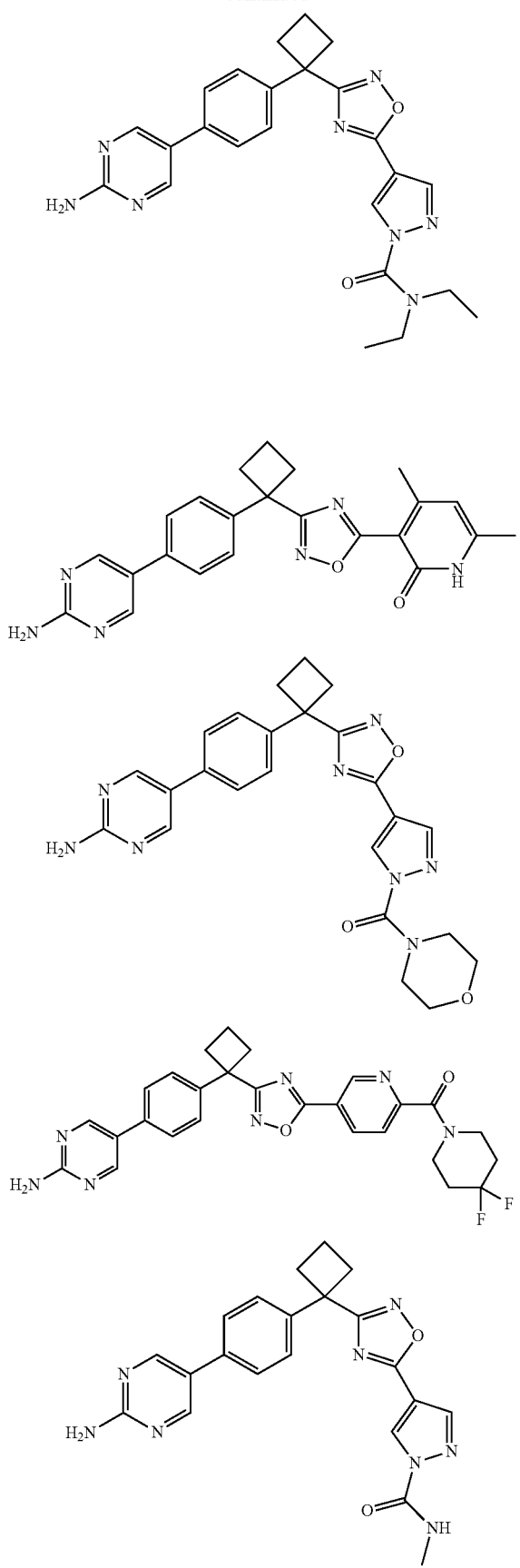
438
-continued
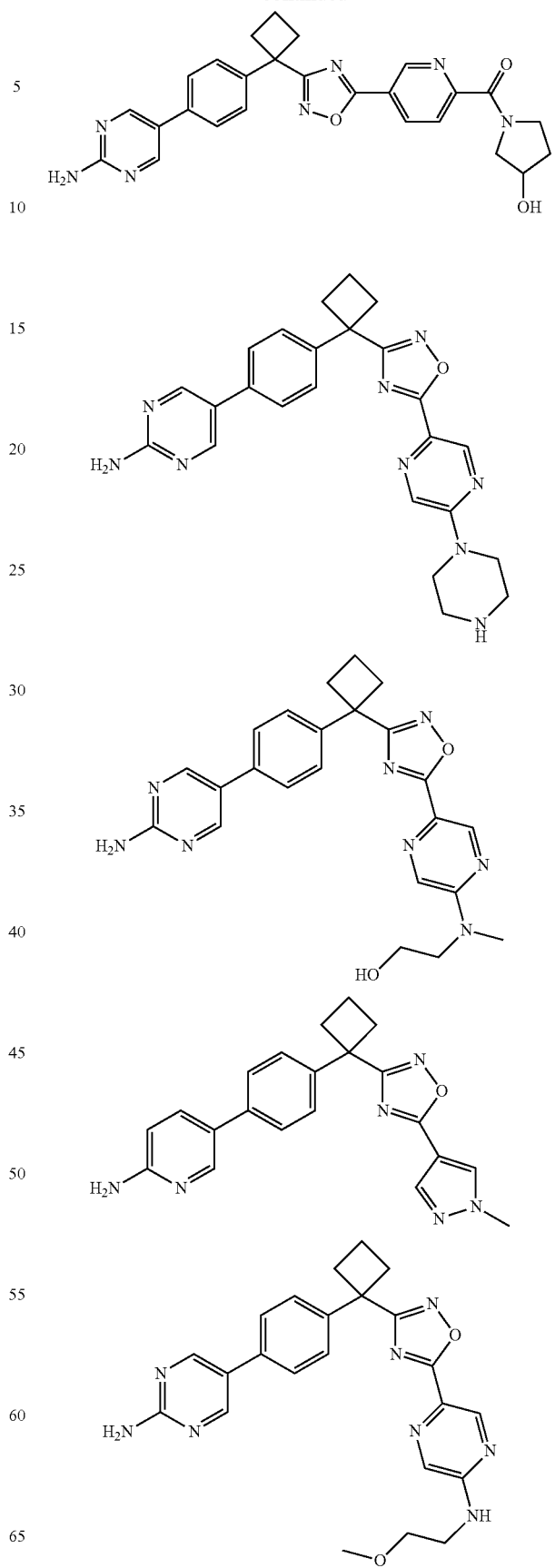

439
-continued
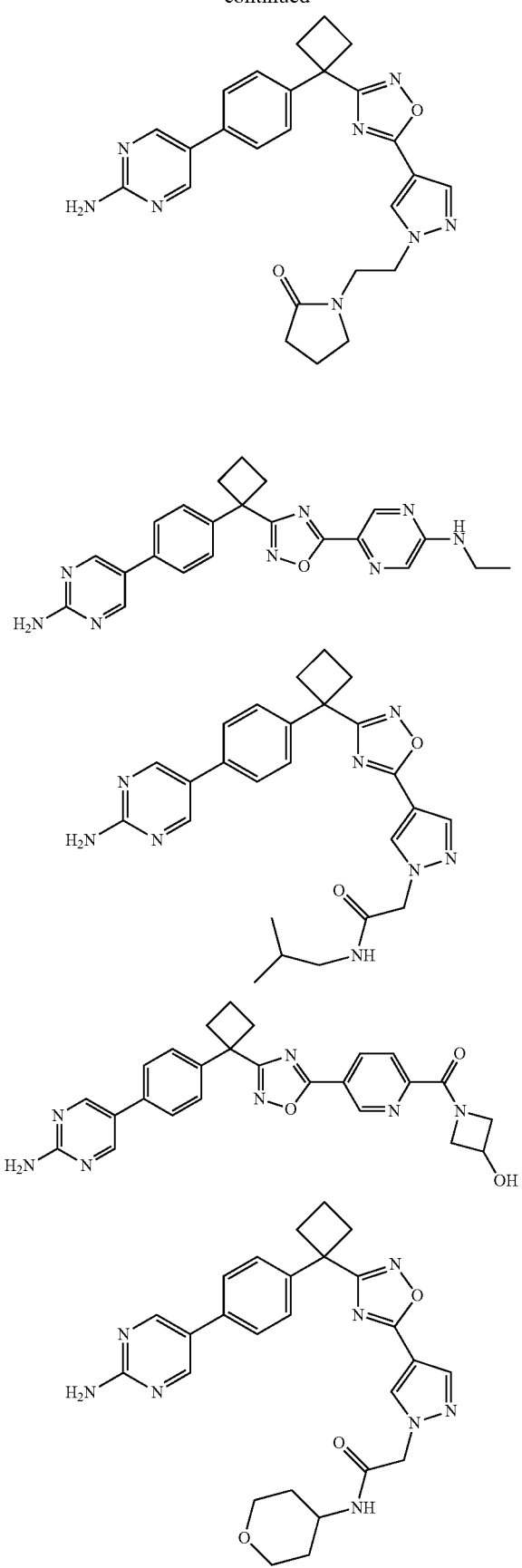
440
-continued
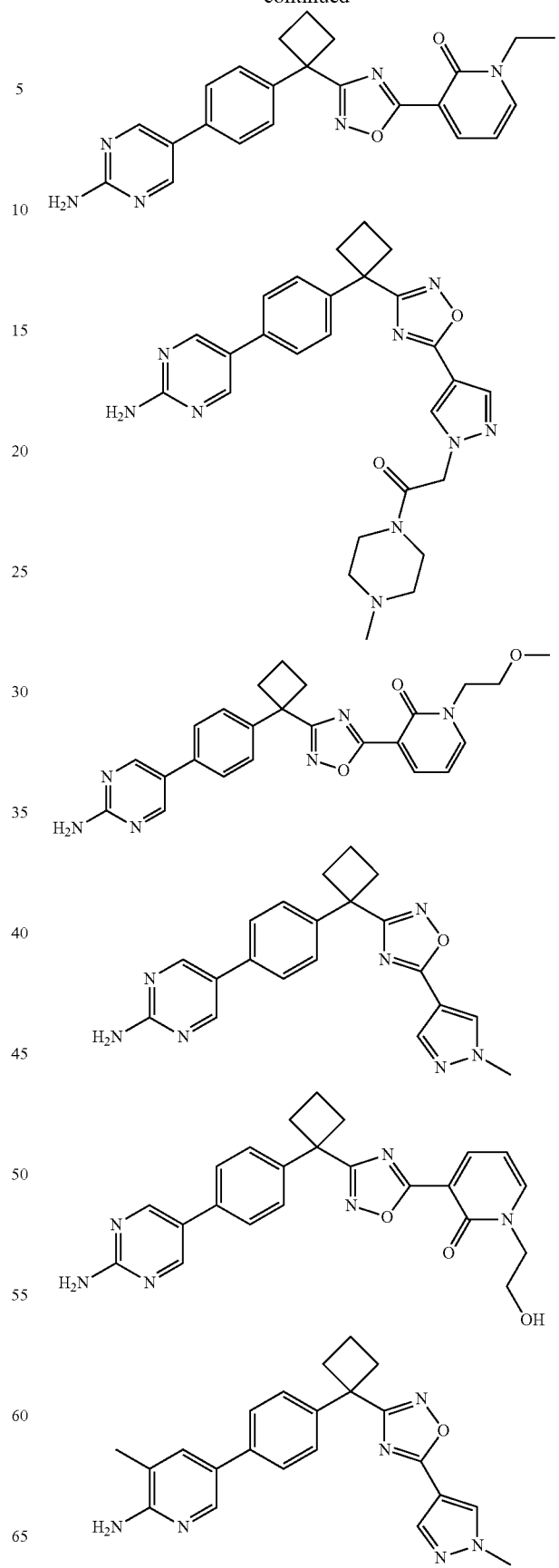

441
-continued
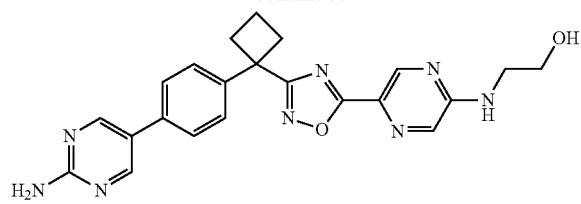
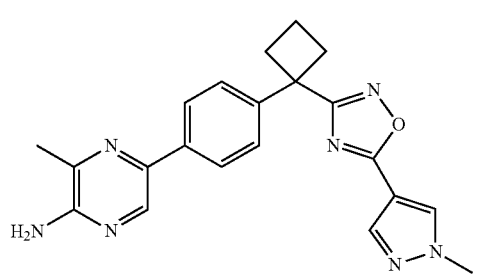
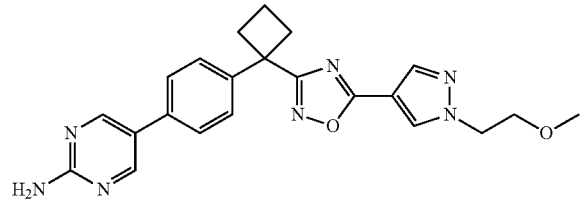
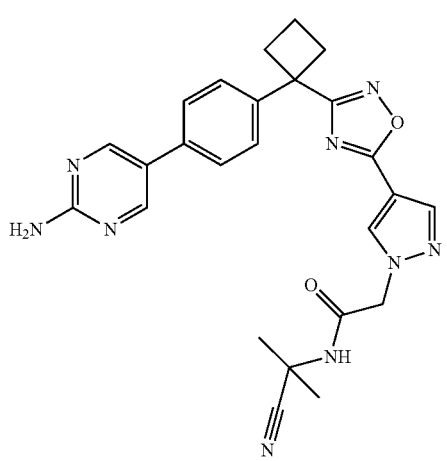
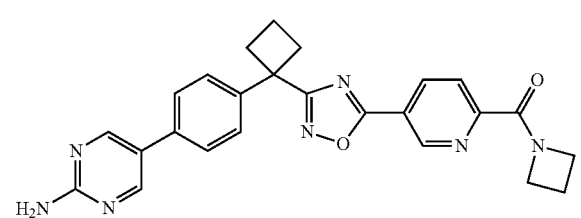
442
-continued
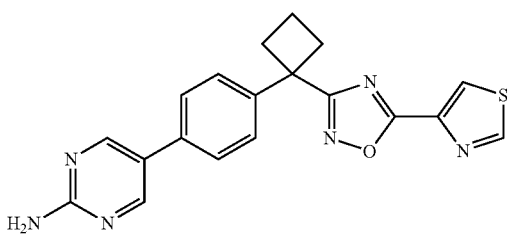
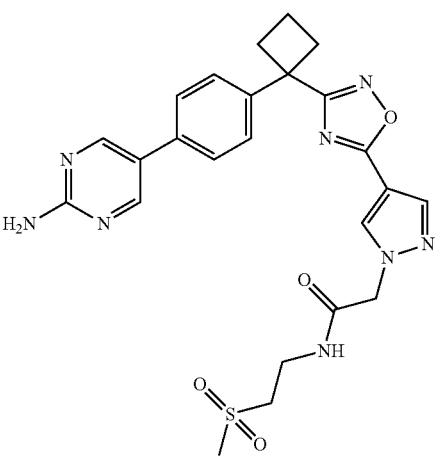
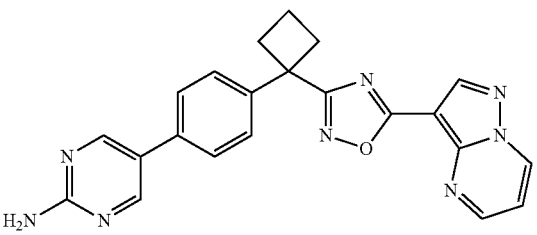

443
-continued
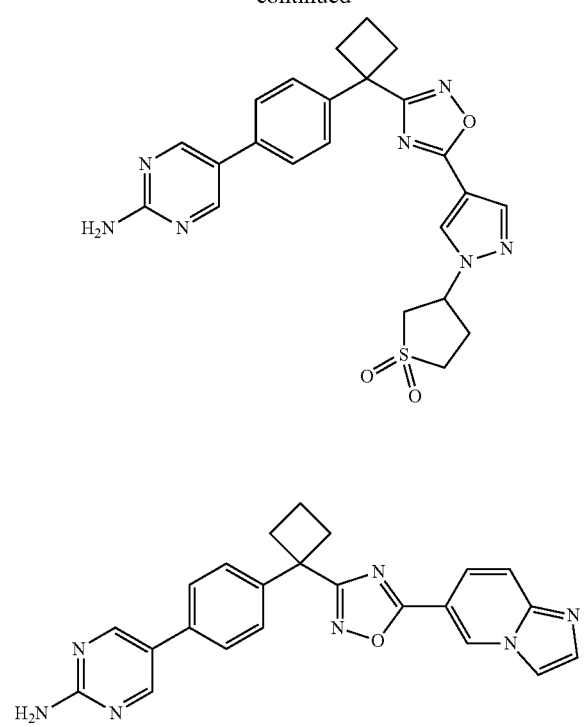
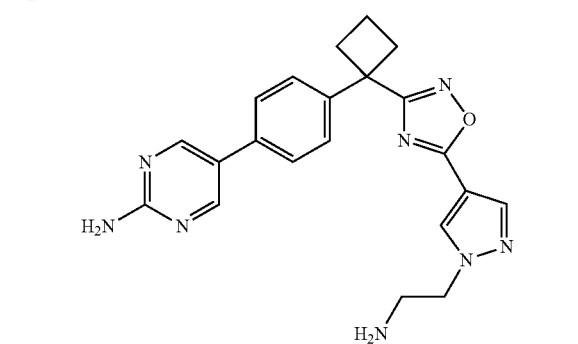
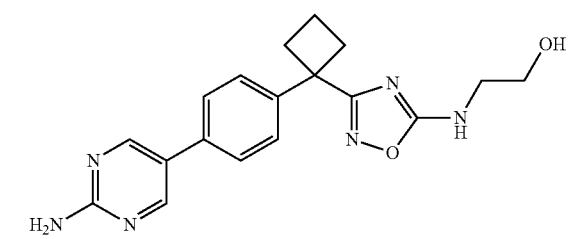
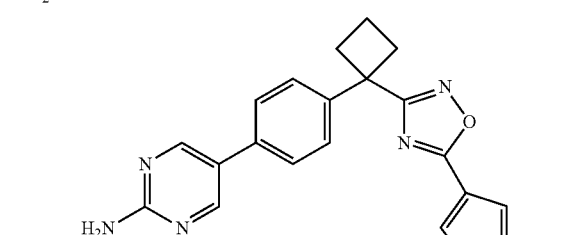
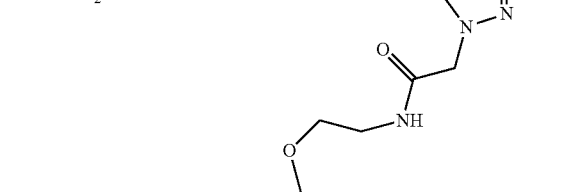
444
-continued
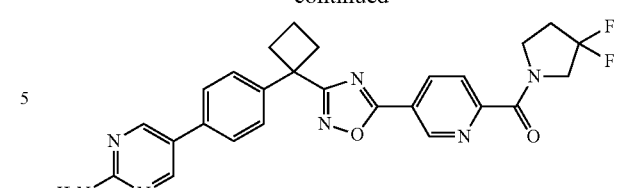
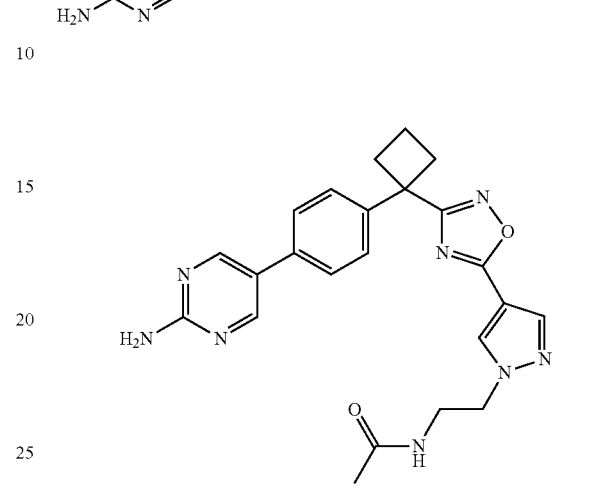
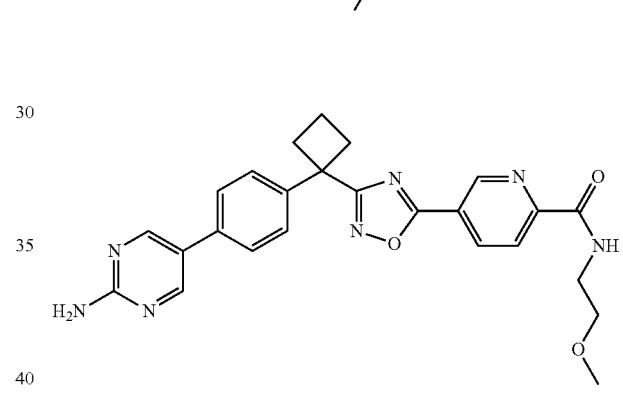
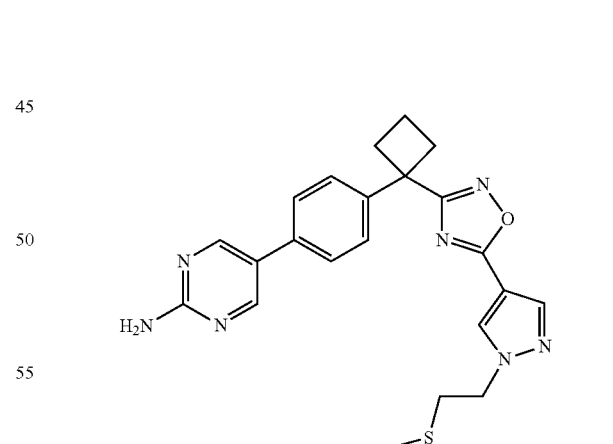
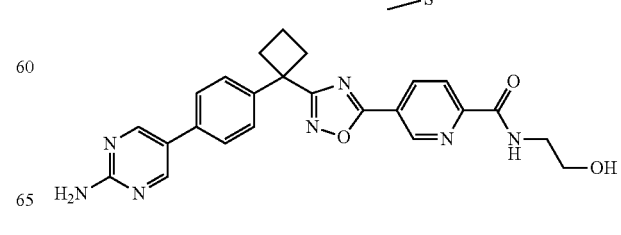

445
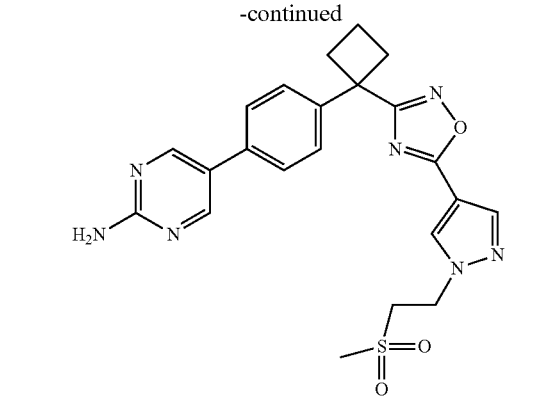
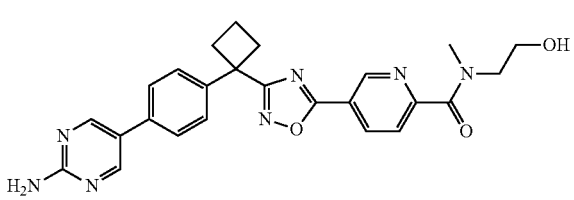
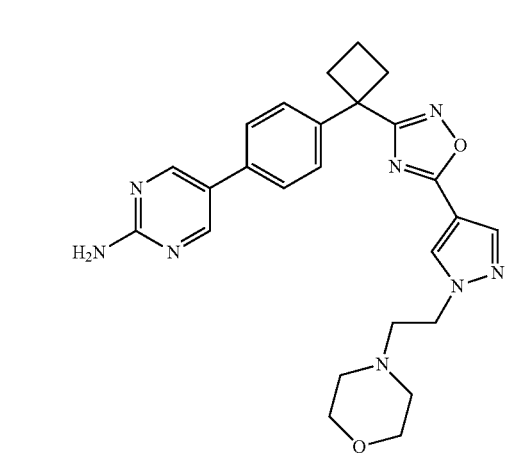
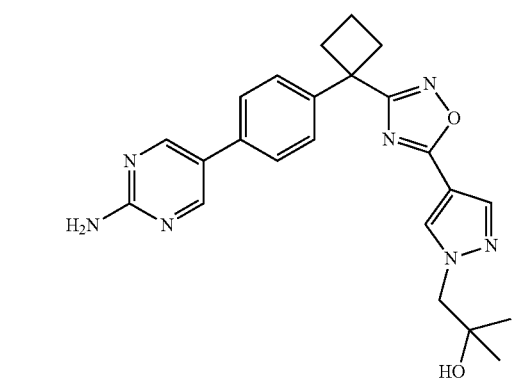
446
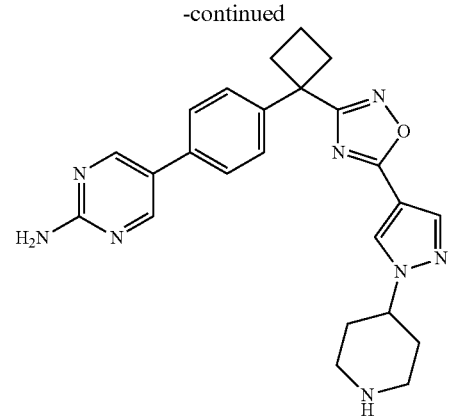
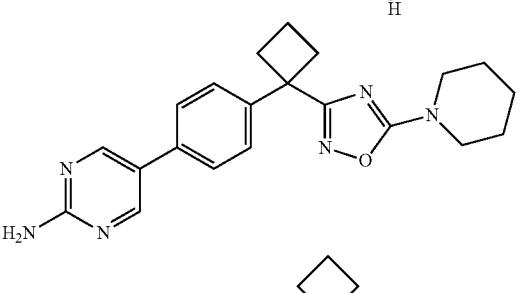
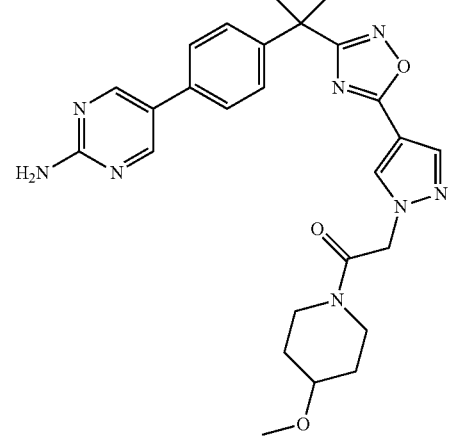
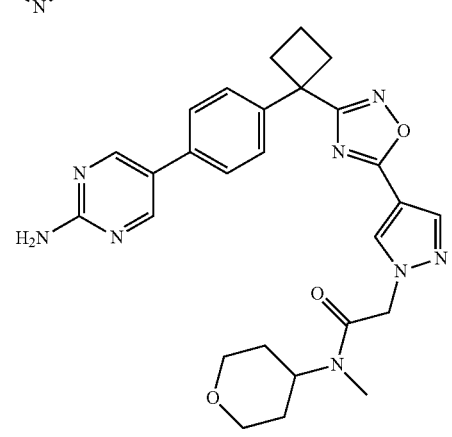

447
-continued
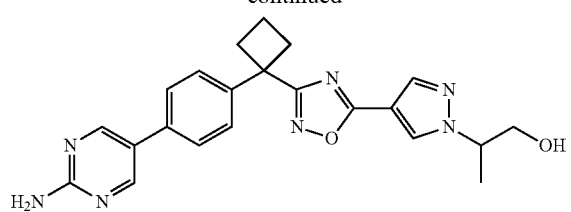
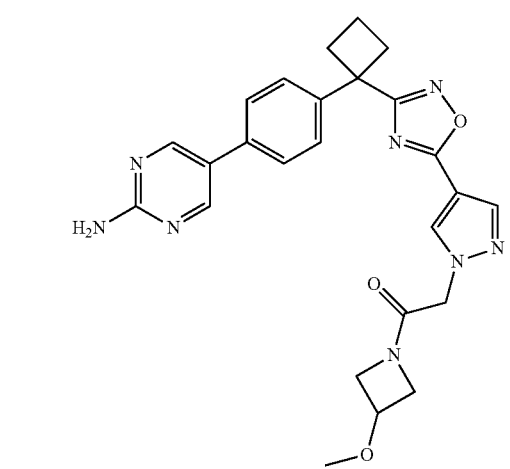
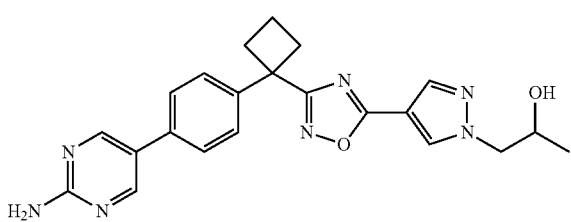
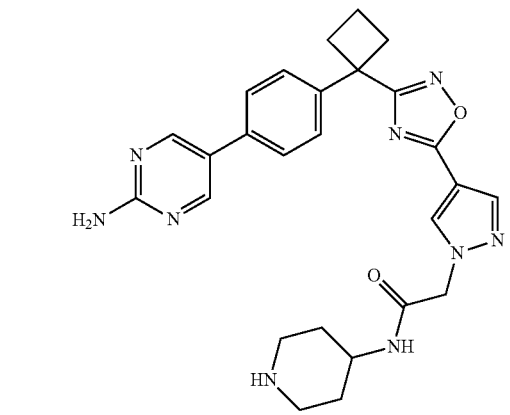
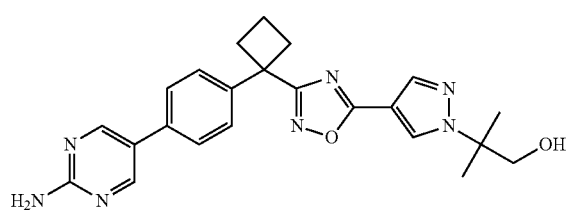
448
-continued
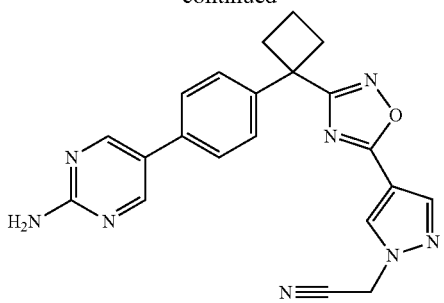
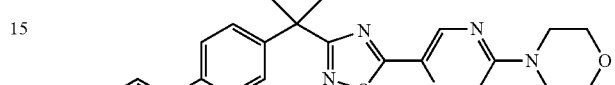
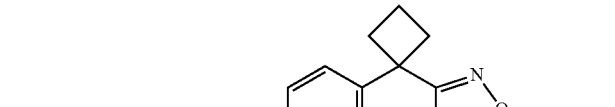
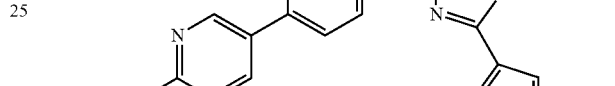
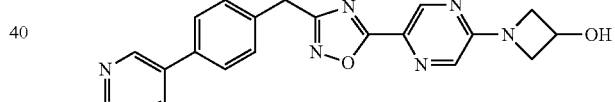
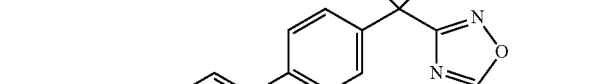
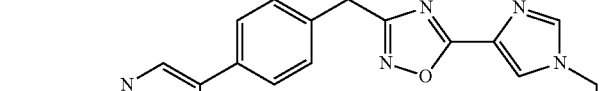

449
-continued
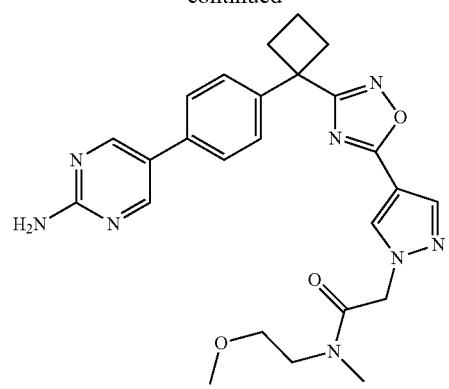
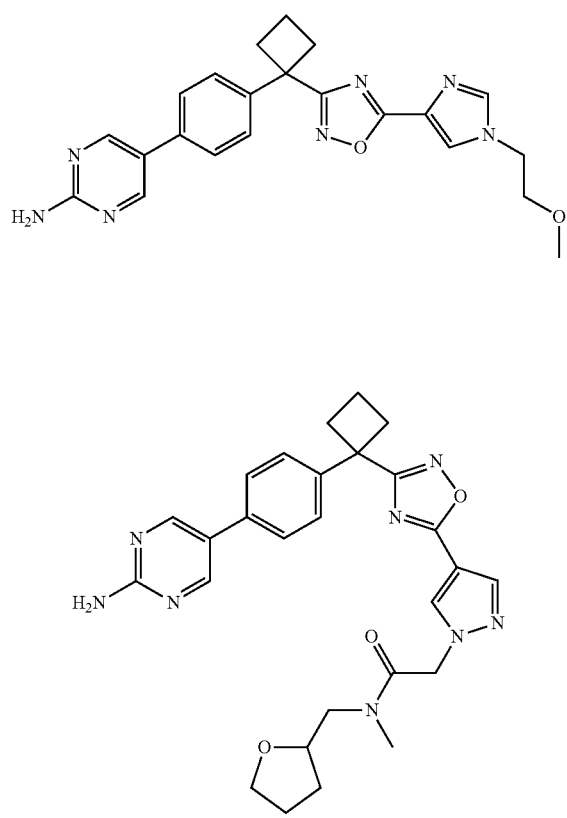
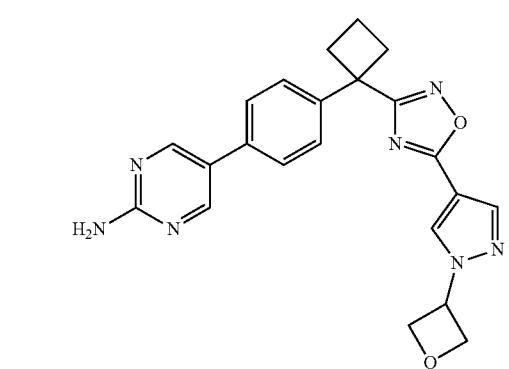
450
-continued
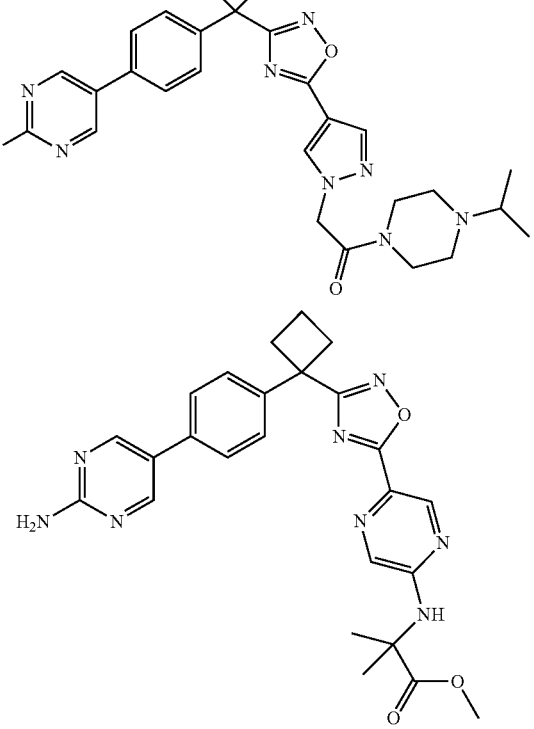
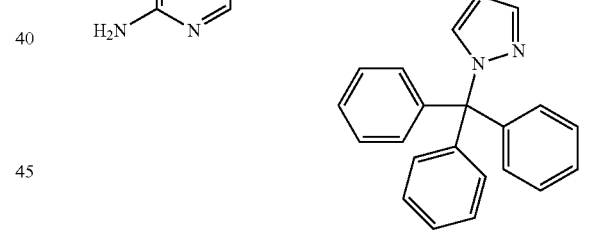
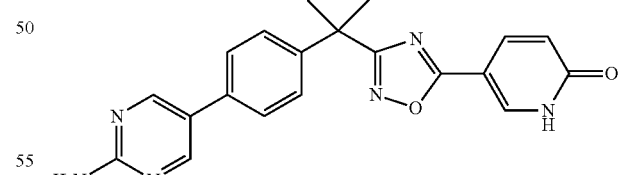
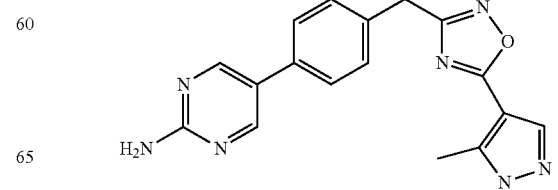

451
-continued
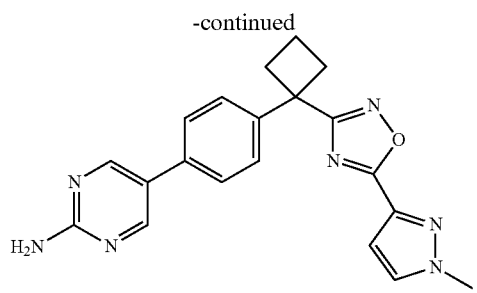
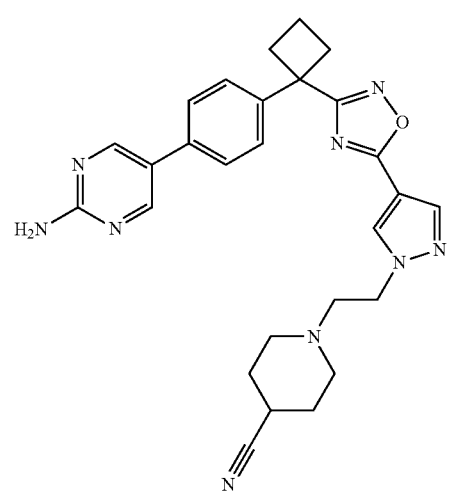
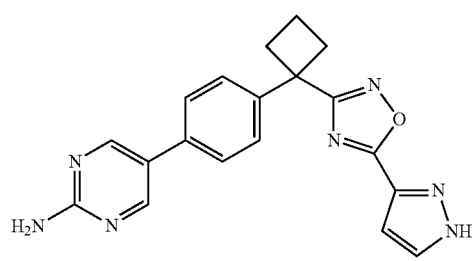
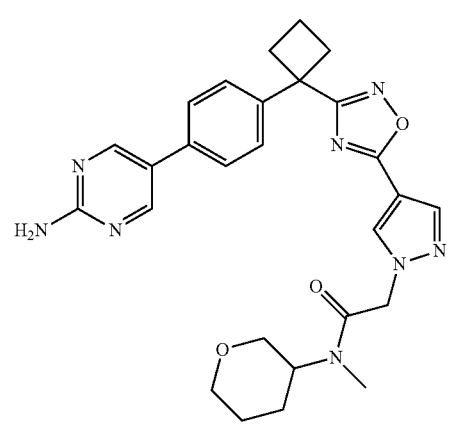
452
-continued
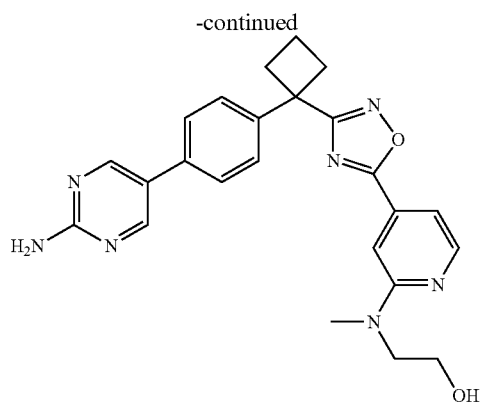
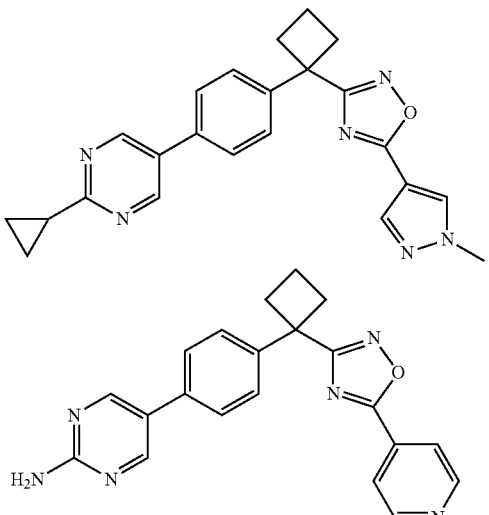
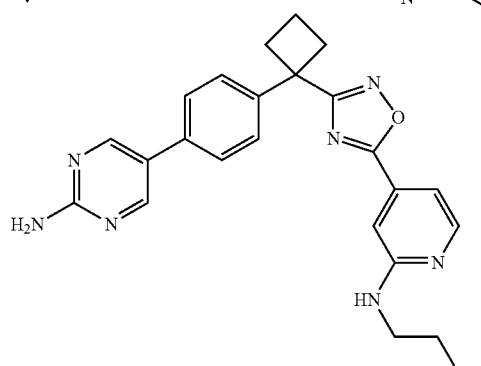
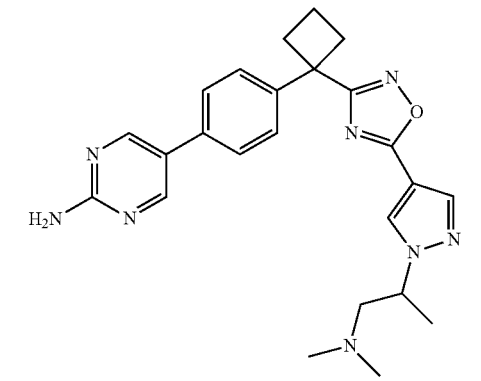
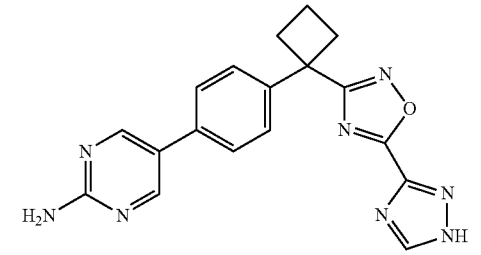

453
-continued
454
-continued
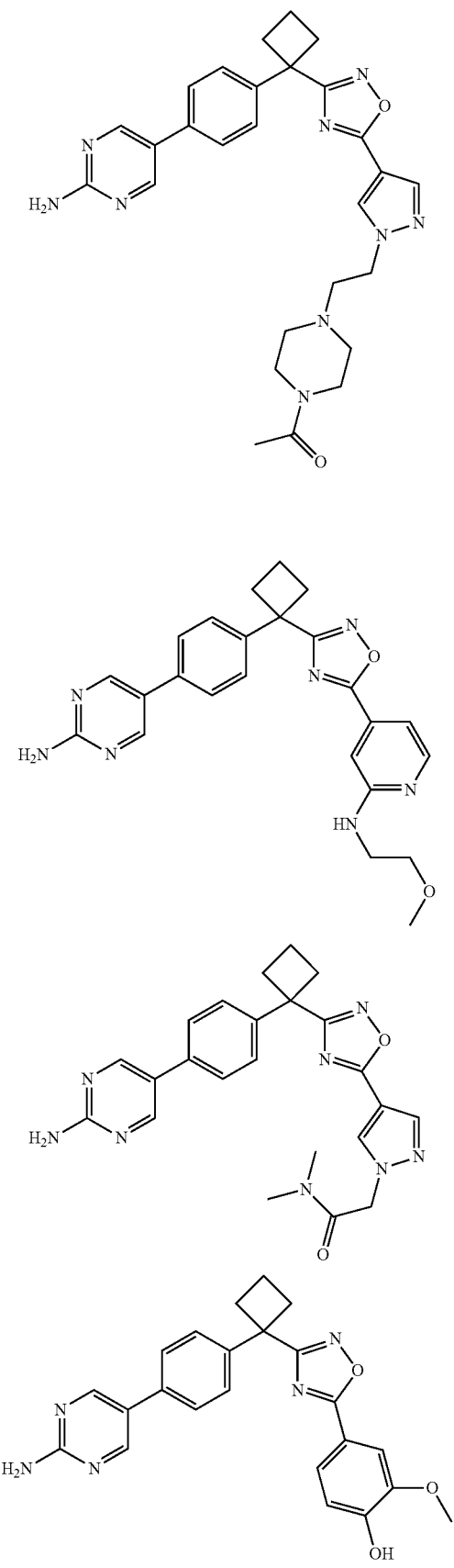
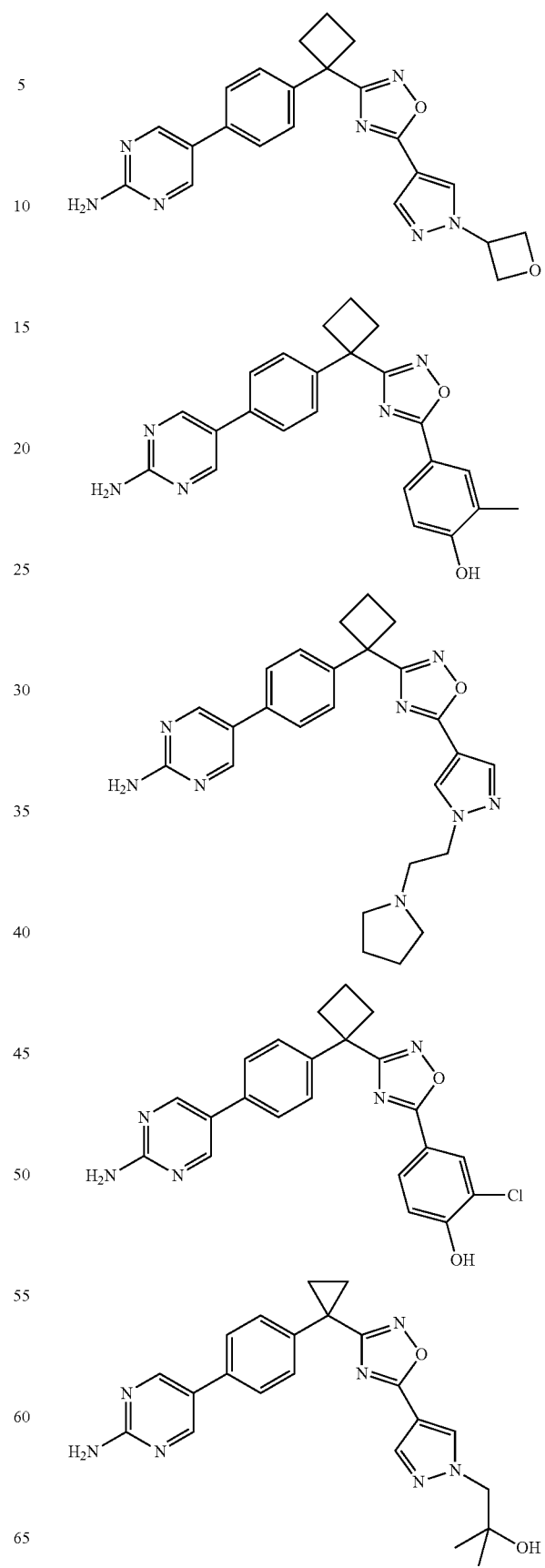

455
-continued
456
-continued
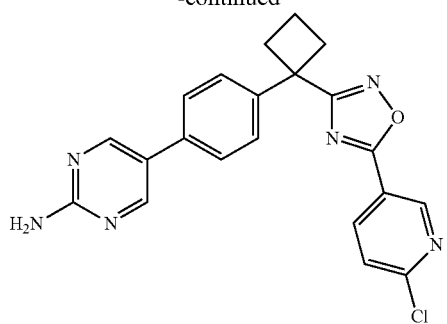
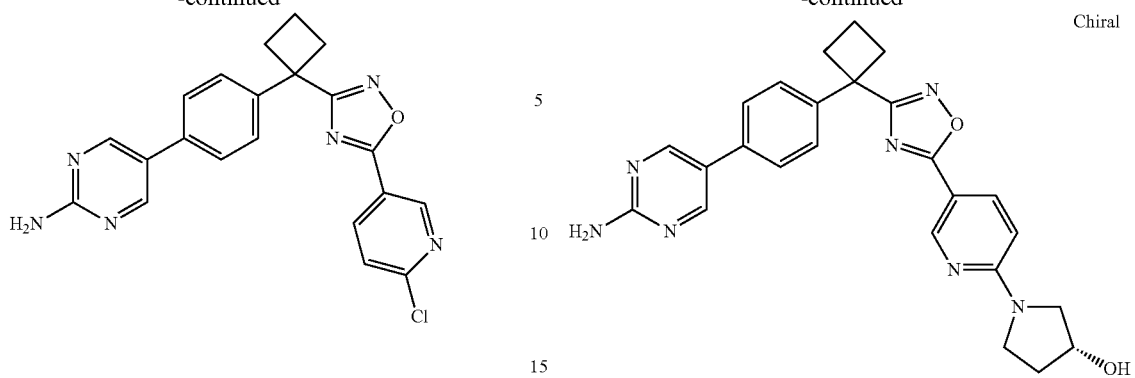
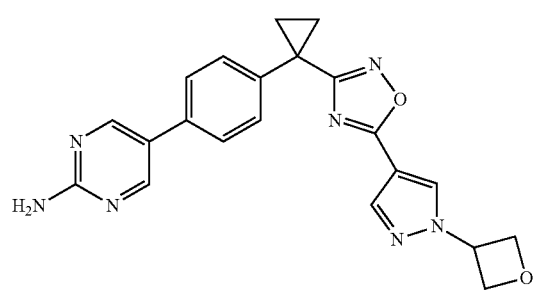
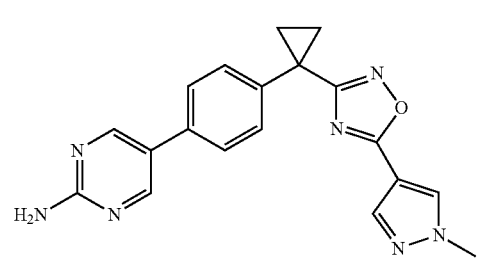
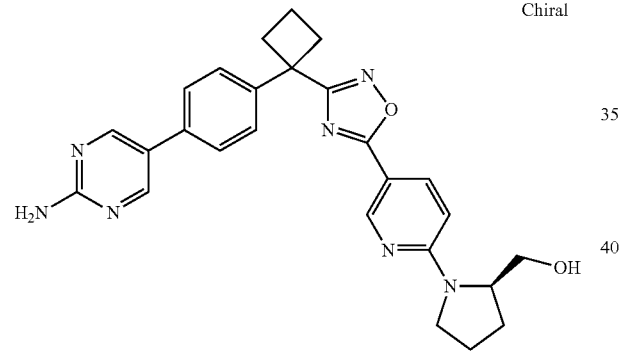
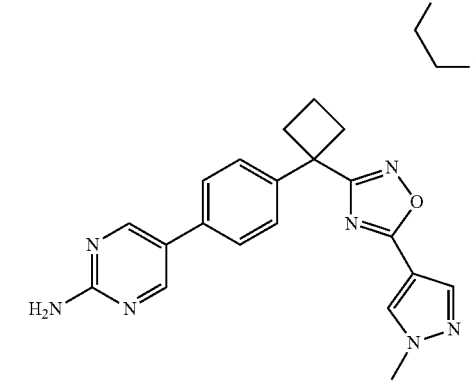
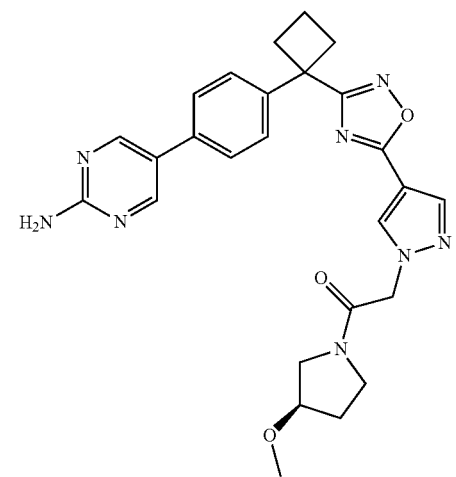
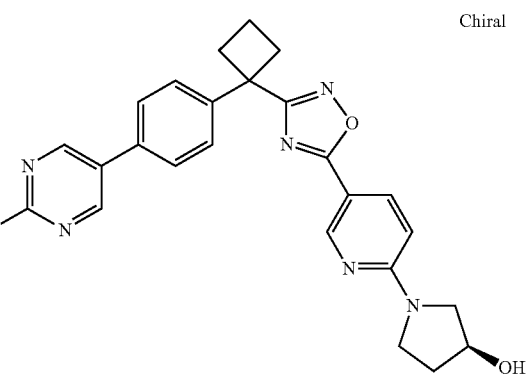

457
-continued
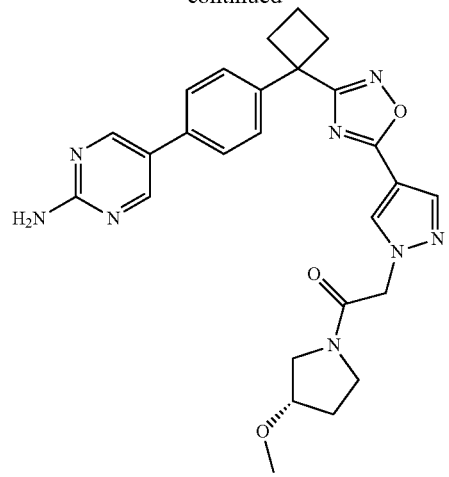
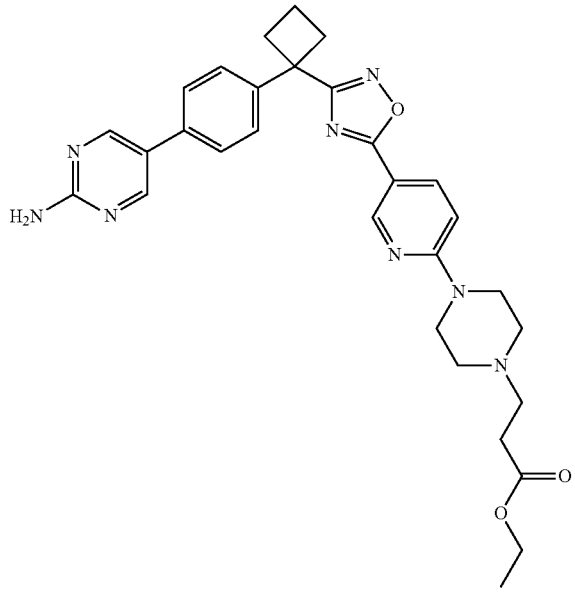
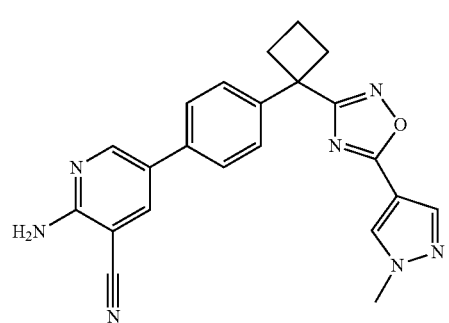
458
-continued
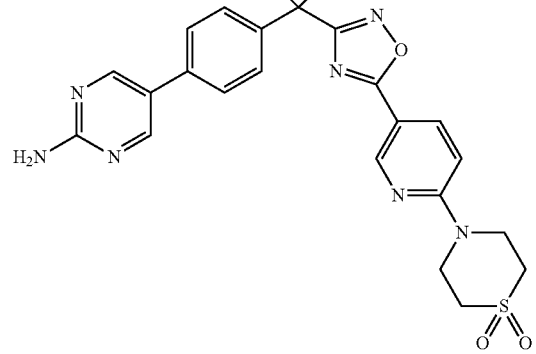
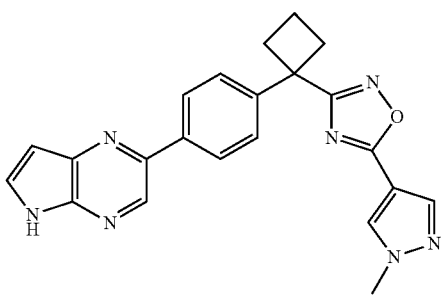
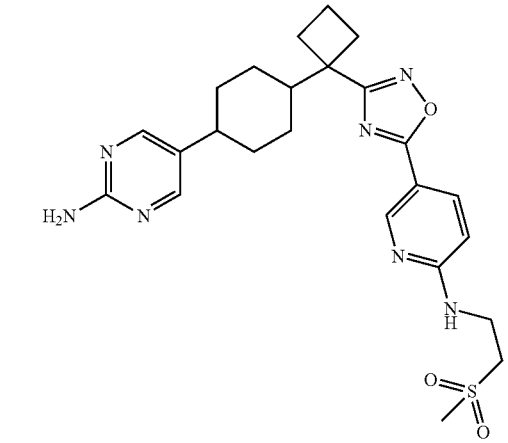
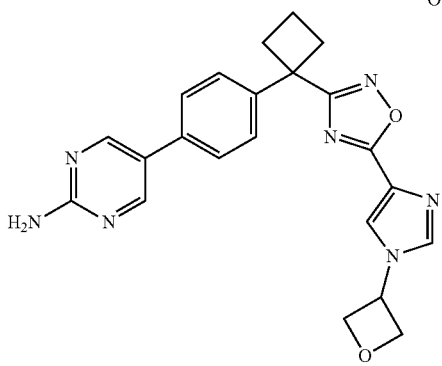

459
-continued
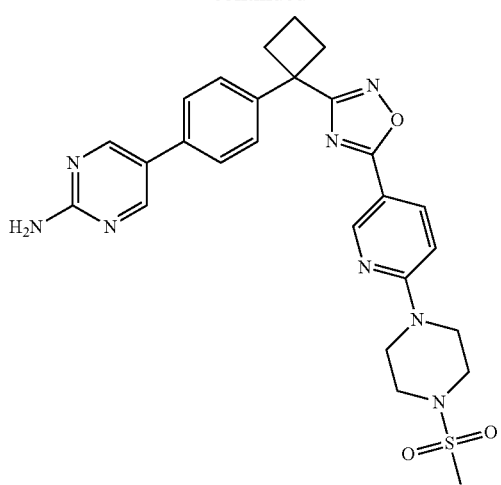
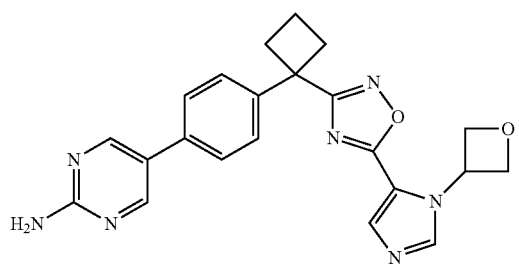
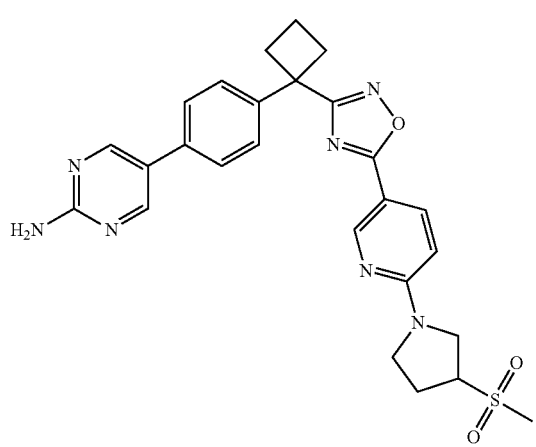
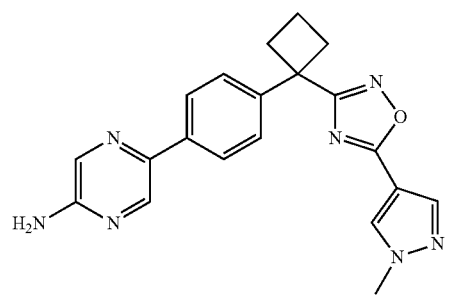
460
-continued
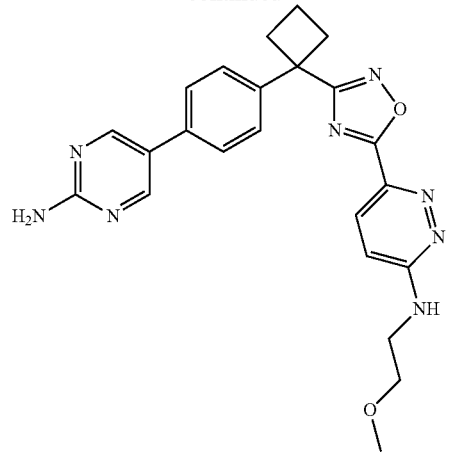
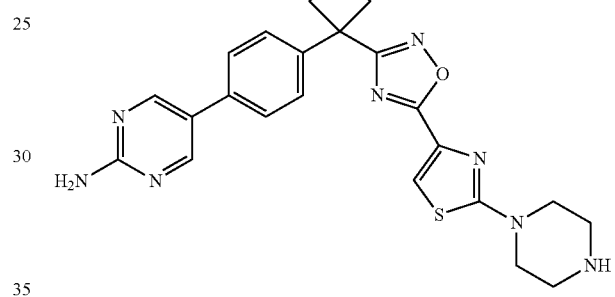
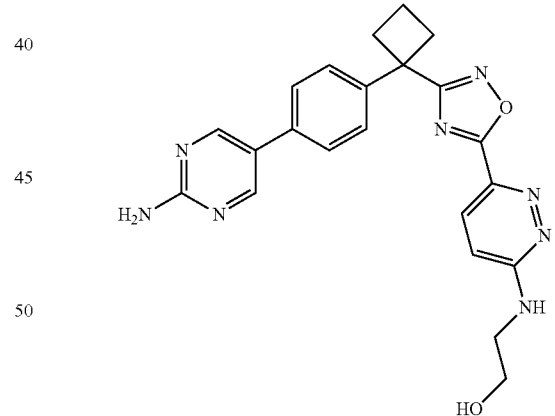
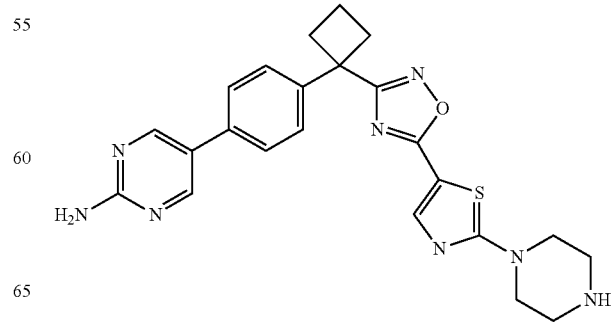

461
-continued
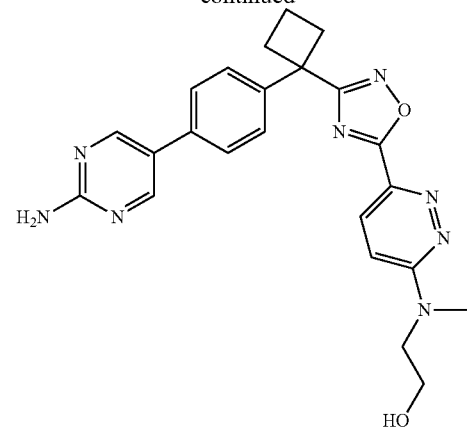
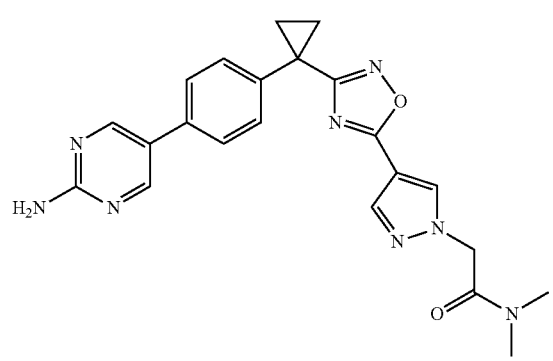
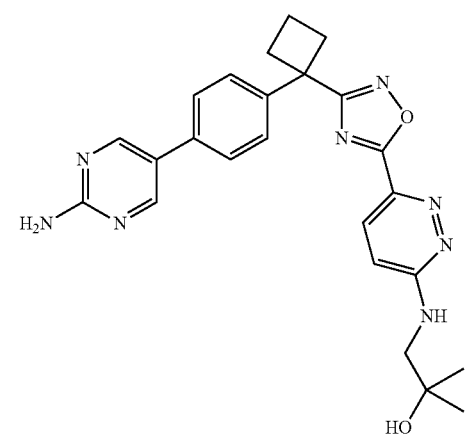
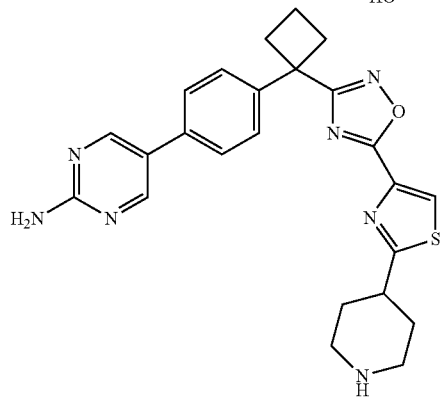
462
-continued
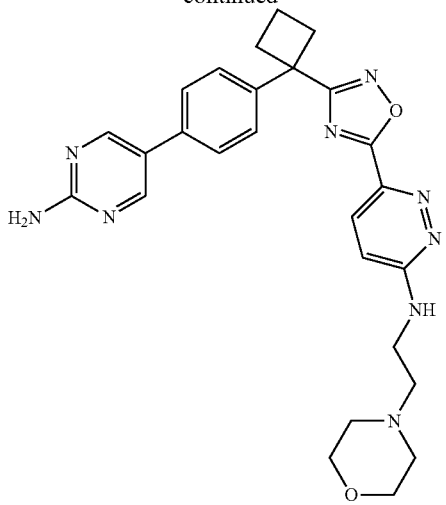
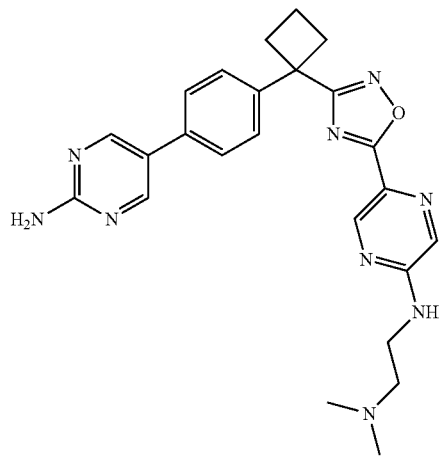
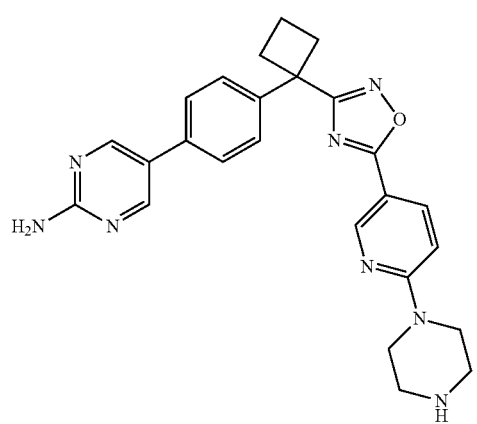

463
-continued
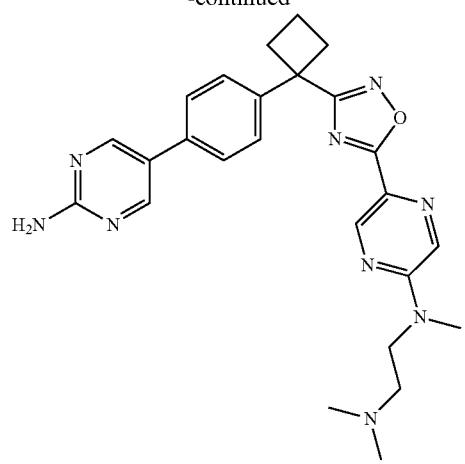
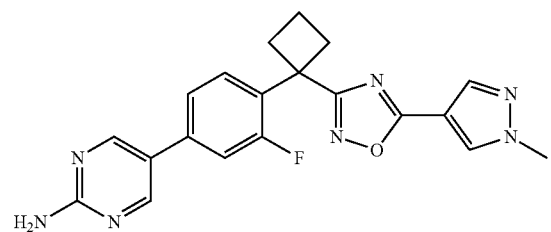
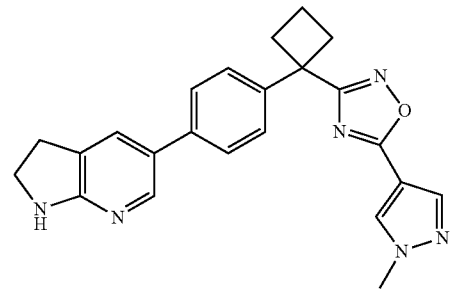
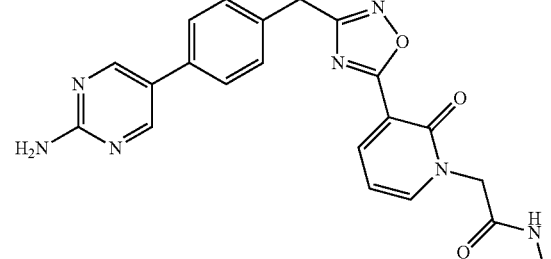
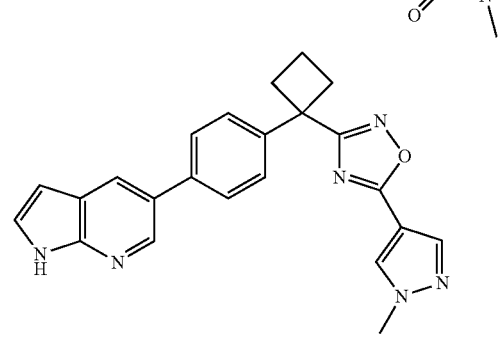
464
-continued
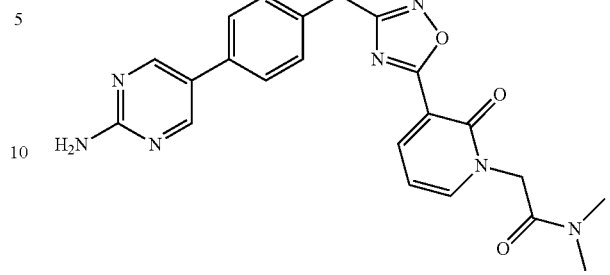
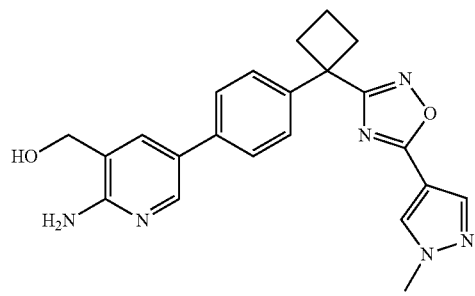
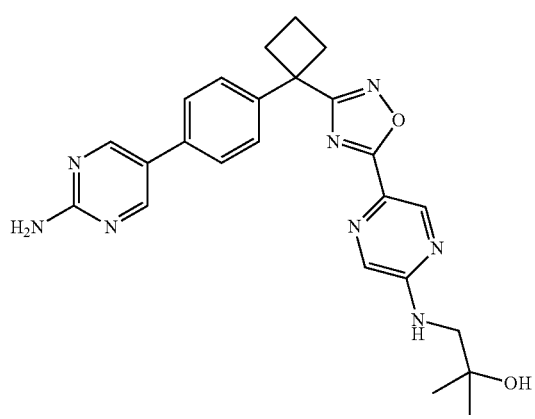
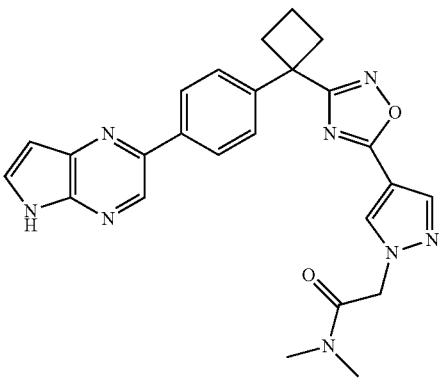

465
-continued
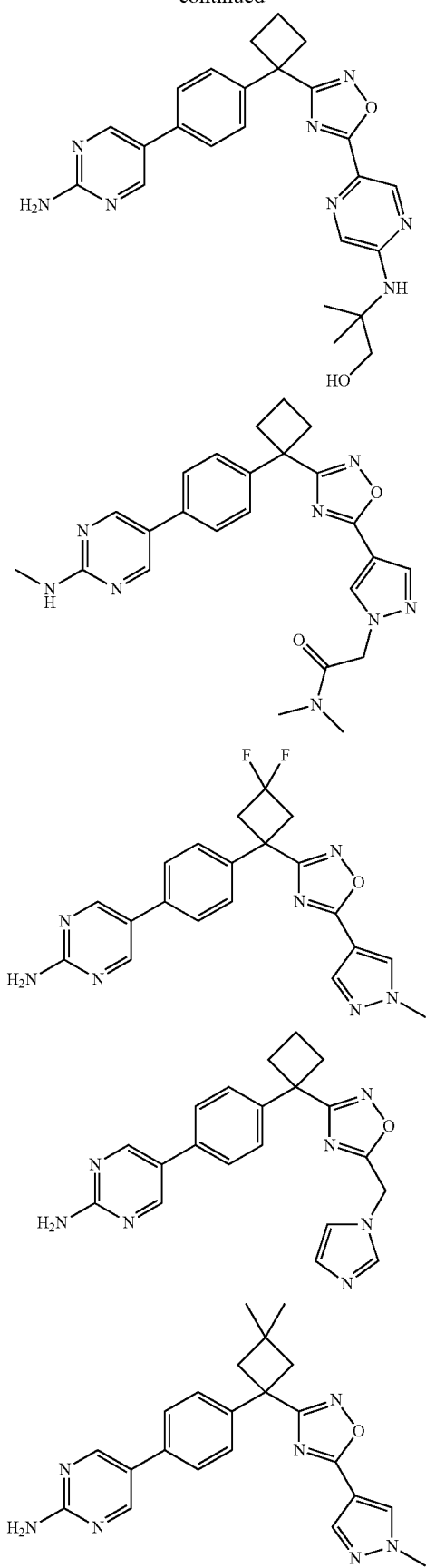
466
-continued
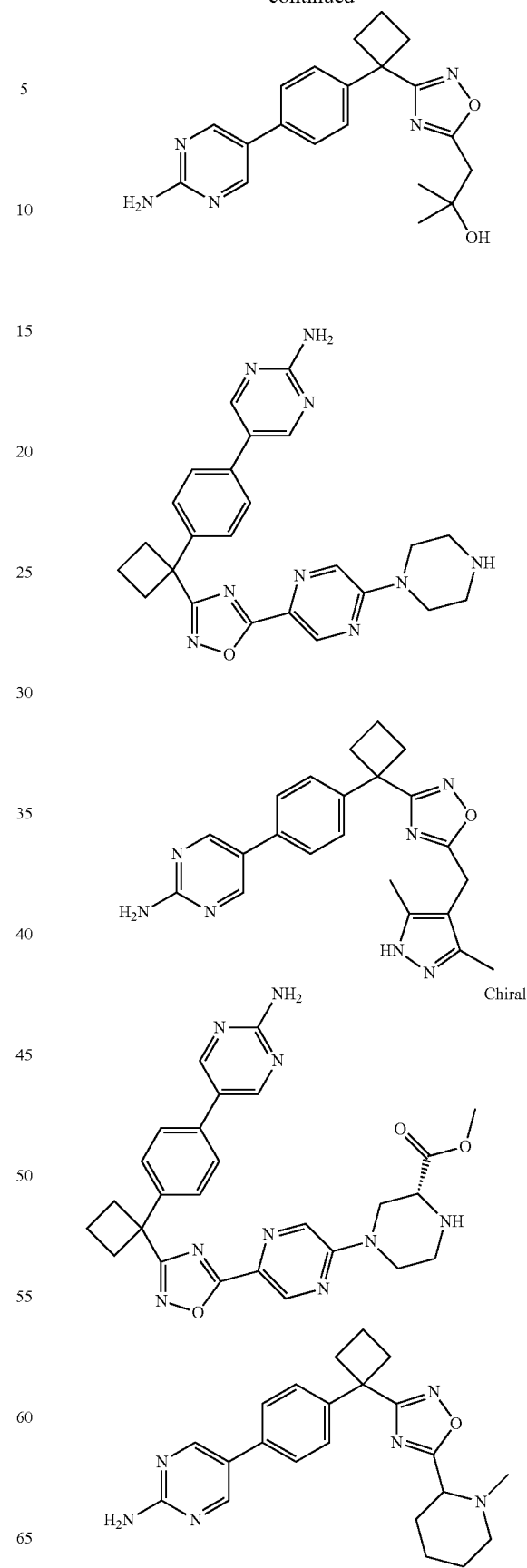

467
-continued
468
-continued
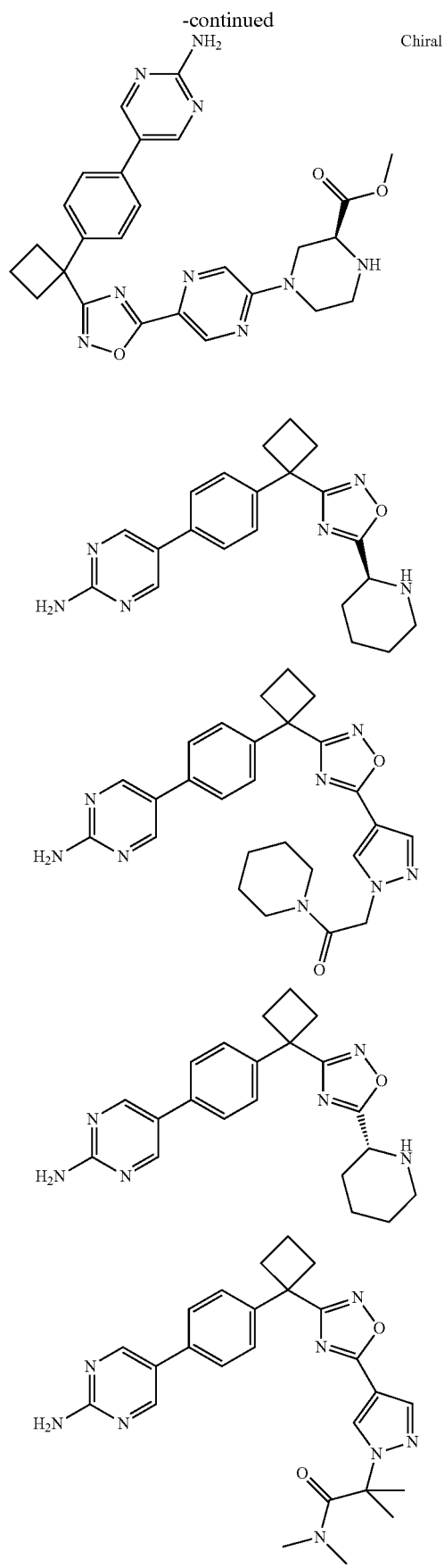
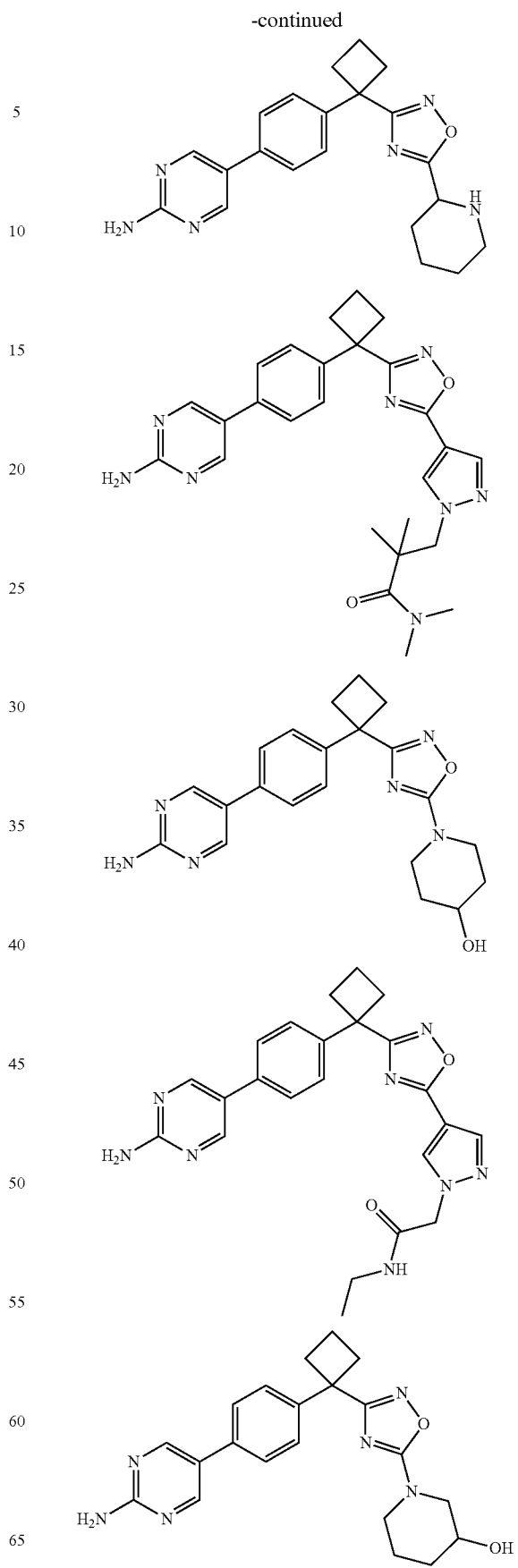

469
-continued
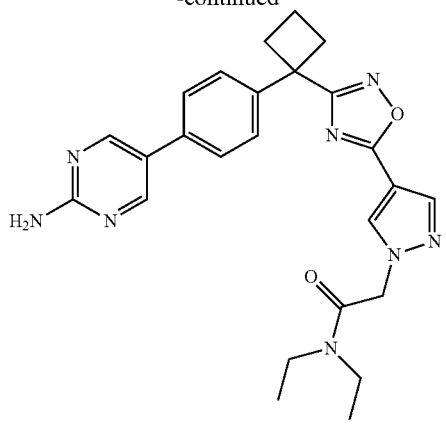
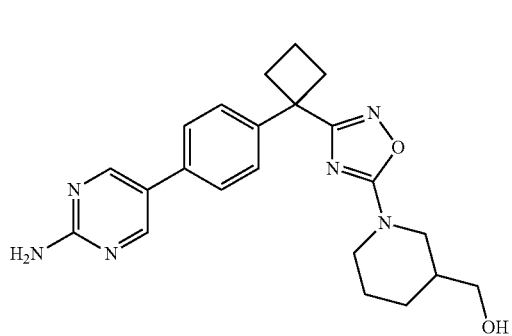
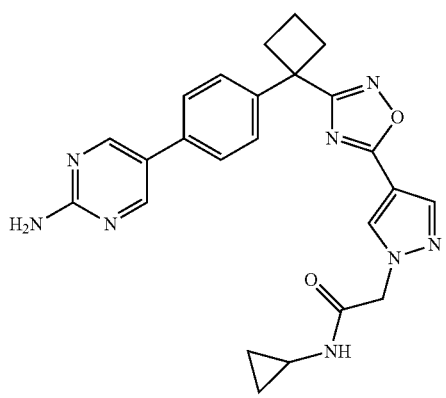
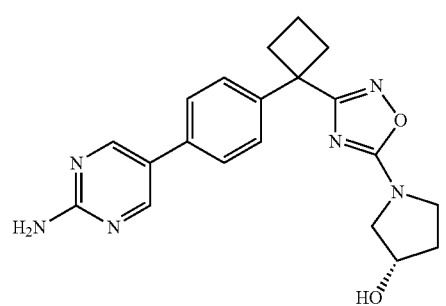
470
-continued
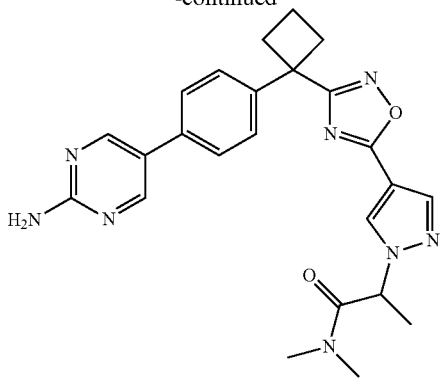
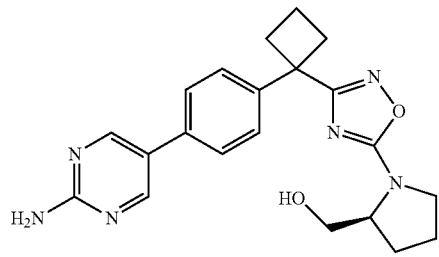
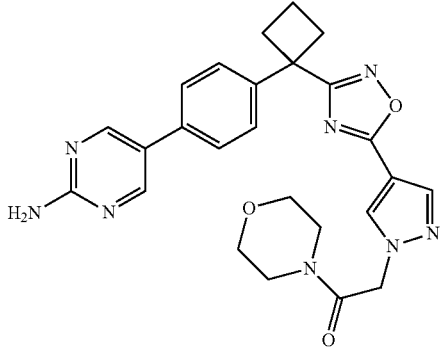
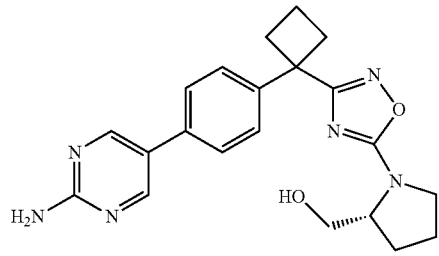
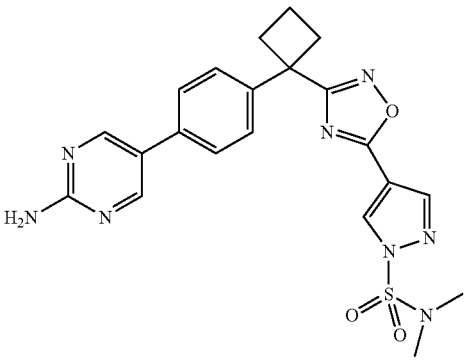

471
-continued
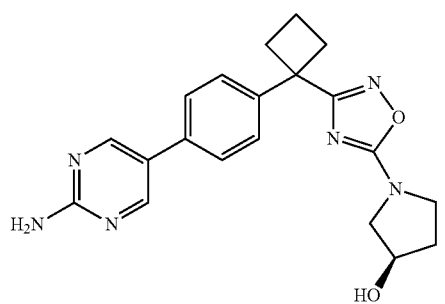
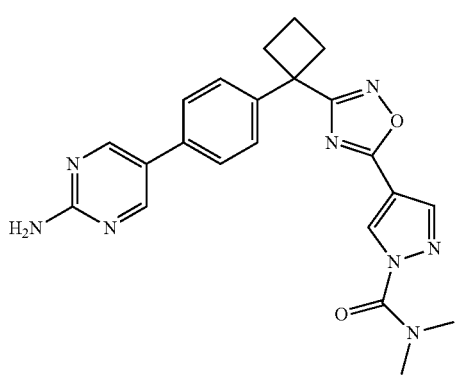
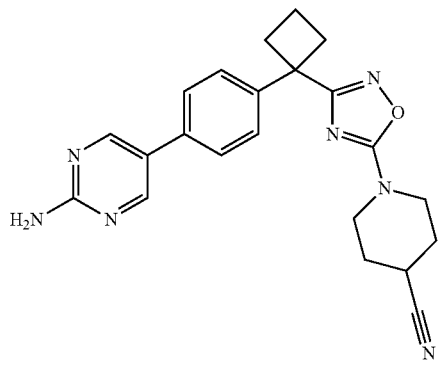
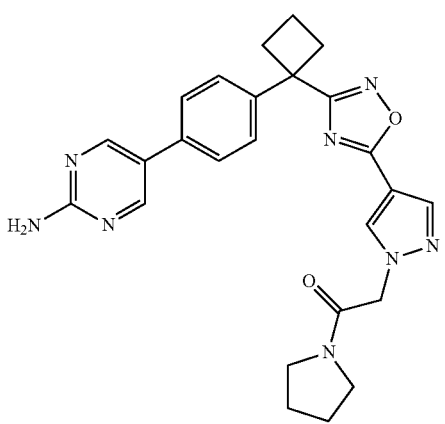
472
-continued
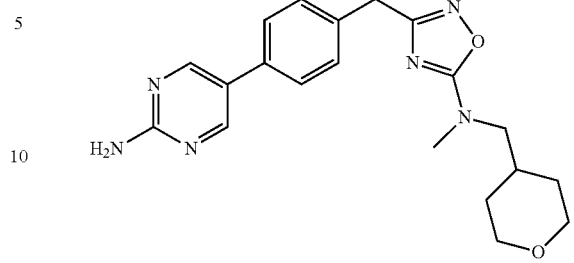
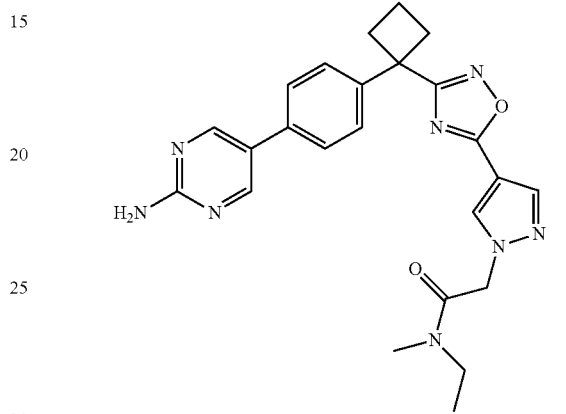
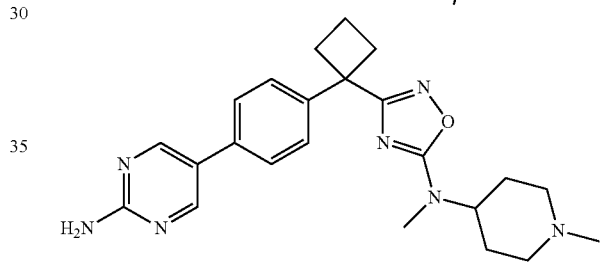
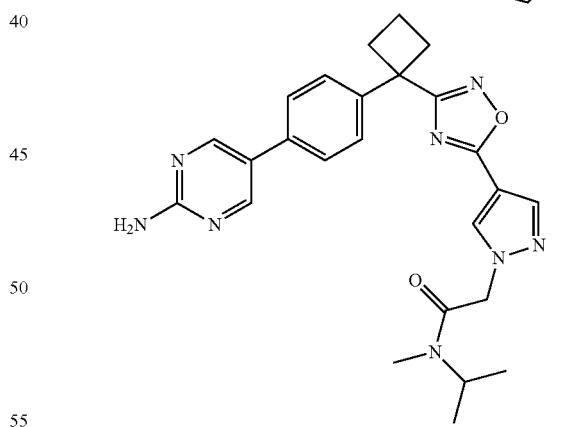
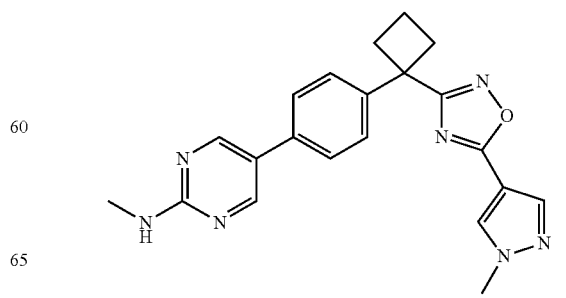

473
-continued
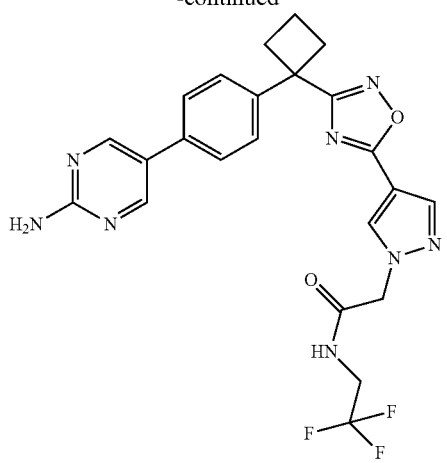
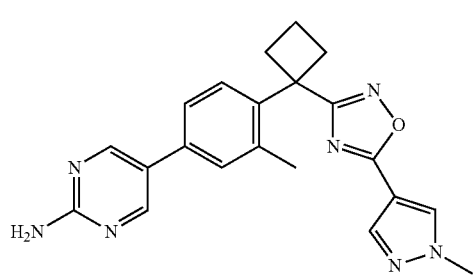
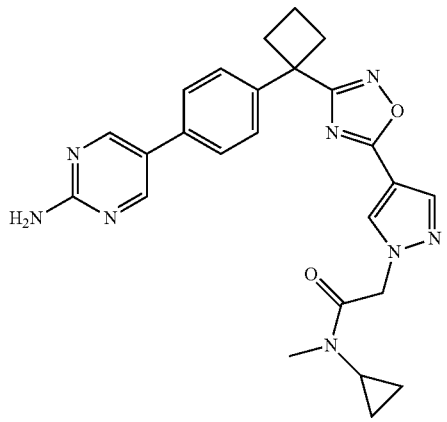
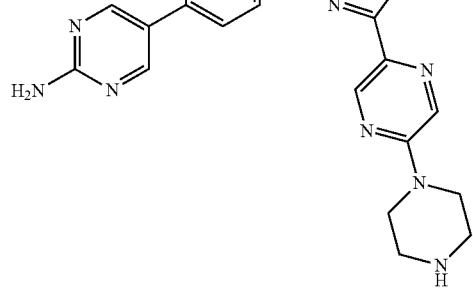
474
-continued
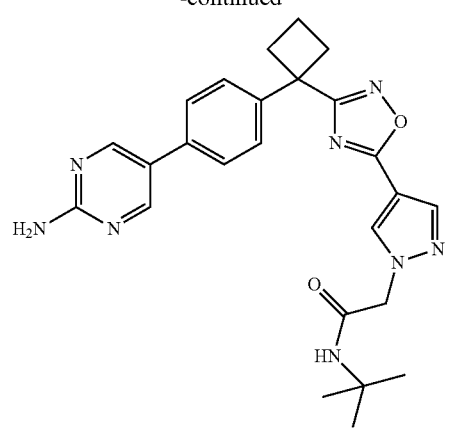
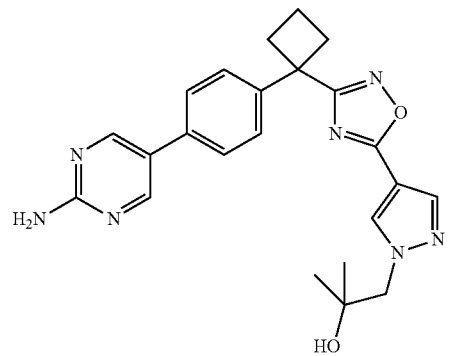
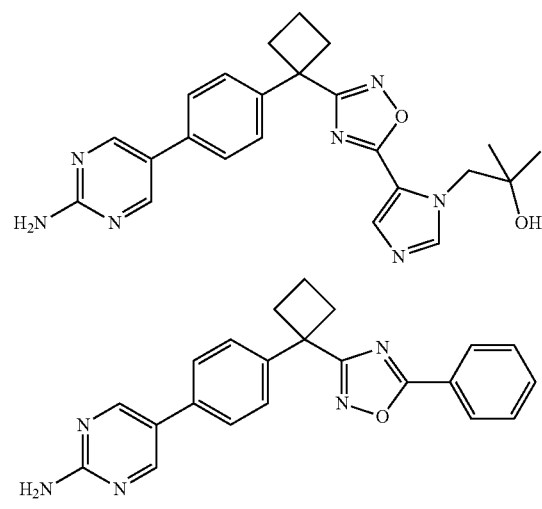

475
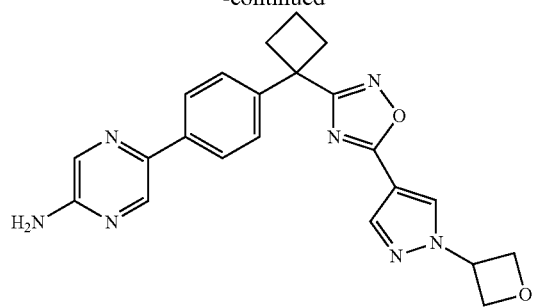
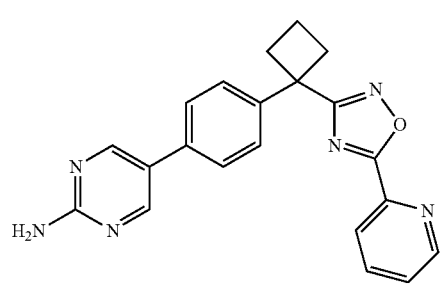
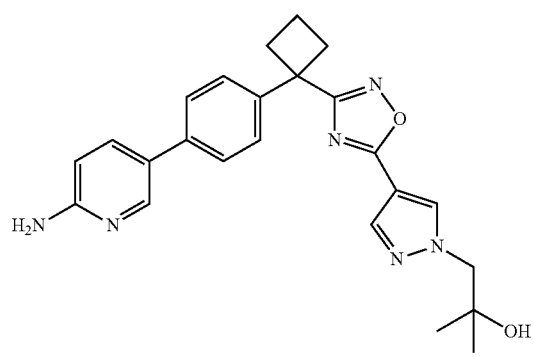
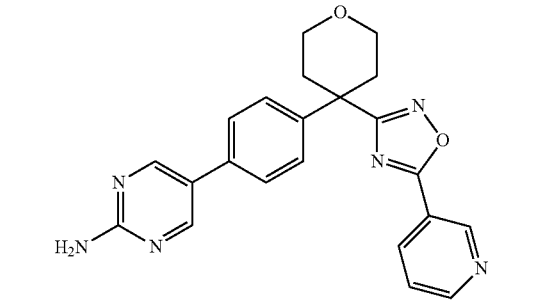
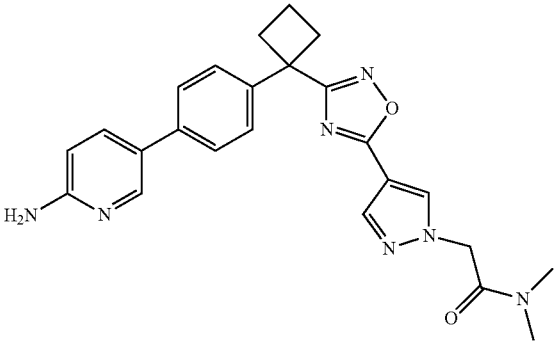
476
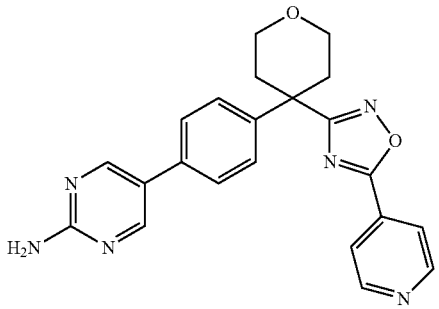
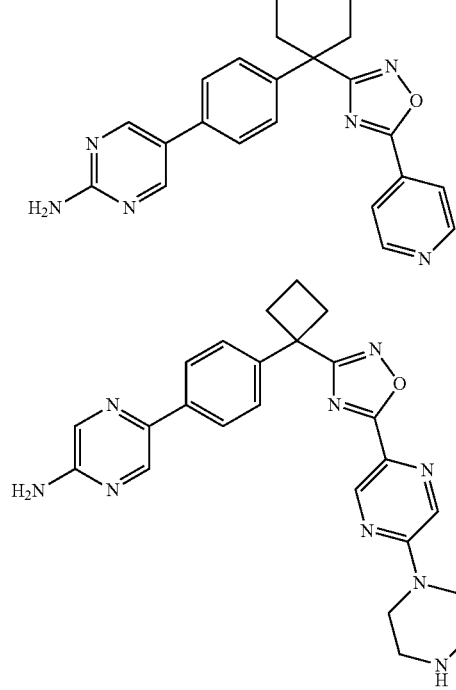
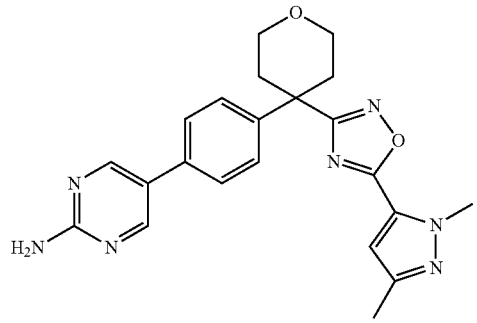
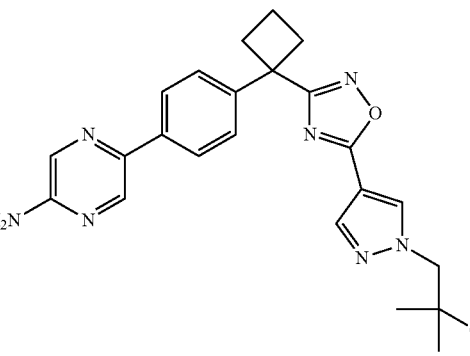
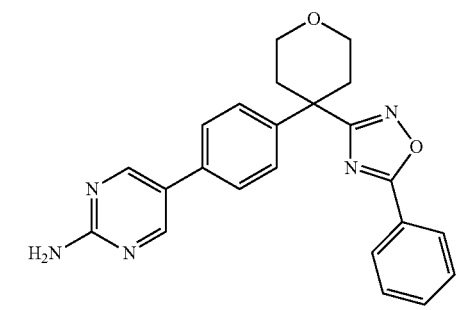

477
-continued
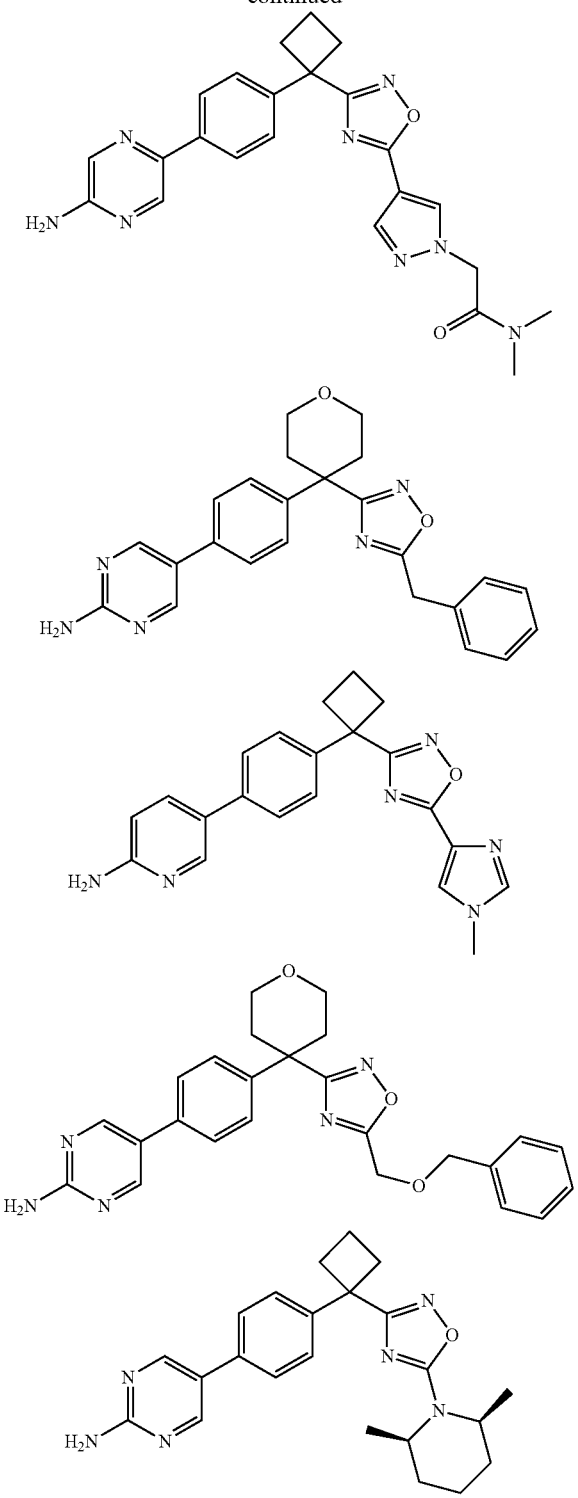
478
-continued
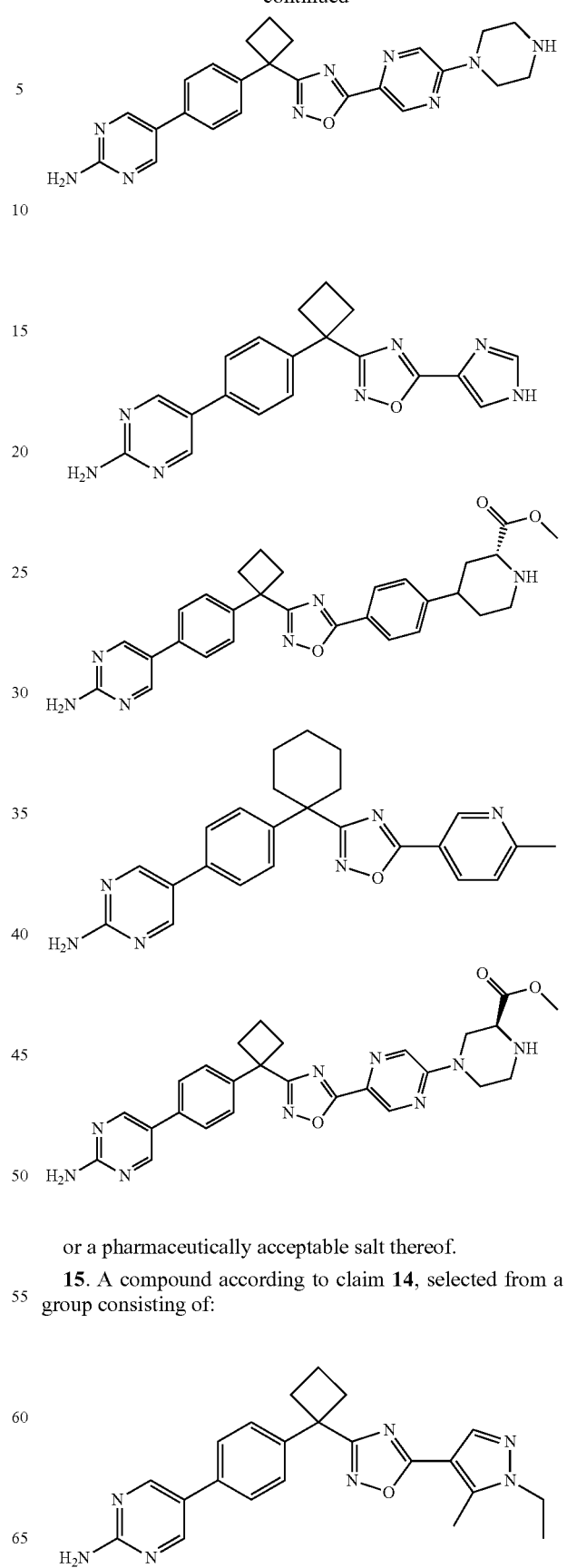
or a pharmaceutically acceptable salt thereof.
15. A compound according to claim 14, selected from a group consisting of:

479
-continued
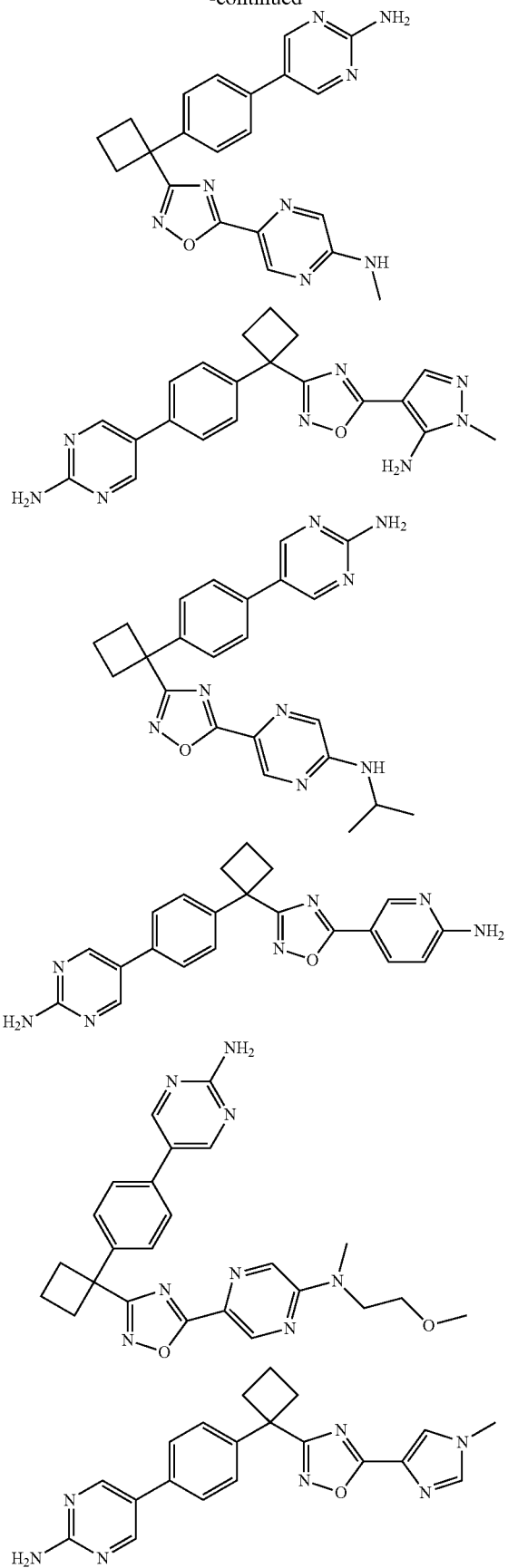
480
-continued
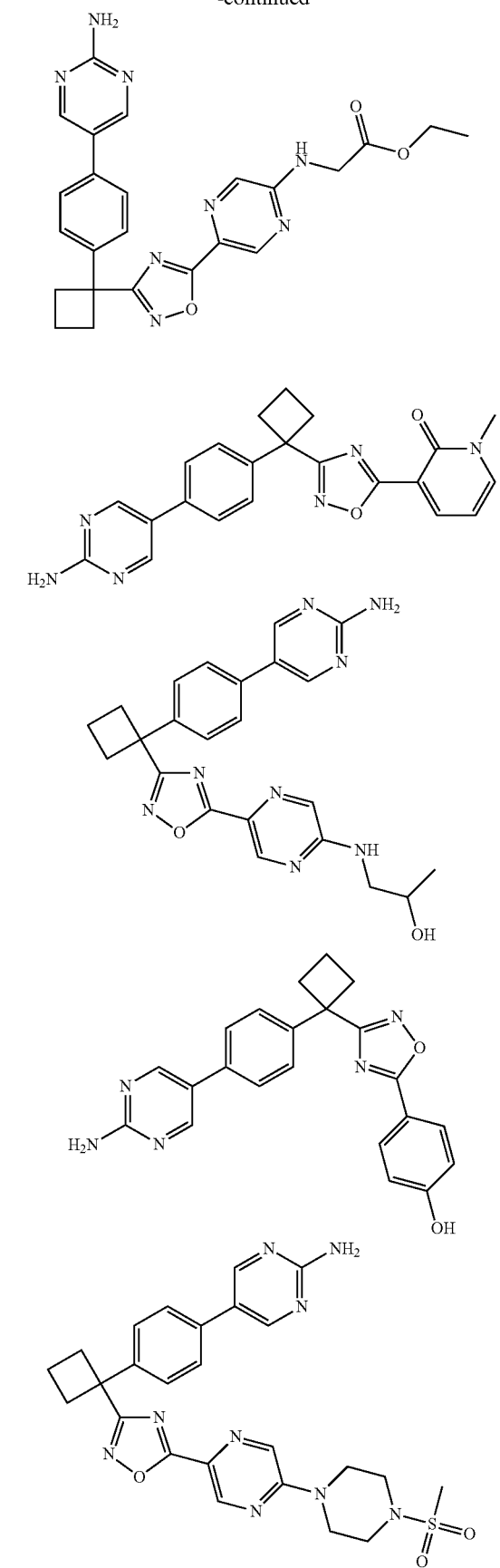

481
-continued
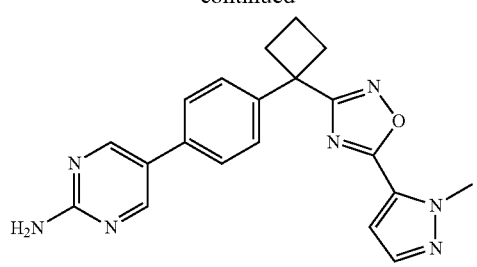
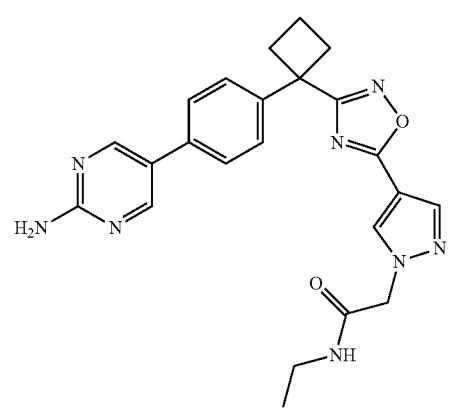
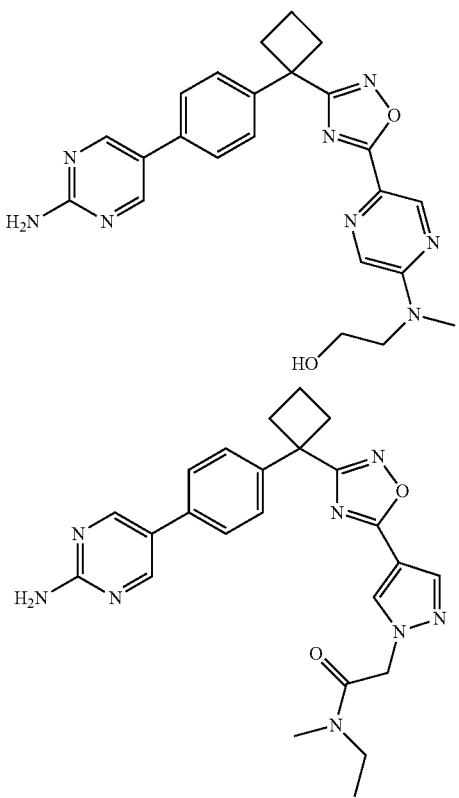
482
-continued
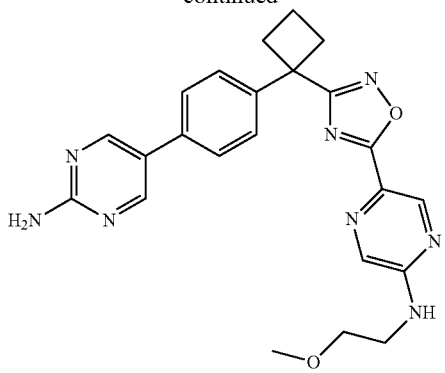
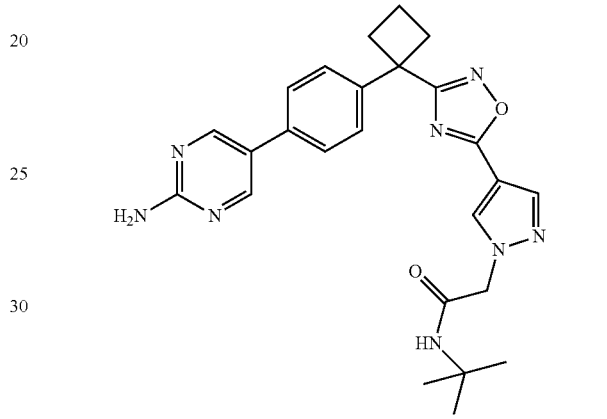
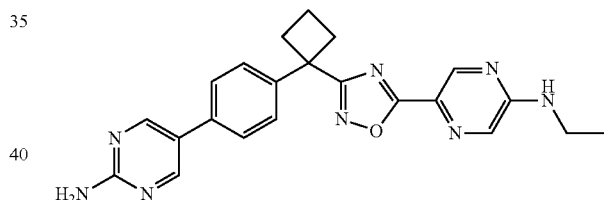
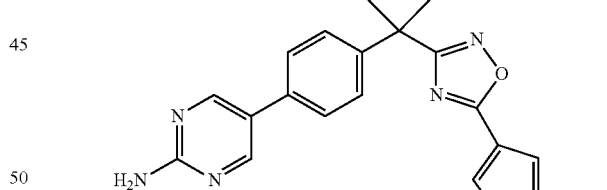
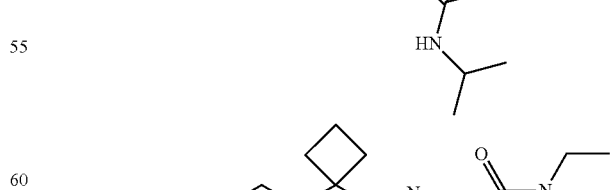
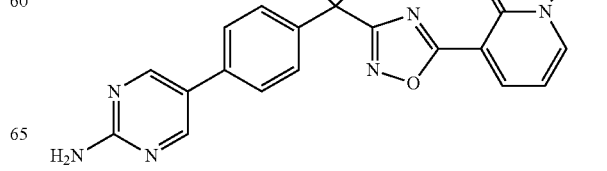

483
-continued
484
-continued
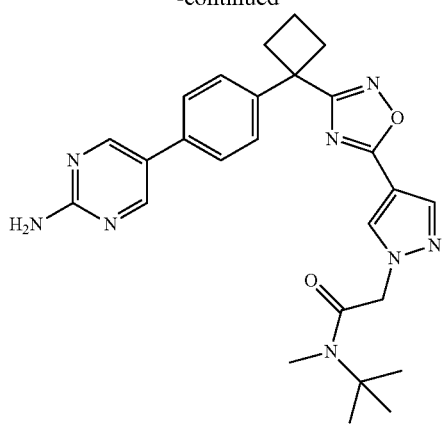
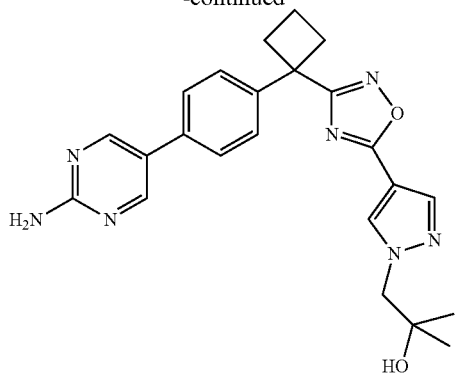
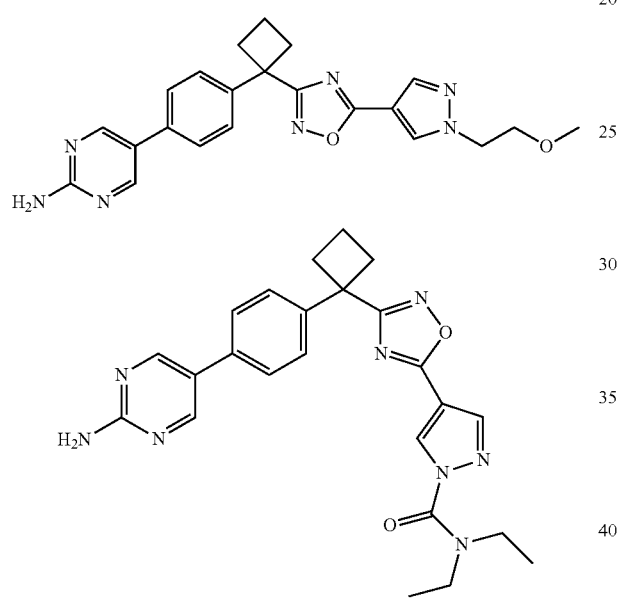
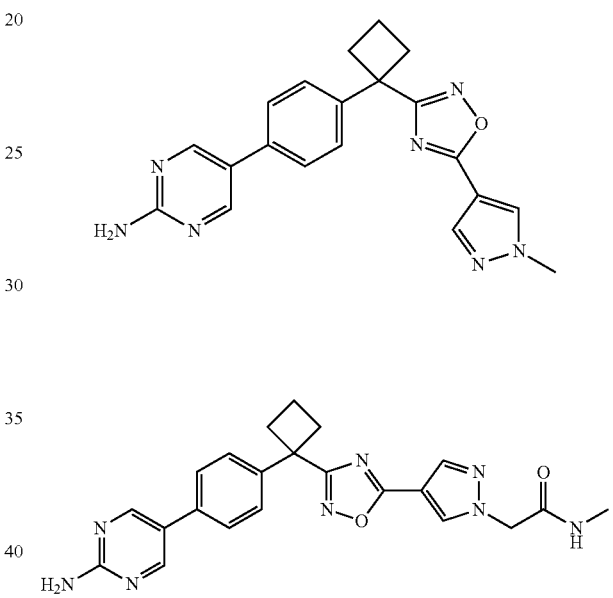
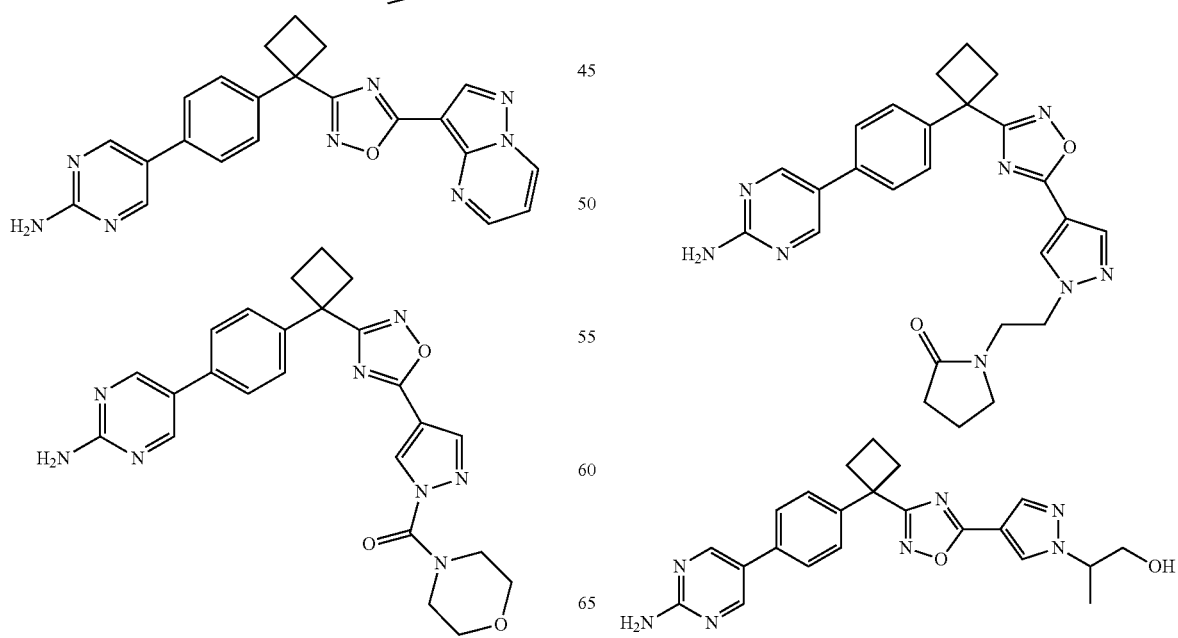

485
-continued
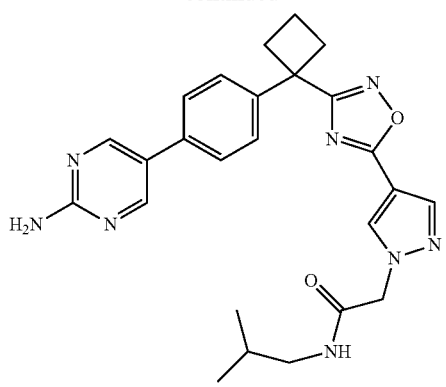
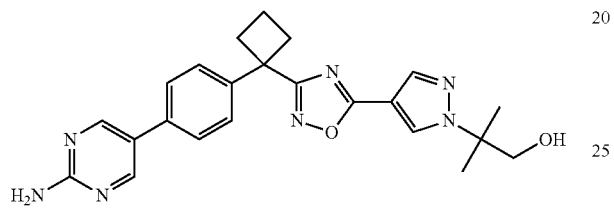
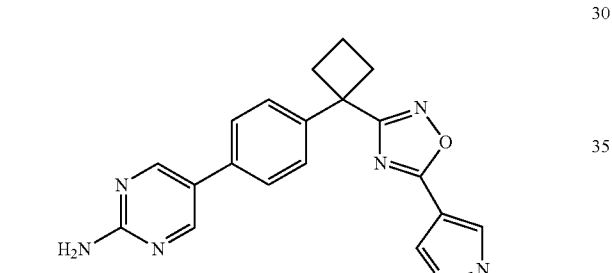
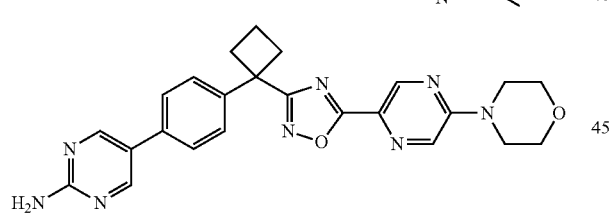
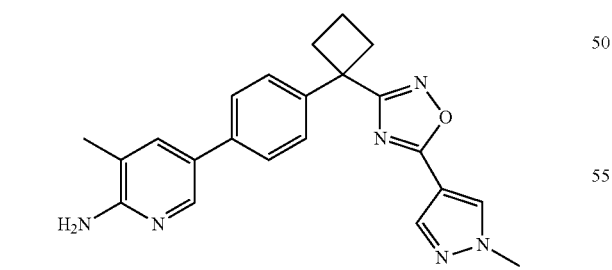
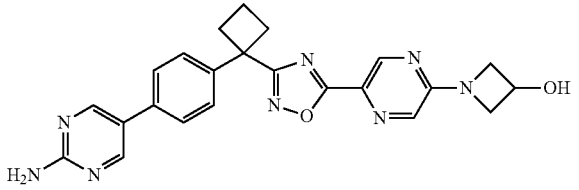
486
-continued
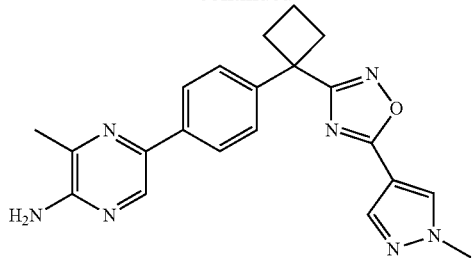
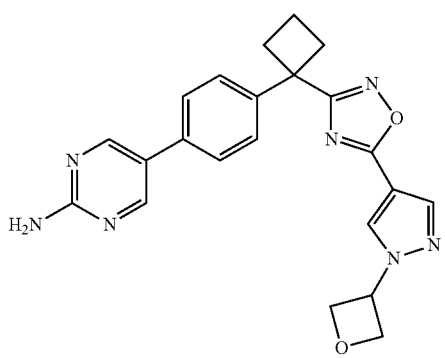
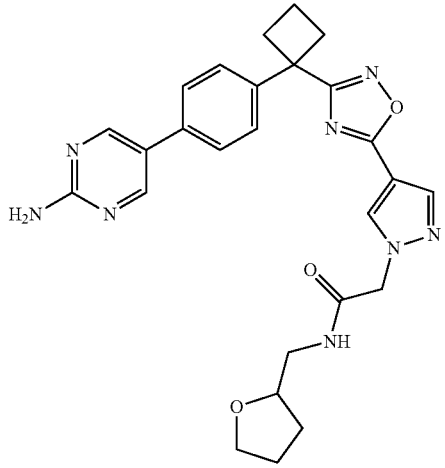
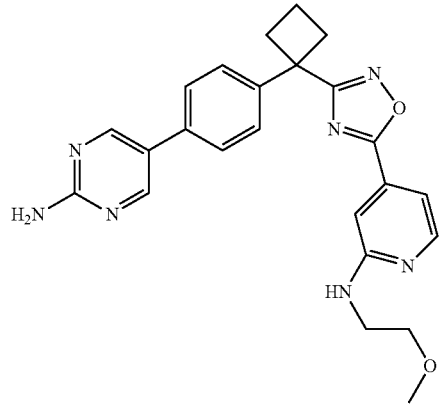

487
-continued
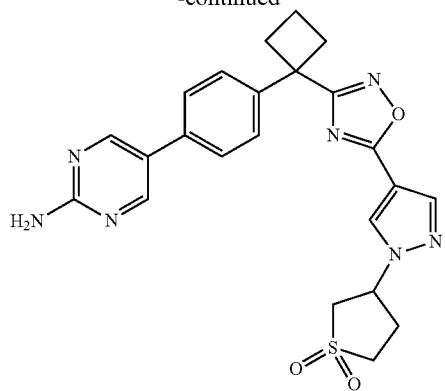
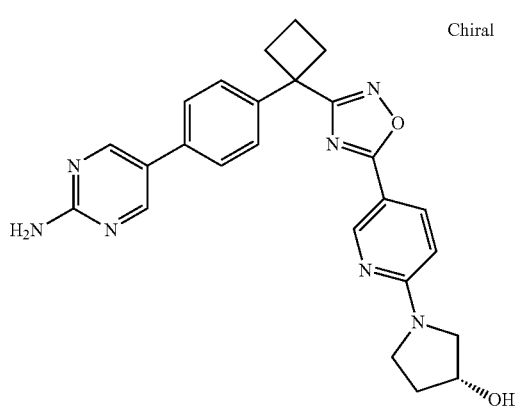
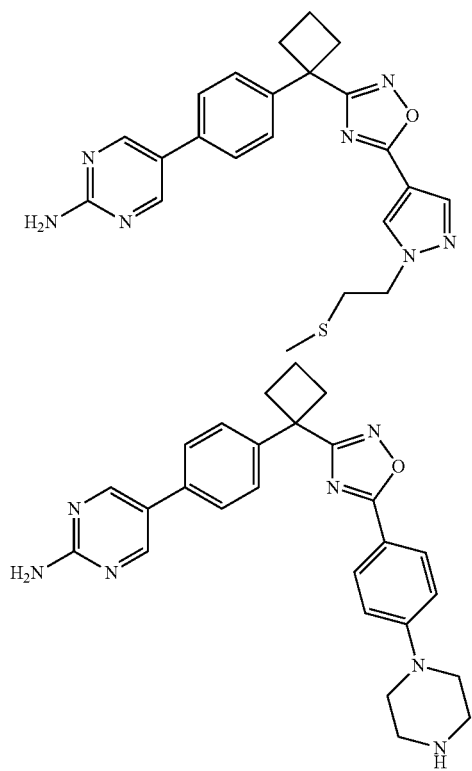
488
-continued
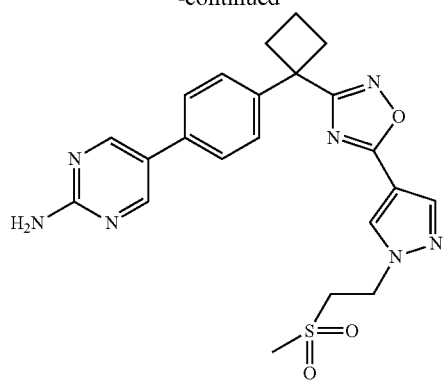
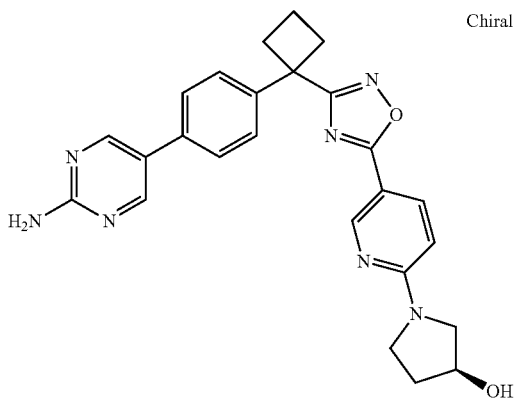
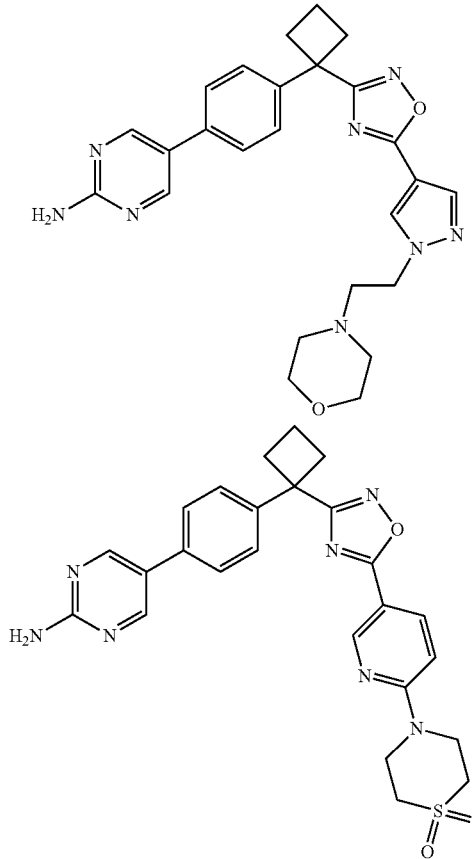

489
-continued
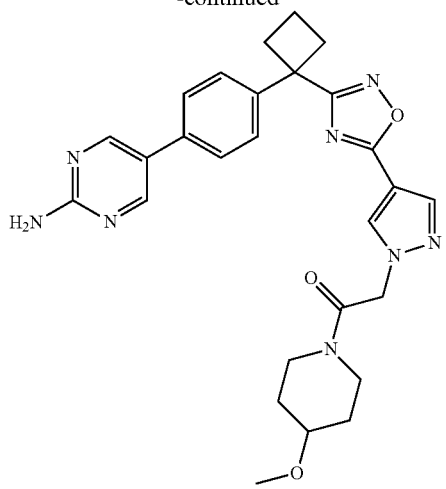
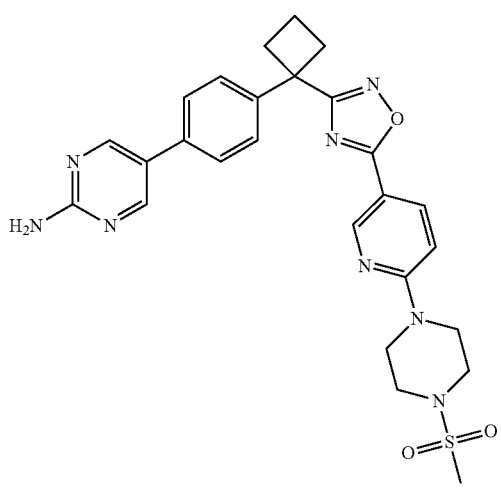
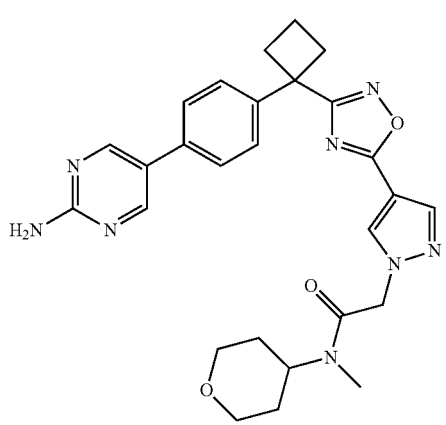
490
-continued
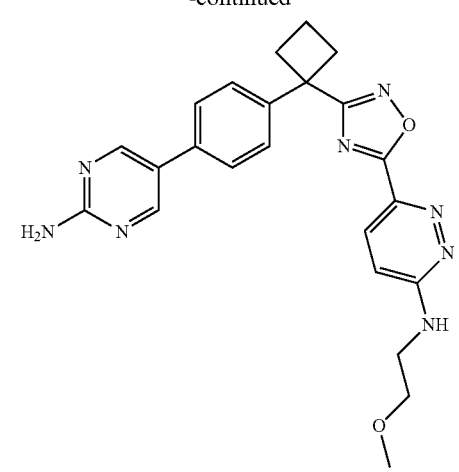
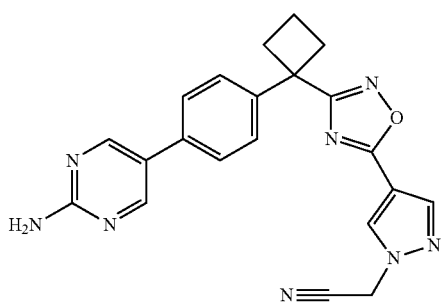
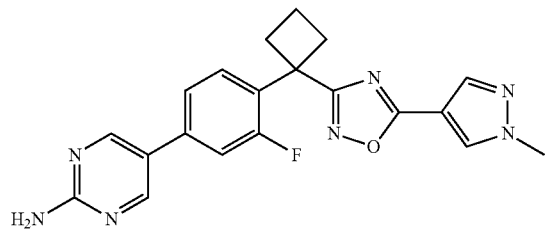
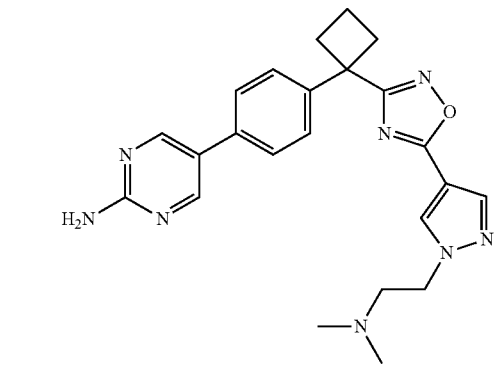

491
-continued
492
-continued
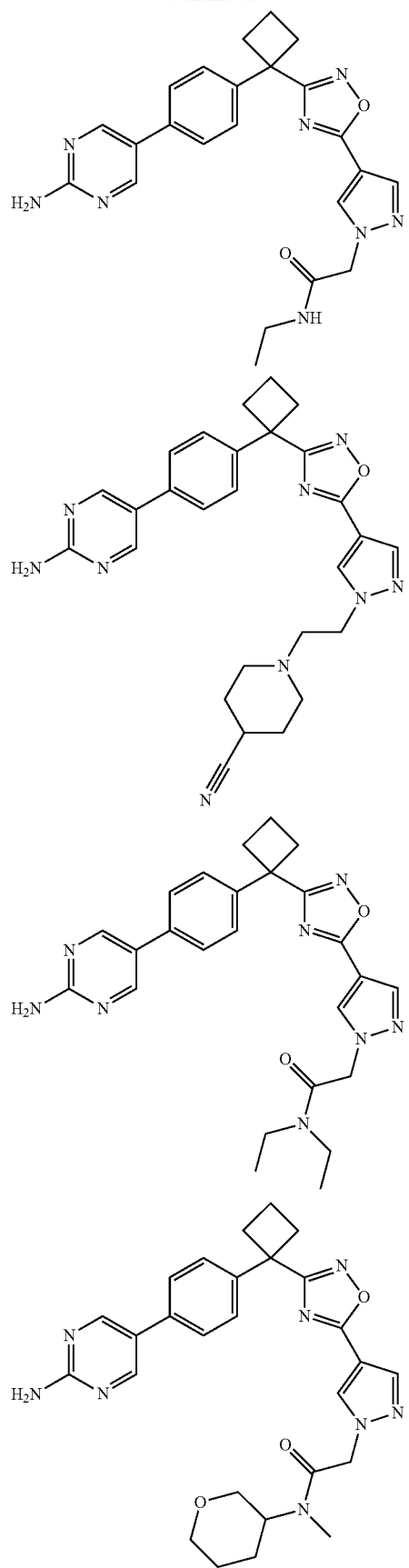
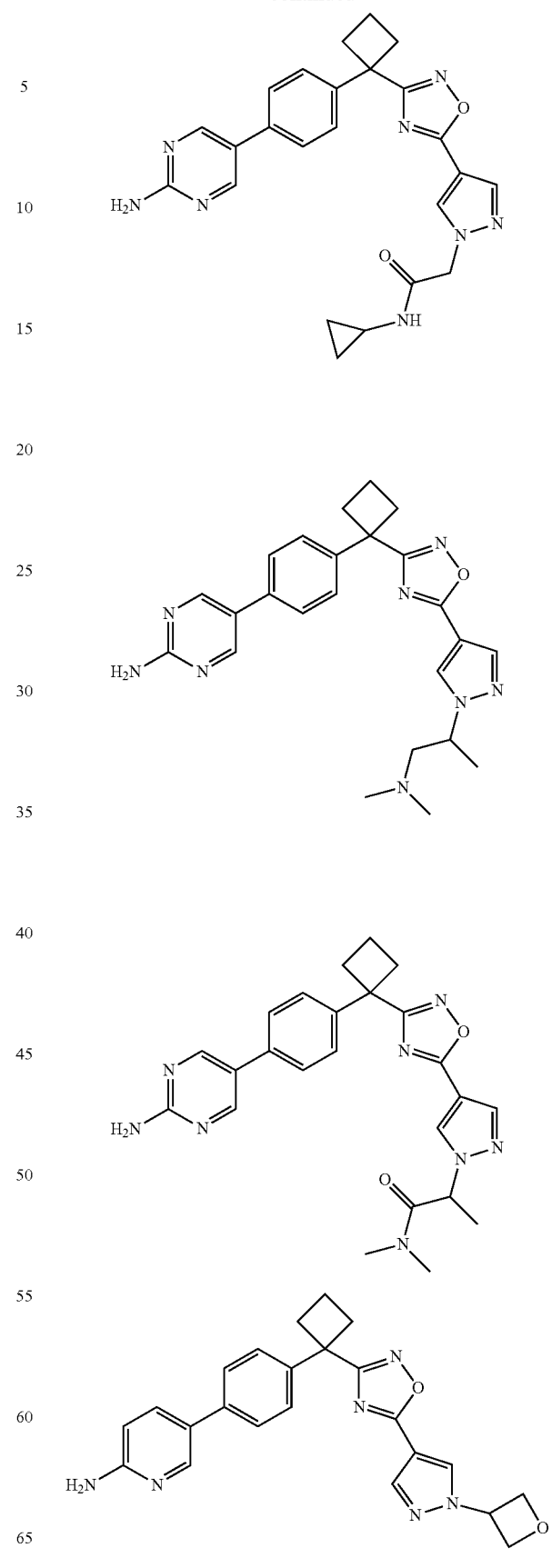

493
-continued
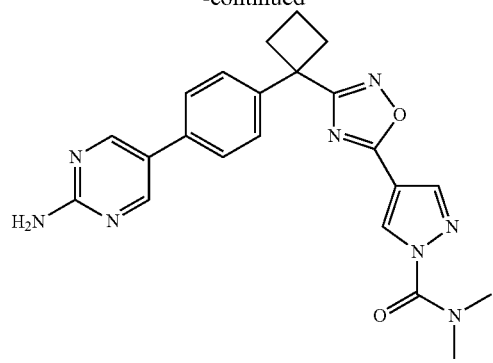
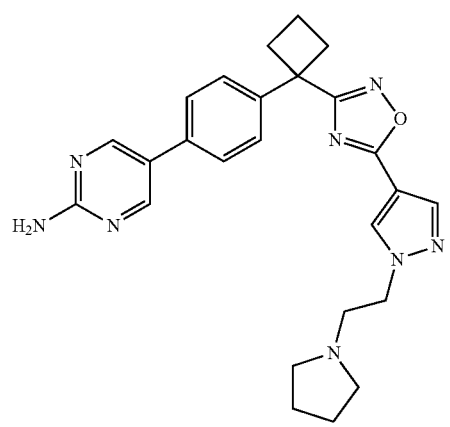
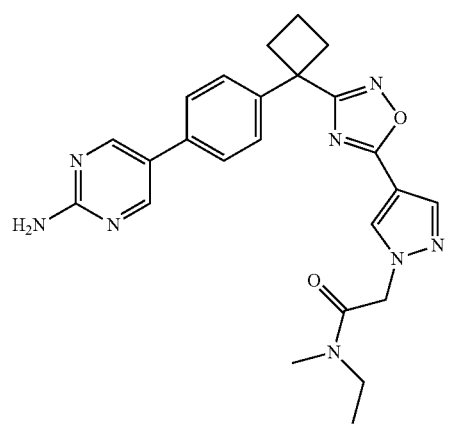
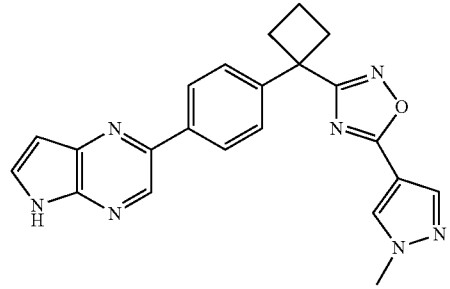
494
-continued
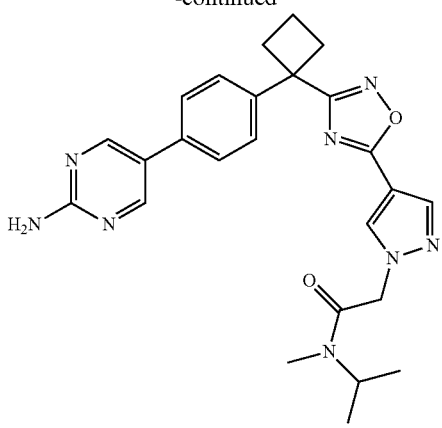
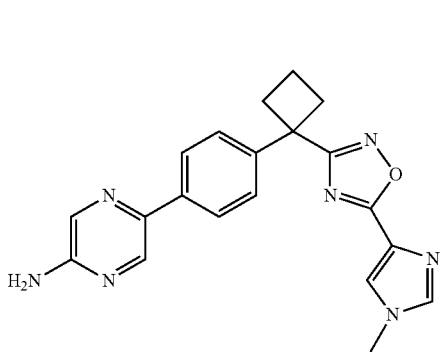
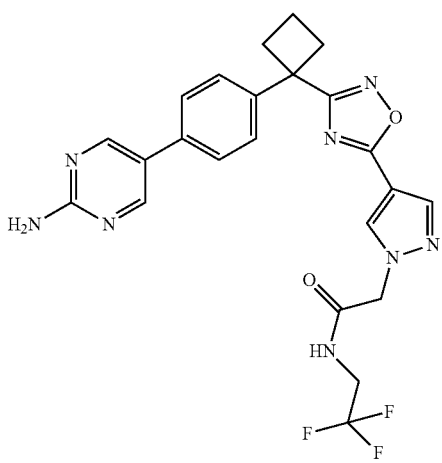
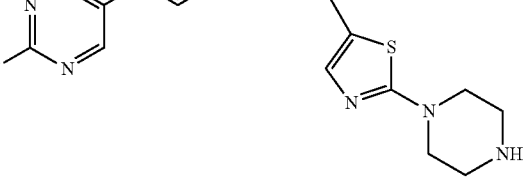

495
-continued
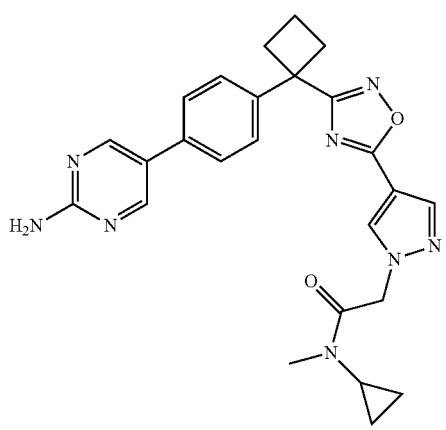
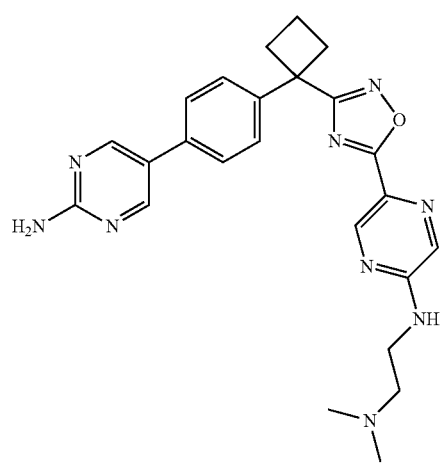
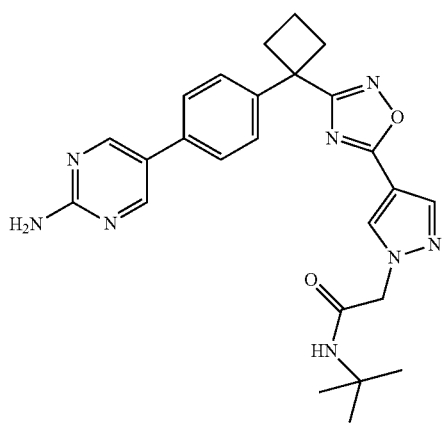
496
-continued
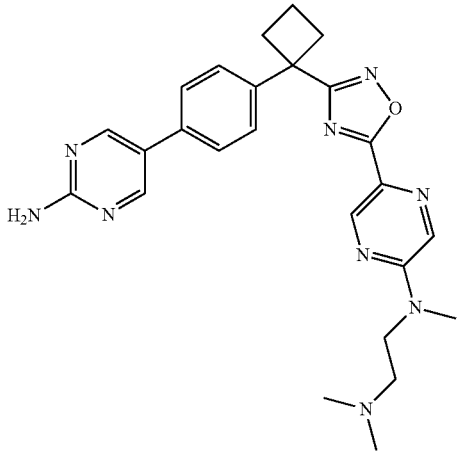
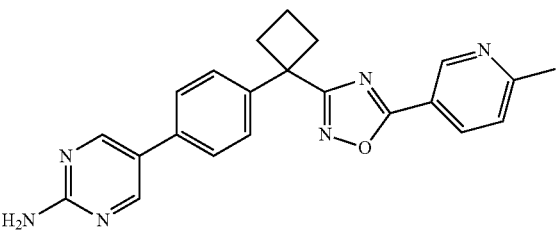
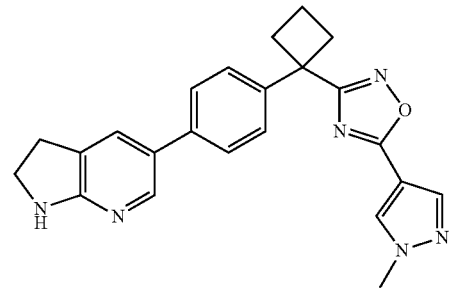
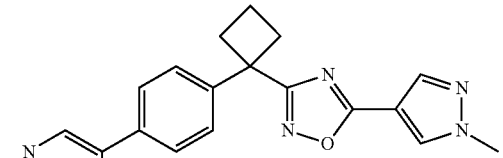
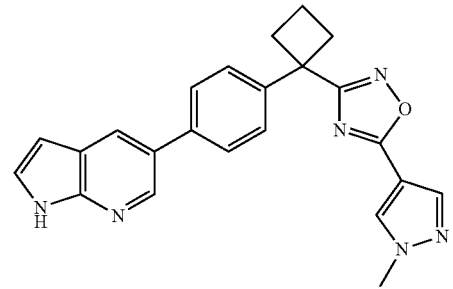

497
-continued
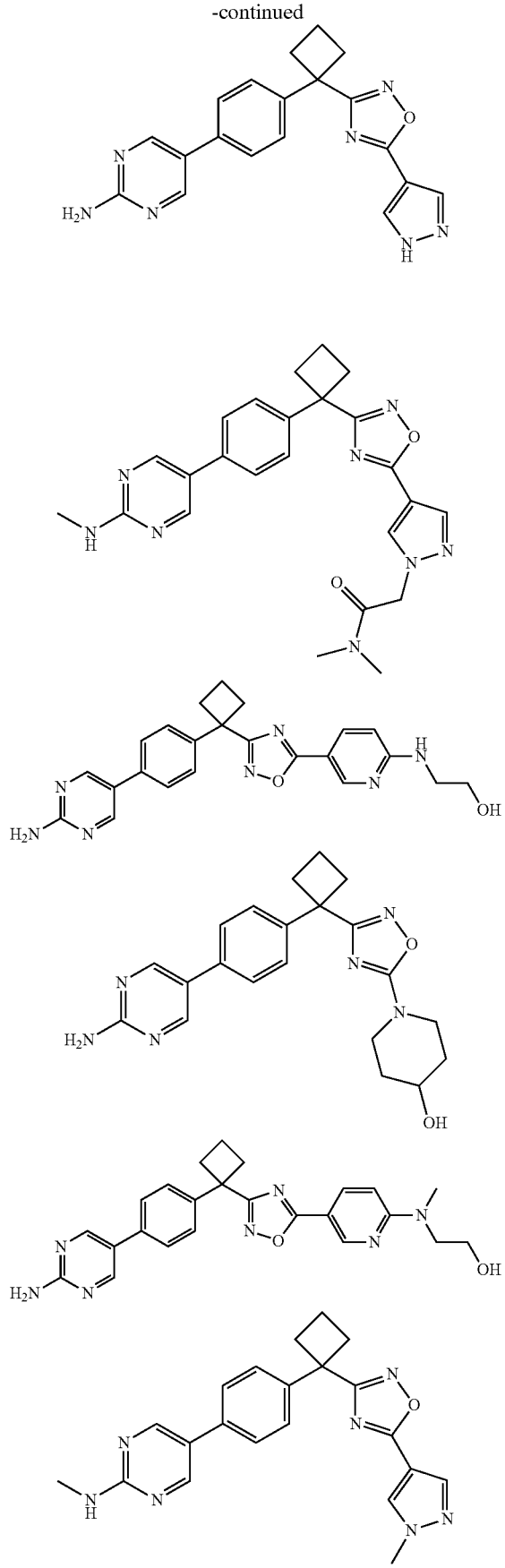
498
-continued
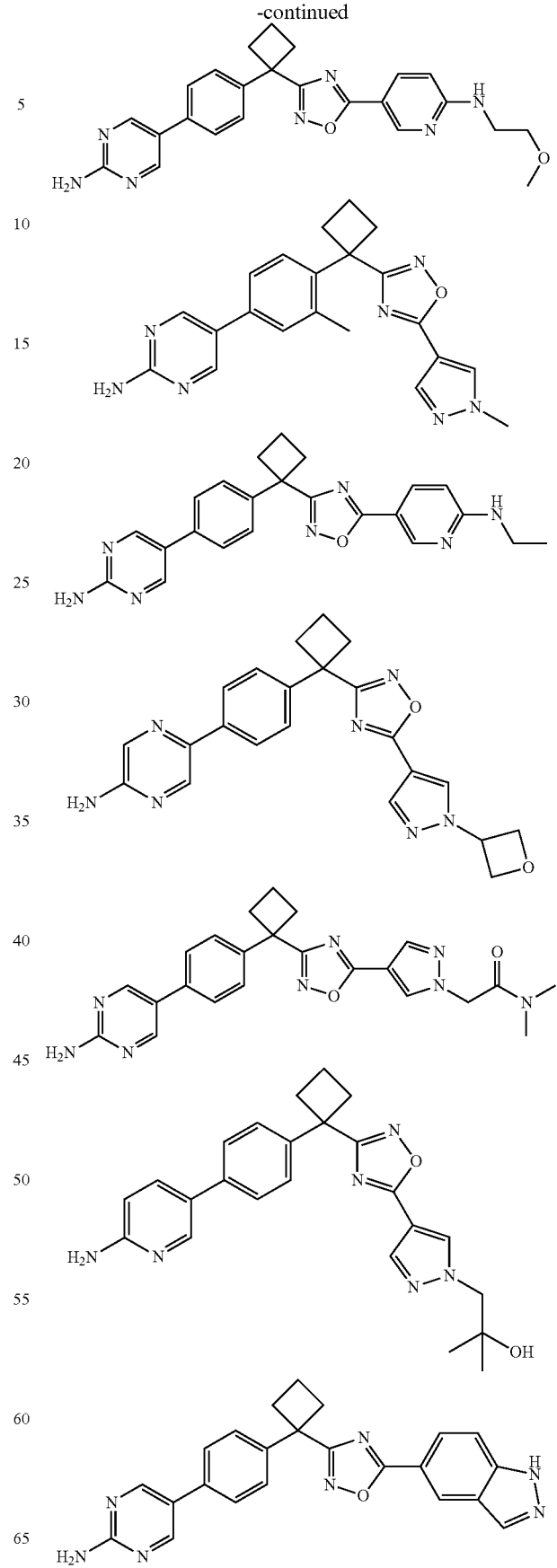

-continued
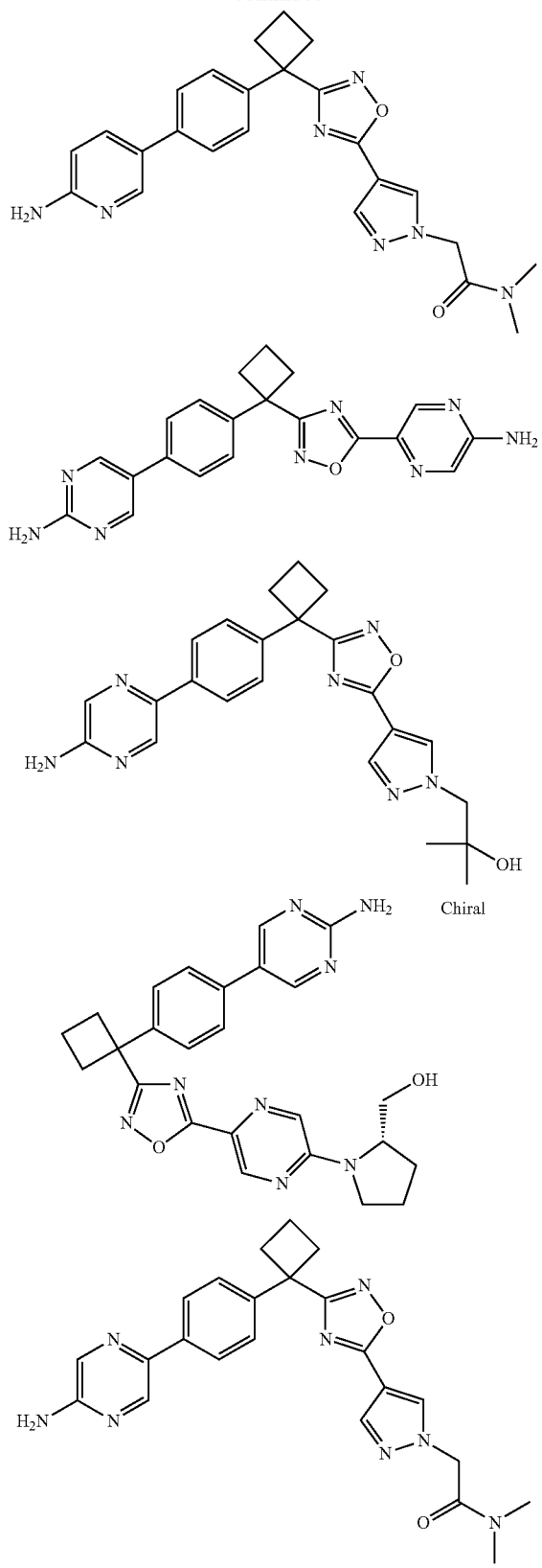
or a pharmaceutically acceptable salt thereof.
16. A compound according to claim 14, selected from a group consisting of:
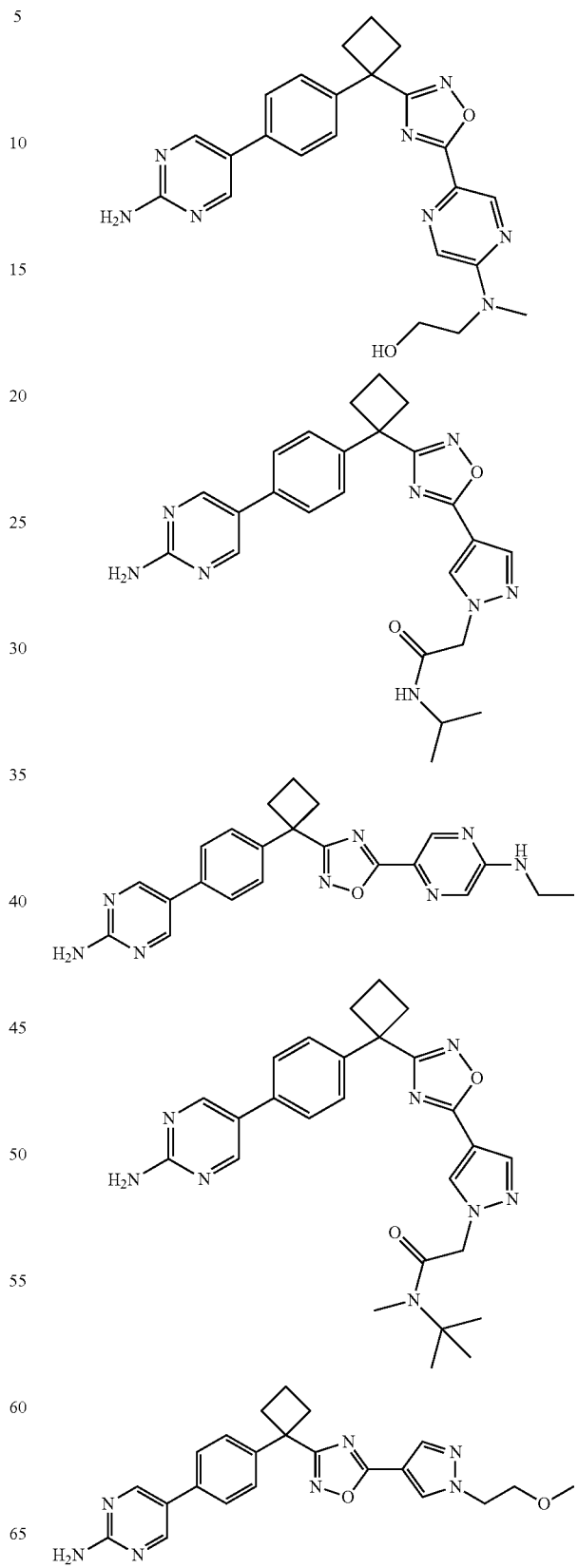

501
-continued
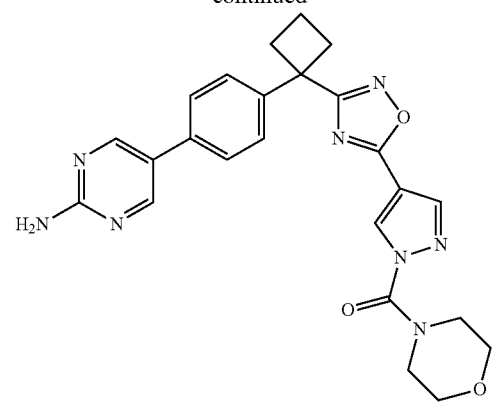
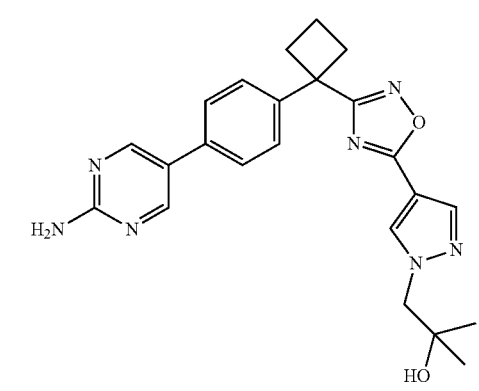
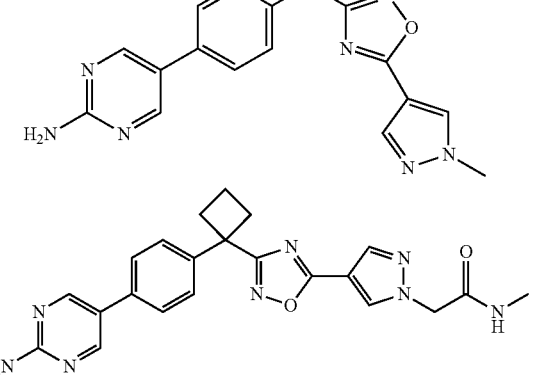
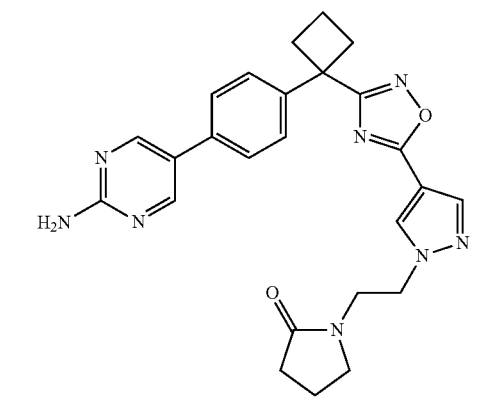
502
-continued
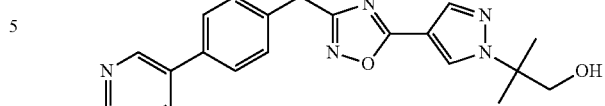
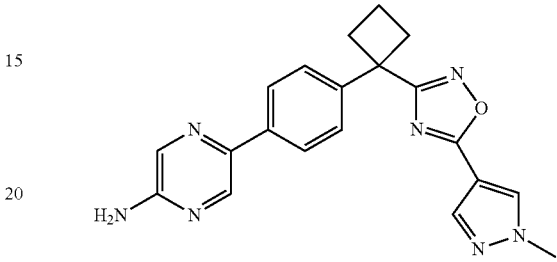
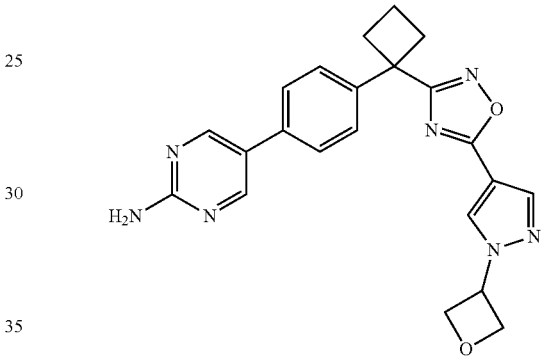
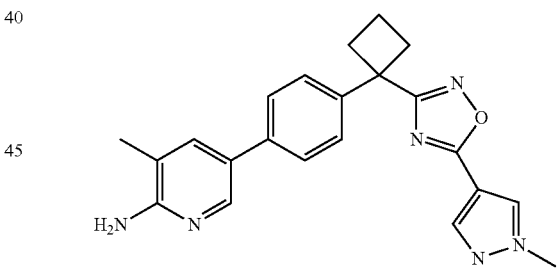
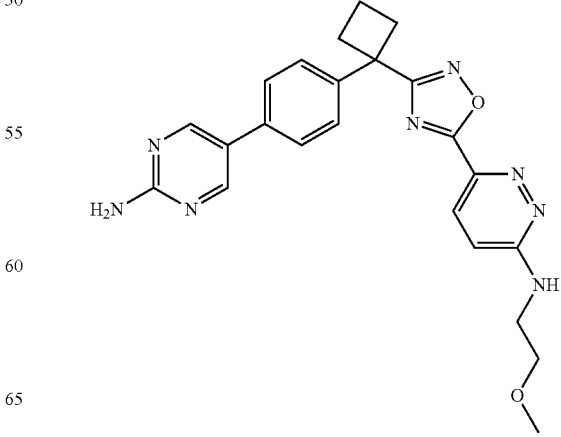

503
-continued
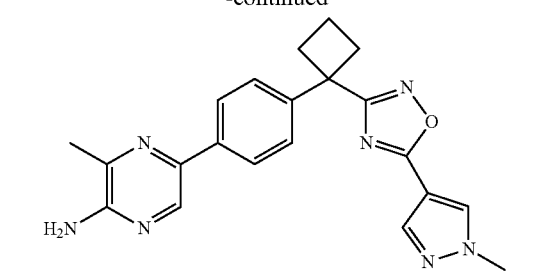
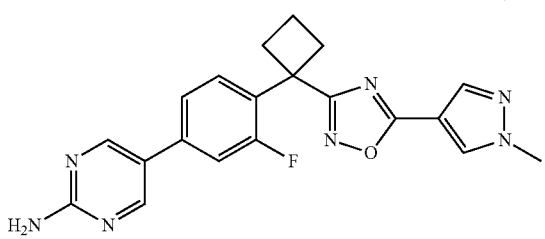
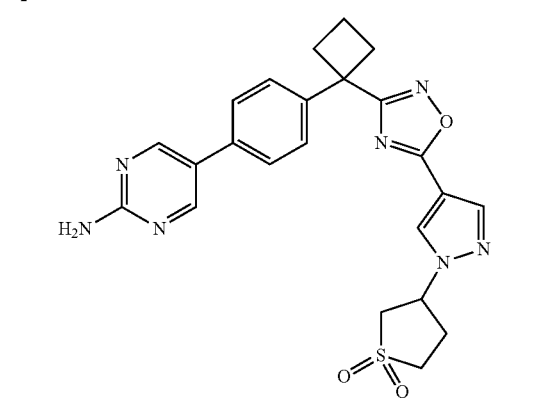
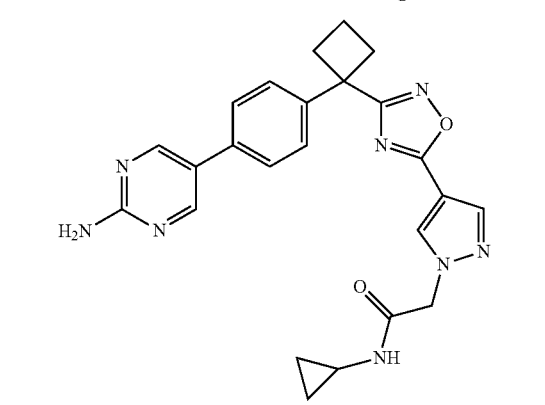
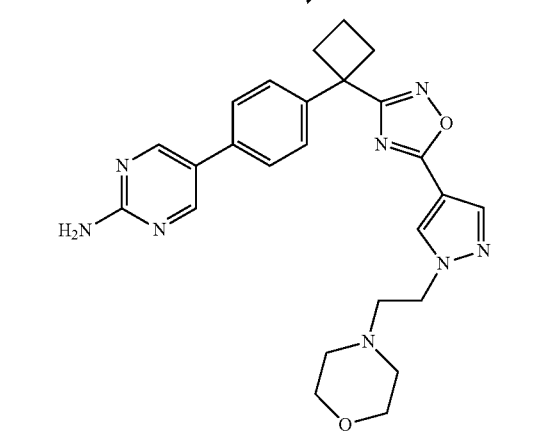
504
-continued
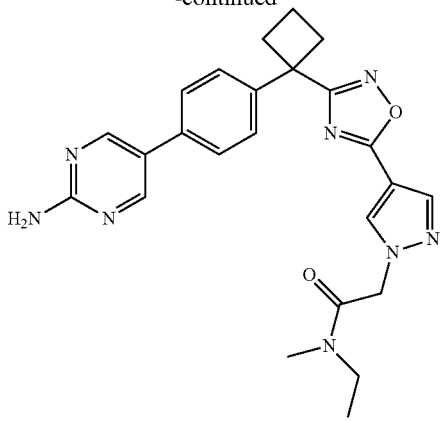
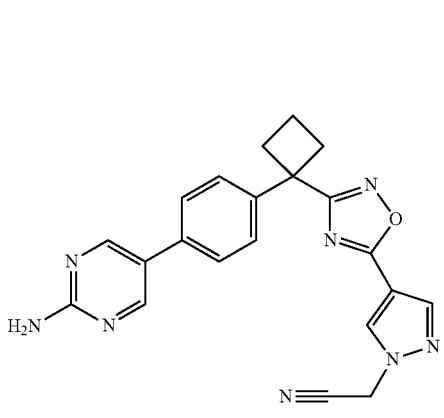

505
-continued
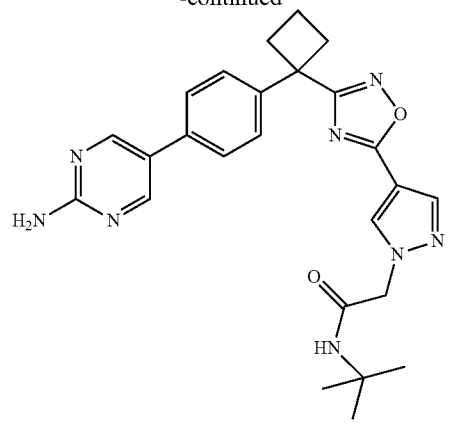
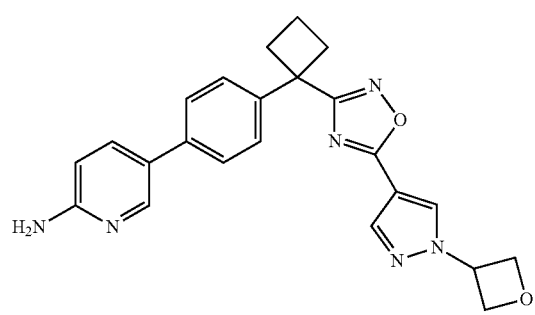
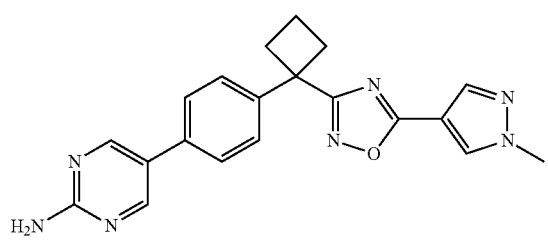
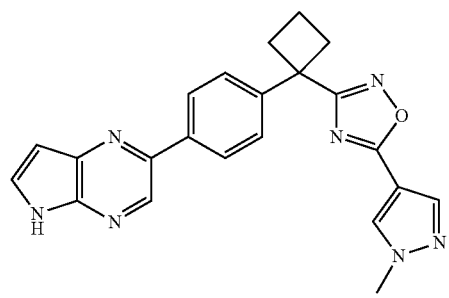
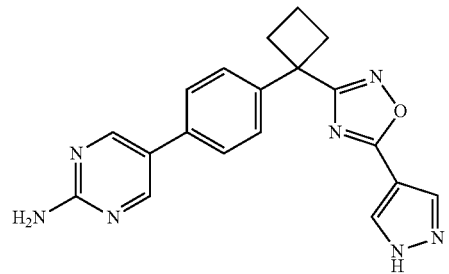
506
-continued
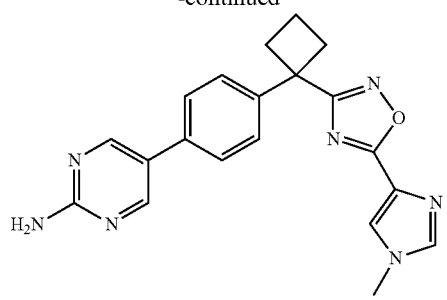
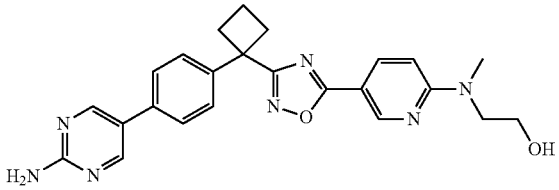
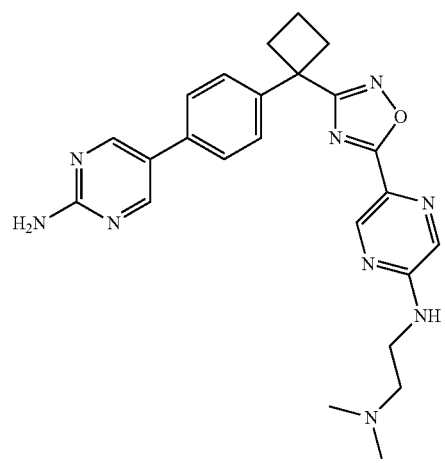
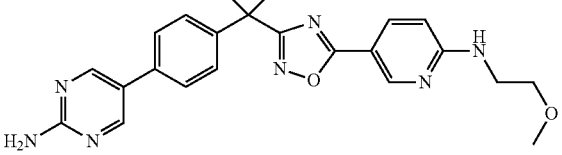
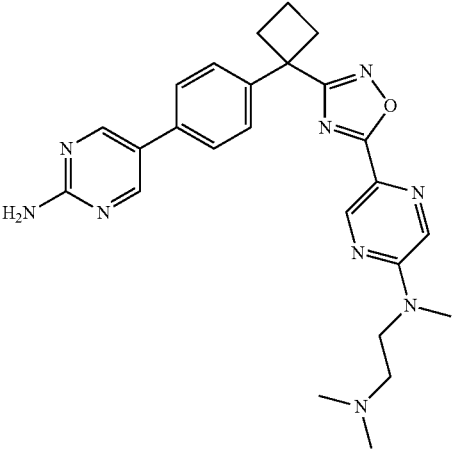

507
-continued
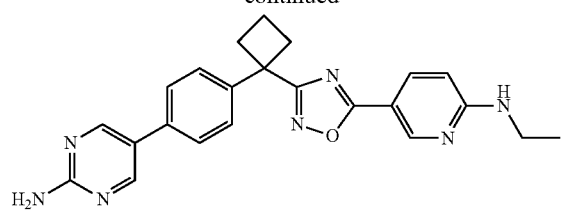
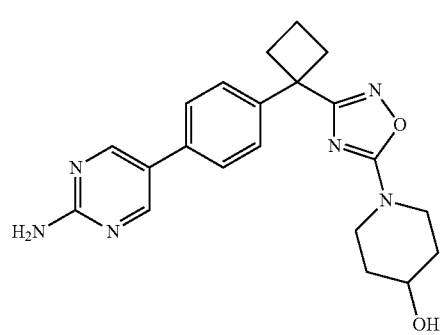
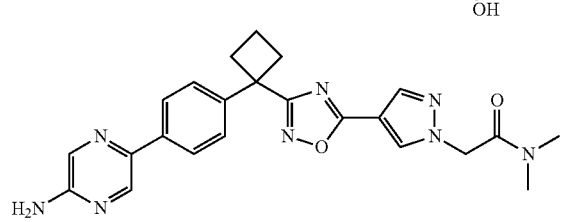
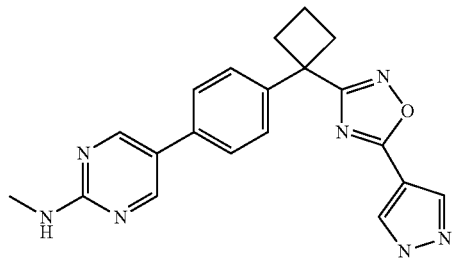
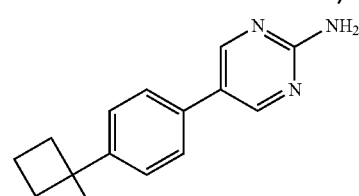
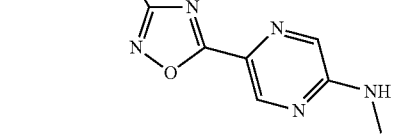
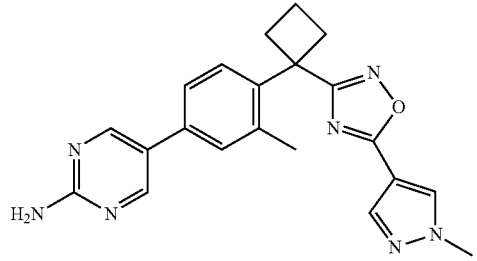
508
-continued
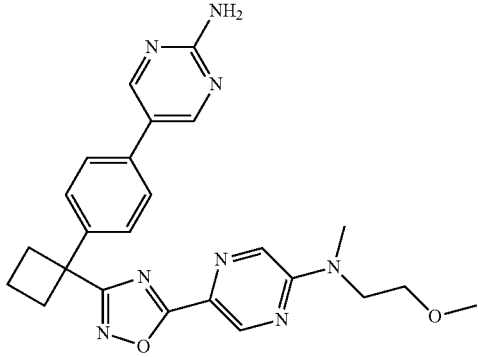
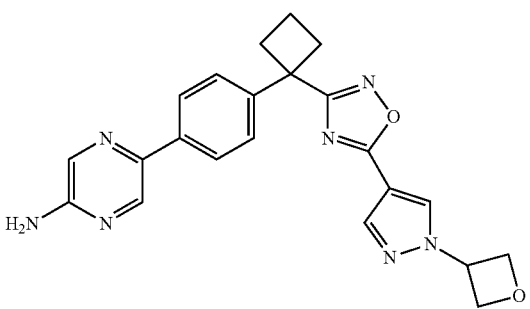
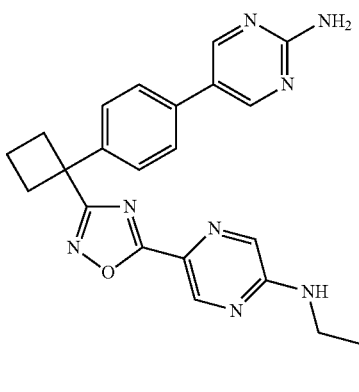
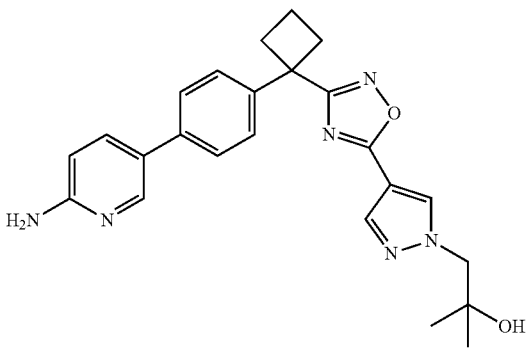

509
-continued

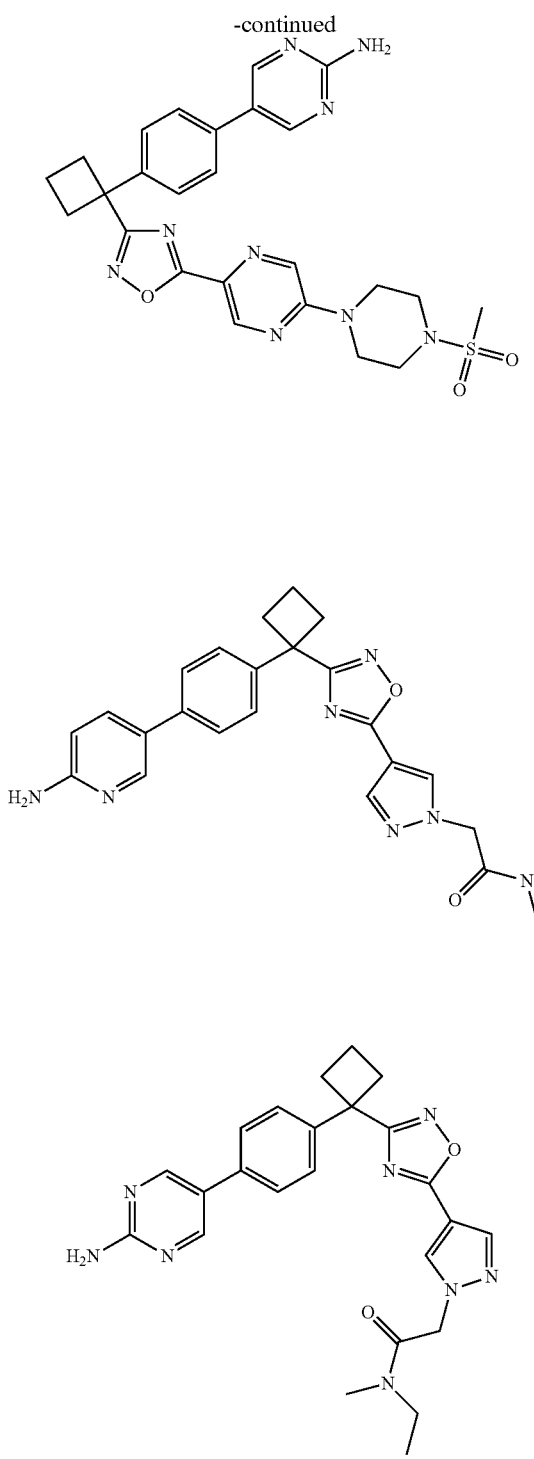

510
-continued

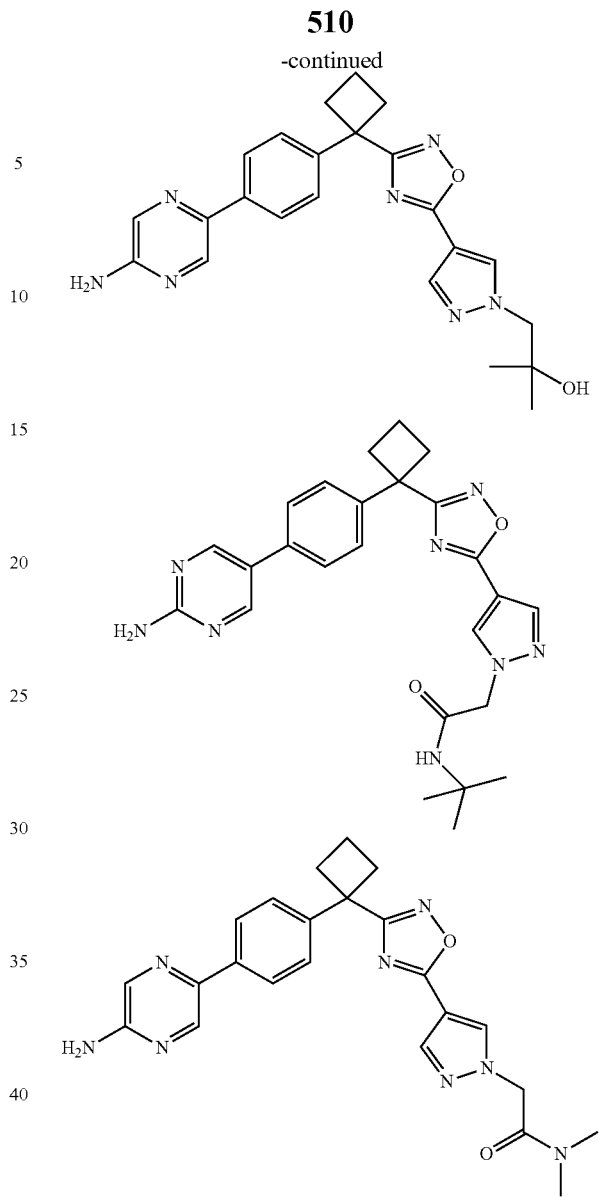

or a pharmaceutically acceptable salt thereof.

17. A pharmaceutical composition comprising a compound according to claim 1, or a pharmaceutically acceptable salt thereof, and a pharmaceutically acceptable excipient and/or carrier.

18. A method of treating atherosclerosis comprising administering an effective amount of a compound according to claim 1 or a pharmaceutically acceptable salt thereof, to a patient in need thereof.

* * * * *